US008420635B2

(12) United States Patent
Matsuda et al.

(10) Patent No.: US 8,420,635 B2
(45) Date of Patent: Apr. 16, 2013

(54) METHOD FOR PREVENTING OR TREATING A GLUCOCORTICOID RECEPTOR-RELATED DISEASE

(75) Inventors: Mamoru Matsuda, Ikoma (JP); Toshiyuki Mori, Ikoma (JP); Kenji Kawashima, Ikoma (JP); Masato Nagatsuka, Ikoma (JP); Sachiko Kobayashi, Ikoma (JP); Minoru Yamamoto, Ikoma (JP); Masatomo Kato, Ikoma (JP); Miwa Takai, Ikoma (JP); Tomoko Oda, Ikoma (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 0 days.

(21) Appl. No.: 13/135,164

(22) Filed: Jun. 28, 2011

(65) Prior Publication Data

US 2011/0263589 A1 Oct. 27, 2011

Related U.S. Application Data

(63) Continuation of application No. 11/992,088, filed as application No. PCT/JP2006/318674 on Sep. 14, 2006, now Pat. No. 8,017,775.

(30) Foreign Application Priority Data

Sep. 14, 2005 (JP) .................................. 2005-266622
Feb. 3, 2006 (JP) .................................. 2006-027128

(51) Int. Cl.
*A61K 31/535* (2006.01)
(52) U.S. Cl.
USPC ....................................... 514/230.5; 514/311
(58) Field of Classification Search ............... 514/230.5, 514/311
See application file for complete search history.

(56) References Cited

U.S. PATENT DOCUMENTS

| 5,688,808 | A | 11/1997 | Jones et al. |
| 5,688,810 | A | 11/1997 | Jones et al. |
| 6,852,719 | B2 | 2/2005 | Liu et al. |
| 7,799,782 | B2 * | 9/2010 | Munson et al. ............ 514/234.5 |
| 2004/0116455 | A1 | 6/2004 | Bekkali et al. |
| 2007/0254917 | A1 | 11/2007 | Higuchi et al. |
| 2009/0298826 | A1 | 12/2009 | Matsuda et al. |
| 2009/0298827 | A1 | 12/2009 | Matsuda et al. |
| 2010/0056504 | A1 | 3/2010 | Matsuda et al. |

FOREIGN PATENT DOCUMENTS

| EP | 1 944 290 A1 | 7/2008 |
| JP | 10-510840 A | 10/1998 |
| JP | 2002-193955 A | 7/2002 |
| WO | WO 96/19458 A2 | 6/1996 |
| WO | WO 96/19458 A3 | 6/1996 |
| WO | WO 2004/018429 A2 | 3/2004 |
| WO | WO 2006/019716 A1 | 2/2006 |
| WO | WO 2007/032556 A1 | 3/2007 |
| WO | WO 2008/111632 A1 | 9/2008 |

OTHER PUBLICATIONS

Hajime Nawata, Sougou Rinsyou, "New horizon of glucocorticoid therapy in 21st century," 54(7), 1951-2076 (2005).
Ku, Yi-Yin; Grieme, Tim; Raje, Prasad; Sharma, Padam; King, Steve; Morton, Edward: "Asymmetric Synthesis of A-240610.0 via a New Atropselective Approach for Axially Chiral Biaryls with Chirality Transfer," Journal of the American Chemical Society, vol. 124, 2002, pp. 4282-4286.
Supplementary European Search Report dated Dec. 2, 2010 in European application No. EP 06 79 8171.
International Search Report for PCT/JP2006/318674 dated Dec. 5, 2006.

* cited by examiner

*Primary Examiner* — Rei-tsang Shiao
(74) *Attorney, Agent, or Firm* — Holtz Holtz Goodman & Chick PC

(57) ABSTRACT

A method of preventing or treating a glucocorticoid receptor-related disease involving administering a therapeutically effective amount of a 1,2-dihydroquinoline compound or a pharmaceutically acceptable salt thereof.

34 Claims, No Drawings

METHOD FOR PREVENTING OR TREATING A GLUCOCORTICOID RECEPTOR-RELATED DISEASE

CROSS-REFERENCE TO RELATED APPLICATIONS

This application is a continuation application of application Ser. No. 11/992,088 (U.S. Pat. No. 8,017,775) filed Mar. 14, 2008, which is a United States national phase application under 35 USC 371 of International application PCT/JP2006/318674 filed Sep. 14, 2006. The entire contents of each of application Ser. No. 11/992,088 and International application PCT/JP2006/318674 are hereby incorporated by reference herein.

TECHNICAL FIELD

The present invention relates to a novel 1-2-dihydroquinoline derivative or a salt thereof, which is useful as a pharmaceutical. The derivative has a glucocorticoid receptor binding activity and is useful as a glucocorticoid receptor modulator having a nonsteroidal structure (a glucocorticoid receptor agonist and/or a glucocorticoid receptor antagonist).

BACKGROUND ART

A glucocorticoid receptor is a 94 kDa ligand-activated intracellular transcriptional factor that is a member of the nuclear receptor superfamily. This receptor is known to regulate the metabolism of carbohydrates, proteins, fats and the like, suppress the immune or inflammatory responses, activate the central nervous system, regulate cardiovascular function, and affect basal and stress-related homeostasis and the like due to its transcriptional regulatory, action. As glucocorticoid receptor-related diseases, metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like are known (SOUGOU RINSYOU, 54(7), 1951-2076 (2005) and JP-A-2002-193955).

Therefore, a compound having a glucocorticoid receptor binding activity is considered to be useful as a preventive and/or therapeutic agent for these diseases.

As such a compound having a glucocorticoid receptor binding activity, glucocorticoid receptor agonists synthesized in the living body such as cortisol and corticosterone, synthetic glucocorticoid receptor agonists such as dexamethasone, prednisone and prednisilone, non-selective glucocorticoid receptor antagonists such as RU486 and the like are known (JP-A-2002-193955).

On the other hand, compounds having a 1,2-dihydroquinoline structure are disclosed as steroid receptor modulators in WO 2004/018429, JP-T-10-0510840 and the like. The compounds disclosed in WO 2004/018429 and JP-T-10-0510840 have a 1,2-dihydroquinoline structure, however, a compound in which any of various substituents has been introduced at the 5-position of the 1,2-dihydroquinoline structure has not been specifically disclosed therein.

DISCLOSURE OF THE INVENTION

It is a very interesting subject to study synthesis of a novel 1,2-dihydroquinoline derivative and to find a pharmacological action of the derivative.

The present inventors conducted studies of synthesis of 1,2-dihydroquinoline derivatives having a novel chemical structure, and succeeded in producing a large number of novel compounds. Further, the present inventors studied the pharmacological actions of the derivatives and as a result, they found that the derivatives have a glucocorticoid receptor binding activity and are useful as a pharmaceutical, and thus the present invention has been completed.

That is, the present invention relates to a compound represented by the following general formula (1) or a salt thereof (hereinafter referred to as "the present compound") and a pharmaceutical composition containing the same. Further, a preferred invention in its pharmaceutical use relates to a glucocorticoid receptor modulator, and its target diseases are glucocorticoid receptor-related diseases, that is, metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like. A particularly preferred invention is an invention relating to a preventive or a therapeutic agent for these diseases.

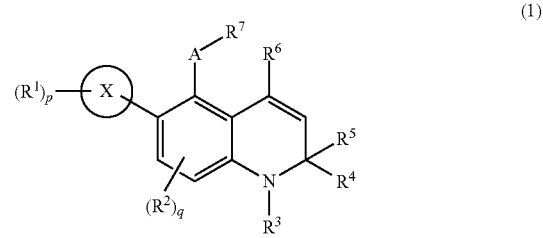

(1)

[The ring X represents a benzene ring or a pyridine ring;

$R^1$ represents a halogen atom, a lower alkyl group which may have at least a substituent, a hydroxy group, a lower alkoxy group which may have at least a substituent, a lower alkenyloxy group which may have at least a substituent, a lower alkylcarbonyl group, an amino group, a nitro group or a cyano group;

p represents an integer of 0 to 5;

in the case where p is 2 to 5, each $R^1$ may be the same or different;

$R^2$ represents a halogen atom, a lower alkyl group which may have at least a substituent, a hydroxy group, an ester of a hydroxy group or a lower alkoxy group which may have at least a substituent;

q represents an integer of 0 to 2;

in the case where q is 2, each $R^2$ may be the same or different;

$R^3$ represents a hydrogen atom, a lower alkyl group which may have at least a substituent, a lower alkenyl group which may have at least a substituent, a lower alkynyl group which may have at least a substituent, an aryl group which may have at least a substituent, a lower alkylcarbonyl group which may have at least a substituent, a lower alkenylcarbonyl group which may have at least a substituent, a lower alkynylcarbonyl group which may have at least a substituent or an arylcarbonyl group which may have at least a substituent;

$R^4$ and $R^5$ may be the same or different and represent a hydrogen atom or a lower alkyl group;

$R^4$ and $R^5$ may be combined together to form a 3- to 8-membered lower cycloalkane ring;

$R^6$ represents a hydrogen atom or a lower alkyl group;

A represents a lower alkylene group or a carbonyl group;

$R^7$ represents $OR^8$, $NR^8R^9$, $SR^8$, $S(O)R^8$ or $S(O)_2R^8$;

$R^8$ represents a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group which may have at least a substituent, a formyl group, a lower alkylcarbonyl group which may have at least a substituent, a lower alkenylcarbonyl group which may have at least a substituent, a lower alkynylcarbonyl group which may have at least a substituent, a lower cycloalkylcarbonyl group which may have at least a substituent, an arylcarbonyl group which may have at least a substituent, a heterocyclic carbonyl group which may have at least a substituent, a carboxy group, a lower alkoxycarbonyl group which may have at least a substituent, a lower alkenyloxycarbonyl group which may have at least a substituent, a lower alkynyloxycarbonyl group which may have at least a substituent, a lower cycloalkyloxycarbonyl group which may have at least a substituent, an aryloxycarbonyl group which may have at least a substituent, a heterocyclic oxycarbonyl group which may have at least a substituent, a lower alkylsulfonyl group which may have at least a substituent, a lower alkenylsulfonyl group which may have at least a substituent, a lower alkynylsulfonyl group which may have at least a substituent, a lower cycloalkylsulfonyl group which may have at least a substituent, an arylsulfonyl group which may have at least a substituent, a heterocyclic sulfonyl group which may have at least a substituent, an aminocarbonyl group, a lower alkylaminocarbonyl group which may have at least a substituent, a lower alkenylaminocarbonyl group which may have at least a substituent, a lower alkynylaminocarbonyl group which may have at least a substituent, a lower cycloalkylaminocarbonyl group which may have at least a substituent, an arylaminocarbonyl group which may have at least a substituent or a heterocyclic aminocarbonyl group which may have at least a substituent;

$R^9$ represents a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group which may have at least a substituent, a formyl group, a lower alkylcarbonyl group which may have at least a substituent, a lower alkenylcarbonyl group which may have at least a substituent, a lower alkynylcarbonyl group which may have at least a substituent, a lower cycloalkylcarbonyl group which may have at least a substituent, an arylcarbonyl group which may have at least a substituent, a heterocyclic carbonyl group which may have at least a substituent, a carboxy group, a lower alkoxycarbonyl group which may have at least a substituent, a lower alkenyloxycarbonyl group which may have at least a substituent, a lower alkynyloxycarbonyl group which may have at least a substituent, a lower cycloalkyloxycarbonyl group which may have at least a substituent, an aryloxycarbonyl group which may have at least a substituent, a heterocyclic oxycarbonyl group which may have at least a substituent, a lower alkylsulfonyl group which may have at least a substituent, a lower alkenylsulfonyl group which may have at least a substituent, a lower alkynylsulfonyl group which may have at least a substituent, a lower cycloalkylsulfonyl group which may have at least a substituent, an arylsulfonyl group which may have at least a substituent, a heterocyclic sulfonyl group which may have at least a substituent, an aminocarbonyl group, a lower alkylaminocarbonyl group which may have at least a substituent, a lower alkenylaminocarbonyl group which may have at least a substituent, a lower alkynylaminocarbonyl group which may have at least a substituent, a lower cycloalkylaminocarbonyl group which may have at least a substituent, an arylaminocarbonyl group which may have at least a substituent or a heterocyclic aminocarbonyl group which may have at least a substituent;

further, in the case where $R^7$ is $NR^8R^9$, $R^8$ and $R^9$ may be combined together to form a 3- to 8-membered nitrogen-containing heterocyclic ring which may have a substituent. Hereinafter the same shall apply.]

The present invention provides a 1-2-dihydroquinoline derivative or a salt thereof, which is useful as a pharmaceutical. The present compound has an excellent glucocorticoid receptor binding activity and is useful as a glucocorticoid receptor modulator. In particular, the present compound is useful as a preventive or therapeutic agent for glucocorticoid receptor-related diseases, that is, metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like.

BEST MODE FOR CARRYING OUT THE INVENTION

Hereinafter, definitions of terms and phrases (atoms, groups and the like) to be used in this specification will be described in detail.

The "halogen atom" refers to a fluorine, chlorine, bromine or iodine atom.

The "lower alkyl group" refers to a straight chain or branched alkyl group having 1 to 8 carbon atoms.

Specific examples thereof include methyl, ethyl, n-propyl, n-butyl, n-pentyl, n-hexyl, n-heptyl, n-octyl, isopropyl, isobutyl, sec-butyl, tert-butyl and isopentyl groups and the like.

The "lower alkenyl group" refers to a straight chain or branched alkenyl group having 2 to 8 carbon atoms. Specific examples thereof include vinyl, propenyl, butenyl, pentenyl, hexenyl, heptenyl, octenyl, isopropenyl, 2-methyl-1-propenyl and 2-methyl-2-butenyl groups and the like.

The "lower alkynyl group" refers to a straight chain or branched alkynyl group having 2 to 8 carbon atoms. Specific examples thereof include ethynyl, propynyl, butynyl, pentynyl, hexynyl, heptynyl, octynyl, isobutynyl and isopentynyl groups and the like.

The "lower cycloalkyl group" refers to a cycloalkyl group having 3 to 8 carbon atoms. Specific examples thereof include cyclopropyl, cyclobutyl, cyclopentyl, cyclohexyl, cycloheptyl and cyclooctyl groups.

The "lower cycloalkane ring" refers to a cycloalkane ring having 3 to 8 carbon atoms. Specific examples thereof include cyclopropane, cyclobutane, cyclopentane, cyclohexane, cycloheptane and cyclooctane rings.

The "aryl group" refers to a residue formed by removing one hydrogen atom from a monocyclic aromatic hydrocarbon group, or bicyclic or tricyclic condensed polycyclic aromatic hydrocarbon having 6 to 14 carbon atoms. Specific examples thereof include phenyl, naphthyl, anthryl and phenanthryl groups and the like.

The "heterocyclic group" refers to a residue formed by removing one hydrogen atom from a saturated or unsaturated monocyclic heterocyclic ring, or a bicyclic or tricyclic condensed polycyclic heterocyclic ring having one or a plurality of heteroatoms selected from a nitrogen atom, an oxygen atom and a sulfur atom in the ring.

Specific examples of the saturated monocyclic heterocyclic ring include pyrrolidine, pyrazolidine, imidazolidine, triazolidine, piperidine, hexahydropyridazine, hexahydropyrimidine, piperazine, homopiperidine and homopiperazine rings and the like having at least a nitrogen atom in the ring, tetrahydrofuran and tetrahydropyran rings and the like having at least an oxygen atom in the ring, tetrahydrothiophene and tetrahydrothiopyran rings and the like having a sulfur atom in the ring, oxazolidine, isoxazolidine and morpholine rings and the like having a nitrogen atom and an oxygen atom in the ring, and thiazolidine, isothiazolidine and thiomorpholine rings and the like having a nitrogen atom and a sulfur atom in the ring.

Further, such a saturated monocyclic heterocyclic ring can be condensed with a benzene ring or the like to form a bicyclic or tricyclic condensed polycyclic heterocyclic ring such as a dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chromane, isochromane, dihydrobenzothiophene, dihydroisobenzothiophene, thiochromane, isothiochromane, dihydrobenzoxazole, dihydrobenzisoxazole, dihydrobenzoxazine, dihydrobenzothiazole, dihydrobenzisothiazole, dihydrobenzothiazine, xanthene, 4a-carbazole, or perimidine ring.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine rings and the like having at least a nitrogen atom in the ring, dihydrofuran, furan, dihydropyran and pyran rings and the like having at least an oxygen atom in the ring, dihydrothiophene, thiophene, dihydrothiopyran and thiopyran rings and the like having a sulfur atom in the ring, dihydrooxazole, oxazole, dihydroisoxazole, isoxazole, dihydrooxazine and oxazine rings and the like having a nitrogen atom and an oxygen atom in the ring, dihydrothiazole, thiazole, dihydroisothiazole, isothiazole, dihydrothiazine and thiazine rings and the like having a nitrogen atom and a sulfur atom in the ring.

Further, such an unsaturated monocyclic heterocyclic ring can be condensed with a benzene ring or the like to form a bicyclic or tricyclic condensed polycyclic heterocyclic ring such as an indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, benzisothiazole, benzothiazine, phenoxanthin, carbazole, β-carboline, phenanthridine, acridine, phenanthroline, phenazine, phenothiazine or phenoxazine ring.

The "lower alkoxy group" refers to a group formed by replacing the hydrogen atom of a hydroxy group with a lower alkyl group. Specific examples thereof include methoxy, ethoxy, n-propoxy, n-butoxy, n-pentoxy, n-hexyloxy, n-heptyloxy, n-octyloxy, isopropoxy, isobutoxy, sec-butoxy, tert-butoxy and isopentoxy groups and the like.

The "lower alkenyloxy group" refers to a group formed by replacing the hydrogen atom of a hydroxy group with a lower alkenyl group. Specific examples thereof include vinyloxy, propenyloxy, butenyloxy, pentenyloxy, hexenyloxy, heptenyloxy, octenyloxy, isopropenyloxy, 2-methyl-1-propenyloxy and 2-methyl-2-butenyloxy groups and the like.

The "lower alkynyloxy group" refers to a group formed by replacing the hydrogen atom of a hydroxy group with a lower alkynyl group. Specific examples thereof include ethynyloxy, propynyloxy, butynyloxy, pentynyloxy, hexynyloxy, heptynyloxy, octynyloxy, isobutynyloxy and isopentynyloxy groups and the like.

The "lower cycloalkyloxy group" refers to a group formed by replacing the hydrogen atom of a hydroxy group with a lower cycloalkyl group. Specific examples thereof include cyclopropyloxy, cyclobutyloxy, cyclopentyloxy, cyclohexyloxy, cycloheptyloxy and cyclooctyloxy groups and the like.

The "aryloxy group" refers to a group formed by replacing the hydrogen atom of a hydroxy group with an aryl group. Specific examples thereof include phenoxy, naphthoxy, anthryloxy and phenanthryloxy groups and the like.

The "heterocyclic oxy group" refers to a group formed by replacing the hydrogen atom of a hydroxy group with a heterocyclic group.

The "lower alkylthio group" refers to a group formed by replacing the hydrogen atom of a mercapto group with a lower alkyl group. Specific examples thereof include methylthio, ethylthio, n-propylthio, n-butylthio, n-pentylthio, n-hexylthio, n-heptylthio, n-octylthio, isopropylthio, isobutylthio, sec-butylthio, tert-butylthio and isopentylthio groups and the like.

The "lower cycloalkylthio group" refers to a group formed by replacing the hydrogen atom of a mercapto group with a lower cycloalkyl group. Specific examples thereof include cyclopropylthio, cyclobutylthio, cyclopentylthio, cyclohexylthio, cycloheptylthio and cyclooctylthio groups.

The "arylthio group" refers to a group formed by replacing the hydrogen atom of a mercapto group with an aryl group. Specific examples thereof include phenylthio, naphthylthio, anthrylthio and phenanthrylthio groups and the like.

The "heterocyclic thio group" refers to a group formed by replacing the hydrogen atom of a mercapto group with a heterocyclic group.

The "lower alkylamino group" refers to a group formed by replacing one or both of the hydrogen atoms of an amino group with a lower alkyl group. Specific examples thereof include methylamino, ethylamino, propylamino, dimethylamino, diethylamino and ethyl(methyl)amino groups and the like.

The "lower alkenylamino group" refers to a group formed by replacing one or both of the hydrogen atoms of an amino group with a lower alkenyl group, or a group formed by replacing one of the hydrogen atoms of an amino group with a lower alkenyl group and the other hydrogen atom with a lower alkyl group. Examples thereof include vinylamino, propenylamino, butenylamino, pentenylamino, hexenylamino, heptenylamino, octenylamino, isopropenylamino, 2-methyl-1-propenylamino, 2-methyl-2-butenylamino, divinylamino and methyl(vinyl)amino groups and the like.

The "lower alkynylamino group" refers to a group formed by replacing one or both of the hydrogen atoms of an amino group with a lower alkynyl group, or a group formed by replacing one of the hydrogen atoms of an amino group with a lower alkynyl group and the other hydrogen atom with a lower alkyl group or a lower alkenyl group. Specific examples thereof include ethynylamino, propynylamino, butynylamino, pentynylamino, hexynylamino, heptynylamino, octynylamino, isobutynylamino, isopentynylamino, diethynylamino, ethynyl(methyl)amino and ethynyl(vinyl)amino groups and the like.

The "lower cycloalkylamino group" refers to a group formed by replacing one or both of the hydrogen atoms of an amino group with a lower cycloalkyl group, or a group formed by replacing one of the hydrogen atoms of an amino group with a lower cycloalkyl group and the other hydrogen atom with a lower alkyl group, a lower alkenyl group or a lower alkynyl group. Specific examples thereof include cyclopropylamino, cyclobutylamino, cyclopentylamino, cyclohexylamino, cycloheptylamino, cyclooctylamino, dicyclohexylamino, cyclohexyl(methyl)amino, cyclohexyl(vinyl)amino and cyclohexyl(ethynyl)amino groups and the like.

The "arylamino group" refers to a group formed by replacing one or both of the hydrogen atoms of an amino group with an aryl group, or a group formed by replacing one of the hydrogen atoms of an amino group with an aryl group and the other hydrogen atom with a lower alkyl group, a lower alkenyl group, a lower alkynyl group or a lower cycloalkyl group. Specific examples thereof include phenylamino, naphthylamino, anthrylamino, phenanthrylamino, diphenylamino, methyl(phenyl)amino, ethyl(phenyl)amino, phenyl(vinyl)amino, ethynyl(phenyl)amino and cyclohexyl(phenyl)amino groups and the like.

The "heterocyclic amino group" refers to a group formed by replacing one or both of the hydrogen atoms of an amino group with a heterocyclic group, or a group formed by replacing one of the hydrogen atoms of an amino group with a heterocyclic group and the other hydrogen atom with a lower alkyl group, a lower alkenyl group, a lower alkynyl group, a lower cycloalkyl group or an aryl group.

The "lower alkylcarbonyl group" refers to a group formed by replacing the hydrogen atom of a formyl group with a lower alkyl group. Specific examples thereof include methylcarbonyl, ethylcarbonyl, n-propylcarbonyl, n-butylcarbonyl, n-pentylcarbonyl, n-hexylcarbonyl, n-heptylcarbonyl, n-octylcarbonyl, isopropylcarbonyl, isobutylcarbonyl, sec-butylcarbonyl, tert-butylcarbonyl and isopentylcarbonyl groups and the like.

The "lower alkenylcarbonyl group" refers to a group formed by replacing the hydrogen atom of a formyl group with a lower alkenyl group. Specific examples thereof include vinylcarbonyl, propenylcarbonyl, butenylcarbonyl, pentenylcarbonyl, hexenylcarbonyl, heptenylcarbonyl, octenylcarbonyl, isopropenylcarbonyl, 2-methyl-1-propenylcarbonyl and 2-methyl-2-butenylcarbonyl groups and the like.

The "lower alkynylcarbonyl group" refers to a group formed by replacing the hydrogen atom of a formyl group with a lower alkynyl group. Specific examples thereof include ethynylcarbonyl, propynylcarbonyl, butynylcarbonyl, pentynylcarbonyl, hexynylcarbonyl, heptynylcarbonyl, octynylcarbonyl, isobutynylcarbonyl and isopentynylcarbonyl groups and the like.

The "lower cycloalkylcarbonyl group" refers to a group formed by replacing the hydrogen atom of a formyl group with a lower cycloalkyl group. Specific examples thereof include cyclopropylcarbonyl, cyclobutylcarbonyl, cyclopentylcarbonyl, cyclohexylcarbonyl, cycloheptylcarbonyl and cyclooctylcarbonyl groups.

The "arylcarbonyl group" refers to a group formed by replacing the hydrogen atom of a formyl group with an aryl group. Specific examples thereof include phenylcarbonyl, naphthylcarbonyl, anthrylcarbonyl and phenanthrylcarbonyl groups and the like.

The "heterocyclic carbonyl group" refers to a group formed by replacing the hydrogen atom of a formyl group with a heterocyclic group.

The "lower alkoxycarbonyl group" refers to a group formed by replacing the hydrogen atom of a formyl group with a lower alkoxy group. Specific examples thereof include methoxycarbonyl, ethoxycarbonyl, n-propoxycarbonyl, n-butoxycarbonyl, n-pentoxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl and isopentoxycarbonyl groups and the like.

The "lower alkenyloxycarbonyl group" refers to a group formed by replacing the hydrogen atom of a formyl group with a lower alkenyloxy group. Specific examples thereof include vinyloxycarbonyl, propenyloxycarbonyl, butenyloxycarbonyl, pentenyloxycarbonyl, hexenyloxycarbonyl, heptenyloxycarbonyl, octenyloxycarbonyl, isopropenyloxycarbonyl, 2-methyl-1-propenyloxycarbonyl and 2-methyl-2-butenyloxycarbonyl groups and the like.

The "lower alkynyloxycarbonyl group" refers to a group formed by replacing the hydrogen atom of a formyl group with a lower alkynyloxy group. Specific examples thereof include ethynyloxycarbonyl, propynyloxycarbonyl, butynyloxycarbonyl, pentynyloxycarbonyl, hexynyloxycarbonyl, heptynyloxycarbonyl, octynyloxycarbonyl, isobutynyloxycarbonyl and isopentynyloxycarbonyl groups and the like.

The "lower cycloalkyloxycarbonyl group" refers to a group formed by replacing the hydrogen atom of a formyl group with a lower cycloalkyloxy group. Specific examples thereof include cyclopropyloxycarbonyl, cyclobutyloxycarbonyl, cyclopentyloxycarbonyl, cyclohexyloxycarbonyl, cycloheptyloxycarbonyl and cyclooctyloxycarbonyl groups and the like.

The "aryloxycarbonyl group" refers to a group formed by replacing the hydrogen atom of a formyl group with an aryloxy group. Specific examples thereof include phenoxycarbonyl, naphthoxycarbonyl, anthryloxycarbonyl and phenanthryloxycarbonyl groups and the like.

The "heterocyclic oxycarbonyl group" refers to a group formed by replacing the hydrogen atom of a formyl group with a heterocyclic oxy group.

The "lower alkylaminocarbonyl group" refers to a group formed by replacing the hydrogen atom of a formyl group with a lower alkylamino group. Specific examples thereof include methylaminocarbonyl, ethylaminocarbonyl, propylaminocarbonyl, dimethylaminocarbonyl, diethylaminocarbonyl and ethylmethylaminocarbonyl groups and the like.

The "lower alkenylaminocarbonyl group" refers to a group formed by replacing the hydrogen atom of a formyl group with a lower alkenylamino group. Specific examples thereof include vinylaminocarbonyl, propenylaminocarbonyl, butenylaminocarbonyl, pentenylaminocarbonyl, hexenylaminocarbonyl, heptenylaminocarbonyl, octenylaminocarbonyl, isopropenylaminocarbonyl, 2-methyl-1-propenylaminocarbonyl, 2-methyl-2-butenylaminocarbonyl, divinylaminocarbonyl and methyl(vinyl)aminocarbonyl groups and the like.

The "lower alkynylaminocarbonyl group" refers to a group formed by replacing the hydrogen atom of a formyl group with a lower alkynylamino group. Specific examples thereof include ethynylaminocarbonyl, propynylaminocarbonyl, butynylaminocarbonyl, pentynylaminocarbonyl, hexynylaminocarbonyl, heptynylaminocarbonyl, octynylaminocarbonyl, isobutynylaminocarbonyl, isopentynylaminocarbonyl, diethynylaminocarbonyl, ethynyl(methyl)aminocarbonyl and ethynyl(vinyl)aminocarbonyl groups and the like.

The "lower cycloalkylaminocarbonyl group" refers to a group formed by replacing the hydrogen atom of a formyl group with a lower cycloalkylamino group. Specific examples thereof include cyclopropylaminocarbonyl, cyclobutylaminocarbonyl, cyclopentylaminocarbonyl, cyclohexylaminocarbonyl, cycloheptylaminocarbonyl, cyclooctylaminocarbonyl, dicyclohexylaminocarbonyl, cyclohexyl(methyl)aminocarbonyl, cyclohexyl(vinyl)aminocarbonyl and cyclohexyl(ethynyl)aminocarbonyl groups and the like.

The "arylaminocarbonyl group" refers to a group formed by replacing the hydrogen atom of a formyl group with an arylamino group. Specific examples thereof include phenylaminocarbonyl, naphthylaminocarbonyl, anthrylaminocarbonyl, phenanthrylaminocarbonyl, diphenylaminocarbonyl, methylphenylaminocarbonyl ethylphenylaminocarbonyl, phenyl(vinyl)aminocarbonyl, ethynyl(phenyl)aminocarbonyl and cyclohexyl(phenyl)aminocarbonyl groups and the like.

The "heterocyclic aminocarbonyl group" refers to a group formed by replacing the hydrogen atom of a formyl group with a heterocyclic amino group.

The "lower alkylsulfinyl group" refers to a group formed by replacing the hydroxy of a sulfinic acid group with a lower alkyl group. Specific examples thereof include methylsulfinyl, ethylsulfinyl, n-propylsulfinyl, n-butylsulfinyl, n-pentylsulfinyl, n-hexylsulfinyl, n-heptylsulfinyl, n-octylsulfinyl, isopropylsulfinyl, isobutylsulfinyl, sec-butylsulfinyl, tert-butylsulfinyl and isopentylsulfinyl groups and the like.

The "arylsulfinyl group" refers to a group formed by replacing the hydroxy of a sulfinic acid group with an aryl group. Specific examples thereof include phenylsulfinyl, naphthylsulfinyl, anthrylsulfinyl and phenanthrylsulfinyl groups and the like.

The "lower alkylsulfonyl group" refers to a group formed by replacing the hydroxy of a sulfonic acid group with a lower alkyl group. Specific examples thereof include methylsulfonyl, ethylsulfonyl, n-propylsulfonyl, n-butylsulfonyl, n-pentylsulfonyl, n-hexylsulfonyl, n-heptylsulfonyl, n-octylsulfonyl, isopropylsulfonyl, isobutylsulfonyl, sec-butylsulfonyl, tert-butylsulfonyl and isopentylsulfonyl groups and the like.

The "lower alkenylsulfonyl group" refers to a group formed by replacing the hydroxy of a sulfonic acid group with a lower alkenyl group. Specific examples thereof include vinylsulfonyl, propenylsulfonyl, butenylsulfonyl, pentenylsulfonyl, hexenylsulfonyl, heptenylsulfonyl, octenylsulfonyl, isopropenylsulfonyl, 2-methyl-1-propenylsulfonyl and 2-methyl-2-butenylsulfonyl groups and the like.

The "lower alkynylsulfonyl group" refers to a group formed by replacing the hydroxy of a sulfonic acid group with a lower alkynyl group. Specific examples thereof include ethynylsulfonyl, propynylsulfonyl, butynylsulfonyl, pentynylsulfonyl, hexynylsulfonyl, heptynylsulfonyl, octynylsulfonyl, isobutynylsulfonyl and isopentynylsulfonyl groups and the like.

The "lower cycloalkylsulfonyl group" refers to a group formed by replacing the hydroxy of a sulfonic acid group with a lower cycloalkyl group. Specific examples thereof include cyclopropylsulfonyl, cyclobutylsulfonyl, cyclopentylsulfonyl, cyclohexylsulfonyl, cycloheptylsulfonyl and cyclooctylsulfonyl groups and the like.

The "heterocyclic sulfonyl group" refers to a group formed by replacing the hydroxy of a sulfonic acid group with a heterocyclic group.

The "arylsulfonyl group" refers to a group formed by replacing the hydroxy of a sulfonic acid group with an aryl group. Specific examples thereof include phenylsulfonyl, naphthylsulfonyl, anthrylsulfonyl and phenanthrylsulfonyl groups and the like.

The "lower alkoxycarbonyloxy group" refers to a group formed by replacing the hydrogen atom of a hydroxy group with a lower alkoxycarbonyl group. Specific examples thereof include methoxycarbonyloxy, ethoxycarbonyloxy, n-propoxycarbonyloxy, n-butoxycarbonyloxy, n-pentoxycarbonyloxy, n-hexyloxycarbonyloxy, n-heptyloxycarbonyloxy, n-octyloxycarbonyloxy, isopropoxycarbonyloxy, isobutoxycarbonyloxy, sec-butoxycarbonyloxy, tert-butoxycarbonyloxy and isopentoxycarbonyloxy groups and the like.

The "aryloxycarbonyloxy group" refers to a group formed by replacing the hydrogen atom of a hydroxy group with an aryloxycarbonyl group. Specific examples thereof include phenoxycarbonyloxy, naphthoxycarbonyloxy, anthryloxycarbonyloxy and phenanthryloxycarbonyloxy groups and the like.

The "lower alkylsulfonyloxy group" refers to a group formed by replacing the hydrogen atom of a hydroxy group with a lower alkylsulfonyl group. Specific examples thereof include methylsulfonyloxy, ethylsulfonyloxy, n-propylsulfonyloxy, n-butylsulfonyloxy, n-pentylsulfonyloxy, n-hexylsulfonyloxy, n-heptylsulfonyloxy, n-octylsulfonyloxy, isopropylsulfonyloxy, isobutylsulfonyloxy, sec-butylsulfonyloxy, tert-butylsulfonyloxy and isopentylsulfonyloxy groups and the like.

The "arylsulfonyloxy group" refers to a group formed by replacing the hydrogen atom of a hydroxy group with an arylsulfonyl group. Specific examples thereof include phenylsulfonyloxy, naphthylsulfonyloxy, anthrylsulfonyloxy and phenanthrylsulfonyloxy groups and the like.

The "lower alkylaminocarbonyloxy group" refers to a group formed by replacing the hydrogen atom of a formyloxy group with a lower alkylamino group. Specific examples thereof include methylaminocarbonyloxy, ethylaminocarbonyloxy, propylaminocarbonyloxy, dimethylaminocarbonyloxy, diethylaminocarbonyloxy and ethyl(methyl)aminocarbonyloxy groups and the like.

The "arylaminocarbonyloxy group" refers to a group formed by replacing the hydrogen atom of a formyloxy group with an arylamino group. Specific examples thereof include phenylaminocarbonyloxy, naphthylaminocarbonyloxy, anthrylaminocarbonyloxy, phenanthrylaminocarbonyloxy, diphenylaminocarbonyloxy, methyl(phenyl)aminocarbonyloxy, ethyl(phenyl)aminocarbonyloxy, phenyl(vinyl)aminocarbonyloxy, ethynyl(phenyl)aminocarbonyloxy and cyclohexyl(phenyl)aminocarbonyloxy groups and the like.

The "3- to 8-membered nitrogen-containing heterocyclic ring" refers to a saturated monocyclic heterocyclic ring containing one or two nitrogen atoms in the ring. Specific examples thereof include aziridine, azetidine, pyrrolidine, piperidine, imidazolidine, pyrazolidine, piperazine and morpholine rings and the like.

The "alkylene group" refers to a straight chain or branched alkylene group having 1 to 8 carbon atoms. Specific examples thereof include methylene, ethylene, trimethylene, tetramethylene, pentamethylene, hexamethylene, heptamethylene, octamethylene, methylmethylene and ethylmethylene groups and the like.

The "ester of a hydroxy group" refers to an ester formed from a hydroxy group and a carboxylic acid.

The "ester of a mercapto group" refers to a thioester formed from a mercapto group and a carboxylic acid.

The "amide of an amino group" refers to an amide formed from an amino group and a carboxylic acid.

The "amide of a lower alkylamino group" refers to an amide formed from a lower alkylamino group and a carboxylic acid.

The "amide of an arylamino group" refers to an amide formed from an arylamino group and a carboxylic acid.

The "amide of a heterocyclic amino group" refers to an amide formed from a heterocyclic amino group and a carboxylic acid.

The "carboxylic acid" refers to a saturated aliphatic monocarboxylic acid, a saturated aliphatic dicarboxylic acid, an unsaturated aliphatic carboxylic acid, a carbocyclic carboxylic acid, a heterocyclic carboxylic acid or the like represented by $R^a COOH$ ($R^a$ represents a hydrogen atom, a lower alkyl group which may have at least a substituent, a lower alkenyl group which may have at least a substituent, an aryl group which may have at least a substituent, a heterocyclic group which may have at least a substituent, a lower alkoxy group which may have at least a substituent or the like). Specific examples thereof include saturated aliphatic monocarboxylic acids such as formic acid, acetic acid, propionic acid, butyric acid, isobutyric acid, valeric acid, isovaleric acid and pivalic acid; saturated aliphatic dicarboxylic acids such as oxalic acid, malonic acid, succinic acid, glutaric acid and adipic acid; unsaturated aliphatic carboxylic acids such as acrylic acid, propionic acid, crotonic acid and cinnamic acid; carbocyclic carboxylic acids such as benzoic acid, phthalic acid, isophthalic acid, terephthalic acid, naphthoic acid, toluic acid, cyclohexane carboxylic acid, and cyclohexane dicarboxylic acid; heterocyclic carboxylic acids such as furancarboxylic acid, thiophenecarboxylic acid, nicotinic acid and isonicotinic acid; and the like. Further, acid anhydrides of these carboxylic acids [$(R^a CO)_2 O$] and acid halides of these carboxylic acids ($R^a COX$, X represents a halogen atom) are also included in the "carboxylic acid".

The "ester of a carboxy group" refers to an ester formed from a carboxy group and an alcohol or a phenol.

The "ester of a sulfinic acid group" refers to an ester formed from a sulfinic acid group and an alcohol or a phenol.

The "ester of a sulfonic acid group" refers to an ester formed from a sulfonic acid group and an alcohol or a phenol.

The "alcohol" refers to a saturated aliphatic hydroxy compound, an unsaturated aliphatic hydroxy compound or the like represented by $R^b OH$ ($R^b$ represents a lower alkyl group which may have at least a substituent, an alkenyl group which may have at least a substituent or the like). Specific examples thereof include saturated aliphatic hydroxy compounds such as methanol, ethanol, propanol, butanol and isopropanol; unsaturated aliphatic hydroxy compounds such as vinyl alcohol; saturated aliphatic hydroxy compounds substituted by at least an aryl group such as benzyl alcohol and phenetyl alcohol; and the like.

The "phenol" refers to a carbocyclic hydroxy compound or the like represented by $R^c OH$ ($R^c$ represents an aryl group which may have at least a substituent or the like). Specific examples thereof include phenol, naphthol, anthrol, phenanthrol and the like.

The "amide of a carboxy group" refers to an acid amide formed from a carboxy group and an amine.

The "amide of a sulfinic acid group" refers to an acid amide formed from a sulfinic acid group and an amine.

The "amide of a sulfonic acid group" refers to an acid amide formed from a sulfonic acid group and an amine.

The "amine" refers to ammonia, a saturated aliphatic amine compound, a carbocyclic amine compound, a heterocyclic amine compound, a saturated cyclic amine compound or the like represented by $HNR^d R^e$ ($R^d$ and $R^e$ may be the same or different and represent a hydrogen atom, a lower alkyl group which may have at least a substituent, an aryl group which may have at least a substituent, a heterocyclic group or the like, or $R^d$ and $R^e$ may be combined together to form a saturated cyclic amine). Specific examples thereof include ammonia; saturated aliphatic amine compounds such as methylamine, ethylamine, propylamine, pentylamine, dimethylamine, diethylamine and ethylmethylamine; saturated aliphatic amine compounds having a substituent such as benzylamine; carbocyclic amine compounds such as phenylamine, naphthylamine, anthrylamine, phenanthrylamine, diphenylamine, methylphenylamine, ethylphenylamine and cyclohexylamine; heterocyclic amine compounds such as furylamine, thienylamine, pyrrolidylamine, pyridylamine, quinolylamine and methylpyridylamine; saturated cyclic amine compounds such as aziridine, azetidine, pyrrolidine, piperidine and 4-methylpiperidine; and the like.

The "lower alkyl group which may have at least a substituent", "lower alkenyl group which may have at least a substituent", "lower alkynyl group which may have at least a substituent", "lower alkoxy group which may have at least a substituent", "lower alkylcarbonyl group which may have at least a substituent", "lower alkenylcarbonyl group which may have at least a substituent", "lower alkynylcarbonyl group which may have at least a substituent", "lower alkoxycarbonyl group which may have at least a substituent", "lower alkenyloxycarbonyl group which may have at least a substituent", "lower alkynyloxycarbonyl group which may have at least a substituent", "lower alkylaminocarbonyl group which may have at least a substituent" and "lower alkylsulfonyloxy group which may have at least a substituent" refer to a "lower alkyl group", a "lower alkenyl group", a "lower alkynyl group", a "lower alkoxy group", a "lower alkylcarbonyl group", a "lower alkenylcarbonyl group", a "lower alkynylcarbonyl group", a "lower alkoxycarbonyl group", a "lower alkenyloxycarbonyl group", a "lower alkynyloxycarbonyl group", a "lower alkylaminocarbonyl group" and a "lower alkylsulfonyloxy group" which may have one or a plurality of substituents selected from the following $\alpha^1$ group, respectively.

[$\alpha^1$ Group]

A halogen atom, a lower cycloalkyl group, an aryl group, an aryl group substituted by at least a halogen atom, an aryl group substituted by at least a lower alkyl group, an aryl group substituted by at least a hydroxy group, an aryl group substituted by at least a lower alkoxy group, a heterocyclic group, a hydroxy group, an ester of a hydroxy group, a lower alkoxy group, a lower alkoxy group substituted by at least a halogen atom, a lower alkenyloxy group, a lower alkynyloxy group, a lower cycloalkyloxy group, an aryloxy group, a heterocyclic oxy group, a mercapto group, an ester of a mercapto group, a lower alkylthio group, a lower alkenylthio group, a lower alkynylthio group, a lower cycloalkylthio group, an arylthio group, a heterocyclic thio group, an amino group, an amide of an amino group, a lower alkylamino group, an amide of a lower alkylamino group, an arylamino group, an amide of an arylamino group, a heterocyclic amino group, an amide of a heterocyclic amino group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, an ester of a carboxy group, an amide of a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfinyl group, an arylsulfinyl group, a lower alkylsulfonyl group, an arylsulfonyl group, a sulfinic acid group, an ester of a sulfinic acid group, an amide of a sulfinic acid group, a sulfonic acid group, an ester of a sulfonic acid group, an amide of a sulfonic acid group, a nitro group and a cyano group.

The "lower cycloalkyl group which may have at least a substituent", "aryl group which may have at least a substituent", "heterocyclic group which may have at least a substituent", "lower cycloalkylcarbonyl group which may have at least a substituent", "arylcarbonyl group which may have at least a substituent", "heterocyclic carbonyl group which may have at least a substituent", "lower cycloalkyloxycarbonyl group which may have at least a substituent", "aryloxycarbonyl group which may have at least a substituent", "heterocyclic oxycarbonyl group which may have at least a substituent", "arylaminocarbonyl group which may have at least a substituent" and "heterocyclic aminocarbonyl group which may have at least a substituent" refer to a "lower cycloalkyl group", an "aryl group", a "heterocyclic group", a "lower cycloalkylcarbonyl group", an "arylcarbonyl group", a "heterocyclic carbonyl group", a "lower cycloalkyloxycarbonyl group", an "aryloxycarbonyl group", a "heterocyclic oxycarbonyl group", an "arylaminocarbonyl group" and a "heterocyclic aminocarbonyl group" which may have one or a plurality of substituents selected from the following $\beta^1$ group, respectively.

[$\beta^1$ Group]

A halogen atom, a lower alkyl group, a lower alkyl group substituted by at least a halogen atom, a lower alkyl group substituted by at least a hydroxy group, a lower alkyl group substituted by at least a lower alkoxy group, a lower alkyl group substituted by at least an amino group, a lower alkyl group substituted by at least a lower alkylamino group, a lower alkyl group substituted by at least a carboxy group, a lower alkyl group substituted by at least a lower alkoxycarbonyl group, a lower alkenyl group, a lower alkynyl group, a lower cycloalkyl group, an aryl group, a heterocyclic group, a hydroxy group, an ester of a hydroxy group, a lower alkoxy group, a lower alkoxy group substituted by at least a halogen atom, a lower alkenyloxy group, a lower alkynyloxy group, a lower cycloalkyloxy group, an aryloxy group, a heterocyclic oxy group, a mercapto group, an ester of a mercapto group, a lower alkylthio group, a lower alkenylthio group; a lower alkynylthio group, a lower cycloalkylthio group, an arylthio group, a heterocyclic thio group, an amino group, an amide of an amino group, a lower alkylamino group, an amide of a lower alkylamino group, an arylamino group, an amide of an arylamino group, a heterocyclic amino group, an amide of a heterocyclic amino group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, an amide of a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfinyl group, an arylsulfinyl group, a lower alkylsulfonyl group, an arylsulfonyl group, a sulfinic acid group, an ester of a sulfinic acid group, an amide of a sulfinic acid group, a sulfonic acid group, an ester of a sulfonic acid group, an amide of a sulfonic acid group, a nitro group, a cyano group, an aminocarbonyloxy group, a lower alkylaminocarbonyloxy group and an arylaminocarbonyloxy group.

The term "a plurality of groups" as used herein means that each group may be the same or different and the number of groups is preferably 1, 2 or 3, and particularly preferably 2. Further, a hydrogen atom and a halogen atom are also included in the concept of the "group".

The "glucocorticoid receptor modulator" as used herein refers to a modulator that exhibits a pharmaceutical action by binding to glucocorticoid receptor. Examples thereof include glucocorticoid receptor agonists, glucocorticoid receptor antagonists and the like.

The "salt" of the present compound is not particularly limited as long as it is a pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumalic acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid or sulfosalicylic acid; quaternary ammonium salts with methyl bromide, methyl iodide or the like; salts with a halogen ion such as a bromine ion, a chlorine ion or an iodine ion; salts with an alkali metal such as lithium, sodium or potassium; salts with an alkaline earth metal such as calcium or magnesium; salts with a metal such as iron or zinc; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine or N,N-bis(phenylmethyl)-1,2-ethanediamine; and the like.

In the case where there are geometrical isomers or optical isomers in the present compound, these isomers are also included in the scope of the present invention.

Further, the present compound may be in the form of a hydrate or a solvate.

Further, in the case where there is proton tautomerism in the present compound, the tautomeric isomers thereof are also included in the present invention.

In the case where there are crystalline polymorphisms in the present compound, the crystalline polymorphisms thereof are also included in the present invention.

(a) Preferred examples of the present compound include compounds in which the respective groups are groups as defined below and salts thereof in the compounds represented by the general formula (1) and salts thereof.

In the general formula (1), (a1) the ring X represents a benzene ring or a pyridine ring; and/or (a2) $R^1$ represents a halogen atom, a lower alkyl group, a hydroxy group, a lower alkoxy group, a lower alkenyloxy group, a lower alkylcarbonyl group, an amino group, a nitro group or a cyano group;

in the case where $R^1$ is a lower alkyl group or a lower alkoxy group, the lower alkyl group or lower alkoxy group may have one or a plurality of groups selected from a halogen atom, an aryl group, an aryl group substituted by at least a halogen atom, an aryl group substituted by at least a lower alkyl group, an aryl group substituted by at least a hydroxy group, an aryl group substituted by at least a lower alkoxy group, a hydroxy group, an ester of a hydroxy group, a lower alkoxy group, an aryloxy group, a carboxy group and an ester of a carboxy group as substituent(s); and/or (a3) p represents an integer of 0 to 3;

in the case where p is 2 or 3, each $R^1$ may be the same or different; and/or (a4) $R^2$ represents a halogen atom, a lower alkyl group, a hydroxy group, an ester of a hydroxy group or a lower alkoxy group; and/or (a5) q represents an integer of 0 to 2;

in the case where q is 2, each $R^2$ may be the same or different; and/or (a6) $R^3$ represents a hydrogen atom, a lower alkyl group, a lower alkenyl group, a lower alkynyl group, an aryl group, a lower alkylcarbonyl group, a lower alkenylcarbonyl group, a lower alkynylcarbonyl group or an arylcarbonyl group;

in the case where $R^3$ is a lower alkyl group or a lower alkylcarbonyl group, the lower alkyl group or lower alkylcarbonyl group may have one or a plurality of aryl groups as substituent(s);

in the case where $R^3$ is an aryl group or an arylcarbonyl group, the aryl group or arylcarbonyl group may have one or a plurality of groups selected from a halogen atom and a lower alkyl group as substituent(s); and/or (a7) $R^4$ and $R^5$ may be the same or different and represent a hydrogen atom or a lower alkyl group; and/or (a8) $R^6$ represents a hydrogen atom or a lower alkyl group; and/or (a9) A represents a lower alkylene group or a carbonyl group; and/or (a10) $R^7$ represents $OR^8$, $NR^8R^9$ or $SR^8$; and/or (a11) $R^8$ represents a lower alkyl group, a lower alkenyl group, a lower alkynyl group, a lower cycloalkyl group, an aryl group, a heterocyclic group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfonyl group, a lower alkenylsulfonyl group, a lower alkynylsulfonyl group, a lower cycloalkylsulfonyl group, an arylsulfonyl group, a heterocyclic sulfonyl group, an aminocarbonyl group, a lower alkylaminocarbonyl group, a lower alkenylaminocarbonyl group, a lower alkynylaminocarbonyl group, a lower cycloalkylaminocarbonyl group, an arylaminocarbonyl group or a heterocyclic aminocarbonyl group; and/or (a12) $R^9$ represents a hydrogen atom, a lower alkyl group, a lower alkenyl group, a lower alkynyl group, a lower cycloalkyl group, an aryl group, a heterocyclic group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfonyl group, a lower alkenylsulfonyl group, a lower alkynylsulfonyl group, a lower cycloalkylsulfonyl group, an arylsulfonyl group, a heterocyclic sulfonyl group, an aminocarbonyl group, a lower alkylaminocarbonyl group, a lower alkenylaminocarbonyl group, a lower alkynylaminocarbonyl group, a lower cycloalkylaminocarbonyl group, an arylaminocarbonyl group or a heterocyclic aminocarbonyl group; and/or (a13) in the case where $R^8$ or $R^9$ is a lower alkyl group, a lower alkenyl group, a lower alkynyl group, a lower alkylcarbonyl group, a lower alkenylcarbonyl group, a lower alkynylcarbonyl group, a lower alkoxycarbonyl group, a lower alkenyloxycarbonyl group, a lower alkynyloxycarbonyl group, a lower alkylsulfonyl group, a lower alkenylsulfonyl group, a lower alkynylsulfonyl group, a lower alkylaminocarbonyl group, a lower alkenylaminocarbonyl group or a lower alkynylaminocarbonyl group, the lower alkyl group, lower alkenyl group, lower alkynyl group, lower alkylcarbonyl group, lower alkenylcarbonyl group, lower alkynylcarbonyl group, lower alkoxycarbonyl group, lower alkenyloxycarbonyl group, lower alkynyloxycarbonyl group, lower alkylsulfonyl group, lower alkenylsulfonyl group, lower alkynylsulfonyl group, lower alkylaminocarbonyl group, lower alkenylaminocarbonyl group or lower alkynylaminocarbonyl group may have one or a plurality of groups selected from a halogen atom, a lower cycloalkyl group, an aryl group, a heterocyclic group, a hydroxy group, an ester of a hydroxy group, a lower alkoxy group, a lower alkoxy group substituted by at least a halogen atom, a lower alkenyloxy group, a lower alkynyloxy group, a lower cycloalkyloxy group, an aryloxy group, a heterocyclic oxy group, a mercapto group, an ester of a mercapto group, a lower alkylthio group, a lower alkenylthio group, a lower alkynylthio group, a lower cycloalkylthio group, an arylthio group, a heterocyclic thio group, an amino group, an amide of an amino group, a lower alkylamino group, an amide of a lower alkylamino group, an arylamino group, an amide of an arylamino group, a heterocyclic amino group, an amide of a heterocyclic amino group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, an amide of a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfinyl group, an arylsulfinyl group, a lower alkylsulfonyl group, an arylsulfonyl group, a sulfinic acid group, an ester of a sulfinic acid group, an amide of a sulfinic acid group, a sulfonic acid group, an ester of a sulfonic acid group, an amide of a sulfonic acid group, a nitro group and a cyano group as substituent(s); and/or (a14) in the case where $R^8$ or $R^9$ is a lower cycloalkyl group, an aryl group, a heterocyclic group, a lower cycloalkylcarbonyl group, an arylcarbonyl group, a heterocyclic carbonyl group, a lower cycloalkyloxycarbonyl group, an aryloxycarbonyl group, a heterocyclic oxycarbonyl group, a lower cycloalkylsulfonyl group, an arylsulfonyl group, a heterocyclic sulfonyl group, a lower cycloalkylaminocarbonyl group, an arylaminocarbonyl group or a heterocyclic aminocarbonyl group, the lower cycloalkyl group, aryl group, heterocyclic group, lower cycloalkylcarbonyl group, arylcarbonyl group, heterocyclic carbonyl group, lower cycloalkyloxycarbonyl group, aryloxycarbonyl group, heterocyclic oxycarbonyl group, lower cycloalkylsulfonyl group, arylsulfonyl group, heterocyclic sulfonyl group, lower cycloalkylaminocarbonyl group, arylaminocarbonyl group or heterocyclic aminocarbonyl group may have one or a plurality of groups selected from a halogen atom, a lower alkyl group, a lower alkyl group substituted by at least a halogen atom, a lower alkyl group substituted by at least a hydroxy group, a lower alkyl group substituted by at least a lower alkoxy group, a lower alkyl group substituted by at least an amino group, a lower alkyl group substituted by at least a lower alkylamino group, a lower alkyl group substituted by at least a carboxy group, a lower alkyl group substituted by at least a lower alkoxycarbonyl group, a lower alkenyl group, a lower alkynyl group, a lower cycloalkyl group, an aryl group, a heterocyclic group, a hydroxy group, an ester of a hydroxy group, a lower alkoxy group, a lower alkoxy group substituted by at least a halogen atom, a lower alkenyloxy group, a lower alkynyloxy group, a lower cycloalkyloxy group, an aryloxy group, a heterocyclic oxy group, a mercapto group, an ester of a mercapto group, a lower alkylthio group, a lower alkenylthio group, a lower alkynylthio group, a lower cycloalkylthio group, an arylthio group, a heterocyclic thio group, an amino group, an amide of an amino group, a lower alkylamino group, an amide of a lower alkylamino group, an arylamino group, an amide of an arylamino group, a heterocyclic amino group, an amide of a heterocyclic amino group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, an amide of a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfinyl group, an arylsulfinyl group, a lower alkylsulfonyl group, an arylsulfonyl group, a sulfinic acid group, an ester of a sulfinic acid group, an amide of a sulfinic acid group, a sulfonic acid group, an ester of a sulfonic acid group, an amide of a sulfonic acid group, a nitro group, a cyano group, an aminocarbonyloxy group, a lower alkylaminocarbonyloxy group and an arylaminocarbonyloxy group as substituent(s); and/or (a15) further, in the case where $R^7$ is $NR^8R^9$, $R^8$ and $R^9$ may be combined together to form a 5- or 6-membered nitrogen-containing heterocyclic ring.

That is, in the compounds represented by the general formula (1), preferred examples include compounds that comprises one or a combination of two or more selected from the above (a1), (a2), (a3), (a4), (a5), (a6), (a7), (a8), (a9), (a10), (a11), (a12), (a13), (a14) and (a15), and salts thereof.

(b) More preferred examples of the present compound include compounds in which the respective groups are groups as defined below and salts thereof in the compounds represented by the general formula (1) and salts thereof.

In the general formula (1), (b1) the ring X represents a benzene ring or a pyridine ring; and/or (b2) $R^1$ represents a halogen atom, a lower alkyl group, a hydroxy group, a lower alkoxy group, a lower alkenyloxy group, a lower alkylcarbonyl group, an amino group or a nitro group;

in the case where $R^1$ is a lower alkyl group or a lower alkoxy group, the lower alkyl group or lower alkoxy group may have one or a plurality of groups selected from a halogen atom, an aryl group, an aryl group substituted by at least a halogen atom, an aryl group substituted by at least a lower alkyl group, an aryl group substituted by at least a lower alkoxy group, a hydroxy group, a lower alkoxy group, an aryloxy group, a carboxy group and an ester of a carboxy group as substituent(s); and/or (b3) p represents an integer of 0 to 3;
in the case where p is 2 or 3, each $R^1$ may be the same or different; and/or (b4) $R^2$ represents a halogen atom, a lower alkyl group, a hydroxy group or a lower alkoxy group; and/or (b5) q represents an integer of 0 to 2;
in the case where q is 2, each $R^2$ may be the same or different; and/or (b6) $R^3$ represents a hydrogen atom, a lower alkyl group, a lower alkenyl group, an aryl group, a lower alkylcarbonyl group, a lower alkenylcarbonyl group or an arylcarbonyl group;

in the case where $R^3$ is a lower alkyl group or a lower alkylcarbonyl group, the lower alkyl group or lower alkylcarbonyl group may have one or a plurality of aryl groups as substituent(s);

in the case where $R^3$ is an aryl group or an arylcarbonyl group, the aryl group or arylcarbonyl group may have one or a plurality of groups selected from a halogen atom and a lower alkyl group as substituent(s); and/or (b7) $R^4$ and $R^5$ may be the same or different and represent a hydrogen atom or a lower alkyl group; and/or (b8) $R^6$ represents a hydrogen atom or a lower alkyl group; and/or (b9) A represents a lower alkylene group or a carbonyl group; and/or (b10) $R^7$ represents $OR^8$, $NR^8R^9$ or $SR^8$; and/or (b11) $R^8$ represents a lower alkyl group, a lower alkenyl group, a lower alkynyl group, a lower cycloalkyl group, an aryl group, a heterocyclic group, a lower alkylcarbonyl group, a lower alkenylcarbonyl group, a lower alkynylcarbonyl group, a lower cycloalkylcarbonyl group, an arylcarbonyl group or a heterocyclic carbonyl group; and/or (b12) $R^9$ represents a hydrogen atom, a lower alkyl group, a lower alkenyl group, a lower alkynyl group, a lower cycloalkyl group, an aryl group, a heterocyclic group, a lower alkylcarbonyl group, a lower alkenylcarbonyl group, a lower alkynylcarbonyl group, a lower cycloalkylcarbonyl group, an arylcarbonyl group or a heterocyclic carbonyl group; and/or (b13) in the case where $R^8$ or $R^9$ is a lower alkyl group, a lower alkenyl group, a lower alkynyl group, a lower alkylcarbonyl group, a lower alkenylcarbonyl group or a lower alkynylcarbonyl group, the lower alkyl group, lower alkenyl group, lower alkynyl group, lower alkylcarbonyl group, lower alkenylcarbonyl group or lower alkynylcarbonyl group may have one or a plurality of groups selected from an aryl group, a hydroxy group and a lower alkoxy group as substituent(s); and/or (b14) in the case where $R^8$ or $R^9$ is a lower cycloalkyl group, an aryl group, a heterocyclic group, a lower cycloalkylcarbonyl group, an arylcarbonyl group or a heterocyclic carbonyl group, the lower cycloalkyl group, aryl group, heterocyclic group, lower cycloalkylcarbonyl group, arylcarbonyl group or heterocyclic carbonyl group may have one or a plurality of groups selected from a halogen atom, a lower alkyl group, a lower alkyl group substituted by at least a halogen atom, a lower alkyl group substituted at least by a hydroxy group, a lower alkyl group substituted by at least a lower alkoxy group, a lower alkyl group substituted by at least an amino group, a lower alkyl group substituted by at least a lower alkylamino group, a lower alkyl group substituted by at least a carboxy group, a lower alkyl group substituted by at least a lower alkoxycarbonyl group, a lower alkenyl group, a lower alkynyl group, an aryl group, a heterocyclic group, a hydroxy group, an ester of a hydroxy group, a lower alkoxy group, a lower alkoxy group substituted by at least a halogen atom, an aryloxy group, a mercapto group, a lower alkylthio group, an amino group, an amide of an amino group, a lower alkylamino group, an amide of a lower alkylamino group, a formyl group, a lower alkylcarbonyl group, a carboxy group, an amide of a carboxy group, a lower alkoxycarbonyl group, a nitro group, a cyano group, an aminocarbonyloxy group and a lower alkylaminocarbonyloxy group as substituent(s); and/or (b15) further, in the case where $R^7$ is $NR^8R^9$, $R^8$ and $R^9$ may be combined together to form a 5- or 6-membered nitrogen-containing heterocyclic ring.

That is, in the compounds represented by the general formula (1), more preferred examples include compounds that comprises one or a combination of two or more selected from the above (b1), (b2), (b3), (b4), (b5), (b6), (b7), (b8), (b9), (b10), (b11), (b12), (b13), (b14) and (b15), and salts thereof.

(c) Further more preferred examples of the present compound include compounds in which the respective groups are groups as defined below and salts thereof in the compounds represented by the general formula (1) and salts thereof.

In the general formula (1), (c1) the ring X represents a benzene ring or a pyridine ring; and/or (c2) $R^1$ represents a halogen atom, a lower alkyl group, a hydroxy group, a lower alkoxy group, a lower alkenyloxy group, a lower alkylcarbonyl group, an amino group or a nitro group;

in the case where $R^1$ is a lower alkyl group or a lower alkoxy group, the lower alkyl group or lower alkoxy group may have one or a plurality of groups selected from a halogen atom, an aryl group, an aryl group substituted by at least a halogen atom, an aryl group substituted by at least a lower alkyl group, an aryl group substituted by at least a lower alkoxy group, a hydroxy group, a lower alkoxy group and an ester of a carboxy group as substituent(s); and/or (c3) p represents an integer of 0 to 3;

in the case where p is 2 or 3, each $R^1$ may be the same or different; and/or (c4) $R^2$ represents a halogen atom, a lower alkyl group or a lower alkoxy group; and/or (c5) q represents 0 or 1; and/or (c6) $R^3$ represents a hydrogen atom, a lower alkyl group, a lower alkenyl group, a lower alkylcarbonyl group, a lower alkenylcarbonyl group or an arylcarbonyl group;

in the case where $R^3$ is a lower alkyl group, the lower alkyl group may have one or a plurality of aryl groups as substituent(s);

in the case where $R^3$ is an arylcarbonyl group, the arylcarbonyl group may have one or a plurality of groups selected from a halogen atom and a lower alkyl group as substituent(s); and/or (c7) $R^4$ and $R^5$ both represent a lower alkyl group; and/or (c8) $R^6$ represents a lower alkyl group; and/or (c9) A represents a lower alkylene group or a carbonyl group; and/or (c10) $R^7$ represents $OR^8$, $NR^8R^9$ or $SR^8$; and/or (c11) $R^8$ represents a lower alkyl group, a lower cycloalkyl group, an aryl group, a heterocyclic group, a lower alkylcarbonyl group, a lower alkenylcarbonyl group, a lower cycloalkylcarbonyl group, an arylcarbonyl group or a heterocyclic carbonyl group; and/or (c12) $R^9$ represents a hydrogen atom, a lower alkyl group, a lower cycloalkyl group, an aryl group, a heterocyclic group, an arylcarbonyl group or a heterocyclic carbonyl group; and/or (c13) in the case where $R^8$ or $R^9$ is a lower alkyl group, the lower alkyl group may have one or a plurality of groups selected from a lower alkoxy group and an aryl group as substituent(s); and/or (c14) in the case where $R^8$ or $R^9$ is an aryl group, an arylcarbonyl group or a heterocyclic carbonyl group, the aryl group, arylcarbonyl group or heterocyclic carbonyl group may have one or a plurality of groups selected from a halogen atom, a lower alkyl group, a lower alkyl group substituted by at least a halogen atom, a lower alkyl group substituted by at least a hydroxy group, a lower alkyl group substituted by at least an amino group, a lower alkyl group substituted by at least a lower alkylamino group, a lower alkyl group substituted by at least a carboxy group, a lower alkyl group substituted by at least a lower alkoxycarbonyl group, a lower alkenyl group, a lower alkynyl group, an aryl group, a hydroxy group, an ester of a hydroxy group, a lower alkoxy group, a lower alkoxy group substituted by at least a halogen atom, an aryloxy group, a lower alkylthio group, an amino group, an amide of an amino group, a lower alkylamino group, an amide of a lower alkylamino group, a formyl group, a lower alkylcarbonyl group, a carboxy group, an amide of a carboxy group, a lower alkoxycarbonyl group, a nitro group, a cyano group and a lower alkylaminocarbonyloxy group as substituent(s); and/or (c15) further, in the case where $R^7$ is $NR^8R^9$, $R^8$ and $R^9$ may be combined together to form a 5- or 6-membered nitrogen-containing heterocyclic ring.

That is, in the compounds represented by the general formula (1), further more preferred examples include compounds that comprises one or a combination of two or more selected from the above (c1), (c2), (c3), (c4), (c5), (c6), (c7), (c8), (c9), (c10), (c11), (c12), (c13), (c14) and (c15), and salts thereof.

(d) Further more preferred examples of the present compound include compounds in which the respective groups are groups as defined below and salts thereof in the compounds represented by the general formula (1) and salts thereof.

In the general formula (1), (d1) the ring X represents a benzene ring; and/or (d2) $R^1$ represents a halogen atom, a lower alkyl group, a hydroxy group, a lower alkoxy group, a lower alkenyloxy group, an amino group or a nitro group;

in the case where $R^1$ is a lower alkyl group, the lower alkyl group may have one or a plurality of halogen atoms as substituent(s);

in the case where $R^1$ is a lower alkoxy group, the lower alkoxy group may have one or a plurality of groups selected from an aryl group, an aryl group substituted by at least a halogen atom, an aryl group substituted by at least a lower alkyl group, an aryl group substituted by at least a lower alkoxy group and a lower alkoxy group as substituent(s); and/or (d3) p represents 2 or 3, and at this time, each $R^1$ may be the same or different; and/or (d4) $R^2$ represents a halogen atom, a lower alkyl group or a lower alkoxy group; and/or (d5) q represents 0 or 1; and/or (d6) $R^3$ represents a hydrogen atom; and/or (d7) $R^4$ and $R^5$ both represent a lower alkyl group; and/or (d8) $R^6$ represents a lower alkyl group; and/or (d9) A represents a lower alkylene group; and/or (d10) $R^7$ represents $OR^8$, $NR^8R^9$ or $SR^8$; and/or (d11) $R^8$ represents an aryl group, an arylcarbonyl group or a heterocyclic carbonyl group; and/or (d12) $R^9$ represents a hydrogen, atom or a lower alkyl group; and/or (d13) in the case where $R^8$ is an aryl group, an arylcarbonyl group or a heterocyclic carbonyl group, the aryl group, arylcarbonyl group or heterocyclic carbonyl group may have one or a plurality of groups selected from a halogen atom, a lower alkyl group, a lower alkyl group substituted by at least a halogen atom, a lower alkyl group substituted by at least a hydroxy group, a lower alkyl group substituted by at least an amino group, a lower alkyl group substituted by at least a lower alkylamino group, a lower alkyl group substituted by at least a carboxy group, a lower alkyl group substituted by at least a lower alkoxycarbonyl group, a lower alkenyl group, a lower alkynyl group, an aryl group, a hydroxy group, an ester of a hydroxy group, a lower alkoxy group, a lower alkoxy group substituted by at least a halogen atom, an aryloxy group, a lower alkylthio group, an amino group, an amide of an amino group, a lower alkylamino group, an amide of a lower alkylamino group, a formyl group, a lower alkylcarbonyl group, a carboxy group, an amide of a carboxy group, a lower alkoxycarbonyl group, a nitro group, a cyano group and a lower alkylaminocarbonyloxy group as substituent(s).

That is, in the compounds represented by the general formula (1), further more preferred examples include compounds that comprises one or a combination of two or more selected from the above (d1), (d2), (d3), (d4), (d5), (d6), (d7), (d8), (d9), (d10), (d11), (d12) and (d13), and salts thereof.

(e) Further more preferred examples of the present compound include compounds that satisfy the following requirement and salts thereof.

A compound which satisfies the requirement of the above (a), (b), (c) and/or (d) and in which $R^7$ is $OR^8$ in the general formula (1) or a salt thereof is preferred, and at this time, a compound in which $R^8$ is a phenyl group, a phenylcarbonyl group or a thiophenecarbonyl group or a salt thereof is particularly preferred.

Incidentally, this $R^8$ may have a substituent, and in the case where $R^8$ is a phenyl group, the phenyl group may be substituted by one or a plurality of groups (particularly one, two or three groups) selected from a halogen atom, a lower alkyl group, a lower alkyl group substituted by at least a halogen atom, a lower alkyl group substituted by at least a hydroxy group, a lower alkyl group substituted by at least a lower alkylamino group, a lower alkyl group substituted by at least a carboxy group, a lower alkyl group substituted by at least a lower alkoxycarbonyl group, a lower alkenyl group, a lower alkynyl group, an aryl group, a hydroxy group, a lower alkoxy group, a lower alkylthio group, an amino group, an amide of an amino group, a lower alkylamino group, an amide of a lower alkylamino group, a formyl group, a lower alkylcarbonyl group, a carboxy group, an amide of a carboxy group, a lower alkoxycarbonyl group, a nitro group and a cyano group. In the case where $R^8$ is a phenylcarbonyl group, the phenylcarbonyl group may be substituted by one or a plurality of groups (particularly one, two or three groups) selected from a halogen atom, a lower alkyl group, a lower alkyl group substituted by at least a halogen atom, a lower alkyl group substituted by at least a hydroxy group, an aryl group, a hydroxy group, an ester of a hydroxy group, a lower alkoxy group, a lower alkoxy group substituted by at least a halogen atom, an aryloxy group, a lower alkylthio group, an amino group, a lower alkylamino group, a lower alkylcarbonyl group, a nitro group and a cyano group. Further, in the case where $R^8$ is a thiophenecarbonyl group, the thiophenecarbonyl group may be substituted by one or a plurality of groups (particularly one, two or three groups) selected from a halogen atom, a lower alkyl group, an aryl group, a lower alkoxy group, a lower alkylthio group, an amide of an amino group and a lower alkylcarbonyl group.

(f) Still other preferred examples of the present compound include compounds that satisfy the following requirement and salts thereof.

A compound which satisfies the requirement of the above (a), (b), (c) and/or (d) and in which $R^7$ is $NR^8R^9$ in the general formula (1) or a salt thereof is preferred, and at this time, a compound in which $R^8$ is a phenyl group or a salt thereof is particularly preferred.

Incidentally, this $R^8$ may have a substituent, and in the case where $R^8$ is a phenyl group, the phenyl group may be substituted by one or a plurality of groups (particularly one, two or three groups) selected from a halogen atom, a lower alkyl group, a lower alkyl group substituted by at least a hydroxy group, a heterocyclic group, a lower alkoxy group, a lower alkylthio group, an amide of an amino group, a lower alkylamino group, an amide of a lower alkylamino group, a lower alkylaminocarbonyloxy group and a cyano group.

(g) Still other preferred examples of the present compound include compounds that satisfy the following requirement and salts thereof.

A compound which satisfies the requirement of the above (a), (b), (c) and/or (d) and in which $R^7$ is $SR^8$ in the general formula (1) or a salt thereof is preferred.

(h) Still further more preferred examples of the present compound include compounds that satisfy the following requirement and salts thereof.

A compound which satisfies the requirement of the above (a), (b), (c), (d), (e), (f) and/or (g) and in which the ring X is a benzene ring in the general formula (1) or a salt thereof.

(i) Still further more preferred examples of the present compound include compounds that satisfy the following requirement and salts thereof.

A compound which satisfies the requirement of the above (a), (b), (c), (d), (e), (f), (g) and/or (h) and in which A is a lower alkylene group in the general formula (1) or a salt thereof is preferred, and at this time, a compound in which the lower alkylene group is a methylene group or a salt thereof is particularly preferred.

(j) Still further more preferred examples of the present compound include compounds that satisfy the following requirement and salts thereof.

A compound which satisfies the requirement of the above (a), (b), (c), (d), (e), (f), (g), (h) and/or (i) and in which $R^3$ is a hydrogen atom in the general formula (1) or a salt thereof.

(k) Particularly preferred examples of the present compound include compounds that satisfy the following requirement and salts thereof.

A compound which satisfies the requirement of the above (a), (b), (c), (d), (e), (f), (g), (h), (i) and/or (j) and in which $R^4$, $R^5$ and $R^6$ are a lower alkyl group in the general formula (1) or a salt thereof is preferred, and at this time, a compound in which each of the lower alkyl groups is a methyl group or a salt thereof is particularly preferred.

(l) Particularly preferred specific examples of the present compound include the following compounds and salts thereof.

5-Acetoxymethyl-6-(2-methoxyphenyl)-2,2,4-trimethyl-1,2-dihydroquinoline

5-Benzoyloxymethyl-6-(2-methoxyphenyl)-2,2,4-trimethyl-1,2-dihydroquinoline 6-(2-Methoxyphenyl)-5-[(thiophene-2-yl)carbonyloxymethyl]-2,2,4-trimethyl-1,2-dihydroquinoline 5-(4-t-Butylbenzoyloxymethyl)-6-(2-methoxyphenyl)-2,2,4-trimethyl-1,2-dihydroquinoline 5-Benzoyloxymethyl-6-(4-fluoro-2-methoxyphenyl)-2,2,4-trim ethyl-1,2-dihydroquinoine 6-(4-Fluoro-2-methoxyphenyl)-5-(3-methoxybenzoyloxymethyl)-2,2,4-trimethyl-1,2-dihydroquinoline 6-(4-Fluoro-2-methoxyphenyl)-5-(2-methoxybenzoyloxymethyl)-2,2,4-trimethyl-1,2-dihydroquinoline 6-(4-Fluoro-2-methoxyphenyl)-5-(4-methoxybenzoyloxymethyl)-2,2,4-trimethyl-1,2-dihydroquinoline 6-(4-Fluoro-2-methoxyphenyl)-5-[(thiophene-2-yl)carbonyloxymethyl]-2,2,4-trimethyl-1,2-dihydroquinoline 6-(4-Fluoro-2-methoxyphenyl)-5-(4-methylbenzoyloxymethyl)-2,2,4-trimethyl-1,2-dihydroquinoline 6-(4-Fluoro-2-methoxyphenyl)-5-(3-methylbenzoyloxymethyl)-2,2,4-trimethyl-1,2-dihydroquinoline 6-(4-Fluoro-2-methoxyphenyl)-5-(2-methylbenzoyloxymethyl)-2,2,4-trimethyl-1,2-dihydroquinoline 6-(4-Fluoro-2-methoxyphenyl)-5-phenoxymethyl-2,2,4-trimethyl-1,2-dihydroquinoline 6-(4-Fluoro-2-methoxyphenyl)-5-(4-methoxyphenoxymethyl)-2,2,4-trimethyl-1,2-dihydroquinoline 6-(4-Fluoro-2-methoxyphenyl)-5-(4-fluorophenoxymethyl)-2,2,4-trimethyl-1,2-dihydroquinoline 6-(4-Fluoro-2-methoxyphenyl)-5-(3-fluorophenoxymethyl)-2,2,4-trimethyl-1,2-dihydroquinoline 6-(4-Fluoro-2-methoxyphenyl)-5-(2-fluorophenoxymethyl)-2,2,4-trimethyl-1,2-dihydroquinoline 6-(4-Fluoro-2-methoxyphenyl)-5-(3-methoxyphenoxymethyl)-2,2,4-trimethyl-1,2-dihydroquinoline 6-(4-Fluoro-2-methoxyphenyl)-5-(2-methoxyphenoxymethyl)-2,2,4-trimethyl-1,2-dihydroquinoline 6-(4,5-Difluoro-2-methoxyphenyl)-5-(3-fluorophenoxymethyl)-2,2,4-trimethyl-1,2-dihydroquinoline 6-(4-Fluoro-2-methoxyphenyl)-5-(4-methylphenoxymethyl)-2,2,4-trimethyl-1,2-dihydroquinoline 6-(4-Fluoro-2-methoxyphenyl)-5-(3-methylphenoxymethyl)-2,2,4-trimethyl-1,2-dihydroquinoline 6-(4-Fluoro-2-methoxyphenyl)-5-(2-methylphenoxymethyl)-2,2,4-trimethyl-1,2-dihydroquinoline 6-(4-Fluoro-2-methoxyphenyl)-5-(2-hydroxymethylphenoxymethyl)-2,2,4-trimethyl-1,2-dihydroquinoline 6-(4-Fluoro-2-methoxyphenyl)-5-(5-fluoro-2-methylphenoxymethyl)-2,2,4-trimethyl-1,2-dihydroquinoline 6-(4-Fluoro-2-methoxyphenyl)-5-(5-chloro-2-methylphenoxymethyl)-2,2,4-trimethyl-1,2-dihydroquinoline 6-(4,5-Difluoro-2-methoxyphenyl)-5-(5-fluoro-2-methylphenoxymethyl)-2,2,4-trimethyl-1,2-dihydroquinoline 6-(4-Fluoro-2-methoxyphenyl)-5-(2-methoxy-5-nitrophenoxymethyl)-2,2,4-trimethyl-1,2-dihydroquinoline 6-(4-Fluoro-2-methoxyphenyl)-5-[2-(2-hydroxyethyl)phenoxymethyl]-2,2,4-trimethyl-1,2-dihydroquinoline 6-(4-Fluoro-2-methoxyphenyl)-5-(2-methyl-5-nitrophenoxymethyl)-2,2,4-trimethyl-1,2-dihydroquinoline 6-(4-Fluoro-2-methoxyphenyl)-5-(2-allylphenoxymethyl)-2,2,4-trimethyl-1,2-dihydroquinoline 6-(5-Chloro-2-methoxyphenyl)-5-[2-(2-hydroxyethyl)phenoxymethyl]-2,2,4-trimethyl-1,2-dihydroquinoline 5-(5-Fluoro-2-methylphenoxymethyl)-6-(4-hydroxy-2-methoxyphenyl)-2,2,4-trimethyl-1,2-dihydroquinoline 5-(5-Fluoro-2-methylphenoxymethyl)-6-(5-hydroxy-2-methoxyphenyl)-2,2,4-trimethyl-1,2-dihydroquinoline 6-(4-Hydroxy-2-methoxyphenyl)-5-(4-methybenzoyloxymethyl)-2,2,4-trimethyl-1,2-dihydroquinoline 6-(2-Methoxyphenyl)-5-phenylaminomethyl-2,2,4-trimethyl-1,2-dihydroquinoline 6-(4-Fluoro-2-methoxyphenyl)-5-phenylaminomethyl-2,2,4-trimethyl-1,2-dihydroquinoline 6-(4-Fluoro-2-methoxyphenyl)-5-(4-methoxyphenylaminomethyl)-2,2,4-trimethyl-1,2-dihydroquinoline 6-(4-Fluoro-2-methoxyphenyl)-5-(4-fluorophenylaminomethyl)-2,2,4-trimethyl-1,2-dihydroquinoline 6-(4-Fluoro-2-methoxyphenyl)-5-(3-fluorophenylaminomethyl)-2,2,4-trimethyl-1,2-dihydroquinoline 6-(4-Fluoro-2-methoxyphenyl)-5-(2-fluorophenylaminomethyl)-2,2,4-trimethyl-1,2-dihydroquinoline 6-(4-Fluoro-2-methoxyphenyl)-5-(3-methoxyphenylaminomethyl)-2,2,4-trimethyl-1,2-dihydroquinoline 6-(4-Fluoro-2-methoxyphenyl)-5-(2-methoxyphenylaminomethyl)-2,2,4-trimethyl-1,2-dihydroquinoline 6-(4,5-Difluoro-2-methoxyphenyl)-5-(2-methoxyphenylaminomethyl)-2,2,4-trimethyl-1,2-dihydroquinoline 6-(4-Fluoro-2-methoxyphenyl)-5-(2-hydroxymethylphenylaminomethyl)-2,2,4-trimethyl-1,2-dihydroquinoline 6-(4-Fluoro-2-methoxyphenyl)-5-(2-methoxy-5-methylphenylaminomethyl)-2,2,4-trimethyl-1,2-dihydroquinoline 6-(4-Fluoro-2-methoxyphenyl)-5-(5-fluoro-2-methylphenylaminomethyl)-2,2,4-trimethyl-1,2-dihydroquinoline 6-(5-Chloro-2-methoxyphenyl)-5-(2-methoxyphenylaminomethyl)-2,2,4-trimethyl-1,2-dihydroquinoline 6-(5-Chloro-2-methoxyphenyl)-5-(5-fluoro-2-methylphenylaminomethyl)-2,2,4-trimethyl-1,2-dihydroquinoline 6-(2-Methoxyphenyl)-5-phenylthiomethyl-2,2,4-trimethyl-1,2-dihydroquinoline 6-(4-Fluoro-2-methoxyphenyl)-5-phenylthiomethyl-2,2,4-trimethyl-1,2-dihydroquinoline 6-(4-Fluoro-2-methoxyphenyl)-5-(2-methoxyphenylthiomethyl)-2,2,4-trimethyl-1,2-dihydroquinoline 6-(4-Fluoro-2-methoxyphenyl)-5-[(5-methylthiophen-2-yl)carbonyloxymethyl]-2,2,4-trimethyl-1,2-dihydroquinoline 6-(4-Fluoro-2-methoxyphenyl)-5-[(4-methylthiophen-2-yl)carbonyloxymethyl]-2,2,4-trimethyl-1,2-dihydroquinoline 5-[(5-Chlorothiophen-2-yl)carbonyloxymethyl]-6-(4-fluoro-2-methoxyphenyl)-2,2,4-trimethyl-1,2-dihydroquinoline 6-(4-Fluoro-2-methoxyphenyl)-5-[(3-methylthiophen-2-yl)carbonyloxymethyl]-2,2,4-trimethyl-1,2-dihydroquinoline 5-[(5-Bromothiophen-2-yl)carbonyloxymethyl]-6-(4-fluoro-2-methoxyphenyl)-2,2,4-trimethyl-1,2-dihydroquinoline 6-(4-Fluoro-2-methoxyphenyl)-5-[(5-methoxythiophen-2-yl)carbonyloxymethyl]-2,2,4-trimethyl-1,2-dihydroquinoline 6-(4-Fluoro-2-methoxyphenyl)-5-[(thiophen-3-yl)carbonyloxy methyl]-2,2,4-trimethyl-1,2-dihydroquinoline 6-(4,5-Difluoro-2-methoxyphenyl)-5-[(5-methylthiophen-2-yl) carbonyloxymethyl]-2,2,4-trimethyl-1,2-dihydroquinoline 6-(5-Chloro-2-methoxyphenyl)-5-(5-methylthiophen-2-yl-carbonyloxymethyl)-2,2,4-trimethyl-1,2-dihydroquinoline 6-(5-Chloro-2-methoxyphenyl)-5-(4-methoxybenzoyloxymethyl)-2,2,4-trimethyl-1,2-dihydroquinoline 6-(5-Chloro-2-methoxyphenyl)-5-(2-methyl-5-nitrophenoxymethyl)-2,2,4-trimethyl-1,2-dihydroquinoline 6-(5-Chloro-2-methoxyphenyl)-5-(5-fluoro-2-methylphenoxymethyl)-2,2,4-trimethyl-1,2-dihydroquinoline 6-(5-Chloro-2-methoxyphenyl)-5-(2-methoxy-5-nitrophenoxymethyl)-2,2,4-trimethyl-1,2-dihydroquinoline 6-(5-Chloro-2-methoxyphenyl)-5-(5-chloro-2-methylphenoxymethyl)-2,2,4-trimethyl-1,2-dihydroquinoline 6-(5-Chloro-2-methoxyphenyl)-5-(5-fluoro-2-methoxyphenoxymethyl)-2,2,4-trimethyl-1,2-dihydroquinoline 6-(5-Chloro-2-methoxyphenyl)-5-(2,5-dimethylphenoxymethyl)-2,2,4-trimethyl-1,2-dihydroquinoline 5-(2-Allylphenoxymethyl)-6-(5-chloro-2-methoxyphenyl)-2,2,4-trimethyl-1,2-dihydroquinoline 5-(5-Fluoro-2-methylphenoxymethyl)-6-(2-methoxy-5-nitrophenyl)-2,2,4-trimethyl-1,2-dihydroquinoline 6-(4-Allyloxy-2-methoxyphenyl)-5-(5-fluoro-2-methylphenoxy methyl)-2,2,4-trimethyl-1,2-dihydroquinoline 6-(5-Allyloxy-2-methoxyphenyl)-5-(5-fluoro-2-methylphenoxy methyl)-2,2,4-trimethyl-1,2-dihydroquinoline 6-(5-Amino-2-methoxyphenyl)-5-(5-fluoro-2-methylphenoxymethyl)-2,2,4-trimethyl-1,2-dihydroquinoline 5-(2-Fluorobenzoyloxymethyl)-6-(4-fluoro-2-methoxyphenyl)-2,2,4-trimethyl-1,2-dihydroquinoline 5-(3-Fluorobenzoyloxymethyl)-6-(4-fluoro-2-methoxyphenyl)-2,2,4-trimethyl-1,2-dihydroquinoline 5-(4-Fluorobenzoyloxymethyl)-6-(4-fluoro-2-methoxyphenyl)-2,2,4-trimethyl-1,2-dihydroquinoline 6-(4-Fluoro-2-methoxyphenyl)-5-(4-methylphenylaminomethyl)-2,2,4-trimethyl-1,2-dihydroquinoline 6-(4-Fluoro-2-methoxyphenyl)-5-(3-methylphenylaminomethyl)-2,2,4-trimethyl-1,2-dihydroquinoline 6-(4-Fluoro-2-methoxyphenyl)-5-(2-methylphenylaminomethyl)-2,2,4-trimethyl-1,2-dihydroquinoline 6-(4-Fluoro-2-methoxyphenyl)-5-(2-methylphenylthiomethyl)-2,2,4-trimethyl-1,2-dihydroquinoline The present compound can be synthesized according to the following procedures. The individual concrete preparation procedures are explained in details in the following examples, [preparation examples]. These examples are intended to make the present invention more clearly understandable, and do not limit the scope of the present invention. The hal shown in the following synthetic routes represents a halogen atom.

The present compound (I)-(a) (the compound that A is methylene group, $R^3$ is H, $R^4$, $R^5$ and $R^6$ is methyl group, $R^7$ is $OR^{8a}$, $R^{8a}$ is such as alkylcarbonyl group, cycloalkylcarbonyl group, arylcarbonyl group, heterocyclic carbonyl group in the general formula (1)) and (I)-(b) (the compound that A is methylene group, $R^3$ is such as alkylcarbonyl group, cycloalkylcarbonyl group, arylcarbonyl group, heterocyclic carbonyl group, $R^4$, $R^5$ and $R^6$ is methyl group, $R^7$ is $OR^{8a}$, $R^{8a}$ is such as alkylcarbonyl group, cycloalkylcarbonyl group, arylcarbonyl group, heterocyclic carbonyl group in the general formula (1)) can be synthesized according to the synthetic route 1. Namely, the compound (I)-(a) or (I)-(b) can be given by the reaction of the compound (II) with a corresponding acid chloride (III)-(a) in an organic solvent such as tetrahydrofuran (hereinafter referred to as THF), 1,4-dioxane, N,N-dimethylformamide (hereinafter referred to as DMF), methylene dichloride in the presence of a base such as triethylamine, diisopropylethylamine (hereinafter referred to as DIEA) at 0° C. to room temperature for 12 hours to 2 days.

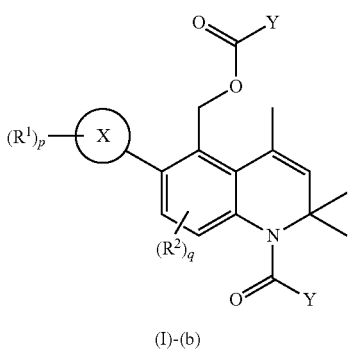

(I)-(b)

The present compound (I)-(a) (the compound that A is methylene group, $R^3$ is H, $R^4$, $R^5$ and $R^6$ is methyl group, $R^7$ is $OR^{8a}$, $R^{8a}$ is such as alkylcarbonyl group, cycloalkylcarbonyl group, arylcarbonyl group, heterocyclic carbonyl group in the general formula (1)) can be also synthesized according to the synthetic route 2. Namely, the compound (IV) can be given by the reaction of the compound (II) with methanesulfonyl chloride in an organic solvent such as methylene dichloride, DMF in the presence of a base such as triethylamine, DIEA at 0° C. to room temperature for 30 minutes to 3 days. The compound (I)-(a) can be given by the reaction of the compound (IV) with a corresponding carboxylic acid (III)-(b) in an organic solvent such as DMF, methylene dichloride in the presence of a base such as potassium carbonate, DIEA, sodium hydride at 50° C. to 100° C. for 1 hour to 2 days.

Synthetic Route 1

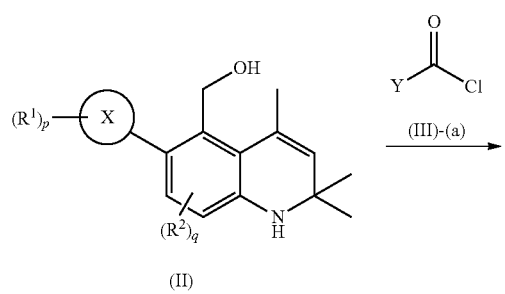

(II)

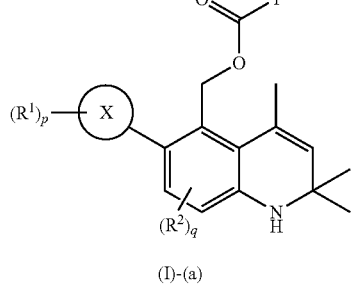

(I)-(a)

Synthetic Route 2

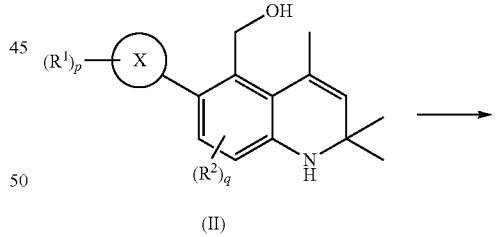

(II)

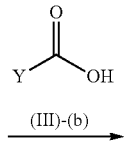

(IV)

-continued

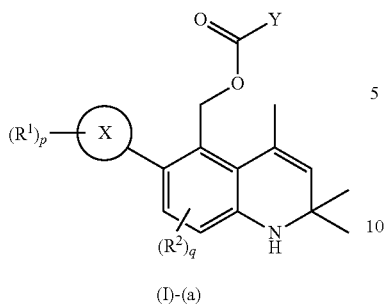

(I)-(a)

The present compound (I)-(a) (the compound that A is methylene group, $R^3$ is H, $R^4$, $R^5$ and $R^6$ is methyl group, $R^7$ is $OR^{8a}$, $R^{8a}$ is such as alkylcarbonyl group, cycloalkylcarbonyl group, arylcarbonyl group, heterocyclic carbonyl group in the general formula (1)) can be also synthesized according to the synthetic route 3. Namely, the compound (I)-(a) can be given by the reaction of the compound (II) with a corresponding carboxylic acid (III)-(b) in an organic solvent such as benzene, toluene in the presence of a phosphine such as triphenylphosphine, tributylphosphine and a reagent such as diethylazodicarboxylate, diisopropylazodicarboxylate, 1,1'-(azodicarbonyl)dipiperidine at room temperature for 1 hour to 2 days.

Synthetic Route 3

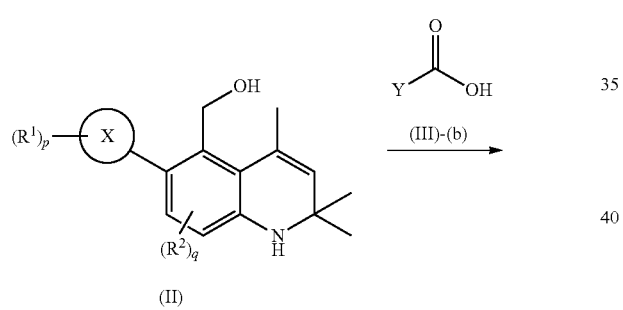

(I)-(a)

The present compound (I)-(c) (the compound that A is methylene group, $R^3$ is H, $R^4$, $R^5$ and $R^6$ is methyl group, $R^7$ is $OR^{8a}$, $NR^8R^9$ or $SR^8$ in the general formula (1)) can be synthesized according to the synthetic route 4. Namely, the compound (I)-(c) can be given by the reaction of the compound (IV) with a corresponding alcohol or phenol (V), amine (VI), thiol or thiophenol (VII) in an organic solvent such as DMF, methylene dichloride in the presence of a base such as potassium carbonate, DIEA, sodium hydride at 50° C. to 100° C. for 1 hour to 2 days.

Synthetic Route 4

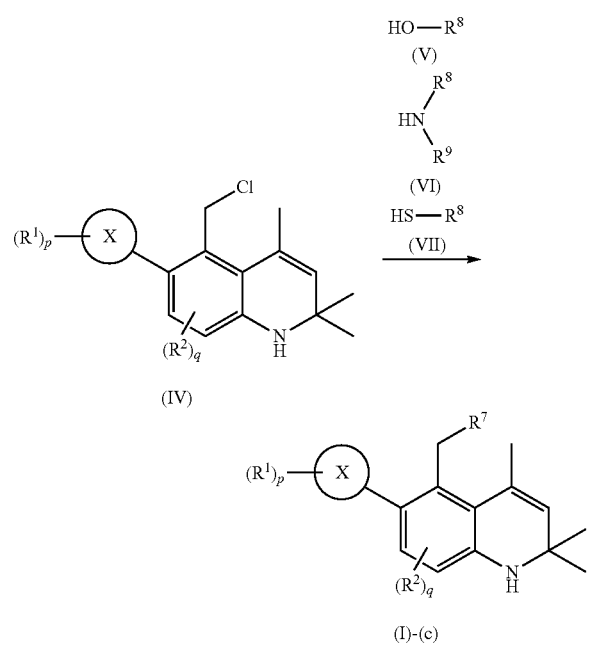

(I)-(c)

The present compound (I)-(d) (the compound that A is methylene group, $R^3$ is H, $R^4$, $R^5$ and $R^6$ is methyl group, $R^7$ is $OR^{8a}$, $R^{8a}$ is aryl group in the general formula (1)) can be synthesized according to the synthetic route 5. Namely, the compound (I)-(d) can be given by the reaction of the compound (II) with a corresponding phenol (V) in an organic solvent such as benzene, toluene in the presence of a phosphine such as triphenylphosphine, tributylphosphine and a reagent such as diethylazodicarboxylate, diisopropylazodicarboxylate, 1,1'-(azodicarbonyl)dipiperidine at room temperature for 1 hour to 2 days.

Synthetic Route 5

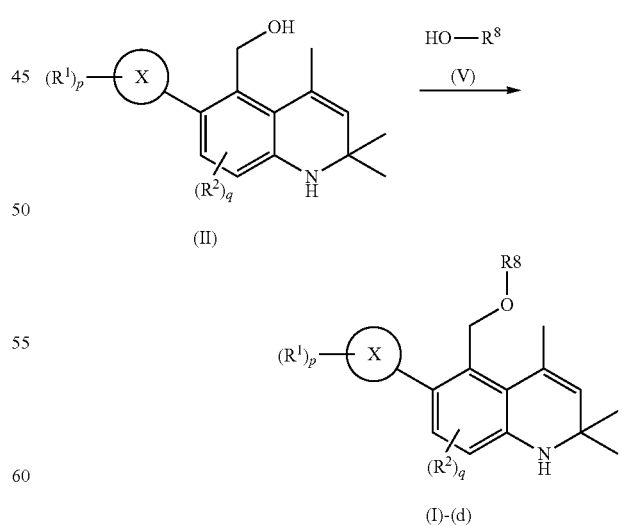

(I)-(d)

The present compound (I)-(e) (the compound that A is carbonyl group, one of the $R^1$ is hydroxyl group at 2 position, $R^3$ is H, $R^4$, $R^5$ and $R^6$ is methyl group, $R^7$ is $NR^8R^9$, p' is an integer from 0 to 4 in the general formula (1)) and (I)-(f) (the compound that A is carbonyl group, one of the R¹ is OR¹⁰ at 2 position (R¹⁰ is such as lower alkyl group, lower alkylcarbonyl group), R³ is H, R⁴, R⁵ and R⁶ is methyl group, R⁷ is NR⁸R⁹, p' is an integer from 0 to 4 in the general formula (1)) can be synthesized according to the synthetic route 6. Namely, the compound (I)-(e) can be given by the reaction of the compound (VIII) with a corresponding amine (VI) in an organic solvent such as diethyl ether, THF in the presence of a base such as butyl lithium at 0° C. to room temperature for 30 minutes to 2 hours. The compound (I)-(f) can be synthesized by the reaction of the compound (I)-(e) with a corresponding halide (IX) in an organic solvent such as DMF, ethanol in the presence of a base such as potassium carbonate, DIEA at room temperature to 100° C. for 1 hour to 24 hours.

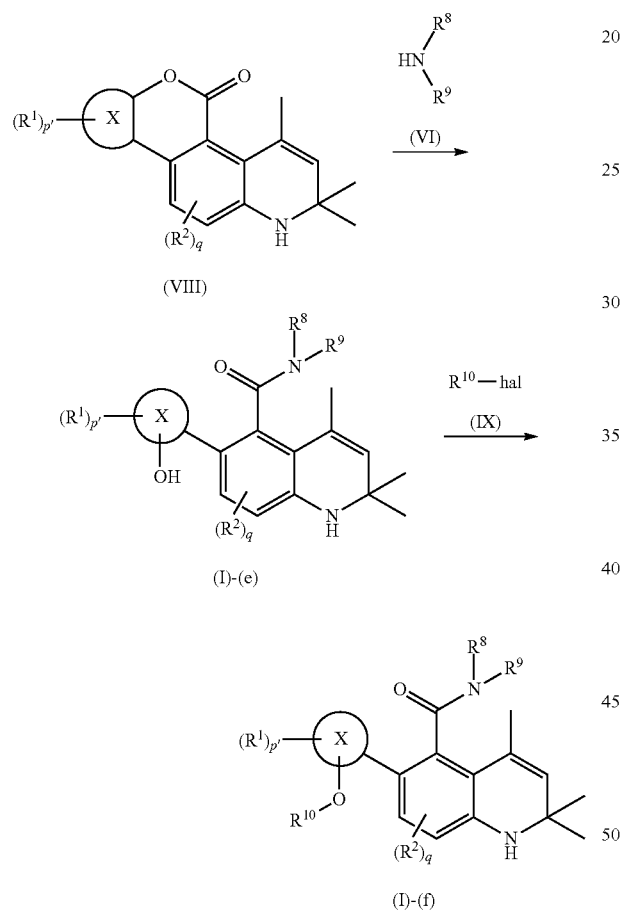

The compound (II)-(a) (the compound that one of the R¹ is OR¹⁰ at 2 position, p' is an integer from 0 to 4 in the above compound (II)) can be synthesized according to the synthetic route 7. Namely, the compound (II)-(b) can be given by the treatment of the compound (VIII) in an organic solvent such as diethyl ether, THF and in the presence of a reductive agent such as lithium aluminium hydride at 0° C. to 50° C. for 1 hour to 1 day. The compound (II)-(a) can be given by the reaction of the compound (II)-(b) with a corresponding halide (IX) in an organic solvent such as DMF, ethanol in the presence of a base such as potassium carbonate, DIEA at room temperature to 100° C. for 1 hour to 24 hours.

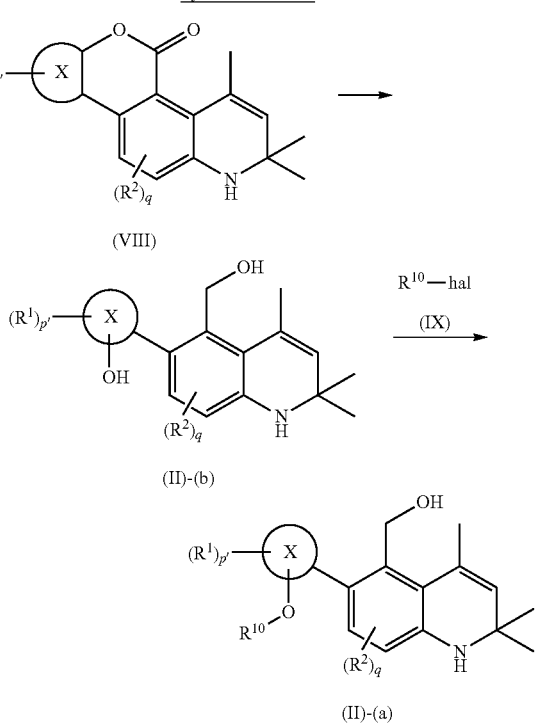

The compound (II)-(c) (the compound that one of the R¹ is H at 2 position, p' is an integer from 0 to 4 in the above compound (II)) can be synthesized according to the synthetic route 8. Namely, the compound (II)-(d) can be given by the reaction of the compound (II)-(b) with trifluoromethanesulfonyl chloride in an organic solvent such as methylene dichloride in the presence of a base such as triethylamine at −30° C. to 0° C. for 30 minutes to 12 hours. The compound (II)-(c) can be synthesized by the treatment of the compound (II)-(d) in an organic solvent such as DMF in the presence of a catalyst such as tetrakis(triphenylphosphine)palladium (0), a base such as trietylamine and formic acid at 60° C. to 100° C. for 1 hour to 24 hours.

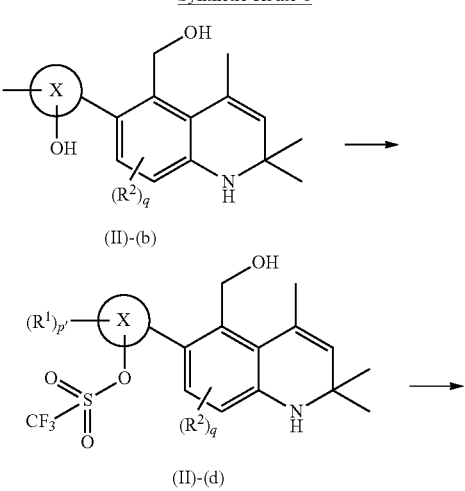

-continued

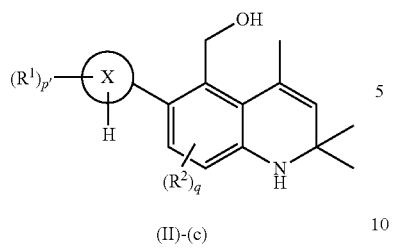

(II)-(c)

The compound (VIII) can be synthesized according to the synthetic route 9. Namely, the compound (XII) can be given by the reaction of a corresponding boronic acid (X)-(a) (the compound which has a benzyloxy group at 2 position) with a halide or triflate (XI) in a solvent such as DMF, ethanol, toluene, water and in the presence of a base such as cesium carbonate, sodium carbonate, tripotassium phosphate and a catalyst such as bis(triphenylphosphine)palladium (II) dichloride, tetrakis(triphenylphosphine)palladium (0) at 50° C. to 120° C. for 12 hours to 2 days. The compound (XIII) can be given by the treatment of the compound (XII) under hydrogen atmosphere in an organic solvent such as methanol, ethanol, 1,4-dioxane, THF in the presence of a catalyst such as palladium carbon, platinum dioxide at room temperature for 2 hours to 2 days. The compound (VIII) can be given by the treatment of the compound (XIII) in acetone in the presence of iodine at 80° C. to 130° C. for 24 hours to 5 days.

-continued

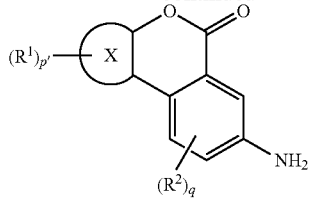

(XIII)

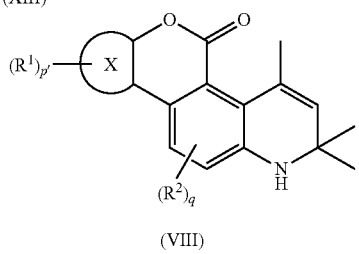

(VIII)

The compound (XIII) in the synthetic route 9 can be also synthesized according to the synthetic route 10. Namely, the compound (XII)-(a) can be given by the treatment of the compound (XII) under hydrogen atmosphere in an organic solvent such as methanol, ethanol, 1,4-dioxane, THF in the presence of a catalyst such as palladium carbon, platinum dioxide at room temperature for 2 hours to 2 days. The compound (XIII) can be given by reflux of the compound (XII)-(a) in pyridine for 2 hours to 1 day.

Synthetic Route 9

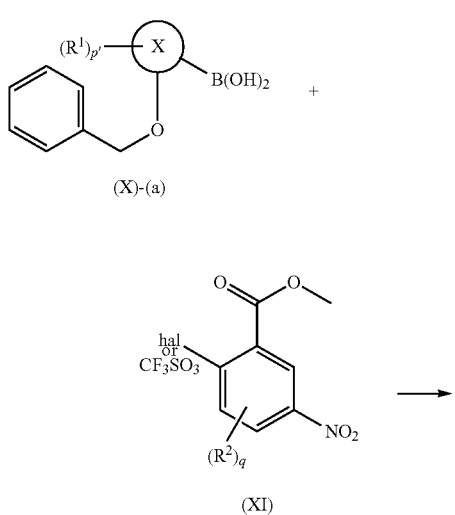

Synthetic Route 10

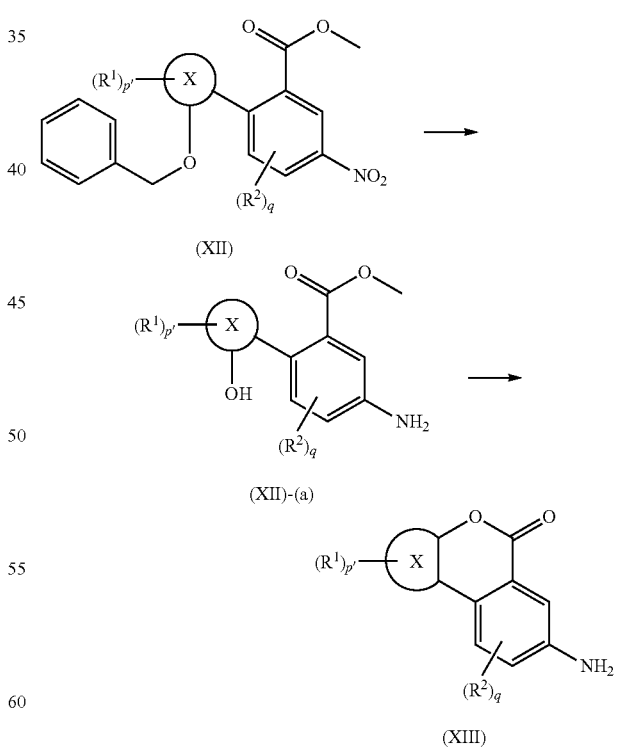

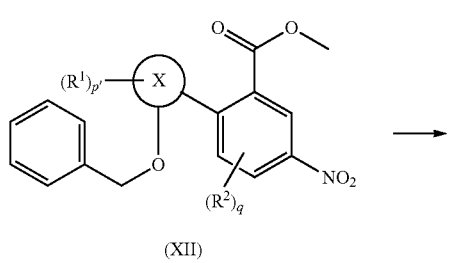

(XII)

The compound (VIII) can be also synthesized according to the synthetic route 11. Namely, the compound (XIV) can be given by the reaction of a corresponding boronic acid (X)-(b) (the compound which has a fluorine atom at 2 position) with a halide or triflate (XI) in a solvent such as DMF, toluene, water in the presence of a base such as cesium carbonate, sodium carbonate, tripotassium phosphate and a catalyst such as bis(triphenylphosphine)palladium (II) dichloride, tetrakis(triphenylphosphine)palladium (0) at 50° C. to 120° C. for 12 hours to 2 days. The compound (XV) can be given by the treatment of the compound (XIV) in a solvent such as water, methanol, ethanol in the presence of a base such as sodium hydroxide at 0° C. to room temperature for 1 hour to 1 day. The compound (XVI) can be given by the treatment of the compound (XV) in an organic solvent such as DMF, THF in the presence of a base such as sodium hydride at room temperature to 100° C. for 1 hour to 2 days. The compound (XIII) can be given by the treatment of the compound (XVI) under hydrogen atmosphere in an organic solvent methanol, ethanol, 1,4-dioxane, THF in the presence of a catalyst such as palladium carbon, platinum dioxide at room temperature for 2 hours to 2 days. The compound (VIII) can be given by the treatment of the compound (XIII) in acetone in the presence of iodine at 80° C. to 130° C. for 24 hours to 5 days.

Synthetic Route 11

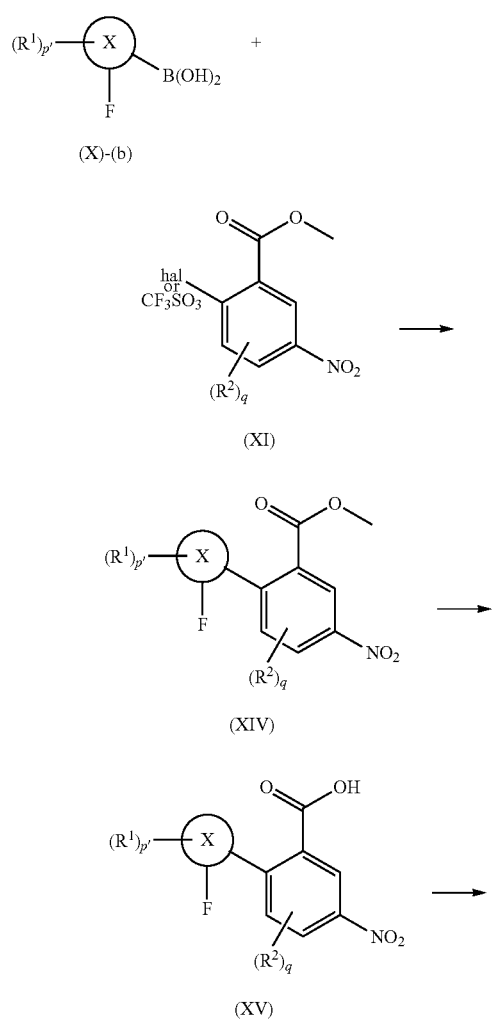

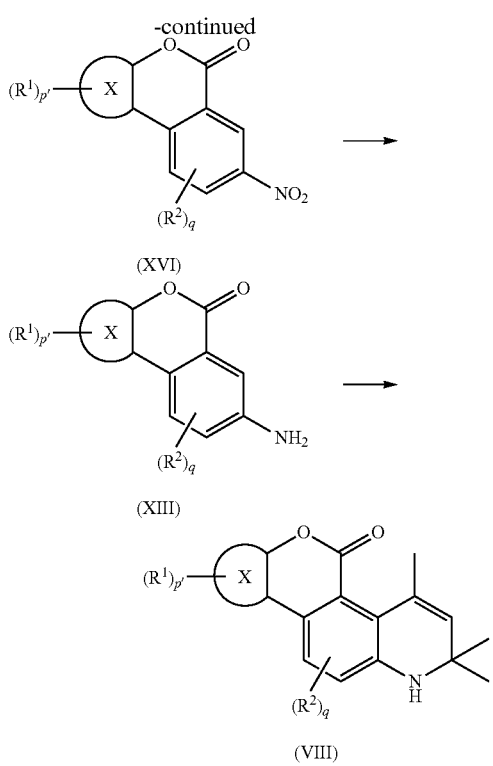

The compound (VIII)-(a) (the compound that ring X is pyridine) can be also synthesized according to the synthetic route 12. Namely, the compound (XVIII) can be given by the reaction of a corresponding boronic acid (XVII) (the compound which has a methoxy group at 2 position) with a halide (XI) in a solvent such as DMF, ethanol, toluene, water in the presence of a base such as cesium carbonate, sodium carbonate, and a catalyst such as bis(triphenylphosphine)palladium (II) dichloride, tetrakis(triphenylphosphine)palladium (0) at 50° C. to 120° C. for 12 hours to 2 days. The compound (XIX) can be given by the treatment of the compound (XVIII) in an organic solvent such as methylene dichloride, methanol, ethanol in the presence of an acid such as boron tribromide, HCl at −78° C. to 0° C. for 1 hour to 12 hours. The compound (XX) can be given by the treatment of the compound (XIX) in a solvent such as water, methanol, ethanol in the presence of a base such as sodium hydroxide at 0° C. to room temperature for 1 hour to 1 day. The compound (XXI) can be given by the treatment of the compound (XX) in an organic solvent of such as DMF, methylene dichloride in the presence of a condensation reagent such as N,N'-dicyclohexylcarbodiimide, O-(7-azabenzotriazol-1-yl)-N,N,N,N-tetramethyluronium-hexafluorophosphate and a base such as DIEA at room temperature to 50° C. for 1 hour to 3 days. The compound (XXII) can be given by the treatment of the compound (XXI) under hydrogen atmosphere in an organic solvent such as methanol, ethanol, 1,4-dioxane, THF in the presence of a catalyst such as palladium carbon, platinum dioxide at room temperature for 2 hours to 2 days. The compound (VIII) can be given by the treatment of the compound (XXII) in acetone in the presence of iodine at 80° C. to 130° C. for 24 hours to 5 days.

Synthetic Route 12

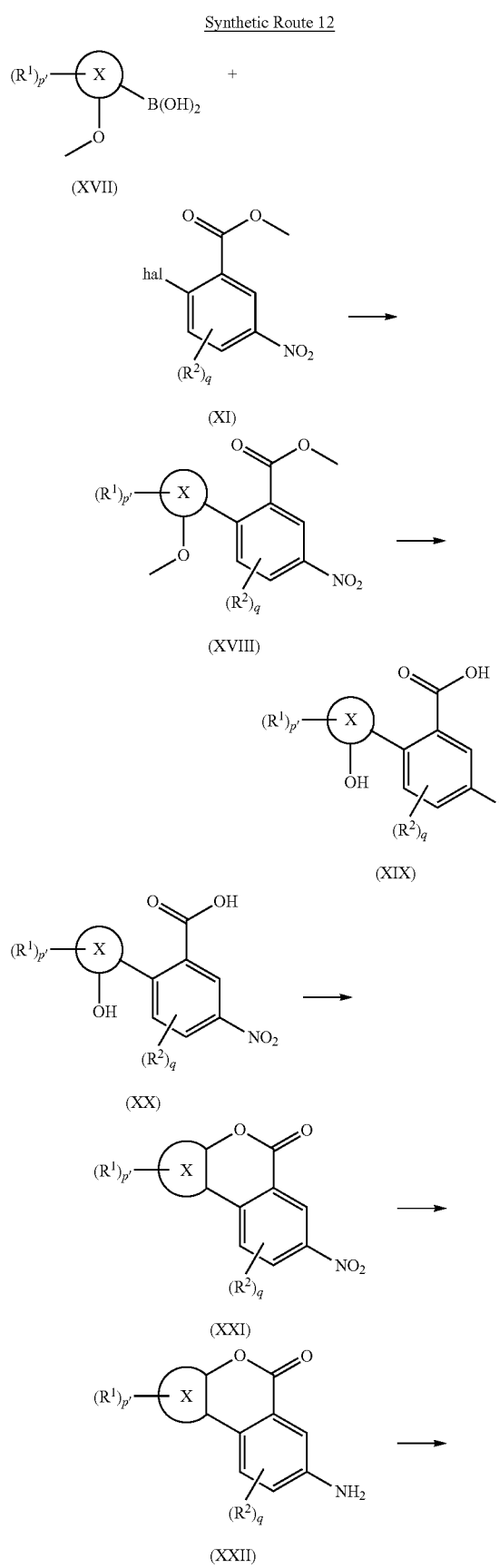

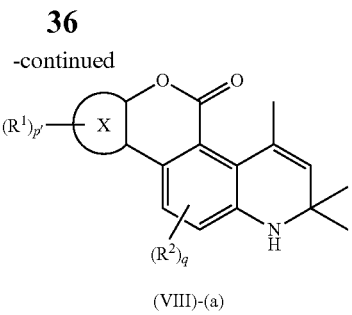

(VIII)-(a)

In order to find the usefulness of the present compound as a pharmaceutical, by using a glucocorticoid receptor competitor assay kit, a glucocorticoid receptor competitor assay was carried out by a fluorescence polarization method. As a result, the present compound showed an excellent glucocorticoid receptor binding activity.

Incidentally, the glucocorticoid receptor is associated with the occurrence of various diseases as described above, therefore, the present compound having an excellent binding activity to the glucocorticoid receptor is useful as a glucocorticoid receptor modulator.

A detailed explanation of this matter will be described in the section of "Pharmacological Test" in Examples described below.

The present compound can be administered either orally or parenterally. Examples of the dosage form include a tablet, a capsule, a granule, a powder, an injection, an eye drop and the like. Such a preparation can be prepared using a commonly used technique.

For example, an oral preparation such as a tablet, a capsule, a granule or a powder can be prepared by optionally adding a necessary amount of an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl p-hydroxybenzoate or benzyl alcohol; a corrigent such as a sweetener, a sour agent or a flavor, or the like.

A parenteral preparation such as an injection or an eye drop can be prepared by optionally adding a necessary amount of a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polyoxyethylene sorbitan monoolate, polyoxy 40 stearate or polyoxyethylene hydrogenated castor oil; a stabilizer such as sodium citrate or sodium edetate; a preservative such as benzalkonium chloride, paraben, benzothonium chloride, p-hydroxybenzoate ester, sodium benzoate, chlorobutanol or sorbic acid; a pH adjusting agent such as hydrochloric acid, citric acid, phosphoric acid, glacial acetic acid, sodium hydroxide, sodium carbonate or sodium hydrogen carbonate; a soothing agent such as benzyl alcohol, or the like.

The dose of the present compound can be appropriately selected depending on the symptoms, age, dosage form or the like. For example, in the case of an oral preparation, it can be administered in an amount of generally 0.01 to 1000 mg, preferably 1 to 100 mg per day in a single dose or several divided doses. Further, in the case of an eye drop, a preparation containing the present compound at a concentration of generally 0.0001% to 10% (w/v), preferably 0.01% to 5% (w/v) can be administered in a single dose or several divided doses.

Hereinafter, Production Examples of the present compound, Preparation Examples and results of Pharmacological Test will be described. However, these examples are described for the purpose of understanding the present invention better and are not meant to limit the scope of the present invention.

EXAMPLES

Production Examples

Reference Example 1

2,2,4-Trimethyl-1,2-dihydro-6-oxa-1-azachrysen-5-one (Reference Compound No. 1-1)

Methyl 2-(2-benzyloxyphenyl)-5-nitrobenzoate (Reference Compound No. 1-1-(1))

A mixture of 2-benzyloxyphenylboronic acid (20.2 g, 88.6 mmol), methyl 2-bromo-5-nitrobenzoate (25.4 g, 97.5 mmol), cesium carbonate (57.7 g, 177 mmol) and bis(triphenylphosphine)palladium(II)dichloride (1.16 g, 1.65 mmol) was suspended in anhydrous N,N-dimethylformamide (300 mL), and then was stirred under argon atmosphere at 80° C. for 3 days. After cooling down, ethyl acetate (500 mL), diethylether (300 mL) and water (500 mL) were added thereto, and then separated. The aqueous layer was extracted with a mixture of ethyl acetate (200 mL) and diethylether (200 mL). The combined organic layer was washed with water (500 mL, twice) and saturated brine (300 mL) successively, dried over anhydrous magnesium sulfate, and then the solvent was removed under reduced pressure. The obtained residue was purified by silica gel column chromatography (hexane-ethyl acetate) to give the titled reference compound (21.0 g) as a pale yellow oil. (Yield 65%)

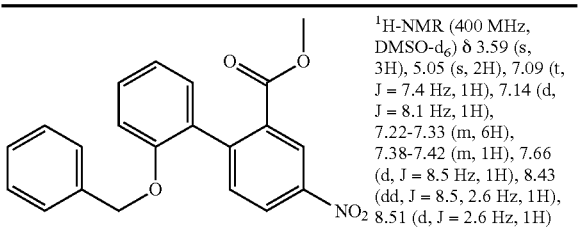

$^1$H-NMR (400 MHz, DMSO-$d_6$) δ 3.59 (s, 3H), 5.05 (s, 2H), 7.09 (t, J = 7.4 Hz, 1H), 7.14 (d, J = 8.1 Hz, 1H), 7.22-7.33 (m, 6H), 7.38-7.42 (m, 1H), 7.66 (d, J = 8.5 Hz, 1H), 8.43 (dd, J = 8.5, 2.6 Hz, 1H), 8.51 (d, J = 2.6 Hz, 1H)

8-Aminobenzo[c]chromen-6-one (Reference Compound No. 1-1(2))

Methyl 2-(2-benzyloxyphenyl)-5-nitrobenzoate (Reference Compound No. 1-1-(1), 21.0 g, 57.8 mmol) was dissolved in a mixture of methanol (135 mL) and tetrahydrofuran (90 mL), then 5% palladium on charcoal (2.19 g) was added thereto, and then the reaction mixture was stirred under hydrogen atmosphere at room temperature overnight. After the unsoluble materials were filtered, the filtrate was removed under reduced pressure. A mixture of ethyl acetate and hexane was added to the obtained residue, and then the mixture was filtered to give the titled reference compound (8.92 g) as a pale yellow solid. (Yield 73%)

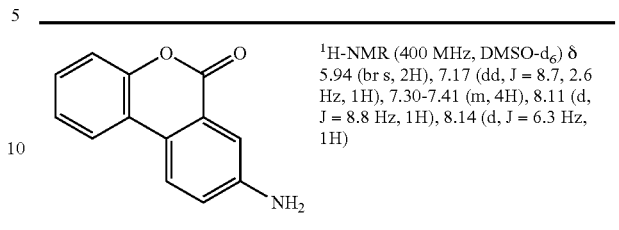

$^1$H-NMR (400 MHz, DMSO-$d_6$) δ 5.94 (br s, 2H), 7.17 (dd, J = 8.7, 2.6 Hz, 1H), 7.30-7.41 (m, 4H), 8.11 (d, J = 8.8 Hz, 1H), 8.14 (d, J = 6.3 Hz, 1H)

2,2,4-Trimethyl-1,2-dihydro-6-oxa-1-azachrysen-5-one (Reference Compound No. 1-1)

In a pressure tube, 8-aminobenzo[c]chromen-6-one (Reference Compound No. 1-1-(2), 8.81 g, 41.7 mmol) was dissolved in acetone (300 ml . . . ), then iodine (4.24 g, 16.7 mmol) was added thereto, then the pressure tube was sealed, and then the reaction mixture was stirred at 105° C. for 2 days. After cooling down, the solvent was removed under reduced pressure. The obtained residue was purified by silica gel column chromatography (hexane-ethyl acetate) to give the titled reference compound (4.83 g) as a yellow solid. (Yield 40%)

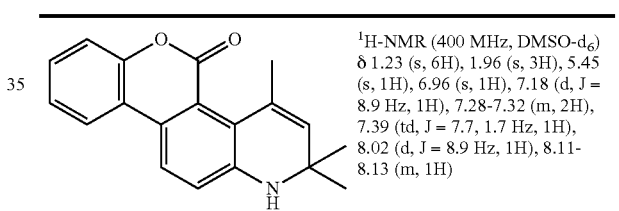

$^1$H-NMR (400 MHz, DMSO-$d_6$) δ 1.23 (s, 6H), 1.96 (s, 3H), 5.45 (s, 1H), 6.96 (s, 1H), 7.18 (d, J = 8.9 Hz, 1H), 7.28-7.32 (m, 2H), 7.39 (td, J = 7.7, 1.7 Hz, 1H), 8.02 (d, J = 8.9 Hz, 1H), 8.11-8.13 (m, 1H)

7,8-Difluoro-2,2,4-trimethyl-1,2-dihydro-6-oxa-1-azachrysen-5-one (Reference Compound No. 1-2)

Methyl 2-(2,3,4-trifluorophenyl)-5-nitrobenzoate (Reference Compound No. 1-2-(1))

A mixture of 2,3,4-trifluorophenylboronic acid (4.70 g, 26.7 mmol), methyl 2-bromo-5-nitrobenzoate (9.02 g, 34.7 mmol), sodium carbonate (8.49 g, 80.1 mmol) and tetrakis(triphenylphosphine)palladium(0) (1.55 g, 1.34 mmol) was suspended in a mixture of toluene (160 mL)-ethanol (40 mL)-water (80 mL), and then the mixture was stirred under nitrogen atmosphere at 95° C. overnight. After cooling down, ethyl acetate (200 mL) and water (200 mL) were added thereto, and then separated. The organic layer was washed with saturated brine (150 mL), dried over anhydrous magnesium sulfate, and then the solvent was removed under reduced pressure. The obtained residue was purified by silica gel column chromatography (hexane-ethyl acetate) to give the titled reference compound (4.37 g) as a brown oil. (Yield 53%)

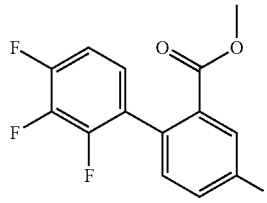

¹H-NMR (400 MHz, DMSO-d₆) δ 3.77 (s, 3H), 7.34 (tdd, J = 8.1, 5.8, 2.1 Hz, 1H), 7.48 (dtd, J = 8.1, 5.8, 2.1 HZ, 1H), 7.78 (d, J = 8.4 Hz, 1H), 8.54 (dd, J = 8.4, 2.5 Hz, 1H), 8.68 (d, J = 2.5 Hz, 1H)

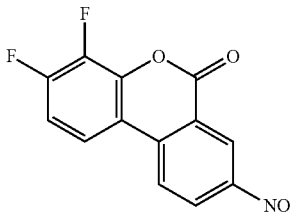

¹H-NMR (400 MHz, DMSO-d₆) δ 7.61 (td, J = 9.6, 5.4 Hz, 1H), 8.38 (ddd, J = 9.6, 7.3, 2.3 HZ, 1H), 8.71 (d, J = 1.5 Hz, 2H), 8.87 (t, J = 1.5, Hz, 1H)

2-(2,3,4-Trifluorophenyl)-5-nitrobenzoic acid (Reference Compound No. 1-2-(2))

Methyl 2-(2,3,4-trifluorophenyl)-5-nitrobenzoate (Reference Compound No. 1-2-(1), 4.37 g, 14.1 mmol) was dissolved in a mixture of tetrahydrofuran (10 mL) and methanol (30 mL), then 1N aqueous NaOH solution (20 mL) was added thereto, and then the reaction mixture was stirred at room temperature overnight. Water (150 mL) and 1N aqueous HCl solution (30 mL) were added to the reaction mixture to acidify, then ethyl acetate (150 mL) was added thereto, and then separated. The organic layer was washed with saturated brine (150 mL), dried over anhydrous magnesium sulfate, and then the solvent was removed under reduced pressure to give the titled reference compound (4.18 g) as a gray solid. (Yield 100%)

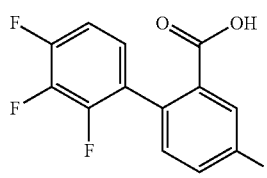

¹H-NMR (400 MHz, DMSO-d₆) δ 7.33 (tdd, J = 8.8, 5.6, 2.2 Hz, 1H), 7.46 (dtd, J = 8.8, 5.6, 2.2 HZ, 1H), 7.74 (d, J = 8.5 Hz, 1H), 8.50 (dd, J = 8.5, 2.5 Hz, 1H), 8.66 (d, J = 2.5 Hz, 1H), 13.67 (br s, 1H)

3,4-Difluoro-8-nitrobenzo[c]chromen-6-one (Reference Compound No. 1-2-(3))

60% Sodium hydride (2.82 g, 70.5 mmol) was suspended in anhydrous N,N-dimethylformamide (60 mL), then under ice cooling, an anhydrous N,N-dimethylformamide solution (40 mL) of 2-(2,3,4-trifluorophenyl)-5-nitrobenzoic acid (Reference Compound No. 1-2-(2), 6.97 g, 23.5 mmol) was added dropwise thereto, and then the reaction mixture was stirred under nitrogen atmosphere at 80° C. for 24 hours. After cooling down, ethyl acetate (400 mL), water (400 mL) and 1N aqueous HCl solution (80 mL) were added, and then separated. The organic layer was washed with saturated brine (200 mL), dried over anhydrous magnesium sulfate, and then the solvent was removed under reduced pressure. Chloroform was added to the obtained solid, and then filtered to give the titled reference compound (3.85 g) as a brown solid. (Yield 59%)

8-Amino-3,4-difluorobenzo[c]chromen-6-one (Reference Compound No. 1-2-(4))

3,4-Difluoro-8-nitrobenzo[c]chromen-6-one (Reference Compound No. 1-2-(3), 3.75 g, 13.5 mmol) was dissolved in 1,4-dioxane (300 mL), then 5% palladium on charcoal (375 mg) was added thereto, and then the reaction mixture was stirred under hydrogen atmosphere (3 kgf/cm²) at room temperature for 4 days. After the mixture was filtered, the filtrate was removed under reduced pressure. 1,4-Dioxane was added to the obtained residue, and then filtered to give the titled reference compound (2.44 g) as an orange solid. (Yield 73%)

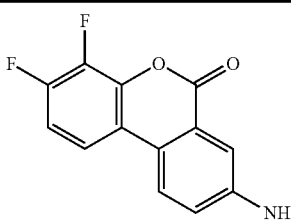

¹H-NMR (400 MHz, DMSO-d₆) δ 6.02 (s, 2H), 7.17 (dd, J = 8.5, 2.4 Hz, 1H), 7.37-7.41 (m, 1H), 7.37 (d, J = 2.4 Hz, 1H), 7.96 (ddd, J = 9.3, 5.4, 2.2 Hz, 1H), 8.08 (d, J = 8.5, Hz, 1H)

7,8-Difluoro-2,2,4-trimethyl-1,2-dihydro-6-oxa-1-azachrysen-5-one (Reference Compound No. 1-2)

In a pressure tube, 8-amino-3,4-difluorobenzo[c]chromen-6-one (Reference Compound No. 1-2-(4), 2.30 g, 9.26 mmol) was dissolved in acetone (60 mL), then iodine (939 mg, 3.70 mmol) was added thereto, then the pressure tube was sealed, and then the reaction mixture was stirred at 110° C. for 5 days. After cooling down, the solvent was removed under reduced pressure. The obtained residue was purified by silica gel column chromatography (chloroform-methanol) to give the titled reference compound (0.95 g) as a yellow solid. (Yield 31%)

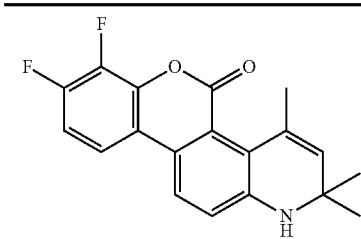

¹H-NMR (500 MHz, DMSO-d₆) δ 1.23 (s, 6H), 1.97 (s, 3H), 5.48 (s, 1H), 7.05 (s, 1H), 7.19 (d, J = 8.9 Hz, 1H), 7.37 (td, J = 9.7, 7.6 Hz, 1H), 7.95 (ddd, J = 9.7, 5.2, 1.8 Hz, 1H), 7.98 (d, J = 8.9, Hz, 1H)

2,2,4-Trimethyl-1,2-dihydro-6-oxa-1,7-diazachrysen-5-one (Reference Compound No. 1-3)

Methyl 2-(2-methoxypyridin-3-yl)-5-nitrobenzoate (Reference Compound No. 1-3-(1))

A mixture of 2-methoxypyridin-3-ylboronic acid (1.00 g, 6.54 mmol), methyl 2-bromo-5-nitrobenzoate (2.21 g, 8.50 mmol), cesium carbonate (6.39 g, 17.6 mmol) and bis(triphenylphosphine)palladium(II) dichloride (230 mg, 0.33 mmol) was suspended in anhydrous N,N-dimethylformamide (15 mL), and then the mixture was stirred under nitrogen atmosphere at 80° C. overnight. After cooling down, water (100 mL) was added thereto, and then the whole was extracted with ethyl acetate (80 mL, twice). The combined organic layer was washed with saturated brine (100 mL), dried over anhydrous magnesium sulfate, and then the solvent was removed under reduced pressure. The obtained residue was purified by silica gel column chromatography (hexane-ethyl acetate) to give the titled reference compound (1.54 g) as a yellow solid. (Yield 81%)

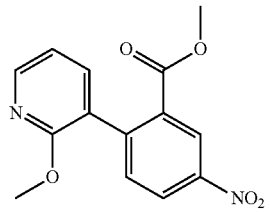 [SMILES: COC(=O)c1cc([N+](=O)[O-])ccc1-c1cccnc1OC]

$^1$H-NMR (500 MHz, DMSO-$d_6$) δ 3.71 (s, 3H), 3.77 (s, 3H), 7.16 (dd, J = 7.3, 5.2 Hz, 1H), 7.71 (d, J = 8.6 Hz, 1H), 7.78 (dd, J = 7.3, 1.8 Hz, 1H), 8.24 (dd, J = 5.2, 1.8 Hz, 1H), 8.47 (dd, J = 8.6, 2.4 Hz, 1H), 8.53 (d, J = 2.4 Hz, 1H)

Methyl 2-(2-hydroxypyridin-3-yl)-5-nitrobenzoate (Reference Compound No. 1-3-(2))

Methyl 2-(2-methoxypyridin-3-yl)-5-nitrobenzoate (Reference Compound No. 1-3-(1), 200 mg, 0.694 mmol) was dissolved in anhydrous dichloromethane (2 mL), then boron tribromide (118 μL, 1.25 mmol) was added thereto at –78° C. The reaction mixture was stirred at 0° C. for 3 hours, and then poured into ice-water (30 mL). Ethyl acetate (50 mL) was added, and then separated. The organic layer was washed with saturated brine (50 mL), dried over anhydrous magnesium sulfate, and then the solvent was removed under reduced pressure. The obtained residue was purified by silica gel column chromatography (hexane-ethyl acetate) to give the titled reference compound (102 mg) as a yellow solid. (Yield 54%)

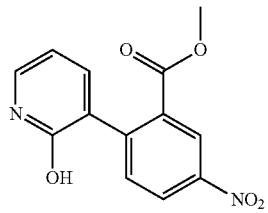 [SMILES: COC(=O)c1cc([N+](=O)[O-])ccc1-c1cccnc1O]

$^1$H-NMR (400 MHz, DMSO-$d_6$) δ 3.78 (s, 3H), 7.13 (dd, J = 7.3, 5.1 Hz, 1H), 7.66 (d, J = 8.5 Hz, 1H), 7.73 (dd, J = 7.3, 1.9 Hz, 1H), 8.22 (dd, J = 5.1, 1.9 Hz, 1H), 8.43 (dd, J = 8.5, 2.5 Hz, 1H), 8.54 (d, J = 2.5 Hz, 1H), 13.29 (s, 1H)

2-(2-Hydroxypyridin-3-yl)-5-nitrobenzoic acid (Reference Compound No. 1-3-(3))

Methyl 2-(2-hydroxypyridin-3-yl)-5-nitrobenzoate (Reference Compound No. 1-3-(2), 300 mg, 1.09 mmol) was dissolved in methanol (2 mL), then conc. HCl (5 mL) was added thereto, and then the reaction mixture was refluxed overnight. The solvent was removed under reduced pressure to give the titled reference compound (263 mg) as a yellow solid. (Yield 93%)

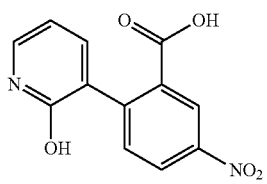

$^1$H-NMR (400 MHz, DMSO-$d_6$) δ 6.32 (t, J = 6.7 Hz, 1H), 7.44 (dd, J = 6.7, 2.1 Hz, 1H), 7.57 (dd, J = 6.7, 2.1 Hz, 1H), 7.61 (d, J = 8.8 Hz, 1H), 8.38 (dd, J = 8.3, 2.6 Hz, 1H), 8.46 (d, J = 2.6 Hz, 1H), 11.77 (br s, 1H), 13.09 (br s, 1H)

8-Nitro-4-azabenzo[c]chromen-6-one (Reference Compound No. 1-3-(4))

2-(2-Hydroxypyridin-3-yl)-5-nitrobenzoic acid (Reference Compound No. 1-3-(3), 50 mg, 0.20 mmol) was dissolved in N,N-dimethylformamide (5 mL), then N,N-diisopropylethylamine (141 μL, 0.81 mmol) and O-(7-azabenzotriazol-1-yl)-N,N,N',N'-tetramethyluronium hexafluorophosphate (154 mg, 0.41 mmol) were added thereto, and then the reaction mixture was stirred at room temperature overnight. Ethyl acetate (30 mL) was added to the reaction mixture, the whole was washed with water (30 mL) and saturated brine (30 mL) successively. The organic layer was dried over anhydrous magnesium sulfate, and then the solvent was removed under reduced pressure. Chloroform was added to the obtained residue, and then filtered to give the titled reference compound (35 mg) as a pale yellow solid. (Yield 71%)

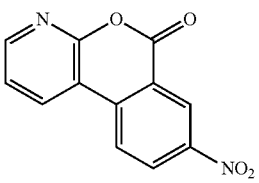 [SMILES: Nc1ccc2c(c1)c(=O)oc1ncccc12]

$^1$H-NMR (400 MHz, DMSO-$d_6$) δ 7.61 (dd, J = 7.9, 4.7 Hz, 1H), 8.61 (dd, J = 4.7, 1.8 Hz, 1H), 8.72 (dd, J = 8.7, 2.4 Hz, 1H), 8.77 (d, J = 8.7 Hz, 1H), 8.88 (d, J = 2.4 Hz, 1H), 9.00 (dd, J = 7.9, 1.8 Hz, 1H)

8-Amino-4-azabenzo[c]chromen-6-one (Reference Compound No. 1-3-(5))

8-Nitro-4-azabenzo[c]chromen-6-one (Reference Compound No. 1-3-(4), 368 mg, 1.52 mmol) was dissolved in methanol (10 mL), then 5% palladium on charcoal (37 mg) was added thereto, and then the reaction mixture was stirred under hydrogen atmosphere at room temperature for 4 days. After the mixture was filtered, the solvent was removed under reduced pressure. Chloroform was added to the obtained residue, and then filtered to give the titled reference compound (298 mg) as a yellow solid. (Yield 92%)

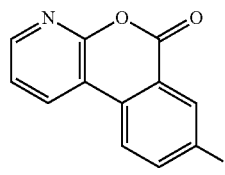

¹H-NMR (500 MHz, DMSO-d₆)
δ 6.05 (br s, 2H), 7.17 (dd, J = 8.6, 2.4 Hz, 1H), 7.39 (d, J = 2.4 Hz, 1H), 7.42 (dd, J = 7.7, 4.6 Hz, 1H), 8.15 (d, J = 8.6 Hz, 1H), 8.31 (dd, J = 4.6, 1.8 Hz, 1H), 8.61 (dd, J = 7.7, 1.8 Hz, 1H)

2,2,4-Trimethyl-1,2-dihydro-6-oxa-1,7-diazachrysen-5-one (Reference Compound No. 1-3)

In a pressure tube, 8-amino-4-azabenzo[c]chromen-6-one (Reference Compound No. 1-3-(5), 258 mg, 1.21 mmol) was dissolved in acetone (10 mL), then iodine (123 mg, 0.48 mmol) was added thereto, then the pressure tube was sealed, and then the reaction mixture was stirred at 105° C. for 1 day. After cooling down, the solvent was removed under reduced pressure. The obtained residue was purified by silica gel column chromatography (hexane-ethyl acetate) to give the titled reference compound (82.5 mg) as a yellow solid. (Yield 23%)

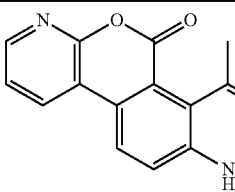

¹H-NMR (400 MHz, DMSO-d₆)
δ 1.24 (s, 6H), 1.98 (s, 3H), 5.49 (s, 1H), 7.08 (s, 1H), 7.19 (d, J = 8.7 Hz, 1H), 7.39 (dd, J = 8.0, 4.6 Hz, 1H), 8.06 (d, J = 8.7 Hz, 1H), 8.30 (dd, J = 4.6, 1.7 Hz, 1H), 8.59 (dd, J = 8.0, 1.7 Hz, 1H)

8-Fluoro-2,2,4,11-Tetramethyl-1,2-dihydro-6-oxa-1-azachrysen-5-one (Reference Compound No. 1-4)

Methyl 2-hydroxy-3-methylbenzoate (Reference Compound No. 1-4-(1))

2-Hydroxy-3-methylbenzoic acid (24.9 g, 0.164 mol) was dissolved in methanol (200 mL), then sulfuric acid (1.75 mL, 32.8 mmol) was added thereto, and then the reaction mixture was refluxed for 7 days. After the reaction mixture was poured into saturated aqueous NaHCO₃ solution (300 mL), methanol was removed under reduced pressure. The aqueous layer was extracted with ethyl acetate (500 mL), then the organic layer was washed with saturated aqueous NaHCO₃ solution (200 mL) and saturated brine (100 mL) successively, dried over anhydrous magnesium sulfate, and then the solvent was removed under reduced pressure to give the titled reference compound (23.0 g) as a pale brown oil. (Yield 84%)

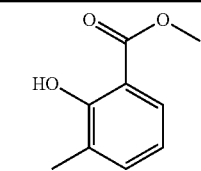

¹H-NMR (500 MHz, DMSO-d₆)
δ 2.20 (s, 3H), 3.91 (s, 3H), 6.87 (t, J = 7.9 Hz, 1H), 7.43-7.45 (m, 1H), 7.66 (dd, J = 7.9, 1.7 Hz, 1H), 10.87 (s, 1H)

Methyl 2-hydroxy-3-methyl-5-nitrobenzoate (Reference Compound No. 1-4-(2))

Methyl 2-hydroxy-3-methylbenzoate (Reference Compound No. 1-4-(1), 22.9 g, 0.138 mol) was dissolved in trifluoroacetic acid (190 mL), then an aqueous solution (90 mL) of sodium nitrate (12.9 g, 152 mmol) was added dropwise thereto over 1 hour at −10° C. After the reaction mixture was stirred at 0° C. for 1.5 hours, it was poured into ice-water (600 mL). The appeared solid was filtered and washed with methanol (100 mL) to give the titled reference compound (18.7 g) as a pale red solid. (Yield 64%)

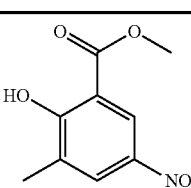

¹H-NMR (400 MHz, DMSO-d₆)
δ 2.30 (s, 3H), 3.97 (s, 3H), 8.34 (d, J = 2.9 Hz, 1H), 8.47 (d, J = 2.9 Hz, 1H), 11.50 (s, 1H)

Methyl 3-methyl-5-nitro-2-trifluoromethylsulfonyloxybenzoate (Reference Compound No. 1-4-(3))

Methyl 2-hydroxy-3-methyl-5-nitrobenzoate (Reference Compound No. 1-4-(2), 6.0 g, 28.4 mmol) was dissolved in tetrahydrofuran (200 mL), then triethylamine (16.7 mL, 120 mmol) and trifluorometanesulfonyl chloride (6.23 mL, 58.5 mmol) were added thereto, and then the reaction mixture was stirred at room temperature overnight. Water (500 mL) was added to the reaction mixture, then the whole was extracted with ethyl acetate (500 mL). The organic layer was washed with 0.2N aqueous NaOH solution (200 mL, twice) and saturated brine (200 mL) successively, dried over anhydrous magnesium sulfate, and then the solvent was removed under reduced pressure. The obtained residue was purified by silica gel column chromatography (hexane-ethyl acetate) to give the titled reference compound (9.32 g) as a pale yellow oil. (Yield 96%)

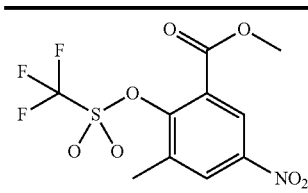

¹H-NMR (500 MHz, DMSO-d₆)
δ 3.32 (s, 3H), 3.92 (s, 3H), 8.51 (d, J = 3.1 Hz, 1H), 8.65 (d, J = 3.1 Hz, 1H)

Methyl 2-(2-benzyloxy-4-fluorophenyl)-3-methyl-5-nitrobenzoate (Reference Compound No. 1-4-(4))

A mixture of methyl 3-methyl-5-nitro-2-trifluoromethylsulfonyloxybenzoate (Reference Compound No. 1-4-(3), 13.26 g, 38.6 mmol), 2-benzyloxy-4-fluorophenylboronic acid (14.3 g, 58.1 mmol), potassium phosphate (21.3 g, 100 mmol) and tetrakis(triphenylphosphine)palladium(0) (3.23 g, 2.80 mmol) was suspended in anhydrous 1,4-dioxane (200 mL), and then the mixture was refluxed for 3 days. After cooling down, ethyl acetate (500 mL) was added thereto, and then the whole was washed with water (500 mL) and saturated brine (50 mL) successively, dried over anhydrous mag-

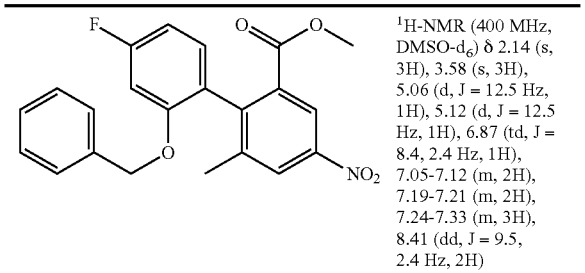

| | $^1$H-NMR (400 MHz, DMSO-d$_6$) δ 2.14 (s, 3H), 3.58 (s, 3H), 5.06 (d, J = 12.5 Hz, 1H), 5.12 (d, J = 12.5 Hz, 1H), 6.87 (td, J = 8.4, 2.4 Hz, 1H), 7.05-7.12 (m, 2H), 7.19-7.21 (m, 2H), 7.24-7.33 (m, 3H), 8.41 (dd, J = 9.5, 2.4 Hz, 2H) |
|---|---|

Methyl 5-amino-2-(4-fluoro-2-hydroxyphenyl)-3-methylbenzoate (Reference Compound No. 1-4-(5))

Methyl 2-(2-benzyloxy-4-fluorophenyl)-3-methyl-5-nitrobenzoate (Reference Compound No. 1-4-(4), 10.7 g, 27.0 mmol) was dissolved in a mixture of methanol (50 mL) and tetrahydrofuran (50 mL), then 10% palladium on charcoal (1.00 g) was added thereto, and then the reaction mixture was stirred under hydrogen atmosphere (3 kgf/cm$^2$) at room temperature for 3 days. After the mixture was filtered, the solvent was removed under reduced pressure. Ethyl acetate was added to the obtained residue, and then filtered to give the titled reference compound (4.79 g) as a pale gray solid. (Yield 64%)

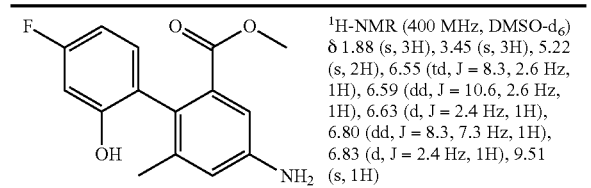

| | $^1$H-NMR (400 MHz, DMSO-d$_6$) δ 1.88 (s, 3H), 3.45 (s, 3H), 5.22 (s, 2H), 6.55 (td, J = 8.3, 2.6 Hz, 1H), 6.59 (dd, J = 10.6, 2.6 Hz, 1H), 6.63 (d, J = 2.4 Hz, 1H), 6.80 (dd, J = 8.3, 7.3 Hz, 1H), 6.83 (d, J = 2.4 Hz, 1H), 9.51 (s, 1H) |
|---|---|

8-Amino-3-fluoro-10-methylbenzo[c]chromen-6-one (Reference Compound No. 1-4-(6))

Methyl 5-amino-2-(4-fluoro-2-hydroxyphenyl)-3-methylbenzoate (Reference Compound No. 1-4-(5), 7.40 g, 26.9 mmol) was dissolved in pyridine (250 mL) and then the reaction mixture was refluxed overnight. The reaction mixture was concentrated under reduced pressure, then ethyl acetate-hexane (1:1) was added to the obtained residue, and then filtered to give the titled reference compound (6.15 g) as a pale yellow solid. (Yield 94%)

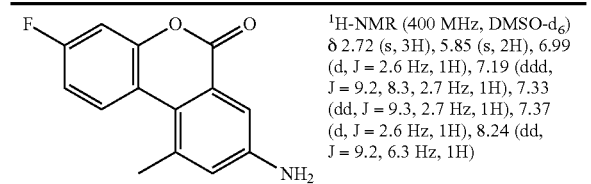

| | $^1$H-NMR (400 MHz, DMSO-d$_6$) δ 2.72 (s, 3H), 5.85 (s, 2H), 6.99 (d, J = 2.6 Hz, 1H), 7.19 (ddd, J = 9.2, 8.3, 2.7 Hz, 1H), 7.33 (dd, J = 9.3, 2.7 Hz, 1H), 7.37 (d, J = 2.6 Hz, 1H), 8.24 (dd, J = 9.2, 6.3 Hz, 1H) |
|---|---|

8-Fluoro-2,2,4,11-tetramethyl-1,2-dihydro-6-oxa-1-azachrysen-5-one (Reference Compound No. 1-4)

In a pressure tube, 8-amino-3-fluoro-10-methylbenzo[c]chromen-6-one (Reference Compound No. 1-4-(6), 6.13 g, 25.2 mmol) was dissolved in acetone (175 mL) and iodine (2.56 g, 10.1 mmol) was added thereto, then the pressure tube was sealed, and then the reaction mixture was stirred at 110° C. for 4 days. After cooling down, the solvent was removed under reduced pressure. The obtained residue was purified by silica gel column chromatography (hexane-ethyl acetate) to give the titled reference compound (6.35 g) as a brown solid. (Yield 78%)

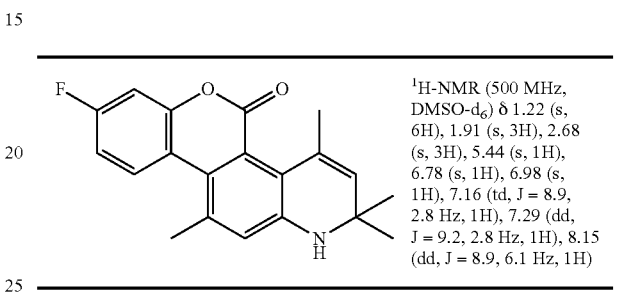

| | $^1$H-NMR (500 MHz, DMSO-d$_6$) δ 1.22 (s, 6H), 1.91 (s, 3H), 2.68 (s, 3H), 5.44 (s, 1H), 6.78 (s, 1H), 6.98 (s, 1H), 7.16 (td, J = 8.9, 2.8 Hz, 1H), 7.29 (dd, J = 9.2, 2.8 Hz, 1H), 8.15 (dd, J = 8.9, 6.1 Hz, 1H) |
|---|---|

Using available compounds, the following Reference Compounds (No. 1-5~1-20) were obtained by a method similar to any ones of Reference Compound No. 1-1~1-4.

| Compound | Structure | $^1$H-NMR |
|---|---|---|
| 8-Fluoro-2,2,4-trimethyl-1,2-dihydro-6-oxa-1-azachrysen-5-one (Reference Compound No. 1-5) | 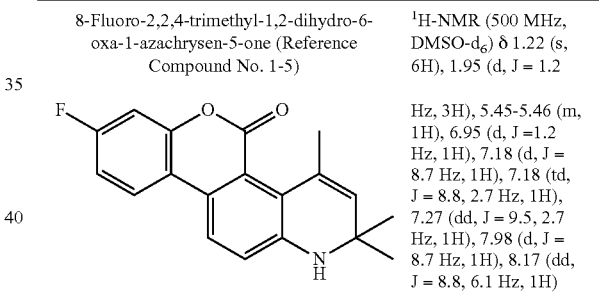 | $^1$H-NMR (500 MHz, DMSO-d$_6$) δ 1.22 (s, 6H), 1.95 (d, J = 1.2 Hz, 3H), 5.45-5.46 (m, 1H), 6.95 (d, J =1.2 Hz, 1H), 7.18 (d, J = 8.7 Hz, 1H), 7.18 (td, J = 8.8, 2.7 Hz, 1H), 7.27 (dd, J = 9.5, 2.7 Hz, 1H), 7.98 (d, J = 8.7 Hz, 1H), 8.17 (dd, J = 8.8, 6.1 Hz, 1H) |
| 9-Chloro-2,2,4-trimethyl-1,2-dihydro-6-oxa-1-azachrysen-5-one (Reference Compound No. 1-6) | 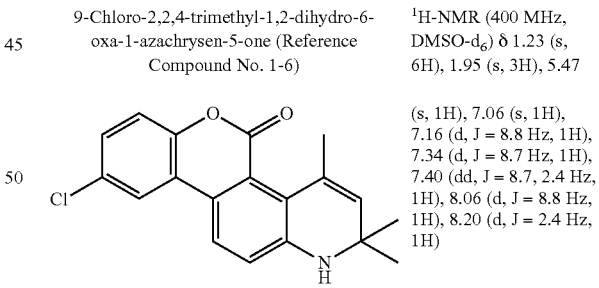 | $^1$H-NMR (400 MHz, DMSO-d$_6$) δ 1.23 (s, 6H), 1.95 (s, 3H), 5.47 (s, 1H), 7.06 (s, 1H), 7.16 (d, J = 8.8 Hz, 1H), 7.34 (d, J = 8.7 Hz, 1H), 7.40 (dd, J = 8.7, 2.4 Hz, 1H), 8.06 (d, J = 8.8 Hz, 1H), 8.20 (d, J = 2.4 Hz, 1H) |
| 9-Fluoro-2,2,4-trimethyl-1,2-dihydro-6-oxa-1-azachrysen-5-one (Reference Compound No. 1-7) | 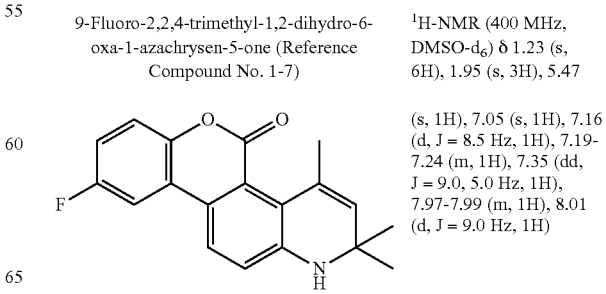 | $^1$H-NMR (400 MHz, DMSO-d$_6$) δ 1.23 (s, 6H), 1.95 (s, 3H), 5.47 (s, 1H), 7.05 (s, 1H), 7.16 (d, J = 8.5 Hz, 1H), 7.19-7.24 (m, 1H), 7.35 (dd, J = 9.0, 5.0 Hz, 1H), 7.97-7.99 (m, 1H), 8.01 (d, J = 9.0 Hz, 1H) |

| Compound | ¹H-NMR |
|---|---|
| 2,2,4,9-Tetramethyl-1,2-dihydro-6-oxa-1-azachrysen-5-one (Reference Compound No. 1-8) 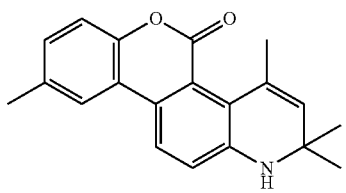 | ¹H-NMR (400 MHz, DMSO-d₆) δ 1.23 (s, 6H), 1.96 (s, 3H), 2.39 (s, 3H), 5.44 (s, 1H), 6.93 (s, 1H), 7.16 (d, J = 8.5 Hz, 1H), 7.17-7.19 (m, 2H), 7.93 (s, 1H), 7.99 (d, J = 8.8 Hz, 1H) |
| 7-Hydroxy-2,2,4-trimethyl-1,2-dihydro-6-oxa-1-azachrysen-5-one (Reference Compound No. 1-9) 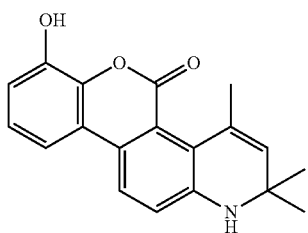 [SMILES: CC1=CC(C)(C)Nc2ccc3c(c21)c(=O)oc1c(O)cccc13] | ¹H-NMR (400 MHz, DMSO-d₆) δ 1.23 (s, 6H), 1.97 (s, 3H), 5.44 (s, 1H), 6.88 (dd, J = 8.0, 1.2 Hz, 1H), 6.93 (s, 1H), 7.08 (t, J = 8.0 Hz, 1H), 7.16 (d, J = 8.8 Hz, 1H), 7.52 (d, J = 8.0 Hz, 1H), 7.94 (d, J = 8.8 Hz, 1H), 9.89 (s, 1H) |
| 10-Methoxy-2,2,4-trimethyl-1,2-dihydro-6-oxa-1-azachrysen-5-one (Reference Compound No. 1-10) 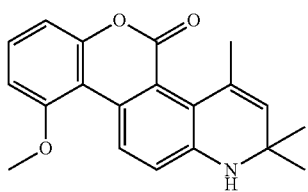 [SMILES: COc1cccc2oc(=O)c3c4c(ccc3c12)NC(C)(C)C=C4C] | ¹H-NMR (400 MHz, DMSO-d₆) δ 1.23 (s, 6H), 1.93 (s, 3H), 3.99 (s, 3H), 5.44 (s, 1H), 6.90 (s, 1H), 6.94 (dd, J = 8.3, 1.0 Hz, 1H), 6.99 (dd, J = 8.3, 1.0 Hz, 1H), 7.12 (d, J = 8.9 Hz, 1H), 7.34 (t, J = 8.3 Hz, 1H), 8.64 (d, J = 8.9 Hz, 1H) |
| 7-Fluoro-2,2,4-trimethyl-1,2-dihydro-6-oxa-1-azachrysen-5-one (Reference Compound No. 1-11) 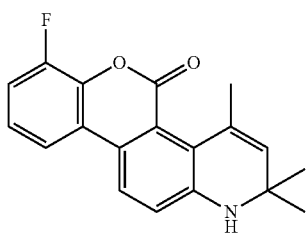 [SMILES: CC1=CC(C)(C)Nc2ccc3c(c21)c(=O)oc1c(F)cccc13] | ¹H-NMR (400 MHz, DMSO-d₆) δ 1.23 (s, 6H), 1.96 (s, 3H), 5.48 (s, 1H), 7.06 (s, 1H), 7.19 (d, J = 8.7 Hz, 1H), 7.27 (td, J = 8.1, 5.4 Hz, 1H), 7.32 (dd, J = 10.5, 8.1 Hz, 1H), 7.92 (d, J = 8.1 Hz, 1H), 8.01 (d, J = 8.7 Hz, 1H) |
| 8,9-Difluoro-2,2,4-trimethyl-1,2-dihydro-6-oxa-1-azachrysen-5-one (Reference Compound No. 1-12) 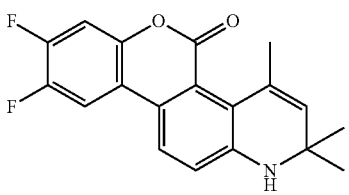 [SMILES: CC1=CC(C)(C)Nc2ccc3c(c21)c(=O)oc1cc(F)c(F)cc13] | ¹H-NMR (400 MHz, DMSO-d₆) δ 1.22 (s, 6H), 1.95 (s, 3H), 5.47 (s, 1H), 7.04 (s, 1H), 7.17 (d, J = 8.8 Hz, 1H), 7.56 (dd, J = 10.9, 7.2 Hz, 1H), 7.97 (d, J = 8.8 Hz, 1H), 8.25 (dd, J = 12.2, 8.8 Hz, 1H) |
| 7,9-Difluoro-2,2,4-trimethyl-1,2-dihydro-6-oxa-1-azachrysen-5-one (Reference Compound No. 1-13) 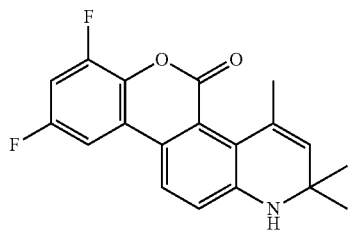 [SMILES: CC1=CC(C)(C)Nc2ccc3c(c21)c(=O)oc1c(F)cc(F)cc13] | ¹H-NMR (500 MHz, DMSO-d₆) δ 1.23 (s, 6H), 1.96 (s, 3H), 5.49 (s, 1H), 7.15 (s, 1H), 7.17 (d, J = 8.6 Hz, 1H), 7.37-7.45 (m, 1H), 7.86 (d, J = 10.1 Hz, 1H), 8.01 (d, J = 8.6 Hz, 1H) |
| 8-Fluoro-11-methoxy-2,2,4-trimethyl-1,2-dihydro-6-oxa-1-azachrysen-5-one (Reference Compound No. 1-14) 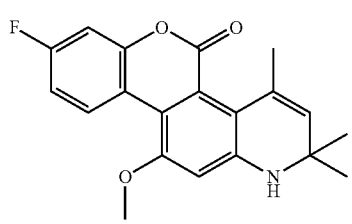 [SMILES: COc1cc2c(c3c(=O)oc4cc(F)ccc4c13)C(C)=CC(C)(C)N2] | ¹H-NMR (500 MHz, DMSO-d₆) δ 1.22 (s, 6H), 1.89 (s, 3H), 3.96 (s, 3H), 5.36 (s, 1H), 6.83 (s, 1H), 6.94 (s, 1H), 7.12 (td, J = 9.0, 2.9 Hz, 1H), 7.24 (dd, J = 9.5, 2.9 Hz, 1H), 8.78 (dd, J = 9.0, 6.7 Hz, 1H) |
| 9-Trifluoromethyl-2,2,4-trimethyl-1,2-dihydro-6-oxa-1-azachrysen-5-one (Reference Compound No. 1-15) 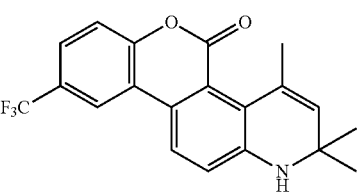 | ¹H-NMR (500 MHz, DMSO-d₆) δ 1.24 (s, 6H), 1.96 (s, 3H), 5.48 (s, 1H), 7.09 (s, 1H), 7.19 (d, J = 8.9 Hz, 1H), 7.50 (d, J = 8.6 Hz, 1H), 7.70 (dd, J = 8.6, 1.8 Hz, 1H), 8.19 (d, J = 8.9 Hz, 1H), 8.46 (d, J = 1.8 Hz, 1H) |
| 12-Chloro-8-fluoro-2,2,4-trimethyl-1,2-dihydro-6-oxa-1-azachrysen-5-one (Reference Compound No. 1-16) 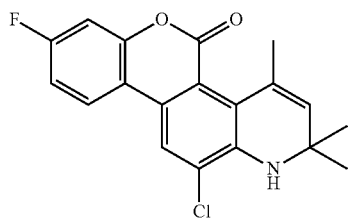 [SMILES: CC1=CC(C)(C)Nc2c(Cl)cc3c(c21)c(=O)oc1cc(F)ccc13] | ¹H-NMR (400 MHz, DMSO-d₆) δ 1.29 (s, 6H), 1.96 (s, 3H), 5.59 (s, 1H), 6.35 (s, 1H), 7.20 (td, J = 8.7, 2.7 Hz, 1H), 7.30 (dd, J = 9.3, 2.7 Hz, 1H), 8.25 (s, 1H), 8.29 (dd, J = 9.3, 6.1 Hz, 1H) |
| 9-Nitro-2,2,4-trimethyl-1,2-dihydro-6-oxa-1-azachrysen-5-one (Reference Compound No. 1-17) 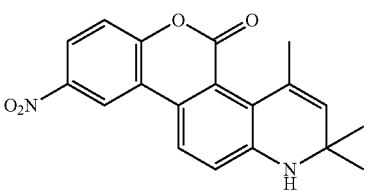 [SMILES: CC1=CC(C)(C)Nc2ccc3c(c21)c(=O)oc1ccc([N+](=O)[O-])cc13] | ¹H-NMR (400 MHz, DMSO-d₆) δ 1.24 (s, 6H), 1.97 (s, 3H), 5.50 (s, 1H), 7.17 (s, 1H), 7.21 (d, J = 8.8 Hz, 1H), 7.54 (d, J = 8.8 Hz, 1H), 8.19 (d, J = 8.8 Hz, 1H), 8.20 (dd, J = 8.8, 2.6 Hz, 1H), 8.92 (d, J = 2.6 Hz, 1H) |

| | |
|---|---|
| 9-Hydroxy-2,2,4-trimethyl-1,2-dihydro-6-oxa-1-azachrysen-5-one (Reference Compound No. 1-18)<br>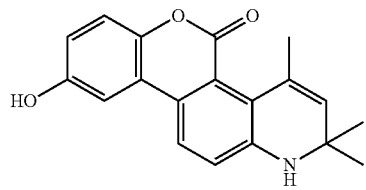 [SMILES: CC1=CC(C)(C)Nc2ccc3c(c21)c(=O)oc1ccc(O)cc13] | $^1$H-NMR (400 MHz, DMSO-d$_6$) δ 1.22 (s, 6H), 1.95 (s, 3H), 5.44 (s, 1H), 6.81 (dd, J = 8.9, 2.7 Hz, 1H), 6.94 (s, 1H), 7.12-7.17 (m, 2H), 7.37 (d, J = 2.7 Hz, 1H), 7.83 (d, J = 8.9 Hz, 1H), 9.49 (s, 1H) |
| 8-Hydroxy-2,2,4-trimethyl-1,2-dihydro-6-oxa-1-azachrysen-5-one (Reference Compound No. 1-19)<br>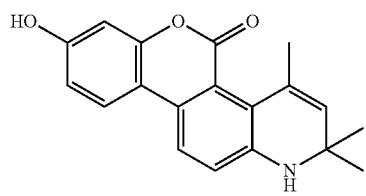 [SMILES: CC1=CC(C)(C)Nc2ccc3c(c21)c(=O)oc1cc(O)ccc13] | $^1$H-NMR (400 MHz, DMSO-d$_6$) δ 1.21 (s, 6H), 1.94 (s, 3H), 5.41 (s, 1H), 6.66 (s, 1H), 6.73 (s, 1H), 6.75 (d, J = 8.6 Hz, 1H), 7.13 (d, J = 8.6 Hz, 1H), 7.85 (d, J = 8.6 Hz, 1H), 7.91 (d, J = 8.6 Hz, 1H), 9.98 (s, 1H) |
| 8-Chloro-2,2,4-trimethyl-1,2-dihydro-6-oxa-1-azachrysen-5-one (Reference Compound No. 1-20)<br>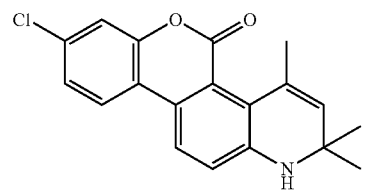 [SMILES: CC1=CC(C)(C)Nc2ccc3c(c21)c(=O)oc1cc(Cl)ccc13] | $^1$H-NMR (400 MHz, DMSO-d$_6$) δ 1.23 (s, 6H), 1.95 (s, 3H), 5.46 (s, 1H), 7.03 (s, 1H), 7.17 (d, J = 8.7 Hz, 1H), 7.35 (dd, J = 8.7, 2.2 Hz, 1H), 7.46 (d, J = 2.2 Hz, 1H), 7.99 (d, J = 8.7 Hz, 1H), 8.13 (d, J = 8.7 Hz, 1H) |

Reference Example 2

7-Methoxy-2,2,4-trimethyl-1,2-dihydro-6-oxa-1-azachrysen-5-one (Reference Compound No. 2-1)

A mixture of 7-Hydroxy-2,2,4-trimethyl-1,2-dihydro-6-oxa-1-azachrysen-5-one (Reference Compound No. 1-9, 430 mg, 1.40 mmol), methyl iodide (87.2 μL, 1.40 mmol) and potassium carbonate (387 mg, 2.80 mmol) was suspended in anhydrous N,N-dimethylformamide (7 mL) and stirred at 50° C. for 3 hours. After cooling down, the reaction mixture was diluted with ethyl acetate (150 mL). The whole was washed with water (150 mL) and saturated brine (200 mL) successively, dried over anhydrous magnesium sulfate, and then the solvent was removed under reduced pressure. The obtained residue was purified by silica gel column chromatography (hexane-ethyl acetate) to give the titled reference compound (384 mg) as a yellow solid. (Yield 85%)

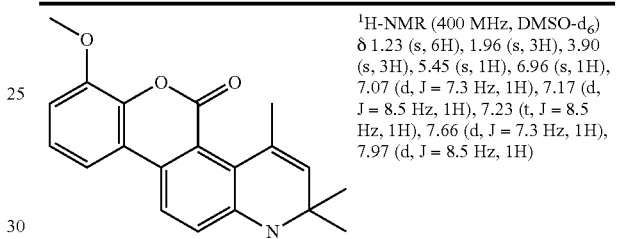

$^1$H-NMR (400 MHz, DMSO-d$_6$) δ 1.23 (s, 6H), 1.96 (s, 3H), 3.90 (s, 3H), 5.45 (s, 1H), 6.96 (s, 1H), 7.07 (d, J = 7.3 Hz, 1H), 7.17 (d, J = 8.5 Hz, 1H), 7.23 (t, J = 8.5 Hz, 1H), 7.66 (d, J = 7.3 Hz, 1H), 7.97 (d, J = 8.5 Hz, 1H)

Using any compounds among Reference Compounds No. 1-9, 1-18, and 1-19, the following Reference Compounds (No. 2-2~2-6) were obtained by a method similar to that of Reference Compound No. 2-1.

| | |
|---|---|
| 7-Methoxymethoxy-2,2,4-trimethyl-1,2-dihydro-6-oxa-1-azachrysen-5-one (Reference Compound No. 2-2)<br>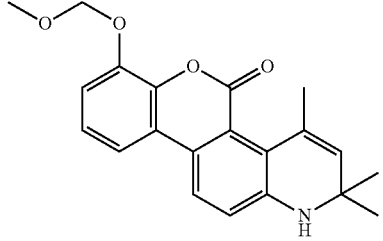 | $^1$H-NMR (400 MHz, DMSO-d$_6$) δ 1.23 (s, 6H), 1.97 (s, 3H), 3.47 (s, 3H), 5.31 (s, 2H), 5.45 (s, 1H), 6.98 (s, 1H), 7.17-7.21 (m, 3H), 7.74 (dd, J = 7.9, 1.6 Hz, 1H), 7.98 (d, J = 8.5 Hz, 1H) |
| 7-Ethoxy-2,2,4-trimethyl-1,2-dihydro-6-oxa-1-azachrysen-5-one (Reference Compound No. 2-3)<br>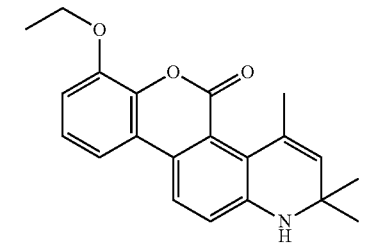 [SMILES: CCOc1cccc2c1oc(=O)c1c3c(ccc12)NC(C)(C)C=C3C] | $^1$H-NMR (500 MHz, DMSO-d$_6$) δ 1.23 (s, 6H), 1.42 (t, J = 7.0 Hz, 3H), 1.96 (s, 3H), 4.15 (q, J = 7.0 Hz, 2H), 5.45 (s, 1H), 6.95 (d, J = 1.1 Hz, 1H), 7.05 (dd, J = 8.3, 1.1 Hz, 1H), 7.17 (d, J = 8.6 Hz, 1H), 7.20 (t, J = 8.6 Hz, 1H), 7.65 (dd, J = 8.3, 1.1 Hz, 1H), 7.97 (d, J = 8.6 Hz, 1H) |

| | |
|---|---|
| 7-Benzyloxy-2,2,4-trimethyl-1,2-dihydro-6-oxa-1-azachrysen-5-one (Reference Compound No. 2-4)<br />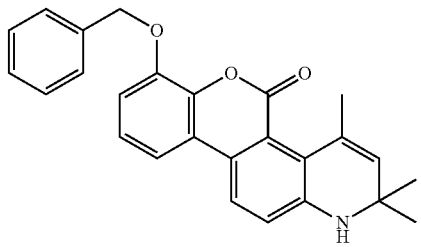 [SMILES: CC1=CC(C)(C)Nc2ccc3c(c21)c(=O)oc1c(OCc2ccccc2)cccc13] | $^1$H-NMR (500 MHz, DMSO-$d_6$)<br />δ 1.23 (s, 6H), 1.96 (s, 3H), 5.23 (s, 2H), 5.45 (s, 1H), 6.96 (d, J = 1.3 Hz, 1H), 7.16 (dd, J = 8.2, 1.3 Hz, 1H), 7.17 (d, J = 8.5 Hz, 1H), 7.21 (t, J = 8.5 Hz, 1H), 7.35-7.39 (m, 1H), 7.43 (t, J = 7.3 Hz, 2H), 7.52-7.54 (m, 2H), 7.68 (dd, J = 8.2, 1.3 Hz, 1H), 7.98 (d, J = 8.5 Hz, 1H) |
| 9-Methoxymethoxy-2,2,4-trimethyl-1,2-dihydro-6-oxa-1-azachrysen-5-one (Reference Compound No. 2-5)<br />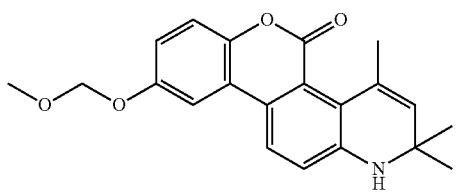 | $^1$H-NMR (400 MHz, DMSO-$d_6$)<br />δ 1.23 (s, 6H), 1.96 (s, 3H), 3.42 (s, 3H), 5.27 (s, 2H), 5.45 (s, 1H), 6.99 (s, 1H), 7.06 (dd, J = 9.0, 2.8 Hz, 1H), 7.17 (d, J = 8.7 Hz, 1H), 7.25 (d, J = 9.0 Hz, 1H), 7.70 (d, J = 2.8 Hz, 1H), 7.98 (d, J = 8.7 Hz, 1H) |
| 8-Methoxymethoxy-2,2,4-trimethyl-1,2-dihydro-6-oxa-1-azachrysen-5-one (Reference Compound No. 2-6)<br />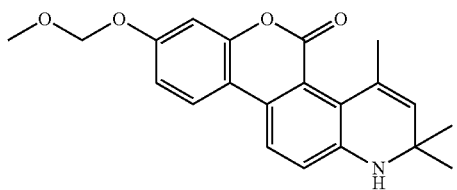 | $^1$H-NMR (400 MHz, DMSO-$d_6$)<br />δ 1.22 (s, 6H), 1.95 (s, 3H), 3.40 (s, 3H), 5.27 (s, 2H), 5.43 (s, 1H), 6.85 (s, 1H), 6.98 (d, J = 9.3 Hz, 1H), 6.99 (s, 1H), 7.16 (d, J = 8.8 Hz, 1H), 7.92 (d, J = 8.8 Hz, 1H), 8.04 (d, J = 9.3 Hz, 1H) |

Reference Example 3

5-Hydroxymethyl-6-(2-hydroxyphenyl)-2,2,4-trimethyl-1,2-dihydroquinoline (Reference Compound No. 3-1)

Under argon atmosphere, lithium aluminum hydride (1.48 g, 39.0 mmol) was suspended in anhydrous tetrahydrofuran (30 mL). A solution of 2,2,4-Trimethyl-1,2-dihydro-6-oxa-1-azachrysen-5-one (Reference Compound No. 1-1, 3.80 g, 13.0 mmol) in anhydrous tetrahydrofuran (40 mL) was added dropwise at 0° C. and the reaction mixture was stirred at the same temperature for 1 hour. Ethyl acetate (15 mL) and water (5 mL) were added dropwise successively to the reaction mixture and then 0.2 N aqueous HCl solution (350 mL) was added thereto. The whole was extracted with ethyl acetate (300 mL, 100 mL). The combined organic layer was washed with water (300 mL) and saturated brine (100 mL) successively, dried over anhydrous magnesium sulfate. The solvent was removed under reduced pressure to give the titled reference compound (4.01 g) as a pale brown solid. (Yield quantitative)

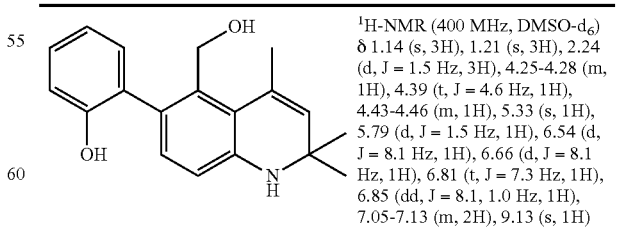

$^1$H-NMR (400 MHz, DMSO-$d_6$)
δ 1.14 (s, 3H), 1.21 (s, 3H), 2.24 (d, J = 1.5 Hz, 3H), 4.25-4.28 (m, 1H), 4.39 (t, J = 4.6 Hz, 1H), 4.43-4.46 (m, 1H), 5.33 (s, 1H), 5.79 (d, J = 1.5 Hz, 1H), 6.54 (d, J = 8.1 Hz, 1H), 6.66 (d, J = 8.1 Hz, 1H), 6.81 (t, J = 7.3 Hz, 1H), 6.85 (dd, J = 8.1, 1.0 Hz, 1H), 7.05-7.13 (m, 2H), 9.13 (s, 1H)

Using any Compounds among Reference Compounds No. 1-2~1-8, 1-10~1-17, 1-20 and 2-1~2-6, the following Reference Compounds (No. 3-2~3-23) were obtained by a method similar to that of Reference Compound No. 3-1.

| | |
|---|---|
| 6-(4-Fluoro-2-hydroxyphenyl)-5-hydroxymethyl-2,2,4-trimethyl-1,2-dihydroquinoline (Reference Compound No. 3-2)<br />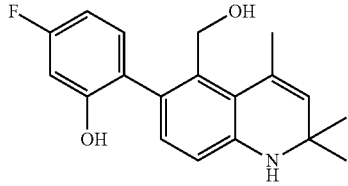 [SMILES: CC1=CC(C)(C)Nc2ccc(-c3ccc(F)cc3O)c(CO)c21] | $^1$H-NMR (400 MHz, DMSO-$d_6$)<br />δ 1.14 (s, 3H), 1.20 (s, 3H), 2.24 (s, 3H), 4.20-4.22 (m, 1H), 4.41 (t, J = 4.4 Hz, 1H), 4.42-4.46 (m, 1H), 5.34 (s, 1H), 5.82 (s, 1H), 6.53 (d, J = 8.0 Hz, 1H), 6.61-6.65 (m, 2H), 6.65 (d, J = 8.0 Hz, 1H), 7.08 (t, J = 7.7 Hz, 1H), 9.64 (s, 1H) |
| 5-Hydroxymethyl-6-(2-hydroxy-5-methylphenyl)-2,2,4-trimethyl-1,2-dihydroquinoline (Reference Compound No. 3-3)<br />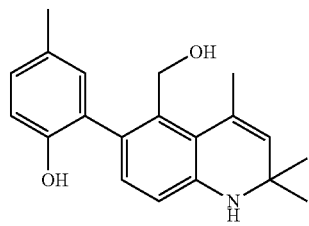 [SMILES: CC1=CC(C)(C)Nc2ccc(-c3cc(C)ccc3O)c(CO)c21] | $^1$H-NMR (400 MHz, DMSO-$d_6$)<br />δ 1.13 (s, 3H), 1.21 (s, 3H), 2.21 (s, 3H), 2.24 (s, 3H), 4.25-4.31 (m, 1H), 4.38-4.40 (m, 2H), 5.33 (s, 1H), 5.78 (s, 1H), 6.53 (d, J = 8.2 Hz, 1H), 6.65 (d, J = 8.2 Hz, 1H), 6.73 (d, J = 8.0 Hz, 1H), 6.87 (s, 1H), 6.90-6.92 (m, 1H), 8.91 (s, 1H) |
| 6-(5-Chloro-2-hydroxyphenyl)-5-hydroxymethyl-2,2,4-trimethyl-1,2-dihydroquinoline (Reference Compound No. 3-4)<br />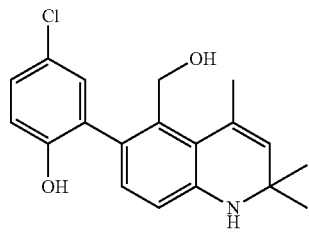 | $^1$H-NMR (400 MHz, DMSO-$d_6$)<br />δ 1.14 (s, 3H), 1.19 (s, 3H), 2.24 (s, 3H), 4.20 (br s, 1H), 4.47 (br s, 2H), 5.34 (s, 1H), 5.87 (s, 1H), 6.54 (d, J = 8.3 Hz, 1H), 6.67 (d, J = 8.3 Hz, 1H), 6.86 (dd, J = 8.6, 2.5 Hz, 1H), 7.09 (d, J = 2.5 Hz, 1H), 7.14 (d, J = 8.6 Hz, 1H), 9.45 (s, 1H) |
| 6-(2-Hydroxy-3-methoxymethoxyphenyl)-5-hydroxymethyl-2,2,4-trimethyl-1,2-dihydroquinoline (Reference Compound No. 3-5)<br />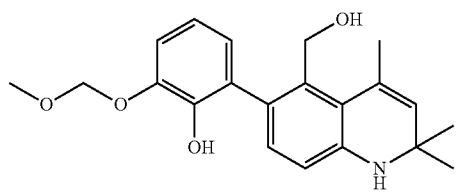 | $^1$H-NMR (500 MHz, DMSO-$d_6$)<br />δ 1.13 (s, 3H), 1.21 (s, 3H), 2.24 (s, 3H), 3.43 (s, 3H), 4.26-4.29 (m, 1H), 4.42-4.46 (m, 1H), 4.42 (t, J = 4.4 Hz, 1H), 5.17 (s, 2H), 5.34 (s, 1H), 5.81 (s, 1H), 6.54 (d, J = 8.2 Hz, 1H), 6.67 (d, J = 8.2 Hz, 1H), 6.73-6.77 (m, 2H), 6.98-7.02 (m, 1H), 8.39 (s, 1H) |
| 6-(2-Hydroxy-3-methoxyphenyl)-5-hydroxymethyl-2,2,4-trimethyl-1,2-dihydroquinoline (Reference Compound No. 3-6)<br />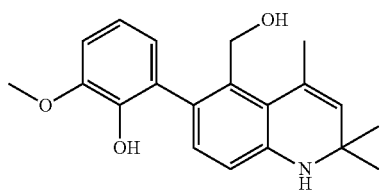 | $^1$H-NMR (400 MHz, DMSO-$d_6$)<br />δ 1.13 (s, 3H), 1.21 (s, 3H), 2.23 (s, 3H), 3.81 (s, 3H), 4.27 (dd, J = 11.8, 4.6 Hz, 1H), 4.37 (t, J = 4.6 Hz, 1H), 4.43 (dd, J = 11.8, 4.6 Hz, 1H), 5.33 (s, 1H), 5.80 (s, 1H), 6.54 (d, J = 8.0 Hz, 1H), 6.66 (d, J = 8.0 Hz, 1H), 6.69 (dd, J = 7.8, 1.4 Hz, 1H), 6.77 (t, J = 7.8 Hz, 1H), 6.90 (dd, J = 7.8, 1.4 Hz, 1H), 8.33 (s, 1H) |

| | |
|---|---|
| 6-(3-Ethoxy-2-hydroxyphenyl)-5-hydroxymethyl-2,2,4-trimethyl-1,2-dihydroquinoline (Reference Compound No. 3-7)<br>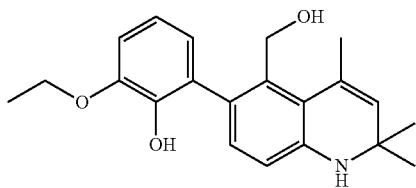 [SMILES: CCOc1cccc(-c2ccc3c(c2CO)C(C)=CC(C)(C)N3)c1O] | $^1$H-NMR (400 MHz, DMSO-d$_6$)<br>δ 1.13 (s, 3H), 1.21 (s, 3H), 1.36 (t, J = 7.0 Hz, 3H), 2.24 (s, 3H), 4.03-4.09 (m, 2H), 4.28 (dd, J = 11.8, 4.6 Hz, 1H), 4.38 (t, J = 4.6 Hz, 1H), 4.44 (dd, J = 11.8, 4.6 Hz, 1H), 5.33 (s, 1H), 5.81 (d, J = 1.6 Hz, 1H), 6.54 (d, J = 8.2 Hz, 1H), 6.66 (d, J = 8.2 Hz, 1H), 6.68 (dd, J = 7.8, 1.6 Hz, 1H), 6.75 (t, J = 7.8 Hz, 1H), 6.89 (dd, J = 7.8, 1.6 Hz, 1H), 8.12 (s, 1H) |
| 6-(3-Benzyloxy-2-hydroxyphenyl)-5-hydroxymethyl-2,2,4-trimethyl-1,2-dihydroquinoline (Reference Compound No. 3-8)<br>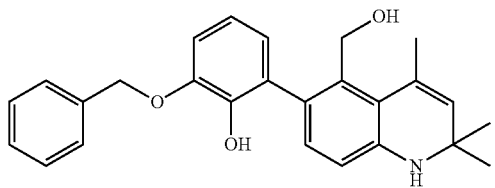 [SMILES: CC1=CC(C)(C)Nc2ccc(-c3cccc(OCc4ccccc4)c3O)c(CO)c21] | $^1$H-NMR (400 MHz, DMSO-d$_6$)<br>δ 1.13 (s, 3H), 1.21 (s, 3H), 2.24 (s, 3H), 4.28 (dd, J = 11.5, 4.5 Hz, 1H), 4.40 (t, J = 4.5 Hz, 1H), 4.45 (dd, J = 11.5, 4.5 Hz, 1H), 5.17 (s, 2H), 5.34 (s, 1H), 5.81 (d, J = 1.7 Hz, 1H), 6.54 (d, J = 8.3 Hz, 1H), 6.67 (d, J = 8.3 Hz, 1H), 6.69 (dd, J = 7.9, 1.7 Hz, 1H), 6.74 (t, J = 7.9 Hz, 1H), 6.95 (dd, J = 7.9, 1.7 Hz, 1H), 7.32 (t, J = 7.1 Hz, 1H), 7.39 (t, J = 7.1 Hz, 2H), 7.52 (d, J = 7.1 Hz, 2H), 8.28 (s, 1H) |
| 6-(2-Hydroxy-6-methoxyphenyl)-5-hydroxymethyl-2,2,4-trimethyl-1,2-dihydroquinoline (Reference Compound No. 3-9)<br>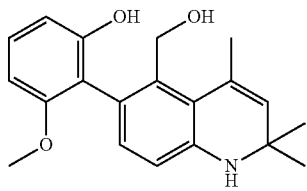 [SMILES: COc1cccc(O)c1-c1ccc2c(c1CO)C(C)=CC(C)(C)N2] | $^1$H-NMR (400 MHz, CDCl$_3$)<br>δ 1.27 (s, 3H), 1.30 (s, 3H), 2.37 (s, 3H), 3.73 (s, 3H), 3.95 (br s, 1H), 4.34 (dd, J = 11.9, 2.7 Hz, 1H), 4.58 (dd, J = 11.9, 9.0 Hz, 1H), 4.94 (s, 1H), 5.51 (s, 1H), 6.58 (dd, J = 8.3, 0.9 Hz, 1H), 6.61 (d, J = 8.1 Hz, 1H), 6.69 (dd, J = 8.3, 0.9 Hz, 1H), 6.83 (d, J = 8.1 Hz, 1H), 7.23 (t, J = 8.3 Hz, 1H) |
| 6-(5-Fluoro-2-hydroxyphenyl)-5-hydroxymethyl-2,2,4-trimethyl-1,2-dihydroquinoline (Reference Compound No. 3-10)<br>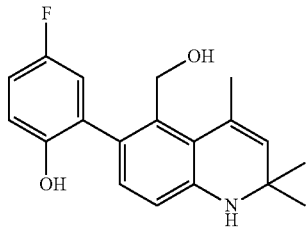 | $^1$H-NMR (500 MHz, DMSO-d$_6$)<br>δ 1.15-1.24 (m, 6H), 2.24 (s, 3H), 4.24 (br s, 1H), 4.45-4.50 (m, 2H), 5.34 (s, 1H), 5.85 (s, 1H), 6.54 (d, J = 8.2 Hz, 1H), 6.68 (d, J = 8.2 Hz, 1H), 6.81-6.84 (m, 1H), 6.89-6.96 (m, 2H), 9.13 (s, 1H) |
| 5-Hydroxymethyl-6-(2-hydroxypyridin-3-yl)-2,2,4-trimethyl-1,2-dihydroquinoline (Reference Compound No. 3-11)<br>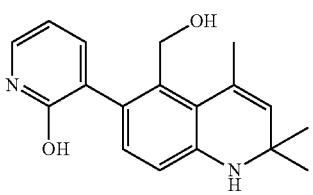 [SMILES: CC1=CC(C)(C)Nc2ccc(-c3cccnc3O)c(CO)c21] | $^1$H-NMR (400 MHz, DMSO-d$_6$)<br>δ 1.16 (s, 6H), 2.26 (s, 3H), 4.31 (s, 2H), 5.06 (t, J = 5.9 Hz, 1H), 5.38 (s, 1H), 5.89 (s, 1H), 6.32 (t, J = 6.7 Hz, 1H), 6.55 (d, J = 8.2 Hz, 1H), 6.68 (d, J = 8.2 Hz, 1H), 7.32-7.41 (m, 1H), 7.37 (dd, J = 6.7, 2.2 Hz, 1H), 11.89 (s, 1H) |

| | |
|---|---|
| 6-(3,4-Difluoro-2-hydroxyphenyl)-5-hydroxymethyl-2,2,4-trimethyl-1,2-dihydroquinoline (Reference Compound No. 3-12) | $^1$H-NMR (400 MHz, DMSO-d$_6$) δ 1.14 (s, 3H), 1.21 (s, 3H), 2.24 (s, 3H), 4.20 (d, J = 10.5 Hz, 1H), 4.44 (d, J = 10.5 Hz, 1H), 4.60 (s, 1H), |
| 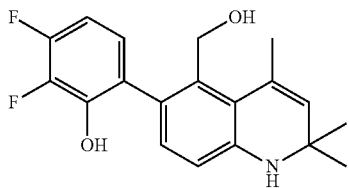 [SMILES: CC1=CC(C)(C)Nc2ccc(-c3ccc(F)c(F)c3O)c(CO)c21] | 5.35 (s, 1H), 5.91 (s, 1H), 6.55 (d, J = 8.2 Hz, 1H), 6.66 (d, J = 8.2 Hz, 1H), 6.81-6.94 (m, 2H), 9.72 (s, 1H) |
| 6-(3-Fluoro-2-hydroxyphenyl)-5-hydroxymethyl-2,2,4-trimethyl-1,2-dihydroquinoline (Reference Compound No. 3-13) | $^1$H-NMR (500 MHz, DMSO-d$_6$) δ 1.14 (s, 3H), 1.21 (s, 3H), 2.25 (s, 3H), 4.25 (d, J = 11.9 Hz, 1H), 4.45 |
| 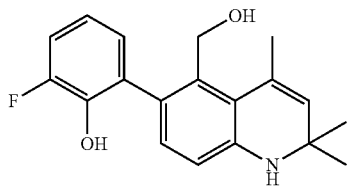 [SMILES: CC1=CC(C)(C)Nc2ccc(-c3cccc(F)c3O)c(CO)c21] | (d, J = 11.9 Hz, 1H), 4.56 (br s, 1H), 5.35 (s, 1H), 5.88 (s, 1H), 6.56 (d, J = 8.2 Hz, 1H), 6.68 (d, J = 8.2 Hz, 1H), 6.81 (td, J = 7.9, 5.2 Hz, 1H), 6.92 (d, J = 7.9 Hz, 1H), 7.10 (ddd, J = 10.8, 7.9, 1.6 Hz, 1H), 9.15 (s, 1H) |
| 6-(4,5-Difluoro-2-hydroxyphenyl)-5-hydroxymethyl-2,2,4-trimethyl-1,2-dihydroquinoline (Reference Compound No. 3-14) | $^1$H-NMR (400 MHz, DMSO-d$_6$) δ 1.17 (s, 6H), 2.24 (s, 3H), 4.18 (br s, 1H), 4.46 (br s, 2H), 5.35 (s, 1H), 5.88 (s, 1H), 6.54 (d, J = 8.2 Hz, |
| 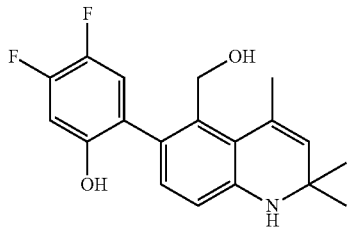 [SMILES: CC1=CC(C)(C)Nc2ccc(-c3cc(F)c(F)cc3O)c(CO)c21] | 1H), 6.67 (d, J = 8.2 Hz, 1H), 6.80 (dd, J = 12.5, 7.3 Hz, 1H), 7.13 (dd, J = 11.5, 9.5 Hz, 1H), 9.58 (br s, 1H) |
| 6-(3,5-Difluoro-2-hydroxyphenyl)-5-hydroxymethyl-2,2,4-trimethyl-1,2-dihydroquinoline (Reference Compound No. 3-15) | $^1$H-NMR (400 MHz, DMSO-d$_6$) δ 1.15 (s, 3H), 1.19 (s, 3H), 2.24 (s, 3H), 4.22 (s, 1H), 4.45 (s, 1H), 4.67 (s, 1H), 5.36 (s, 1H), 5.94 (s, 1H), |
| 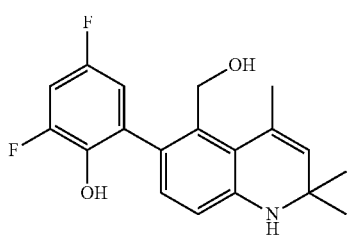 [SMILES: CC1=CC(C)(C)Nc2ccc(-c3cc(F)cc(F)c3O)c(CO)c21] | 6.56 (d, J = 8.1 Hz, 1H), 6.69 (d, J = 8.1 Hz, 1H), 6.78-6.85 (m, 1H), 7.10-7.19 (m, 1H), 9.11 (s, 1H) |
| 6-(4-Fluoro-2-hydroxyphenyl)-5-hydroxymethyl-2,2,4,7-tetramethyl-1,2-dihydroquinoline (Reference Compound No. 3-16) | $^1$H-NMR (500 MHz, DMSO-d$_6$) δ 1.15 (s, 3H), 1.16 (s, 3H), 1.75 (s, 3H), 2.22 (s, 3H), 4.06 (d, J = 11.6 Hz, 1H), 4.20 (br s, 1H), 4.32 (d, J = |
| 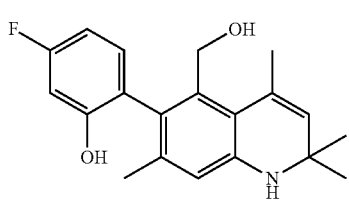 [SMILES: CC1=CC(C)(C)Nc2cc(C)c(-c3ccc(F)cc3O)c(CO)c21] | 11.6 Hz, 1H), 5.29 (s, 1H), 5.68 (s, 1H), 6.42 (s, 1H), 6.62 (td, J = 8.4, 2.7 Hz, 1H), 6.65 (dd, J = 11.0, 2.7 Hz, 1H), 6.98 (dd, J = 8.4, 7.3 Hz, 1H), 9.47 (br s, 1H) |

| Compound | NMR |
|---|---|
| 6-(4-Fluoro-2-hydroxyphenyl)-5-hydroxymethyl-7-methoxy-2,2,4-trimethyl-1,2-dihydroquinoline (Reference Compound No. 3-17) 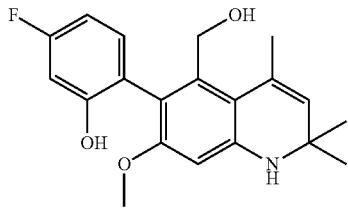 [SMILES: COc1cc2c(c(CO)c1-c1ccc(F)cc1O)C(C)=CC(C)(C)N2] | $^1$H-NMR (400 MHz, DMSO-d$_6$) δ 1.12 (s, 3H), 1.19 (s, 3H), 2.21 (s, 3H), 3.51 (s, 3H), 4.14 (d, J = 11.7 Hz, 1H), 4.23 (d, J = 11.7 Hz, 1H), 5.18 (s, 1H), 5.79 (s, 1H), 6.23 (s, 1H), 6.36-6.44 (m, 2H), 6.85 (t, J = 7.9 Hz, 1H) |
| 5-Hydroxymethyl-6-(2-hydroxy-5-trifluoromethylphenyl)-2,2,4-trimethyl-1,2-dihydroquinoline (Reference Compound No. 3-18) 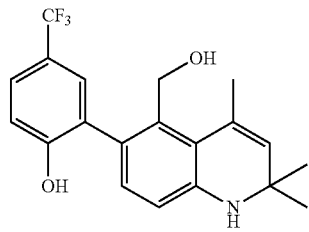 [SMILES: CC1=CC(C)(C)Nc2ccc(-c3cc(C(F)(F)F)ccc3O)c(CO)c21] | $^1$H-NMR (400 MHz, DMSO-d$_6$) δ 1.15 (s, 3H), 1.20 (s, 3H), 2.24 (s, 3H), 4.15 (d, J = 11.8 Hz, 1H), 4.50 (d, J = 11.8 Hz, 1H), 5.35 (s, 1H), 5.89 (s, 1H), 6.56 (d, J = 8.2 Hz, 1H), 6.69 (d, J = 8.2 Hz, 1H), 7.01 (d, J = 8.5 Hz, 1H), 7.40 (d, J = 2.0 Hz, 1H), 7.47 (dd, J = 8.5, 2.0 Hz, 1H), 10.06 (br s, 1H) |
| 8-Chloro-6-(4-fluoro-2-hydroxyphenyl)-5-hydroxymethyl-2,2,4-trimethyl-1,2-dihydroquinoline (Reference Compound No. 3-19) 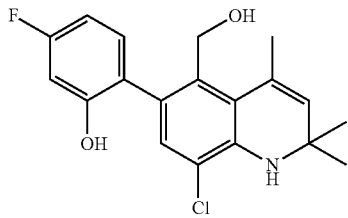 [SMILES: CC1=CC(C)(C)Nc2c(Cl)cc(-c3ccc(F)cc3O)c(CO)c21] | $^1$H-NMR (400 MHz, DMSO-d$_6$) δ 1.21 (s, 3H), 1.27 (s, 3H), 2.25 (s, 3H), 4.20 (s, 1H), 4.45 (s, 2H), 5.26 (s, 1H), 5.47 (s, 1H), 6.59-6.70 (m, 2H), 6.84 (s, 1H), 7.12 (t, J = 7.9 Hz, 1H), 9.79 (s, 1H) |
| 5-Hydroxymethyl-6-(2-hydroxy-5-nitrophenyl)-2,2,4-trimethyl-1,2-dihydroquinoline (Reference Compound No. 3-20) 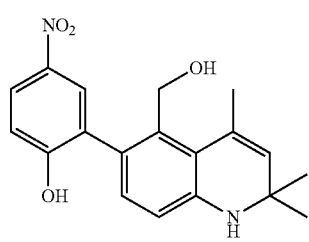 | $^1$H-NMR (400 MHz, DMSO-d$_6$) δ 1.17 (br s, 6H), 2.24 (s, 3H), 4.10 (br s, 1H), 4.50 (br s, 1H), 5.36 (s, 1H), 5.94 (s, 1H), 6.57 (d, J = 8.3 Hz, 1H), 6.72 (d, J = 8.3 Hz, 1H), 7.02 (d, J = 9.0 Hz, 1H), 7.99 (d, J = 3.0 Hz, 1H), 8.08 (dd, J = 9.0, 3.0 Hz, 1H) |

| | |
|---|---|
| 6-(2-Hydroxy-5-methoxymethoxyphenyl)-5-hydroxymethyl-2,2,4-trimethyl-1,2-dihydroquinoline (Reference Compound No. 3-21) 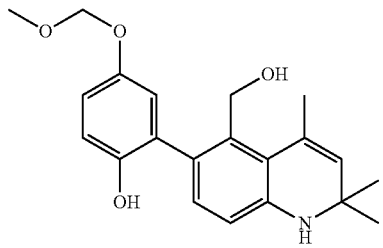 | $^1$H-NMR (400 MHz, DMSO-d$_6$) δ 1.13 (s, 3H), 1.21 (s, 3H), 2.24 (s, 3H), 3.37 (s, 3H), 4.25-4.33 (m, 1H), 4.40-4.44 (m, 1H), 4.46 (s, 1H), 5.07 (s, 2H), 5.34 (s, 1H), 5.82 (s, 1H), 6.54 (d, J = 8.3 Hz, 1H), 6.68 (d, J = 8.3 Hz, 1H), 6.74-6.82 (m, 3H), 8.83 (s, 1H) |
| 6-(2-Hydroxy-4-methoxymethoxyphenyl)-5-hydroxymethyl-2,2,4-trimethyl-1,2-dihydroquinoline (Reference Compound No. 3-22) 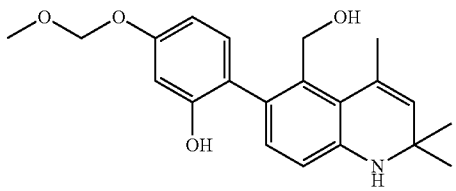 | $^1$H-NMR (500 MHz, DMSO-d$_6$) δ 1.13 (s, 3H), 1.20 (s, 3H), 2.23 (s, 3H), 3.39 (s, 3H), 4.26 (dd, J = 11.0, 6.6 Hz, 1H), 4.33 (t, J = 6.6 Hz, 1H), 4.44 (dd, J = 11.0, 6.6 Hz, 1H), 5.14 (s, 2H), 5.33 (s, 1H), 5.76 (s, 1H), 6.49 (dd, J = 8.4, 2.6 Hz, 1H), 6.53 (d, J = 8.3 Hz, 1H), 6.56 (d, J = 2.6 Hz, 1H), 6.65 (d, J = 8.3 Hz, 1H), 6.97 (d, J = 8.4 Hz, 1H), 9.23 (s, 1H) |
| 6-(4-Chloro-2-hydroxyphenyl)-5-hydroxymethyl-2,2,4-trimethyl-1,2-dihydroquinoline (Reference Compound No. 3-23) 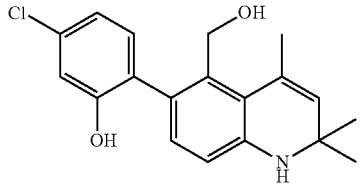 [SMILES: CC1=CC(C)(C)Nc2ccc(-c3ccc(Cl)cc3O)c(CO)c21] | $^1$H-NMR (500 MHz, DMSO-d$_6$) δ 1.14 (s, 3H), 1.20 (s, 3H), 2.24 (s, 3H), 4.19 (d, J = 11.3 Hz, 1H), 4.46 (d, J = 11.3 Hz, 1H), 5.34 (s, 1H), 5.83 (s, 1H), 6.54 (d, J = 8.0 Hz, 1H), 6.65 (d, J = 8.0 Hz, 1H), 6.84 (dd, J = 8.1, 2.0 Hz, 1H), 6.87 (d, J = 2.0 Hz, 1H), 7.08 (d, J = 8.1 Hz, 1H), 9.65 (br s, 1H) |

Reference Example 4

5-Hydroxymethyl-6-(2-methoxyphenyl)-2,2,4-trimethyl-1,2-dihydroquinoline (Reference Compound No. 4-1)

5-Hydroxymethyl-6-(2-methoxyphenyl)-1,2,2,4-tetramethyl-1,2-dihydroquinoline (Reference Compound No. 4-2)

A mixture of 5-hydroxymethyl-6-(2-hydroxyphenyl)-2,2,4-trimethyl-1,2-dihydroquinoline (Reference Compound No. 3-1, 4.01 g, 13.6 mmol), methyl iodide (847 μL, 13.6 mmol) and potassium carbonate (3.76 g, 27.2 mmol) was suspended in anhydrous N,N-dimethylformamide (70 mL) and stirred at 50° C. for 4 hours. After cooling down, the reaction mixture was diluted with ethyl acetate (200 mL) and diethylether (300 mL). The whole was washed with water (500 mL, 300 mL) and saturated brine (200 mL) successively, dried over anhydrous magnesium sulfate, and then the solvent was removed under reduced pressure. The obtained residue was purified by silica gel column chromatography (hexane-ethyl acetate) to give the titled Reference Compound No. 4-1 (3.01 g, Yield 71%) and the titled reference compound No. 4-2 (380 mg, Yield 9%) as a pale yellow solid respectively.

| | | |
|---|---|---|
| Reference Compound No. 4-1 | 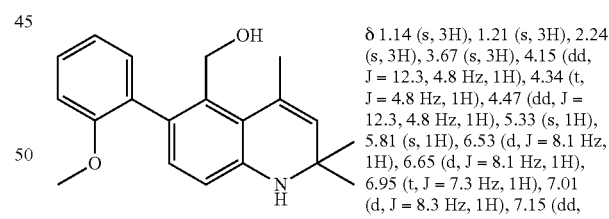 | $^1$H-NMR (400 MHz, DMSO-d$_6$) δ 1.14 (s, 3H), 1.21 (s, 3H), 2.24 (s, 3H), 3.67 (s, 3H), 4.15 (dd, J = 12.3, 4.8 Hz, 1H), 4.34 (t, J = 4.8 Hz, 1H), 4.47 (dd, J = 12.3, 4.8 Hz, 1H), 5.33 (s, 1H), 5.81 (s, 1H), 6.53 (d, J = 8.1 Hz, 1H), 6.65 (d, J = 8.1 Hz, 1H), 6.95 (t, J = 7.3 Hz, 1H), 7.01 (d, J = 8.3 Hz, 1H), 7.15 (dd, J = 7.6, 1.7 Hz, 1H), 7.26-7.30 (m, 1H) |
| Reference Compound No. 4-2 | 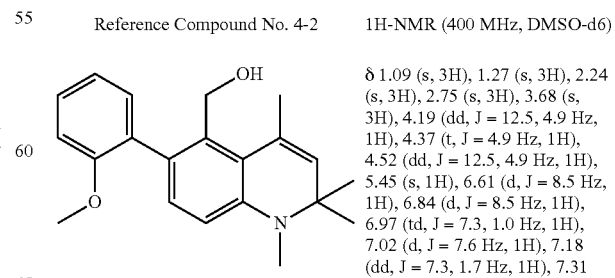 | 1H-NMR (400 MHz, DMSO-d6) δ 1.09 (s, 3H), 1.27 (s, 3H), 2.24 (s, 3H), 2.75 (s, 3H), 3.68 (s, 3H), 4.19 (dd, J = 12.5, 4.9 Hz, 1H), 4.37 (t, J = 4.9 Hz, 1H), 4.52 (dd, J = 12.5, 4.9 Hz, 1H), 5.45 (s, 1H), 6.61 (d, J = 8.5 Hz, 1H), 6.84 (d, J = 8.5 Hz, 1H), 6.97 (td, J = 7.3, 1.0 Hz, 1H), 7.02 (d, J = 7.6 Hz, 1H), 7.18 (dd, J = 7.3, 1.7 Hz, 1H), 7.31 (m, 1H) |

Using any compounds among Reference Compounds No. 3-1~3-10 and 3-12~3-23, the following Reference Compounds (No. 4-3~4-32) were obtained by a method similar to that of Reference Compound No. 4-1 and No. 4-2.

6-(4-Fluoro-2-methoxyphenyl)-5-hydroxymethyl-2,2,4-trimethyl-1,2-dihydroquinoline (Reference Compound No. 4-3)

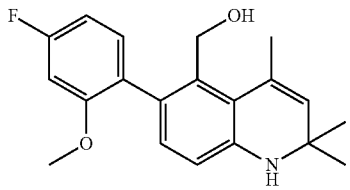

¹H-NMR (400 MHz, DMSO-$d_6$)
δ 1.14 (s, 3H), 1.20 (s, 3H), 2.23 (s, 3H), 3.69 (s, 3H), 4.09 (dd, J = 12.1, 4.7 Hz, 1H), 4.38 (t, J = 4.7 Hz, 1H), 4.45 (dd, J = 12.1, 4.7 Hz, 1H), 5.33 (s, 1H), 5.84 (s, 1H), 6.52 (d, J = 8.2 Hz, 1H), 6.63 (d, J = 8.2 Hz, 1H), 6.77 (td, J = 8.4, 2.5 Hz, 1H), 6.90 (dd, J = 11.6, 2.5 Hz, 1H), 7.16 (dd, J = 8.4, 7.2 Hz, 1H)

5-Hydroxymethyl-6-(2-methoxy-5-methylphenyl)-2,2,4-trimethyl-1,2-dihydroquinoline (Reference Compound No. 4-4)

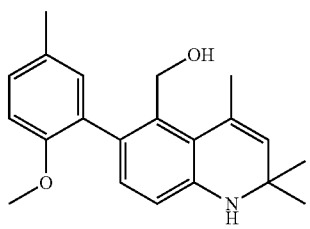

¹H-NMR (400 MHz, DMSO-$d_6$)
δ 1.13 (s, 3H), 1.21 (s, 3H), 2.23 (s, 3H), 2.25 (s, 3H), 3.63 (s, 3H), 4.15 (d, J = 12.1 Hz, 1H), 4.31 (br s, 1H), 4.45 (d, J = 12.1 Hz, 1H), 5.32 (s, 1H), 5.80 (s, 1H), 6.52 (d, J = 8.2 Hz, 1H), 6.64 (d, J = 8.2 Hz, 1H), 6.89 (d, J = 8.4 Hz, 1H), 6.95 (d, J = 1.9 Hz, 1H), 7.07 (dd, J = 8.4, 1.9 Hz, 1H)

5-Hydroxymethyl-6-(2-methoxy-5-methylphenyl)-1,2,2,4-tetramethyl-1,2-dihydroquinoline (Reference Compound No. 4-5)

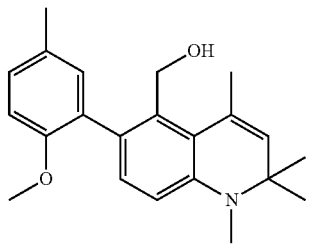 [SMILES: COc1ccc(C)cc1-c1ccc2c(c1CO)C(C)=CC(C)(C)N2C]

¹H-NMR (500 MHz, DMSO-$d_6$)
δ 1.08 (s, 3H), 1.27 (s, 3H), 2.24 (s, 3H), 2.26 (s, 3H), 2.74 (s, 3H), 3.64 (s, 3H), 4.21 (dd, J = 12.5, 5.3 Hz, 1H), 4.34 (t, J = 5.3 Hz, 1H), 4.51 (dd, J = 12.5, 5.3 Hz, 1H), 5.45 (s, 1H), 6.60 (d, J = 8.6 Hz, 1H), 6.83 (d, J = 8.6 Hz, 1H), 6.91 (d, J = 8.5 Hz, 1H), 6.98 (d, J = 1.9 Hz, 1H), 7.10 (dd, J = 8.5, 1.9 Hz, 1H)

6-(5-Chloro-2-methoxyphenyl)-5-hydroxymethyl-2,2,4-trimethyl-1,2-dihydroquinoline (Reference Compound No. 4-6)

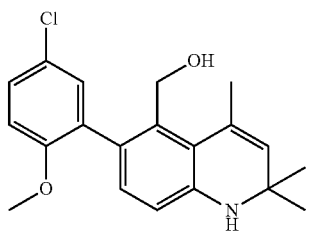

¹H-NMR (400 MHz, DMSO-$d_6$)
δ 1.14 (s, 3H), 1.20 (s, 3H), 2.23 (s, 3H), 3.68 (s, 3H), 4.08 (d, J = 11.8 Hz, 1H), 4.46 (br s, 1H), 4.48 (d, J = 11.8 Hz, 1H), 5.34 (s, 1H), 5.90 (s, 1H), 6.53 (d, J = 8.3 Hz, 1H), 6.65 (d, J = 8.3 Hz, 1H), 7.03 (d, J = 8.8 Hz, 1H), 7.18 (d, J = 2.7 Hz, 1H), 7.33 (dd, J = 8.7, 2.7 Hz, 1H)

5-Hydroxymethyl-6-(2-methoxy-3-methoxymethoxyphenyl)-2,2,4-trimethyl-1,2-dihydroquinoline (Reference Compound No. 4-7)

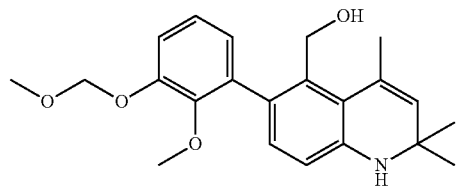

¹H-NMR (400 MHz, DMSO-$d_6$)
δ 1.14 (s, 3H), 1.21 (s, 3H), 2.24 (s, 3H), 3.42 (s, 3H), 3.43 (s, 3H), 4.21 (dd, J = 12.0, 4.5 Hz, 1H), 4.38 (t, J = 4.5 Hz, 1H), 4.46 (dd, J = 12.0, 4.5 Hz, 1H), 5.22 (s, 2H), 5.34 (s, 1H), 5.87 (s, 1H), 6.55 (d, J = 8.2 Hz, 1H), 6.70 (d, J = 8.2 Hz, 1H), 6.85 (d, J = 6.9 Hz, 1H), 7.02 (t, J = 6.9 Hz, 1H), 7.08 (d, J = 6.9 Hz, 1H)

| | |
|---|---|
| 6-(2,3-Dimethoxyphenyl)-5-hydroxymethyl-2,2,4-trimethyl-1,2-dihydroquinoline (Reference Compound No. 4-8)<br />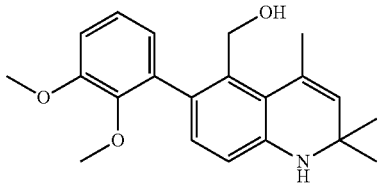 | $^1$H-NMR (400 MHz, DMSO-$d_6$) δ 1.14 (s, 3H), 1.21 (s, 3H), 2.24 (s, 3H), 3.39 (s, 3H), 3.81 (s, 3H), 4.21 (d, J = 12.0 Hz, 1H), 4.36 (br s, 1H), 4.43 (d, J = 12.0 Hz, 1H), 5.34 (s, 1H), 5.86 (s, 1H), 6.54 (d, J = 8.2 Hz, 1H), 6.69 (d, J = 8.2 Hz, 1H), 6.78 (dd, J = 7.8, 1.6 Hz, 1H), 6.99 (dd, J = 7.8, 1.6 Hz, 1H), 7.04 (t, J = 7.8 Hz, 1H) |
| 6-(3-Ethoxy-2-methoxyphenyl)-5-hydroxymethyl-2,2,4-trimethyl-1,2-dihydroquinoline (Reference Compound No. 4-9)<br />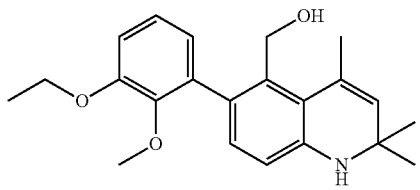 [SMILES: CCOc1cccc(-c2ccc3c(c2CO)C(C)=CC(C)(C)N3)c1OC] | $^1$H-NMR (400 MHz, DMSO-$d_6$) δ 1.14 (s, 3H), 1.21 (s, 3H), 1.37 (t, J = 7.0 Hz, 3H), 2.24 (s, 3H), 3.42 (s, 3H), 4.04-4.09 (m, 2H), 4.21 (dd, J = 12.1, 4.6 Hz, 1H), 4.35 (t, J = 4.6 Hz, 1H), 4.44 (dd, J = 12.1, 4.6 Hz, 1H), 5.34 (s, 1H), 5.85 (s, 1H), 6.54 (d, J = 8.2 Hz, 1H), 6.68 (d, J = 8.2 Hz, 1H), 6.76 (dd, J = 7.8, 1.8 Hz, 1H), 6.97 (dd, J = 7.8, 1.8 Hz, 1H), 7.02 (t, J = 7.8 Hz, 1H) |
| 6-(3-Benzyloxy-2-methoxyphenyl)-5-hydroxymethyl-2,2,4-trimethyl-1,2-dihydroquinoline (Reference Compound No. 4-10)<br />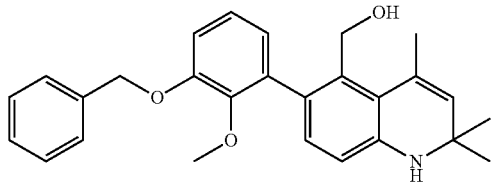 [SMILES: COc1c(OCc2ccccc2)cccc1-c1ccc2c(c1CO)C(C)=CC(C)(C)N2] | $^1$H-NMR (400 MHz, DMSO-$d_6$) δ 1.14 (s, 3H), 1.21 (s, 3H), 2.24 (s, 3H), 3.44 (s, 3H), 4.22 (dd, J = 12.1, 4.6 Hz, 1H), 4.37 (t, J = 4.6 Hz, 1H), 4.45 (dd, J = 12.1, 4.6 Hz, 1H), 5.15 (s, 2H), 5.34 (s, 1H), 5.86 (s, 1H), 6.55 (d, J = 8.2 Hz, 1H), 6.70 (d, J = 8.2 Hz, 1H), 6.80 (dd, J = 7.8, 1.7 Hz, 1H), 7.03 (t, J = 7.8 Hz, 1H), 7.08 (dd, J = 7.8, 1.7 Hz, 1H), 7.34 (t, J = 7.2 Hz, 1H), 7.41 (t, J = 7.2 Hz, 2H), 7.50 (d, J = 7.2 Hz, 2H) |
| 6-(2,6-Dimethoxyphenyl)-5-hydroxymethyl-2,2,4-trimethyl-1,2-dihydroquinoline (Reference Compound No. 4-11)<br />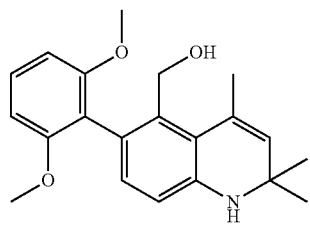 [SMILES: COc1cccc(OC)c1-c1ccc2c(c1CO)C(C)=CC(C)(C)N2] | $^1$H-NMR (500 MHz, DMSO-$d_6$) δ 1.18 (s, 6H), 2.22 (d, J = 1.2 Hz, 3H), 3.63 (s, 6H), 3.96-3.98 (m, 1H), 4.23 (d, J = 5.2 Hz, 2H), 5.29 (s, 1H), 5.75 (s, 1H), 6.49 (d, J = 8.1 Hz, 1H), 6.55 (d, J = 8.1 Hz, 1H), 6.69 (d, J = 8.3 Hz, 2H), 7.25 (t, J = 8.3 Hz, 1H) |
| 5-Hydroxymethyl-6-(2-methoxycarbonylmethoxyphenyl)-2,2,4-trimethyl-1,2-dihydroquinoline (Reference Compound No. 4-12)<br />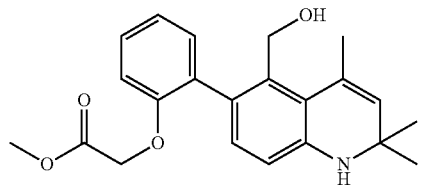 | $^1$H-NMR (400 MHz, DMSO-$d_6$) δ 1.14 (s, 3H), 1.21 (s, 3H), 2.24 (s, 3H), 3.66 (s, 3H), 4.21 (dd, J = 12.6, 5.1 Hz, 1H), 4.31 (t, J = 5.1 Hz, 1H), 4.53 (dd, J = 12.6, 5.1 Hz, 1H), 4.67 (d, J = 16.5 Hz, 1H), 4.73 (d, J = 16.5 Hz, 1H), 5.33 (s, 1H), 5.83 (s, 1H), 6.54 (d, J = 8.3 Hz, 1H), 6.69 (d, J = 8.3 Hz, 1H), 6.89 (d, J = 8.1 Hz, 1H), 7.00 (t, J = 7.0 Hz, 1H), 7.19 (dd, J = 7.6, 1.7 Hz, 1H), 7.22-7.28 (m, 1H) |

6-(2-Ethoxyphenyl)-5-hydroxymethyl-2,2,4-trimethyl-1,2-dihydroquinoline (Reference Compound No. 4-13)

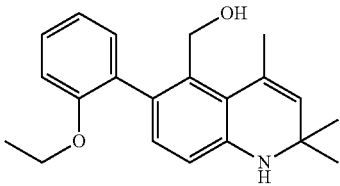 [SMILES: CCOc1ccccc1-c1ccc2c(c1CO)C(C)=CC(C)(C)N2]

$^1$H-NMR (400 MHz, DMSO-$d_6$) δ 1.11 (s, 3H), 1.19 (t, J = 6.9 Hz, 3H), 1.23 (s, 3H), 2.22 (s, 3H), 3.94 (q, J = 6.9 Hz, 2H), 4.15 (dd, J = 12.7, 5.0 Hz, 1H), 4.37 (t, J = 5.0 Hz, 1H), 4.55 (dd, J = 12.7, 5.0 Hz, 1H), 5.32 (s, 1H), 5.83 (s, 1H), 6.54 (d, J = 8.1 Hz, 1H), 6.67 (d, J = 8.1 Hz, 1H), 6.92-7.01 (m, 2H), 7.17 (dd, J = 7.3, 1.7 Hz, 1H), 7.24-7.28 (m, 1H)

6-(2-Benzyloxyphenyl)-5-hydroxymethyl-2,2,4-trimethyl-1,2-dihydroquinoline (Reference Compound No. 4-14)

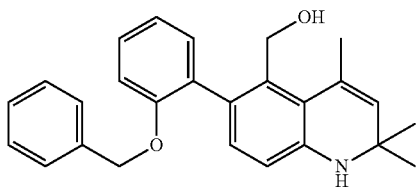 [SMILES: CC1=CC(C)(C)Nc2ccc(-c3ccccc3OCc3ccccc3)c(CO)c21]

$^1$H-NMR (400 MHz, DMSO-$d_6$) δ 1.11 (s, 3H), 1.22 (s, 3H), 2.12 (s, 3H), 4.18 (dd, J = 12.4, 4.1 Hz, 1H), 4.36 (t, J = 4.1 Hz, 1H), 4.46-4.55 (m, 1H), 4.99 (d, J = 12.2 Hz, 1H), 5.03 (d, J = 12.2 Hz, 1H), 5.31 (s, 1H), 5.82 (s, 1H), 6.55 (d, J = 8.3 Hz, 1H), 6.70 (d, J = 8.3 Hz, 1H), 6.99 (t, J = 7.4 Hz, 1H), 7.09 (d, J = 7.6 Hz, 1H), 7.21 (dd, J = 7.3, 1.7 Hz, 1H), 7.23-7.34 (m, 6H)

1-Benzyl-6-(2-benzyloxyphenyl)-5-hydroxymethyl-2,2,4-trimethyl-1,2-dihydroquinoline (Reference Compound No. 4-15)

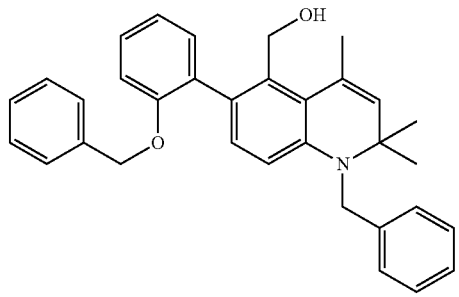 [SMILES: CC1=CC(C)(C)N(Cc2ccccc2)c2ccc(-c3ccccc3OCc3ccccc3)c(CO)c21]

$^1$H-NMR (400 MHz, DMSO-$d_6$) δ 1.20 (s, 3H), 1.33 (s, 3H), 2.17 (s, 3H), 4.22 (dd, J = 12.8, 4.3 Hz, 1H), 4.42 (t, J = 4.9 Hz, 1H), 4.46 (s, 1H), 4.53-4.64 (m, 2H), 4.98 (d, J = 11.9 Hz, 1H), 5.03 (d, J = 11.9 Hz, 1H), 5.49 (s, 1H), 6.35 (d, J = 8.5 Hz, 1H), 6.70 (d, J = 8.5 Hz, 1H), 6.98 (t, J = 7.3 Hz, 1H), 7.08 (d, J = 7.6 Hz, 1H), 7.16-7.38 (m, 12H)

5-Hydroxymethyl-6-(2-methoxyphenyl)-2,2,4-trimethyl-1,2-dihydroquinoline (Reference Compound No. 4-16)

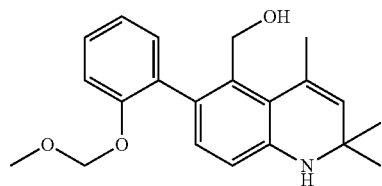

$^1$H-NMR (400 MHz, DMSO-$d_6$) δ 1.14 (s, 3H), 1.20 (s, 3H), 2.24 (s, 3H), 3.22 (s, 3H), 4.18 (dd, J = 12.2, 4.4 Hz, 1H), 4.38 (t, J = 4.4 Hz, 1H), 4.51 (dd, J = 12.2, 4.4 Hz, 1H), 5.02 (d, J = 6.6 Hz, 1H), 5.05 (d, J = 6.6 Hz, 1H), 5.33 (s, 1H), 5.83 (s, 1H), 6.54 (d, J = 8.1 Hz, 1H), 6.68 (d, J = 8.1 Hz, 1H), 7.02 (td, J = 7.4, 1.0 Hz, 1H), 7.11 (dd, J = 8.3, 1.0 Hz, 1H), 7.20 (dd, J = 7.6, 1.7 Hz, 1H), 7.23-7.29 (m, 1H)

6-(5-Fluoro-2-methoxyphenyl)-5-hydroxymethyl-2,2,4-trimethyl-1,2-dihydroquinoline (Reference Compound No. 4-17)

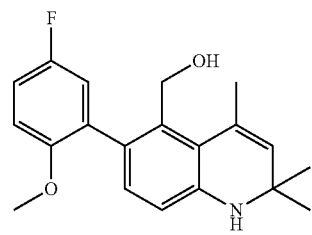 [SMILES: COc1ccc(F)cc1-c1ccc2c(c1CO)C(C)=CC(C)(C)N2]

$^1$H-NMR (500 MHz, DMSO-$d_6$) δ 1.14 (s, 3H), 1.20 (s, 3H), 2.24 (d, J = 0.9 Hz, 3H), 3.65 (s, 3H), 4.10 (d, J = 11.6 Hz, 1H), 4.43-4.45 (m, 1H), 4.48 (d, J = 11.6 Hz, 1H), 5.34 (s, 1H), 5.87 (s, 1H), 6.53 (d, J = 8.1 Hz, 1H), 6.66 (d, J = 8.1 Hz, 1H), 6.98-7.02 (m, 2H), 7.08-7.12 (m, 1H)

6-(3,4-Difluoro-2-methoxyphenyl)-5-hydroxymethyl-2,2,4-trimethyl-1,2-dihydroquinoline (Reference Compound No. 4-18)

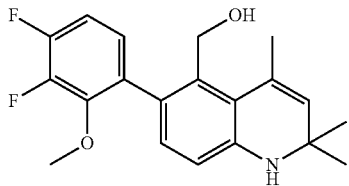 [SMILES: COc1c(-c2ccc3c(c2CO)C(C)=CC(C)(C)N3)ccc(F)c1F]

¹H-NMR (500 MHz, DMSO-d₆) δ 1.15 (s, 3H), 1.20 (s, 3H), 2.24 (s, 3H), 3.58 (s, 3H), 4.14 (d, J = 11.0 Hz, 1H), 4.47 (d, J = 11.0 Hz, 1H), 4.50-4.52 (m, 1H), 5.36 (s, 1H), 5.95 (s, 1H), 6.56 (d, J = 8.1 Hz, 1H), 6.69 (d, J = 8.1 Hz, 1H), 7.05 (ddd, J = 8.9, 6.1, 1.8 Hz, 1H), 7.15 (td, J = 8.9, 7.6 Hz, 1H)

6-(3-Fluoro-2-methoxyphenyl)-5-hydroxymethyl-2,2,4-trimethyl-1,2-dihydroquinoline (Reference Compound No. 4-19)

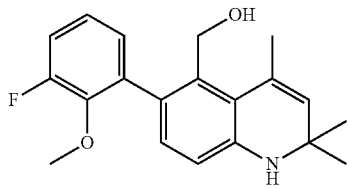 [SMILES: COc1c(F)cccc1-c1ccc2c(c1CO)C(C)=CC(C)(C)N2]

¹H-NMR (400 MHz, DMSO-d₆) δ 1.15 (s, 3H), 1.21 (s, 3H), 2.25 (s, 3H), 3.52 (s, 3H), 4.17-4.19 (m, 1H), 4.46-4.50 (m, 1H), 4.48 (s, 1H), 5.35 (s, 1H), 5.93 (s, 1H), 6.57 (d, J = 8.2 Hz, 1H), 6.71 (d, J = 8.2 Hz, 1H), 7.03-7.05 (m, 1H), 7.09 (td, J = 8.0, 5.0 Hz, 1H), 7.20 (ddd, J = 11.4, 8.0, 1.8 Hz, 1H)

6-(4,5-Difluoro-2-methoxyphenyl)-5-hydroxymethyl-2,2,4-trimethyl-1,2-dihydroquinoline (Reference Compound No. 4-20)

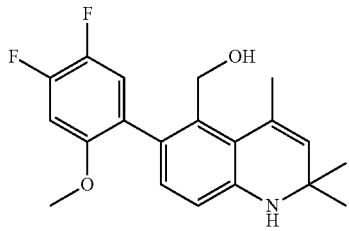 [SMILES: COc1cc(F)c(F)cc1-c1ccc2c(c1CO)C(C)=CC(C)(C)N2]

¹H-NMR (500 MHz, DMSO-d₆) δ 1.14 (s, 3H), 1.19 (s, 3H), 2.23 (s, 3H), 3.67 (s, 3H), 4.05-4.08 (m, 1H), 4.45-4.49 (m, 2H), 5.34 (s, 1H), 5.89 (s, 1H), 6.53 (d, J = 8.2 Hz, 1H), 6.65 (d, J = 8.2 Hz, 1H), 7.14 (dd, J = 13.1, 7.3 Hz, 1H), 7.22 (dd, J = 11.3, 9.5 Hz, 1H)

6-(3,5-Difluoro-2-methoxyphenyl)-5-hydroxymethyl-2,2,4-trimethyl-1,2-dihydroquinoline (Reference Compound No. 4-21)

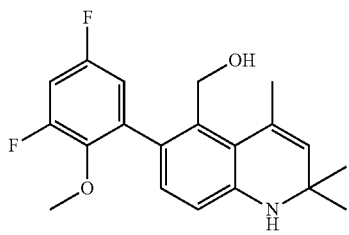 [SMILES: COc1c(F)cc(F)cc1-c1ccc2c(c1CO)C(C)=CC(C)(C)N2]

¹H-NMR (400 MHz, DMSO-d₆) δ 1.17 (s, 3H), 1.19 (s, 3H), 2.25 (s, 3H), 3.47 (s, 3H), 4.16 (s, 1H), 4.50 (s, 1H), 4.57 (t, J = 4.6 Hz, 1H), 5.36 (s, 1H), 5.99 (s, 1H), 6.57 (d, J = 8.3 Hz, 1H), 6.73 (d, J = 8.3 Hz, 1H), 6.92-6.99 (m, 1H), 7.22-7.31 (m, 1H)

6-(4-Fluoro-2-methoxyphenyl)-5-hydroxymethyl-2,2,4,7-tetramethyl-1,2-dihydroquinoline (Reference Compound No. 4-22)

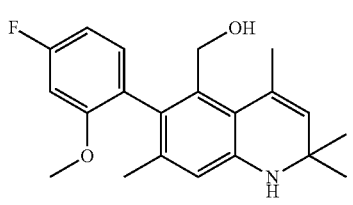 [SMILES: COc1cc(F)ccc1-c1c(C)cc2c(c1CO)C(C)=CC(C)(C)N2]

¹H-NMR (400 MHz, DMSO-d₆) δ 1.16 (s, 6H), 1.70 (s, 3H), 2.22 (s, 3H), 3.67 (s, 3H), 3.95 (dd, J = 11.5, 4.6 Hz, 1H), 4.22 (t, J = 4.6 Hz, 1H), 4.32 (dd, J = 11.5, 4.6 Hz, 1H), 5.28 (s, 1H), 5.69 (s, 1H), 6.41 (s, 1H), 6.77 (td, J = 8.4, 2.5 Hz, 1H), 6.92 (dd, J = 11.5, 2.5 Hz, 1H), 7.07 (dd, J = 8.4, 7.3 Hz, 1H)

| Compound | ¹H-NMR |
|---|---|
| 6-(4-Fluoro-2-methoxyphenyl)-5-hydroxymethyl-7-methoxy-2,2,4-trimethyl-1,2-dihydroquinoline (Reference Compound No. 4-23)<br>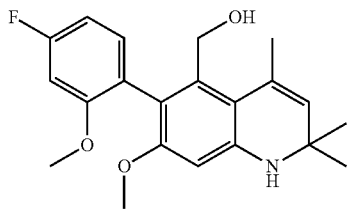 [SMILES: COc1cc(F)ccc1-c1c(OC)cc2c(c1CO)C(C)=CC(C)(C)N2] | ¹H-NMR (400 MHz, DMSO-$d_6$)<br>δ 1.16 (s, 3H), 1.17 (s, 3H), 2.20 (s, 3H), 3.51 (s, 3H), 3.65 (s, 3H), 3.96 (dd, J = 11.5, 4.5 Hz, 1H), 4.25 (t, J = 4.5 Hz, 1H), 4.32 (dd, J = 11.5, 4.5 Hz, 1H), 5.19 (s, 1H), 5.87 (s, 1H), 6.23 (s, 1H), 6.72 (td, J = 8.4, 2.4 Hz, 1H), 6.86 (dd, J = 11.5, 2.4 Hz, 1H), 7.06 (dd, J = 8.4, 7.3 Hz, 1H) |
| 6-(2-Ethoxy-4-fluorophenyl)-5-hydroxymethyl-2,2,4-trimethyl-1,2-dihydroquinoline (Reference Compound No. 4-24)<br>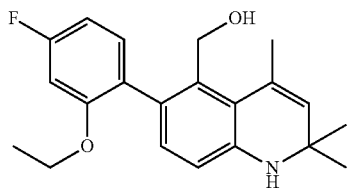 [SMILES: CCOc1cc(F)ccc1-c1ccc2c(c1CO)C(C)=CC(C)(C)N2] | ¹H-NMR (400 MHz, DMSO-$d_6$)<br>δ 1.11 (s, 3H), 1.19 (t, J = 7.0 Hz, 3H), 1.23 (s, 3H), 2.22 (s, 3H), 3.97 (q, J = 7.0 Hz, 2H), 4.09 (dd, J = 12.6, 3.8 Hz, 1H), 4.40-4.43 (m, 1H), 4.54 (dd, J = 12.6, 6.1 Hz, 1H), 5.32 (s, 1H), 5.84 (s, 1H), 6.53 (d, J = 8.3 Hz, 1H), 6.65 (d, J = 8.3 Hz, 1H), 6.77 (td, J = 8.4, 2.5 Hz, 1H), 6.88 (dd, J = 11.6, 2.5 Hz, 1H), 7.18 (dd, J = 8.4, 7.3 Hz, 1H) |
| 6-(4-Fluoro-2-propoxyphenyl)-5-hydroxymethyl-2,2,4-trimethyl-1,2-dihydroquinoline (Reference Compound No. 4-25)<br>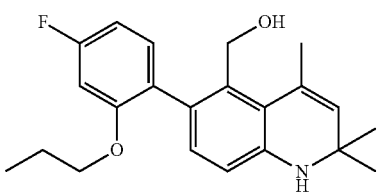 [SMILES: CCCOc1cc(F)ccc1-c1ccc2c(c1CO)C(C)=CC(C)(C)N2] | ¹H-NMR (400 MHz, DMSO-$d_6$)<br>δ 0.82 (t, J = 7.4 Hz, 3H), 1.11 (s, 3H), 1.22 (s, 3H), 1.51-1.63 (m, 2H), 2.21 (s, 3H), 3.80-3.90 (m, 2H), 4.09 (dd, J = 12.5, 4.9 Hz, 1H), 4.41 (t, J = 4.9 Hz, 1H), 4.53 (dd, J = 12.5, 4.9 Hz, 1H), 5.32 (s, 1H), 5.83 (s, 1H), 6.53 (d, J = 8.1 Hz, 1H), 6.64 (d, J = 8.1 Hz, 1H), 6.76 (td, J = 8.3, 2.4 Hz, 1H), 6.88 (dd, J = 11.5, 2.4 Hz, 1H), 7.18 (dd, J = 8.3, 7.1 Hz, 1H) |
| 6-(4-Fluoro-2-isopropoxyphenyl)-5-hydroxymethyl-2,2,4-trimethyl-1,2-dihydroquinoline (Reference Compound No. 4-26)<br>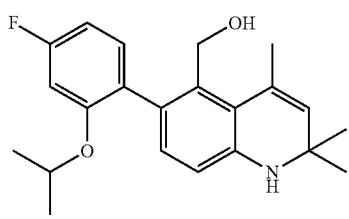 [SMILES: CC1=CC(C)(C)Nc2ccc(-c3ccc(F)cc3OC(C)C)c(CO)c21] | ¹H-NMR (400 MHz, DMSO-$d_6$)<br>δ 1.08 (d, J = 6.1 Hz, 3H), 1.10 (s, 3H), 1.18 (d, J = 6.1 Hz, 3H), 1.23 (s, 3H), 2.22 (s, 3H), 4.09 (dd, J = 12.6, 3.9 Hz, 1H), 4.40 (dd, J = 5.8, 3.9 Hz, 1H), 4.46-4.57 (m, 2H), 5.32 (s, 1H), 5.83 (s, 1H), 6.53 (d, J = 8.1 Hz, 1H), 6.64 (d, J = 8.1 Hz, 1H), 6.76 (td, J = 8.3, 2.5 Hz, 1H), 6.89 (dd, J = 11.6, 2.5 Hz, 1H) 7.18 (dd, J = 8.3, 7.3 Hz, 1H) |
| 5-Hydroxymethyl-6-(2-methoxy-5-trifluoromethylphenyl)-2,2,4-trimethyl-1,2-dihydroquinoline (Reference Compound No. 4-27)<br>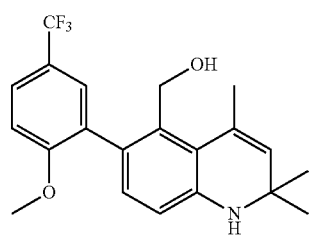 | ¹H-NMR (400 MHz, DMSO-$d_6$)<br>δ 1.14 (s, 3H), 1.20 (s, 3H), 2.24 (s, 3H), 3.77 (s, 3H), 4.01-4.06 (m, 1H), 4.46-4.51 (m, 2H), 5.35 (s, 1H), 5.92 (s, 1H), 6.55 (d, J = 8.2 Hz, 1H), 6.67 (d, J = 8.2 Hz, 1H), 7.20 (d, J = 8.6 Hz, 1H), 7.47 (d, J = 2.0 Hz, 1H), 7.66 (dd, J = 8.6, 2.0 Hz, 1H) |

| | |
|---|---|
| 8-Chloro-6-(4-fluoro-2-methoxyphenyl)-5-hydroxymethyl-2,2,4-trimethyl-1,2-dihydroquinoline (Reference Compound No. 4-28)<br />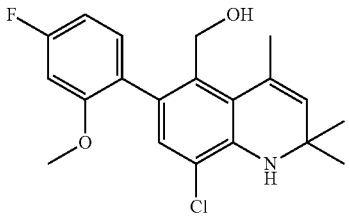 [SMILES: COc1cc(F)ccc1-c1cc(Cl)c2c(c1CO)C(C)=CC(C)(C)N2] | $^1$H-NMR (400 MHz, DMSO-d$_6$) δ 1.20 (s, 3H), 1.28 (s, 3H), 2.24 (s, 3H), 3.71 (s, 3H), 4.09 (dd, J = 12.5, 4.8 Hz, 1H), 4.44 (dd, J = 12.5, 4.8 Hz, 1H), 4.54 (t, J = 4.8 Hz, 1H), 5.28 (s, 1H), 5.47 (s, 1H), 6.79 (td, J = 8.5, 2.7 Hz, 1H), 6.82 (s, 1H), 6.94 (dd, J = 11.5, 2.7 Hz, 1H), 7.19 (dd, J = 8.5, 7.1 Hz, 1H) |
| 5-Hydroxymethyl-6-(2-methoxy-5-nitrophenyl)-2,2,4-trimethyl-1,2-dihydroquinoline (Reference Compound No. 4-29)<br />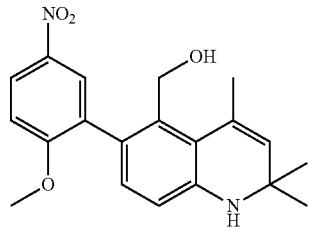 [SMILES: COc1ccc([N+](=O)[O-])cc1-c1ccc2c(c1CO)C(C)=CC(C)(C)N2] | $^1$H-NMR (500 MHz, DMSO-d$_6$) δ 1.16 (s, 3H), 1.20 (s, 3H), 2.24 (s, 3H), 3.84 (s, 3H), 4.00 (dd, J = 12.1, 4.7 Hz, 1H), 4.49 (dd, J = 12.1, 4.7 Hz, 1H), 4.54 (t, J = 4.7 Hz, 1H), 5.36 (s, 1H), 5.96 (s, 1H), 6.57 (d, J = 8.1 Hz, 1H), 6.71 (d, J = 8.1 Hz, 1H), 7.25 (d, J = 9.2 Hz, 1H), 8.03 (d, J = 3.1 Hz, 1H), 8.24 (dd, J = 9.2, 3.1 Hz, 1H) |
| 5-Hydroxymethyl-6-(2-methoxy-5-methoxymethoxyphenyl)-2,2,4-trimethyl-1,2-dihydroquinoline (Reference Compound No. 4-30)<br />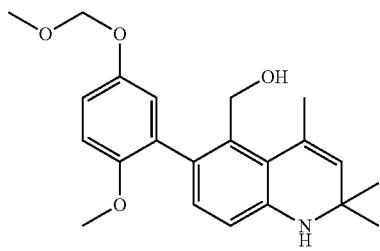 | $^1$H-NMR (400 MHz, DMSO-d$_6$) δ 1.13 (s, 3H), 1.21 (s, 3H), 2.24 (s, 3H), 3.38 (s, 3H), 3.62 (s, 3H), 4.15 (dd, J = 12.2, 4.7 Hz, 1H), 4.38 (t, J = 4.7 Hz, 1H), 4.47 (dd, J = 12.2, 4.7 Hz, 1H), 5.11 (d, J = 6.5 Hz, 1H), 5.13 (d, J = 6.5 Hz, 1H), 5.33 (s, 1H), 5.84 (s, 1H), 6.53 (d, J = 8.2 Hz, 1H), 6.66 (d, J = 8.2 Hz, 1H), 6.85 (d, J = 2.6 Hz, 1H), 6.90-6.96 (m, 2H) |
| 5-Hydroxymethyl-6-(2-methoxy-4-methoxymethoxyphenyl)-2,2,4-trimethyl-1,2-dihydroquinoline (Reference Compound No. 4-31)<br />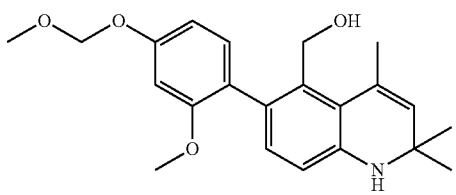 | $^1$H-NMR (400 MHz, DMSO-d$_6$) δ 1.13 (s, 3H), 1.20 (s, 3H), 2.23 (s, 3H), 3.41 (s, 3H), 3.65 (s, 3H), 4.14 (d, J = 12.2 Hz, 1H), 4.33 (br s, 1H), 4.45 (d, J = 12.2 Hz, 1H), 5.22 (s, 2H), 5.32 (s, 1H), 5.78 (s, 1H), 6.51 (d, J = 8.3 Hz, 1H), 6.61-6.64 (m, 2H), 6.66 (d, J = 2.4 Hz, 1H), 7.05 (d, J = 8.3 Hz, 1H) |
| 6-(4-Chloro-2-methoxyphenyl)-5-hydroxymethyl-2,2,4-trimethyl-1,2-dihydroquinoline (Reference Compound No. 4-32)<br />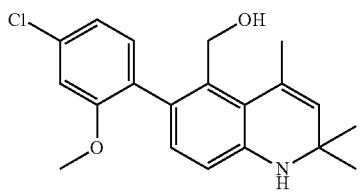 [SMILES: COc1cc(Cl)ccc1-c1ccc2c(c1CO)C(C)=CC(C)(C)N2] | $^1$H-NMR (400 MHz, DMSO-d$_6$) δ 1.14 (s, 3H), 1.20 (s, 3H), 2.23 (s, 3H), 3.70 (s, 3H), 4.07 (dd, J = 11.7, 3.7 Hz, 1H), 4.40-4.42 (m, 1H), 4.46 (dd, J = 11.7, 5.7 Hz, 1H), 5.33 (s, 1H), 5.86 (s, 1H), 6.53 (d, J = 8.3 Hz, 1H), 6.63 (d, J = 8.3 Hz, 1H), 7.00 (dd, J = 8.0, 2.0 Hz, 1H), 7.07 (d, J = 2.0 Hz, 1H), 7.16 (d, J = 8.0 Hz, 1H) |

Reference Example 5

5-Chloromethyl-6-(2-methoxyphenyl)-2,2,4-trimethyl-1,2-dihydroquinoline (Reference Compound No. 5-1)

5-Hydroxymethyl-6-(2-methoxyphenyl)-2,2,4-trimethyl-1,2-dihydroquinoline (Reference Compound No. 4-1, 2.00 g, 6.46 mmol) was dissolved in anhydrous dichloromethane (32 mL) and then triethylamine (1.35 mL, 9.69 mmol) and methanesulfonyl chloride (55 µL, 7.11 mmol) were added thereto at 0° C. The reaction mixturer was stirred at room temperature overnight. Ethyl acetate (500 mL), water (200 mL), and saturated brine (200 mL) were added to the reaction mixture and separated. The water layer was extracted with ethyl acetate (150 mL) and the organic layer was combined. The organic layer was washed with saturated brine (200 mL), dried over anhydrous magnesium sulfate, and then the solvent was removed under reduced pressure. The obtained residue was purified by silica gel column chromatography (hexane-ethyl acetate) to give the titled reference compound (1.07 g) as a pale yellow solid. (Yield 50%)

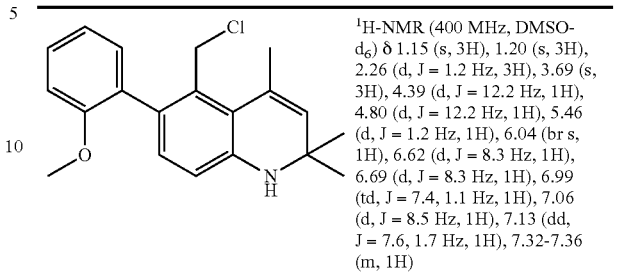

$^1$H-NMR (400 MHz, DMSO-$d_6$) δ 1.15 (s, 3H), 1.20 (s, 3H), 2.26 (d, J = 1.2 Hz, 3H), 3.69 (s, 3H), 4.39 (d, J = 12.2 Hz, 1H), 4.80 (d, J = 12.2 Hz, 1H), 5.46 (d, J = 1.2 Hz, 1H), 6.04 (br s, 1H), 6.62 (d, J = 8.3 Hz, 1H), 6.69 (d, J = 8.3 Hz, 1H), 6.99 (td, J = 7.4, 1.1 Hz, 1H), 7.06 (d, J = 8.5 Hz, 1H), 7.13 (dd, J = 7.6, 1.7 Hz, 1H), 7.32-7.36 (m, 1H)

Using any compounds among Reference Compounds No. 4-3, 4-4, 4-6, 4-11, 4-17, 4-18, 4-20~4-27 and 4-32, the following Reference Compounds (No. 5-2~5-16) were obtained by a method similar to that of Reference Compound No. 5-1

5-Chloromethyl-6-(4-fluoro-2-methoxyphenyl)-2,2,4-trimethyl-1,2-dihydroquinoline (Reference Compound No. 5-2)

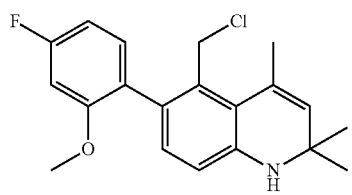

$^1$H-NMR (400 MHz, DMSO-$d_6$) δ 1.15 (s, 3H), 1.20 (s, 3H), 2.26 (s, 3H), 3.70 (s, 3H), 4.36 (d, J = 12.1 Hz, 1H), 4.77 (d, J = 12.1 Hz, 1H), 5.46 (s, 1H), 6.05 (br s, 1H), 6.61 (d, J = 8.3 Hz, 1H), 6.67 (d, J = 8.3 Hz, 1H), 6.81 (td, J = 8.4, 2.5 Hz, 1H), 6.96 (dd, J = 11.5, 2.5 Hz, 1H), 7.14 (dd, J = 8.4, 7.2 Hz, 1H)

5-Chloromethyl-6-(2-methoxy-5-methylphenyl)-2,2,4-trimethyl-1,2-dihydroquinoline (Reference Compound No. 5-3)

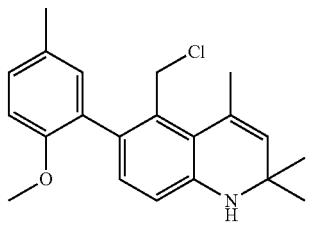

$^1$H-NMR (400 MHz, DMSO-$d_6$) δ 1.14 (s, 3H), 1.20 (s, 3H), 2.26 (s, 6H), 3.65 (s, 3H), 4.41 (d, J = 11.9 Hz, 1H), 4.80 (d, J = 11.9 Hz, 1H), 5.46 (s, 1H), 6.05 (br s, 1H), 6.62 (d, J = 8.3 Hz, 1H), 6.68 (d, J = 8.3 Hz, 1H), 6.93-6.95 (m, 2H), 7.13 (dd, J = 8.3, 1.7 Hz, 1H)

5-Chloromethyl-6-(2,6-dimethoxyphenyl)-2,2,4-trimethyl-1,2-dihydroquinoline (Reference Compound No. 5-4)

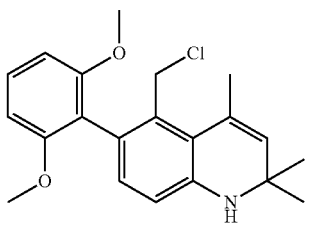

$^1$H-NMR (400 MHz, DMSO-$d_6$) δ 1.18 (s, 6H), 2.25 (d, J = 1.2 Hz, 3H), 3.64 (s, 6H), 4.49 (s, 2H), 5.42 (s, 1H), 5.95 (s, 1H), 6.58 (s, 2H), 6.71 (d, J = 8.5 Hz, 2H), 7.29 (t, J = 8.5 Hz, 1H)

| | |
|---|---|
| 6-(5-Chloro-2-methoxyphenyl)-5-chloromethyl-2,2,4-trimethyl-1,2-dihydroquinoline (Reference Compound No. 5-5)<br>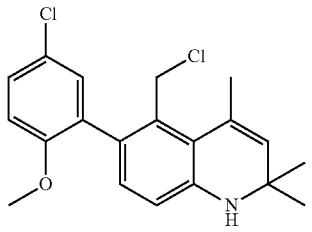 | $^1$H-NMR (400 MHz, DMSO-d$_6$) δ 1.16 (s, 3H), 1.20 (s, 3H), 2.26 (s, 3H), 3.70 (s, 3H), 4.36 (d, J = 12.0 Hz, 1H), 4.79 (d, J = 12.0 Hz, 1H), 5.47 (s, 1H), 6.11 (br s, 1H), 6.62 (d, J = 8.3 Hz, 1H), 6.70 (d, J = 8.3 Hz, 1H), 7.09 (d, J = 8.9 Hz, 1H), 7.15 (d, J = 2.7 Hz, 1H), 7.39 (dd, J = 8.9, 2.7 Hz, 1H) |
| 5-Chloromethyl-6-(5-fluoro-2-methoxyphenyl)-2,2,4-trimethyl-1,2-dihydroquinoline (Reference Compound No. 5-6)<br>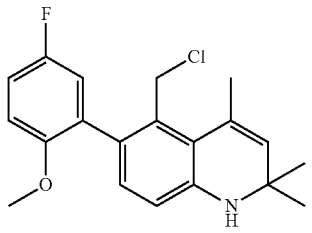 | $^1$H-NMR (400 MHz, DMSO-d$_6$) δ 1.16 (s, 3H), 1.20 (s, 3H), 2.26 (d, J = 1.2 Hz, 3H), 3.68 (s, 3H), 4.38 (d, J = 12.1 Hz, 1H), 4.81 (d, J = 12.1 Hz, 1H), 5.47 (s, 1H), 6.12 (br s, 1H), 6.63 (d, J = 8.2 Hz, 1H), 6.71 (d, J = 8.2 Hz, 1H), 6.97 (dd, J = 9.0, 3.2 Hz, 1H), 7.06 (dd, J = 9.0, 4.6 Hz, 1H), 7.16 (dd, J = 8.3, 3.2 Hz, 1H) |
| 5-Chloromethyl-6-(4,5-difluoro-2-methoxyphenyl)-2,2,4-trimethyl-1,2-dihydroquinoline (Reference Compound No. 5-7)<br>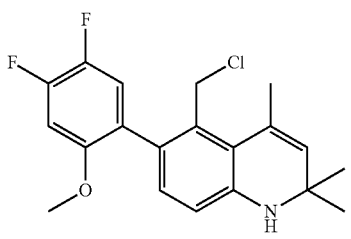 | $^1$H-NMR (400 MHz, DMSO-d$_6$) δ 1.15 (s, 3H), 1.19 (s, 3H), 2.26 (s, 3H), 3.69 (s, 3H), 4.36 (d, J = 12.1 Hz, 1H), 4.79 (d, J = 12.1 Hz, 1H), 5.47 (s, 1H), 6.12 (br s, 1H), 6.62 (d, J = 8.2 Hz, 1H), 6.69 (d, J = 8.2 Hz, 1H), 7.18-7.23 (m, 2H) |
| 5-Chloromethyl-6-(3,5-difluoro-2-methoxyphenyl)-2,2,4-trimethyl-1,2-dihydroquinoline (Reference Compound No. 5-8)<br>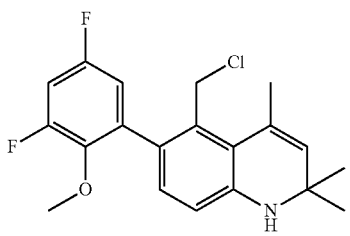 | $^1$H-NMR (500 MHz, DMSO-d$_6$) δ 1.16 (s, 3H), 1.20 (s, 3H), 2.27 (s, 3H), 3.52 (s, 3H), 4.45 (d, J = 12.2 Hz, 1H), 4.86 (d, J = 12.2 Hz, 1H), 5.49 (s, 1H), 6.21 (s, 1H), 6.66 (d, J = 8.2 Hz, 1H), 6.79 (d, J = 8.2 Hz, 1H), 6.93 (ddd, J = 8.9, 3.1, 1.8 Hz, 1H), 7.32-7.36 (m, 1H) |
| 5-Chloromethyl-6-(4-fluoro-2-methoxyphenyl)-2,2,4,7-tetramethyl-1,2-dihydroquinoline (Reference Compound No. 5-9)<br>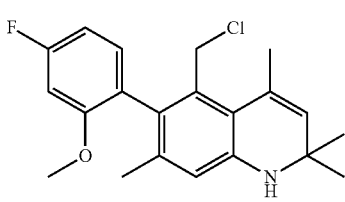 | $^1$H-NMR (400 MHz, DMSO-d$_6$) δ 1.15 (s, 3H), 1.17 (s, 3H), 1.71 (s, 3H), 2.24 (s, 3H), 3.69 (s, 3H), 4.24 (d, J = 11.1 Hz, 1H), 4.66 (d, J = 11.1 Hz, 1H), 5.40 (s, 1H), 5.92 (br s, 1H), 6.50 (s, 1H), 6.82 (td, J = 8.4, 2.5 Hz, 1H), 6.99 (dd, J = 11.5, 2.5 Hz, 1H), 7.04 (dd, J = 8.4, 7.1 Hz, 1H) |

| | |
|---|---|
| 5-Chloromethyl-6-(4-fluoro-2-methoxyphenyl)-7-methoxy-2,2,4-trimethyl-1,2-dihydroquinoline (Reference Compound No. 5-10)<br>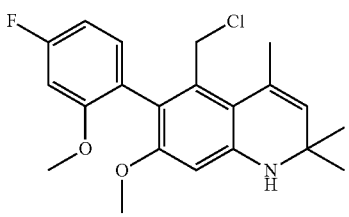 | $^1$H-NMR (400 MHz, DMSO-d$_6$) δ 1.16 (s, 3H), 1.18 (s, 3H), 2.23 (s, 3H), 3.53 (s, 3H), 3.66 (s, 3H), 4.24 (d, J = 12.2 Hz, 1H), 4.65 (d, J = 12.2 Hz, 1H), 5.30 (s, 1H), 6.08 (s, 1H), 6.32 (s, 1H), 6.77 (td, J = 8.4, 2.5 Hz, 1H), 6.92 (dd, J = 11.6, 2.5 Hz, 1H), 7.06 (dd, J = 8.4, 7.3 Hz, 1H) |
| 5-Chloromethyl-6-(2-ethoxy-4-fluorophenyl)-2,2,4-trimethyl-1,2-dihydroquinoline (Reference Compound No. 5-11)<br>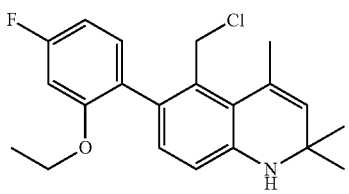 | $^1$H-NMR (500 MHz, DMSO-d$_6$) δ 1.12 (s, 3H), 1.18 (t, J = 7.0 Hz, 3H), 1.22 (s, 3H), 2.25 (s, 3H), 3.97-4.02 (m, 2H), 4.36 (d, J = 11.9 Hz, 1H), 4.85 (d, J = 11.9 Hz, 1H), 5.46 (s, 1H), 6.06 (br s, 1H), 6.62 (d, J = 7.9 Hz, 1H), 6.68 (d, J = 7.9 Hz, 1H), 6.80 (td, J = 8.3, 2.4 Hz, 1H), 6.94 (dd, J = 11.6, 2.4 Hz, 1H), 7.17 (dd, J = 8.3, 7.3 Hz, 1H) |
| 5-Chloromethyl-6-(4-fluoro-2-propoxyphenyl)-2,2,4-trimethyl-1,2-dihydroquinoline (Reference Compound No. 5-12)<br>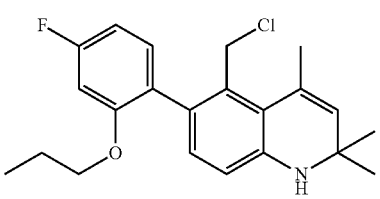 | $^1$H-NMR (400 MHz, DMSO-d$_6$) δ 0.79 (t, J = 7.3 Hz, 3H), 1.13 (s, 3H), 1.21 (s, 3H), 1.50-1.62 (m, 2H), 2.24 (s, 3H), 3.88 (t, J = 6.3 Hz, 2H), 4.34 (d, J = 12.0 Hz, 1H), 4.84 (d, J = 12.0 Hz, 1H), 5.47 (s, 1H), 6.05 (s, 1H), 6.62 (d, J = 8.3 Hz, 1H), 6.68 (d, J = 8.3 Hz, 1H), 6.81 (td, J = 8.4, 2.4 Hz, 1H), 6.94 (dd, J = 11.5, 2.4 Hz, 1H), 7.17 (dd, J = 8.4, 7.1 Hz, 1H) |
| 5-Chloromethyl-6-(4-fluoro-2-isopropoxyphenyl)-2,2,4-trimethyl-1,2-dihydroquinoline (Reference Compound No. 5-13)<br>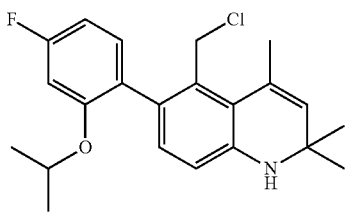 | $^1$H-NMR (400 MHz, CDCl$_3$) δ 1.12 (d, J = 6.0 Hz, 3H), 1.21 (d, J = 6.0 Hz, 3H), 1.24 (s, 3H), 1.31 (s, 3H), 2.36 (s, 3H), 4.30-4.38 (m, 1H), 4.44 (d, J = 11.7 Hz, 1H), 4.84 (br s, 1H), 5.56 (br s, 1H), 6.64-6.78 (m, 4H), 7.21 (t, J = 7.4 Hz, 1H) |
| 5-Chloromethyl-6-(3,4-difluoro-2-methoxyphenyl)-2,2,4-trimethyl-1,2-dihydroquinoline (Reference Compound No.5-14)<br>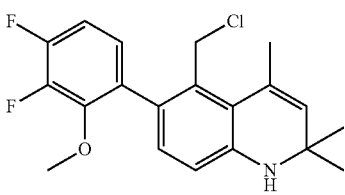 | $^1$H-NMR (400 MHz, DMSO-d$_6$) δ 1.16 (s, 3H), 1.20 (s, 3H), 2.27 (s, 3H), 3.64 (s, 3H), 4.43 (d, J = 12.2 Hz, 1H), 4.83 (d, J = 12.2 Hz, 1H), 5.48 (s, 1H), 6.17 (s, 1H), 6.65 (d, J = 8.2 Hz, 1H), 6.75 (d, J = 8.2 Hz, 1H), 7.03 (ddd, J = 8.7, 6.3, 2.2 Hz, 1H), 7.16-7.23 (m, 1H) |

-continued

| | |
|---|---|
| 5-Chloromethyl-6-(2-methoxy-5-trifluoromethylphenyl)-2,2,4-trimethyl-1,2-dihydroquinoline (Reference Compound No. 5-15) 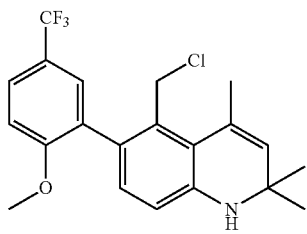 | $^1$H-NMR (400 MHz, DMSO-d$_6$) δ 1.16 (s, 3H), 1.20 (s, 3H), 2.27 (s, 3H), 3.78 (s, 3H), 4.32 (d, J = 12.1 Hz, 1H), 4.79 (d, J = 12.1 Hz, 1H), 5.47 (s, 1H), 6.13 (s, 1H), 6.64 (d, J = 8.2 Hz, 1H), 6.72 (d, J = 8.2 Hz, 1H), 7.26 (d, J = 8.7 Hz, 1H), 7.42 (d, J = 2.0 Hz, 1H), 7.73 (dd, J = 8.7, 2.0 Hz, 1H) |
| 6-(4-Chloro-2-methoxyphenyl)-5-chloromethyl-2,2,4-trimethyl-1,2-dihydroquinoline (Reference Compound No. 5-16) 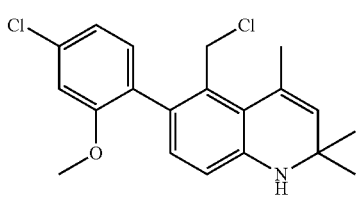 | $^1$H-NMR (500 MHz, DMSO-d$_6$) δ 1.15 (s, 3H), 1.20 (s, 3H), 2.26 (s, 3H), 3.72 (s, 3H), 4.35 (d, J = 12.1 Hz, 1H), 4.78 (d, J = 12.1 Hz, 1H), 5.46 (s, 1H), 6.09 (br s, 1H), 6.62 (d, J = 8.1 Hz, 1H), 6.67 (d, J = 8.1 Hz, 1H), 7.05 (dd, J = 8.2, 1.9 Hz, 1H), 7.13 (d, J = 1.9 Hz, 1H), 7.14 (d, J = 8.2 Hz, 1H) |

Reference Example 6

5-Hydroxymethyl-6-(2-trifluoromethylsulfonyloxyphenyl)-2,2,4-trimethyl-1,2-dihydroquinoline (Reference Compound No. 6-1)

5-Hydroxymethyl-6-(2-hydroxyphenyl)-2,2,4-trimethyl-1,2-dihydroquinoline (Reference Compound No. 3-1, 293 mg, 0.992 mmol) was dissolved in anhydrous dichloromethane (5 mL) and then triethylamine (167 μL, 1.20 mmol) and trifluoromethanesulfonyl chloride (106 μL, 0.996 mmol) were added thereto at 0° C. After the reaction mixture was stirred at 0° C. for 1 hour, it was diluted with chloroform (20 mL). The whole was washed with saturated aqueous NaHCO$_3$ solution (20 mL) and then the solvent was removed under reduced pressure. The obtained residue was purified by silica gel column chromatography (hexane-ethyl acetate) to give the titled reference compound (177 mg) as an orange solid. (Yield 42%)

| | |
|---|---|
| 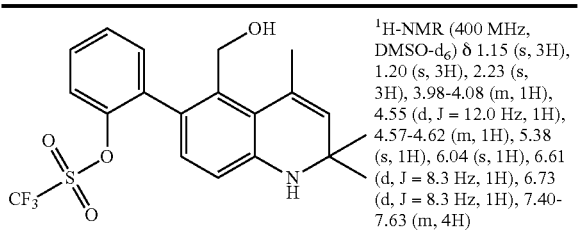 | $^1$H-NMR (400 MHz, DMSO-d$_6$) δ 1.15 (s, 3H), 1.20 (s, 3H), 2.23 (s, 3H), 3.98-4.08 (m, 1H), 4.55 (d, J = 12.0 Hz, 1H), 4.57-4.62 (m, 1H), 5.38 (s, 1H), 6.04 (s, 1H), 6.61 (d, J = 8.3 Hz, 1H), 6.73 (d, J = 8.3 Hz, 1H), 7.40-7.63 (m, 4H) |

Using Reference Compound No. 3-2, the following Reference Compound (No. 6-2) was obtained by a method similar to that of Reference Compound No. 6-1.

| | |
|---|---|
| 6-(4-Fluoro-2-trifluoromethylsulfonyloxyphenyl)-5-hydroxymethyl-2,2,4-trimethyl-1,2-dihydroquinoline (References Compound No. 6-2) 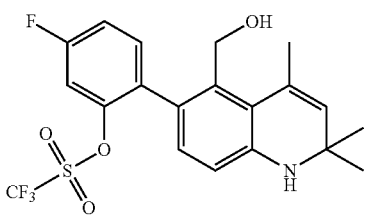 [SMILES: CC1=CC(C)(C)Nc2ccc(-c3ccccc3OS(=O)(=O)C(F)(F)F)c(CO)c21] | $^1$H-NMR (400 MHz, DMSO-d$_6$) δ 1.15 (s, 3H), 1.18 (s, 3H), 2.23 (s, 3H), 4.00 (d, J = 11.9 Hz, 1H), 4.53 (d, J = 11.9 Hz, 1H), 4.68 (br s, 1H), 5.39 (s, 1H), 6.06 (s, 1H), 6.60 (d, J = 8.2 Hz, 1H), 6.72 (d, J = 8.2 Hz, 1H), 7.43 (td, J = 8.5, 2.5 Hz, 1H), 7.49 (dd, J = 8.6, 2.5 Hz, 1H), 7.64 (dd, J = 8.5, 6.4 Hz, 1H) |

Reference Example 7

5-Hydroxymethyl-6-phenyl-2,2,4-trimethyl-1,2-dihydroquinoline (Reference Compound No. 7-1)

5-Hydroxymethyl-6-(2-trifluoromethylsulfonyloxyphenyl)-2,2,4-trimethyl-1,2-dihydroquinoline (Reference Compound No. 6-1, 136 mg, 0.318 mmol) was dissolved in anhydrous N,N-dimethylformamide (1.5 mL), then the solvent was bubbled with argon for 2 minutes, and then tetrakis(triphenylphosphine)palladium(0) (35.6 mg, 0.0308 mmol), triethylamine (221 μL, 1.59 mmol) and formic acid (60 μL, 1.6 mmol) were added thereto. After the reaction mixture was stirred at 60° C. for 10 hours, it was diluted with ethyl acetate (50 mL). The whole was washed with saturated NaHCO$_3$ solution (30 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled reference compound (93.0 mg) as a yellow oil. (quantative)

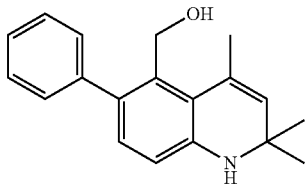 [SMILES: CC1=CC(C)(C)Nc2ccc(-c3ccccc3)c(CO)c21]

| | |
|---|---|
| (structure) | ¹H-NMR (400 MHz, DMSO-d₆) δ 1.17 (s, 6H), 2.28 (s, 3H), 4.43 (d, J = 4.4 Hz, 2H), 4.62-4.72 (m, 1H), 5.37 (s, 1H), 5.89 (s, 1H), 6.59 (d, J = 8.1 Hz, 1H), 6.78 (d, J = 8.1 Hz, 1H), 7.23-7.62 (m, 5H) |

Using Reference Compound No. 6-2, the following Reference Compound (No. 7-2) was obtained by a method similar to that of Reference Compound No. 7-1.

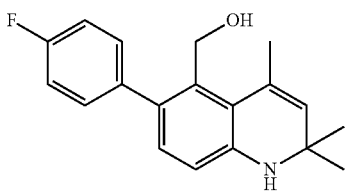

| | |
|---|---|
| 6-(4-Fluorophenyl)-5-hydroxymethyl-2,2,4-trimethyl-1,2-dihydroquinoline (Reference Compound No. 7-2) | ¹H-NMR (500 MHz, DMSO-d₆) δ 1.17 (s, 6H), 2.27 (s, 3H), 4.38 (d, J = 4.3 Hz, 2H), 4.72 (t, J = 4.3 Hz, 1H), 5.38 (s, 1H), 5.90 (s, 1H), 6.58 (d, J = 8.2 Hz, 1H), 6.77 (d, J = 8.2 Hz, 1H), 7.17 (t, J = 8.8 Hz, 2H), 7.37 (dd, J = 8.8, 5.7 Hz, 2H) |

Reference Example 8

Methyl 5-amino-2-bromobenzoate (Reference Compound No. 8)

Methyl 2-Bromo-5-nitrobenzoate (25.3 g, 97.3 mmol) was dissolved in anhydrous methanol (50 mL), and tin (II) chloride (93.3 g, 487 mmol) was added thereto, and then the reaction mixture was refluxed for 2 hours. After cooling down, ethyl acetate (500 mL) and water (100 mL) were added thereto, and the mixture was neutralized with 4N aqueous NaOH solution, and then it was filtered on celite. The filtrate was concentrated under reduced pressure, and ethyl acetate (200 mL) was added thereto, and then it was washed with saturated NaHCO₃ solution (200 mL, twice), water (200 mL) and saturated brine (200 mL) successively. The organic layer was dried over anhydrous magnesium sulfate and the solvent was removed under reduced pressure to give the titled reference compound (21.0 g) as a yellow oil. (Yield 94%)

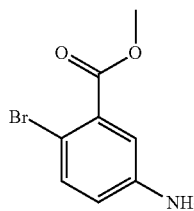

¹H-NMR (400 MHz, DMSO-d₆) δ 3.80 (s, 3H), 5.55 (s, 2H), 6.63 (dd, J = 8.8, 2.8 Hz, 1H), 6.94 (d, J = 2.8 Hz, 1H), 7.29 (d, J = 8.8 Hz, 1H)

Reference Example 9

Methyl 3-amino-4-chlorobenzoate (Reference Compound No. 9)

3-Amino-4-chlorobenzoic acid (20.9 g, 0.122 mol) and cecium carbonate (79.5 g, 0.244 mol) were suspended in N,N-dimethylformamide (500 mL), and methyl iodide (7.60 mL, 0.122 mol) was added thereto, and then the reaction mixture was stirred under argon atmosphere at room temperature for 2 hours. Ethyl acetate (250 mL) and diethyl ether (500 mL) were added to the reaction mixture and then the whole was washed with water (1 L). The aqueous layer was extracted with ethyl acetate/diethylether (2/1) (300 mL, 3 times). The combined organic layer was washed with water (500 mL, 4 times) and saturated brine (300 mL) successively. The organic layer was dried over anhydrous magnesium sulfate and then the solvent was removed under reduced pressure to give the titled reference compound (21.82 g) as a pale brown solid. (Yield 97%)

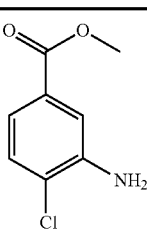

¹H-NMR (400 MHz, CDCl₃) δ 3.89 (s, 3H), 4.16 (br s, 2H), 7.30 (d, J = 8.3 Hz, 1H), 7.35 (dd, J = 8.3, 1.8 Hz, 1H), 7.44 (d, J = 1.8 Hz, 1H)

Reference Example 10

Methyl 5-amino-2-bromo-4-chlorobenzoate (Reference Compound No. 10)

Methyl 3-amino-4-chlorobenzoate (Reference Compound No. 9, 12.0 g, 64.7 mmol) was dissolved in N,N-dimethylformamide (250 mL), and after cooling down to 0° C., N-bromosuccinimide (11.5 g, 64.6 mmol) was added thereto, and then the reaction mixture was stirred under argon atmosphere at room temperature for 30 minutes. Ethyl acetate (200 mL) and diethyl ether (200 mL) were added to the reaction mixture and then the whole was washed with 1% aqueous sodium hyposulfite solution (500 mL). The aqueous layer was extracted with ethyl acetate/diethylether (1/1) (200 mL). The combined organic layer was washed with water (400 mL, 4 times) and saturated brine (300 mL) successively, dried over anhydrous magnesium sulfate and then the solvent was removed under reduced pressure. The obtained residue was filtered with hexane (15 mL) to give the titled reference compound (15.74 g) as a pale brown solid. (Yield 92%)

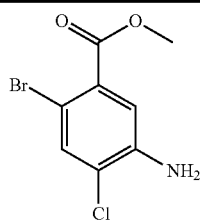

¹H-NMR (500 MHz, CDCl₃) δ 3.91 (s, 3H), 4.16 (br s, 2H), 7.24 (s, 1H), 7.54 (s, 1H)

Reference Example 11

Methyl (2-hydroxyphenyl)acetate (Reference Compound No. 11-1)

2-Hydroxyphenylacetic acid (302.7 mg, 1.99 mmol) was dissolved in anhydrous methanol (10 mL), and sulfuric acid (0.2 mL) was added thereto, and then the reaction mixture was stirred at 90° C. for 6 hours. The reaction mixture was concentrated under reduced pressure. Ethyl acetate (50 mL), 1N aqueous NaOH solution (5 mL), and saturated aqueous NaHCO₃ solution (30 mL) were added to the reaction mixture and separated. The organic layer was washed with saturated brine (30 mL), dried over anhydrous magnesium sulfate. The solvent was removed under reduced pressure to give the titled reference compound (242.4 mg) as a yellow solid. (Yield 73%)

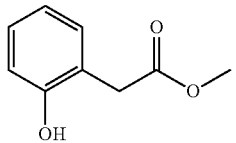

¹H-NMR (500 MHz, DMSO-d₆) δ 3.55 (s, 2H), 3.58 (s, 3H), 6.73 (td, J = 7.8, 1.1 Hz, 1H), 6.79 (dd, J = 7.8, 1.1 Hz, 1H), 7.06 (td, J = 7.8, 1.1 Hz, 1H), 7.09 (d, J = 7.8 Hz, 1H), 9.46 (s, 1H)

Using available compounds, the following Reference Compound (No. 11-2) was obtained by a method similar to that of Reference Compound No. 11-1.

Methyl 2-hydroxy-4-nitrobenzoate (Reference Compound No. 11-2)

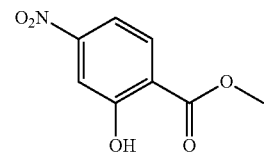

¹H-NMR (400 MHz, DMSO-d₆) δ 3.89 (s, 3H), 7.71 (dd, J = 8.5, 2.2 Hz, 1H), 7.75 (d, J = 2.2 Hz, 1H), 7.93 (d, J = 8.5 Hz, 1H), 10.99 (s, 1H)

Example 1

5-(2-Fluorobenzoyloxymethyl)-6-(4-fluoro-2-methoxyphenyl)-2,2,4-trimethyl-1,2-dihydroquinoline (Compound No. 1-1)

1-(2-Fluorobenzoyl)-5-(2-fluorobenzoyloxymethyl)-6-(4-fluoro-2-methoxyphenyl)-2,2,4-trimethyl-1,2-dihydroquinoline (Compound No. 1-2)

6-(4-Fluoro-2-methoxyphenyl)-5-hydroxymethyl-2,2,4-trimethyl-1,2-dihydroquinoline (Reference Compound 4-3, 60.0 mg, 0.183 mmol) was dissolved in anhydrous tetrahydrofuran (1 mL), then triethylamine (81.0 μL, 0.581 mmol) and 2-fluorobenzoyl chloride (51.0 μL, 0.427 mmol) were added thereto. The reaction mixture was stirred at room temperature overnight. It was diluted with ethyl acetate (100 mL). The whole was washed with water (100 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled Compound 1-1 (43.0 mg, Yield 52%) as a colorless solid and the titled Compound 1-2 (18.3 mg, Yield 17%) as a pale yellow oil.

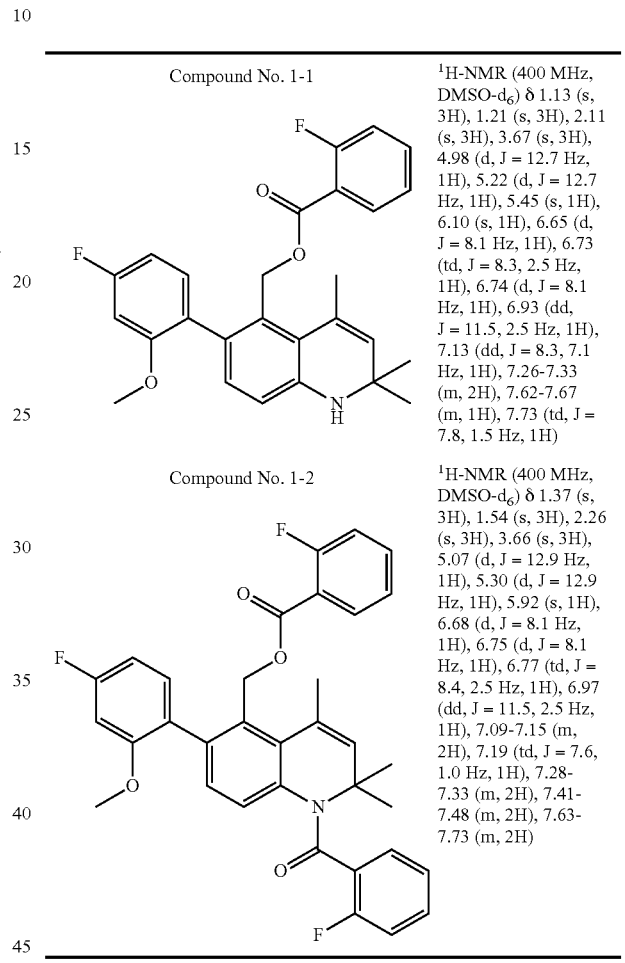

Compound No. 1-1

¹H-NMR (400 MHz, DMSO-d₆) δ 1.13 (s, 3H), 1.21 (s, 3H), 2.11 (s, 3H), 3.67 (s, 3H), 4.98 (d, J = 12.7 Hz, 1H), 5.22 (d, J = 12.7 Hz, 1H), 5.45 (s, 1H), 6.10 (s, 1H), 6.65 (d, J = 8.1 Hz, 1H), 6.73 (td, J = 8.3, 2.5 Hz, 1H), 6.74 (d, J = 8.1 Hz, 1H), 6.93 (dd, J = 11.5, 2.5 Hz, 1H), 7.13 (dd, J = 8.3, 7.1 Hz, 1H), 7.26-7.33 (m, 2H), 7.62-7.67 (m, 1H), 7.73 (td, J = 7.8, 1.5 Hz, 1H)

Compound No. 1-2

¹H-NMR (400 MHz, DMSO-d₆) δ 1.37 (s, 3H), 1.54 (s, 3H), 2.26 (s, 3H), 3.66 (s, 3H), 5.07 (d, J = 12.9 Hz, 1H), 5.30 (d, J = 12.9 Hz, 1H), 5.92 (s, 1H), 6.68 (d, J = 8.1 Hz, 1H), 6.75 (d, J = 8.1 Hz, 1H), 6.77 (td, J = 8.4, 2.5 Hz, 1H), 6.97 (dd, J = 11.5, 2.5 Hz, 1H), 7.09-7.15 (m, 2H), 7.19 (td, J = 7.6, 1.0 Hz, 1H), 7.28-7.33 (m, 2H), 7.41-7.48 (m, 2H), 7.63-7.73 (m, 2H)

Using any compounds among Reference Compounds No. 3-11, 4-1~4-10, 4-12~4-16, 4-18, 4-19, 4-22, 7-1 and 7-2, the following Compounds (No. 1-3~1-58) were obtained by a method similar to that of Compounds No. 1-1 and 1-2.

5-Acetoxymethyl-6-(2-methoxyphenyl)-2,2,4-trimethyl-1,2-dihydroquinoline (Compound No. 1-3)

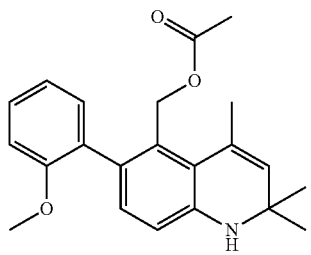

¹H-NMR (500 MHz, DMSO-d₆) δ 1.17 (s, 3H), 1.20 (s, 3H), 1.86 (s, 3H), 2.05 (s, 3H), 3.68 (s, 3H), 4.68 (d, J = 12.5 Hz, 1H), 4.94 (d, J = 12.5 Hz, 1H), 5.42 (s, 1H), 6.01 (d, J = 1.8 Hz, 1H), 6.62 (d, J = 8.2 Hz, 1H), 6.71 (s, 1H), 6.94 (td, J = 7.4, 1.1 Hz, 1H), 7.02 (d, J = 7.6 Hz, 1H), 7.07 (dd, J = 7.6, 1.8 Hz, 1H), 7.28-7.31 (m, 1H)

| | |
|---|---|
| 5-Cyclohexylcarbonyloxymethyl-6-(2-methoxyphenyl)-2,2,4-trimethyl-1,2-dihydroquinoline (Compound No. 1-4) 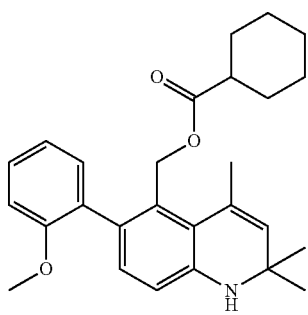 | $^1$H-NMR (400 MHz, DMSO-$d_6$) δ 1.05-1.28 (m, 5H), 1.16 (s, 3H), 1.20 (s, 3H), 1.48-1.62 (m, 3H), 1.66-1.72 (m, 2H), 2.03 (s, 3H), 2.11-2.19 (m, 1H), 3.68 (s, 3H), 4.66 (d, J = 12.7 Hz, 1H), 4.97 (d, J = 12.7 Hz, 1H), 5.41 (s, 1H), 6.03 (s, 1H), 6.63 (d, J = 8.2 Hz, 1H), 6.73 (d, J = 8.2 Hz, 1H), 6.94 (t, J = 7.3 Hz, 1H), 7.02 (d, J = 7.6 Hz, 1H), 7.09 (dd, J = 7.6, 1.7 Hz, 1H), 7.27-7.32 (m, 1H) |
| 5-Benzoyloxymethyl-6-(2-methoxyphenyl)-2,2,4-trimethyl-1,2-dihydroquinoline (Compound No. 1-5) 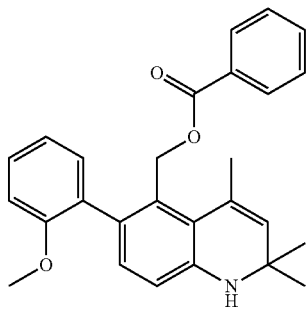 [SMILES: COc1ccccc1-c1ccc2c(c1COCc1ccccc1)C(C)=CC(C)(C)N2] | $^1$H-NMR (400 MHz, DMSO-$d_6$) δ 1.15 (s, 3H), 1.23 (s, 3H), 2.09 (s, 3H), 3.66 (s, 3H), 5.00 (d, J = 12.8 Hz, 1H), 5.23 (d, J =12.8 Hz, 1H), 5.46 (s, 1H), 6.09 (s, 1H), 6.67 (d, J = 8.3 Hz, 1H), 6.77 (d, J = 8.3 Hz, 1H), 6.91 (t, J = 7.4 Hz, 1H), 7.02 (d, J = 7.8 Hz, 1H), 7.13 (dd, J = 7.4, 1.8 Hz, 1H), 7.27-7.31 (m, 1H), 7.47 (t, J = 7.4 Hz, 2H), 7.61 (t, J = 7.4 Hz, 1H), 7.81 (d, J = 7.4 Hz, 2H) |
| 1-Benzoyl-5-benzoylmethyl-6-(2-methoxyphenyl)-2,2,4-trimethyl-1,2-dihydroquinoline (Compound No. 1-6) 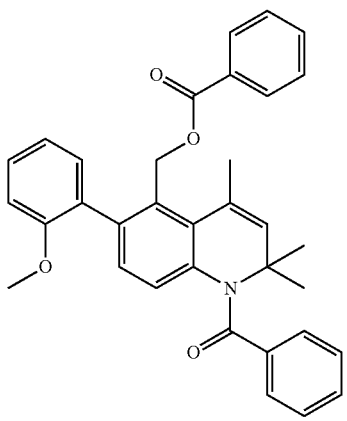 | $^1$H-NMR (400 MHz, DMSO-$d_6$) δ 1.38 (s, 3H), 1.55 (s, 3H), 2.29 (s, 3H), 3.65 (s, 3H), 5.10 (d, J = 13.1 Hz, 1H), 5.33 (d, J = 13.1 Hz, 1H), 5.93 (s, 1H), 6.52 (d, J = 8.3 Hz, 1H), 6.74 (d, J = 8.3 Hz, 1H), 6.94 (t, J = 7.4 Hz, 1H), 7.05 (d, J = 7.8 Hz, 1H), 7.11 (dd, J = 7.6, 1.7 Hz, 1H), 7.31-7.36 (m, 1H), 7.38 (t, J = 7.3 Hz, 2H), 7.44-7.54 (m, 5H), 7.63 (t, J = 7.4 Hz, 1H), 7.81 (d, J = 7.1 Hz, 2H) |

| | |
|---|---|
| 5-Acryloyloxymethyl-6-(2-methoxyphenyl)-2,2,4-trimethyl-1,2-dihydroquinoline (Compound No. 1-7) 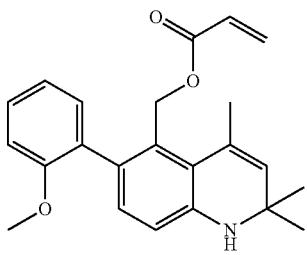 | $^1$H-NMR (400 MHz, CDCl$_3$) δ 1.25 (s, 3H), 1.28 (s, 3H), 2.14 (s, 3H), 3.73 (s, 3H), 3.86 (br s, 1H), 4.94 (d, J = 12.8 Hz, 1H), 5.23 (d, J = 12.8 Hz, 1H), 5.49 (s, 1H), 5.73 (dd, J = 10.5, 1.5 Hz, 1H), 6.00 (dd, J = 17.3, 10.5 Hz, 1H), 6.27 (dd, J = 17.3, 1.5 Hz, 1H), 6.60 (d, J = 8.3 Hz, 1H), 6.88-6.89 (m, 1H), 6.90-6.91 (m, 1H), 6.95 (d, J = 7.3 Hz, 1H), 7.17 (d, J = 7.6 Hz, 1H), 7.29 (d, J = 7.6 Hz, 1H) |
| 6-(2-Methoxyphenyl)-5-[(thiophene-2-yl)carbonyloxymethyl]-2,2,4-trimethyl-1,2-dihydroquinoline (Compound No. 1-8) 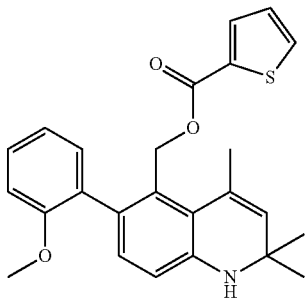 | $^1$H-NMR (400 MHz, CDCl$_3$) δ 1.24 (s, 3H), 1.29 (s, 3H), 2.19 (s, 3H), 3.44 (br s, 1H), 3.70 (s, 3H), 5.07 (d, J = 12.7 Hz, 1H), 5.37 (d, J = 12.7 Hz, 1H), 5.50 (s, 1H), 6.61 (d, J = 8.1 Hz, 1H), 6.87-6.94 (m, 3H), 7.03 (dd, J = 4.9, 3.7 Hz, 1H), 7.21 (d, J = 7.6 Hz, 1H), 7.25-7.29 (m, 1H), 7.48 (dd, J = 4.9, 1.2 Hz, 1H), 7.68 (dd, J = 3.7, 1.2 Hz, 1H). |
| 1-Acryloyl-5-acryloyloxymethyl-6-(2-methoxyphenyl)-2,2,4-trimethyl-1,2-dihydroquinoline (Compound No. 1-9) 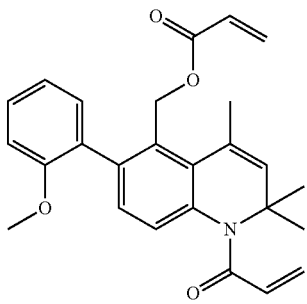 | $^1$H-NMR (400 MHz, DMSO-d$_6$) δ 1.37 (s, 3H), 1.50 (s, 3H), 2.16 (s, 3H), 3.70 (s, 3H), 4.89 (d, J = 12.8 Hz, 1H), 5.15 (d, J = 12.8 Hz, 1H), 5.67 (dd, J = 9.5, 2.7 Hz, 1H), 5.84 (s, 1H), 5.89 (dd, J = 10.4, 1.5 Hz, 1H), 6.04 (dd, J = 17.3, 10.4 Hz, 1H), 6.18 (dd, J = 17.3, 1.5 Hz, 1H), 6.23 (dd, J = 16.8, 2.7 Hz, 1H), 6.26 (dd, J = 16.8, 9.5 Hz, 1H), 6.87 (d, J = 7.9 Hz, 1H), 6.99 (t, J = 7.9 Hz, 1H), 7.04 (d, J = 7.9 Hz, 1H), 7.09 (d, J = 7.5 Hz, 1H), 7.16 (d, J = 7.5 Hz, 1H), 7.38 (t, J = 7.9 Hz, 1H) |
| 5-(4-t-Butylbenzoyloxymethyl)-6-(2-methoxyphenyl)-2,2,4-trimethyl-1,2-dihydroquinoline (Compound No. 1-10) 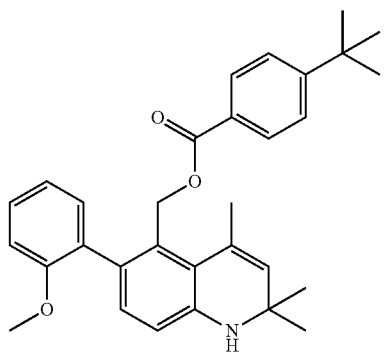 | $^1$H-NMR (400 MHz, CDCl$_3$) δ 1.27 (s, 3H), 1.31 (s, 12H), 2.18 (s, 3H), 3.70 (s, 3H), 5.08 (d, J = 12.8 Hz, 1H), 5.38 (d, J = 12.8 Hz, 1H), 5.51 (s, 1H), 6.62 (d, J = 8.1 Hz, 1H), 6.88-6.93 (m, 3H), 7.20 (d, J = 7.6 Hz, 1H), 7.26 (t, J = 7.6 Hz, 1H), 7.38 (d, J = 8.7 Hz, 2H), 7.87 (d, J = 8.7 Hz, 2H) |

1-(4-t-Butylbenzoyl)-5-(4-t-butylbenzoyl-oxymethyl)-6-(2-methoxyphenyl)-2,2,4-trimethyl-1,2-dihydroquinoline (Compound No. 1-11)

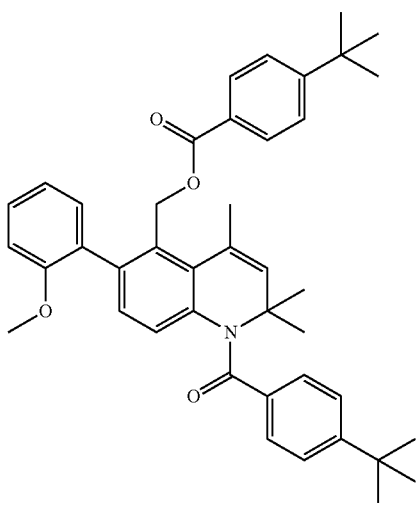

$^1$H-NMR (400 MHz, CDCl$_3$) δ 1.28 (s, 9H), 1.33 (s, 9H), 1.56 (s, 3H), 1.63 (s, 3H), 2.29 (s, 3H), 3.70 (s, 3H), 5.12 (d, J = 12.9 Hz, 1H), 5.41 (d, J = 12.9 Hz, 1H), 5.79 (s, 1H), 6.57 (d, J = 8.3 Hz, 1H), 6.75 (d, J = 8.3 Hz, 1H), 6.88-6.94 (m, 2H), 7.15 (d, J = 7.6 Hz, 1H), 7.25-7.29 (m, 1H), 7.31 (d, J = 8.7 Hz, 2H), 7.41 (d, J = 8.8 Hz, 2H), 7.56 (d, J = 8.7 Hz, 2H), 7.87 (d, J = 8.8 Hz, 2H)

6-(2-Methoxyphenyl)-5-(2-naphthoyloxy-methyl)-2,2,4-trimethyl-1,2-dihydroquinoline (Compound No. 1-12)

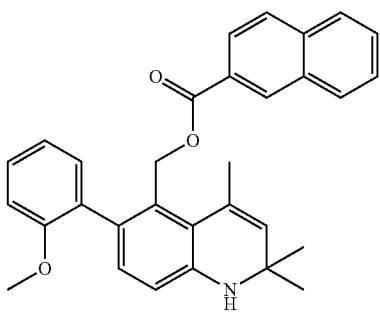

$^1$H-NMR (400 MHz, CDCl$_3$) δ 1.62 (s, 3H), 1.64 (s, 3H), 2.54 (s, 3H), 2.64 (br s, 1H), 3.68 (s, 3H), 4.39 (d, J = 12.2 Hz, 1H), 4.69 (d, J = 12.2 Hz, 1H), 5.86 (s, 1H), 6.54 (s, 2H), 6.94-7.02 (m, 3H), 7.30 (m, 1H), 7.44-7.55 (m, 3H), 7.68 (d, J = 8.5 Hz, 1H), 7.77 (d, J = 8.1 Hz, 1H), 7.82 (d, J = 7.6 Hz, 1H), 8.17 (s, 1H)

5-Butyryloxymethyl-6-(2-methoxy-phenyl)-2,2,4-trimethyl-1,2-dihydro-quinoline (Compound No. 1-13)

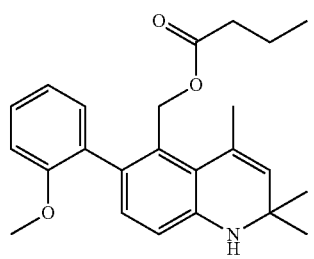

$^1$H-NMR (400 MHz, CDCl$_3$) δ 0.86 (t, J = 7.6 Hz, 3H), 1.25 (s, 3H), 1.27 (s, 3H), 1.54 (qt, J = 7.6, 7.6 Hz, 2H), 2.14 (s, 3H), 2.13-2.16 (m, 2H), 3.73 (s, 3H), 3.86 (br s, 1H), 4.84 (d, J = 12.5 Hz, 1H), 5.15 (d, J = 12.5 Hz, 1H), 5.48 (s, 1H), 6.58 (d, J = 8.1 Hz, 1H), 6.88 (d, J = 8.1 Hz, 1H), 6.90 (d, J = 7.7 Hz, 1H), 6.94 (t, J = 7.7 Hz, 1H), 7.17 (d, J = 7.7 Hz, 1H), 7.28 (t, J = 7.7 Hz, 1H)

-continued

5-Benzoyloxymethyl-6-(4-fluoro-2-methoxyphenyl)-2,2,4-trimethyl-1,2-dihydroquinoline (Compound No. 1-14)

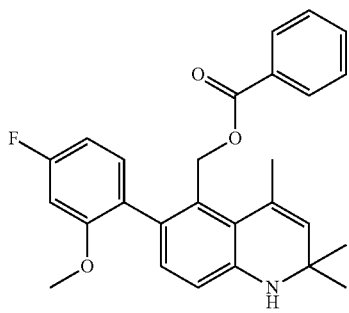

$^1$H-NMR (400 MHz, DMSO-d$_6$) δ 1.14 (s, 3H), 1.23 (s, 3H), 2.10 (s, 3H), 3.67 (s, 3H), 4.99 (d, J = 12.7 Hz, 1H), 5.21 (d, J = 12.7 Hz, 1H), 5.46 (s, 1H), 6.11 (s, 1H), 6.66 (d, J = 8.2 Hz, 1H), 6.72 (td, J = 8.3, 2.7 Hz, 1H), 6.75 (d, J = 8.2 Hz, 1H), 6.92 (dd, J = 11.3, 2.7 Hz, 1H), 7.14 (dd, J = 8.3, 7.1 Hz, 1H), 7.47 (t, J = 8.0 Hz, 2H), 7.60-7.64 (m, 1H), 7.82 (dd, J = 8.0, 1.2 Hz, 2H)

5-(3-Fluorobenzoyloxymethyl)-6-(4-fluoro-2-methoxyphenyl)-2,2,4-trimethyl-1,2-dihydroquinoline (Compound No. 1-15)

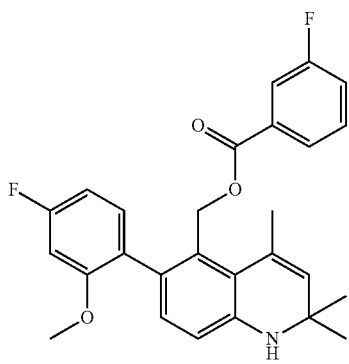

$^1$H-NMR (400 MHz, DMSO-d$_6$) δ 1.13 (s, 3H), 1.23 (s, 3H), 2.10 (s, 3H), 3.67 (s, 3H), 5.03 (d, J = 12.7 Hz, 1H), 5.23 (d, J = 12.7 Hz, 1H), 5.47 (s, 1H), 6.13 (s, 1H), 6.67 (d, J = 8.2 Hz, 1H), 6.74 (td, J = 8.5, 2.5 Hz, 1H), 6.76 (d, J = 8.2 Hz, 1H), 6.92 (dd, J = 11.5, 2.5 Hz, 1H), 7.15 (dd, J = 8.5, 7.1 Hz, 1H), 7.47-7.57 (m, 3H), 7.65-7.67 (m, 1H)

6-(4-Fluoro-2-methoxyphenyl)-5-(3-methoxybenzoyloxymethyl)-2,2,4-trimethyl-1,2-dihydroquinoline (Compound No. 1-16)

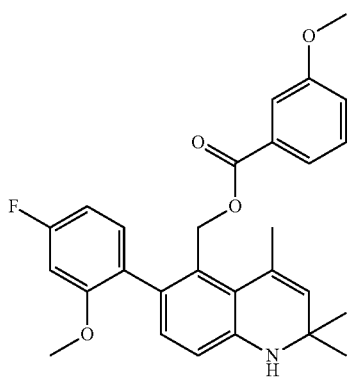

$^1$H-NMR (400 MHz, DMSO-d$_6$) δ 1.13 (s, 3H), 1.22 (s, 3H), 2.10 (s, 3H), 3.67 (s, 3H), 3.77 (s, 3H), 4.99 (d, J = 12.8 Hz, 1H), 5.20 (d, J = 12.8 Hz, 1H), 5.47 (s, 1H), 6.01 (s, 1H), 6.66 (d, J = 8.1 Hz, 1H), 6.74 (td, J = 8.3, 2.6 Hz, 1H), 6.75 (d, J = 8.1 Hz, 1H), 6.93 (dd, J = 11.5, 2.6 Hz, 1H), 7.14 (dd, J = 8.3, 7.1 Hz, 1H), 7.19 (dt, J = 6.8, 2.6 Hz, 1H), 7.30 (dd, J = 2.0, 1.0 Hz, 1H), 7.37-7.42 (m, 2H)

| Compound | NMR |
|---|---|
| 5-(4-Fluorobenzoyloxymethyl)-6-(4-fluoro-2-methoxyphenyl)-2,2,4-trimethyl-1,2-dihydroquinoline (Compound No. 1-17) 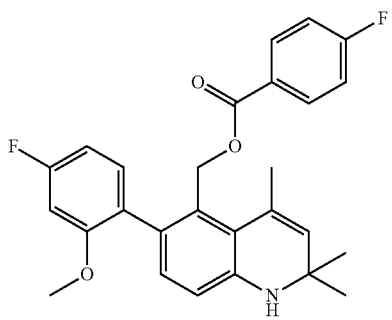 | $^1$H-NMR (500 MHz, DMSO-d$_6$) δ 1.13 (s, 3H), 1.22 (s, 3H), 2.10 (s, 3H), 3.66 (s, 3H), 4.99 (d, J = 12.8 Hz, 1H), 5.20 (d, J = 12.8 Hz, 1H), 5.46 (s, 1H), 6.10 (s, 1H), 6.66 (d, J = 8.2 Hz, 1H), 6.72 (td, J = 8.3, 2.4 Hz, 1H), 6.74 (d, J = 8.2 Hz, 1H), 6.91 (dd, J = 11.6, 2.4 Hz, 1H), 7.14 (dd, J = 8.3, 7.0 Hz, 1H), 7.31 (t, J = 8.9 Hz, 2H), 7.87 (dd, J = 8.9, 5.5 Hz, 2H) |
| 6-(4-Fluoro-2-methoxyphenyl)-5-(2-methoxybenzoyloxymethyl)-2,2,4-trimethyl-1,2-dihydroquinoline (Compound No. 1-18) 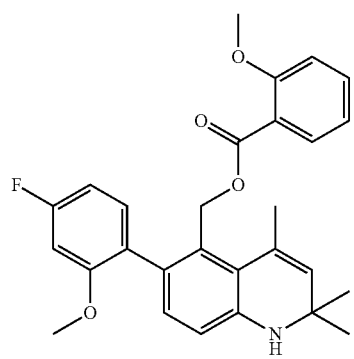 | $^1$H-NMR (400 MHz, DMSO-d$_6$) δ 1.15 (s, 3H), 1.21 (s, 3H), 2.13 (s, 3H), 3.67 (s, 3H), 3.75 (s, 3H), 4.89 (d, J = 12.7 Hz, 1H), 5.14 (d, J = 12.7 Hz, 1H), 5.46 (s, 1H), 6.07 (s, 1H), 6.63 (d, J = 8.2 Hz, 1H), 6.72 (d, J = 8.2 Hz, 1H), 6.73-6.78 (m, 1H), 6.92-6.97 (m, 2H), 7.10 (d, J = 8.3 Hz, 1H), 7.12 (dd, J = 8.3, 7.1 Hz, 1H), 7.46-7.52 (m, 2H) |
| 6-(4-Fluoro-2-methoxyphenyl)-5-(4-methoxybenzoyloxymethyl)-2,2,4-trimethyl-1,2-dihydroquinoline (Compound No. 1-19) 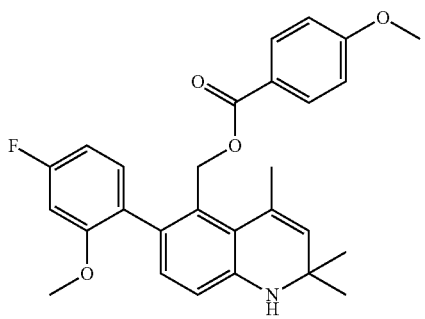 | $^1$H-NMR (400 MHz, DMSO-d$_6$) δ 1.15 (s, 3H), 1.22 (s, 3H), 2.09 (s, 3H), 3.67 (s, 3H), 3.81 (s, 3H), 4.93 (d, J = 12.7 Hz, 1H), 5.16 (d, J = 12.7 Hz, 1H), 5.45 (s, 1H), 6.09 (s, 1H), 6.65 (d, J = 8.2 Hz, 1H), 6.72 (td, J = 8.4, 2.5 Hz, 1H), 6.74 (d, J = 8.2 Hz, 1H), 6.92 (dd, J = 11.5, 2.5 Hz, 1H), 6.99 (d, J = 8.9 Hz, 2H), 7.14 (dd, J = 8.4, 7.2 Hz, 1H), 7.77 (d, J = 8.9 Hz, 2H) |
| 5-Butyryloxymethyl-6-(4-fluoro-2-methoxyphenyl)-2,2,2-trimethyl-1,2-dihydroquinoline (Compound No. 1-20) 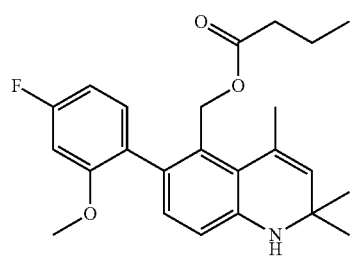 | $^1$H-NMR (500 MHz, DMSO-d$_6$) δ 0.79 (t, J = 7.5 Hz, 3H), 1.16 (s, 3H), 1.19 (s, 3H), 1.39-1.47 (m, 2H), 2.05 (s, 3H), 2.13 (t, J = 7.5 Hz, 2H), 3.70 (s, 3H), 4.67 (d, J = 12.5 Hz, 1H), 4.94 (d, J = 12.5 Hz, 1H), 5.42 (s, 1H), 6.03 (s, 1H), 6.61 (d, J = 8.2 Hz, 1H), 6.70 (d, J = 8.2 Hz, 1H), 6.75 (td, J = 8.3, 2.5 Hz, 1H), 6.92 (dd, J = 11.5, 2.5 Hz, 1H), 7.08 (dd, J = 8.3, 7.0 Hz, 1H) |

| | |
|---|---|
| 6-(4-Fluoro-2-methoxyphenyl)-5-[(thiophene-2-yl)carbonyloxymethyl]-2,2,4-trimethyl-1,2-dihydroquinoline (Compound No. 1-21) 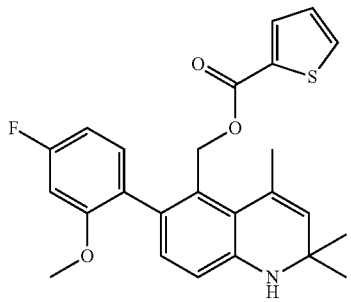 | $^1$H-NMR (500 MHz, DMSO-$d_6$) δ 1.13 (s, 3H), 1.21 (s, 3H), 2.10 (s, 3H), 3.67 (s, 3H), 4.93 (d, J = 12.7 Hz, 1H), 5.18 (d, J = 12.7 Hz, 1H), 5.45 (s, 1H), 6.09 (s, 1H), 6.65 (d, J = 8.1 Hz, 1H), 6.71-6.74 (m, 1H), 6.74 (d, J = 8.1 Hz, 1H), 6.92 (dd, J = 11.6, 2.4 Hz, 1H), 7.13 (dd, J = 8.6, 7.0 Hz, 1H), 7.17 (dd, J = 5.0, 3.7 Hz, 1H), 7.66 (dd, J = 3.7, 1.2 Hz, 1H), 7.90 (dd, J = 5.0, 1.2 Hz, 1H) |
| 5-Acetoxymethyl-6-(2-methoxyphenyl)-1,2,2,4-tetramethyl-1,2-dihydroquinoline (Compound No. 1-22) 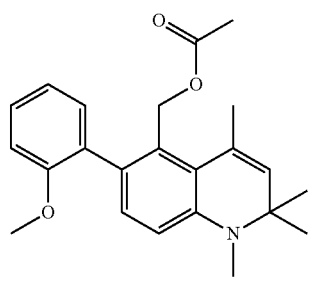 | $^1$H-NMR (500 MHz, DMSO-$d_6$) δ 1.15 (s, 3H), 1.23 (s, 3H), 1.84 (s, 3H), 2.07 (d, J = 1.2 Hz, 3H), 2.77 (s, 3H), 3.69 (s, 3H), 4.74 (d, J = 12.5 Hz, 1H), 4.99 (d, J = 12.5 Hz, 1H), 5.56 (d, J = 1.2 Hz, 1H), 6.71 (d, J = 8.6 Hz, 1H), 6.90 (d, J = 8.6 Hz, 1H), 6.97 (td, J = 7.4, 1.1 Hz, 1H), 7.04 (d, J = 7.6 Hz, 1H), 7.11 (dd, J = 7.5, 1.7 Hz, 1H), 7.30-7.33 (m, 1H) |
| 5-Cyclohexylcarbonyloxymethyl-6-(2-methoxyphenyl)-1,2,2,4-tetramethyl-1,2-dihydroquinoline (Compound No. 1-23) 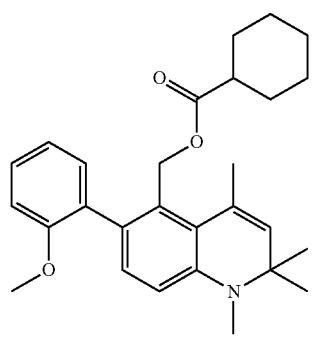 | $^1$H-NMR (400 MHz, DMSO-$d_6$) δ 1.10-1.28 (m, 5H), 1.14 (s, 3H), 1.23 (s, 3H), 1.50-1.60 (m, 3H), 1.65-1.70 (m, 2H), 2.05 (s, 3H), 2.10-2.18 (m, 1H), 2.77 (s, 3H), 3.69 (s, 3H), 4.72 (d, J = 12.7 Hz, 1H), 5.01 (d, J = 12.7 Hz, 1H), 5.55 (s, 1H), 6.71 (d, J = 8.4 Hz, 1H), 6.91 (d, J = 8.4 Hz, 1H), 6.96 (t, J = 7.5 Hz, 1H), 7.04 (d, J = 8.3 Hz, 1H), 7.13 (dd, J = 7.5, 1.6 Hz, 1H), 7.30-7.34 (m, 1H) |

| | |
|---|---|
| 5-Benzoyloxymethyl-6-(2-methoxyphenyl)-1,2,2,4-tetramethyl-1,2-dihydroquinoline (Compound No. 1-24)<br />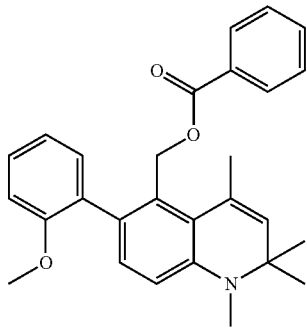 | $^1$H-NMR (400 MHz, DMSO-d$_6$) δ 1.10 (s, 3H), 1.27 (s, 3H), 2.12 (s, 3H), 2.80 (s, 3H), 3.67 (s, 3H), 5.05 (d, J = 13.1 Hz, 1H), 5.28 (d, J = 13.1 Hz, 1H), 5.59 (s, 1H), 6.75 (d, J = 8.5 Hz, 1H), 6.94 (t, J = 7.3 Hz, 1H), 6.96 (d, J = 8.5 Hz, 1H), 7.04 (d, J = 8.3 Hz, 1H), 7.18 (dd, J = 7.3, 1.7 Hz, 1H), 7.29-7.34 (m, 1H), 7.47 (t, J = 7.5 Hz, 2H), 7.61 (t, J = 7.5 Hz, 1H), 7.80 (d, J = 7.5 Hz, 2H) |
| 5-Benzoyloxymethyl-6-(2-methoxy-5-methylphenyl)-2,2,4-trimethyl-1,2-dihydroquinoline (Compound No. 1-25)<br />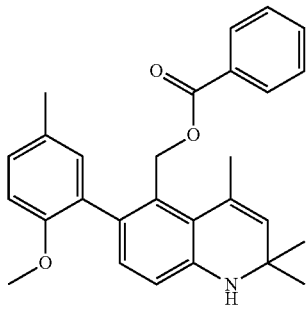 | $^1$H-NMR (400 MHz, DMSO-d$_6$) δ 1.16 (s, 3H), 1.22 (s, 3H), 2.09 (s, 3H), 2.11 (s, 3H), 3.62 (s, 3H), 4.96 (d, J = 12.8 Hz, 1H), 5.22 (d, J = 12.8 Hz, 1H), 5.46 (s, 1H), 6.07 (s, 1H), 6.66 (d, J = 8.2 Hz, 1H), 6.77 (d, J = 8.2 Hz, 1H), 6.90 (d, J = 8.3 Hz, 1H), 6.93 (d, J = 2.0 Hz, 1H), 7.06 (dd, J = 8.3, 2.0 Hz, 1H), 7.46-7.50 (m, 2H), 7.60-7.64 (m, 1H), 7.83 (d, J = 8.2 Hz, 2H), |
| 5-Benzoyloxymethyl-6-(2-methoxy-5-methylphenyl)-1,2,2,4-tetramethyl-1,2-dihydroquinoline (Compound No. 1-26)<br />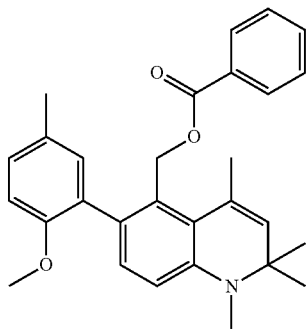 | $^1$H-NMR (400 MHz, DMSO-d$_6$) δ 1.19 (s, 3H), 1.25 (s, 3H), 2.21 (s, 3H), 2.13 (s, 3H), 2.79 (s, 3H), 3.63 (s, 3H), 5.02 (d, J = 12.9 Hz, 1H), 5.27 (d, J = 12.9 Hz, 1H), 5.58-5.59 (m, 1H), 6.75 (d, J = 8.8 Hz, 1H), 6.91-6.98 (m, 3H), 7.08 (d, J = 8.3 Hz, 1H), 7.45-7.49 (m, 2H), 7.60-7.67 (m, 1H), 7.81 (d, J = 8.3 Hz, 2H) |

| | |
|---|---|
| 5-Benzoyloxymethyl-6-(5-chloro-2-methoxyphenyl)-2,2,4-trimethyl-1,2-dihydroquinoline (Compound No. 1-27) 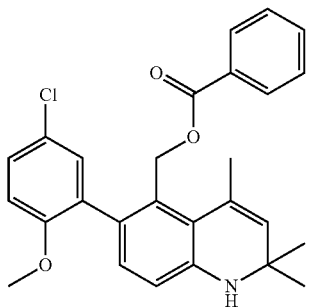 | $^1$H-NMR (400 MHz, DMSO-d$_6$) δ 1.14 (s, 3H), 1.22 (s, 3H), 2.11 (s, 3H), 3.66 (s, 3H), 4.98 (d, J = 12.7 Hz, 1H), 5.23 (d, J = 12.7 Hz, 1H), 5.47 (s, 1H), 6.16 (br s, 1H), 6.67 (d, J = 8.3 Hz, 1H), 6.78 (d, J = 8.3 Hz, 1H), 7.04 (d, J = 8.8 Hz, 1H), 7.16 (d, J = 2.8 Hz, 1H), 7.32 (dd, J = 8.8, 2.8 Hz, 1H), 7.47 (t, J = 7.8 Hz, 2H), 7.62 (t, J = 7.8 Hz, 1H), 7.82 (dd, J = 7.8, 1.2 Hz, 2H) |
| 5-Benzoyloxymethyl-6-(2-methoxy-3-methoxymethoxyphenyl)-2,2,4-trimethyl-1,2-dihydroquinoline (Compound No. 1-28) 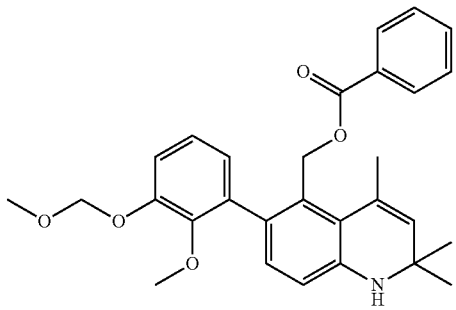 | $^1$H-NMR (500 MHz, DMSO-d$_6$) δ 1.15 (s, 3H), 1.22 (s, 3H), 2.09 (s, 3H), 3.41 (s, 3H), 3.44 (s, 3H), 5.04 (d, J = 12.8 Hz, 1H), 5.20 (d, J = 6.7 Hz, 1H), 5.23 (d, J = 6.7 Hz, 1H), 5.29 (d, J = 12.8 Hz, 1H), 5.46 (s, 1H), 6.14 (s, 1H), 6.69 (d, J = 8.2 Hz, 1H), 6.84 (dd, J = 7.9, 1.5 Hz, 1H), 6.85 (d, J = 8.2 Hz, 1H), 6.99 (t, J = 7.9 Hz, 1H), 7.08 (dd, J = 7.9, 1.5 Hz, 1H), 7.45-7.48 (m, 2H), 7.60-7.63 (m, 1H), 7.81-7.83 (m, 2H) |
| 5-Benzoyloxymethyl-6-(2,3-dimethoxyphenyl)-2,2,4-trimethyl-1,2-dihydroquinoline (Compound No. 1-29) 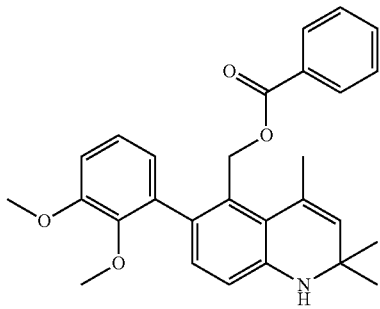 | $^1$H-NMR (400 MHz, DMSO-d$_6$) δ 1.16 (s, 3H), 1.22 (s, 3H), 2.08 (s, 3H), 3.41 (s, 3H), 3.81 (s, 3H), 5.03 (d, J = 12.8 Hz, 1H), 5.28 (d, J = 12.8 Hz, 1H), 5.46 (s, 1H), 6.12 (s, 1H), 6.69 (d, J = 8.2 Hz, 1H), 6.76-6.78 (m, 1H), 6.83 (d, J = 8.2 Hz, 1H), 7.00-7.01 (m, 2H), 7.47 (t, J = 7.4 Hz, 2H), 7.61 (t, J = 7.4 Hz, 1H), 7.82 (d, J = 7.4 Hz, 2H) |
| 5-Benzoyloxymethyl-6-(3-ethoxy-2-methylphenyl)-2,2,4-trimethyl-1,2-dihydroquinoline (Compound No. 1-30) 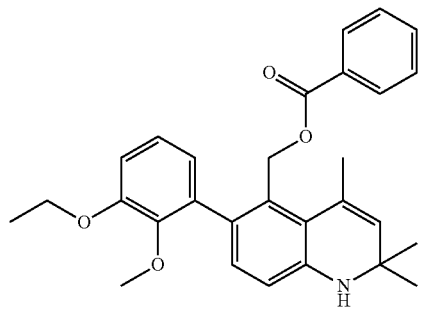 | $^1$H-NMR (500 MHz, DMSO-d$_6$) δ 1.16 (s, 3H), 1.22 (s, 3H), 1.36 (t, J = 7.0 Hz, 3H), 2.08 (s, 3H), 3.44 (s, 3H), 4.01-4.09 (m, 2H), 5.03 (d, J = 12.8 Hz, 1H), 5.28 (d, J = 12.8 Hz, 1H), 5.46 (s, 1H), 6.11 (s, 1H), 6.68 (d, J = 8.1 Hz, 1H), 6.75-6.77 (m, 1H), 6.83 (d, J = 8.1 Hz, 1H), 6.97-6.99 (m, 2H), 7.47 (t, J = 7.5 Hz, 2H), 7.61 (t, J = 7.5 Hz, 1H), 7.82 (d, J = 7.5 Hz, 2H) |

| | |
|---|---|
| 5-Benzoyloxymethyl-6-(3-benzyloxy-2-methoxyphenyl)-2,2,4-trimethyl-1,2-dihydroquinoline (Compound No. 1-31) 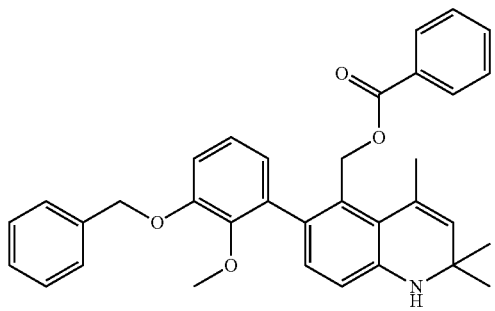 | $^1$H-NMR (400 MHz, DMSO-d$_6$) δ 1.16 (s, 3H), 1.22 (s, 3H), 2.09 (s, 3H), 3.46 (s, 3H), 5.05 (d, J = 12.8 Hz, 1H), 5.12 (d, J = 12.1 Hz, 1H), 5.16 (d, J = 12.1 Hz, 1H), 5.29 (d, J = 12.8 Hz, 1H), 5.46 (s, 1H), 6.13 (s, 1H), 6.69 (d, J = 8.3 Hz, 1H), 6.79 (d, J = 7.8 Hz, 1H), 6.84 (d, J = 8.3 Hz, 1H), 7.00 (t, J = 7.8 Hz, 1H), 7.09 (d, J = 7.8 Hz, 1H), 7.33 (t, J = 7.2 Hz, 1H), 7.40 (t, J = 7.2 Hz, 2H), 7.46 (t, J = 7.4 Hz, 2H), 7.48 (d, J = 7.2 Hz, 2H), 7.61 (t, J = 7.4 Hz, 1H), 7.83 (d, J = 7.4 Hz, 2H) |
| 5-Benzoyloxymethyl-6-(2-methoxycarbonyl-methoxyphenyl)-2,2,4-trimethyl-1,2-dihydroquinoline (Compound No. 1-32) 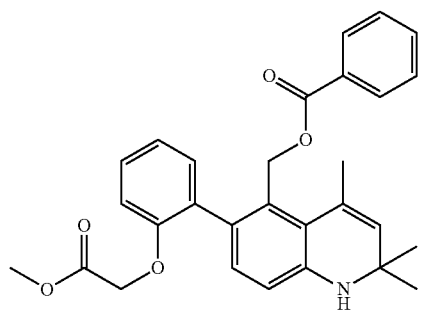 | $^1$H-NMR (400 MHz, DMSO-d$_6$) δ 1.10 (s, 3H), 1.24 (s, 3H), 2.13 (s, 3H), 3.64 (s, 3H), 4.69 (d, J = 16.4 Hz, 1H), 4.77 (d, J = 16.4 Hz, 1H), 5.06 (d, J = 13.1 Hz, 1H), 5.38 (d, J = 13.1 Hz, 1H), 5.45 (s, 1H), 6.09 (s, 1H), 6.67 (d, J = 8.2 Hz, 1H), 6.81 (d, J = 8.2 Hz, 1H), 6.94 (d, J = 8.3 Hz, 1H), 6.97 (t, J = 7.3 Hz, 1H), 7.20 (dd, J = 7.3, 1.7 Hz, 1H), 7.25-7.29 (m, 1H), 7.46 (t, J = 7.4 Hz, 2H), 7.61 (t, J = 7.4 Hz, 1H), 7.81 (d, J = 7.4 Hz, 2H) |
| 5-Benzoyloxymethyl-6-(2-ethoxyphenyl)-2,2,4-trimethyl-1,2-dihydroquinoline (Compound No. 1-33) 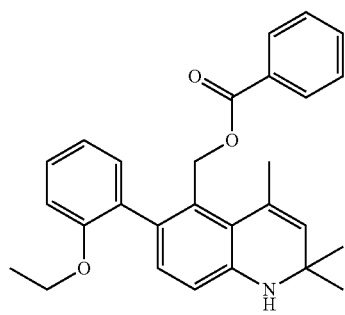 | $^1$H-NMR (400 MHz, DMSO-d$_6$) δ 1.10 (s, 3H), 1.20 (t, J = 7.0 Hz, 3H), 1.26 (s, 3H), 2.09 (s, 3H), 3.91-4.04 (m, 2H), 5.01 (d, J = 13.0 Hz, 1H), 5.32 (d, J = 13.0 Hz, 1H), 5.46 (s, 1H), 6.09 (s, 1H), 6.67 (d, J = 8.3 Hz, 1H), 6.79 (d, J = 8.3 Hz, 1H), 6.94 (t, J = 7.3 Hz, 1H), 7.02 (d, J = 8.3 Hz, 1H), 7.18 (dd, J = 7.3, 1.7 Hz, 1H), 7.24-7.32 (m, 1H), 7.46 (t, J = 7.8 Hz, 2H), 7.61 (t, J = 7.8 Hz, 1H), 7.80 (dd, J = 7.8, 1.3 Hz, 2H) |

1-Benzoyl-5-benzoyloxymethyl-6-(2-ethoxyphenyl)-2,2,4-trimethyl-1,2-dihydroquinoline (Compound No. 1-34)

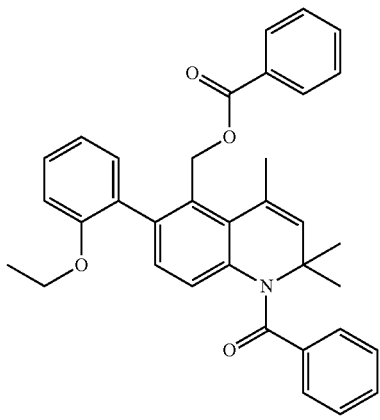

$^{1}$H-NMR (400 MHz, DMSO-d$_6$) δ 1.12 (t, J = 6.8 Hz, 3H), 1.36 (s, 3H), 1.58 (s, 3H), 2.29 (s, 3H), 3.85-4.00 (m, 2H), 5.12 (d, J = 12.9 Hz, 1H), 5.38 (d, J = 12.9 Hz, 1H), 5.94 (s, 1H), 6.52 (d, J = 8.3 Hz, 1H), 6.73 (d, J = 8.3 Hz, 1H), 6.94 (t, J = 7.4 Hz, 1H), 7.02 (dd, J = 8.1, 4.2 Hz, 1H), 7.15 (dd, J = 7.6, 1.7 Hz, 1H), 7.25-7.55 (m, 8H), 7.57-7.67 (m, 1H), 7.81 (d, J = 7.4 Hz, 2H)

5-Benzoyloxymethyl-6-phenyl-2,2,4-trimethyl-1,2-dihydroquinoline (Compound No. 1-35)

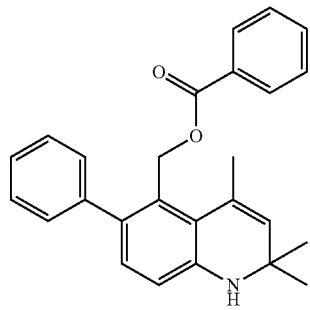

$^{1}$H-NMR (400 MHz, DMSO-d$_6$) δ 1.18 (s, 6H), 2.12 (s, 3H), 5.23 (s, 2H), 5.48 (s, 1H), 6.14 (s, 1H), 6.71 (d, J = 8.3 Hz, 1H), 6.90 (d, J = 8.3 Hz, 1H), 7.28-7.38 (m, 5H), 7.49 (t, J = 7.8 Hz, 2H), 7.64 (t, J = 7.8 Hz, 1H), 7.87 (dd, J = 8.3, 1.2 Hz, 2H)

5-Benzoyloxymethyl-6-(2-benzyloxyphenyl)-2,2,4-trimethyl-1,2-dihydroquinoline (Compound No. 1-36)

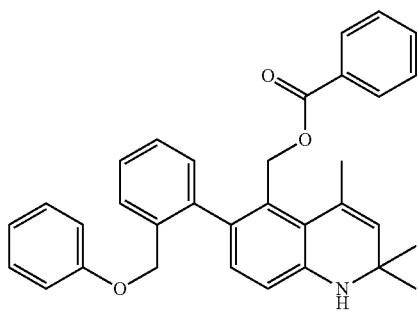

$^{1}$H-NMR (400 MHz, DMSO-d$_6$) δ 1.10 (s, 3H), 1.24 (s, 3H), 1.92 (s, 3H), 4.98-5.09 (m, 3H), 5.24 (d, J = 12.9 Hz, 1H), 5.43 (s, 1H), 6.09 (s, 1H), 6.68 (d, J = 8.2 Hz, 1H), 6.82 (d, J = 8.2 Hz, 1H), 6.94-7.03 (m, 1H), 7.09-7.35 (m, 8H), 7.39-7.46 (m, 2H), 7.55-7.62 (m, 1H), 7.72-7.80 (m, 2H)

| Compound | NMR |
|---|---|
| 5-Benzoyloxymethyl-1-benzyl-6-(2-benzyloxyphenyl)-2,2,4-trimethyl-1,2-dihydroquinoline (Compound No. 1-37) 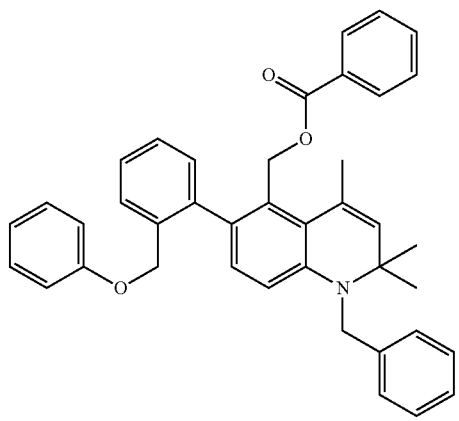 | $^1$H-NMR (400 MHz, DMSO-d$_6$) δ 1.17 (s, 3H), 1.34 (s, 3H), 1.98 (s, 3H), 4.50 (d, J = 18.0 Hz, 1H), 4.62 (d, J = 18.0 Hz, 1H), 5.00 (d, J = 12.1 Hz, 1H), 5.05 (d, J = 12.1 Hz, 1H), 5.10 (d, J = 13.2 Hz, 1H), 5.30 (d, J = 13.2 Hz, 1H), 5.61 (s, 1H), 6.48 (d, J = 8.5 Hz, 1H), 6.82 (d, J = 8.5 Hz, 1H), 6.97 (t, J = 7.4 Hz, 1H), 7.14 (d, J = 8.3 Hz, 1H), 7.17-7.39 (m, 12H), 7.44 (t, J = 7.9 Hz, 2H), 7.60 (t, J = 7.4 Hz, 1H), 7.79 (d, J = 7.4 Hz, 2H) |
| 5-Benzoyloxymethyl-6-(2-methoxymethoxyphenyl)-2,2,4-trimethyl-1,2-dihydroquinoline (Compound No. 1-38) 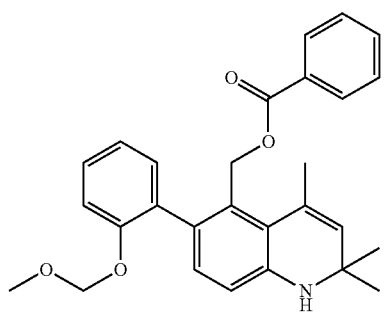 | $^1$H-NMR (400 MHz, DMSO-d$_6$) δ 1.15 (s, 3H), 1.22 (s, 3H), 2.09 (s, 3H), 3.21 (s, 3H), 4.99-5.01 (m, 3H), 5.29 (d, J = 12.7 Hz, 1H), 5.46 (s, 1H), 6.11 (s, 1H), 6.68 (d, J = 8.2 Hz, 1H), 6.81 (d, J = 8.2 Hz, 1H), 6.98 (t, J = 7.4 Hz, 1H), 7.11-7.21 (m, 2H), 7.23-7.38 (m, 1H), 7.41-7.54 (m, 2H), 7.62 (t, J = 7.4 Hz, 1H), 7.82 (d, J = 6.8 Hz, 2H) |
| 5-Acryloyloxymethyl-6-(2-methoxyphenyl)-1,2,2,4-tetramethyl-1,2-dihydroquinoline (Compound No. 1-39) 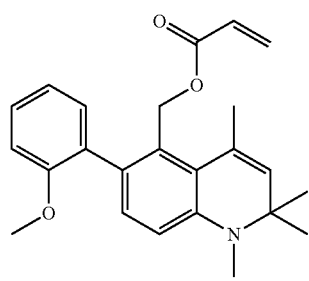 | $^1$H-NMR (500 MHz, DMSO-d$_6$) δ 1.13 (s, 3H), 1.24 (s, 3H), 2.06 (s, 3H), 2.78 (s, 3H), 3.68 (s, 3H), 4.85 (d, J = 12.8 Hz, 1H), 5.10 (d, J = 12.8 Hz, 1H), 5.56 (s, 1H), 5.86 (dd, J = 10.4, 1.6 Hz, 1H), 6.01 (dd, J = 17.2, 10.4 Hz, 1H), 6.16 (dd, J = 17.2, 1.6 Hz, 1H), 6.72 (d, J = 8.6 Hz, 1H), 6.92 (d, J = 8.6 Hz, 1H), 6.95 (td, J = 7.6, 1.0 Hz, 1H), 7.04 (d, J = 7.6 Hz, 1H), 7.13 (dd, J = 7.6, 1.8 Hz, 1H), 7.32 (td, J = 7.6, 1.8 Hz, 1H) |

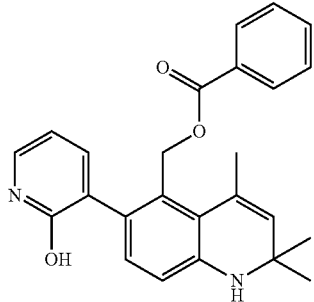

5-ベンゾイルオキシメチル-6-(2-
ヒドロキシピリジン-3-イル)-2,2,4-
トリメチル-1,2-ジヒドロキノリン
5-Benzoyloxymethyl-6-(2-hydroxypyridin-
3-yl)-2,2,4-trimethyl-1,2-dihydroquinoline
(Compound No. 1-40)

$^1$H-NMR (500 MHz, DMSO-d$_6$) δ
1.16 (s, 6H), 2.27 (s, 3H), 5.19 (s,
1H), 5.37 (s, 2H), 6.50 (s, 1H), 6.59
(d, J = 8.6 Hz, 1H), 7.04 (dd, J =
7.6, 4.9 Hz, 1H), 7.48-7.52 (m, 3H),
7.63 (t, J = 7.3 Hz, 1H), 7.94-7.96
(m, 3H), 8.01 (dd, J = 7.6, 1.8 Hz,
1H), 12.94 (br s, 1H)

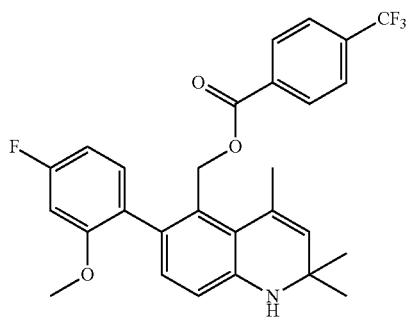

6-(4-Fluoro-2-methoxyphenyl)-5-(4-trifluoro-
methylbenzoyloxymethyl)-2,2,4-trimethyl-
1,2-dihydroquinoline (Compound No. 1-41)

$^1$H-NMR (400 MHz, DMSO-d$_6$) δ
1.13 (s, 3H), 1.22 (s, 3H), 2.11 (s,
3H), 3.66 (s, 3H), 5.04 (d, J = 12.7
Hz, 1H), 5.26 (d, J = 12.7 Hz, 1H),
5.47 (s, 1H), 6.12 (s, 1H), 6.66 (d,
J = 8.2 Hz, 1H), 6.71 (dd, J = 8.4,
2.4 Hz, 1H), 6.75 (d, J = 8.2 Hz, 1H),
6.91 (dd, J = 11.5, 2.4 Hz, 1H),
7.14 (dd, J = 8.4, 7.1 Hz, 1H), 7.87
(d, J = 8.2 Hz, 2H), 8.00 (d, J = 8.2
Hz, 2H)

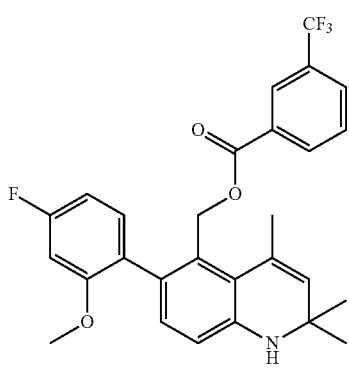

6-(4-Fluoro-2-methoxyphenyl)-5-(3-
trifluoromethylbenzoyloxymethyl)-2,2,4-
trimethyl-1,2-dihydroquinoline
(Compound No. 1-42)

$^1$H-NMR (400 MHz, DMSO-d$_6$) δ
1.10 (s, 3H), 1.22 (s, 3H), 2.11 (s,
3H), 3.67 (s, 3H), 5.08 (d, J = 12.9
Hz, 1H), 5.27 (d, J = 12.9 Hz, 1H),
5.47 (s, 1H), 6.13 (s, 1H), 6.67 (d,
J = 8.2 Hz, 1H), 6.74 (td, J = 8.8,
3.1 Hz, 1H), 6.76 (d, J = 8.2 Hz, 1H),
6.93 (dd, J = 11.4, 2.6 Hz, 1H),
7.16 (dd, J = 8.1, 7.1 Hz, 1H), 7.75
(t, J = 8.1 Hz, 1H), 8.01-8.03 (m, 2H),
8.11 (d, J = 7.8 Hz, 1H)

| | |
|---|---|
| 6-(4-Fluoro-2-methoxyphenyl)-5-(2-trifluoromethylbenzoyloxymethyl)-2,2,4-trimethyl-1,2-dihydroquinoline (Compound No. 1-43)<br />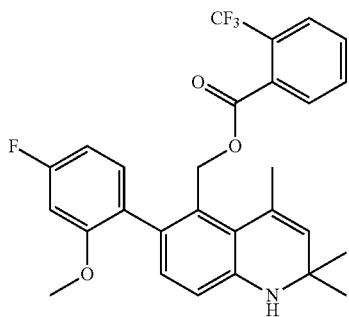 | $^1$H-NMR (400 MHz, DMSO-$d_6$) δ 1.14 (s, 3H), 1.20 (s, 3H), 2.11 (s, 3H), 3.68 (s, 3H), 5.00 (d, J = 12.6 Hz, 1H), 5.26 (d, J = 12.6 Hz, 1H), 5.46 (s, 1H), 6.10 (s, 1H), 6.65 (d, J = 8.3 Hz, 1H), 6.73 (d, J = 8.3 Hz, 1H), 6.78 (td, J = 8.3, 2.6 Hz, 1H), 6.95 (dd, J = 11.5, 2.6 Hz, 1H), 7.12 (dd, J = 8.3, 7.1 Hz, 1H), 7.59-7.65 (m, 1H), 7.73-7.79 (m, 2H), 7.82-7.87 (m, 1H) |
| 6-(4-Fluoro-2-methoxyphenyl)-5-(4-methylbenzoyloxymethyl)-2,2,4-trimethyl-1,2-dihydroquinoline (Compound No. 1-44)<br />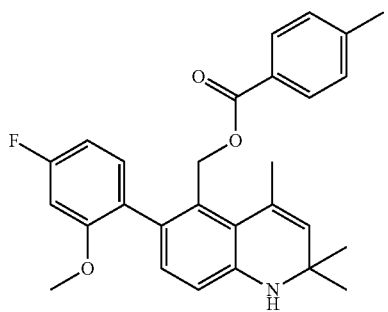 | $^1$H-NMR (400 MHz, DMSO-$d_6$) δ 1.14 (s, 3H), 1.22 (s, 3H), 2.08 (s, 3H), 2.35 (s, 3H), 3.67 (s, 3H), 4.95 (d, J = 12.8 Hz, 1H), 5.18 (d, J = 12.8 Hz, 1H), 5.45 (s, 1H), 6.10 (s, 1H), 6.65 (d, J = 8.3 Hz, 1H), 6.69-6.76 (m, 2H), 6.92 (dd, J = 11.5, 2.7 Hz, 1H), 7.14 (dd, J = 8.3, 7.1 Hz, 1H), 7.28 (d, J = 7.8 Hz, 2H), 7.71 (d, J = 8.3 Hz, 2H) |
| 6-(4-Fluoro-2-methoxyphenyl)-5-(3-methylbenzoyloxymethyl)-2,2,4-trimethyl-1,2-dihydroquinoline (Compound No. 1-45)<br />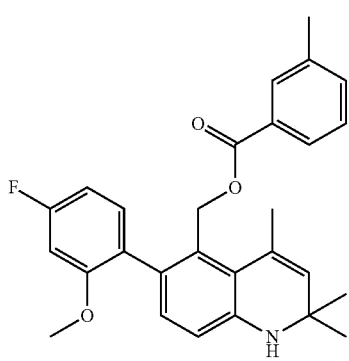 | $^1$H-NMR (400 MHz, DMSO-$d_6$) δ 1.16 (s, 3H), 1.23 (s, 3H), 2.08 (s, 3H), 2.32 (s, 3H), 3.67 (s, 3H), 4.97 (d, J = 12.7 Hz, 1H), 5.19 (d, J = 12.7 Hz, 1H), 5.46 (s, 1H), 6.11 (s, 1H), 6.66 (d, J = 8.3 Hz, 1H), 6.73 (td, J = 8.4, 2.5 Hz, 1H), 6.75 (d, J = 8.3 Hz, 1H), 6.92 (dd, J = 11.5, 2.5 Hz, 1H), 7.14 (dd, J = 8.4, 7.1 Hz, 1H), 7.36 (t, J = 7.6 Hz, 1H), 7.43 (d, J = 7.6 Hz, 1H), 7.61-7.62 (m, 2H) |

| | |
|---|---|
| 6-(4-Fluoro-2-methoxyphenyl)-5-(2-methylbenzoyloxymethyl)-2,2,4-trimethyl-1,2-dihydroquinoline (Compound No. 1-46) 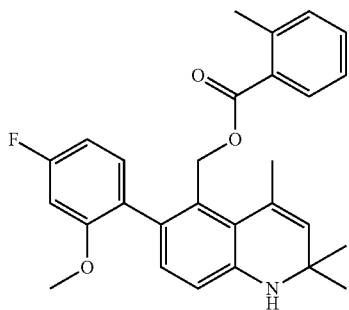 | $^1$H-NMR (500 MHz, DMSO-d$_6$) δ 1.16 (s, 3H), 1.22 (s, 3H), 2.10 (s, 3H), 2.39 (s, 3H), 3.66 (s, 3H), 4.97 (d, J = 12.8 Hz, 1H), 5.20 (d, J = 12.8 Hz, 1H), 5.46 (s, 1H), 6.09 (s, 1H), 6.66 (d, J = 8.4 Hz, 1H), 6.74 (d, J = 8.4 Hz, 1H), 6.73-6.77 (m, 1H), 6.93 (dd, J = 11.3, 2.5 Hz, 1H), 7.12 (dd, J = 8.3, 7.2 Hz, 1H), 7.25 (t, J = 7.7 Hz, 1H), 7.28 (d, J = 7.7 Hz, 1H), 7.44 (t, J = 7.7 Hz, 1H), 7.69 (d, J = 7.7 Hz, 1H) |
| 5-(4-t-Butylbenzoyloxymethyl)-6-(4-fluoro-2-methoxyphenyl)-2,2,4-trimethyl-1,2-dihydroquinoline (Compound No. 1-47) 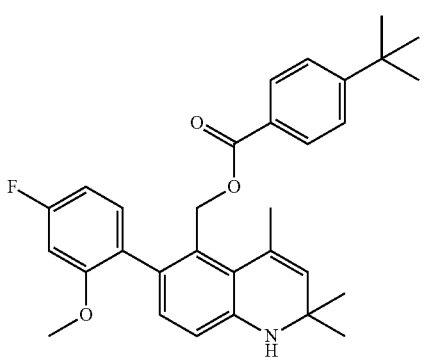 | $^1$H-NMR (500 MHz, DMSO-d$_6$) δ 1.15 (s, 3H), 1.23 (s, 3H), 1.28 (s, 9H), 2.08 (s, 3H), 3.67 (s, 3H), 4.94 (d, J = 12.8 Hz, 1H), 5.18 (d, J = 12.8 Hz, 1H), 5.46 (s, 1H), 6.09 (s, 1H), 6.66 (d, J = 8.1 Hz, 1H), 6.71-6.76 (m, 1H), 6.75 (d, J = 8.1 Hz, 1H), 6.92 (dd, J = 11.3, 2.5 Hz, 1H), 7.14 (dd, J = 8.4, 7.2 Hz, 1H), 7.49 (d, J = 8.9 Hz, 2H), 7.75 (d, J = 8.9 Hz, 2H) |
| 5-Cyclohexylcarbonyloxymethyl-6-(4-fluoro-2-methoxyphenyl)-2,2,4-trimethyl-1,2-dihydroquinoline (Compound No. 1-48) 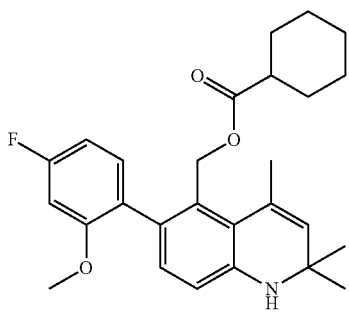 | $^1$H-NMR (400 MHz, DMSO-d$_6$) δ 1.15-1.23 (m, 5H), 1.15 (s, 3H), 1.19 (s, 3H), 1.51-1.70 (m, 5H), 2.03 (s, 3H), 2.12-2.20 (m, 1H), 3.70 (s, 3H), 4.64 (d, J = 12.6 Hz, 1H), 4.94 (d, J = 12.6 Hz, 1H), 5.42 (s, 1H), 6.05 (s, 1H), 6.61 (d, J = 8.2 Hz, 1H), 6.70 (d, J = 8.2 Hz, 1H), 6.76 (td, J = 8.4, 2.5 Hz, 1H), 6.93 (dd, J = 11.5, 2.5 Hz, 1H), 7.09 (dd, J = 8.4, 7.1 Hz, 1H) |

| | |
|---|---|
| 6-(4-Fluoro-2-methoxyphenyl)-5-[(pyridin-3-yl)carbonyloxymethyl]-2,2,4-trimethyl-1,2-dihydroquinoline (Compound No. 1-49)<br>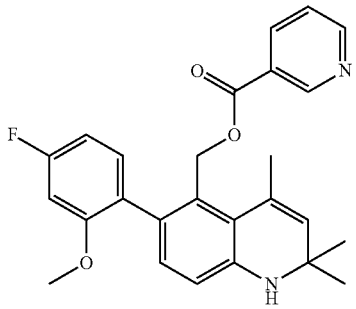 | $^1$H-NMR (400 MHz, DMSO-$d_6$) δ 1.11 (s, 3H), 1.22 (s, 3H), 2.12 (s, 3H), 3.67 (s, 3H), 5.06 (d, J = 12.7 Hz, 1H), 5.26 (d, J = 12.7 Hz, 1H), 5.47 (s, 1H), 6.12 (s, 1H), 6.66 (d, J = 8.3 Hz, 1H), 6.73 (td, J = 8.5, 2.6 Hz, 1H), 6.75 (d, J = 8.3 Hz, 1H), 6.92 (dd, J = 11.5, 2.6 Hz, 1H), 7.15 (dd, J = 8.5, 7.1 Hz, 1H), 7.53 (ddd, J = 7.9, 4.8, 0.8 Hz, 1H), 8.11-8.14 (m, 1H), 8.78 (dd, J = 4.8, 1.7 Hz, 1H), 8.92 (dd, J = 2.2, 0.8 Hz, 1H) |
| 6-(4-Fluorophenyl)-5-[(thiophen-2-yl)carbonyloxymethyl]-2,2,4-trimethyl-1,2-dihydroquinoline (Compound No. 1-50)<br>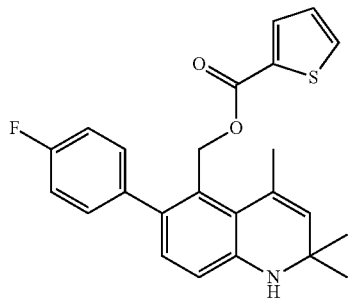 | $^1$H-NMR (400 MHz, DMSO-$d_6$) δ 1.16 (s, 6H), 2.12 (s, 3H), 5.17 (s, 2H), 5.47 (s, 1H), 6.15 (s, 1H), 6.70 (d, J = 8.2 Hz, 1H), 6.87 (d, J = 8.2 Hz, 1H), 7.17 (t, J = 8.7 Hz, 2H), 7.20 (dd, J = 5.1, 3.7 Hz, 1H), 7.32 (dd, J = 8.7, 5.6 Hz, 2H), 7.72 (dd, J = 3.7, 1.2 Hz, 1H), 7.93 (dd, J = 5.1, 1.2 Hz, 1H) |
| 6-(3,4-Difluoro-2-methoxyphenyl)-5-[(thiophen-2-yl)carbonyloxymethyl]-2,2,4-trimethyl-1,2-dihydroquinoline (Compound No. 1-51)<br>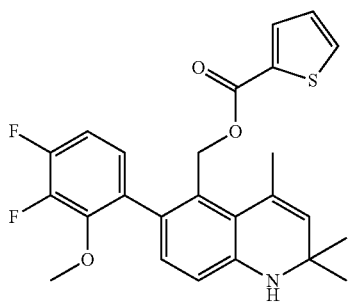 | $^1$H-NMR (400 MHz, DMSO-$d_6$) δ 1.14 (s, 3H), 1.20 (s, 3H), 2.11 (s, 3H), 3.61 (s, 3H), 5.00 (d, J = 12.8 Hz, 1H), 5.23 (d, J = 12.8 Hz, 1H), 5.47 (s, 1H), 6.21 (s, 1H), 6.69 (d, J = 8.2 Hz, 1H), 6.82 (d, J = 8.2 Hz, 1H), 7.00-7.16 (m, 2H), 7.17 (dd, J = 4.9, 3.7 Hz, 1H), 7.67 (dd, J = 3.7, 1.2 Hz, 1H), 7.91 (dd, J = 4.9, 1.2 Hz, 1H) |

| Compound | NMR |
|---|---|
| 5-[(4-Bromothiophen-2-yl)carbonyloxymethyl]-6-(4-fluoro-2-methoxyphenyl)-2,2,4-trimethyl-1,2-dihydroquinoline (Compound No. 1-52) 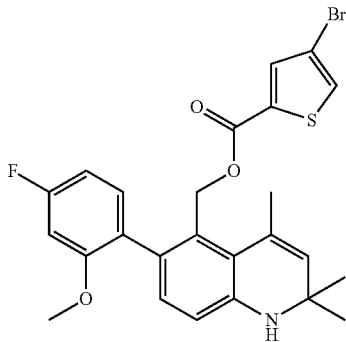 | $^1$H-NMR (500 MHz, DMSO-d$_6$) δ 1.13 (s, 3H), 1.21 (s, 3H), 2.09 (s, 3H), 3.67 (s, 3H), 4.97 (d, J = 12.7 Hz, 1H), 5.20 (d, J = 12.7 Hz, 1H), 5.46 (s, 1H), 6.11 (s, 1H), 6.65 (d, J = 8.2 Hz, 1H), 6.74 (d, J = 8.2 Hz, 1H), 6.74 (td, J = 8.5, 2.5 Hz, 1H), 6.92 (dd, J = 11.5, 2.5 Hz, 1H), 7.13 (dd, J = 8.5, 7.2 Hz, 1H), 7.60 (d, J = 1.5 Hz, 1H), 8.04 (d, J = 1.5 Hz, 1H) |
| 6-(4-Fluoro-2-methoxyphenyl)-5-(4-phenylbenzoyl-oxymethyl)-2,2,4-trimethyl-1,2-dihydroquinoline (Compound No. 1-53) 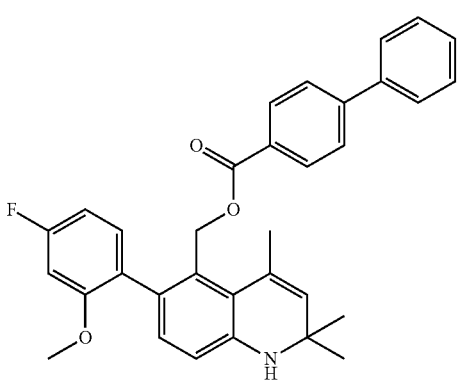 | $^1$H-NMR (500 MHz, DMSO-d$_6$) δ 1.16 (s, 3H), 1.23 (s, 3H), 2.12 (s, 3H), 3.68 (s, 3H), 5.00 (d, J = 12.5 Hz, 1H), 5.23 (d, J = 12.5 Hz, 1H), 5.47 (s, 1H), 6.11 (s, 1H), 6.67 (d, J = 8.1 Hz, 1H), 6.74 (td, J = 8.3, 2.7 Hz, 1H), 6.76 (d, J = 8.1 Hz, 1H), 6.93 (dd, J = 11.3, 2.7 Hz, 1H), 7.16 (dd, J = 8.3, 7.2 Hz, 1H), 7.42 (t, J = 6.9 Hz, 1H), 7.49 (t, J = 6.9 Hz, 2H), 7.73 (d, J = 6.9 Hz, 2H), 7.78 (d, J = 8.7 Hz, 2H), 7.90 (d, J = 8.7 Hz, 2H) |
| 6-(4-Fluoro-2-methoxyphenyl)-5-(4-trifluoromethoxy-benzoyloxymethyl)-2,2,4-trimethyl-1,2-dihydroquinoline (Compound No. 1-54) 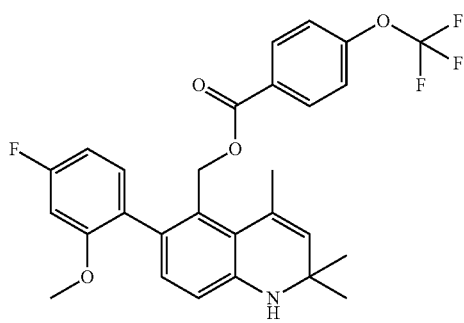 | $^1$H-NMR (400 MHz, DMSO-d$_6$) δ 1.13 (s, 3H), 1.22 (s, 3H), 2.11 (s, 3H), 3.66 (s, 3H), 5.00 (d, J = 12.5 Hz, 1H), 5.23 (d, J = 12.5 Hz, 1H), 5.46 (s, 1H), 6.11 (s, 1H), 6.65 (d, J = 8.3 Hz, 1H), 6.73 (td, J = 8.3, 2.6 Hz, 1H), 6.75 (d, J = 8.3 Hz, 1H), 6.91 (dd, J = 11.5, 2.6 Hz, 1H), 7.14 (dd, J = 8.3, 7.1 Hz, 1H), 7.47 (dt, J = 8.9, 1.7 Hz, 2H), 7.93 (dt, J = 8.9, 1.7 Hz, 2H) |

| Compound | NMR |
|---|---|
| 6-(4-Fluoro-2-methoxyphenyl)-5-(4-dimethyl-aminobenzoyloxymethyl)-2,2,4-trimethyl-1,2-dihydroquinoline (Compound No. 1-55) 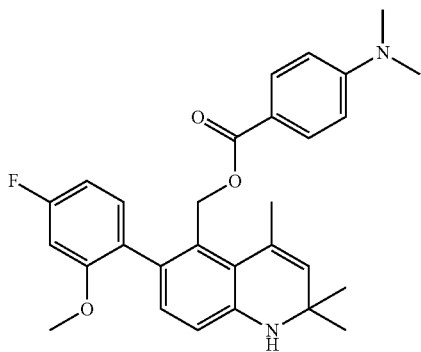 | $^1$H-NMR (400 MHz, DMSO-$d_6$) δ 1.16 (s, 3H), 1.23 (s, 3H), 2.07 (s, 3H), 2.97 (s, 6H), 3.67 (s, 3H), 4.86 (d, J = 12.8 Hz, 1H), 5.10 (d, J = 12.8 Hz, 1H), 5.44 (s, 1H), 6.07 (s, 1H), 6.65 (d, J = 8.2 Hz, 1H), 6.66 (d, J = 9.2 Hz, 2H), 6.72 (td, J = 8.4, 2.5 Hz, 1H), 6.74 (d, J = 8.2 Hz, 1H), 6.92 (dd, J = 11.5, 2.5 Hz, 1H), 7.13 (dd, J = 8.4, 7.2 Hz, 1H), 7.63 (d, J = 9.2 Hz, 2H) |
| 6-(3-Fluoro-2-methoxyphenyl)-5-[(thiophene-2-yl)carbonyloxymethyl]-2,2,4-trimethyl-1,2-dihydroquinoline (Compound No. 1-56) 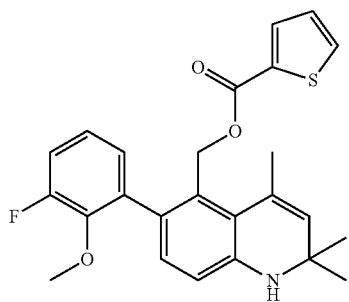 | $^1$H-NMR (400 MHz, DMSO-$d_6$) δ 1.15 (s, 3H), 1.20 (s, 3H), 2.11 (s, 3H), 3.54 (s, 3H), 5.00 (d, J = 12.7 Hz, 1H), 5.25 (d, J = 12.7 Hz, 1H), 5.46 (s, 1H), 6.19 (s, 1H), 6.70 (d, J = 8.2 Hz, 1H), 6.84 (d, J = 8.2 Hz, 1H), 7.00-7.03 (m, 1H), 7.06 (td, J = 7.8, 5.0 Hz, 1H), 7.17 (dd, J = 5.0, 3.8 Hz, 1H), 7.22 (ddd, J = 11.0, 7.8, 2.2 Hz, 1H), 7.66 (dd, J = 3.8, 1.3 Hz, 1H), 7.91 (dd, J = 5.0, 1.3 Hz, 1H) |
| 6-(4-Fluoro-2-methoxyphenyl)-5-[(thiophen-2-yl)carbonyloxymethyl]-2,2,4,7-tetramethyl-1,2-dihydroquinoline (Compound No. 1-57) 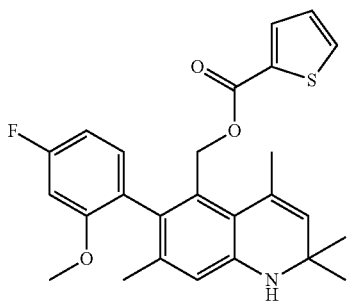 | $^1$H-NMR (400 MHz, DMSO-$d_6$) δ 1.17 (s, 3H), 1.18 (s, 3H), 1.75 (s, 3H), 2.06 (s, 3H), 3.63 (s, 3H), 4.76 (d, J = 12.2 Hz, 1H), 5.06 (d, J = 12.2 Hz, 1H), 5.39 (s, 1H), 5.97 (s, 1H), 6.54 (s, 1H), 6.66 (td, J = 8.3, 2.6 Hz, 1H), 6.91 (dd, J = 11.6, 2.6 Hz, 1H), 7.00 (dd, J = 8.3, 7.2 Hz, 1H), 7.18 (dd, J = 5.0, 3.7 Hz, 1H), 7.68 (dd, J = 3.7, 1.2 Hz, 1H), 7.92 (dd, J = 5.0, 1.2 Hz, 1H) |

| | |
|---|---|
| 6-(4-Fluoro-2-methoxyphenyl)-5-(phenoxy-carbonyloxymethyl)-2,2,4-trimethyl-1,2-dihydroquinoline (Compound No. 1-58)<br>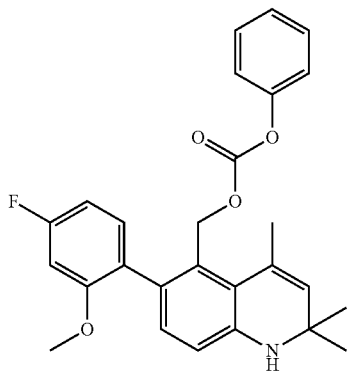 | $^1$H-NMR (400 MHz, DMSO-$d_6$) δ 1.17 (s, 3H), 1.21 (s, 3H), 2.14 (s, 3H), 3.71 (s, 3H), 4.93 (d, J = 12.5 Hz, 1H), 5.17 (d, J = 12.5 Hz, 1H), 5.46 (s, 1H), 6.10 (s, 1H), 6.65 (d, J = 8.2 Hz, 1H), 6.73 (d, J = 8.2 Hz, 1H), 6.81 (td, J = 8.4, 2.5 Hz, 1H), 6.95 (dd, J = 11.5, 2.5 Hz, 1H), 7.07-7.12 (m, 3H), 7.25 (t, J = 7.6 Hz, 1H), 7.39 (t, J = 7.6 Hz, 2H) |

Example 2

1-Acryloyl-5-benzoyloxymethyl-6-(4-fluoro-2-methoxyphenyl)-2,2,4-trimethyl-1,2-dihydroquinoline (Compound No. 2-1)

5-Benzoyloxymethyl-6-(4-fluoro-2-methoxyphenyl)-2,2,4-trimethyl-1,2-dihydroquinoine (Compound 1-14, 35.7 mg, 0.0827 mmol) was dissolved in anhydrous tetrahydrofuran (1 mL), then triethylamine (115 μL, 0.825 mmol) and acryloyl chloride (40.4 μL, 0.497 mmol) were added thereto. The reaction mixture was stirred at room temperature overnight. It was diluted with ethyl acetate (100 mL). The whole was washed with water (50 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (3.0 mg) as a pale yellow oil. (Yield 7%)

| | |
|---|---|
| 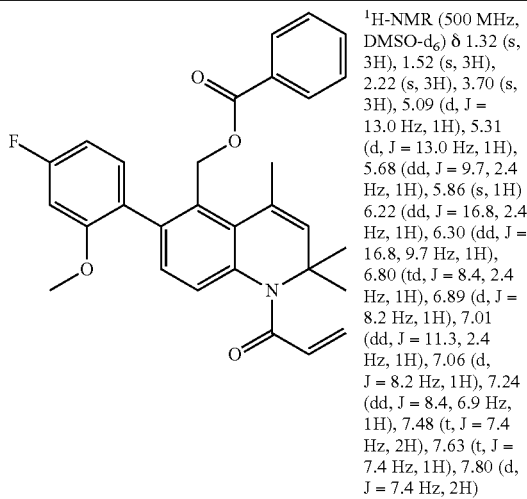 | $^1$H-NMR (500 MHz, DMSO-$d_6$) δ 1.32 (s, 3H), 1.52 (s, 3H), 2.22 (s, 3H), 3.70 (s, 3H), 5.09 (d, J = 13.0 Hz, 1H), 5.31 (d, J = 13.0 Hz, 1H), 5.68 (dd, J = 9.7, 2.4 Hz, 1H), 5.86 (s, 1H) 6.22 (dd, J = 16.8, 2.4 Hz, 1H), 6.30 (dd, J = 16.8, 9.7 Hz, 1H), 6.80 (td, J = 8.4, 2.4 Hz, 1H), 6.89 (d, J = 8.2 Hz, 1H), 7.01 (dd, J = 11.3, 2.4 Hz, 1H), 7.06 (d, J = 8.2 Hz, 1H), 7.24 (dd, J = 8.4, 6.9 Hz, 1H), 7.48 (t, J = 7.4 Hz, 2H), 7.63 (t, J = 7.4 Hz, 1H), 7.80 (d, J = 7.4 Hz, 2H) |

Using any compounds among Compounds No. 1-7, 1-8, 1-25, 3-4, and 10-1, the following Compounds (No. 2-2~2-6) were obtained by a method similar to that of Compound No. 2-1.

| | |
|---|---|
| 1-Acryloyl-6-(2-methoxyphenyl)-5-[(thiophen-2-yl)carbonyloxymethyl]-2,2,4-trimethyl-1,2-dihydroquinoline (Compound No. 2-2)<br>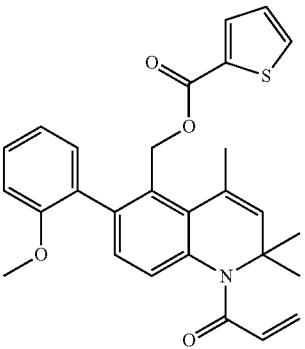 | $^1$H-NMR (400 MHz, DMSO-$d_6$) δ 1.32 (s, 3H), 1.51 (s, 3H), 2.21 (s, 3H), 3.69 (s, 3H), 5.05 (d, J = 12.8 Hz, 1H), 5.29 (d, J = 12.8 Hz, 1H), 5.68 (dd, J = 9.8, 2.4 Hz, 1H), 5.84 (s, 1H), 6.22 (dd, J = 16.8, 2.4 Hz, 1H), 6.31 (dd, J = 16.8, 9.8 Hz, 1H), 6.89 (d, J = 8.2 Hz, 1H), 6.99 (t, J = 7.7 Hz, 1H), 7.07 (d, J = 8.2 Hz, 1H), 7.10 (d, J = 7.7 Hz, 1H), 7.17 (dd, J = 4.9, 3.7 Hz, 1H), 7.21 (d, J = 7.7 Hz, 1H), 7.38 (t, J = 7.7 Hz, 1H), 7.65 (dd, J = 3.7, 1.2 Hz, 1H), 7.91 (dd, J = 4.9, 1.2 Hz, 1H) |

| Compound | 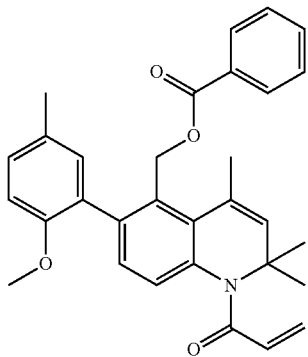<br>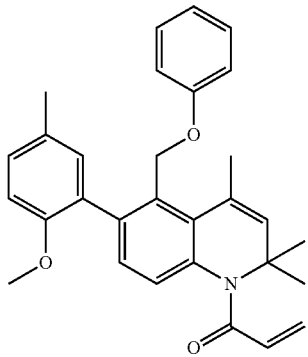<br>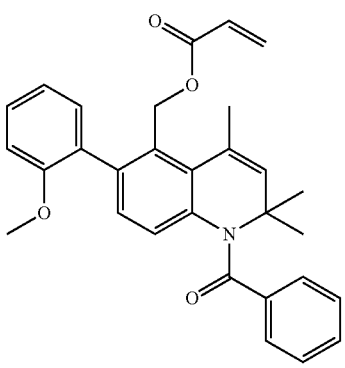 | NMR |
|---|---|---|
| 1-Acryloyl-5-benzoyloxymethyl-6-(2-methoxy-5-methylphenyl)-2,2,4-trimethyl-1,2-dihydroquinoline (Compound No. 2-3) | | $^1$H-NMR (400 MHz, DMSO-$d_6$) δ 1.36 (s, 3H), 1.51 (s, 3H), 2.15 (s, 3H), 2.21 (s, 3H), 3.65 (s, 3H), 5.07 (d, J = 12.7 Hz, 1H), 5.32 (d, J = 12.7 Hz, 1H), 5.68 (dd, J = 9.6, 2.5 Hz, 1H), 5.86 (s, 1H), 6.22 (dd, J = 16.8, 2.5 Hz, 1H), 6.31 (dd, J = 16.8, 9.6 Hz, 1H), 6.89 (d, J = 8.3 Hz, 1H), 6.98 (d, J = 8.4 Hz, 1H), 6.96-7.01 (m, 1H), 7.07 (d, J = 8.3 Hz, 1H), 7.15 (d, J = 8.4 Hz, 1H), 7.47-7.51 (m, 2H), 7.61-7.65 (m, 1H), 7.80-7.82 (m, 2H) |
| 1-Acryloyl-6-(2-methoxy-5-methylphenyl)-5-phenoxymethyl-2,2,4-trimethyl-1,2-dihydroquinoline (Compound No. 2-4) | | $^1$H-NMR (400 MHz, DMSO-$d_6$) δ 1.35 (s, 3H), 1.44 (s, 3H), 2.16 (s, 3H), 2.19 (s, 3H), 3.69 (s, 3H), 4.60 (d, J = 11.4 Hz, 1H), 5.14 (d, J = 11.4 Hz, 1H), 5.66 (dd, J = 9.2, 2.9 Hz, 1H), 5.80 (s, 1H), 6.20 (dd, J = 16.8, 2.9 Hz, 1H), 6.27 (dd, J = 16.8, 9.2 Hz, 1H), 6.72 (d, J = 7.8 Hz, 2H), 6.84 (d, J = 8.2 Hz, 1H), 6.86 (t, J = 7.3 Hz, 1H), 6.96 (d, J = 8.4 Hz, 1H), 7.02 (d, J = 2.0 Hz, 1H), 7.05 (d, J = 8.2 Hz, 1H), 7.12 (dd, J = 8.4, 2.0 Hz, 1H), 7.16-7.20 (m, 2H) |
| 5-Acryloylmethyl-1-benzoyl-6-(2-methoxyphenyl)-2,2,4-trimethyl-1,2-dihydroquinoline (Compound No. 2-5) | | $^1$H-NMR (400 MHz, DMSO-$d_6$) δ 1.42 (s, 3H), 1.52 (s, 3H), 2.23 (s, 3H), 3.66 (s, 3H), 4.88 (d, J = 12.9 Hz, 1H), 5.14 (d, J = 12.9 Hz, 1H), 5.90 (dd, J = 10.3, 1.7 Hz, 1H), 5.91 (s, 1H), 6.05 (dd, J = 17.2, 10.3 Hz, 1H), 6.19 (dd, J = 17.2, 1.7 Hz, 1H), 6.50 (d, J = 8.3 Hz, 1H), 6.70 (d, J = 8.3 Hz, 1H), 6.93 (td, J = 7.3, 0.9 Hz, 1H), 7.03-7.06 (m, 2H), 7.31-7.35 (m, 1H), 7.37 (t, J = 7.6 Hz, 2H), 7.45 (t, J = 7.6 Hz, 1H), 7.51 (d, J = 7.6 Hz, 2H) |
| 1-Acryloyl-6-(2-methoxyphenyl)-5-phenylthiomethyl-2,2,4-trimethyl-1,2-dihydroquinoline (Compound No. 2-6) | 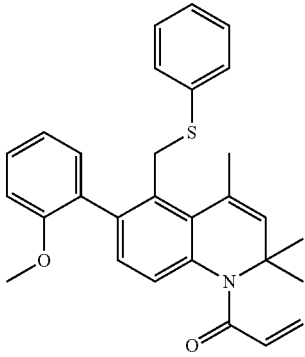 | $^1$H-NMR (400 MHz, DMSO-$d_6$) δ 1.32 (s, 3H), 1.57 (s, 3H), 2.33 (s, 3H) 3.72 (s, 3H), 3.94 (d, J = 12.4 Hz, 1H), 4.37 (d, J = 12.4 Hz, 1H), 5.65 (dd, J = 8.8, 3.4 Hz, 1H), 5.83 (s, 1H), 6.19 (dd, J = 16.9, 3.4 Hz, 1H), 6.25 (dd, J = 16.9, 8.8 Hz, 1H), 6.77 (d, J = 8.3 Hz, 1H), 6.93-6.98 (m, 4H), 7.04-7.09 (m, 2H), 7.11-7.20 (m, 3H), 7.33-7.37 (m, 1H) |

Example 3

6-(2-Methoxyphenyl)-5-phenoxymethyl-2,2,4-trimethyl-1,2-dihydroquinoline (Compound No. 3-1)

A mixture of 5-chloromethyl-6-(2-methoxyphenyl)-2,2,4-trimethyl-1,2-dihydroquinoline (Reference Compound 5-1, 52 mg, 0.16 mmol), phenol (42 μL, 0.48 mmol) and potassium carbonate (88 mg, 0.64 mmol) was suspended in anhydrous N,N-dimethylformamide (2 mL), and stirred 80° C. for 5 hours. After cooling down, the reaction mixture was diluted with ethyl acetate (60 mL). The whole was washed with water (50 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled compound (24 mg) as a colorless oil. (Yield 39%)

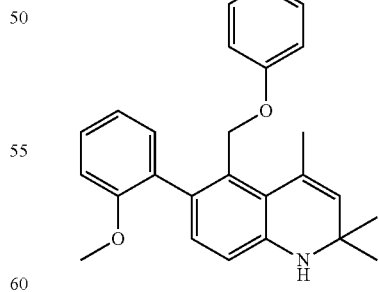

$^1$H-NMR (500 MHz, DMSO-$d_6$) δ 1.11 (s, 3H), 1.17 (s, 3H), 2.08 (s, 3H), 3.70 (s, 3H), 4.55 (d, J = 11.5 Hz, 1H), 5.02 (d, J = 11.5 Hz, 1H), 5.39 (s, 1H), 5.95 (s, 1H), 6.62 (d, J = 8.2 Hz, 1H), 6.67 (d, J = 7.9 Hz, 2H), 6.75 (d, J = 8.2 Hz, 1H), 6.82 (t, J = 7.3 Hz, 1H), 6.89 (td, J = 7.4, 1.0 Hz, 1H), 7.01 (d, J = 7.6 Hz, 1H), 7.13-7.17 (m, 3H), 7.24-7.27 (m, 1H)

Using any compounds among Reference Compounds No. 5-2, 5-3, 5-7~5-9, and 5-14~5-16, the following Compounds (No. 3-2~3-102) were obtained by a method similar to that of Compound No. 3-1.

| | |
|---|---|
| 6-(4-Fluoro-2-methoxyphenyl)-5-phenoxy-methyl-2,2,4-trimethyl-1,2-dihydroquinoline (Compound No. 3-2)<br/>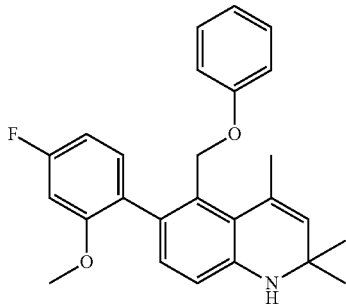 | $^1$H-NMR (400 MHz, DMSO-d$_6$) δ 1.12 (s, 3H), 1.17 (s, 3H), 2.08 (s, 3H), 3.71 (s, 3H), 4.51 (d, J = 11.1 Hz, 1H), 5.00 (d, J = 11.1 Hz, 1H), 5.39 (s, 1H), 5.99 (s, 1H), 6.62 (d, J = 8.3 Hz, 1H), 6.67-6.71 (m, 3H), 6.73 (d, J = 8.3 Hz, 1H), 6.84 (t, J = 7.3 Hz, 1H), 6.91 (dd, J = 11.3, 2.3 Hz, 1H), 7.13-7.19 (m, 3H) |
| 6-(4-Fluoro-2-methoxyphenyl)-5-(4-methoxyphenoxymethyl)-2,2,4-trimethyl-1,2-dihydroquinoline (Compound No. 3-3)<br/>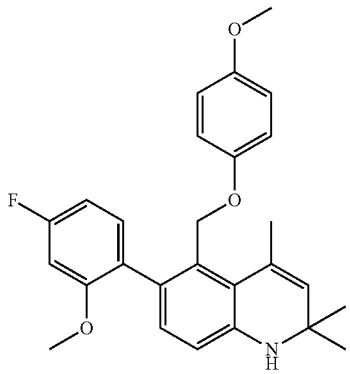 | $^1$H-NMR (400 MHz, DMSO-d$_6$) δ 1.13 (s, 3H), 1.17 (s, 3H), 2.09 (s, 3H), 3.64 (s, 3H), 3.70 (s, 3H), 4.43 (d, J = 11.1 Hz, 1H), 4.93 (d, J = 11.1 Hz, 1H), 5.39 (s, 1H), 5.98 (s, 1H), 6.60 (d, J = 8.2 Hz, 1H), 6.61 (d, J = 9.1 Hz, 2H), 6.67-6.73 (m, 1H), 6.71 (d, J = 8.2 Hz, 1H), 6.73 (d, J = 9.1 Hz, 2H), 6.91 (dd, J = 11.5, 2.4 Hz, 1H), 7.13 (dd, J = 8.4, 7.1 Hz, 1H) |
| 6-(2-Methoxy-5-methylphenyl)-5-phenoxymethyl-2,2,4-trimethyl-1,2-dihydroquinoline (Compound No. 3-4)<br/>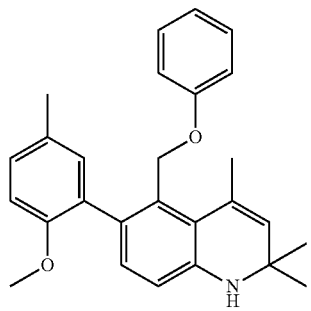 | $^1$H-NMR (400 MHz, DMSO-d$_6$) δ 1.13 (s, 3H), 1.17 (s, 3H), 2.09 (s, 3H), 2.13 (s, 3H), 3.65 (s, 3H), 4.51 (d, J = 11.4 Hz, 1H), 5.03 (d, J = 11.4 Hz, 1H), 5.39 (s, 1H), 5.95 (s, 1H), 6.61 (d, J = 8.3 Hz, 1H), 6.69-6.76 (m, 3H), 6.82-6.89 (m, 2H), 6.96 (d, J = 2.0 Hz, 1H), 7.02 (d, J = 8.3 Hz, 1H), 7.15-7.18 (m, 2H) |

| | | |
|---|---|---|
| 6-(4-Fluoro-2-methoxyphenyl)-5-(4-fluorophenoxymethyl)-2,2,4-trimethyl-1,2-dihydroquinoline (Compound No. 3-5) 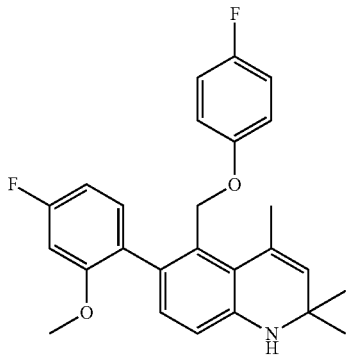 | $^1$H-NMR (400 MHz, DMSO-d$_6$) δ 1.12 (s, 3H), 1.16 (s, 3H), 2.08 (s, 3H), 3.71 (s, 3H), 4.48 (d, J = 11.4 Hz, 1H), 4.98 (d, J = 11.4 Hz, 1H), 5.39 (s, 1H), 6.00 (s, 1H), 6.61 (d, J = 8.1 Hz, 1H), 6.68-6.73 (m, 4H), 6.91 (dd, J = 11.5, 2.4 Hz, 1H), 7.12 (t, J = 8.9 Hz, 2H), 7.14 (dd, J = 8.3, 7.1 Hz, 1H) | |
| 6-(4-Fluoro-2-methoxyphenyl)-5-(3-fluorophenoxymethyl)-2,2,4-trimethyl-1,2-dihydroquinoline (Compound No. 3-6) 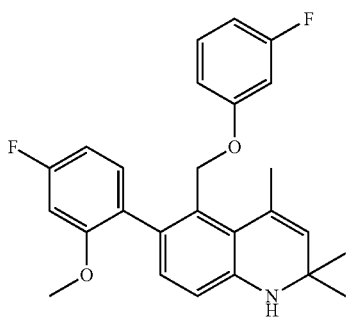 | $^1$H-NMR (400 MHz, DMSO-d$_6$) δ 1.11 (s, 3H), 1.15 (s, 3H), 2.08 (s, 3H), 3.71 (s, 3H), 4.52 (d, J = 11.5 Hz, 1H), 5.02 (d, J =11.5 Hz, 1H), 5.40 (s, 1H), 6.01 (s, 1H), 6.52-6.57 (m, 1H), 6.62 (d, J = 8.2 Hz, 1H), 6.64-6.71 (m, 3H), 6.73 (d, J = 8.2 Hz, 1H), 6.91 (dd, J = 11.5, 2.4 Hz, 1H), 7.14 (dd, J = 8.4, 7.2 Hz, 1H), 7.16-7.22 (m, 1H) | |
| 6-(4-Fluoro-2-methoxyphenyl)-5-(2-fluorophenoxymethyl)-2,2,4-trimethyl-1,2-dihydroquinoline (Compound No. 3-7) 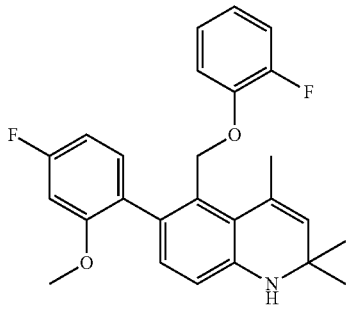 | $^1$H-NMR (400 MHz, DMSO-d$_6$) δ 1.11 (s, 3H), 1.15 (s, 3H), 2.11 (s, 3H), 3.70 (s, 3H) 4.57 (d, J = 11.5 Hz, 1H), 5.10 (d, J = 11.5 Hz, 1H), 5.40 (s, 1H), 6.02 (s, 1H), 6.62 (d, J = 8.1 Hz, 1H), 6.67-6.85 (m, 3H), 6.73 (d, J = 8.1 Hz, 1H), 6.90-6.97 (m, 2H), 7.07-7.15 (m, 2H) | |

| | |
|---|---|
| 6-(4-Fluoro-2-methoxyphenyl)-5-(3-methoxyphenoxymethyl)-2,2,4-trimethyl-1,2-dihydroquinoline (Compound No. 3-8) 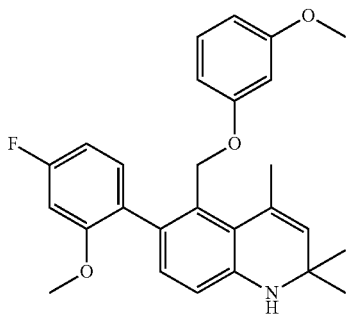 | $^1$H-NMR (400 MHz, DMSO-d$_6$) δ 1.13 (s, 3H), 1.17 (s, 3H), 2.08 (s, 3H), 3.66 (s, 3H), 3.71 (s, 3H), 4.49 (d, J = 11.2 Hz, 1H), 4.99 (d, J = 11.2 Hz, 1H), 5.39 (s, 1H), 5.99 (s, 1H), 6.25 (t, J = 2.1 Hz, 1H), 6.30 (dd, J = 8.2, 2.1 Hz, 1H), 6.43 (dd, J = 8.2, 2.1 Hz, 1H), 6.62 (d, J = 8.2 Hz, 1H), 6.67-6.72 (m, 1H), 6.73 (d, J = 8.2 Hz, 1H), 6.91 (dd, J = 11.5, 2.4 Hz, 1H), 7.06 (t, J = 8.2 Hz, 1H), 7.15 (dd, J = 8.3, 7.3 Hz, 1H) |
| 6-(4-Fluoro-2-methoxyphenyl)-5-(2-methoxyphenoxymethyl)-2,2,4-trimethyl-1,2-dihydroquinoline (Compound No. 3-9) 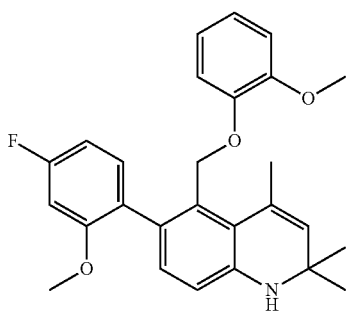 | $^1$H-NMR (500 MHz, DMSO-d$_6$) δ 1.16 (s, 3H), 1.17 (s, 3H), 2.10 (s, 3H), 3.66 (s, 3H), 3.69 (s, 3H), 4.44 (d, J = 11.3 Hz, 1H), 5.03 (d, J = 11.3 Hz, 1H), 5.38 (s, 1H), 5.98 (s, 1H), 6.61 (d, J = 8.2 Hz, 1H), 6.64 (td, J = 8.1, 1.8 Hz, 2H), 6.71 (d, J = 8.2 Hz, 1H), 6.71 (d, J = 8.1 Hz, 1H), 6.80 (td, J = 7.9, 2.0 Hz, 1H), 6.87 (dd, J = 8.1, 1.5 Hz, 1H), 6.89 (dd, J = 11.3, 2.0 Hz, 1H), 7.12 (dd, J = 7.9, 7.3 Hz, 1H) |
| 5-(4-Acetyl-3-fluorophenoxymethyl)-6-(4-fluoro-2-methoxyphenyl)-2,2,4-trimethyl-1,2-dihydroquinoline (Compound No. 3-10) 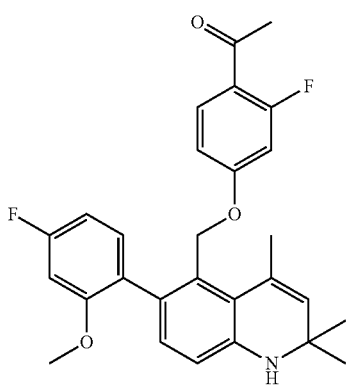 | $^1$H-NMR (500 MHz, DMSO-d$_6$) δ 1.11 (s, 3H), 1.15 (s, 3H), 2.07 (s, 3H), 2.47 (d, J = 4.6 Hz, 3H), 3.71 (s, 3H), 4.63 (d, J = 11.6 Hz, 1H), 5.10 (d, J = 11.6 Hz, 1H), 5.41 (s, 1H), 6.04 (s, 1H), 6.63 (d, J = 8.2 Hz, 1H), 6.64-6.68 (m, 2H), 6.71 (td, J = 8.3, 2.4 Hz, 1H), 6.75 (d, J = 8.2 Hz, 1H), 6.92 (dd, J = 11.3, 2.4 Hz, 1H), 7.15 (dd, J = 8.3, 7.0 Hz, 1H), 7.68 (t, J = 9.0 Hz, 1H) |

| Compound | | NMR |
|---|---|---|
| 6-(4-Fluoro-2-methoxyphenyl)-5-(quinolin-6-yloxymethyl)-2,2,4-trimethyl-1,2-dihydroquinoline (Compound No. 3-11) 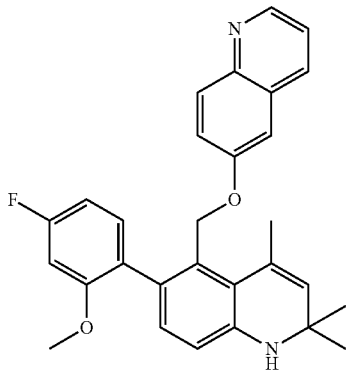 | | $^1$H-NMR (400 MHz, DMSO-d$_6$) δ 1.11 (s, 3H), 1.17 (s, 3H), 2.10 (s, 3H), 3.73 (s, 3H), 4.67 (d, J = 11.5 Hz, 1H), 5.14 (d, J = 11.5 Hz, 1H), 5.41 (s, 1H), 6.01 (s, 1H), 6.63 (d, J = 8.3 Hz, 1H), 6.71 (td, J = 8.3, 2.5 Hz, 1H), 6.76 (d, J = 8.3 Hz, 1H), 6.91 (dd, J = 11.5, 2.5 Hz, 1H), 7.06 (d, J = 2.7 Hz, 1H), 7.21 (dd, J = 8.3, 7.1 Hz, 1H), 7.24 (dd, J = 9.2, 2.7 Hz, 1H), 7.42 (dd, J = 7.9, 4.3 Hz, 1H), 7.83 (d, J = 9.2 Hz, 1H), 8.10 (d, J = 7.9 Hz, 1H), 8.69 (dd, J = 4.3, 1.7 Hz, 1H) |
| 6-(3,4-Difluoro-2-methoxyphenyl)-5-phenoxymethyl-2,2,4-trimethyl-1,2-dihydroquinoline (Compound No. 3-12) 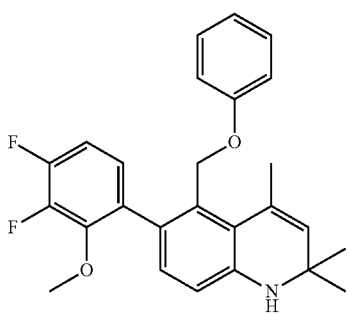 | | $^1$H-NMR (500 MHz, DMSO-d$_6$) δ 1.15 (s, 3H), 1.18 (s, 3H), 2.07 (s, 3H), 3.64 (s, 3H), 4.55 (d, J = 11.2 Hz, 1H), 5.04 (d, J = 11.2 Hz, 1H), 5.42 (s, 1H), 6.11 (s, 1H), 6.66 (d, J = 8.2 Hz, 1H), 6.74 (d, J = 8.3 Hz, 2H), 6.80 (d, J = 8.2 Hz, 1H), 6.86 (t, J = 7.5 Hz, 1H), 7.01-7.08 (m, 2H), 7.19 (dd, J = 8.3, 7.5 Hz, 2H) |
| 6-(3,5-Difluoro-2-methoxyphenyl)-5-(3-fluorophenoxymethyl)-2,2,4-trimethyl-1,2-dihydroquinoline (Compound No. 3-13) 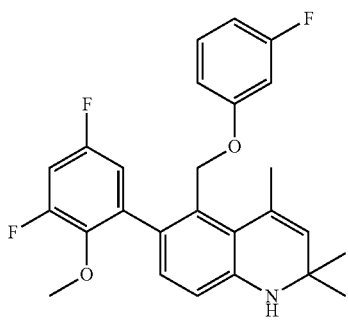 | | $^1$H-NMR (400 MHz, DMSO-d$_6$) δ 1.17 (s, 6H), 2.08 (s, 3H), 3.54 (s, 3H), 4.55 (d, J = 10.7 Hz, 1H), 5.12 (d, J = 10.7 Hz, 1H), 5.44 (s, 1H), 6.18 (s, 1H), 6.59-6.74 (m, 4H), 6.85 (d, J = 8.3 Hz, 1H), 6.89 (ddd, J = 9.2, 3.2, 1.7 Hz, 1H), 7.17-7.26 (m, 2H) |

| | |
|---|---|
| 6-(4,5-Difluoro-2-methoxyphenyl)-5-(3-fluorophenoxymethyl)-2,2,4-trimethyl-1,2-dihydroquinoline (Compound No. 3-14)<br>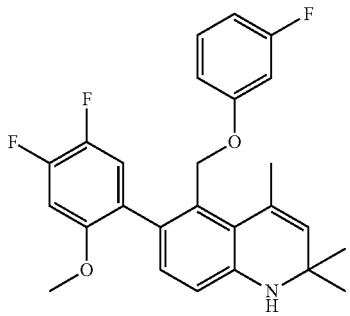 | $^1$H-NMR (500 MHz, DMSO-d$_6$) δ 1.14 (s, 6H), 2.08 (s, 3H), 3.69 (s, 3H), 4.50 (d, J = 11.3 Hz, 1H), 5.04 (d, J = 11.3 Hz, 1H), 5.41 (s, 1H), 6.08 (s, 1H), 6.58-6.60 (m, 2H), 6.62 (d, J = 8.2 Hz, 1H), 6.68 (t, J = 9.0 Hz, 1H), 6.76 (d, J = 8.2 Hz, 1H), 7.14 (dd, J = 12.8, 7.0 Hz, 1H), 7.16-7.23 (m, 2H) |
| 6-(4-Fluoro-2-methoxyphenyl)-5-(3-fluorophenoxymethyl)-2,2,4,7-tetramethyl-1,2-dihydroquinoline (Compound No. 3-15)<br>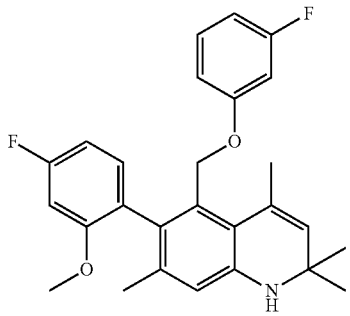 | $^1$H-NMR (400 MHz, DMSO-d$_6$) δ 1.11 (s, 3H), 1.19 (s, 3H), 1.75 (s, 3H), 2.04 (s, 3H), 3.69 (s, 3H), 4.34 (d, J = 10.7 Hz, 1H), 4.87 (d, J = 10.7 Hz, 1H), 5.35 (s, 1H), 5.88 (s, 1H), 6.51 (s, 1H), 6.57-6.68 (m, 4H), 6.89 (dd, J = 11.5, 2.4 Hz, 1H), 7.02 (dd, J = 8.4, 7.2 Hz, 1H), 7.16-7.22 (m, 1H) |
| 6-(4-Fluoro-2-methoxyphenyl)-5-(5-oxo-5,6,7,8-tetrahydronaphthalen-2-yloxymethyl)-2,2,4-trimethyl-1,2-dihydroquinoline (Compound No. 3-16)<br>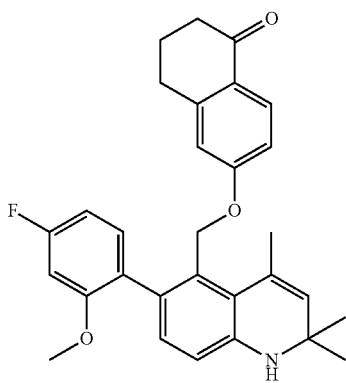 | $^1$H-NMR (500 MHz, DMSO-d$_6$) δ 1.10 (s, 3H), 1.16 (s, 3H), 1.94-1.98 (m, 2H), 2.06 (s, 3H), 2.47 (t, J = 6.6 Hz, 2H), 2.79-2.82 (m, 2H), 3.71 (s, 3H), 4.61 (d, J = 11.6 Hz, 1H), 5.09 (d, J = 11.6 Hz, 1H), 5.40 (s, 1H), 6.01 (s, 1H), 6.61 (d, J = 2.3 Hz, 1H), 6.62 (d, J = 8.2 Hz, 1H), 6.66 (dd, J = 8.9, 2.3 Hz, 1H), 6.72 (td, J = 8.4, 2.4 Hz, 1H), 6.74 (d, J = 8.2 Hz, 1H), 6.92 (dd, J = 11.6, 2.4 Hz, 1H), 7.16 (dd, J = 8.4, 7.2 Hz, 1H), 7.70 (d, J = 8.9 Hz, 1H) |

| | |
|---|---|
| 5-(4-Chlorophenoxymethyl)-6-(4-fluoro-2-methoxyphenyl)-2,2,4-trimethyl-1,2-dihydroquinoline (Compound No. 3-17)<br />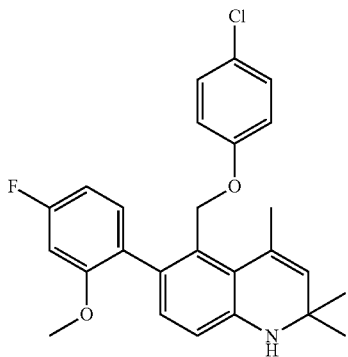 | $^1$H-NMR (400 MHz, DMSO-d$_6$) δ 1.11 (s, 3H), 1.16 (s, 3H), 2.06 (s, 3H), 3.71 (s, 3H), 4.51 (d, J = 11.7 Hz, 1H), 4.99 (d, J = 11.7 Hz, 1H), 5.39 (s, 1H), 6.00 (s, 1H), 6.61 (d, J = 8.3 Hz, 1H), 6.67-6.75 (m, 1H), 6.71 (d, J = 9.0 Hz, 2H), 6.73 (d, J = 8.3 Hz, 1H), 6.91 (dd, J = 11.5, 2.4 Hz, 1H), 7.14 (dd, J = 8.4, 7.2 Hz, 1H), 7.20 (d, J = 9.0 Hz, 2H) |
| 5-(4-Acetylphenoxymethyl)-6-(4-fluoro-2-methoxyphenyl)-2,2,4-trimethyl-1,2-dihydroquinoline (Compound No. 3-18)<br />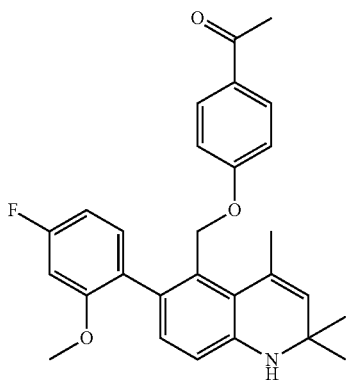 | $^1$H-NMR (400 MHz, DMSO-d$_6$) δ 1.10 (s, 3H), 1.16 (s, 3H), 2.06 (s, 3H), 2.46 (s, 3H), 3.71 (s, 3H), 4.62 (d, J = 11.7 Hz, 1H), 5.09 (d, J = 11.7 Hz, 1H), 5.40 (s, 1H), 6.02 (s, 1H), 6.63 (d, J = 8.3 Hz, 1H), 6.70 (td, J = 8.4, 2.4 Hz, 1H), 6.75 (d, J = 8.3 Hz, 1H), 6.80 (d, J = 8.7 Hz, 2H), 6.91 (dd, J = 11.5, 2.4 Hz, 1H), 7.17 (dd, J = 8.4, 7.1 Hz, 1H), 7.81 (d, J = 8.7 Hz, 2H) |
| 6-(4-Fluoro-2-methoxyphenyl)-5-(3-nitrophenoxymethyl)-2,2,4-trimethyl-1,2-dihydroquinoline (Compound No. 3-19)<br />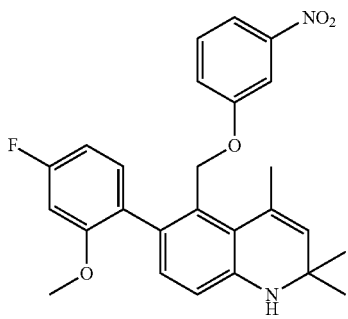 | $^1$H-NMR (400 MHz, DMSO-d$_6$) δ 1.02 (s, 3H), 1.15 (s, 3H), 2.12 (s, 3H), 3.72 (s, 3H), 4.68 (d, J = 12.2 Hz, 1H), 5.19 (d, J = 12.2 Hz, 1H), 5.41 (s, 1H), 6.02 (s, 1H), 6.62 (d, J = 8.3 Hz, 1H), 6.72 (t, 1H), 6.72 (td, J = 8.3, 2.4 Hz, 1H), 6.75 (d, J = 8.3 Hz, 1H), 6.92 (dd, J = 11.5, 2.4 Hz, 1H), 7.15 (dd, J = 8.1, 2.2 Hz, 1H), 7.19 (dd, J = 8.3, 7.1 Hz, 1H), 7.38 (t, J = 2.2 Hz, 1H), 7.45 (t, J = 8.1 Hz, 1H), 7.71 (dd, J = 8.1, 2.2 Hz, 1H) |

| | |
|---|---|
| 6-(4-Fluoro-2-methoxyphenyl)-5-(4-methylphenoxymethyl)-2,2,4-trimethyl-1,2-dihydroquinoline (Compound No. 3-20) 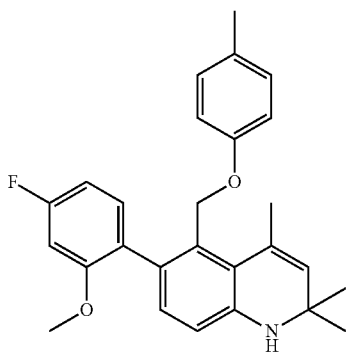 | $^1$H-NMR (400 MHz, DMSO-d$_6$) δ 1.13 (s, 3H), 1.17 (s, 3H), 2.07 (s, 3H), 2.16 (s, 3H), 3.71 (s, 3H), 4.45 (d, J = 11.2 Hz, 1H), 4.94 (d, J = 11.2 Hz, 1H), 5.39 (s, 1H), 5.98 (s, 1H), 6.58 (d, J = 8.3 Hz, 2H), 6.61 (d, J = 8.3 Hz, 1H), 6.69 (td, J = 8.4, 2.5 Hz, 1H), 6.72 (d, J = 8.3 Hz, 1H), 6.91 (dd, J = 11.5, 2.5 Hz, 1H), 6.96 (d, J = 8.3 Hz, 2H), 7.14 (dd, J = 8.4, 7.2 Hz, 1H) |
| 6-(4-Fluoro-2-methoxyphenyl)-5-(3-methylphenoxymethyl)-2,2,4-trimethyl-1,2-dihydroquinoline (Compound No. 3-21) 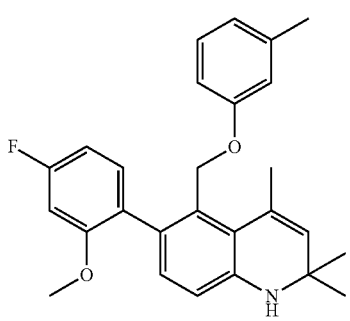 | $^1$H-NMR (400 MHz, DMSO-d$_6$) δ 1.12 (s, 3H), 1.17 (s, 3H), 2.07 (s, 3H), 2.18 (s, 3H), 3.71 (s, 3H), 4.48 (d, J = 11.4 Hz, 1H), 4.98 (d, J = 11.4 Hz, 1H), 5.39 (s, 1H), 5.99 (s, 1H), 6.47-6.50 (m, 2H), 6.61 (d, J = 8.2 Hz, 1H), 6.65 (d, J = 7.3 Hz, 1H), 6.69-6.73 (m, 1H), 6.72 (d, J = 8.2 Hz, 1H), 6.92 (dd, J = 11.5, 2.4 Hz, 1H), 7.03 (t, J = 7.7 Hz, 1H), 7.15 (dd, J = 8.3, 7.3 Hz, 1H) |
| 6-(4-Fluoro-2-methoxyphenyl)-5-(2-methylphenoxymethyl)-2,2,4-trimethyl-1,2-dihydroquinoline (Compound No. 3-22) 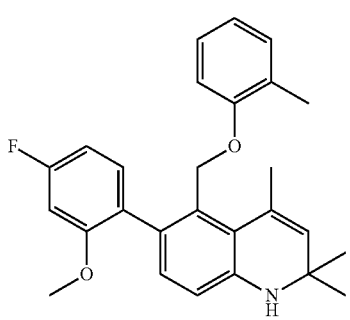 | $^1$H-NMR (400 MHz, DMSO-d$_6$) δ 1.08 (s, 3H), 1.17 (s, 3H), 2.03 (s, 3H), 2.05 (s, 3H), 3.74 (s, 3H), 4.56 (d, J = 11.9 Hz, 1H), 5.01 (d, J = 11.9 Hz, 1H), 5.39 (s, 1H), 6.01 (s, 1H), 6.53 (d, J = 7.8 Hz, 1H), 6.62 (d, J = 8.3 Hz, 1H), 6.70-6.74 (m, 1H), 6.74 (d, J = 8.3 Hz, 1H), 6.75 (td, J = 7.6, 2.4 Hz, 1H), 6.94 (dd, J = 11.5, 2.4 Hz, 1H), 6.95-7.00 (m, 1H), 7.03-7.05 (m, 1H), 7.18 (dd, J = 8.4, 7.2 Hz, 1H) |

6-(4-Fluoro-2-methoxyphenyl)-5-(3-oxo-2,3-dihydrobenzofuran-6-yloxymethyl)-2,2,4-trimethyl-1,2-dihydroquinoline (Compound No. 3-23)

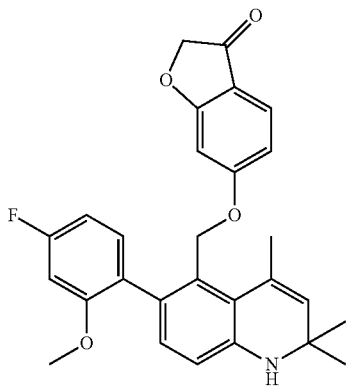

$^1$H-NMR (400 MHz, DMSO-d$_6$) δ 1.12 (s, 3H), 1.15 (s, 3H), 2.06 (s, 3H), 3.71 (s, 3H), 4.63 (d, J = 11.7 Hz, 1H), 4.70 (s, 2H), 5.11 (d, J = 11.7 Hz, 1H), 5.41 (s, 1H), 6.05 (s, 1H), 6.51-6.54 (m, 2H), 6.64 (d, J = 8.2 Hz, 1H), 6.71 (td, J = 8.5, 2.6 Hz, 1H), 6.75 (d, J = 8.2 Hz, 1H), 6.92 (dd, J = 11.5, 2.6 Hz, 1H), 7.14 (dd, J = 8.5, 7.1 Hz, 1H), 7.43 (d, J = 9.0 Hz, 1H)

5-(4-Cyanophenoxymethyl)-6-(4-fluoro-2-methoxyphenyl)-2,2,4-trimethyl-1,2-dihydroquinoline (Compound No. 3-24)

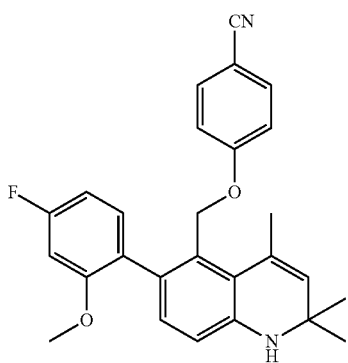

$^1$H-NMR (400 MHz, DMSO-d$_6$) δ 1.10 (s, 3H), 1.14 (s, 3H), 2.05 (s, 3H), 3.71 (s, 3H), 4.62 (d, J = 11.6 Hz, 1H), 5.09 (d, J = 11.6 Hz, 1H), 5.40 (s, 1H), 6.03 (s, 1H), 6.63 (d, J = 8.1 Hz, 1H), 6.69 (td, J = 8.4, 2.6 Hz, 1H), 6.74 (d, J = 8.1 Hz, 1H), 6.87 (d, J = 9.0 Hz, 2H), 6.90 (dd, J = 11.6, 2.6 Hz, 1H), 7.15 (dd, J = 8.4, 7.1 Hz, 1H), 7.64 (d, J = 9.0 Hz, 2H)

5-(3-Clorophenoxymethyl)-6-(4-fluoro-2-methoxyphenyl)-2,2,4-trimethyl-1,2-dihydroquinoline (Compound No. 3-25)

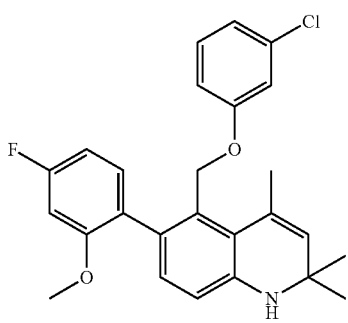

$^1$H-NMR (500 MHz, DMSO-d$_6$) δ 1.09 (s, 3H), 1.16 (s, 3H), 2.08 (s, 3H), 3.71 (s, 3H), 4.54 (d, J = 11.6 Hz, 1H), 5.05 (d, J = 11.6 Hz, 1H), 5.40 (s, 1H), 6.00 (s, 1H), 6.61 (d, J = 8.2 Hz, 1H), 6.67 (dd, J = 8.1, 2.2 Hz, 1H), 6.71-6.72 (m, 1H), 6.72 (td, J = 8.2, 2.5 Hz, 1H), 6.73 (d, J = 8.2 Hz, 1H), 6.89 (dd, J = 8.1, 2.2 Hz, 1H), 6.92 (dd, J = 11.5, 2.5 Hz, 1H), 7.14 (dd, J = 8.2, 6.7 Hz, 1H), 7.18 (t, J = 8.1 Hz, 1H)

| Compound | NMR |
|---|---|
| 6-(4-Fluoro-2-methoxyphenyl)-5-(2-hydroxymethylphenoxymethyl)-2,2,4-trimethyl-1,2-dihydroquinoline (Compound No. 3-26) 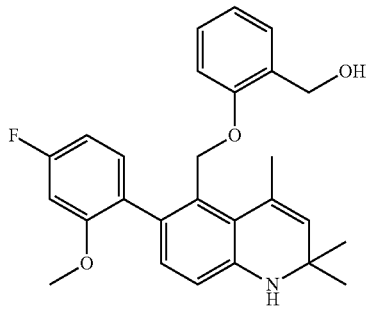 | $^1$H-NMR (500 MHz, DMSO-$d_6$) δ 1.10 (s, 3H), 1.18 (s, 3H), 2.01 (s, 3H), 3.73 (s, 3H), 4.39 (dd, J = 15.1, 5.8 Hz, 1H), 4.43 (dd, J = 15.1, 5.8 Hz, 1H), 4.55 (d, J =11.8 Hz, 1H), 4.84 (t, J = 5.8 Hz, 1H), 5.01 (d, J = 11.8 Hz, 1H), 5.39 (s, 1H), 6.01 (s, 1H), 6.55 (d, J = 7.5 Hz, 1H), 6.62 (d, J = 8.2 Hz, 1H), 6.71-6.75 (m, 1H), 6.74 (d, J = 8.2 Hz, 1H), 6.83 (t, J = 7.5 Hz, 1H), 6.93 (dd, J = 11.6, 1.9 Hz, 1H), 7.03 (td, J = 8.1, 1.9 Hz, 1H), 7.18 (dd, J = 8.1, 7.0 Hz, 1H), 7.30 (d, J = 7.5 Hz, 1H) |
| 6-(4-Fluoro-2-methoxyphenyl)-5-(4-methylthiophenoxymethyl)-2,2,4-trimethyl-1,2-dihydroquinoline (Compound No. 3-27) 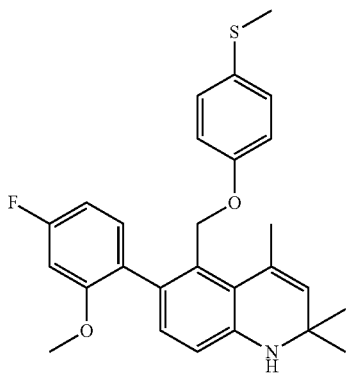 | $^1$H-NMR (500 MHz, DMSO-$d_6$) δ 1.12 (s, 3H), 1.16 (s, 3H), 2.07 (s, 3H), 2.37 (s, 3H), 3.71 (s, 3H), 4.49 (d, J = 11.5 Hz, 1H), 4.97 (d, J = 11.5 Hz, 1H), 5.39 (s, 1H), 5.98 (s, 1H), 6.61 (d, J = 8.2 Hz, 1H), 6.67 (d, J = 8.8 Hz, 2H), 6.66-6.73 (m, 1H), 6.72 (d, J = 8.2 Hz, 1H), 6.91 (dd, J = 11.6, 2.4 Hz, 1H), 7.11 (d, J = 8.8 Hz, 2H), 7.14 (dd, J = 8.4, 7.2 Hz, 1H) |
| 5-(4-Ethoxyphenoxymethyl)-6-(4-fluoro-2-methoxyphenyl)-2,2,4-trimethyl-1,2-dihydroquinoline (Compound No. 3-28) 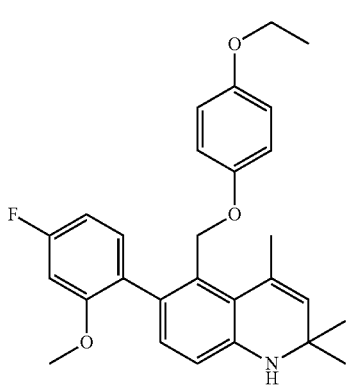 | $^1$H-NMR (400 MHz, DMSO-$d_6$) δ 1.13 (s, 3H), 1.17 (s, 3H), 1.26 (t, J = 7.0 Hz, 3H), 2.08 (s, 3H), 3.70 (s, 3H), 3.89 (q, J = 7.0 Hz, 2H), 4.42 (d, J = 11.2 Hz, 1H), 4.93 (d, J = 11.2 Hz, 1H), 5.39 (s, 1H), 5.97 (s, 1H), 6.59-6.62 (m, 3H), 6.67-6.72 (m, 4H), 6.90 (dd, J = 11.5, 2.4 Hz, 1H), 7.13 (dd, J = 8.3, 7.1 Hz, 1H) |

| Compound | 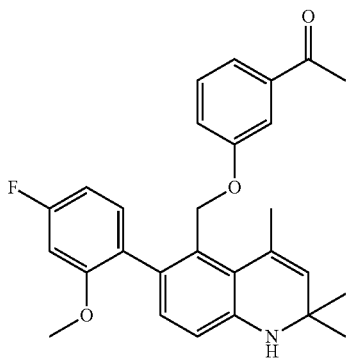 <br> 5-(3-Acetylphenoxymethyl)-6-(4-fluoro-2-methoxyphenyl)-2,2,4-trimethyl-1,2-dihydroquinoline (Compound No. 3-29) | $^1$H-NMR (400 MHz, DMSO-d$_6$) δ 1.08 (s, 3H), 1.17 (s, 3H), 2.09 (s, 3H), 2.49 (s, 3H), 3.71 (s, 3H), 4.59 (d, J = 11.6 Hz, 1H), 5.09 (d, J = 11.6 Hz, 1H), 5.40 (s, 1H), 6.00 (s, 1H), 6.61 (d, J = 8.3 Hz, 1H), 6.70 (td, J = 8.5, 2.5 Hz, 1H), 6.73 (d, J = 8.3 Hz, 1H), 6.90 (dd, J = 11.5, 2.5 Hz, 1H), 6.97 (ddd, J = 8.2, 2.6, 0.8 Hz, 1H), 7.16-7.20 (m, 2H), 7.32 (t, J = 7.8 Hz, 1H), 7.46 (dt, J = 7.8, 1.2 Hz, 1H) |
|---|---|---|
| | 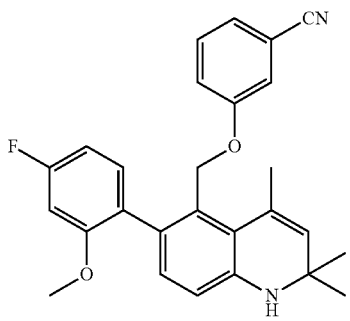 <br> 5-(3-Cyanophenoxymethyl)-6-(4-fluoro-2-methoxyphenyl)-2,2,4-trimethyl-1,2-dihydroquinoline (Compound No. 3-30) | $^1$H-NMR (400 MHz, DMSO-d$_6$) δ 1.09 (s, 3H), 1.14 (s, 3H), 2.08 (s, 3H), 3.71 (s, 3H), 4.59 (d, J = 11.7 Hz, 1H), 5.09 (d, J = 11.7 Hz, 1H), 5.41 (s, 1H), 6.02 (s, 1H), 6.62 (d, J = 8.2 Hz, 1H), 6.70 (td, J = 8.4, 2.6 Hz, 1H), 6.74 (d, J = 8.2 Hz, 1H), 6.92 (dd, J = 11.6, 2.6 Hz, 1H), 7.03 (dd, J = 7.9, 2.3 Hz, 1H), 7.12 (d, J = 2.3 Hz, 1H), 7.14 (dd, J = 8.4, 7.2 Hz, 1H), 7.30 (d, J = 7.9 Hz, 1H), 7.37 (t, J = 7.9 Hz, 1H) |
| | 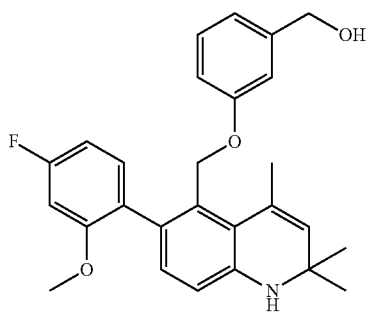 <br> 6-(4-Fluoro-2-methoxyphenyl)-5-(3-hydroxymethylphenoxymethyl)-2,2,4-trimethyl-1,2-dihydroquinoline (Compound No. 3-31) | $^1$H-NMR (400 MHz, DMSO-d$_6$) δ 1.13 (s, 3H), 1.18 (s, 3H), 2.06 (s, 3H), 3.71 (s, 3H), 4.38 (d, J = 5.9 Hz, 2H), 4.49 (d, J = 11.0 Hz, 1H), 4.98 (d, J = 11.0 Hz, 1H), 5.09 (t, J = 5.9 Hz, 1H), 5.39 (s, 1H), 5.99 (s, 1H), 6.56 (dd, J = 7.7, 2.1 Hz, 1H), 6.61 (dd, J = 8.2 Hz, 1H), 6.66-6.72 (m, 2H), 6.80 (d, J = 7.7 Hz, 1H), 6.72 (d, J = 8.2 Hz, 1H), 6.91 (dd, J = 11.5, 2.4 Hz, 1H), 7.11 (t, J = 7.7 Hz, 1H), 7.15 (dd, J = 8.3, 7.3 Hz, 1H) |

| | | |
|---|---|---|
| 5-(2-Cyanophenoxymethyl)-6-(4-fluoro-2-methoxyphenyl)-2,2,4-trimethyl-1,2-dihydroquinoline (Compound No. 3-32) 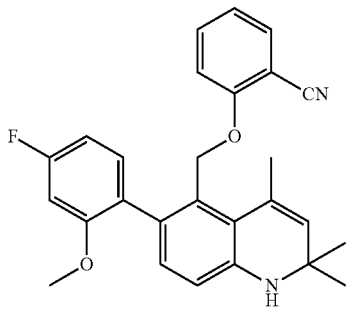 | | $^1$H-NMR (500 MHz, DMSO-d$_6$) δ 1.05 (s, 3H), 1.12 (s, 3H), 2.10 (s, 3H), 3.73 (s, 3H), 4.66 (d, J = 11.9 Hz, 1H), 5.20 (d, J = 11.9 Hz, 1H), 5.41 (s, 1H), 6.04 (s, 1H), 6.64 (d, J = 8.3 Hz, 1H), 6.72 (td, J = 8.4, 2.4 Hz, 1H), 6.76 (d, J = 8.3 Hz, 1H), 6.80 (d, J = 8.6 Hz, 1H), 6.93 (dd, J = 11.3, 2.4 Hz, 1H), 6.98 (t, J = 7.6 Hz, 1H), 7.20 (dd, J = 8.4, 7.2 Hz, 1H), 7.45-7.49 (m, 1H), 7.63 (dd, J = 7.6, 1.5 Hz, 1H) |
| 5-(2-Ethylphenoxymethyl)-6-(4-fluoro-2-methoxyphenyl)-2,2,4-trimethyl-1,2-dihydroquinoline (Compound No. 3-33) 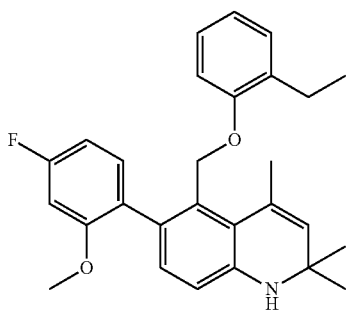 | | $^1$H-NMR (500 MHz, DMSO-d$_6$) δ 1.02 (t, J = 7.4 Hz, 3H), 1.10 (s, 3H), 1.18 (s, 3H), 2.01 (s, 3H), 2.45-2.49 (m, 2H), 3.73 (s, 3H), 4.57 (d, J = 11.6 Hz, 1H), 5.01 (d, J =11.6 Hz, 1H), 5.37 (s, 1H), 6.02 (s, 1H), 6.58 (d, J = 7.6 Hz, 1H), 6.64 (d, J = 8.2 Hz, 1H), 6.72-6.78 (m, 2H), 6.75 (d, J = 8.2 Hz, 1H), 6.93 (dd, J = 11.3, 2.4 Hz, 1H), 7.00 (td, J = 7.6, 1.5 Hz, 1H), 7.05 (dd, J = 7.6, 1.5 Hz, 1H), 7.16 (dd, J = 8.3, 7.3 Hz, 1H) |
| 5-(2-Ethoxyphenoxymethyl)-6-(4-fluoro-2-methoxyphenyl)-2,2,4-trimethyl-1,2-dihydroquinoline (Compound No. 3-34) 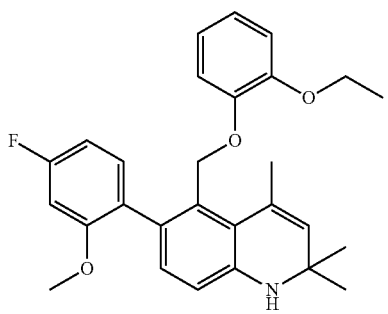 | | $^1$H-NMR (400 MHz, DMSO-d$_6$) δ 1.14 (s, 3H), 1.17 (s, 3H), 1.23 (t, J = 6.9 Hz, 3H), 2.11 (s, 3H), 3.71 (s, 3H), 3.90 (q, J = 6.9 Hz, 2H), 4.47 (d, J = 11.7 Hz, 1H), 5.05 (d, J = 11.7 Hz, 1H), 5.38 (s, 1H), 5.98 (s, 1H), 6.59 (dd, J = 7.8, 1.6 Hz, 1H), 6.61 (d, J = 8.2 Hz, 1H), 6.67 (td, J = 8.3, 2.5 Hz, 1H), 6.71 (td, J = 7.8, 1.6 Hz, 1H), 6.71 (d, J = 8.2 Hz, 1H), 6.78 (td, J = 7.8, 1.6 Hz, 1H), 6.85 (dd, J = 7.8, 1.6 Hz, 1H), 6.91 (dd, J = 11.5, 2.5 Hz, 1H), 7.13 (dd, J = 8.3, 7.3 Hz, 1H) |

| | |
|---|---|
| 5-(4-Carbamoylphenoxymethyl)-6-(4-fluoro-2-methoxyphenyl)-2,2,4-trimethyl-1,2-dihydroquinoline (Compound No. 3-35) 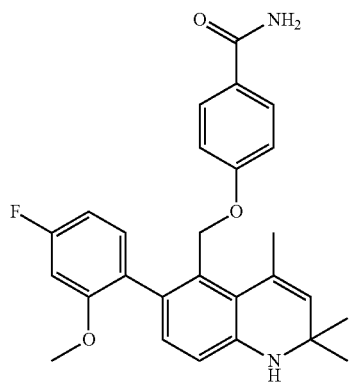 | $^1$H-NMR (400 MHz, DMSO-d$_6$) δ 1.11 (s, 3H), 1.15 (s, 3H), 2.07 (s, 3H), 3.71 (s, 3H), 4.57 (d, J = 11.5 Hz, 1H), 5.05 (d, J = 11.5 Hz, 1H), 5.40 (s, 1H), 6.01 (s, 1H), 6.62 (d, J = 8.2 Hz, 1H), 6.70 (td, J = 8.5, 2.6 Hz, 1H), 6.73 (d, J = 8.8 Hz, 2H), 6.74 (d, J = 8.2 Hz, 1H), 6.91 (dd, J = 11.5, 2.6 Hz, 1H), 7.12 (br s, 1H), 7.16 (dd, J = 8.5, 7.2 Hz, 1H), 7.71 (d, J = 8.8 Hz, 2H), 7.75 (br s, 1H) |
| 6-(4-Fluoro-2-methoxyphenyl)-5-(4-nitrophenoxymethyl)-2,2,4-trimethyl-1,2-dihydroquinoline (Compound No. 3-36) 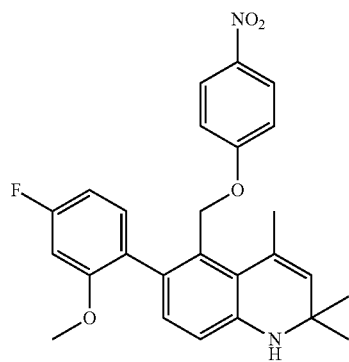 | $^1$H-NMR (400 MHz, DMSO-d$_6$) δ 1.09 (s, 3H), 1.15 (s, 3H), 2.06 (s, 3H), 3.71 (s, 3H), 4.68 (d, J = 11.7 Hz, 1H), 5.15 (d, J = 11.7 Hz, 1H), 5.41 (s, 1H), 6.06 (s, 1H), 6.64 (d, J = 8.3 Hz, 1H), 6.70 (td, J = 8.4, 2.5 Hz, 1H), 6.75 (d, J = 8.3 Hz, 1H), 6.89-6.93 (m, 1H), 6.91 (d, J = 9.3 Hz, 2H), 7.17 (dd, J = 8.4, 7.1 Hz, 1H), 8.09 (d, J = 9.3 Hz, 2H) |
| 5-(2-Carbamoylphenoxymethyl)-6-(4-fluoro-2-methoxyphenyl)-2,2,4-trimethyl-1,2-dihydroquinoline (Compound No. 3-37) 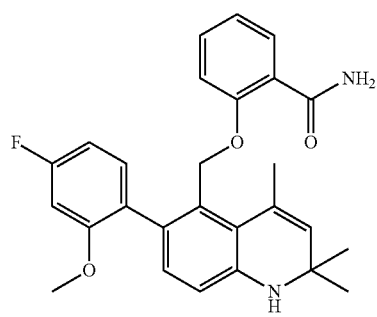 | $^1$H-NMR (400 MHz, DMSO-d$_6$) δ 1.14 (s, 3H), 1.18 (s, 3H), 2.01 (s, 3H), 3.64 (s, 3H), 4.81 (d, J = 10.7 Hz, 1H), 5.05 (d, J = 10.7 Hz, 1H), 5.42 (s, 1H), 6.10 (s, 1H), 6.68 (d, J = 8.3 Hz, 1H), 6.72 (td, J = 8.3, 2.5 Hz, 1H), 6.76 (d, J = 8.3 Hz, 1H), 6.86-6.95 (m, 2H), 6.99 (t, J = 7.6 Hz, 1H), 7.14 (dd, J = 8.3, 7.1 Hz, 1H), 7.33 (s, 1H), 7.34-7.41 (m, 1H), 7.50 (s, 1H), 7.88 (dd, J = 7.6, 1.7 Hz, 1H) |

| | |
|---|---|
| 6-(4-Fluoro-2-methoxyphenyl)-5-(2-nitrophenoxymethyl)-2,2,4-trimethyl-1,2-dihydroquinoline (Compound No. 3-38) 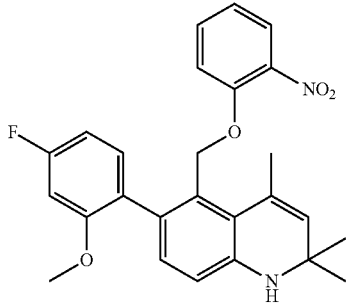 | $^1$H-NMR (400 MHz, DMSO-d$_6$) δ 1.06 (s, 3H), 1.12 (s, 3H), 2.06 (s, 3H), 3.71 (s, 3H), 4.67 (d, J = 11.7 Hz, 1H), 5.21 (d, J = 11.7 Hz, 1H), 5.38 (s, 1H), 6.04 (s, 1H), 6.63 (d, J = 8.3 Hz, 1H), 6.69 (td, J = 8.4, 2.5 Hz, 1H), 6.75 (d, J = 8.3 Hz, 1H), 6.90-6.94 (m, 2H) 6.98-7.02 (m, 1H), 7.14 (dd, J = 8.4, 7.1 Hz, 1H), 7.44-7.48 (m, 1H), 7.77 (dd, J = 8.1, 1.7 Hz, 1H) |
| 6-(4-Fluoro-2-methoxyphenyl)-5-(2-methylthiophenoxymethyl)-2,2,4-trimethyl-1,2-dihydroquinoline (Compound No. 3-39) 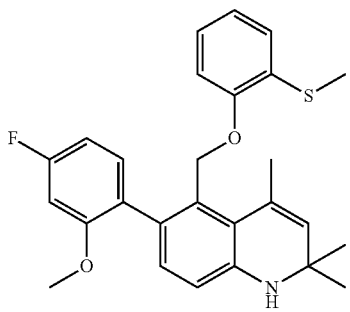 | $^1$H-NMR (400 MHz, DMSO-d$_6$) δ 1.15 (s, 3H), 1.16 (s, 3H), 2.05 (s, 3H), 2.30 (s, 3H), 3.71 (s, 3H), 4.49 (d, J = 11.2 Hz, 1H), 5.06 (d, J = 11.2 Hz, 1H), 5.37 (s, 1H), 6.01 (s, 1H), 6.59-6.69 (m, 2H), 6.63 (d, J = 8.3 Hz, 1H), 6.75 (d, J = 8.3 Hz, 1H), 6.86 (td, J = 7.6, 1.5 Hz, 1H), 6.91 (dd, J = 11.5, 2.4 Hz, 1H), 6.97 (td, J = 7.6, 1.5 Hz, 1H), 7.08 (dd, J = 7.6, 1.5 Hz, 1H), 7.21 (dd, J = 8.4, 7.2 Hz, 1H) |
| 6-(4-Fluoro-2-methoxyphenyl)-5-(4-hydroxymethylphenoxymethyl)-2,2,4-trimethyl-1,2-dihydroquinoline (Compound No. 3-40) 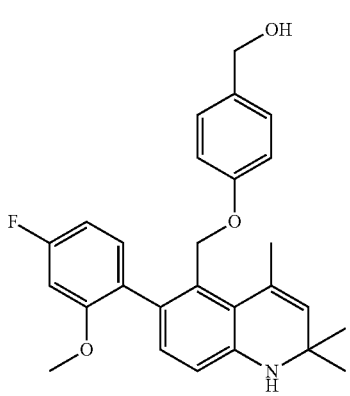 | $^1$H-NMR (400 MHz, DMSO-d$_6$) δ 1.13 (s, 3H), 1.17 (s, 3H), 2.07 (s, 3H), 3.71 (s, 3H), 4.34 (d, J = 5.9 Hz, 2H), 4.48 (d, J = 11.2 Hz, 1H), 4.95-4.99 (m, 2H), 5.39 (s, 1H), 5.98 (s, 1H), 6.61 (d, J = 8.3 Hz, 1H), 6.65 (d, J = 8.5 Hz, 2H), 6.67-6.73 (m, 1H), 6.72 (d, J = 8.3 Hz, 1H), 6.91 (dd, J = 11.5, 2.7 Hz, 1H), 7.10 (d, J = 8.5 Hz, 2H), 7.15 (dd, J = 8.3, 7.1 Hz, 1H) |

| | |
|---|---|
| 6-(4-Fluoro-2-methoxyphenyl)-5-(1-naphthoxymethyl)-2,2,4-trimethyl-1,2-dihydroquinoline (Compound No. 3-41)<br>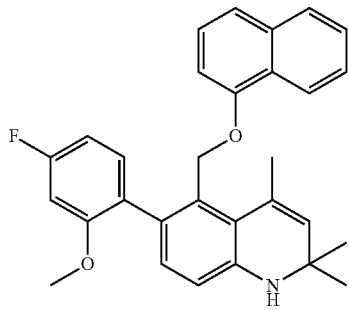 | $^1$H-NMR (500 MHz, DMSO-d$_6$) δ 1.11 (s, 3H), 1.19 (s, 3H), 2.04 (s, 3H), 3.72 (s, 3H), 4.78 (d, J = 11.3 Hz, 1H), 5.16 (d, J = 11.3 Hz, 1H), 5.38 (s, 1H), 6.06 (s, 1H), 6.63-6.70 (m, 2H), 6.67 (d, J = 7.9 Hz, 1H), 6.78 (d, J = 7.9 Hz, 1H), 6.92 (dd, J = 11.6, 2.4 Hz, 1H), 7.20 (dd, J = 8.4, 7.2 Hz, 1H), 7.28 (t, J = 7.9 Hz, 1H), 7.36-7.43 (m, 2H), 7.46-7.49 (m, 1H), 7.80 (d, J = 7.9 Hz, 1H), 8.04 (d, J = 8.6 Hz, 1H) |
| 5-(2-Chlorophenoxymethyl)-6-(4-fluoro-2-methoxyphenyl)-2,2,4-trimethyl-1,2-dihydroquinoline (Compound No. 3-42)<br>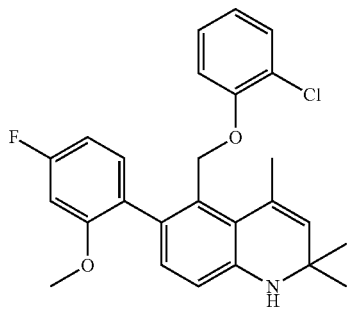 | $^1$H-NMR (400 MHz, DMSO-d$_6$) δ 1.10 (s, 3H), 1.15 (s, 3H), 2.08 (s, 3H), 3.72 (s, 3H), 4.56 (d, J = 11.7 Hz, 1H), 5.12 (d, J = 11.7 Hz, 1H), 5.39 (s, 1H), 6.03 (s, 1H), 6.63 (d, J = 8.2 Hz, 1H), 6.69 (td, J = 8.5, 2.6 Hz, 1H), 6.74 (dd, J = 8.2, 1.5 Hz, 1H), 6.75 (d, J = 8.2 Hz, 1H), 6.84 (td, J = 7.6, 1.5 Hz, 1H), 6.92 (dd, J = 11.6, 2.6 Hz, 1H), 7.12 (ddd, J = 8.2, 7.6, 1.6 Hz, 1H), 7.19 (dd, J = 8.5, 7.1 Hz, 1H), 7.33 (dd, J = 7.6, 1.6 Hz, 1H) |
| 6-(4-Fluoro-2-methoxyphenyl)-5-(2-methyl-1-naphthoxymethyl)-2,2,4-trimethyl-1,2-dihydroquinoline (Compound No. 3-43)<br>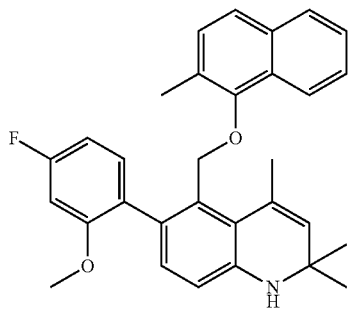 | $^1$H-NMR (400 MHz, DMSO-d$_6$) δ 1.23 (s, 3H), 1.30 (s, 3H), 1.97 (s, 3H), 2.38 (s, 3H), 3.52 (s, 3H), 4.73 (d, J = 12.8 Hz, 1H), 5.38 (d, J = 12.8 Hz, 1H), 5.51 (s, 1H), 6.00 (s, 1H), 6.20-6.24 (m, 1H), 6.29 (td, J = 8.4, 2.5 Hz, 1H), 6.53 (d, J = 8.2 Hz, 1H), 6.60 (d, J = 8.2 Hz, 1H), 6.68 (dd, J = 11.6, 2.5 Hz, 1H), 7.16 (d, J = 8.3 Hz, 1H), 7.24-7.20 (m, 1H), 7.31-7.35 (m, 1H), 7.48 (d, J = 8.3 Hz, 1H), 7.60 (d, J = 8.1 Hz, 1H), 7.75 (d, J = 8.1 Hz, 1H) |
| 6-(4-Fluoro-2-methoxyphenyl)-5-(2,3,5-trimethylphenoxymethyl)-2,2,4-trimethyl-1,2-dihydroquinoline (Compound No. 3-44)<br>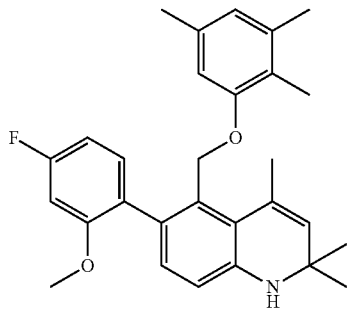 | $^1$H-NMR (400 MHz, DMSO-d$_6$) δ 1.07 (s, 3H), 1.19 (s, 3H), 1.91 (s, 3H), 2.04 (s, 3H), 2.09 (s, 3H), 2.10 (s, 3H), 3.74 (s, 3H), 4.53 (d, J = 11.8 Hz, 1H), 4.99 (d, J = 11.8 Hz, 1H), 5.38 (s, 1H), 6.00 (s, 1H), 6.17 (s, 1H), 6.45 (s, 1H), 6.61 (d, J = 8.2 Hz, 1H), 6.73 (d, J = 8.2 Hz, 1H), 6.76 (td, J = 8.4, 2.4 Hz, 1H), 6.95 (dd, J = 11.5, 2.4 Hz, 1H), 7.17 (dd, J = 8.4, 7.1 Hz, 1H) |

6-(4,5-Difluoro-2-methoxyphenyl)-5-(2-methylphenoxymethyl)-2,2,4-trimethyl-1,2-dihydroquinoline (Compound No. 3-45)

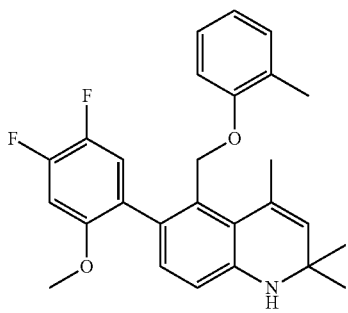

$^1$H-NMR (500 MHz, DMSO-d$_6$) δ 1.11 (s, 3H), 1.17 (s, 3H), 2.03 (s, 3H), 2.05 (s, 3H), 3.72 (s, 3H), 4.54 (d, J = 11.6 Hz, 1H), 5.02 (d, J = 11.6 Hz, 1H), 5.40 (s, 1H), 6.08 (s, 1H), 6.58 (d, J = 7.7 Hz, 1H), 6.64 (d, J = 8.1 Hz, 1H), 6.74 (t, J = 7.7 Hz, 1H), 6.77 (d, J = 8.1 Hz, 1H), 6.95-7.03 (m, 1H), 7.05 (d, J = 7.7 Hz, 1H), 7.17 (dd, J = 13.1, 7.0 Hz, 1H), 7.23 (dd, J = 11.3, 9.5 Hz, 1H)

5-(2,3-Dimethylphenoxymethyl)-6-(4-fluoro-2-methoxyphenyl)-2,2,4-trimethyl-1,2-dihydroquinoline (Compound No. 3-46)

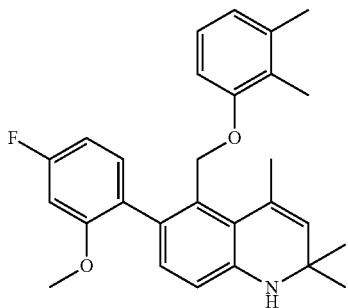

$^1$H-NMR (500 MHz, DMSO-d$_6$) δ 1.09 (s, 3H), 1.18 (s, 3H), 1.96 (s, 3H), 2.01 (s, 3H), 2.14 (s, 3H), 3.73 (s, 3H), 4.53 (d, J = 11.5 Hz, 1H), 4.97 (d, J = 11.5 Hz, 1H), 5.38 (s, 1H), 6.06 (s, 1H), 6.41 (d, J = 7.9 Hz, 1H), 6.64 (d, J = 7.9 Hz, 1H), 6.62 (d, J = 8.1 Hz, 1H), 6.74 (dd, J = 8.4, 2.5 Hz, 1H), 6.74 (d, J = 8.1 Hz, 1H), 6.87 (t, J = 7.9 Hz, 1H), 6.93 (dd, J = 11.3, 2.5 Hz, 1H), 7.16 (dd, J = 8.4, 7.0 Hz, 1H)

5-(2,6-Dimethylphenoxymethyl)-6-(4-fluoro-2-methoxyphenyl)-2,2,4-trimethyl-1,2-dihydroquinoline (Compound No. 3-47)

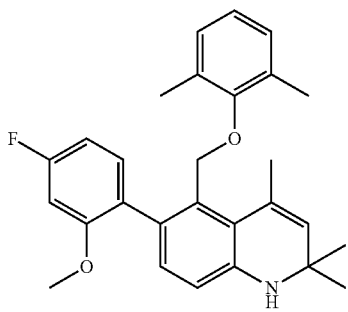

$^1$H-NMR (400 MHz, DMSO-d$_6$) δ 1.15 (s, 3H), 1.25 (s, 3H), 1.80 (s, 6H), 2.33 (s, 3H), 3.60 (s, 3H), 4.50 (d, J = 12.8 Hz, 1H), 5.16 (d, J = 12.8 Hz, 1H), 5.43 (s, 1H), 5.95 (s, 1H), 6.49 (td, J = 8.2, 2.3 Hz, 1H), 6.51 (t, J = 7.5 Hz, 1H), 6.60 (br s, 2H), 6.74-6.82 (m, 2H), 6.78 (d, J = 7.5 Hz, 2H)

| | |
|---|---|
| 6-(4-Fluoro-2-methoxyphenyl)-5-(5-fluoro-2-methylphenoxymethyl)-2,2,4-trimethyl-1,2-dihydroquinoline (Compound No. 3-48)<br />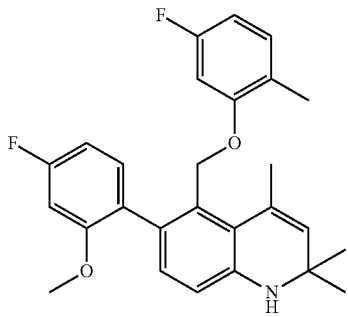 | $^1$H-NMR (400 MHz, DMSO-d$_6$) δ 1.06 (s, 3H), 1.15 (s, 3H), 2.01 (s, 3H), 2.06 (s, 3H), 3.74 (s, 3H), 4.58 (d, J = 12.1 Hz, 1H), 5.05 (d, J = 12.1 Hz, 1H), 5.39 (s, 1H), 6.03 (s, 1H), 6.36 (dd, J = 11.5, 2.4 Hz, 1H), 6.53 (td, J = 8.4, 2.4 Hz, 1H), 6.62 (d, J = 8.1 Hz, 1H), 6.75 (d, J = 8.1 Hz, 1H), 6.76 (td, J = 8.2, 2.2 Hz, 1H), 6.95 (dd, J = 11.5, 2.2 Hz, 1H), 7.03 (t, J = 7.7 Hz, 1H), 7.16 (dd, J = 8.4, 7.1 Hz, 1H) |
| 5-(3,5-Dimethylphenoxymethyl)-6-(4-fluoro-2-methoxyphenyl)-2,2,4-trimethyl-1,2-dihydroquinoline (Compound No. 3-49)<br />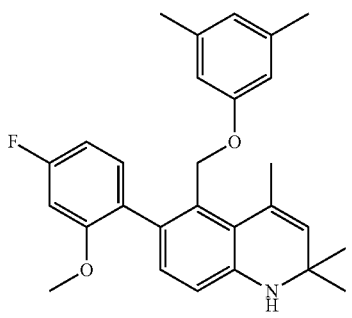 | $^1$H-NMR (400 MHz, DMSO-d$_6$) δ 1.11 (s, 3H), 1.18 (s, 3H), 2.08 (s, 3H), 2.13 (s, 6H), 3.70 (s, 3H), 4.47 (d, J = 11.4 Hz, 1H), 4.97 (d, J = 11.4 Hz, 1H), 5.39 (s, 1H), 5.97 (s, 1H), 6.28 (s, 2H), 6.47 (s, 1H), 6.60 (d, J = 8.2 Hz, 1H), 6.71 (d, J = 8.2 Hz, 1H), 6.73 (td, J = 8.3, 2.4 Hz, 1H), 6.92 (dd, J = 11.5, 2.4 Hz, 1H), 7.14 (dd, J = 8.3, 7.1 Hz, 1H) |
| 6-(4-Fluoro-2-methoxyphenyl)-5-(2,3,6-trimethylphenoxymethyl)-2,2,4-trimethyl-1,2-dihydroquinoline (Compound No. 3-50)<br />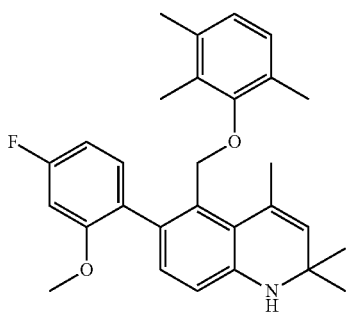 | $^1$H-NMR (400 MHz, DMSO-d$_6$) δ 1.15 (s, 3H), 1.26 (s, 3H), 1.69 (s, 3H), 1.75 (s, 3H), 2.03 (s, 3H), 2.33 (s, 3H), 3.60 (s, 3H), 4.45 (d, J = 12.7 Hz, 1H), 5.16 (d, J = 12.7 Hz, 1H), 5.44 (s, 1H), 5.94 (s, 1H), 6.37-6.48 (m, 2H), 6.57 (d, J = 8.3 Hz, 1H), 6.59 (d, J = 8.3 Hz, 1H), 6.67 (d, J = 8.1 Hz, 1H), 6.69 (d, J = 8.1 Hz, 1H), 6.78 (dd, J = 11.5, 2.2 Hz, 1H) |

| | |
|---|---|
| 6-(4-Fluoro-2-methoxyphenyl)-5-(2-methoxycarbonylphenoxymethyl)-2,2,4-trimethyl-1,2-dihydroquinoline (Compound No. 3-51) 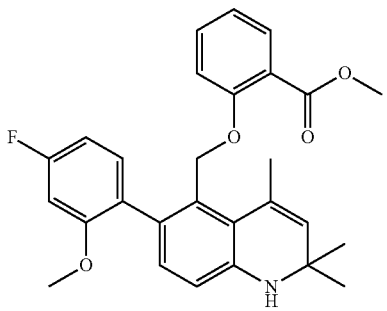 | $^1$H-NMR (500 MHz, DMSO-d$_6$) δ 1.05 (s, 3H), 1.13 (s, 3H), 2.10 (s, 3H), 3.72 (s, 3H), 3.73 (s, 3H), 4.56 (d, J = 11.9 Hz, 1H), 5.13 (d, J = 11.9 Hz, 1H), 5.36 (s, 1H), 5.97 (s, 1H), 6.60 (d, J = 8.2 Hz, 1H), 6.66-6.70 (m, 2H), 6.73 (d, J = 8.2 Hz, 1H), 6.89 (t, J = 7.5 Hz, 1H), 6.92 (dd, J = 11.6, 2.4 Hz, 1H), 7.21 (dd, J = 8.2, 7.0 Hz, 1H), 7.29-7.32 (m, 1H), 7.53 (dd, J = 7.6, 1.8 Hz, 1H) |
| 6-(4-Fluoro-2-methoxyphenyl)-5-(pyridin-3-yloxymethyl)-2,2,4-trimethyl-1,2-dihydroquinoline (Compound No. 3-52) 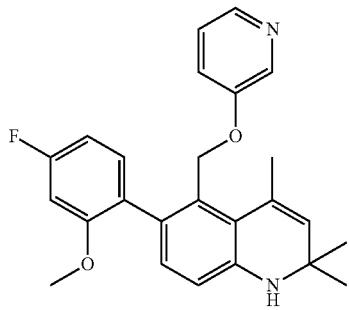 | $^1$H-NMR (500 MHz, DMSO-d$_6$) δ 1.09 (s, 3H), 1.15 (s, 3H), 2.10 (s, 3H), 3.71 (s, 3H), 4.59 (d, J = 11.6 Hz, 1H), 5.09 (d, J = 11.6 Hz, 1H), 5.41 (s, 1H), 6.01 (s, 1H), 6.62 (d, J = 8.2 Hz, 1H), 6.70 (td, J = 8.5, 2.6 Hz, 1H), 6.74 (d, J = 8.2 Hz, 1H), 6.91 (dd, J = 11.5, 2.6 Hz, 1H), 7.07-7.09 (m, 1H), 7.15 (dd, J = 8.5, 7.0 Hz, 1H), 7.19 (dd, J = 8.6, 4.6 Hz, 1H), 8.04 (d, J = 2.7 Hz, 1H), 8.06 (dd, J = 4.6, 1.2 Hz, 1H) |
| 6-(4-Fluoro-2-methoxyphenyl)-5-(3-methoxycarbonylphenoxymethyl)-2,2,4-trimethyl-1,2-dihydroquinoline (Compound No. 3-53) 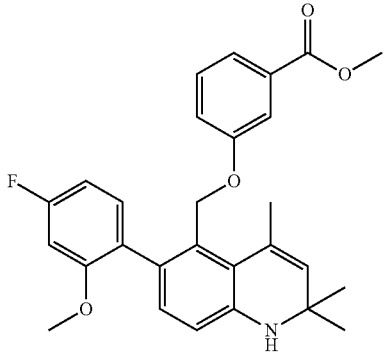 | $^1$H-NMR (400 MHz, DMSO-d$_6$) δ 1.02 (s, 3H), 1.17 (s, 3H), 2.10 (s, 3H), 3.72 (s, 3H), 3.81 (s, 3H), 4.61 (d, J = 12.0 Hz, 1H), 5.10 (d, J = 12.0 Hz, 1H), 5.40 (s, 1H), 6.00 (s, 1H), 6.60 (d, J = 8.1 Hz, 1H), 6.73 (td, J = 8.4, 2.6 Hz, 1H), 6.73 (d, J = 8.1 Hz, 1H), 6.92 (dd, J = 11.5, 2.6 Hz, 1H), 6.96 (ddd, J = 8.0, 2.5, 1.2 Hz, 1H), 7.15 (dd, J = 2.5, 1.2 Hz, 1H), 7.18 (dd, J = 8.4, 7.2 Hz, 1H), 7.30 (t, J = 8.0 Hz, 1H), 7.44 (dt, J = 8.0, 1.2 Hz, 1H) |

| | |
|---|---|
| 5-(3-Dimethylaminophenyoxymethyl)-6-(4-fluoro-2-methoxyphenyl)-2,2,4-trimethyl-1,2-dihydroquinoline (Compound No. 3-54)<br/>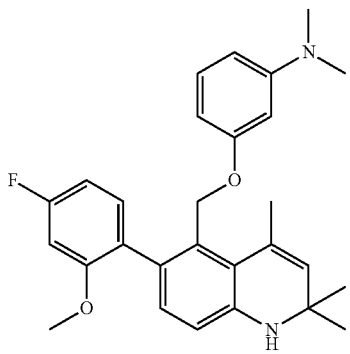 | $^1$H-NMR (400 MHz, DMSO-d$_6$) δ 1.14 (s, 3H), 1.18 (s, 3H), 2.09 (s, 3H), 2.80 (s, 6H), 3.71 (s, 3H), 4.46 (d, J = 11.1 Hz, 1H), 4.97 (d, J = 11.1 Hz, 1H), 5.39 (s, 1H), 5.97-6.03 (m, 3H), 6.23 (dd, J = 8.1, 2.4 Hz, 1H), 6.60 (d, J = 8.2 Hz, 1H), 6.70 (td, J = 8.4, 2.6 Hz, 1H), 6.72 (d, J = 8.2 Hz, 1H), 6.91 (dd, J = 11.5, 2.6 Hz, 1H), 6.94 (t, J = 8.1 Hz, 1H), 7.14 (dd, J = 8.4, 7.2 Hz, 1H) |
| 6-(4-Fluoro-2-methoxyphenyl)-5-(2-trifluoromethylphenoxymethyl)-2,2,4-trimethyl-1,2-dihydroquinoline (Compound No. 3-55)<br/>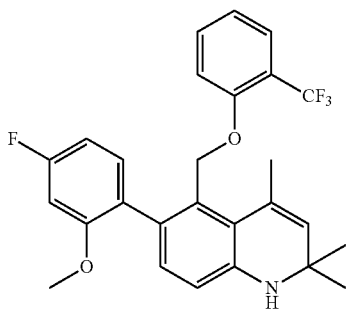 | $^1$H-NMR (500 MHz, DMSO-d$_6$) δ 1.11 (s, 3H), 1.14 (s, 3H), 2.02 (s, 3H), 3.71 (s, 3H), 4.58 (d, J = 11.5 Hz, 1H), 5.14 (d, J = 11.5 Hz, 1H), 5.37 (s, 1H), 6.04 (s, 1H), 6.65 (d, J = 8.2 Hz, 1H), 6.67 (td, J = 8.3, 2.5 Hz, 1H), 6.76 (d, J = 8.2 Hz, 1H), 6.90 (d, J = 7.9 Hz, 1H), 6.93 (dd, J = 11.5, 2.5 Hz, 1H), 7.00 (t, J = 7.9 Hz, 1H), 7.16 (dd, J = 8.3, 7.0 Hz, 1H), 7.46 (td, J = 7.9, 1.5 Hz, 1H), 7.54 (dd, J = 7.9, 1.5 Hz, 1H) |
| 6-(4-Fluoro-2-methoxyphenyl)-5-(5-chloro-2-methylphenoxymethyl)-2,2,4-trimethyl-1,2-dihydroquinoline (Compound No. 3-56)<br/>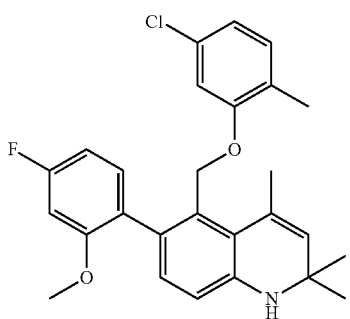 | $^1$H-NMR (500 MHz, DMSO-d$_6$) δ 1.00 (s, 3H), 1.17 (s, 3H), 2.02 (s, 3H), 2.09 (s, 3H), 3.74 (s, 3H), 4.60 (d, J = 12.2 Hz, 1H), 5.11 (d, J = 12.2 Hz, 1H), 5.39 (s, 1H), 6.02 (s, 1H), 6.46 (s, 1H), 6.61 (d, J = 8.1 Hz, 1H), 6.74 (d, J = 8.1 Hz, 1H), 6.76 (d, J = 7.9 Hz, 1H), 6.78 (td, J = 8.7, 2.4 Hz, 1H), 6.96 (dd, J = 11.5, 2.4 Hz, 1H), 7.04 (d, J = 7.9 Hz, 1H), 7.18 (dd, J = 8.7, 7.2 Hz, 1H) |

| Compound | NMR |
|---|---|
| 6-(4,5-Difluoro-2-methoxyphenyl)-5-(5-fluoro-2-methylphenoxymethyl)-2,2,4-trimethyl-1,2-dihydroquinoline (Compound No. 3-57) 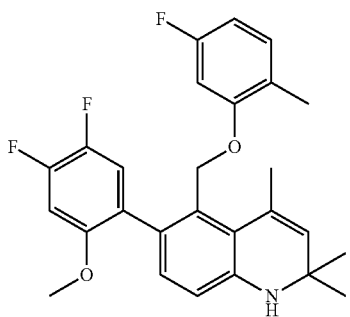 | $^1$H-NMR (400 MHz, DMSO-d$_6$) δ 1.10 (s, 3H), 1.14 (s, 3H), 2.01 (s, 3H), 2.05 (s, 3H), 3.72 (s, 3H), 4.57 (d, J = 12.0 Hz, 1H), 5.05 (d, J = 12.0 Hz, 1H), 5.41 (s, 1H), 6.10 (s, 1H), 6.44 (dd, J = 11.5, 2.4 Hz, 1H), 6.55 (td, J = 8.4, 2.4 Hz, 1H), 6.63 (d, J = 8.2 Hz, 1H), 6.77 (d, J = 8.2 Hz, 1H), 7.03-7.07 (m, 1H), 7.18 (dd, J = 13.2, 7.1 Hz, 1H), 7.20 (dd, J = 11.2, 9.3 Hz, 1H) |
| 5-(2,5-Dimethylphenoxymethyl)-6-(4-fluoro-2-methoxyphenyl)-2,2,4-trimethyl-1,2-dihydroquinoline (Compound No. 3-58) 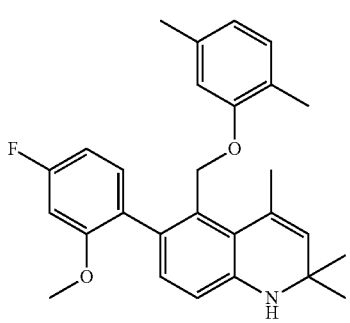 | $^1$H-NMR (400 MHz, DMSO-d$_6$) δ 1.05 (s, 3H), 1.18 (s, 3H), 1.99 (s, 3H), 2.06 (s, 3H), 2.13 (s, 3H), 3.74 (s, 3H), 4.56 (d, J = 12.0 Hz, 1H), 5.03 (d, J = 12.0 Hz, 1H), 5.38 (s, 1H), 6.00 (s, 1H), 6.28 (s, 1H), 6.52 (d, J = 7.7 Hz, 1H), 6.61 (d, J = 8.1 Hz, 1H), 6.73 (d, J = 8.1 Hz, 1H), 6.77 (td, J = 8.4, 2.5 Hz, 1H), 6.89 (d, J = 7.7 Hz, 1H), 6.96 (dd, J = 11.5, 2.5 Hz, 1H), 7.19 (dd, J = 8.4, 7.2 Hz, 1H) |
| 6-(4-Fluoro-2-methoxyphenyl)-5-(2-methoxy-5-methylphenoxymethyl)-2,2,4-trimethyl-1,2-dihydroquinoline (Compound No. 3-59) 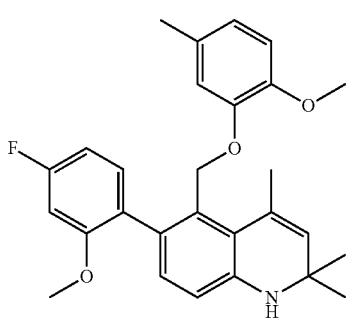 | $^1$H-NMR (400 MHz, DMSO-d$_6$) δ 1.15 (s, 3H), 1.18 (s, 3H), 2.11 (s, 6H), 3.62 (s, 3H), 3.69 (s, 3H), 4.43 (d, J = 11.5 Hz, 1H), 5.02 (d, J = 11.5 Hz, 1H), 5.38 (s, 1H), 5.98 (s, 1H), 6.42 (d, J = 1.7 Hz, 1H), 6.57-6.60 (m, 1H), 6.61 (d, J = 8.1 Hz, 1H), 6.67 (td, J = 8.4, 2.5 Hz, 1H), 6.71 (d, J = 8.1 Hz, 1H), 6.74 (d, J = 8.1 Hz, 1H), 6.90 (dd, J = 11.5, 2.5 Hz, 1H), 7.13 (dd, J = 8.4, 7.1 Hz, 1H) |

| | |
|---|---|
| 6-(4-Fluoro-2-methoxyphenyl)-5-(2-methyl-3-nitrophenoxymethyl)-2,2,4-trimethyl-1,2-dihydroquinoline (Compound No. 3-60) 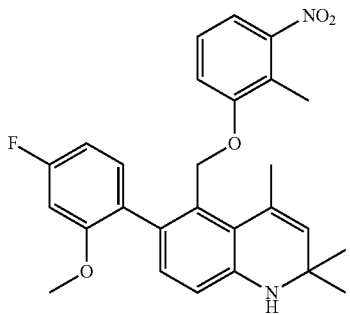 | $^1$H-NMR (400 MHz, DMSO-d$_6$) δ 1.03 (s, 3H), 1.15 (s, 3H), 2.06 (s, 3H), 2.15 (s, 3H), 3.74 (s, 3H), 4.71 (d, J = 12.1 Hz, 1H), 5.14 (d, J = 12.1 Hz, 1H), 5.14 (s, 1H), 6.04 (s, 1H), 6.63 (d, J = 8.3 Hz, 1H), 6.74-6.79 (m, 1H), 6.75 (d, J = 8.3 Hz, 1H), 6.85 (d, J = 7.9 Hz, 1H), 6.95 (dd, J = 11.5, 2.7 Hz, 1H), 7.18 (dd, J = 8.3, 7.1 Hz, 1H), 7.21 (t, J = 7.9 Hz, 1H), 7.32 (d, J = 7.9 Hz, 1H) |
| 6-(4-Fluoro-2-methoxyphenyl)-5-(2-methoxy-5-nitrophenoxymethyl)-2,2,4-trimethyl-1,2-dihydroquinoline (Compound No. 3-61) 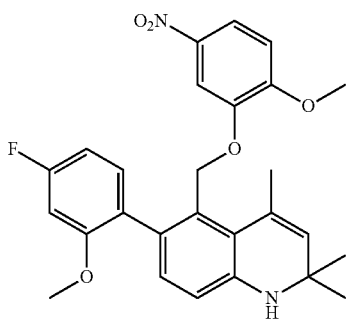 | $^1$H-NMR (400 MHz, DMSO-d$_6$) δ 1.04 (s, 3H), 1.17 (s, 3H), 2.13 (s, 3H), 3.70 (s, 3H), 3.82 (s, 3H), 4.62 (d, J = 11.8 Hz, 1H), 5.23 (d, J = 11.8 Hz, 1H), 5.39 (s, 1H), 6.01 (s, 1H), 6.61 (d, J = 8.3 Hz, 1H), 6.68 (td, J = 8.4, 2.6 Hz, 1H), 6.73 (d, J = 8.3 Hz, 1H), 6.90 (dd, J = 11.5, 2.6 Hz, 1H), 7.09 (d, J = 9.0 Hz, 1H), 7.13 (dd, J = 8.4, 7.2 Hz, 1H), 7.30 (d, J = 2.7 Hz, 1H), 7.81 (dd, J = 9.0, 2.7 Hz, 1H) |
| 6-(4-Fluoro-2-methoxyphenyl)-5-[2-(1-propenyl)phenoxymethyl]-2,2,4-trimethyl-1,2-dihydroquinoline (Compound No. 3-62) 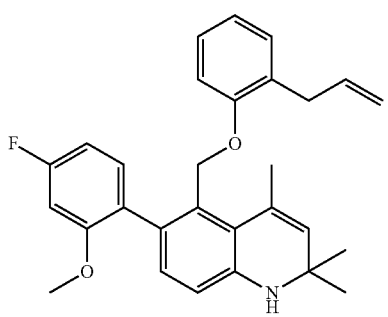 | $^1$H-NMR (400 MHz, DMSO-d$_6$) δ 1.16 (s, 3H), 1.22 (s, 3H), 1.76 (dd, J = 6.6, 1.7 Hz, 3H), 1.99 (s, 3H), 3.71 (s, 3H), 4.60 (d, J = 11.4 Hz, 1H), 4.98 (d, J = 11.4, Hz, 1H), 5.40 (s, 1H), 6.05 (s, 1H), 6.15 (dd, J = 16.0, 6.6 Hz, 1H), 6.53 (dd, J = 16.0, 1.7 Hz, 1H), 6.61-6.82 (m, 2H), 6.65 (d, J = 8.1 Hz, 1H), 6.75 (d, J = 8.1 Hz, 1H), 6.80 (t, J = 7.4 Hz, 1H), 6.93 (dd, J = 11.5, 2.4 Hz, 1H), 7.04 (t, J = 7.7 Hz, 1H), 7.15 (dd, J = 8.5, 7.1 Hz, 1H), 7.35 (dd, J = 7.7, 1.5 Hz, 1H) |

| | |
|---|---|
| 5-(3-Ethynylphenoxymethyl)-6-(4-fluoro-2-methoxyphenyl)-2,2,4-trimethyl-1,2-dihydroquinoline (Compound No. 3-63) 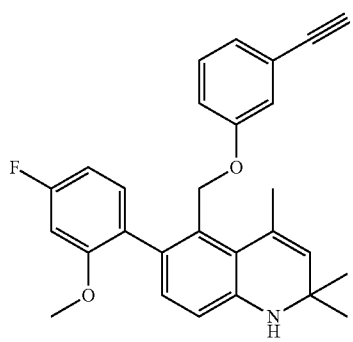 | $^1$H-NMR (500 MHz, DMSO-d$_6$) δ 1.09 (s, 3H), 1.16 (s, 3H), 2.09 (s, 3H), 3.71 (s, 3H), 4.13 (s, 1H), 4.53 (d, J = 11.8 Hz, 1H), 5.04 (d, J = 11.8 Hz, 1H), 5.40 (s, 1H), 5.99 (s, 1H), 6.61 (d, J = 7.9 Hz, 1H), 6.70 (dd, J = 8.4, 2.5 Hz, 1H), 6.72-6.75 (m, 3H), 6.92 (dd, J = 11.6, 2.5 Hz, 1H), 6.95 (d, J = 7.6 Hz, 1H), 7.13-7.18 (m, 2H) |
| 6-(4-Fluoro-2-methoxyphenyl)-5-(3-phenylphenoxymethyl)-2,2,4-trimethyl-1,2-dihydroquinoline (Compound No. 3-64) 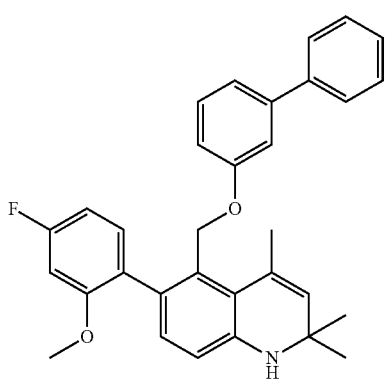 | $^1$H-NMR (400 MHz, DMSO-d$_6$) δ 1.08 (s, 3H), 1.16 (s, 3H), 2.13 (s, 3H), 3.71 (s, 3H), 4.59 (d, J = 11.6 Hz, 1H), 5.12 (d, J = 11.6 Hz, 1H), 5.40 (s, 1H), 6.00 (s, 1H), 6.68-6.75 (m, 2H), 6.62 (d, J = 8.3 Hz, 1H), 6.74 (d, J = 8.3 Hz, 1H), 6.89-6.93 (m, 2H), 7.12-7.17 (m, 2H), 7.25 (t, J = 7.9 Hz, 1H), 7.35-7.37 (m, 1H), 7.43 (t, J = 7.9 Hz, 2H), 7.55 (d, J = 7.9 Hz, 2H) |
| 5-(3,5-Difluorophenoxymethyl)-6-(4-fluoro-2-methoxyphenyl)-2,2,4-trimethyl-1,2-dihydroquinoline (Compound No. 3-65) 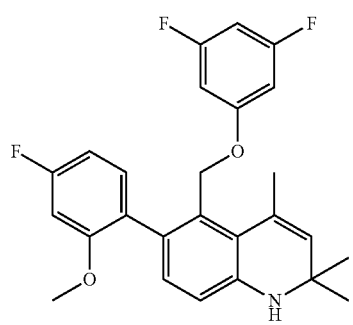 | $^1$H-NMR (500 MHz, DMSO-d$_6$) δ 1.12 (s, 3H), 1.14 (s, 3H), 2.07 (s, 3H), 3.71 (s, 3H), 4.54 (d, J = 11.6 Hz, 1H), 5.04 (d, J = 11.6 Hz, 1H), 5.41 (s, 1H), 6.03 (s, 1H), 6.45 (dd, J = 9.4, 2.2 Hz, 2H), 6.62 (d, J = 8.2 Hz, 1H), 6.68 (tt, J = 9.4, 2.2 Hz, 1H), 6.71 (td, J = 8.3, 2.6 Hz, 1H), 6.74 (d, J = 8.2 Hz, 1H), 6.92 (dd, J = 11.5, 2.6 Hz, 1H), 7.13 (dd, J = 8.3, 7.0 Hz, 1H) |

| | |
|---|---|
| 5-(3,5-Dichlorophenoxymethyl)-6-(4-fluoro-2-methoxyphenyl)-2,2,4-trimethyl-1,2-dihydroquinoline (Compound No. 3-66) 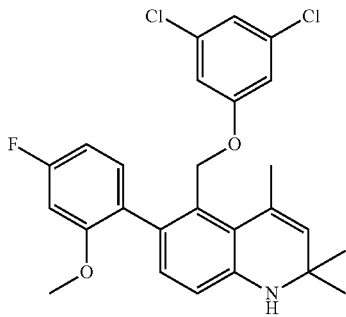 | $^1$H-NMR (400 MHz, DMSO-d$_6$) δ 1.06 (s, 3H), 1.15 (s, 3H), 2.09 (s, 3H), 3.72 (s, 3H), 4.57 (d, J = 12.0 Hz, 1H), 5.10 (d, J = 12.0 Hz, 1H), 5.41 (s, 1H), 6.03 (s, 1H), 6.62 (d, J = 8.3 Hz, 1H), 6.72-6.77 (m, 4H), 6.93 (dd, J = 11.5, 2.4 Hz, 1H), 7.04 (t, J = 1.8 Hz, 1H), 7.14 (dd, J = 8.3, 7.1 Hz, 1H) |
| 5-(5-Fluoro-2-methoxyphenoxymethyl)-6-(4-fluoro-2-methoxyphenyl)-2,2,4-trimethyl-1,2-dihydroquinoline (Compound No. 3-67) 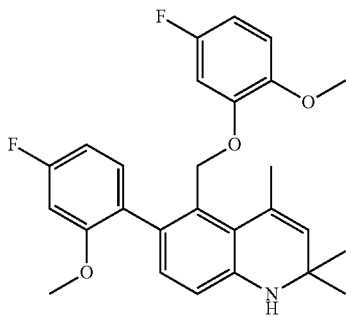 | $^1$H-NMR (500 MHz, DMSO-d$_6$) δ 1.14 (s, 3H), 1.15 (s, 3H), 2.09 (s, 3H), 3.65 (s, 3H), 3.69 (s, 3H), 4.45 (d, J = 11.3 Hz, 1H), 5.04 (d, J = 11.3 Hz, 1H), 5.39 (s, 1H), 6.01 (s, 1H), 6.54 (dd, J = 10.5, 3.0 Hz, 1H), 6.59 (td, J = 8.8, 3.0 Hz, 1H), 6.62 (d, J = 8.2 Hz, 1H), 6.66 (td, J = 8.4, 2.5 Hz, 1H), 6.73 (d, J = 8.2 Hz, 1H), 6.86 (dd, J = 8.8, 5.5 Hz, 1H), 6.90 (dd, J = 11.5, 2.5 Hz, 1H), 7.12 (dd, J = 8.4, 7.2 Hz, 1H) |
| 6-(4-Fluoro-2-methoxyphenyl)-5-[2-(2-hydroxyethyl)phenoxymethyl]-2,2,4-trimethyl-1,2-dihydroquinoline (Compound No. 3-68) 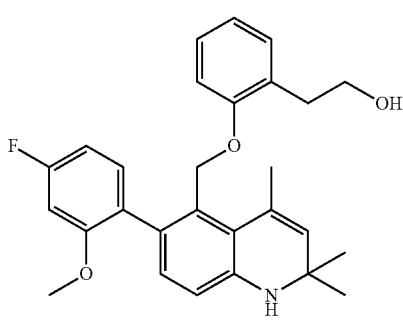 | $^1$H-NMR (400 MHz, DMSO-d$_6$) δ 1.12 (s, 3H), 1.17 (s, 3H), 2.02 (s, 3H), 2.63 (t, J = 7.2 Hz, 2H), 3.40-3.51 (m, 2H), 3.72 (s, 3H), 4.44 (t, J = 5.2 Hz, 1H), 4.51 (d, J = 11.5 Hz, 1H), 5.00 (d, J = 11.5 Hz, 1H), 5.38 (s, 1H), 6.02 (s, 1H), 6.59 (d, J = 7.6 Hz, 1H), 6.63 (d, J = 8.3 Hz, 1H), 6.68-6.79 (m, 2H), 6.74 (d, J = 8.3 Hz, 1H), 6.93 (dd, J = 11.5, 2.4 Hz, 1H), 7.01 (td, J = 7.6, 1.7 Hz, 1H), 7.06 (dd, J = 7.6, 1.7 Hz, 1H), 7.17 (dd, J = 8.3, 7.1 Hz, 1H) |

5-(2-Isopropylphenoxymethyl)-6-(4-fluoro-2-methoxyphenyl)-2,2,4-trimethyl-1,2-dihydroquinoline (Compound No. 3-69)

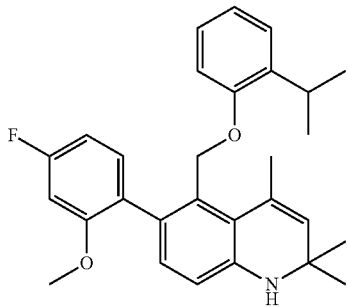

$^1$H-NMR (400 MHz, DMSO-d$_6$) δ 1.05 (d, J = 6.8 Hz, 3H), 1.06 (d, J = 6.8 Hz, 3H), 1.11 (s, 3H), 1.19 (s, 3H), 2.00 (s, 3H), 3.11-3.22 (m, 1H), 3.72 (s, 3H), 4.57 (d, J = 11.5 Hz, 1H), 4.99 (d, J = 11.5 Hz, 1H), 5.36 (s, 1H), 6.04 (s, 1H), 6.60 (d, J = 7.6 Hz, 1H), 6.64 (d, J = 8.3 Hz, 1H), 6.69-6.78 (m, 1H), 6.75 (d, J = 8.3 Hz, 1H), 6.80 (t, J = 7.0 Hz, 1H), 6.93 (dd, J = 11.5, 2.4 Hz, 1H), 7.00 (td, J = 7.6, 1.5 Hz, 1H), 7.11 (dd, J = 7.6, 1.5 Hz, 1H), 7.16 (dd, J = 8.4, 7.2 Hz, 1H)

5-(3-Ethylphenoxymethyl)-6-(4-fluoro-2-methoxyphenyl)-2,2,4-trimethyl-1,2-dihydroquinoline (Compound No. 3-70)

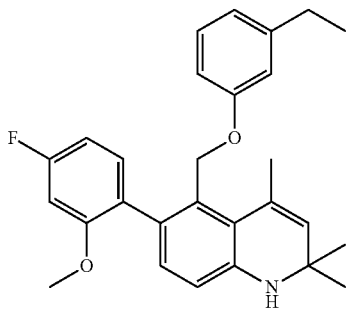

$^1$H-NMR (400 MHz, DMSO-d$_6$) δ 1.09 (t, J = 7.6 Hz, 3H), 1.10 (s, 3H), 1.17 (s, 3H), 2.09 (s, 3H), 2.47 (q, J = 7.6 Hz, 2H), 3.71 (s, 3H), 4.50 (d, J = 11.5 Hz, 1H), 5.00 (d, J = 11.5 Hz, 1H), 5.39 (s, 1H), 5.98 (s, 1H), 6.46-6.52 (m, 1H), 6.50 (s, 1H), 6.60 (d, J = 8.1 Hz, 1H), 6.66-6.75 (m, 2H), 6.72 (d, J = 8.1 Hz, 1H), 6.91 (dd, J = 11.5, 2.4 Hz, 1H), 7.05 (t, J = 8.1 Hz, 1H), 7.15 (dd, J = 8.4, 7.2 Hz, 1H)

5-(3-Isopropylphenoxymethyl)-6-(4-fluoro-2-methoxyphenyl)-2,2,4-trimethyl-1,2-dihydroquinoline (Compound No. 3-71)

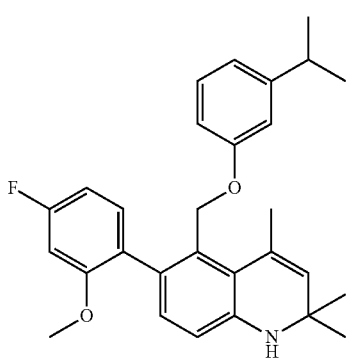

$^1$H-NMR (400 MHz, DMSO-d$_6$) δ 1.10 (s, 3H), 1.10 (d, J = 6.8 Hz, 3H), 1.11 (d, J = 6.8 Hz, 3H), 1.17 (s, 3H), 2.11 (s, 3H), 2.69-2.80 (m, 1H), 3.71 (s, 3H), 4.51 (d, J = 11.5 Hz, 1H), 5.02 (d, J = 11.5 Hz, 1H), 5.39 (s, 1H), 5.98 (s, 1H), 6.45-6.53 (m, 2H), 6.60 (d, J = 8.3 Hz, 1H), 6.67-6.76 (m, 2H), 6.73 (d, J = 8.3 Hz, 1H), 6.91 (dd, J = 11.6, 2.6 Hz, 1H), 7.05 (t, J = 7.8 Hz, 1H), 7.15 (dd, J = 8.3, 7.1 Hz, 1H)

| Compound | NMR |
|---|---|
| 6-(4-Fluoro-2-methoxyphenyl)-5-(2-methyl-5-nitrophenoxymethyl)-2,2,4-trimethyl-1,2-dihydroquinoline (Compound No. 3-72)<br />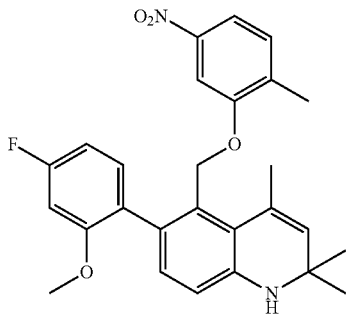 | $^1$H-NMR (400 MHz, DMSO-d$_6$) δ 0.91 (s, 3H), 1.18 (s, 3H), 2.12 (s, 3H), 2.18 (s, 3H), 3.75 (s, 3H), 4.75 (d, J = 12.7 Hz, 1H), 5.28 (d, J = 12.7 Hz, 1H), 5.40 (s, 1H), 6.04 (s, 1H), 6.61 (d, J = 8.2 Hz, 1H), 6.76 (d, J = 8.2 Hz, 1H), 6.80 (td, J = 8.5, 2.8 Hz, 1H), 6.96 (dd, J = 11.5, 2.8 Hz, 1H), 7.14 (d, J = 2.2 Hz, 1H), 7.25 (dd, J = 8.5, 7.1 Hz, 1H), 7.33 (d, J = 8.3 Hz, 1H), 7.63 (dd, J = 8.3, 2.2 Hz, 1H) |
| 6-(4-Fluoro-2-methoxyphenyl)-5-(2-propylphenoxymethyl)-2,2,4-trimethyl-1,2-dihydroquinoline (Compound No. 3-73)<br />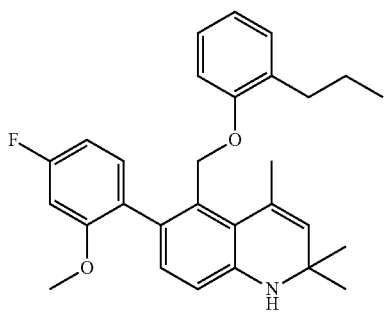 | $^1$H-NMR (400 MHz, DMSO-d$_6$) δ 0.81 (t, J = 7.4 Hz, 3H), 1.11 (s, 3H), 1.19 (s, 3H), 1.45 (sextet, J = 7.4 Hz, 2H), 2.02 (s, 3H), 2.38-2.46 (m, 2H), 3.72 (s, 3H), 4.57 (d, J = 11.9 Hz, 1H), 5.00 (d, J = 11.9 Hz, 1H), 5.37 (s, 1H), 6.02 (s, 1H), 6.56 (d, J = 8.1 Hz, 1H), 6.63 (d, J = 8.1 Hz, 1H), 6.75 (d, J = 8.1 Hz, 1H), 6.72-6.77 (m, 2H), 6.94 (dd, J = 11.5, 2.2 Hz, 1H), 7.00 (td, J = 8.1, 2.2 Hz, 1H), 7.03 (dd, J = 7.3, 1.7 Hz, 1H), 7.16 (dd, J = 8.1, 7.1 Hz, 1H) |
| 6-(4-Fluoro-2-methoxyphenyl)-5-(2-allylphenoxymethyl)-2,2,4-trimethyl-1,2-dihydroquinoline (Compound No. 3-74)<br />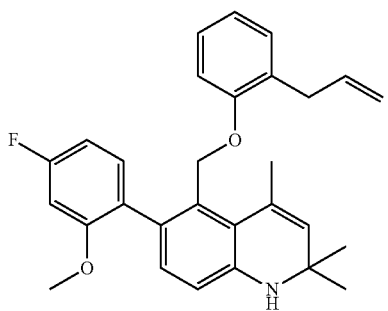 | $^1$H-NMR (500 MHz, DMSO-d$_6$) δ 1.09 (s, 3H), 1.18 (s, 3H), 2.02 (s, 3H), 3.16-3.25 (m, 2H), 3.73 (s, 3H), 4.58 (d, J = 11.6 Hz, 1H), 4.92-4.97 (m, 2H), 5.02 (d, J = 11.6 Hz, 1H), 5.38 (s, 1H), 5.87 (ddt, J = 17.1, 10.1, 6.7 Hz, 1H), 6.02 (s, 1H), 6.59 (d, J = 8.2 Hz, 1H), 6.63 (d, J = 8.1 Hz, 1H), 6.73 (td, J = 8.2, 2.2 Hz, 1H), 6.75 (d, J = 8.1 Hz, 1H), 6.78 (td, J = 7.4, 0.7 Hz, 1H), 6.94 (dd, J = 11.6, 2.2 Hz, 1H), 7.01-7.04 (m, 2H), 7.16 (dd, J = 8.2, 7.0 Hz, 1H) |

| | |
|---|---|
| 6-(4-Fluoro-2-methoxyphenyl)-5-(3-trifluoromethylphenoxymethyl)-2,2,4-trimethyl-1,2-dihydroquinoline (Compound No. 3-75)<br />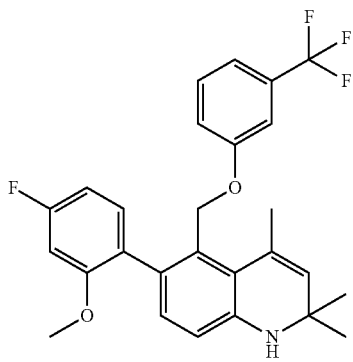 | $^1$H-NMR (400 MHz, DMSO-d$_6$) δ 1.03 (s, 3H), 1.15 (s, 3H), 2.11 (s, 3H), 3.71 (s, 3H), 4.62 (d, J = 12.0 Hz, 1H), 5.14 (d, J = 12.0 Hz, 1H), 5.40 (s, 1H), 6.00 (s, 1H), 6.61 (d, J = 8.2 Hz, 1H), 6.71 (td, J = 8.3, 2.6 Hz, 1H), 6.74 (d, J = 8.2 Hz, 1H), 6.89 (s, 1H), 6.91 (dd, J = 11.6, 2.6 Hz, 1H), 6.96 (dd, J = 8.2, 2.1 Hz, 1H), 7.13-7.18 (m, 2H), 7.36-7.40 (m, 1H) |
| 6-(4-Fluoro-2-methoxyphenyl)-5-(3-trifluoromethoxyphenoxymethyl)-2,2,4-trimethyl-1,2-dihydroquinoline (Compound No. 3-76)<br />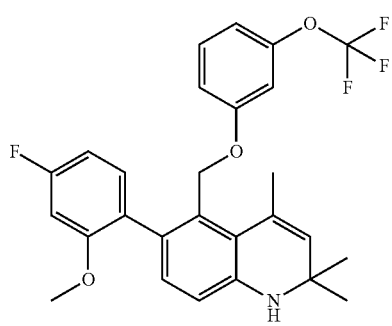 | $^1$H-NMR (400 MHz, DMSO-d$_6$) δ 1.07 (s, 3H), 1.14 (s, 3H), 2.10 (s, 3H), 3.71 (s, 3H), 4.58 (d, J = 11.9 Hz, 1H), 5.08 (d, J = 11.9 Hz, 1H), 5.40 (s, 1H), 6.01 (s, 1H), 6.61 (s, 1H), 6.62 (d, J = 8.1 Hz, 1H), 6.70 (t, J = 8.4, 2.4 Hz, 1H), 6.73 (dd, J = 8.0, 2.3 Hz, 1H), 6.74 (d, J = 8.1 Hz, 1H), 6.82 (dt, J = 8.0, 1.0 Hz, 1H), 6.91 (dd, J = 11.5, 2.4 Hz, 1H), 7.14 (dd, J = 8.4, 7.1 Hz, 1H), 7.27 (t, J = 8.0 Hz, 1H) |
| 6-(4-Fluoro-2-methoxyphenyl)-5-(2-isopropyl-5-methylphenoxymethyl)-2,2,4-trimethyl-1,2-dihydroquinoline Compound No. 3-77)<br />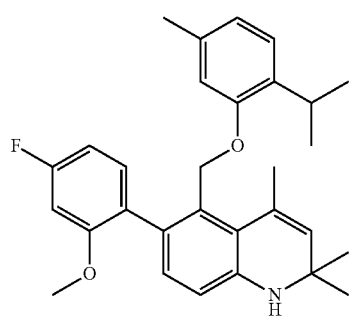 | $^1$H-NMR (400 MHz, DMSO-d$_6$) δ 1.03 (d, J = 6.8 Hz, 3H), 1.04 (d, J = 6.8 Hz, 3H), 1.09 (s, 3H), 1.19 (s, 3H), 2.02 (s, 3H), 2.15 (s, 3H), 3.07-3.14 (m, 1H), 3.72 (s, 3H), 4.57 (d, J = 11.6 Hz, 1H), 5.00 (d, J = 11.6 Hz, 1H), 5.36 (s, 1H), 6.02 (s, 1H), 6.36 (s, 1H), 6.60 (d, J = 7.4 Hz, 1H), 6.63 (d, J = 8.1 Hz, 1H), 6.74 (d, J = 8.1 Hz, 1H), 6.73-6.78 (m, 1H), 6.93-6.98 (m, 1H), 6.97 (d, J = 7.4 Hz, 1H), 7.16 (dd, J = 8.3, 7.1 Hz, 1H) |

| | |
|---|---|
| 6-(4-Fluoro-2-methoxyphenyl)-5-(2-phenylphenoxymethyl)-2,2,4-trimethyl-1,2-dihydroquinoline (Compound No. 3-78) 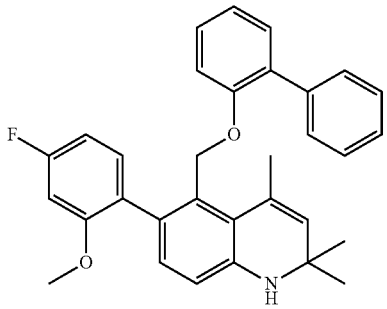 | $^1$H-NMR (500 MHz, DMSO-d$_6$) δ 1.12 (s, 3H), 1.17 (s, 3H), 2.03 (s, 3H), 3.65 (s, 3H), 4.51 (d, J = 11.9 Hz, 1H), 5.06 (d, J = 11.9 Hz, 1H), 5.40 (s, 1H), 5.40 (s, 1H), 6.00 (s, 1H), 6.59 (d, J = 8.3 Hz, 1H), 6.69 (d, J = 8.4, 2.6 Hz, 1H), 6.69 (d, J = 8.3 Hz, 1H), 6.76 (d, J = 7.6 Hz, 1H), 6.90 (dd, J = 11.6, 2.6 Hz, 1H), 6.93 (td, J = 7.6, 1.10 Hz, 1H), 6.98 (dd, J = 8.4, 7.2 Hz, 1H), 7.17 (td, J = 7.6, 1.8 Hz, 1H), 7.21 (dd, J = 7.6, 1.8 Hz, 1H), 7.24-7.27 (m, 1H), 7.33 (t, J = 7.7 Hz, 2H), 7.39 (d, J = 7.7 Hz, 2H) |
| 5-(2-t-Butoxycarbonylaminophenoxymethyl)-6-(4-fluoro-2-methoxyphenyl)-2,2,4-trimethyl-1,2-dihydroquinoline (Compound No. 3-79) 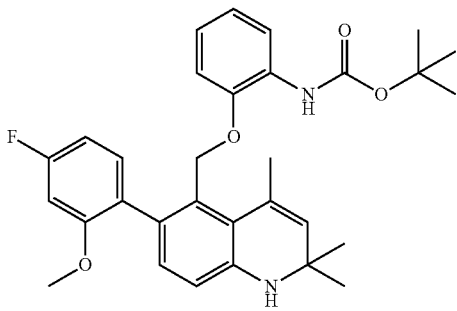 | $^1$H-NMR (500 MHz, DMSO-d$_6$) δ 1.11 (s, 3H), 1.20 (s, 3H), 1.44 (s, 9H), 2.04 (s, 3H), 3.72 (s, 3H), 4.68 (d, J = 11.6 Hz, 1H), 5.04 (d, J = 11.6 Hz, 1H), 5.44 (s, 1H), 6.08 (s, 1H), 6.63-6.66 (m, 1H), 6.65 (d, J = 8.2 Hz, 1H), 6.71-6.75 (m, 1H), 6.76 (d, J = 8.2 Hz, 1H), 6.79-6.87 (m, 2H), 6.94 (dd, J = 11.6, 2.4 Hz, 1H), 7.14 (s, 1H), 7.18 (dd, J = 8.2, 7.3, Hz 1H), 7.76 (d, J = 7.0 Hz, 1H) |
| 6-(4-Fluoro-2-methoxyphenyl)-5-(2-trifluoromethoxyphenoxymethyl)-2,2,4-trimethyl-1,2-dihydroquinoline (Compound No. 3-80) 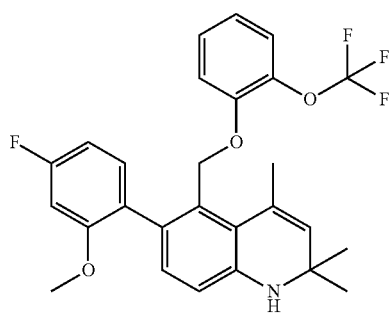 | $^1$H-NMR (400 MHz, DMSO-d$_6$) δ 1.10 (s, 3H), 1.15 (s, 3H), 2.04 (s, 3H), 3.71 (s, 3H), 4.58 (d, J = 11.5 Hz, 1H), 5.11 (d, J = 11.5 Hz, 1H), 5.37 (s, 1H), 6.04 (s, 1H), 6.64 (d, J = 8.1 Hz, 1H), 6.69 (td, J = 8.4, 2.6 Hz, 1H), 6.75 (d, J = 8.1 Hz, 1H), 6.87 (dd, J = 8.4, 1.3 Hz, 1H), 6.89-6.95 (m, 2H), 7.14 (dd, J = 8.3, 7.1 Hz, 1H), 7.19 (td, J = 8.0, 1.3 Hz, 1H), 7.26 (dt, J = 8.0, 1.3 Hz, 1H) |

| Compound | ¹H-NMR |
|---|---|
| 5-(3-Chloro-2-methylphenoxymethyl)-6-(4-fluoro-2-methoxyphenyl)-2,2,4-trimethyl-1,2-dihydroquinoline (Compound No. 3-81) 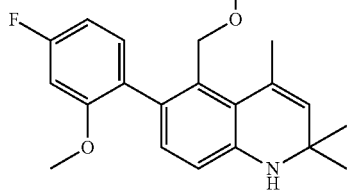 | ¹H-NMR (400 MHz, DMSO-d₆) δ 1.06 (s, 3H), 1.16 (s, 3H), 2.04 (s, 3H), 2.10 (s, 3H), 3.73 (s, 3H), 4.61 (d, J = 12.0 Hz, 1H), 5.05 (d, J = 12.0 Hz, 1H), 5.40 (s, 1H), 6.03 (s, 1H), 6.53 (d, J = 8.0 Hz, 1H), 6.62 (d, J = 8.2 Hz, 1H), 6.74 (d, J = 8.2 Hz, 1H), 6.76 (td, J = 8.4, 2.3 Hz, 1H), 6.89 (d, J = 8.0 Hz, 1H), 6.94 (dd, J = 11.5, 2.3 Hz, 1H), 7.00 (t, J = 8.0 Hz, 1H), 7.17 (dd, J = 8.3, 7.1 Hz, 1H) |
| 6-(4-Fluoro-2-methoxyphenyl)-5-(5-isopropyl-2-methylphenoxymethyl)-2,2,4-trimethyl-1,2-dihydroquinoline (Compound No. 3-82) 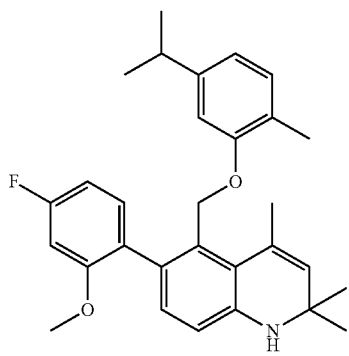 | ¹H-NMR (400 MHz, DMSO-d₆) δ 1.01 (s, 3H), 1.06 (d, J = 6.8 Hz, 3H), 1.07 (d, J = 6.8 Hz, 3H), 1.17 (s, 3H), 2.00 (s, 3H), 2.08 (s, 3H), 2.64-2.69 (m, 1H), 3.74 (s, 3H), 4.58 (d, J = 12.1 Hz, 1H), 5.07 (d, J = 12.1 Hz, 1H), 5.38 (s, 1H), 5.99 (s, 1H), 6.29 (d, J = 1.3 Hz, 1H), 6.58 (d, J = 7.7, 1.3 Hz, 1H), 6.61 (d, J = 8.3 Hz, 1H), 6.75 (d, J = 8.3 Hz, 1H), 6.76 (td, J = 8.4, 2.4 Hz, 1H), 6.92 (d, J = 7.7 Hz, 1H), 6.95 (dd, J = 11.5, 2.4 Hz, 1H), 7.18 (dd, J = 8.4, 7.1 Hz, 1H) |
| 6-(4-Fluoro-2-methoxyphenyl)-5-(2-methoxy-5-methoxycarbonylphenoxy-methyl)-2,2,4-trimethyl-1,2-dihydroquinoline (Compound No. 3-83) 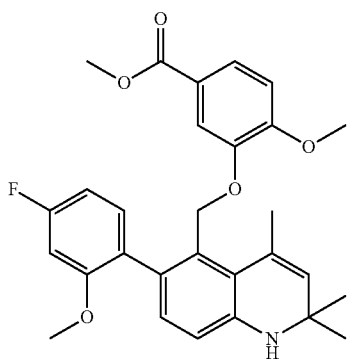 | ¹H-NMR (400 MHz, DMSO-d₆) δ 1.06 (s, 3H), 1.19 (s, 3H), 2.14 (s, 3H), 3.69 (s, 3H), 3.74 (s, 3H), 3.76 (s, 3H), 4.55 (d, J = 11.7 Hz, 1H), 5.13 (d, J = 11.7 Hz, 1H), 5.38 (s, 1H), 5.99 (s, 1H), 6.60 (d, J = 8.1 Hz, 1H), 6.68 (td, J = 8.4, 2.5 Hz, 1H), 6.70 (d, J = 8.1 Hz, 1H), 6.90 (dd, J = 11.5, 2.5 Hz, 1H), 6.98 (d, J = 8.7 Hz, 1H), 7.04 (d, J = 2.0 Hz, 1H), 7.10 (dd, J = 8.4, 7.2 Hz, 1H), 7.49 (dd, J = 8.7, 2.0 Hz, 1H) |

| | |
|---|---|
| 5-(2-Acetyl-5-fluorophenoxymethyl)-6-(4-fluoro-2-methoxyphenyl)-2,2,4-trimethyl-1,2-dihydroquinoline (Compound No. 3-84)<br>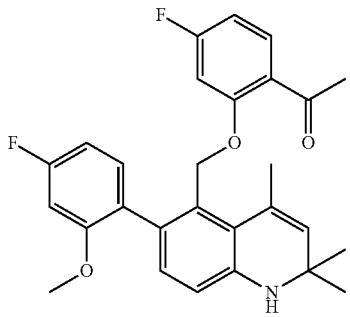 | $^1$H-NMR (500 MHz, DMSO-d$_6$) δ 1.11 (s, 3H), 1.15 (s, 3H), 2.05 (s, 3H), 2.38 (s, 3H), 3.64 (s, 3H), 4.83 (d, J = 11.6 Hz, 1H), 5.09 (d, J = 11.6 Hz, 1H), 5.42 (s, 1H), 6.08 (s, 1H), 6.67 (d, J = 8.3 Hz, 1H), 6.76 (d, J = 8.3 Hz, 1H), 6.74-6.76 (m, 3H), 6.91 (dd, J = 11.6, 2.4 Hz, 1H), 7.12 (dd, J = 8.4, 7.2 Hz, 1H), 7.63 (dd, J = 8.7, 7.0 Hz, 1H) |
| 5-(2,5-Diclorophenoxymethyl)-6-(4-fluoro-2-methoxyphenyl)-2,2,4-trimethyl-1,2-dihydroquinoline (Compound No. 3-85)<br>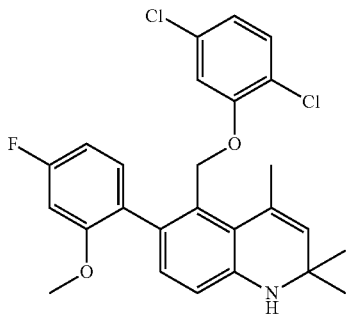 | $^1$H-NMR (500 MHz, DMSO-d$_6$) δ 1.04 (s, 3H), 1.15 (s, 3H), 2.12 (s, 3H), 3.73 (s, 3H), 4.61 (d, J = 12.2 Hz, 1H), 5.20 (d, J = 12.2 Hz, 1H), 5.39 (s, 1H), 6.04 (s, 1H), 6.63 (d, J = 8.2 Hz, 1H), 6.72 (d, J = 2.3 Hz, 1H), 6.74 (td, J = 8.3, 2.6 Hz, 1H), 6.76 (d, J = 8.2 Hz, 1H), 6.90 (dd, J = 8.4, 2.3 Hz, 1H), 6.94 (dd, J = 11.5, 2.6 Hz, 1H), 7.18 (dd, J = 8.3, 7.2 Hz, 1H), 7.35 (d, J = 8.4 Hz, 1H) |
| 6-(4-Fluoro-2-methoxyphenyl)-5-(3-fluoro-5-methylphenoxymethyl)-2,2,4-trimethyl-1,2-dihydroquinoline (Compound No. 3-86)<br>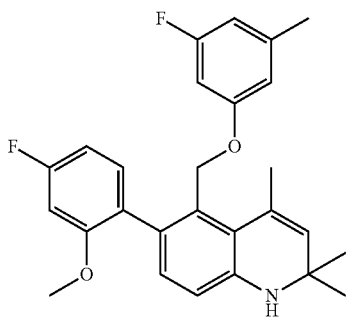 | $^1$H-NMR (400 MHz, DMSO-d$_6$) δ 1.11 (s, 3H), 1.16 (s, 3H), 2.07 (s, 3H), 2.19 (s, 3H), 3.71 (s, 3H), 4.50 (d, J = 11.6 Hz, 1H), 5.00 (d, J = 11.6 Hz, 1H), 5.40 (s, 1H), 6.00 (s, 1H), 6.32 (dt, J = 11.1, 2.1 Hz, 1H), 6.36 (br s, 1H), 6.49 (d, J = 9.8 Hz, 1H), 6.61 (d, J = 8.3 Hz, 1H), 6.72 (td, J = 8.4, 2.6 Hz, 1H), 6.73 (d, J = 8.3 Hz, 1H), 6.92 (dd, J = 11.5, 2.6 Hz, 1H), 7.13 (dd, J = 8.4, 7.2 Hz, 1H) |

| | |
|---|---|
| 6-(4-Fluoro-2-methoxyphenyl)-5-(2-methoxycarbonyl-5-nitrophenoxymethyl)-2,2,4-trimethyl-1,2-dihydroquinoline (Compound No. 3-87) 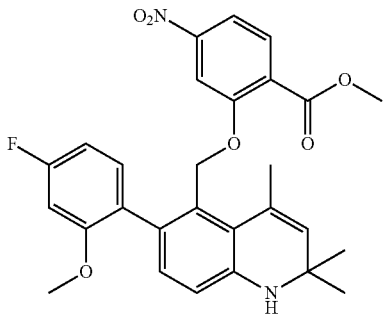 | $^1$H-NMR (500 MHz, DMSO-d$_6$) δ 0.88 (s, 3H), 1.15 (s, 3H), 2.14 (s, 3H), 3.73 (s, 3H), 3.81 (s, 3H), 4.76 (d, J = 12.8 Hz, 1H), 5.37 (d, J = 12.8 Hz, 1H), 5.37 (s, 1H), 6.00 (s, 1H), 6.60 (d, J = 8.1 Hz, 1H), 6.76 (d, J = 8.1 Hz, 1H), 6.76 (td, J = 8.4, 2.5 Hz, 1H), 6.94 (dd, J = 11.3, 2.5 Hz, 1H), 7.25 (dd, J = 8.4, 6.9 Hz, 1H), 7.26 (s, 1H), 7.72 (dd, J = 8.4, 1.8 Hz, 1H), 7.75 (d, J = 8.4 Hz, 1H) |
| 5-(2-Acetyl-5-chlorophenoxymethyl)-6-(4-fluoro-2-methoxyphenyl)-2,2,4-trimethyl-1,2-dihydroquinoline (Compound No. 3-88) 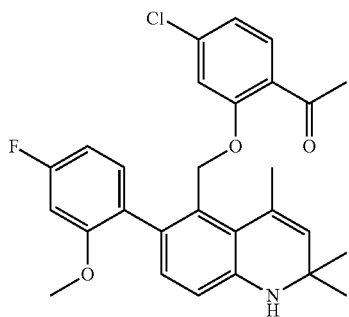 | $^1$H-NMR (400 MHz, DMSO-d$_6$) δ 1.07 (s, 3H), 1.16 (s, 3H), 2.06 (s, 3H), 2.39 (s, 3H), 3.64 (s, 3H), 4.84 (d, J = 12.0 Hz, 1H), 5.14 (d, J = 12.0 Hz, 1H), 5.41 (s, 1H), 6.08 (s, 1H), 6.66 (d, J = 8.2 Hz, 1H), 6.76 (td, J = 8.4, 2.7 Hz, 1H), 6.76 (d, J = 8.2 Hz, 1H), 6.89 (d, J = 1.9 Hz, 1H), 6.92 (dd, J = 11.5, 2.7 Hz, 1H), 7.00 (dd, J = 8.3, 1.9 Hz, 1H), 7.14 (dd, J = 8.4, 7.1 Hz, 1H), 7.53 (d, J = 8.3 Hz, 1H) |
| 6-(4-Fluoro-2-methoxyphenyl)-5-(5-methoxycarbonyl-2-methylphenoxymethyl)-2,2,4-trimethyl-1,2-dihydroquinoline (Compound No. 3-89) 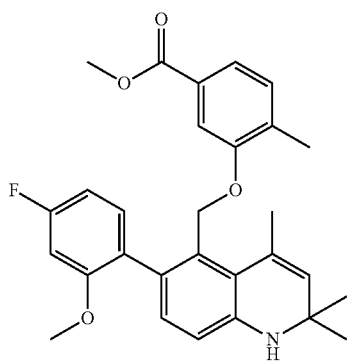 | $^1$H-NMR (500 MHz, DMSO-d$_6$) δ 0.91 (s, 3H), 1.20 (s, 3H), 2.10 (s, 3H), 2.13 (s, 3H), 3.75 (s, 3H), 3.80 (s, 3H), 4.67 (d, J = 12.4 Hz, 1H), 5.18 (d, J = 12.4 Hz, 1H), 5.38 (s, 1H), 6.00 (s, 1H), 6.60 (d, J = 8.2 Hz, 1H), 6.74 (d, J = 8.2 Hz, 1H), 6.81 (td, J = 8.3, 2.5 Hz, 1H), 6.93 (d, J = 1.2 Hz, 1H), 6.95 (dd, J = 11.5, 2.5 Hz, 1H), 7.18 (d, J = 7.6 Hz, 1H), 7.26 (dd, J = 8.3, 7.3 Hz, 1H), 7.35 (dd, J = 7.6, 1.2 Hz, 1H) |

| | |
|---|---|
| 5-(5-Cyano-2-methoxyphenoxymethyl)-6-(4-fluoro-2-methoxyphenyl)-2,2,4-trimethyl-1,2-dihydroquinoline (Compound No. 3-90)<br />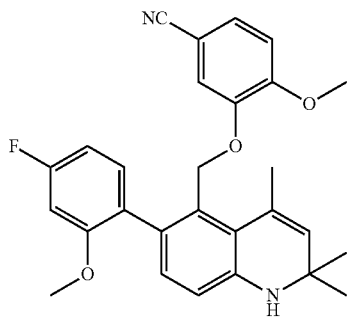 | $^{1}$H-NMR (500 MHz, DMSO-d$_6$) δ 1.13 (s, 3H), 1.15 (s, 3H), 2.09 (s, 3H), 3.69 (s, 3H), 3.77 (s, 3H), 4.50 (d, J = 11.6 Hz, 1H), 5.11 (d, J = 11.6 Hz, 1H), 5.39 (s, 1H), 6.01 (s, 1H), 6.62 (d, J = 8.2 Hz, 1H), 6.65 (td, J = 8.4, 2.6 Hz, 1H), 6.72 (d, J = 8.2 Hz, 1H), 6.90 (dd, J = 11.5, 2.6 Hz, 1H), 6.99 (d, J = 2.1 Hz, 1H), 7.04 (d, J = 8.5 Hz, 1H), 7.09 (dd, J = 8.4, 7.2 Hz, 1H), 7.33 (dd, J = 8.5, 2.1 Hz, 1H) |
| 5-(2-Cyano-5-nitrophenoxymethyl)-6-(4-fluoro-2-methoxyphenyl)-2,2,4-trimethyl-1,2-dihydroquinoline (Compound No. 3-91)<br />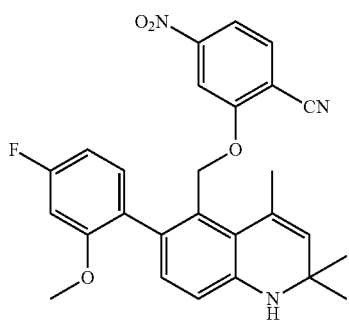 | $^{1}$H-NMR (500 MHz, DMSO-d$_6$) δ 0.88 (s, 3H), 1.16 (s, 3H), 2.17 (s, 3H), 3.74 (s, 3H), 4.88 (d, J = 12.8 Hz, 1H), 5.42 (s, 1H), 5.47 (d, J = 12.8 Hz, 1H), 6.07 (s, 1H), 6.63 (d, J = 8.3 Hz, 1H), 6.77-6.81 (m, 1H), 6.79 (d, J = 8.3 Hz, 1H), 6.95 (dd, J = 11.5, 2.6 Hz, 1H), 7.26 (dd, J = 8.3, 7.0 Hz, 1H), 7.35 (d, J = 2.1 Hz, 1H), 7.79 (dd, J = 8.6, 2.1 Hz, 1H), 7.98 (d, J = 8.6 Hz, 1H) |
| 5-(2,5-Difluorophenoxymethyl)-6-(4-fluoro-2-methoxyphenyl)-2,2,4-trimethyl-1,2-dihydroquinoline (Compound No. 3-92)<br />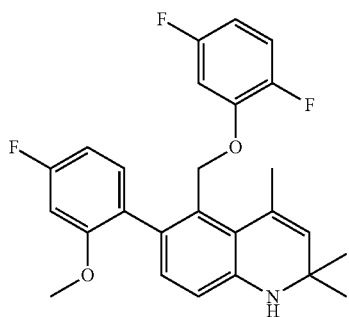 | $^{1}$H-NMR (400 MHz, DMSO-d$_6$) δ 1.11 (s, 3H), 1.13 (s, 3H), 2.10 (s, 3H), 3.70 (s, 3H), 4.59 (d, J = 11.7 Hz, 1H), 5.11 (d, J = 11.7 Hz, 1H), 5.41 (s, 1H), 6.05 (s, 1H), 6.62-7.73 (m, 3H), 6.63 (d, J = 8.1 Hz, 1H), 6.75 (d, J = 8.1 Hz, 1H), 6.93 (dd, J = 11.6, 2.6 Hz, 1H), 7.11 (dd, J = 8.4, 7.2 Hz, 1H), 7.13-7.18 (m, 1H) |

| | |
|---|---|
| 6-(4-Fluoro-2-methoxyphenyl)-5-(5-fluoro-2-nitrophenoxymethyl)-2,2,4-trimethyl-1,2-dihydroquinoline (Compound No. 3-93)<br />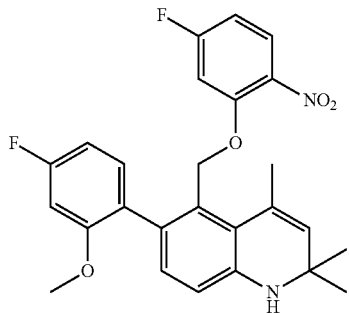 | $^1$H-NMR (400 MHz, DMSO-d$_6$) δ 1.06 (s, 3H), 1.10 (s, 3H), 2.09 (s, 3H), 3.71 (s, 3H), 4.71 (d, J = 12.2 Hz, 1H), 5.23 (d, J = 12.2 Hz, 1H), 5.38 (s, 1H), 6.08 (s, 1H), 6.64 (d, J = 8.2 Hz, 1H), 6.70 (td, J = 8.3, 2.4 Hz, 1H), 6.76 (d, J = 8.2 Hz, 1H), 6.82 (dd, J = 11.1, 2.5 Hz, 1H), 6.84-6.89 (m, 1H), 6.93 (dd, J = 11.5, 2.4 Hz, 1H), 7.11 (dd, J = 8.3, 7.1 Hz, 1H), 7.93 (dd, J = 8.0, 6.1 Hz, 1H) |
| 6-(4-Fluoro-2-methoxyphenyl)-5-(5-formyl-2-methylphenoxymethyl)-2,2,4-trimethyl-1,2-dihydroquinoline (Compound No. 3-94)<br />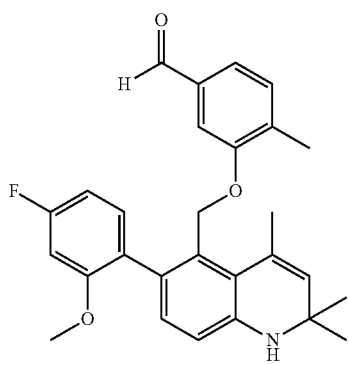 | $^1$H-NMR (500 MHz, DMSO-d$_6$) δ 0.99 (s, 3H), 1.18 (s, 3H), 2.07 (s, 3H), 2.15 (s, 3H), 3.74 (s, 3H), 4.69 (d, J = 11.9 Hz, 1H), 5.81 (d, J = 11.9 Hz, 1H), 5.39 (s, 1H), 6.02 (s, 1H), 6.62 (d, J = 8.1 Hz, 1H), 6.75 (d, J = 8.1 Hz, 1H), 6.78 (td, J = 8.4, 2.7 Hz, 1H), 6.92 (d, J = 0.9 Hz, 1H), 6.95 (dd, J = 11.5, 2.7 Hz, 1H), 7.26 (dd, J = 8.4, 7.0 Hz, 1H), 7.30 (d, J = 7.6 Hz, 1H), 7.33 (dd, J = 7.6, 0.9 Hz, 1H), 9.78 (s, 1H) |
| 5-(2-Chloro-5-fluorophenoxymethyl)-6-(4-fluoro-2-methoxyphenyl)-2,2,4-trimethyl-1,2-dihydroquinoline (Compound No. 3-95)<br />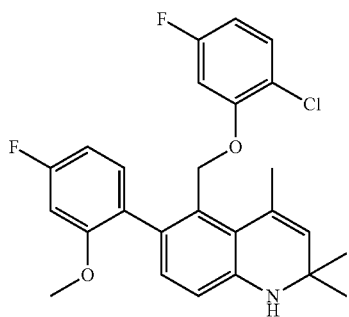 | $^1$H-NMR (400 MHz, DMSO-d$_6$) δ 1.09 (s, 3H), 1.12 (s, 3H), 2.09 (s, 3H), 3.72 (s, 3H), 4.59 (d, J = 12.0 Hz, 1H), 5.14 (d, J = 12.0 Hz, 1H), 5.40 (s, 1H), 6.06 (s, 1H), 6.64 (d, J = 8.3 Hz, 1H), 6.65 (dd, J = 10.9, 2.8 Hz, 1H), 6.70 (td, J = 8.4, 2.4 Hz, 1H), 6.71 (td, J = 8.4, 2.1 Hz, 1H), 6.76 (d, J = 8.3 Hz, 1H), 6.93 (dd, J = 11.5, 2.7 Hz, 1H), 7.17 (dd, J = 8.5, 7.1 Hz, 1H), 7.36 (dd, J = 8.8, 6.2 Hz, 1H) |

| | |
|---|---|
| 5-[2-(2-Hydroxyethyl)phenoxymethyl]-6-(2-methoxy)-5-methylphenyl)-2,2,4-trimethyl-1,2-dihydroquinoline (Compound No. 3-96) 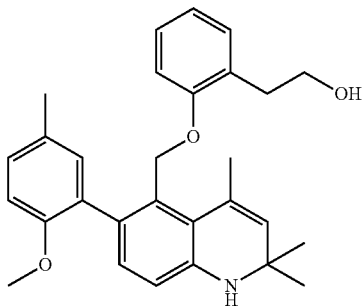 | $^1$H-NMR (400 MHz, DMSO-d$_6$) δ 1.13 (s, 3H), 1.17 (s, 3H), 2.03 (s, 3H), 2.15 (s, 3H), 2.61-2.67 (m, 2H), 3.44-3.49 (m, 2H), 3.67 (s, 3H), 4.43 (t, J = 5.2 Hz, 1H), 4.52 (d, J = 11.5 Hz, 1H), 5.02 (d, J = 11.5 Hz, 1H), 5.38 (s, 1H), 5.97 (s, 1H), 6.58 (d, J = 7.6 Hz, 1H), 6.63 (d, J = 8.2 Hz, 1H), 6.74 (td, J = 7.6, 0.9 Hz, 1H), 6.76 (d, J = 8.2 Hz, 1H), 6.90 (d, J = 8.1 Hz, 1H), 6.98 (d, J = 1.9 Hz, 1H), 6.98-7.08 (m, 3H) |
| 5-[2-(2-Hydroxyethyl)phenoxymethyl]-6-(2-methoxy-5-trifluoromethylphenyl)-2,2,4-trimethyl-1,2-dihydroquinoline (Compound No. 3-97) 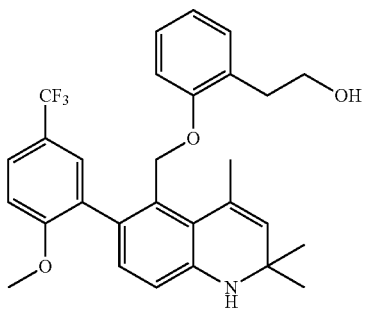 | $^1$H-NMR (500 MHz, DMSO-d$_6$) δ 1.15 (s, 3H), 1.18 (s, 3H), 2.04 (s, 3H), 2.56-2.71 (m, 2H), 3.42-3.48 (m, 2H), 3.79 (s, 3H), 4.43 (t, J = 5.4 Hz, 1H), 4.44 (d, J = 11.6 Hz, 1H), 5.01 (d, J = 11.6 Hz, 1H), 5.41 (s, 1H), 6.09 (s, 1H), 6.59 (d, J = 7.5 Hz, 1H), 6.66 (d, J = 8.3 Hz, 1H), 6.75 (t, J = 7.5 Hz, 1H), 6.80 (d, J = 8.3 Hz, 1H), 6.98 (t, J = 7.5 Hz, 1H), 7.05 (d, J = 7.5 Hz, 1H), 7.21 (d, J = 8.7 Hz, 1H), 7.45 (d, J = 2.3 Hz, 1H), 7.62 (dd, J = 8.7, 2.3 Hz, 1H) |
| 6-(5-Chloro-2-methoxyphenyl)-5-[2-(2-Hydroxyethyl)phenoxymethyl]-2,2,4-trimethyl-1,2-dihydroquinoline (Compound No. 3-98) 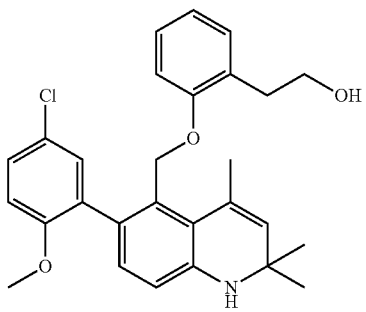 | $^1$H-NMR (500 MHz, DMSO-d$_6$) δ 1.15 (s, 3H), 1.17 (s, 3H), 2.02 (s, 3H), 2.60-2.69 (m, 2H), 3.45-3.49 (m, 2H), 3.70 (s, 3H), 4.43 (t, J = 5.2 Hz, 1H), 4.48 (d, J = 11.0 Hz, 1H), 5.01 (d, J = 11.0 Hz, 1H), 5.40 (s, 1H), 6.07 (s, 1H), 6.62 (d, J = 7.9 Hz, 1H), 6.65 (d, J = 8.1 Hz, 1H), 6.76 (t, J = 7.3 Hz, 1H), 6.77 (d, J = 8.1 Hz, 1H), 7.00-7.03 (m, 1H), 7.04 (d, J = 8.9 Hz, 1H), 7.07 (d, J = 7.3 Hz, 1H), 7.18 (d, J = 2.6 Hz, 1H), 7.29 (dd, J = 8.9, 2.6 Hz, 1H) |

6-(5-Fluoro-2-methoxyphenyl)-5-[2-(2-hydroxyethyl)phenoxymethyl]-2,2,4-trimethyl-1,2-dihydroquinoline (Compound No. 3-99)

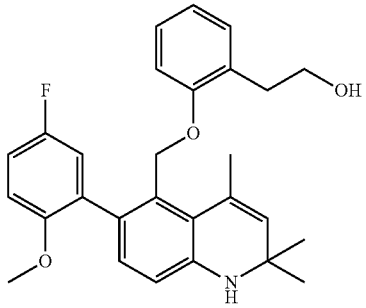

$^1$H-NMR (500 MHz, DMSO-d$_6$) δ 1.13 (s, 3H), 1.18 (s, 3H), 2.02 (s, 3H), 2.63 (q, J = 6.4 Hz, 2H), 3.46 (q, J = 6.4 Hz, 2H), 3.69 (s, 3H), 4.42 (t, J = 6.4 Hz, 1H), 4.53 (d, J = 11.3 Hz, 1H), 5.03 (d, J = 11.3 Hz, 1H), 5.39 (s, 1H), 6.05 (s, 1H), 6.61 (d, J = 8.2 Hz, 1H), 6.64 (d, J = 8.2 Hz, 1H), 6.76 (t, J = 8.2 Hz, 1H), 6.78 (d, J = 8.2 Hz, 1H), 6.99-7.03 (m, 2H), 7.02 (dd, J = 8.6, 2.9 Hz, 1H), 7.07 (d, J = 8.2 Hz, 1H), 7.08 (d, J = 8.2 Hz, 1H)

5-(2-Cyano-5-nitrophenoxymethyl)-6-(2-methoxy-5-trifluoromethylphenyl)-2,2,4-trimethyl-1,2-dihydroquinoline (Compound No. 3-100)

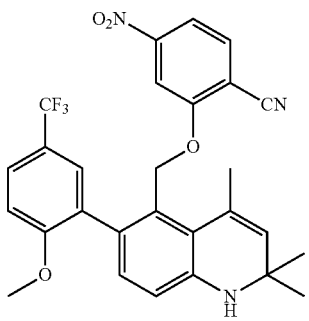

$^1$H-NMR (500 MHz, DMSO-d$_6$) δ 0.97 (s, 3H), 1.16 (s, 3H), 2.17 (s, 3H), 3.82 (s, 3H), 4.78 (d, J = 12.5 Hz, 1H), 5.45 (s, 1H), 5.49 (d, J = 12.5 Hz, 1H), 6.17 (s, 1H), 6.67 (d, J = 8.2 Hz, 1H), 6.85 (d, J = 8.2 Hz, 1H), 7.23 (d, J = 8.7 Hz, 1H), 7.41 (d, J = 2.0 Hz, 1H), 7.52 (d, J = 2.0 Hz, 1H), 7.63 (dd, J = 8.7, 2.0 Hz, 1H), 7.79 (dd, J = 8.6, 2.0 Hz, 1H), 7.98 (d, J = 8.6 Hz, 1H)

5-(5-Formyl-2-methylphenoxymethyl)-6-(2-methoxy-5-trifluoromethylphenyl)-2,2,4-trimethyl-1,2-dihydroquinoline (Compound No. 3-101)

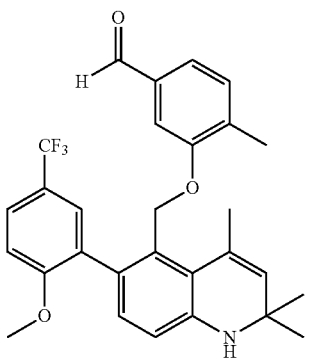

$^1$H-NMR (400 MHz, DMSO-d$_6$) δ 1.05 (s, 3H), 1.18 (s, 3H), 2.09 (s, 3H), 2.15 (s, 3H), 3.81 (s, 3H), 4.58 (d, J = 12.1 Hz, 1H), 5.20 (d, J = 12.1 Hz, 1H), 5.42 (s, 1H), 6.11 (s, 1H), 6.65 (d, J = 8.3 Hz, 1H), 6.81 (d, J = 8.3 Hz, 1H), 6.96 (s, 1H), 7.23 (d, J = 8.5 Hz, 1H), 7.25-7.34 (m, 2H), 7.53 (d, J = 2.1 Hz, 1H), 7.63 (dd, J = 8.8, 2.1 Hz, 1H), 9.77 (s, 1H)

| Compound | NMR |
|---|---|
| 6-(4-Chloro-2-methoxyphenyl)-5-[2-(2-hydroxyethyl)phenoxymethyl]-2,2,4-trimethyl-1,2-dihydroquinoline (Compound No. 3-102) 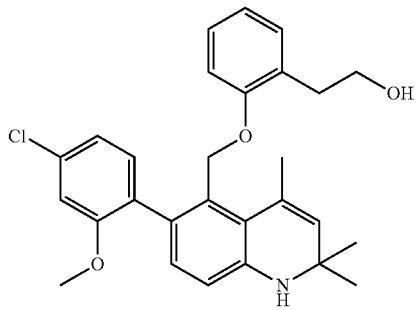 | $^1$H-NMR (400 MHz, DMSO-$d_6$) δ 1.12 (s, 3H), 1.17 (s, 3H), 2.01 (s, 3H), 2.62 (t, J = 7.2 Hz, 2H), 3.45 (br s, 2H), 3.74 (s, 3H), 4.43 (t, J = 5.1 Hz, 1H), 4.50 (d, J = 12.8 Hz, 1H), 5.00 (d, J = 12.8 Hz, 1H), 5.39 (s, 1H), 6.04 (s, 1H), 6.61 (d, J = 7.5 Hz, 1H), 6.64 (d, J = 8.2 Hz, 1H), 6.75 (d, J = 8.2 Hz, 1H), 6.76 (t, J = 7.5 Hz, 1H), 6.96 (dd, J = 8.1, 2.0 Hz, 1H), 7.01 (t, J = 7.5 Hz, 1H), 7.07 (d, J = 7.5 Hz, 1H), 7.09 (d, J = 2.0 Hz, 1H), 7.17 (d, J = 8.1 Hz, 1H) |

Example 4

5-Benzyloxymethyl-6-(2-methoxyphenyl)-2,2,4-trimethyl-1,2-dihydroquinoline (Compound No. 4-1)

60% Sodium hydride (30 mg, 0.75 mmol) was suspended in anhydrous tetrahydrofuran (1 mL), and benzylalcohol (78 µL, 0.75 mmol) was added thereto under argon atmosphere at 0° C. After the reaction mixture was stirred at room temperature for 30 minutes, a solution of 5-chloromethyl-6-(2-methoxyphenyl)-2,2,4-trimethyl-1,2-dihydroquinoline (Reference Compound 5-1, 50 mg, 0.15 mmol) in anhydrous tetrahydrofuran solution (1.5 mL) was added thereto. The reaction mixture was stirred at 50° C. for 7 hours. After cooling down, ethyl acetate (50 mL) was added thereto. The whole was washed with water (50 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled compound (4.0 mg) as a colorless solid. (Yield 7%)

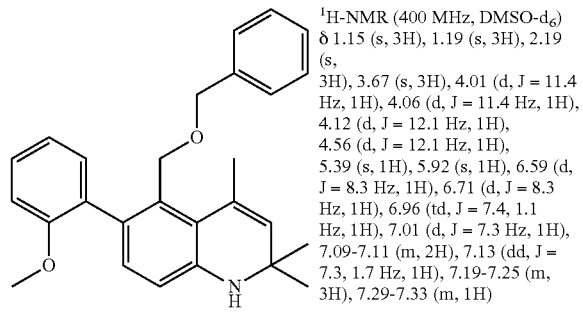

$^1$H-NMR (400 MHz, DMSO-$d_6$) δ 1.15 (s, 3H), 1.19 (s, 3H), 2.19 (s, 3H), 3.67 (s, 3H), 4.01 (d, J = 11.4 Hz, 1H), 4.06 (d, J = 11.4 Hz, 1H), 4.12 (d, J = 12.1 Hz, 1H), 4.56 (d, J = 12.1 Hz, 1H), 5.39 (s, 1H), 5.92 (s, 1H), 6.59 (d, J = 8.3 Hz, 1H), 6.71 (d, J = 8.3 Hz, 1H), 6.96 (td, J = 7.4, 1.1 Hz, 1H), 7.01 (d, J = 7.3 Hz, 1H), 7.09-7.11 (m, 2H), 7.13 (dd, J = 7.3, 1.7 Hz, 1H), 7.19-7.25 (m, 3H), 7.29-7.33 (m, 1H)

Using Compound No. 5-2, the following Compounds (No. 4-2~4-6) were obtained by a method similar to that of Compound No. 4-1.

| Compound | NMR |
|---|---|
| 5-Benzyloxymethyl-6-(4-fluoro-2-methoxyphenyl)-2,2,4-trimethyl-1,2-dihydroquinoline (Compound No. 4-2) 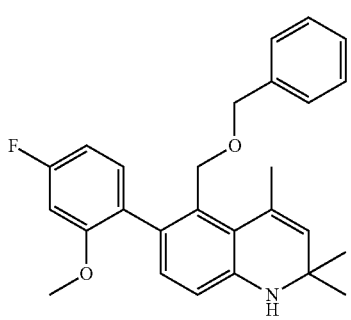 | $^1$H-NMR (500 MHz, DMSO-$d_6$) δ 1.15 (s, 3H), 1.18 (s, 3H), 2.19 (s, 3H), 3.67 (s, 3H), 4.04 (d, J = 11.6 Hz, 1H), 4.06 (d, J = 11.6 Hz, 1H), 4.09 (d, J = 11.6 Hz, 1H), 4.52 (d, J = 11.6 Hz, 1H), 5.39 (s, 1H), 5.93 (s, 1H), 6.58 (d, J = 8.2 Hz, 1H), 6.68 (d, J = 8.2 Hz, 1H), 6.76 (td, J = 8.4, 2.6 Hz, 1H), 6.89 (dd, J = 11.5, 2.6 Hz, 1H), 7.10-7.11 (m, 2H), 7.12 (dd, J = 8.4, 7.2 Hz, 1H), 7.21-7.26 (m, 3H) |

-continued

| | |
|---|---|
| 6-(4-Fluoro-2-methoxyphenyl)-5-(thiophen-2-ylmethoxymethyl)-2,2,4-trimethyl-1,2-dihydroquinoline (Compound No. 4-3)<br>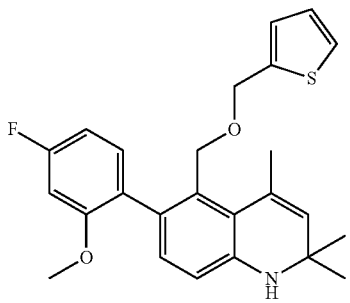 | $^1$H-NMR (400 MHz, DMSO-d$_6$)<br>δ 1.16 (s, 3H), 1.18 (s, 3H), 2.16 (s, 3H), 3.68 (s, 3H), 4.05 (d, J = 11.7 Hz, 1H), 4.19 (d, J = 12.3 Hz, 1H), 4.24 (d, J = 12.3 Hz, 1H), 4.52 (d, J = 11.7 Hz, 1H), 5.37 (s, 1H), 5.94 (s, 1H), 6.58 (d, J = 8.1 Hz, 1H), 6.68 (d, J = 8.1 Hz, 1H), 6.75 (td, J = 8.4, 2.4 Hz, 1H), 6.82 (dd, J = 3.5, 1.2 Hz, 1H), 6.90 (dd, J = 4.9, 3.5 Hz, 1H), 6.90 (dd, J = 11.7, 2.4 Hz, 1H), 7.12 (dd, J = 8.4, 7.1 Hz, 1H), 7.41 (dd, J = 4.9, 1.2 Hz, 1H) |
| 6-(4-Fluoro-2-methoxyphenyl)-5-(4-methylbenzyloxymethyl)-2,2,4-trimethyl-1,2-dihydroquinoline (Compound No. 4-4)<br>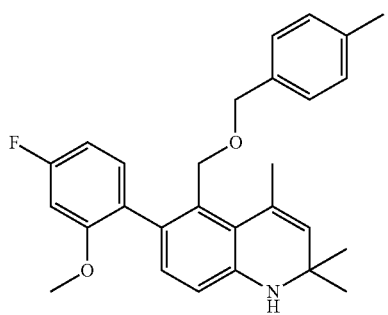 | $^1$H-NMR (400 MHz, DMSO-d$_{63}$)<br>δ 1.15 (s, 3H), 1.18 (s, 3H), 2.17 (s, 3H), 2.25 (s, 3H), 3.67 (s, 3H), 3.99 (d, J = 11.4 Hz, 1H), 4.03 (d, J = 11.7 Hz, 1H), 4.04 (d, J = 11.4 Hz, 1H), 4.49 (d, J = 11.7 Hz, 1H), 5.38 (s, 1H), 5.93 (s, 1H), 6.58 (d, J = 8.1 Hz, 1H), 6.67 (d, J = 8.1 Hz, 1H), 6.75 (td, J = 8.4, 2.4 Hz, 1H), 6.89 (dd, J = 11.5, 2.4 Hz, 1H), 6.98 (d, J = 7.9 Hz, 2H), 7.04 (d, J = 7.9 Hz, 2H), 7.10 (dd, J = 8.4, 7.2 Hz, 1H) |
| 6-(4-Fluoro-2-methoxyphenyl)-5-(3-methylbenzyloxymethyl)-2,2,4-trimethyl-1,2-dihydroquinoline (Compound No. 4-5)<br>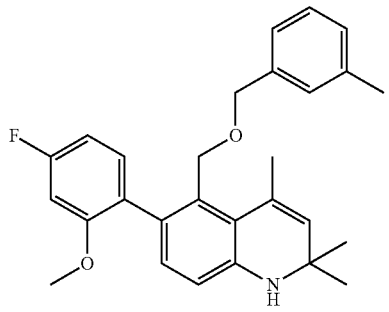 | $^1$H-NMR (400 MHz, DMSO-d$_6$)<br>δ 1.15 (s, 3H), 1.19 (s, 3H), 2.18 (s, 3H), 2.23 (s, 3H), 3.67 (s, 3H), 4.00 (d, J = 11.7 Hz, 1H), 4.05 (d, J = 11.7 Hz, 2H), 4.51 (d, J = 11.7 Hz, 1H), 5.39 (s, 1H), 5.94 (s, 1H), 6.58 (d, J = 8.3 Hz, 1H), 6.68 (d, J = 8.3 Hz, 1H), 6.75 (td, J = 8.4, 2.4 Hz, 1H), 6.88-6.91 (m, 2H), 6.90 (dd, J = 11.2, 2.4 Hz, 1H), 7.02 (d, J = 7.7 Hz, 1H), 7.10-7.14 (m, 2H) |
| 6-(4-Fluoro-2-methoxyphenyl)-5-(2-phenylethoxymethyl)-2,2,4-trimethyl-1,2-dihydroquinoline (Compound No. 4-6)<br>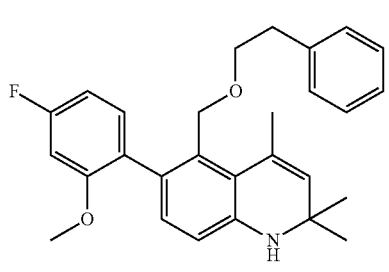 | $^1$H-NMR (500 MHz, CDCl$_3$)<br>δ 1.24 (s, 3H), 1.27 (s, 3H), 2.18 (s, 3H), 2.69 (t, J = 7.1 Hz, 2H), 3.22-3.31 (m, 2H), 3.68 (s, 3H), 3.80 (br s, 1H), 4.08 (d, J = 11.9 Hz, 1H), 4.58 (d, J = 11.9 Hz, 1H), 5.43 (s, 1H), 6.52 (d, J = 8.2 Hz, 1H), 6.58-6.64 (m, 2H), 6.80 (d, J = 8.2 Hz, 1H), 7.09-7.26 (m, 6H) |

Example 5

5-Benzoyloxymethyl-6-(3-hydroxy-2-methoxyphenyl)-2,2,4-trimethyl-1,2-dihydroquinoline (Compound No. 5-1)

5-Benzoyloxymethyl-6-(2-methoxy-3-methoxymethoxylphenyl)-2,2,4-trimethyl-1,2-dihydroquinoline (Compound 1-28, 228 mg, 0.481 mmol) was dissolved in 1,4-dioxane (4 mL), and 4N HCl/1,4-dioxane (1 mL) was added thereto, and then the reaction mixture was stirred at room temperature for 45 minutes. The solvent was removed under reduced pressure, and the obtained residue was purified by silica gel column chromatography (hexane-ethyl acetate) to give the titled compound (14.0 mg) as a colorless solid. (Yield 7%)

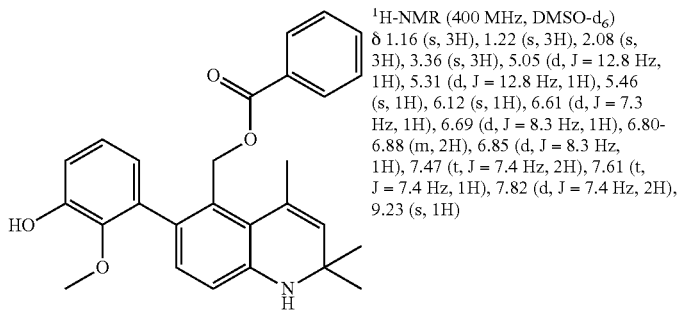

$^1$H-NMR (400 MHz, DMSO-$d_6$)
δ 1.16 (s, 3H), 1.22 (s, 3H), 2.08 (s, 3H), 3.36 (s, 3H), 5.05 (d, J = 12.8 Hz, 1H), 5.31 (d, J = 12.8 Hz, 1H), 5.46 (s, 1H), 6.12 (s, 1H), 6.61 (d, J = 7.3 Hz, 1H), 6.69 (d, J = 8.3 Hz, 1H), 6.80-6.88 (m, 2H), 6.85 (d, J = 8.3 Hz, 1H), 7.47 (t, J = 7.4 Hz, 2H), 7.61 (t, J = 7.4 Hz, 1H), 7.82 (d, J = 7.4 Hz, 2H), 9.23 (s, 1H)

Using any compounds among Reference Compound No. 2-6, Compounds 1-38, 13-4 and 13-49~13-50, the following Compounds (No. 5-2~5-5) were obtained by a method similar to that of Compound No. 5-1.

5-Benzoyloxymethyl-6-(2-hydroxyphenyl)-2,2,4-trimethyl-1,2-dihydroquinoline (Compound No. 5-2)

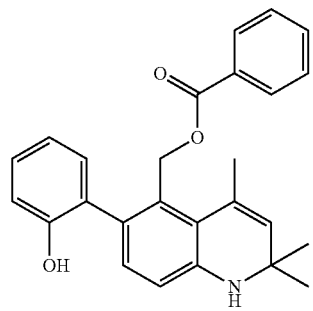

$^1$H-NMR (400 MHz, DMSO-$d_6$)
δ 1.16 (s, 3H), 1.23 (s, 3H), 2.07 (s, 3H), 5.05 (d, J = 12.9 Hz, 1H), 5.31 (d, J = 12.9 Hz, 1H), 5.46 (s, 1H), 6.08 (s, 1H), 6.68 (d, J = 8.3 Hz, 1H), 6.75 (t, J = 6.8 Hz, 1H), 6.80 (d, J = 8.3 Hz, 1H), 6.87 (d, J = 8.1 Hz, 1H), 7.04-7.15 (m, 2H), 7.41-7.51 (m, 2H), 7.61 (t, J = 7.8 Hz, 1H), 7.82 (dd, J = 7.8, 1.2 Hz, 2H), 9.31 (s, 1H)

5-(5-Fluoro-2-methylphenoxymethyl)-6-(4-hydroxy-2-methoxyphenyl)-2,2,4-trimethyl-1,2-dihydroquinoline (Compound No. 5-3)

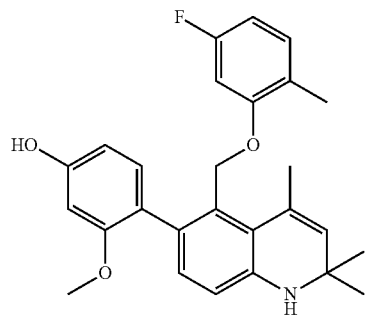

$^1$H-NMR (400 MHz, DMSO-$d_6$)
δ 1.00 (s, 3H), 1.14 (s, 3H), 2.01 (s, 3H), 2.08 (s, 3H), 3.67 (s, 3H), 4.63 (d, J = 12.1 Hz, 1H), 5.08 (d, J = 122.1 Hz, 1H), 5.37 (s, 1H), 5.90 (s, 1H), 6.29 (dd, J = 11.5, 2.4 Hz, 1H), 6.36 (dd, J = 8.1, 2.3 Hz, 1H), 6.45 (d, J = 2.3 Hz, 1H), 6.50 (td, J = 8.4, 2.4 Hz, 1H), 6.58 (d, J = 8.1 Hz, 1H), 6.73 (d, J = 8.1 Hz, 1H), 6.94 (d, J = 8.1 Hz, 1H), 7.00-7.04 (m, 1H), 9.46 (s, 1H)

| | |
|---|---|
| 5-(5-Fluoro-2-methylphenoxymethyl)-6-(5-hydroxy-2-methoxyphenyl)-2,2,4-trimethyl-1,2-dihydroquinoline (Compound No. 5-4) 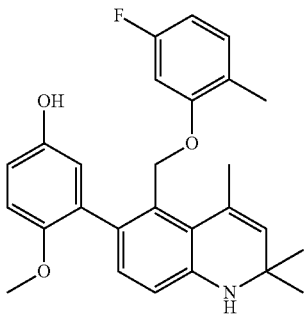 | $^1$H-NMR (400 MHz, DMSO-d$_6$) δ 1.02 (s, 3H), 1.15 (s, 3H), 2.01 (s, 3H), 2.06 (s, 3H), 3.61 (s, 3H), 4.65 (d, J = 12.2 Hz, 1H), 5.10 (d, J = 12.2 Hz, 1H), 5.38 (s, 1H), 5.99 (s, 1H), 6.33 (dd, J = 11.5, 2.4 Hz, 1H), 6.51 (td, J = 8.4, 2.4 Hz, 1H), 6.59 (d, J = 2.9 Hz, 1H), 6.61 (d, J = 8.3 Hz, 1H), 6.67 (dd, J = 8.8, 2.9 Hz, 1H), 6.75 (d, J = 8.3 Hz, 1H), 6.85 (d, J = 8.8 Hz, 1H), 7.00-7.04 (m, 1H), 8.93 (s, 1H). |
| 6-(4-Hydroxy-2-methoxyphenyl)-5-(4-methylbenzoyloxymethyl)-2,2,4-trimethyl-1,2-dihydroquinoline (Compound No. 5-5) 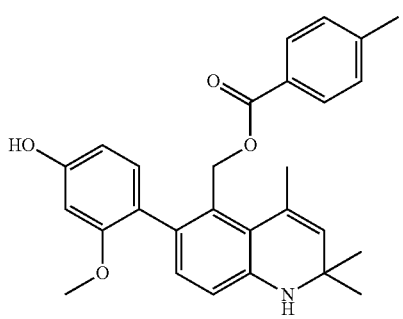 | $^1$H-NMR (500 MHz, DMSO-d$_6$) δ 1.15 (s, 3H), 1.22 (s, 3H), 2.06 (s, 3H), 2.35 (s, 3H), 3.60 (s, 3H), 4.96 (d, J = 12.7 Hz, 1H), 5.19 (d, J = 12.7 Hz, 1H), 5.43 (s, 1H), 6.00 (s, 1H), 6.31 (dd, J = 8.2, 2.4 Hz, 1H), 6.41 (d, J = 2.4 Hz, 1H), 6.63 (d, J = 8.2 Hz, 1H), 6.73 (d, J = 8.2 Hz, 1H), 6.89 (d, J = 8.2 Hz, 1H), 7.27 (d, J = 8.1 Hz, 2H), 7.72 (d, J = 8.1 Hz, 2H), 9.42 (s, 1H). |

Example 6

6-(2-Methoxyphenyl)-5-[(pyrrolidin-1-yl)methyl]-2,2,4-trimethyl-1,2-dihydroquinoline (Compound No. 6-1)

A mixture of 5-chloromethyl-6-(2-methoxyphenyl)-2,2,4-trimethyl-1,2-dihydroquinoline (Reference Compound No. 5-1, 41.2 mg, 0.126 mmol), pyrrolidine (52.6 μL, 0.630 mmol) and potassium carbonate (34.8 mg, 0.252 mmol) was suspended in anhydrous N,N-dimethylformamide mL), and the reaction mixture was stirred at 50° C. for 1 hour. After cooling down, it was diluted with ethyl acetate (50 mL). The whole was washed with water (50 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (36.1 mg) as a colorless solid: (Yield 79%)

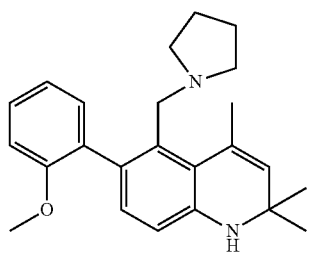 [SMILES: COc1ccccc1-c1ccc2c(c1CN1CCCC1)C(C)=CC(C)(C)N2]

$^1$H-NMR (500 MHz, DMSO-d$_6$) δ 1.08 (s, 3H), 1.21 (s, 3H), 1.43-1.51 (m, 4H), 1.97-2.09 (m, 4H), 2.13 (d, J = 1.4 Hz, 3H), 3.07 (d, J = 13.1 Hz, 1H), 3.68 (s, 3H), 3.73 (d, J = 13.1 Hz, 1H), 5.29 (d, J = 1.4 Hz, 1H), 5.77 (s, 1H), 6.53 (d, J = 7.9 Hz, 1H), 6.64 (d, J = 7.9 Hz, 1H), 6.94 (td, J = 7.3, 0.9 Hz, 1H), 6.99 (d, J = 7.6 Hz, 1H), 7.03 (dd, J = 7.3, 1.8 Hz, 1H), 7.27-7.29 (m, 1H)

Using any compounds among Reference Compound No. 5-1~5-10 and No. 5-14~5-16, the following Compounds (No. 6-2~6-86) were obtained by a method similar to that of Compound No. 6-1.

| | |
|---|---|
| 6-(2-Methoxyphenyl)-5-phenylaminomethyl-2,2,4-trimethyl-1,2-dihydroquinoline (Compound No. 6-2) 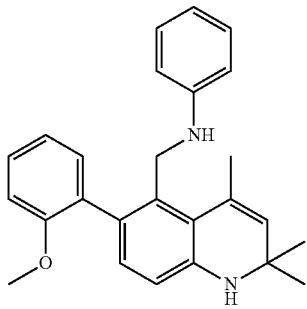 | $^1$H-NMR (400 MHz, DMSO-d$_6$) δ 1.17 (s, 3H), 1.20 (s, 3H), 2.10 (s, 3H), 3.69 (s, 3H), 3.76 (d, J = 12.3 Hz, 1H), 3.97 (d, J = 12.3 Hz, 1H), 5.08 (s, 1H), 5.35 (s, 1H), 5.90 (s, 1H), 6.43 (d, J = 8.0 Hz, 2H), 6.45 (t, J = 8.0 Hz, 1H), 6.58 (d, J = 8.2 Hz, 1H), 6.68 (d, J = 8.2 Hz, 1H), 6.87 (t, J = 7.4 Hz, 1H), 6.96 (t, J = 8.0 Hz, 2H), 6.97 (d, J = 7.6 Hz, 1H), 7.17 (dd, J = 7.6, 1.7 Hz, 1H), 7.20-7.24 (m, 1H) |
| 6-(2-Methoxyphenyl)-5-propylaminomethyl-2,2,4-trimethyl-1,2-dihydroquinoline (Compound No. 6-3) 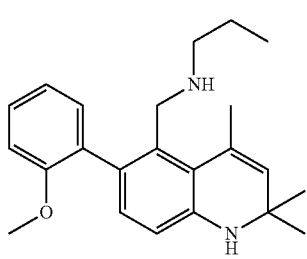 | $^1$H-NMR (400 MHz, DMSO-d$_6$) δ 0.69 (t, J = 7.4 Hz, 3H), 1.03 (br s, 1H), 1.13 (s, 3H), 1.13-1.21 (m, 2H), 1.19 (s, 3H), 2.09 (t, J = 6.8 Hz, 2H), 2.23 (s, 3H), 3.37 (d, J = 12.5 Hz, 1H), 3.48 (d, J = 12.5 Hz, 1H), 3.68 (s, 3H), 5.36 (s, 1H), 5.81 (s, 1H), 6.51 (d, J = 8.1 Hz, 1H), 6.61 (d, J = 8.1 Hz, 1H), 6.95 (td, J = 7.3, 1.0 Hz, 1H), 7.02 (d, J = 7.6 Hz, 1H), 7.08 (dd, J = 7.3, 1.7 Hz, 1H), 7.28-7.32 (m, 1H) |
| 5-Benzylaminomethyl-6-(2-methoxyphenyl)-2,2,4-trimethyl-1,2-dihydroquinoline (Compound No. 6-4) 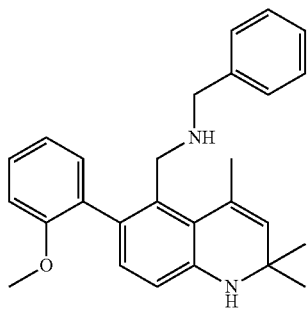 | $^1$H-NMR (400 MHz, DMSO-d$_6$) δ 1.14 (s, 3H), 1.19 (s, 3H), 1.51 (br s, 1H), 2.21 (s, 3H), 3.31 (s, 2H), 3.42 (d, J = 12.3 Hz, 1H), 3.53 (d, J = 12.3 Hz, 1H), 3.60 (s, 3H), 5.37 (s, 1H), 5.83 (s, 1H), 6.52 (d, J = 8.1 Hz, 1H), 6.62 (d, J = 8.1 Hz, 1H), 6.95 (td, J = 7.3, 1.0 Hz, 1H), 6.99 (d, J = 8.1 Hz, 1H), 7.02-7.04 (m, 2H), 7.09 (dd, J = 7.3, 1.7 Hz, 1H), 7.12-7.21 (m, 3H), 7.29-7.33 (m, 1H) |
| 5-Cyclohexylaminomethyl-6-(2-methoxyphenyl)-2,2,4-trimethyl-1,2-dihydroquinoline (Compound No. 6-5) 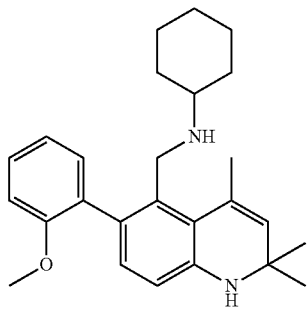 | $^1$H-NMR (400 MHz, DMSO-d$_6$) δ 0.70-0.80 (m, 2H), 0.89-1.05 (m, 3H), 1.13 (s, 3H), 1.19 (s, 3H), 1.37-1.52 (m, 5H), 1.80-1.88 (m, 1H), 2.25 (s, 3H), 3.44 (d, J = 12.3 Hz, 1H), 3.49 (d, J = 12.3 Hz, 1H), 3.68 (s, 3H), 5.36 (s, 1H), 5.82 (s, 1H), 6.50 (d, J = 8.2 Hz, 1H), 6.61 (d, J = 8.2 Hz, 1H), 6.95 (t, J = 7.3 Hz, 1H), 7.03 (d, J = 8.1 Hz, 1H), 7.08 (dd, J = 7.3, 1.7 Hz, 1H), 7.28-7.33 (m, 1H) |

| | |
|---|---|
| 6-(2-Methoxyphenyl)-5-[(N-methyl-N-phenylamino)methyl]-2,2,4-trimethyl-1,2-dihydroquinoline (Compound No. 6-6) 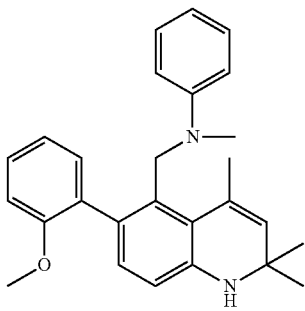 | ¹H-NMR (400 MHz, DMSO-d₆) δ 1.15 (s, 3H), 1.20 (s, 3H), 1.92 (s, 3H), 2.38 (s, 3H), 3.70 (s, 3H), 4.04 (d, J = 13.4 Hz, 1H), 4.31 (d, J = 13.4 Hz, 1H), 5.34 (s, 1H), 5.95 (s, 1H), 6.57-6.62 (m, 3H), 6.63 (d, J = 8.3 Hz, 1H), 6.72 (d, J = 8.3 Hz, 1H), 6.93 (t, J = 7.3 Hz, 1H), 6.99 (d, J = 8.1 Hz, 1H), 7.04 (dd, J = 7.4, 1.8 Hz, 1H), 7.09 (t, J = 7.9 Hz, 2H), 7.23-7.27 (m, 1H) |
| 5-(4-Chlorophenylaminomethyl)-6-(2-methoxyphenyl)-2,2,4-trimethyl-1,2-dihydroquinoline (Compound No. 6-7) 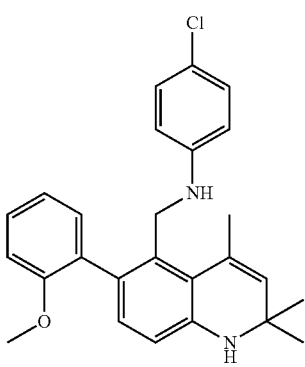 | ¹H-NMR (400 MHz, DMSO-d₆) δ 1.16 (s, 3H), 1.19 (s, 3H), 2.08 (s, 3H), 3.68 (s, 3H), 3.68-3.73 (m, 1H), 3.97 (dd, J = 12.2, 4.5 Hz, 1H), 5.35 (s, 1H), 5.44 (t, J = 4.5 Hz, 1H), 5.91 (s, 1H), 6.43 (d, J = 8.8 Hz, 2H), 6.58 (d, J = 8.3 Hz, 1H), 6.69 (d, J = 8.3 Hz, 1H), 6.87 (t, J = 7.4 Hz, 1H), 6.95-6.98 (m, 1H), 6.97 (d, J = 8.8 Hz, 2H), 7.17 (dd, J = 7.3, 1.7 Hz, 1H), 7.20-7.24 (m, 1H) |
| 5-(3,5-Difluorophenylaminomethyl)-6-(2-methoxyphenyl)-2,2,4-trimethyl-1,2-dihydroquinoline (Compound No. 6-8) 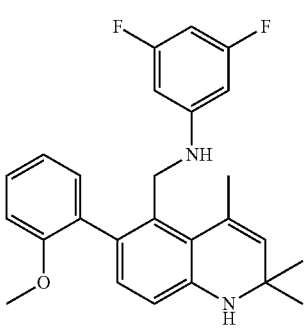 | ¹H-NMR (400 MHz, DMSO-d₆) δ 1.17 (s, 3H), 1.18 (s, 3H), 2.08 (s, 3H), 3.66-3.73 (m, 1H), 3.68 (s, 3H), 3.98-4.05 (m, 1H), 5.37 (s, 1H), 5.93 (s, 1H), 6.03-6.18 (m, 3H), 6.59 (d, J = 8.2 Hz, 1H), 6.70 (d, J = 8.2 Hz, 1H), 6.88 (t, J = 7.6 Hz, 1H), 6.98 (d, J = 7.6 Hz, 1H), 7.15 (dd, J = 7.6, 1.7 Hz, 1H), 7.21-7.26 (m, 1H) |

-continued 5-(3-Dimethylaminocarbonyloxyphenylaminomethyl)-6-(2-methoxyphenyl)-2,2,4-trimethyl-1,2-dihydroquinoline (Compound No. 6-9)

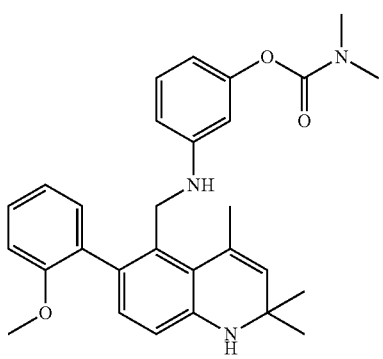

$^1$H-NMR (400 MHz, DMSO-$d_6$)
δ 1.17 (s, 3H), 1.21 (s, 3H), 2.09 (s, 3H), 2.86 (s, 3H), 2.98 (s, 3H), 3.69 (s, 3H), 3.72 (dd, J = 12.3, 3.5 Hz, 1H), 3.98 (dd, J = 12.3, 4.0 Hz, 1H), 5.36 (s, 2H), 5.90 (s, 1H), 6.15-6.18 (m, 2H), 6.28 (d, J = 8.1 Hz, 1H), 6.58 (d, J = 8.1 Hz, 1H), 6.68 (d, J = 8.1 Hz, 1H), 6.88 (t, J = 7.4 Hz, 1H), 6.93 (t, J = 8.1 Hz, 1H), 6.98 (d, J = 7.8 Hz, 1H), 7.17 (dd, J = 7.4, 1.6 Hz, 1H), 7.21-7.25 (m, 1H)

6-(5-Fluoro-2-methoxyphenyl)-5-phenylaminomethyl-2,2,4-trimethyl-1,2-dihydroquinoline (Compound No. 6-10)

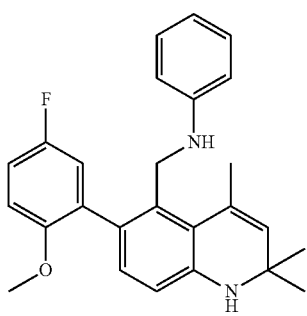

$^1$H-NMR (400 MHz, CDCl$_3$)
δ 1.25 (s, 3H), 1.30 (s, 3H), 2.21 (d, J = 1.5 Hz, 3H), 3.69 (s, 3H), 3.80-3.90 (m, 2H), 3.96 (d, J = 12.3 Hz, 1H), 4.18 (d, J = 12.3 Hz, 1H), 5.48 (d, J = 1.5 Hz, 1H), 6.42 (d, J = 8.5 Hz, 1H), 6.42 (d, J = 8.8 Hz, 1H), 6.55 (d, J = 8.1 Hz, 1H), 6.62 (t, J = 7.5 Hz, 1H), 6.75-6.78 (m, 1H), 6.82 (d, J = 8.1 Hz, 1H), 6.87-6.94 (m, 2H), 7.09 (dd, J = 8.5, 7.5 Hz, 2H)

6-(2,6-Dimethoxyphenyl)-5-phenylaminomethyl-2,2,4-trimethyl-1,2-dihydroquinoline (Compound No. 6-11)

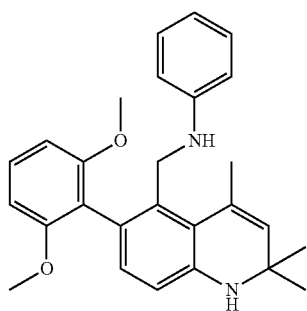

$^1$H-NMR (500 MHz, DMSO-$d_6$)
δ 1.18 (s, 6H), 2.12, 2.25 (d, J = 1.5 Hz, 3H), 3.64 (s, 3H), 3.66 (s, 3H), 3.80 (s, 1H), 4.49-5.04 (m, 2H), 5.33, 5.42 (d, J = 1.5 Hz, 1H), 5.85, 5.95 (s, 1H), 6.41-7.31 (m, 10H)

| Compound | Structure | NMR |
|---|---|---|
| 6-(2-Methoxy-5-methylphenyl)-5-phenylaminomethyl-2,2,4-trimethyl-1,2-dihydroquinoline (Compound No. 6-12) | 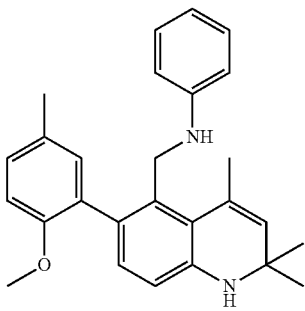 | $^1$H-NMR (400 MHz, DMSO-$d_6$) δ 1.17 (s, 3H), 1.20 (s, 3H), 2.21 (s, 3H), 2.15 (s, 3H), 3.65 (s, 3H), 3.78 (d, J = 11.8 Hz, 1H), 3.96 (d, J = 11.8 Hz, 1H), 5.02 (s, 1H), 5.36 (s, 1H), 5.90 (br s, 1H), 6.44-6.48 (m, 3H), 6.58 (d, J = 8.0 Hz, 1H), 6.69 (d, J = 8.0 Hz, 1H), 6.85 (d, J = 8.3 Hz, 1H), 6.95-7.01 (m, 4H) |
| 6-(4-Fluoro-2-methoxyphenyl)-5-phenylaminomethyl-2,2,4-trimethyl-1,2-dihydroquinoline (Compound No. 6-13) | 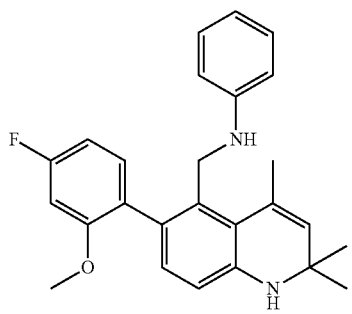 | $^1$H-NMR (400 MHz, DMSO-$d_6$) δ 1.17 (s, 3H), 1.20 (s, 3H), 2.10 (s, 3H), 3.67-3.72 (m, 1H), 3.70 (s, 3H), 3.98 (dd, J = 12.1, 4.5 Hz, 1H), 5.12 (t, J = 4.5 Hz, 1H), 5.36 (s, 1H), 5.92 (s, 1H), 6.43 (d, J = 7.4 Hz, 2H), 6.46 (t, J = 7.4 Hz, 1H), 6.57 (d, J = 8.0 Hz, 1H), 6.65-6.69 (m, 1H), 6.67 (d, J = 8.0 Hz, 1H), 6.86 (dd, J = 11.5, 2.7 Hz, 1H), 6.97 (t, J = 7.4 Hz, 2H), 7.19 (dd, J = 8.3, 7.1 Hz, 1H) |
| 6-(4-Fluoro-2-methoxyphenyl)-5-(4-methoxyphenylaminomethyl)-2,2,4-trimethyl-1,2-dihydroquinoline (Compound No. 6-14) | 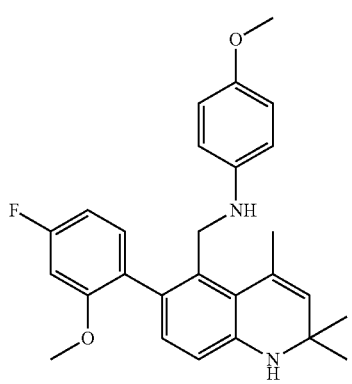 | $^1$H-NMR (400 MHz, DMSO-$d_6$) δ 1.16 (s, 3H), 1.19 (s, 3H), 2.12 (s, 3H), 3.59 (s, 3H), 3.64-3.71 (m, 1H), 3.70 (s, 3H), 3.91 (dd, J = 11.8, 4.8 Hz, 1H), 4.67 (t, J = 4.8 Hz, 1H), 5.35 (s, 1H), 5.91 (s, 1H), 6.40 (d, J = 9.0 Hz, 2H), 6.56 (d, J = 8.0 Hz, 1H), 6.61 (d, J = 8.0 Hz, 2H), 6.65 (d, J = 8.0 Hz, 1H), 6.67 (td, J = 8.4, 2.5 Hz, 1H), 6.86 (dd, J = 11.5, 2.5 Hz, 1H), 7.18 (dd, J = 8.4, 7.1 Hz, 1H) |

6-(5-Chloro-2-methoxphenyl)-5-phenyl-aminomethyl-2,2,4-trimethyl-1,2-dihydroquinoline (Compound No. 6-15)

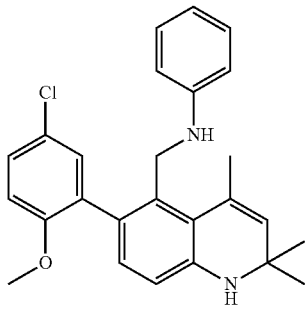

$^1$H-NMR (400 MHz, DMSO-$d_6$)
δ 1.18 (s, 3H), 1.19 (s, 3H), 2.11 (s, 3H), 3.69 (s, 3H), 3.65-3.75 (m, 1H), 4.00 (d, J = 15.4 Hz, 1H), 5.18 (s, 1H), 5.36 (s, 1H), 5.97 (s, 1H), 6.44-6.48 (m, 3H), 6.58 (d, J = 8.2 Hz, 1H), 6.69 (d, J = 8.2 Hz, 1H), 6.95-6.99 (m, 3H), 7.22-7.26 (m, 2H)

6-(4-Fluoro-2-methoxyphenyl)-5-(4-fluoro-phenylaminomethyl)-2,2,4-trimethyl-1,2-dihydroquinoline (Compound No. 6-16)

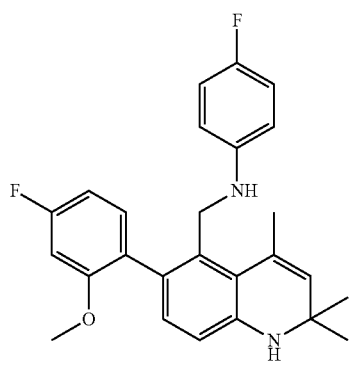

$^1$H-NMR (400 MHz, DMSO-$d_6$)
δ 1.16 (s, 3H), 1.19 (s, 3H), 2.10 (s, 3H), 3.64 (dd, J = 12.1, 4.5, 1H), 3.69 (s, 3H), 3.95 (dd, J = 12.1, 4.5 Hz, 1H), 5.14 (t, J = 4.5 Hz, 1H), 5.36 (s, 1H), 5.92 (s, 1H), 6.41 (dd, J = 9.0, 4.5, 2H), 6.57 (d, J = 8.2 Hz, 1H), 6.64-6.69 (m, 1H), 6.66 (d, J = 8.2 Hz, 1H), 6.80 (t, J = 9.0 Hz, 2H), 6.86 (dd, J = 11.5, 2.4 Hz, 1H), 7.18 (t, J = 8.3, 7.3 Hz, 1H)

6-(4-Fluoro-2-methoxyphenyl)-5-(3-fluoro-phenylaminomethyl)-2,2,4-trimethyl-1,2-dihydroquinoline (Compound No. 6-17)

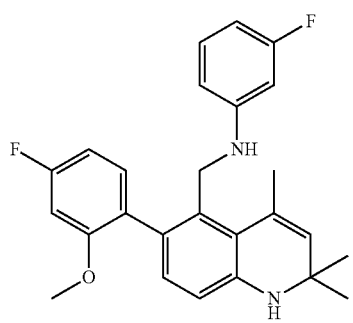

$^1$H-NMR (400 MHz, DMSO-$d_6$)
δ 1.17 (s, 3H), 1.18 (s, 3H), 2.09 (s (s, 3H), 3.64-3.71 (m, 1H), 3.69 (s, 3H), 4.00 (dd, J = 12.6, 4.7 Hz, 1H), 5.36 (s, 1H), 5.64 (s, 1H), 5.93 (s, 1H), 6.16-6.22 (m, 2H), 6.26 (d, J = 7.6 Hz, 1H), 6.58 (d, J = 8.3 Hz, 1H), 6.62-6.70 (m, 1H), 6.67 (d, J = 8.3 Hz, 1H), 6.87 (dd, J = 11.5, 2.4 Hz, 1H), 6.92-6.98 (m, 1H), 7.18 (dd, J = 8.3, 7.3 Hz, 1H)

| | |
|---|---|
| 6-(4-Fluoro-2-methoxyphenyl)-5-(2-fluorophenylaminomethyl)-2,2,4-trimethyl-1,2-dihydroquinoline (Compound No. 6-18) 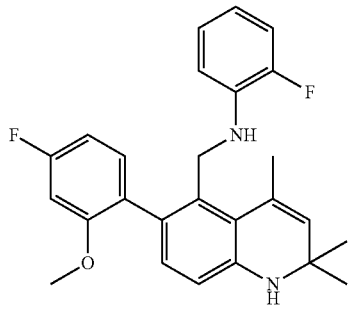 | $^1$H-NMR (400 MHz, CDCl$_3$) δ 1.24 (s, 3H), 1.30 (s, 3H), 2.20 (s, 3H), 3.69 (s, 3H), 3.93 (d, J = 12.0 Hz, 1H), 4.09 (br s, 1H), 4.20 (d, J = 12.0 Hz, 1H), 5.49 (s, 1H), 6.46 (t, d, J = 8.4, 1.3 Hz, 1H), 6.52-6.61 (m, 3H), 6.64 (dd, J = 8.3, 2.4 Hz, 1H), 6.81 (d, J = 8.1 Hz, 1H), 6.86-6.91 (m, 2H), 7.08 (dd, J = 8.3, 6.8 Hz, 1H) |
| 6-(4-Fluoro-2-methoxyphenyl)-5-(3-methoxyphenylaminomethyl)-2,2,4-trimethyl-1,2-dihydroquinoline (Compound No. 6-19) 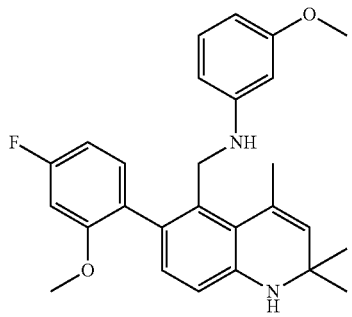 | $^1$H-NMR (400 MHz, DMSO-d$_6$) δ 1.17 (s, 3H), 1.19 (s, 3H), 2.10 (s, 3H), 3.61 (s, 3H), 3.66-3.70 (m, 1H), 3.70 (s, 3H), 3.96 (dd, J = 12.3, 4.1 Hz, 1H), 5.16 (t, J = 4.1 Hz, 1H), 5.36 (s, 1H), 5.92 (s, 1H), 5.99 (s, 1H), 6.04-6.07 (m, 2H), 6.57 (d, J = 8.3 Hz, 1H), 6.66 (d, J = 8.3 Hz, 1H), 6.65-6.70 (m, 1H), 6.84-6.89 (m, 2H), 7.18 (dd, J = 8.3, 7.1 Hz, 1H) |
| 6-(4-Fluoro-2-methoxyphenyl)-5-(2-methoxyphenylaminomethyl)-2,2,4-trimethyl-1,2-dihydroquinoline (Compound No. 6-20) 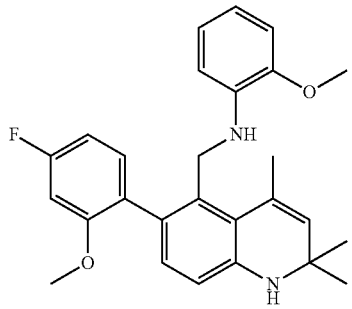 | $^1$H-NMR (500 MHz, DMSO-d$_6$) δ 1.14 (s, 3H), 1.21 (s, 3H), 2.07 (s, 3H), 3.67 (s, 3H), 3.71 (s, 3H), 3.81 (dd, J = 12.1, 4.1 Hz, 1H), 3.99-4.02 (m, 1H), 4.19-4.21 (m, 1H), 5.39 (s, 1H), 5.99 (s, 1H), 6.34 (d, J = 7.9 Hz, 1H), 6.51 (td, J = 7.7, 1.4 Hz, 1H), 6.59 (d, J = 8.1 Hz, 1H), 6.67 (d, J = 8.1 Hz, 1H), 6.66-6.75 (m, 3H), 6.86 (dd, J = 11.5, 2.6 Hz, 1H), 7.09 (dd, J = 8.2, 7.0 Hz, 1H) |

| | |
|---|---|
| 6-(4-Fluoro-2-methoxyphenyl)-5-(1-oxo-4-methylbenzoxazin-6-ylaminomethyl)-2,2,4-trimethyl-1,2-dihydroquinoline (Compound No. 6-21)<br>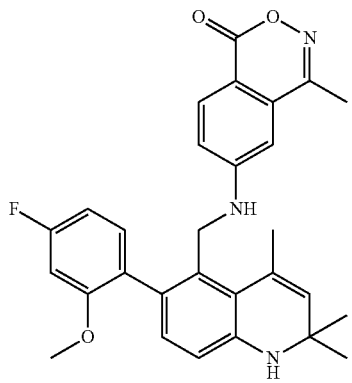 | $^1$H-NMR (500 MHz, DMSO-$d_6$) δ 1.16 (s, 3H), 1.17 (s, 3H), 2.09 (s, 3H), 2.35 (s, 3H), 3.69 (s, 3H), 3.86 (dd, J = 13.4, 3.9 Hz, 1H), 4.24 (dd, J = 13.4, 3.9 Hz, 1H), 5.40 (s, 1H), 6.00 (s, 1H), 6.50 (br s, 1H), 6.62 (d, J = 8.2 Hz, 1H), 6.65 (t,d J = 8.3, 2.5 Hz, 1H), 6.71 (d, J = 8.2 Hz, 1H), 6.84 (dd, J = 11.5, 2.5 Hz, 1H), 6.97 (br s, 1H), 7.14 (br s, 1H), 7.17 (dd, J = 8.3, 7.0 Hz, 1H), 7.80 (d, J = 8.9 Hz, 1H) |
| 6-(4-Fluoro-2-methoxyphenyl)-5-(2-methylthiophenylaminomethyl)-2,2,4-trimethyl-1,2-dihydroquinoline (Compound No. 6-22)<br>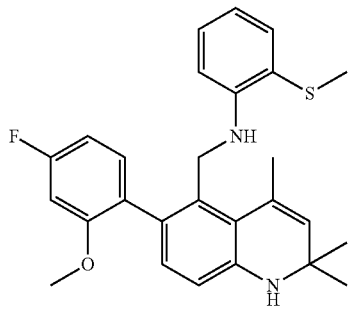 | $^1$H-NMR (400 MHz, DMSO-$d_6$) δ 1.16 (s, 3H), 1.20 (s, 3H), 2.03 (s, 3H), 2.20 (s, 3H), 3.67 (s, 3H), 3.70 (d, J = 4.1 Hz, 1H), 4.00 (d, J = 4.1 Hz, 1H), 4.74 (t, J = 4.1 Hz, 1H), 5.40 (s, 1H), 6.07 (s, 1H), 6.39 (d, J = 7.6 Hz, 1H), 6.55 (td, J = 7.5, 1.1 Hz, 1H), 6.63 (d, J = 8.3 Hz, 1H), 6.72 (d, J = 8.3 Hz, 1H), 6.74 (td, J = 9.5, 2.4 Hz, 1H), 6.90 (dd, J = 11.5, 2.4 Hz, 1H), 7.04-7.08 (m, 1H), 7.14 (dd, J = 8.2, 7.2 Hz, 1H), 7.26 (dd, J = 7.6, 1.5 Hz, 1H) |
| 5-(2-Acetylaminophenylaminomethyl)-6-(4-fluoro-2-methoxyphenyl)-2,2,4-trimethyl-1,2-dihydroquinoline (Compound No. 6-23)<br>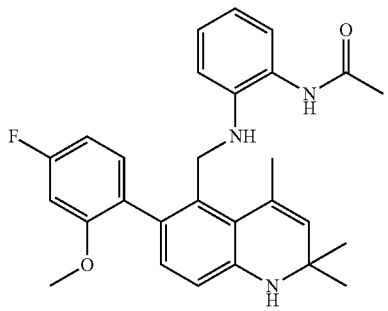 | $^1$H-NMR (500 MHz, DMSO-$d_6$) δ 1.17 (s, 3H), 1.22 (s, 3H), 1.95 (s, 3H), 2.01 (s, 3H), 3.70 (s, 3H), 3.76 (dd, J = 12.7, 4.1 Hz, 1H), 4.06 (dd, J = 12.7, 4.1 Hz, 1H), 4.46 (t, J = 4.1 Hz, 1H), 5.36 (s, 1H), 5.99 (s, 1H), 6.39 (t, J = 7.3 Hz, 1H), 6.53 (t, J = 7.3 Hz, 1H), 6.60 (d, J = 8.2 Hz, 1H), 6.70 (d, J = 8.2 Hz, 1H), 6.66-6.73 (m, 1H), 6.89 (dd, J = 11.3, 2.4 Hz, 1H), 6.93 (t, J = 7.3 Hz, 1H), 7.08 (d, J = 7.3 Hz, 1H), 7.15 (dd, J = 8.2, 7.0 Hz, 1H), 9.16 (s, 1H) |

5-(2-Ethoxyphenylaminomethyl)-6-(4-fluoro-2-methoxyphenyl)-2,2,4-trimethyl-1,2-dihydroquinoline (Compound No. 6-24)

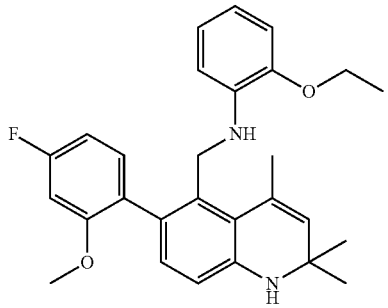

¹H-NMR (400 MHz, CDCl₃)
δ 1.15 (s, 3H), 1.21 (s, 3H), 1.26 (t, J = 7.0 Hz, 3H), 2.04 (s, 3H), 3.67 (s, 3H), 3.90-3.98 (m, 4H), 4.12-4.14 (m, 1H), 5.40 (s, 1H), 6.03 (s, 1H), 6.31 (d, J = 7.7 Hz, 1H), 6.49 (t, J = 7.7 Hz, 1H), 6.60 (d, J = 8.1 Hz, 1H), 6.66-6.76 (m, 4H), 6.89 (dd, J = 11.4, 2.6 Hz, 1H), 7.11 (dd, J = 8.2, 7.2 Hz, 1H)

6-(3,4-Difluoro-2-methoxyphenyl)-5-(2-methoxyphenylaminomethyl)-2,2,4-trimethyl-1,2-dihydroquinoline (Compound No. 6-25)

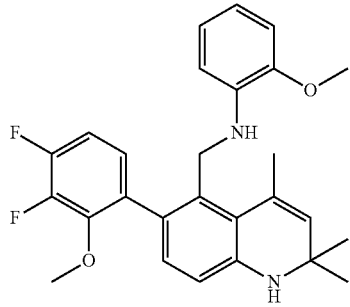

¹H-NMR (400 MHz, DMSO-d₆)
δ 1.15 (s, 3H), 1.22 (s, 3H), 2.06 (m, 3H), 3.65 (m, 3H), 3.69 (s, 3H), 3.92 (dd, J = 12.6, 4.9 Hz, 1H), 4.02 (dd, J = 12.6, 4.9 Hz, 1H), 4.18 (t, J = 4.9 Hz, 1H), 5.42 (s, 1H), 6.12 (s, 1H), 6.34 (dd, J = 7.7, 1.3 Hz, 1H), 6.52 (td, J = 7.7, 1.5 Hz, 1H), 6.63 (d, J = 8.3 Hz, 1H), 6.66-6.70 (m, 1H), 6.74 (dd, J = 7.7, 1.2 Hz, 1H), 6.76 (d, J = 8.3 Hz, 1H), 6.99 (ddd, J = 8.4, 6.1, 2.0 Hz, 1H), 7.06-7.12 (m, 1H)

6-(3,5-Difluoro-2-methoxyphenyl)-5-(2-methoxyphenylaminomethyl)-2,2,4-trimethyl-1,2-dihydroquinoline (Compound No. 6-26)

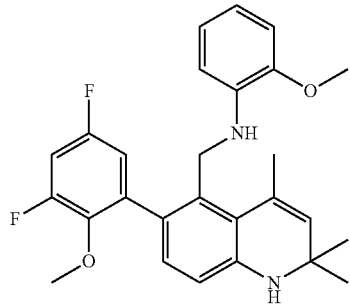

¹H-NMR (400 MHz, DMSO-d₆)
δ 1.16 (s, 3H), 1.22 (s, 3H), 2.08 (s, 3H), 3.54 (s, 3H), 3.69 (s, 3H), 3.91 (dd, J = 12.8, 4.9 Hz, 1H), 4.08 (dd, J = 12.8, 4.9 Hz, 1H), 4.22 (t, J = 4.9 Hz, 1H), 5.43 (s, 1H), 6.16 (s, 1H), 6.35 (dd, J = 7.8, 1.2 Hz, 1H), 6.52 (td, J = 7.8, 1.5 Hz, 1H), 6.64 (d, J = 8.3 Hz, 1H), 6.65-6.71 (m, 1H), 6.74 (dd, J = 7.8, 1.2 Hz, 1H), 6.80 (d, J = 8.3 Hz, 1H), 6.90 (ddd, J = 9.0, 3.0, 1.5 Hz, 1H), 7.19-7.25 (m, 1H)

| | |
|---|---|
| 6-(4,5-Difluoro-2-methoxyphenyl)-5-(2-methoxyphenylaminomethyl)-2,2,4-trimethyl-1,2-dihydroquinoline (Compound No. 6-27)<br>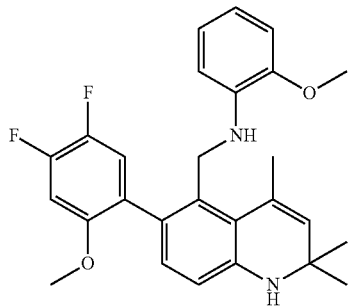 | $^1$H-NMR (400 MHz, DMSO-$d_6$) δ 1.15 (s, 3H), 1.21 (s, 3H), 2.07 (s, 3H), 3.65 (s, 3H), 3.71 (s, 3H), 3.82-3.88 (m, 1H), 3.95-4.02 (m, 1H), 4.18-4.22 (m, 1H), 5.40 (s, 1H), 6.06 (s, 1H), 6.36 (d, J = 7.8 Hz, 1H), 6.52 (t, J = 7.8 Hz, 1H), 6.59 (d, J = 8.2 Hz, 1H), 6.66-6.70 (m, 1H), 6.69 (d, J = 8.2 Hz, 1H), 6.74 (dd, J = 7.8, 1.2 Hz, 1H), 7.10 (dd, J = 12.9, 7.3 Hz, 1H), 7.18 (dd, J = 11.0, 9.5 Hz, 1H) |
| 6-(4-Fluoro-2-methoxyphenyl)-5-(2-methoxyphenylaminomethyl)-2,2,4,7-tetramethyl-1,2-dihydroquinoline (Compound No. 6-28)<br>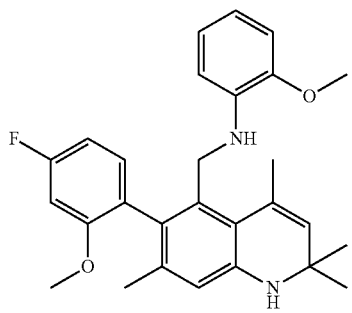 | $^1$H-NMR (400 MHz, DMSO-$d_6$) δ 1.14 (s, 3H), 1.20 (s, 3H), 1.71 (s, 3H), 2.06 (s, 3H), 3.65 (dd, J = 11.7, 2.9 Hz, 1H), 3.67 (s, 3H), 3.73 (s, 3H), 3.96 (dd, J = 11.7, 6.7 Hz, 1H), 4.14 (dd, J = 6.7, 2.9 Hz, 1H), 5.33 (s, 1H), 5.86 (s, 1H), 6.33 (d, J = 7.8 Hz, 1H), 6.47-6.51 (m, 1H), 6.49 (s, 1H), 6.64-6.73 (m, 3H), 6.86 (dd, J = 11.5, 2.4 Hz, 1H), 6.99 (dd, J = 8.3, 7.1 Hz, 1H) |
| 6-(4-Fluoro-2-methoxyphenyl)-7-methoxy-5-(2-methoxyphenylaminomethyl)-2,2,4-trimethyl-1,2-dihydroquinoline (Compound No. 6-29)<br>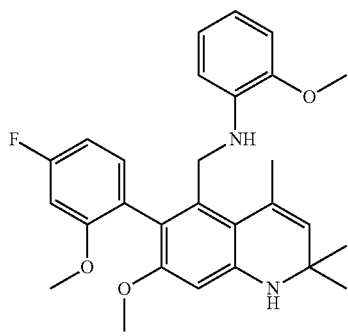 | $^1$H-NMR (400 MHz, DMSO-$d_6$) δ 1.15 (s, 3H), 1.20 (s, 3H), 2.04 (s, 3H), 3.53 (s, 3H), 3.60-3.65 (m, 1H), 3.64 (s, 3H), 3.72 (s, 3H), 3.92-3.97 (m, 1H), 4.13-4.15 (m, 1H), 5.23 (s, 1H), 6.03 (s, 1H), 6.30 (s, 1H), 6.32 (d, J = 7.8 Hz, 1H), 6.49 (td, J = 7.8, 1.4 Hz, 1H), 6.64-6.69 (m, 2H), 6.73 (dd, J = 7.8, 1.2 Hz, 1H), 6.81 (dd, J = 11.5, 2.4 Hz, 1H), 6.98 (dd, J = 8.3, 7.1 Hz, 1H) |

| | |
|---|---|
| 5-(3-t-Butylphenylaminomethyl)-6-(4-fluoro-2-methoxyphenyl)-2,2,4-trimethyl-1,2-dihydroquinoline (Compound No. 6-30) 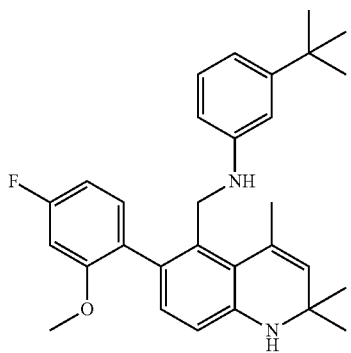 | $^1$H-NMR (400 MHz, DMSO-d$_6$) δ 1.15 (s, 3H), 1.17 (s, 9H), 1.20 (s, 3H), 2.12 (s, 3H), 3.70 (s, 3H), 3.76 (dd, J = 12.1, 4.6 Hz, 1H), 3.98 (dd, J = 12.1, 4.6 Hz, 1H), 4.92 (t, J = 4.6 Hz, 1H), 5.36 (s, 1H), 5.91 (s, 1H), 6.21 (dd, J = 7.9, 1.5 Hz, 1H), 6.49-6.52 (m, 2H), 6.57 (d, J = 8.1 Hz, 1H), 6.65-6.70 (m, 1H), 6.66 (d, J = 8.1 Hz, 1H), 6.86 (dd, J = 11.1, 2.8 Hz, 1H), 6.89 (t, J = 7.9 Hz, 1H), 7.18 (dd, J = 8.3, 7.1 Hz, 1H) |
| 5-(3-Cyanophenylaminomethyl)-6-(4-fluoro-2-methoxyphenyl)-2,2,4-trimethyl-1,2-dihydroquinoline (Compound No. 6-31) 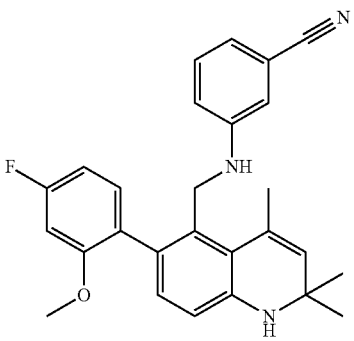 | $^1$H-NMR (500 MHz, DMSO-d$_6$) δ 1.16 (s, 3H), 1.18 (s, 3H), 2.08 (s, 3H), 3.66-3.69 (m, 1H), 3.69 (s, 3H), 4.05 (dd, J = 12.2, 4.9 Hz, 1H), 5.37 (s, 1H), 5.93-5.94 (m, 2H), 6.58 (d, J = 8.2 Hz, 1H), 6.66 (td, J = 8.4, 2.5 Hz, 1H), 6.68 (d, J = 8.2 Hz, 1H), 6.71 (d, J = 1.6 Hz, 1H), 6.74 (dd, J = 8.0, 1.6 Hz, 1H), 6.82 (d, J = 8.0 Hz, 1H), 6.86 (dd, J = 11.3, 2.5 Hz, 1H), 7.13 (t, J = 8.0 Hz, 1H), 7.17 (dd, J = 8.4, 7.2 Hz, 1H) |
| 6-(4-Fluoro-2-methoxyphenyl)-5-(4-isopropylphenylaminomethyl)-2,2,4-trimethyl-1,2-dihydroquinoline (Compound No. 6-32) 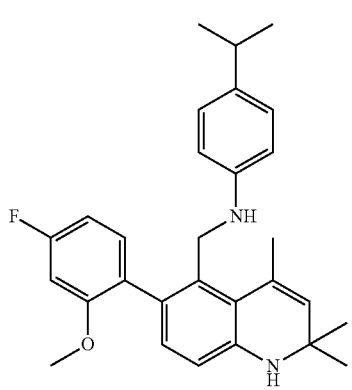 | $^1$H-NMR (400 MHz, DMSO-d$_6$) δ 1.10 (d, J = 6.8 Hz, 6H), 1.16 (s, 3H), 1.19 (s, 3H), 2.10 (s, 3H), 2.61-2.73 (m, 1H), 3.66-3.72 (m, 1H), 3.71 (s, 3H), 3.95 (dd, J = 12.3, 4.9 Hz, 1H), 4.87 (t, J = 4.9 Hz, 1H), 5.35 (s, 1H), 5.91 (s, 1H), 6.37 (d, J = 8.5 Hz, 2H), 6.56 (d, J = 8.3 Hz, 1H), 6.64-6.71 (m, 1H), 6.65 (d, J = 8.3 Hz, 1H), 6.82-6.90 (m, 1H), 6.85 (d, J = 8.5 Hz, 2H), 7.19 (dd, J = 8.3, 7.1 Hz, 1H) |

| | |
|---|---|
| 6-(4-Fluoro-2-methoxyphenyl)-5-(4-methylthiophenylaminomethyl)-2,2,4-trimethyl-1,2-dihydroquinoline (Compound No. 6-33)<br>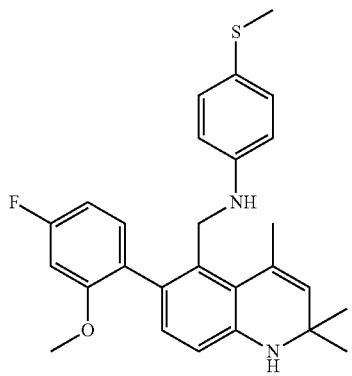 | $^1$H-NMR (400 MHz, DMSO-$d_6$) δ 1.17 (s, 3H), 1.19 (s, 3H), 2.09 (s, 3H), 2.30 (s, 3H), 3.66 (d, J = 12.5 Hz, 1H), 3.70 (s, 3H), 3.97 (d, J = 12.5 Hz, 1H), 5.34 (s, 1H), 5.36 (s, 1H), 5.92 (s, 1H), 6.42 (d, J = 8.7 Hz, 2H), 6.57 (d, J = 8.1 Hz, 1H), 6.66-6.68 (m, 1H), 6.66 (d, J = 8.1 Hz, 1H), 6.86 (dd, J = 11.5, 2.4 Hz, 1H), 7.00 (d, J = 8.7 Hz, 2H), 7.18 (dd, J = 8.3, 7.1 Hz, 1H) |
| 6-(4-Fluoro-2-methoxyphenyl)-5-(3-hydroxymethylphenylaminomethyl)-2,2,4-trimethyl-1,2-dihydroquinoline (Compound No. 6-34)<br>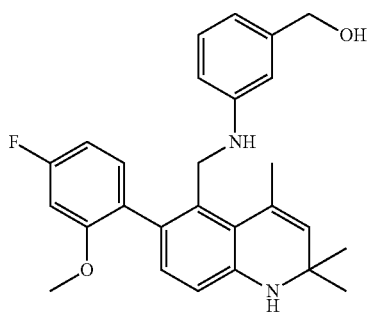 | $^1$H-NMR (500 MHz, DMSO-$d_6$) δ 1.17 (s, 3H), 1.20 (s, 3H), 2.09 (s, 3H), 3.67-3.70 (m, 1H), 3.70 (s, 3H), 3.97 (dd, J = 12.2, 4.6 Hz, 1H), 4.30 (d, J = 5.8 Hz, 2H), 4.93 (t, J = 5.8 Hz, 1H), 5.08 (br s, 1H), 5.35 (s, 1H), 5.91 (s, 1H), 6.31 (d, J = 7.7 Hz, 1H), 6.41 (s, 1H), 6.44 (d, J = 7.7 Hz, 1H), 6.57 (d, J = 8.2 Hz, 1H), 6.66 (d, J = 8.2 Hz, 1H), 6.68 (td, J = 8.3, 2.6 Hz, 1H), 6.87 (dd, J = 11.5, 2.6 Hz, 1H), 6.92 (t, J = 7.7 Hz, 1H), 7.20 (dd, J = 8.3, 7.3 Hz, 1H) |
| 6-(4-Fluoro-2-methoxyphenyl)-5-(4-methylphenylaminomethyl)-2,2,4-trimethyl-1,2-dihydroquinoline (Compound No. 6-35)<br>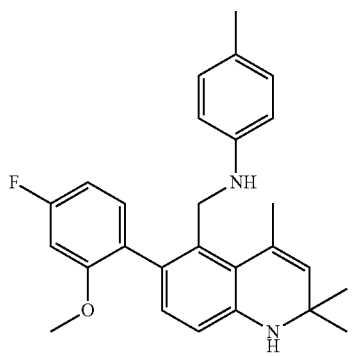 | $^1$H-NMR (400 MHz, DMSO-$d_6$) δ 1.17 (s, 3H), 1.19 (s, 3H), 2.10 (s, 6H), 3.65-3.70 (m, 1H), 3.70 (s, 3H), 3.92 (dd, J = 12.0, 4.5 Hz, 1H), 4.87 (t, J = 4.5 Hz, 1H), 5.35 (s, 1H), 5.92 (s, 1H), 6.35 (d, J = 8.2 Hz, 2H), 6.56 (d, J = 8.3 Hz, 1H), 6.66 (d, J = 8.3 Hz, 1H), 6.67 (td, J = 8.5, 2.6 Hz, 1H), 6.79 (d, J = 8.2 Hz, 2H), 6.86 (dd, J = 11.5, 2.6 Hz, 1H), 7.18 (dd, J = 8.5, 7.1 Hz, 1H) |

| | |
|---|---|
| 6-(4-Fluoro-2-methoxyphenyl)-5-(3-methylphenylaminomethyl)-2,2,4-trimethyl-1,2-dihydroquinoline (Compound No. 6-36)<br>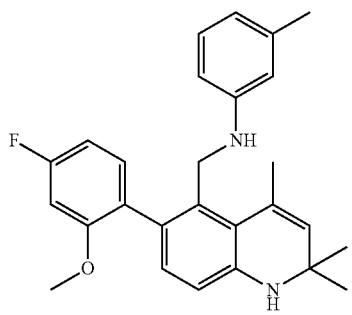 | $^1$H-NMR (400 MHz, DMSO-$d_6$)<br>δ 1.17 (s, 3H), 1.20 (s, 3H), 2.09 (s, 3H), 2.11 (s, 3H), 3.67-3.70 (m, 1H), 3.70 (s, 3H), 3.96 (d, J = 12.1, 4.7 Hz, 1H), 5.00 (t, J = 4.7 Hz, 1H), 5.36 (s, 1H), 5.91 (s, 1H), 6.24-6.28 (m, 2H), 6.29 (d, J = 7.3 Hz, 1H), 6.57 (d, J = 8.2 Hz, 1H), 6.66 (d, J = 8.2 Hz, 1H), 6.68 (td, J = 8.4, 2.6 Hz, 1H), 6.83-6.87 (m, 1H), 6.87 (dd, J = 11.5, 2.6 Hz, 1H), 7.19 (dd, J = 8.4, 7.1 Hz, 1H) |
| 6-(4-Fluoro-2-methoxyphenyl)-5-(2-methylphenylaminomethyl)-2,2,4-trimethyl-1,2-dihydroquinoline (Compound No. 6-37)<br>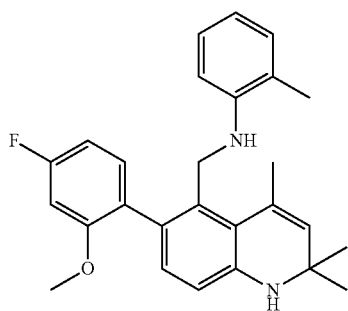 | $^1$H-NMR (400 MHz, DMSO-$d_6$)<br>δ 1.13 (s, 3H), 1.21 (s, 3H), 1.93 (s, 3H), 2.03 (s, 3H), 3.72 (s, 3H), 3.82 (t, J = 4.5 Hz, 1H), 3.89 (dd, J = 12.6, 4.5 Hz, 1H), 4.04 (dd, J = 12.6, 4.5 Hz, 1H), 5.40 (s, 1H), 6.01 (s, 1H), 6.30 (d, J = 7.4 Hz, 1H), 6.47 (t, J = 7.4 Hz, 1H), 6.60 (d, J = 8.2 Hz, 1H), 6.70 (d, J = 8.2 Hz, 1H), 6.74 (td, J = 8.4, 2.6 Hz, H), 6.91 (d, J = 7.4 Hz, 1H), 6.90-6.93 (m, 1H), 6.92 (dd, J = 11.5, 2.6 Hz, 1H), 7.19 (dd, J = 8.4, 7.1 Hz, 1H) |
| 5-(4-t-Butylphenylaminomethyl)-6-(4-fluoro-2-methoxyphenyl)-2,2,4-trimethyl-1,2-dihydroquinoline (Compound No. 6-38)<br>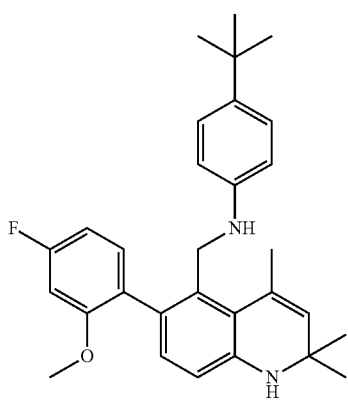 | $^1$H-NMR (400 MHz, DMSO-$d_6$)<br>δ 1.16 (s, 3H), 1.17 (s, 9H), 1.19 (s, 3H), 2.10 (s, 3H), 3.71 (s, 3H), 3.67-3.71 (m, 1H), 3.95 (dd, J = 12.0, 4.6 Hz, 1H), 4.88 (t, J = 4.6 Hz, 1H), 5.35 (s, 1H), 5.91 (s, 1H), 6.38 (d, J = 8.7 Hz, 2H), 6.56 (d, J = 8.3 Hz, 1H), 6.65 (d, J = 8.3 Hz, 1H), 6.68 (t, d, J = 8.4, 2.6 Hz, 1H), 6.87 (dd, J = 11.5, 2.6 Hz, 1H), 7.00 (d, J = 8.7 Hz, 2H), 7.19 (dd, J = 8.4, 7.1 Hz, 1H) |

| | |
|---|---|
| 6-(4-Fluoro-2-methoxyphenyl)-5-(3-isopropylphenylaminomethyl)-2,2,4-trimethyl-1,2-dihydroquinoline (Compound No. 6-39)<br>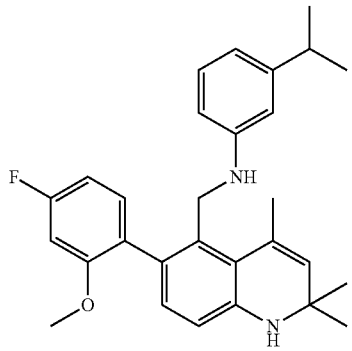 | $^1$H-NMR (500 MHz, DMSO-d$_6$) δ 1.10 (d, J = 6.8 Hz, 6H), 1.15 (s, 3H), 1.20 (s, 3H), 2.11 (s, 3H), 2.65 (sextet, J = 6.8 Hz, 1H), 3.70 (s, 3H), 3.74 (dd, J = 12.2, 4.7 Hz, 1H), 3.98 (dd, J = 12.2, 4.7 Hz, 1H), 4.95 (t, J = 4.7 Hz, 1H), 5.36 (s, 1H), 5.90 (s, 1H), 6.22 (d, J = 7.7 Hz, 1H), 6.31 (s, 1H), 6.36 (d, J = 7.7 Hz, 1H), 6.57 (d, J = 8.1 Hz, 1H), 6.66 (d, J = 8.1 Hz, 1H), 6.68 (td, J = 8.3, 2.6 Hz, 1H), 6.86 (dd, J = 11.5, 2.6 Hz, 1H), 6.88 (t, J = 7.7 Hz, 1H), 7.18 (dd, J = 8.3, 7.0 Hz, 1H) |
| 5-(3-Ethylphenylaminomethyl)-6-(4-fluoro-2-methoxyphenyl)-2,2,4-trimethyl-1,2-dihydroquinoline (Compound No. 6-40)<br>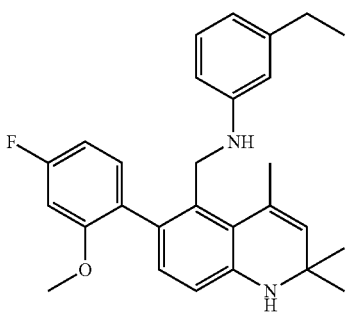 | $^1$H-NMR (400 MHz, DMSO-d$_6$) δ 1.08 (t, J = 7.6 Hz, 3H), 1.16 (s, 3H), 1.20 (s, 3H), 2.10 (s, 3H), 2.40 (q, J = 7.6 Hz, 2H), 3.70 (s, 3H), 3.70-3.73 (m, 1H), 3.97 (dd, J = 12.1, 4.6 Hz, 1H), 4.99 (t, J = 4.6 Hz, 1H), 5.36 (s, 1H), 5.91 (s, 1H), 6.24 (d, J = 7.7 Hz, 1H), 6.27 (s, 1H), 6.33 (d, J = 7.7 Hz, 1H), 6.57 (d, J = 8.2 Hz, 1H), 6.66 (d, J = 8.2 Hz, 1H), 6.68 (td, J = 8.4, 2.4 Hz, 1H), 6.87 (dd, J = 11.4, 2.4 Hz, 1H), 6.87 (t, J = 7.7 Hz, 1H), 7.18 (dd, J = 8.4, 7.1 Hz, 1H) |
| 6-(4-Fluoro-2-methoxyphenyl)-5-(2-hydroxymethylphenylaminomethyl)-2,2,4-trimethyl-1,2-dihydroquinoline (Compound No. 6-41)<br>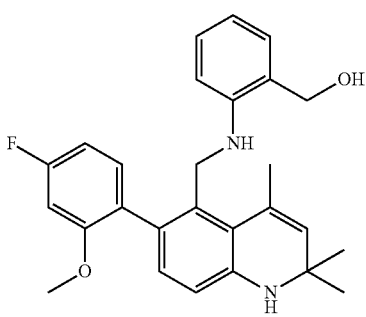 | $^1$H-NMR (400 MHz, DMSO-d$_6$) δ 1.15 (s, 3H), 1.20 (s, 3H), 2.02 (s, 3H), 3.70 (s, 3H), 3.81 (dd, J = 12.6, 4.6 Hz, 1H), 4.08 (dd, J = 12.6, 4.6 Hz, 1H), 4.29 (d, J = 5.3 Hz, 1H), 4.84 (t, J = 4.6 Hz, 1H), 4.99 (t, J = 5.3 Hz, 1H), 5.36 (s, 1H), 5.98 (s, 1H), 6.34 (d, J = 7.8 Hz, 1H), 6.49 (td, J = 7.3, 0.8 Hz, 2H), 6.59 (d, J = 8.2 Hz, 1H), 6.69 (d, J = 8.2 Hz, 1H), 6.70 (td, J = 8.4, 2.8 Hz, 1H), 6.89 (dd, J = 11.6, 2.8 Hz, 1H), 6.96 (dd, J = 7.3, 1.2 Hz, 1H), 6.98-7.02 (m, 1H), 7.15 (dd, J = 8.4, 7.2 Hz, 1H) |

| | |
|---|---|
| 6-(4-Fluoro-2-methoxyphenyl)-5-[3-(1-hydroxyethyl)phenylaminomethyl]-2,2,4-trimethyl-1,2-dihydroquinoline (Compound No. 6-42)<br>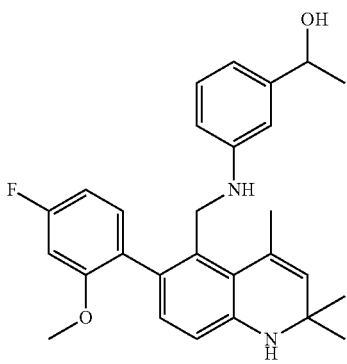 | $^{1}$H-NMR (400 MHz, DMSO-d$_{6}$) δ 1.16 (s, 3H), 1.20 (s, 3H), 1.22 (d, J = 6.3 Hz, 3H), 2.10 (s, 3H), 3.71 (s, 3H), 3.71-3.75 (m, 1H), 3.97 (dd, J = 11.0, 5.4 Hz, 1H), 4.40-4.51 (m, 1H), 4.90-4.91 (m, 1H), 5.00-5.05 (m, 1H), 5.36 (s, 1H), 5.92 (s, 1H), 6.28 (d, J = 7.7 Hz, 1H), 6.44 (s, 1H), 6.46 (d, J = 7.7 Hz, 1H), 6.57 (d, J = 8.3 Hz, 1H), 6.66 (d, J = 8.3 Hz, 1H), 6.68 (td, J = 8.7, 2.8 Hz, 1H), 6.87 (dd, J = 12.0, 2.8 Hz, 1H), 6.91 (t, J = 7.7 Hz, 1H), 7.20 (dd, J = 8.7, 7.8 Hz, 1H) |
| 6-(4-Fluoro-2-methoxyphenyl)-5-(2-methoxy-5-methylphenylaminomethyl)-2,2,4-trimethyl-1,2-dihydroquinoline (Compound No. 6-43)<br>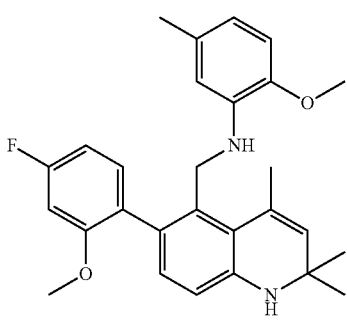 | $^{1}$H-NMR (400 MHz, DMSO-d$_{6}$) δ 1.14 (s, 3H), 1.21 (s, 3H), 2.07 (s, 3H), 2.10 (s, 3H), 3.66 (s, 3H), 3.67 (s, 3H), 3.80 (dd, J = 12.3, 2.9 Hz, 1H), 4.00 (dd, J = 12.3, 7.0 Hz, 1H), 4.14-4.17 (m, 1H), 5.39 (s, 1H), 5.99 (s, 1H), 6.14 (d, J = 1.3 Hz, 1H), 6.30 (dd, J = 8.1, 1.3 Hz, 1H), 6.59 (d, J = 8.2 Hz, 1H), 6.60 (d, J = 8.1 Hz, 1H), 6.67 (d, J = 8.2 Hz, 1H), 6.73 (td, J = 8.4, 2.4 Hz, 1H), 6.87 (dd, J = 11.5, 2.4 Hz, 1H), 7.09 (dd, J = 8.4, 7.1 Hz, 1H) |
| 5-(3-Dimethylaminophenylaminomethyl)-6-(4-fluoro-2-methoxyphenyl)-2,2,4-trimethyl-1,2-dihydroquinoline (Compound No. 6-44)<br>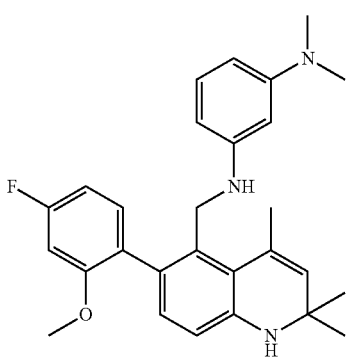 | $^{1}$H-NMR (500 MHz, DMSO-d$_{6}$) δ 1.17 (s, 3H), 1.20 (s, 3H), 2.12 (s, 3H), 2.76 (s, 6H), 3.69-3.75 (m, 1H), 3.71 (s, 3H), 3.92-3.96 (m, 1H), 4.77 (s, 1H), 5.36 (s, 1H), 5.80-5.83 (m, 2H), 5.90-5.94 (m, 2H), 6.57 (d, J = 8.3 Hz, 1H), 6.66 (d, J = 8.3 Hz, 1H), 6.69 (td, J = 8.4, 2.5 Hz, 1H), 6.78 (t, J = 8.0 Hz, 1H), 6.87 (dd, J = 11.5, 2.5 Hz, 1H), 7.18 (dd, J = 8.4, 7.0 Hz, 1H) |

| | |
|---|---|
| 5-(2-Ethylphenylaminomethyl)-6-(4-fluoro-2-methoxyphenyl)-2,2,4-trimethyl-1,2-dihydroquinoline (Compound No. 6-45)<br>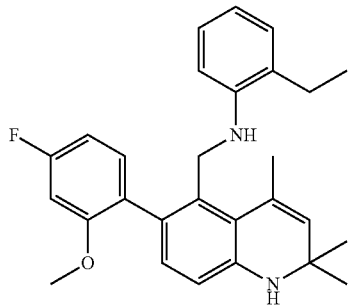 | $^1$H-NMR (400 MHz, DMSO-d$_6$) δ 1.04 (t, J = 7.5 Hz, 3H), 1.13 (s, 3H), 1.21 (s, 3H), 2.01 (s, 3H), 2.28-2.34 (m, 2H), 3.71 (s, 3H), 3.86-3.90 (m, 1H), 4.02-4.06 (m, 1H), 4.76 (br s, 1H), 5.38 (s, 1H), 6.02 (s, 1H), 6.31 (d, J = 7.8 Hz, 1H), 6.47-6.52 (m, 1H), 6.61 (d, J = 8.3 Hz, 1H), 6.71 (d, J = 8.3 Hz, 1H), 6.74 (td, J = 8.3, 2.5 Hz, 1H), 6.87-6.94 (m, 3H), 7.19 (dd, J = 8.3, 7.1 Hz, 1H) |
| 5-(2,4-Dimethoxyphenylaminomethyl)-6-(4-fluoro-2-methoxyphenyl)-2,2,4-trimethyl-1,2-dihydroquinoline (Compound No. 6-46)<br>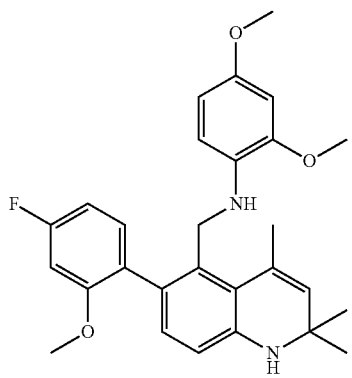 | $^1$H-NMR (500 MHz, DMSO-d$_6$) δ 1.15 (s, 3H), 1.21 (s, 3H), 2.08 (s, 3H), 3.62 (s, 3H), 3.66 (s, 3H), 3.71 (s, 3H), 3.72-3.76 (m, 1H), 3.86-3.87 (m, 1H), 3.93-3.97 (m, 1H), 5.38 (s, 1H), 5.97 (s, 1H), 6.26 (br s, 2H), 6.41 (s, 1H), 6.58 (d, J = 8.2 Hz, 1H), 6.66 (d, J = 8.2 Hz, 1H), 6.72 (td, J = 8.3, 2.5 Hz, 1H), 6.86 (dd, J = 11.5, 2.5 Hz, 1H), 7.08 (dd, J = 8.3, 7.0 Hz, 1H) |
| 6-(4-Fluoro-2-methoxyphenyl)-5-(2-isopropylphenylaminomethyl)-2,2,4-trimethyl-1,2-dihydroquinoline (Compound No. 6-47)<br>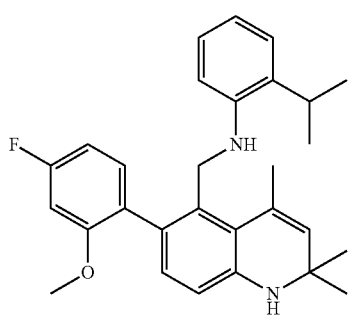 | $^1$H-NMR (500 MHz, DMSO-d$_6$) δ 1.07 (d, J = 6.8 Hz, 3H), 1.09 (d, J = 6.8 Hz, 3H), 1.13 (s, 3H), 1.21 (s, 3H), 2.01 (s, 3H), 2.64-2.75 (m, 1H), 3.71 (s, 3H), 3.83-3.95 (m, 2H), 3.98-4.07 (m, 1H), 5.38 (s, 1H), 6.03 (s, 1H), 6.32 (d, J = 7.6 Hz, 1H), 6.56 (t, J = 7.1 Hz, 1H), 6.61 (d, J = 8.3 Hz, 1H), 6.69-6.78 (m, 1H), 6.71 (d, J = 8.3 Hz, 1H), 6.88-6.96 (m, 2H), 6.99 (dd, J = 7.6, 1.5 Hz, 1H), 7.18 (dd, J = 8.4, 7.2 Hz, 1H) |

| | |
|---|---|
| 6-(4-Fluoro-2-methoxyphenyl)-5-(3-methylthiophenylaminomethyl)-2,2,4-trimethyl-1,2-dihydroquinoline (Compound No. 6-48)<br>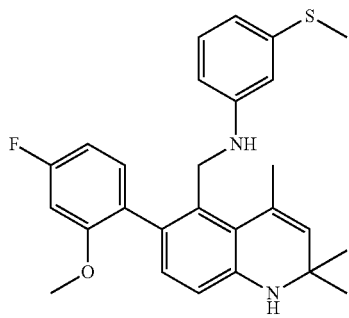 | $^1$H-NMR (400 MHz, DMSO-d$_6$) δ 1.16 (s, 3H), 1.19 (s, 3H), 2.10 (s, 3H), 2.34 (s, 3H), 3.64-3.73 (m, 1H), 3.70 (s, 3H), 3.99 (dd, J = 12.0, 4.3 Hz, 1H), 5.30 (t, J = 4.3 Hz, 1H), 5.36 (s, 1H), 5.92 (s, 1H), 6.22 (dd, J = 8.1, 1.5 Hz, 1H), 6.30-6.38 (m, 2H), 6.57 (d, J = 8.3 Hz, 1H), 6.61-6.73 (m, 1H), 6.66 (d, J = 8.3 Hz, 1H), 6.84-6.94 (m, 2H), 7.19 (dd, J = 8.3, 7.3 Hz, 1H) |
| 6-(4-Fluoro-2-methoxyphenyl)-5-(4-hydroxymethylphenylaminomethyl)-2,2,4-trimethyl-1,2-dihydroquinoline (Compound No. 6-49)<br>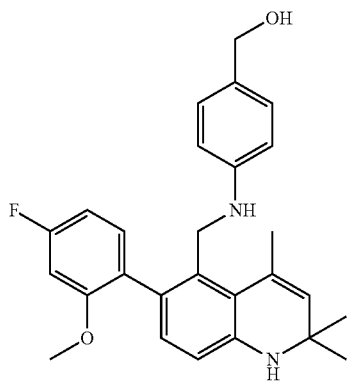 | $^1$H-NMR (400 MHz, DMSO-d$_6$) δ 1.17 (s, 3H), 1.19 (s, 3H), 2.10 (s, 3H), 3.69 (d, J = 10.0 Hz, 1H), 3.70 (s, 3H), 3.93-3.96 (m, 1H), 4.25 (d, J = 5.6 Hz, 2H), 4.75 (t, J = 5.6 Hz, 1H), 5.05 (br s, 1H), 5.35 (s, 1H), 5.92 (s, 1H), 6.40 (d, J = 8.4 Hz, 2H), 6.57 (d, J = 8.2 Hz, 1H), 6.61-6.70 (m, 1H), 6.66 (d, J = 8.2 Hz, 1H), 6.87 (dd, J = 11.4, 2.6 Hz, 1H), 6.93 (d, J = 8.4 Hz, 2H), 7.17-7.21 (m, 1H) |
| 5-(4-Ethylphenylaminomethyl)-6-(4-fluoro-2-methoxyphenyl)-2,2,4-trimethyl-1,2-dihydroquinoline (Compound No. 6-50)<br>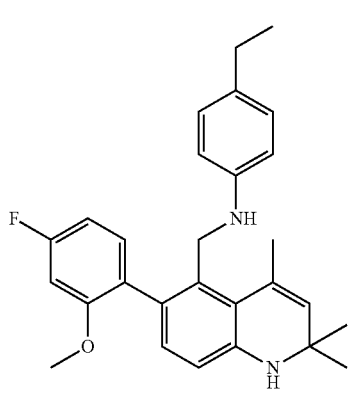 | $^1$H-NMR (400 MHz, DMSO-d$_6$) δ 1.10 (t, J = 7.6 Hz, 3H), 1.12 (s, 3H), 1.17 (s, 3H), 2.07 (s, 3H), 2.44-2.48 (m, 1H), 3.71 (s, 3H), 4.46 (d, J = 11.2 Hz, 1H), 4.95 (d, J = 11.2 Hz, 1H), 5.38 (s, 1H), 5.98 (s, 1H), 6.61 (d, J = 8.2 Hz, 1H), 6.61 (d, J = 8.4 Hz, 2H), 6.70 (td, J = 8.4, 2.5 Hz, 1H), 6.72 (d, J = 8.2 Hz, 1H), 6.91 (dd, J = 11.5, 2.5 Hz, 1H), 6.99 (d, J = 8.4 Hz, 2H), 7.14 (dd, J = 8.4, 7.1 Hz, 1H) |

| | |
|---|---|
| 5-(3,5-Dimethylphenylaminomethyl)-6-(4-fluoro-2-methoxyphenyl)-2,2,4-trimethyl-1,2-dihydroquinoline (Compound No. 6-51)<br>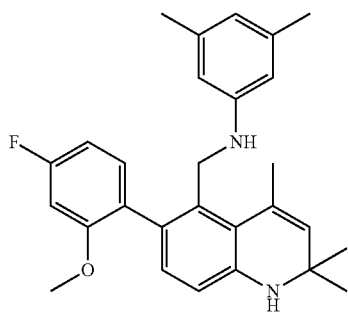 | $^1$H-NMR (400 MHz, DMSO-d$_6$) δ 1.16 (s, 3H), 1.20 (s, 3H), 2.07 (s, 6H), 2.08 (s, 3H), 3.64-3.72 (m, 1H), 3.70 (s, 3H), 3.95 (dd, J = 12.5, 4.5 Hz, 1H), 4.91 (t, J = 4.5 Hz, 1H), 5.35 (s, 1H), 5.91 (s, 1H), 6.05 (s, 2H), 6.12 (s, 1H), 6.56 (d, J = 8.3 Hz, 1H), 6.66 (d, J = 8.3 Hz, 1H), 6.66-6.73 (m, 1H), 6.88 (dd, J = 11.5, 2.4 Hz, 1H), 7.19 (dd, J = 8.2, 7.2 Hz, 1H) |
| 5-(2,3-Dimethylphenylaminomethyl)-6-(4-fluoro-2-methoxyphenyl)-2,2,4-trimethyl-1,2-dihydroquinoline (Compound No. 6-52)<br>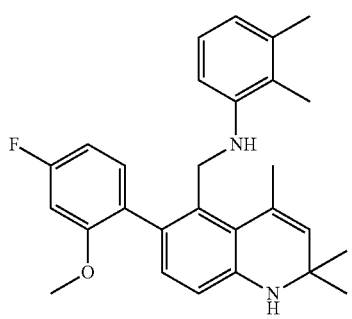 | $^1$H-NMR (400 MHz, DMSO-d$_6$) δ 1.14 (s, 3H), 1.21 (s, 3H), 1.83 (s, 3H), 2.01 (s, 3H), 2.14 (s, 3H), 3.71 (s, 3H), 3.78 (t, J = 4.9 Hz, 1H), 3.88 (dd, J = 12.3, 4.9 Hz, 1H), 3.99 (dd, J = 12.3, 4.9 Hz, 1H), 5.39 (s, 1H), 6.02 (s, 1H), 6.20 (d, J = 7.8 Hz, 1H), 6.40 (d, J = 7.8 Hz, 1H), 6.60 (d, J = 8.1 Hz, 1H), 6.70 (d, J = 8.1 Hz, 1H), 6.74 (td, J = 8.3, 2.5 Hz, 1H), 6.81 (t, J = 7.8 Hz, 1H), 6.91 (dd, J = 11.4, 2.5 Hz, 1H), 7.18 (dd, J = 8.3, 7.1 Hz, 1H) |
| 5-(2,5-Dimethylphenylaminomethyl)-6-(4-fluoro-2-methoxyphenyl)-2,2,4-trimethyl-1,2-dihydroquinoline (Compound No. 6-53)<br>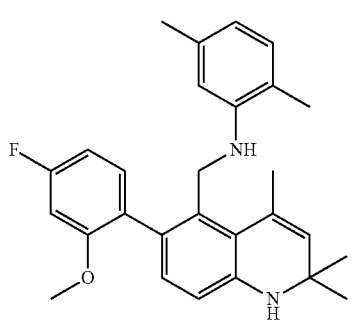 | $^1$H-NMR (500 MHz, DMSO-d$_6$) δ 1.12 (s, 3H), 1.21 (s, 3H), 1.88 (s, 3H), 2.03 (s, 3H), 2.12 (s, 3H), 3.72 (s, 3H), 3.75 (t, J = 4.7 Hz, 1H), 3.90 (dd, J = 12.5, 4.7 Hz, 1H), 4.03 (dd, J = 12.5, 4.7 Hz, 1H), 5.40 (s, 1H), 6.01 (s, 1H), 6.10 (s, 1H), 6.28 (d, J = 7.6 Hz, 1H), 6.60 (d, J = 8.2 Hz, 1H), 6.70 (d, J = 8.2 Hz, 1H), 6.73-6.79 (m, 1H), 6.77 (d, J = 7.6 Hz, 1H), 6.93 (dd, J = 11.6, 2.4 Hz, 1H), 7.19 (dd, J = 8.2, 7.0 Hz, 1H) |

| Compound | NMR |
|---|---|
| 6-(4-Fluoro-2-methoxyphenyl)-5-(5-methoxy-2-methylphenylaminomethyl)-2,2,4-trimethyl-1,2-dihydroquinoline (Compound No. 6-54)<br>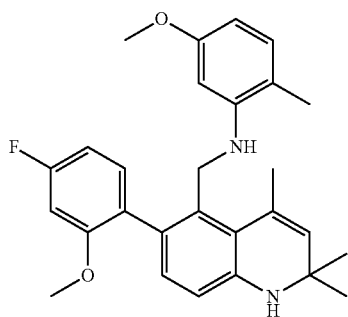 | $^1$H-NMR (400 MHz, DMSO-$d_6$) δ 1.13 (s, 3H), 1.21 (s, 3H), 1.86 (s, 3H), 2.03 (s, 3H), 3.60 (s, 3H), 3.71 (s, 3H), 3.81-3.91 (m, 2H), 3.97-4.05 (m, 1H), 5.40 (s, 1H), 5.84 (d, J = 2.4 Hz, 1H), 6.02 (s, 1H), 6.05 (dd, J = 8.1, 2.4 Hz, 1H), 6.60 (d, J = 8.3 Hz, 1H), 6.70 (d, J = 8.3 Hz, 1H), 6.74 (td, J = 8.4, 2.6 Hz, 1H), 6.79 (d, J = 8.1 Hz, 1H), 6.92 (dd, J = 11.4, 2.6 Hz, 1H), 7.19 (dd, J = 8.4, 7.1 Hz, 1H) |
| 6-(4-Fluoro-2-methoxyphenyl)-5-[4-(1-hydroxyethyl)phenylaminomethyl]-2,2,4-trimethyl-1,2-dihydroquinoline (Compound No. 6-55)<br>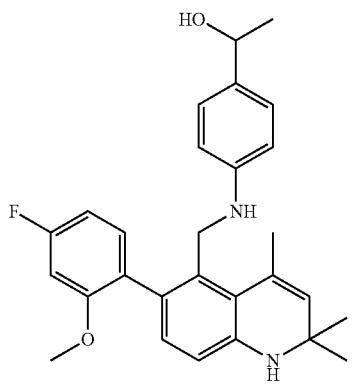 | $^1$H-NMR (400 MHz, DMSO-$d_6$) δ 1.17 (s, 3H), 1.19 (s, 3H), 1.22 (d, J = 6.3 Hz, 3H), 2.10 (s, 3H), 3.67-3.70 (m, 1H), 3.70 (s, 3H), 3.95 (dd, J = 11.8, 4.6 Hz, 1H), 4.47-4.53 (m, 1H), 4.74 (d, J = 3.9 Hz, 1H), 4.99 (t, J = 4.6 Hz, 1H), 5.35 (s, 1H), 5.91 (s, 1H), 6.39 (d, J = 8.5 Hz, 2H), 6.57 (d, J = 8.2 Hz, 1H), 6.66 (d, J = 8.2 Hz, 1H), 6.68 (td, J = 8.4, 2.5 Hz, 1H), 6.87 (dd, J = 11.5, 2.5 Hz, 1H), 6.95 (d, J = 8.5 Hz, 2H), 7.19 (dd, J = 8.4, 7.3 Hz, 1H) |
| 5-(2-t-Butylphenylaminomethyl)-6-(4-fluoro-2-methoxyphenyl)-2,2,4-trimethyl-1,2-dihydroquinoline (Compound No. 6-56)<br>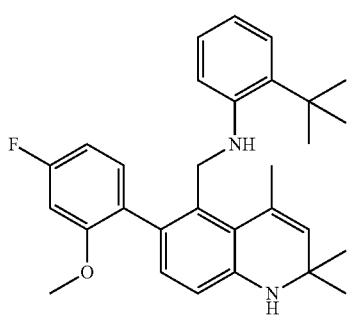 | $^1$H-NMR (500 MHz, DMSO-$d_6$) δ 1.16 (s, 3H), 1.20 (s, 3H), 1.23 (s, 9H), 2.01 (s, 3H), 3.64 (s, 3H), 3.73 (t, J = 4.0 Hz, 1H), 3.92 (d, J = 1.07 Hz, 1H), 4.05 (d, J = 10.7 Hz, 1H), 5.38 (s, 1H), 6.08 (s, 1H), 6.34 (d, J = 7.3 Hz, 1H), 6.54 (td, J = 7.7, 1.1 Hz, 1H), 6.64 (d, J = 8.2 Hz, 1H), 6.73 (d, J = 8.2 Hz, 1H), 6.75 (td, J = 8.4, 2.6 Hz, 1H), 6.91 (dd, J = 11.6, 2.6 Hz, 1H), 6.95-6.99 (m, 1H), 7.08 (dd, J = 7.7, 1.8 Hz, 1H), 7.10 (dd, J = 8.4, 7.2 Hz, 1H) |

| Compound | Structure | NMR |
|---|---|---|
| 6-(4-Fluoro-2-methoxyphenyl)-5-(5-fluoro-2-methylphenylaminomethyl)-2,2,4-trimethyl-1,2-dihydroquinoline (Compound No. 6-57) | 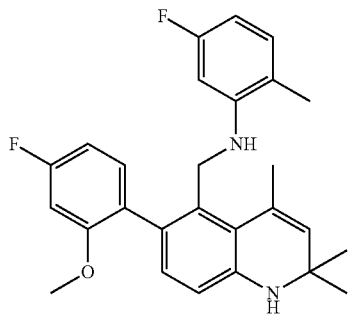 | $^1$H-NMR (400 MHz, DMSO-d$_6$) δ 1.11 (s, 3H), 1.19 (s, 3H), 1.90 (s, 3H), 2.04 (s, 3H), 3.72 (s, 3H), 3.88 (dd, J = 12.8, 4.3 Hz, 1H), 4.05 (dd, J = 12.8, 4.3 Hz, 1H), 4.20 (t, J = 4.3 Hz, 1H), 5.40 (s, 1H), 6.01 (s, 1H), 6.04 (dd, J = 12.1, 2.5 Hz, 1H), 6.20 (td, J = 8.1, 2.5 Hz, 1H), 6.60 (d, J = 8.2 Hz, 1H), 6.70 (d, J = 8.2 Hz, 1h), 6.75 (td, J = 8.3, 2.5 Hz, 1H), 6.87 (t, J = 8.1 Hz, 1H), 6.92 (dd, J = 11.6, 2.5 Hz, 1H), 7.19 (dd, J = 8.3, 7.1 Hz, 1H) |
| 6-(4-Fluoro-2-methoxyphenyl)-5-(1-naphtylaminomethyl)-2,2,4-trimethyl-1,2-dihydroquinoline (Compound No. 6-58) | 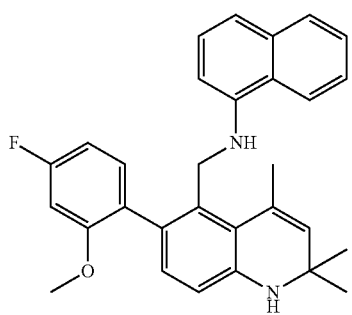 | $^1$H-NMR (400 MHz, DMSO-d$_6$) δ 1.16 (s, 3H), 1.21 (s, 3H), 2.07 (s, 3H), 3.69 (s, 3H), 3.97 (dd, J = 12.2, 4.8 Hz, 1H), 4.11 (dd, J = 12.2, 3.8 Hz, 1H), 5.36 (s, 1H), 5.98 (s, 1H), 6.28 (d, J = 7.6 Hz, 1H), 6.62 (d, J = 8.2 Hz, 1H), 6.65 (td, J = 8.1, 2.5 Hz, 1H), 6.71 (d, J = 8.2 Hz, 1H), 6.84 (dd, J = 11.6, 2.5 Hz, 1H), 7.06 (d, J = 7.8 Hz, 1H), 7.17 (t, J = 8.1 Hz, 1H), 7.25 (t, J = 7.1 Hz, 1H), 7.35 (t, J = 7.1 Hz, 1H), 7.40 (t, J = 6.7 Hz, 1H), 7.71 (d, J = 7.1 Hz, 1H), 7.94 (d, J = 8.5 Hz, 1H) |
| 6-(4,5-Difluoro-2-methoxyphenyl)-5-(2-methylphenylaminomethyl)-2,2,4-trimethyl-1,2-dihydroquinoline (Compound No. 6-59) | 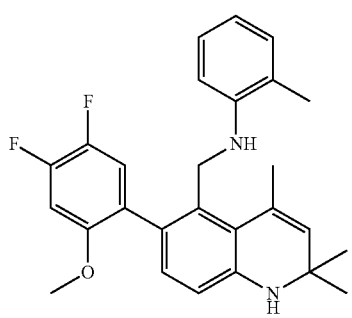 | $^1$H-NMR (400 MHz, DMSO-d$_6$) δ 1.14 (s, 3H), 1.20 (s, 3H), 1.95 (s, 3H), 2.03 (s, 3H), 3.70 (s, 3H), 3.85 (dd, J = 12.3, 4.4 Hz, 1H), 3.94 (t, J = 4.4 Hz, 1H), 4.06 (dd, J = 12.3, 4.4 Hz, 1H), 5.41 (s, 1H), 6.07 (s, 1H), 6.32 (d, J = 7.7 Hz, 1H), 6.47 (t, J = 7.7 Hz, 1H), 6.60 (d, J = 8.3 Hz, 1H), 6.72 (d, J = 8.3 Hz, 1H), 6.88-6.94 (m, 1H), 6.91 (d, J = 7.7 Hz, 1H), 7.15 (dd, J = 13.1, 7.2 Hz, 1H), 7.29 (dd, J = 11.1, 9.4 Hz, 1H) |

| Compound | ¹H-NMR |
|---|---|
| 6-(4-Fluoro-2-methoxyphenyl)-5-(2-methyl-1-naphtylaminomethyl)-2,2,4-trimethyl-1,2-dihydroquinoline (Compound No. 6-60) 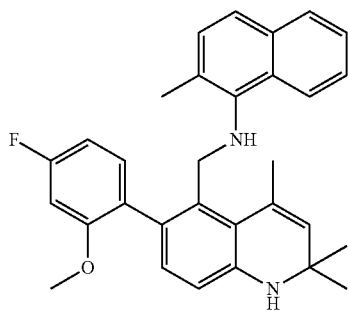 | ¹H-NMR (400 MHz, DMSO-$d_6$) δ 1.18 (s, 3H), 1.22 (s, 3H), 1.97 (s, 3H), 2.05 (s, 3H), 3.54-3.58 (m, 1H), 3.58 (s, 3H), 4.14 (dd, J = 13.4, 6.8 Hz, 1H), 4.37 (dd, J = 13.4, 3.8 Hz, 1H), 5.39 (s, 1H), 5.99 (s, 1H), 6.46 (td, J = 8.3, 2.4 Hz, 1H), 6.57 (d, J = 8.1 Hz, 1H), 6.62 (d, J = 8.1 Hz, 1H), 6.66 (dd, J = 8.3, 7.1 Hz, 1H), 6.76 (dd, J = 11.5, 2.4 Hz, 1H), 7.12 (d, J = 8.3 Hz, 1H), 7.20-7.24 (m, 1H), 7.29-7.34 (m, 1H), 7.32 (d, J = 8.1 Hz, 1h), 7.63 (d, J = 8.4 Hz, 1H), 7.71 (d, J = 7.6 Hz, 1H) |
| 5-(2-Ethyl-6-methylphenylaminomethyl)-6-(4-fluoro-2-methoxyphenyl)-2,2,4-trimethyl-1,2-dihydroquinoline (Compound No. 6-61) 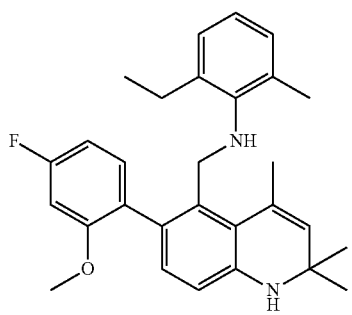 | ¹H-NMR (400 MHz, DMSO-$d_6$) δ 0.87 (t, J = 7.6 Hz, 3H), 1.16 (s, 3H), 1.25 (s, 3H), 1.89 (s, 3H), 2.15 (s, 3H), 2.23 (q, J = 7.6 Hz, 2H), 3.02-3.04 (m, 1H), 3.63 (s, 3H), 3.90 (dd, J = 13.1, 6.3 Hz, 1H), 4.15 (dd, J = 13.1, 3.9 Hz, 1H), 5.45 (s, 1H), 6.03 (s, 1H), 6.58 (d, J = 8.1 Hz, 1H), 6.58-6.67 (m, 2H), 6.66 (d, J = 8.1 Hz, 1H), 6.78-7.86 (m, 4H) |
| 5-(3-Chloro-2-methylphenylaminomethyl)-6-(4-fluoro-2-methoxyphenyl)-2,2,4-trimethyl-1,2-dihydroquinoline (Compound No. 6-62) 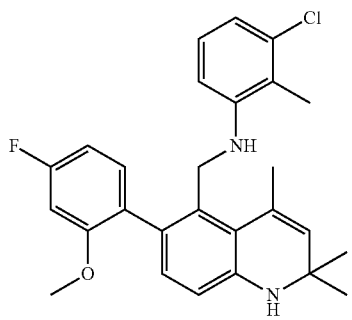 | ¹H-NMR (400 MHz, DMSO-$d_6$) δ 1.11 (s, 3H), 1.19 (s, 3H), 2.01 (s, 6H), 3.72 (s, 3H), 3.88 (dd, J = 133.0, 4.5 Hz, 1H), 4.05-4.08 (m, 1H), 4.27 (t, J = 4.5 Hz, 1H), 5.40 (s, 1H), 6.01 (s, 1H), 6.26 (d, J = 7.8 Hz, 1H), 6.56-6.60 (m, 1H), 6.60 (d, J = 8.3 Hz, 1H), 6.70 (d, J = 8.3 Hz, 1H), 6.74 (td, J = 8.4, 2.5 Hz, 1H), 6.86-6.93 (m, 2H), 7.20 (dd, J = 8.2, 7.2 Hz, 1H) |

| | |
|---|---|
| 5-(2,6-Dimethylphenylaminomethyl)-6-(4-fluoro-2-methoxyphenyl)-2,2,4-trimethyl-1,2-dihydroquinoline (Compond No. 6-63) 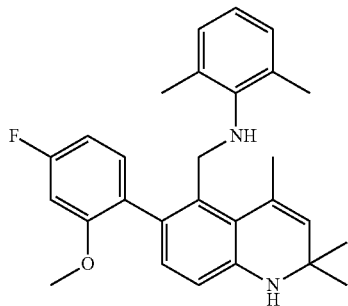 | $^1$H-NMR (400 MHz, DMSO-$d_6$) δ 1.15 (s, 3H), 1.23 (s, 3H), 1.87 (s, 6H), 2.13 (s, 3H), 3.02 (dd, J = 6.4, 3.3 Hz, 1H), 3.62 (s, 3H), 3.94 (dd, J = 13.0, 6.4 Hz, 1H), 4.15 (dd, J = 13.0, 3.3 Hz, 1H), 5.43 (s, 1H), 6.02 (s, 1H), 6.58 (d, J = 8.2 Hz, 1H), 6.58 (t, J = 7.6 Hz, 1H), 6.62 (td, J = 8.6, 2.9 Hz, 1H), 6.66 (d, J = 8.2 Hz, 1H), 6.78 (d, J = 7.6 Hz, 2H), 6.82 (dd, J = 8.6, 7.2 Hz, 1H), 6.85 (dd, J = 11.5, 2.9 Hz, 1H) |
| 5-(4-Dimethylaminophenylaminomethyl)-6-(4-fluoro-2-methoxyphenyl)-2,2,4-trimethyl-1,2-dihydroquinoline (Compound No. 6-64) 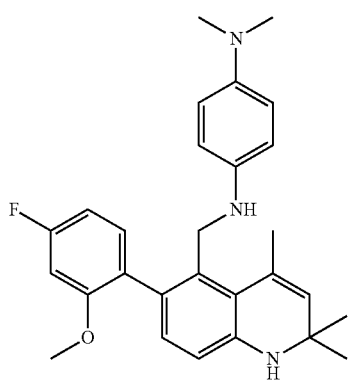 | $^1$H-NMR (400 MHz, DMSO-$d_6$) δ 1.16 (s, 3H), 1.20 (s, 3H), 2.12 (s, 3H), 2.67 (s, 6H), 3.65-3.70 (m, 1H), 3.70 (s, 3H), 3.89 (dd, J = 11.1, 5.2 Hz, 1H), 4.40 (t, J = 5.1 Hz, 1H), 5.35 (s, 1H), 5.90 (s, 1H), 6.38 (d, J = 8.7 Hz, 2H), 6.54 (d, J = 8.7 Hz, 2H), 6.56 (d, J = 8.1 Hz, 1H), 6.65 (d, J = 8.1 Hz, 1H), 6.68 (td, J = 8.3, 2.6 Hz, 1H), 6.87 (dd, J = 11.5, 2.6 Hz, 1H), 7.18 (dd, J = 8.3, 7.1 Hz, 1H) |
| 5-(2,6-Dimethoxyphenylaminomethyl)-6-(4-fluoro-2-methoxyphenyl)-2,2,4-trimethyl-1,2-dihydroquinoline (Compound No. 6-65) 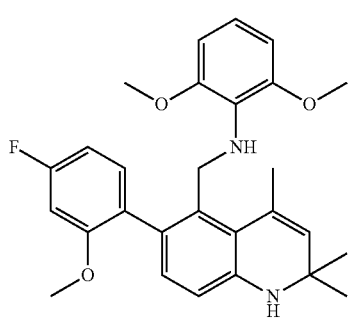 | $^1$H-NMR (400 MHz, DMSO-$d_6$) δ 1.15 (s, 3H), 1.22 (s, 3H), 2.20 (s, 3H), 3.60 (s, 6H), 3.64 (s, 3H), 4.07 (dd, J = 12.9, 6.0 Hz, 1H), 4.27 (dd, J = 12.9, 5.1 Hz, 1H), 5.41 (s, 1H), 5.96 (s, 1H), 6.48 (d, J = 7.7 Hz, 2H), 6.56 (d, J = 8.2 Hz, 1H), 6.60 (dd, J = 8.8, 7.7 Hz, 1H), 6.66 (d, J = 8.2 Hz, 1H), 6.69 (td, J = 8.6, 2.4 Hz, 1H), 6.86 (dd, J = 11.5, 2.4 Hz, 1H), 7.05 (dd, J = 8.6, 7.1 Hz, 1H) |

6-(2-Methoxy-5-methylphenyl)-5-(2-methoxy-5-methylphenylaminomethyl)-2,2,4-trimethyl-1,2-dihydroquinoline (Compound No. 6-66)

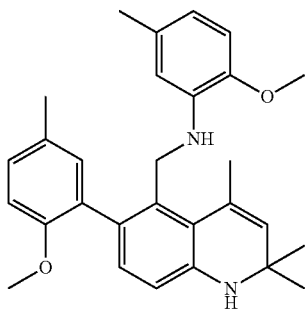

$^1$H-NMR (400 MHz, DMSO-d$_6$) δ 1.13 (s, 3H), 1.21 (s, 3H), 2.08 (s, 3H), 2.09 (s, 3H), 2.20 (s, 3H), 3.61 (s, 3H), 3.67 (s, 3H), 3.84 (dd, J = 12.2, 3.5 Hz, 1H), 4.00 (dd, J = 12.2, 6.6 Hz, 1H), 4.22 (dd, J = 6.6, 3.5 Hz, 1H), 5.39 (s, 1H), 5.94 (s, 1H), 6.14 (s, 1H), 6.29 (d, J = 8.1 Hz, 1H), 6.58 (d, J = 8.3 Hz, 1H), 6.60 (d, J = 8.1 Hz, 1H), 6.68 (d, J = 8.3 Hz, 1H), 6.85 (d, J = 8.3 Hz, 1H), 6.89 (d, J = 2.2 Hz, 1H), 7.04 (dd, J = 8.3, 2.2 Hz, 1H)

6-(2-Methoxy-5-trifluoromethylphenyl)-5-(3-methylphenylaminomethyl)-2,2,4-trimethyl-1,2-dihydroquinoline (Compound No. 6-67)

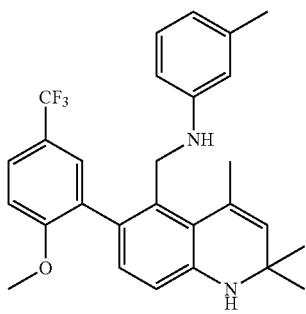

$^1$H-NMR (400 MHz, DMSO-d$_6$) δ 1.17 (s, 3H), 1.20 (s, 3H), 2.09 (s, 3H), 2.11 (s, 3H), 3.61 (dd, J = 12.1, 4.1 Hz, 1H), 3.77 (s, 3H), 4.01 (dd, J = 12.1, 4.1 Hz, 1H), 5.11 (t, J = 4.1 Hz, 1H), 5.37 (s, 1H), 5.98 (s, 1H), 6.21 (br s, 2H), 6.27 (d, J = 7.7 Hz, 1H), 6.59 (d, J = 8.2 Hz, 1H), 6.70 (d, J = 8.2 Hz, 1H), 6.82 (t, J = 7.7 Hz, 1H), 7.15 (d, J = 8.5 Hz, 1H), 7.53 (d, J = 2.2 Hz, 1H), 7.57 (d, J = 8.5 Hz, 1H)

5-(2-Methoxy-5-methylphenylaminomethyl)-6-(2-methoxy-5-trifluoromethylphenyl)-2,2,4-trimethyl-1,2-dihydroquinoline (Compound No. 6-68)

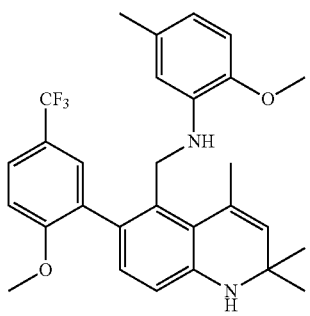

$^1$H-NMR (400 MHz, DMSO-d$_6$) δ 1.14 (s, 3H), 1.22 (s, 3H), 2.08 (s, 3H), 2.09 (s, 3H), 3.66 (s, 3H), 3.74 (s, 3H), 3.85 (dd, J = 12.7, 3.7 Hz, 1H), 3.97 (dd, J = 12.7, 6.5 Hz, 1H), 4.15-4.18 (m, 1H), 5.41 (s, 1H), 6.06 (s, 1H), 6.12 (s, 1H), 6.29 (d, J = 8.1 Hz, 1H), 6.59 (d, J = 8.1 Hz, 1H), 6.61 (d, J = 8.1 Hz, 1H), 6.72 (d, J = 8.1 Hz, 1H), 7.17 (d, J = 8.6 Hz, 1H), 7.38 (d, J = 2.2 Hz, 1H), 7.61 (dd, d, J = 8.6, 2.2 Hz, 1H)

| | | |
|---|---|---|
| 5-(2-Methoxyphenylaminomethyl)-6-(2-methoxy-5-trifluoromethylphenyl)-2,2,4-trimethyl-1,2-dihydroquinoline (Compound No. 6-69) 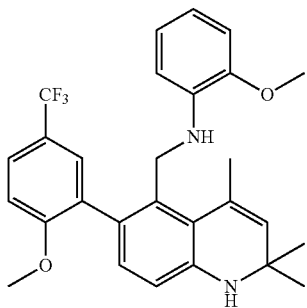 | | $^1$H-NMR (500 MHz, DMSO-d$_6$) δ 1.16 (s, 3H), 1.21 (s, 3H), 2.09 (s, 3H), 3.70 (s, 3H), 3.74 (s, 3H), 3.85 (dd, J = 12.5, 3.8 Hz, 1H), 3.97 (dd, J = 12.5, 6.7 Hz, 1H), 4.19-4.21 (m, 1H), 5.41 (s, 1H), 6.06 (s, 1H), 6.32 (d, J = 7.8 Hz, 1H), 6.50 (t, J = 7.8 Hz, 1H), 6.62 (dd, J = 8.3 Hz, 1H), 6.65 (t, J = 7.8 Hz, 1H), 6.72 (d, J = 8.3 Hz, 1H), 6.73 (d, J = 7.8 Hz, 1H), 7.16 (d, J = 8.7 Hz, 1H), 7.38 (d, J = 2.4 Hz, 1H), 7.61 (dd, J = 8.7, 2.4 Hz, 1H) |
| 5-(2-Ethoxyphenylaminomethyl)-6-(2-methoxy-5-trifluoromethylphenyl)-2,2,4-trimethyl-1,2-dihydroquinoline (Compound No. 6-70) 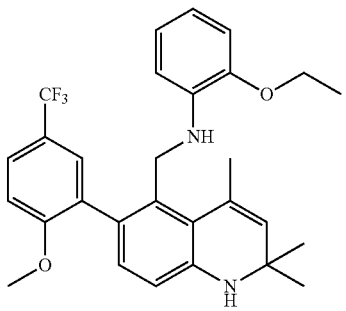 | | $^1$H-NMR (400 MHz, DMSO-d$_6$) δ 1.16 (s, 3H), 1.21 (s, 3H), 1.26 (t, J = 7.0 Hz, 3H), 2.06 (s, 3H), 3.74 (s, 3H), 3.87-3.98 (m, 4H), 4.13-4.14 (m, 1H), 5.42 (s, 1H), 6.10 (s, 1H), 6.29 (d, J = 7.8 Hz, 1H), 6.49 (t, J = 7.8 Hz, 1H), 6.63 (d, J = 8.2 Hz, 1H), 6.65 (t, J = 7.8 Hz, 1H), 6.72 (d, J = 7.8 Hz, 1H), 6.75 (d, J = 8.2 Hz, 1H), 7.18 (d, J = 8.7 Hz, 1H), 7.40 (d, J = 82.0 Hz, 1H), 7.63 (dd, J = 8.7, 2.0 Hz, 1H) |
| 5-(3-Ethylphenylaminomethyl)-6-(2-methoxy-5-trifluoromethylphenyl)-2,2,4-trimethyl-1,2-dihydroquinoline (Compound No. 6-71) 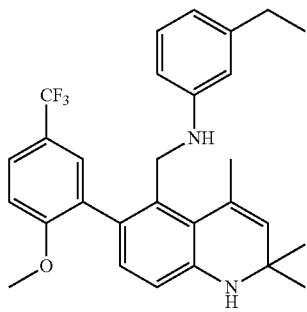 | | $^1$H-NMR (500 MHz, DMSO-d$_6$) δ 1.07 (t, J = 7.6 Hz, 3H), 1.17 (s, 3H), 1.20 (s, 3H), 2.12 (s, 3H), 2.38 (q, J = 7.6 Hz, 2H), 3.63 (dd, J = 12.3, 3.6 Hz, 1H), 3.77 (s, 3H), 4.03 (dd, J = 12.3, 5.0 Hz, 1H), 5.09-5.11 (m, 1H), 5.37 (s, 1H), 5.97 (s, 1H), 6.21 (d, J = 7.7 Hz, 1H), 6.25 (s, 1H), 6.30 (d, J = 7.7 Hz, 1H), 6.59 (d, J = 8.3 Hz, 1H), 6.71 (d, J = 8.3 Hz, 1H), 6.84 (t, J = 7.7 Hz, 1H), 7.15 (d, J = 8.6 Hz, 1H), 7.53 (d, J = 2.4 Hz, 1H), 7.56 (d, J = 8.6 Hz, 1H) |

| | |
|---|---|
| 6-(5-Chloro-2-methoxyphenyl)-5-(2-methoxyphenylaminomethyl)-2,2,4-trimethyl-1,2-dihydroquinoline (Compound No. 6-72)<br>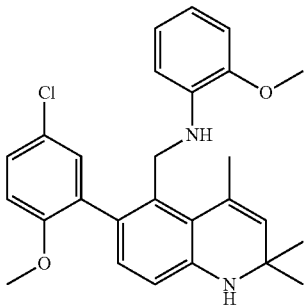 | $^1$H-NMR (500 MHz, DMSO-d$_6$)<br>δ 1.15 (s, 3H), 1.21 (s, 3H), 2.08 (s, 3H), 3.66 (s, 3H), 3.72 (s, 3H), 3.84 (dd, J = 12.5, 3.8 Hz, 1H), 4.00 (dd, J = 12.5, 6.3 Hz, 1H), 4.21 (dd, J = 6.3, 3.8 Hz, 1H), 5.40 (s, 1H), 6.03 (s, 1H), 6.35 (dd, J = 7.8, 1.3 Hz, 1H), 6.51 (td, J = 7.8, 1.3 Hz, 1H), 6.60 (d, J = 8.3 Hz, 1H), 6.66 (d, J = 7.8, 1.3 Hz, 1H), 6.70 (d, J = 8.3 Hz, 1H), 6.73 (dd, J = 7.8, 1.3 Hz, 1H), 6.98 (d, J = 8.7 Hz, 1H), 7.10 (d, J = 2.8 Hz, 1H), 7.27 (dd, J = 8.7, 2.8 Hz, 1H) |
| 6-(5-Chloro-2-methoxphenyl)-5-(2-methoxy-5-methylphenylaminomethyl)-2,2,4-trimethyl-1,2-dihydroquinoline (Compound No. 6-73)<br>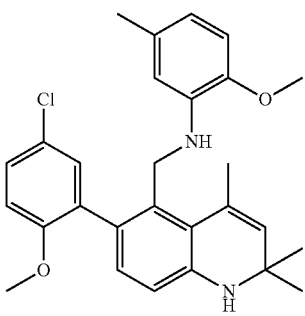 | $^1$H-NMR (500 MHz, DMSO-d$_6$)<br>δ 1.13 (s, 3H), 1.21 (s, 3H), 2.08 (s, 3H), 2.09 (s, 3H), 3.66 (s, 3H), 3.67 (s, 3H), 3.85 (dd, J = 12.5, 3.4 Hz, 1H), 3.99 (dd, J = 12.5, 6.6 Hz, 1H), 4.18 (dd, J = 6.6, 3.4 Hz, 1H), 5.40 (s, 1H), 6.03 (s, 1H), 6.14 (s, 1H), 6.29 (d, J = 8.2 Hz, 1H), 6.59 (d, J = 8.3 Hz, 1H), 6.60 (d, J = 8.2 Hz, 1H), 6.69 (d, J = 8.3 Hz, 1H), 6.99 (d, J = 8.9 Hz, 1H), 7.11 (d, J = 2.6 Hz, 1H), 7.29 (dd, J = 8.9, 2.6 Hz, 1H) |
| 6-(5-Fluoro-2-methoxyphenyl)-5-(2-methoxy-5-methylphenylaminomethyl)-2,2,4-trimethyl-1,2-dihydroquinoline (Compound No. 6-74)<br>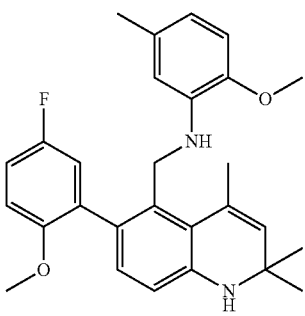 | $^1$H-NMR (400 MHz, DMSO-d$_6$)<br>δ 1.14 (s, 3H), 1.21 (s, 3H), 2.08 (s, 3H), 2.09 (s, 3H), 3.64 (s, 3H), 3.66 (s, 3H), 3.85 (dd, J = 12.7, 3.6 Hz, 1H), 4.01 (dd, J = 12.7, 6.6 Hz, 1H), 4.20 (dd, J = 6.6, 3.6 Hz, 1H), 5.40 (s, 1H), 6.03 (s, 1H), 6.14 (d, J = 1.5 Hz, 1H), 6.29 (dd, J = 8.1, 1.5 Hz, 1H), 6.59 (d, J = 8.1 Hz, 1H), 6.60 (d, J = 8.1 Hz, 1H), 6.70 (d, J = 8.1 Hz, 1H), 6.94 (dd, J = 9.0, 3.3 Hz, 1H), 6.96 (dd, J = 8.9, 4.8 Hz, 1H), 7.07 (td, J = 8.9, 3.3 Hz, 1H) |

| | |
|---|---|
| 6-(5-Fluoro-2-methoxyphenyl)-5-(2-methoxyphenylaminomethyl)-2,2,4-trimethyl-1,2-dihydroquinoline (Compound No. 6-75)<br>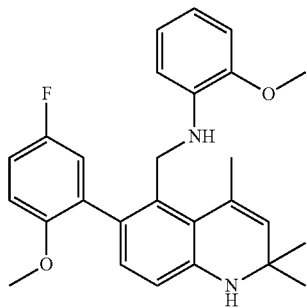 | $^1$H-NMR (500 MHz, DMSO-$d_6$)<br>δ 1.15 (s, 3H), 1.21 (s, 3H), 2.08 (s, 3H), 3.64 (s, 3H), 3.71 (s, 3H), 3.86 (dd, J = 12.4, 3.6 Hz, 1H), 4.01 (dd, J = 12.4, 6.5 Hz, 1H), 4.23 (dd, J = 6.5, 3.6 Hz, 1H), 5.40 (s, 1H), 6.02 (s, 1H), 6.35 (dd, J = 7.7, 1.2 Hz, 1H), 6.51 (td, J = 7.7, 1.2 Hz, 1H), 6.60 (d, J = 8.1 Hz, 1H), 6.67 (td, J = 7.7, 1.2 Hz, 1H), 6.71 (d, J = 8.1 Hz, 1H), 6.73 (dd, J = 7.7, 1.2 Hz, 1H), 6.93 (dd, J = 9.0, 3.3 Hz, 1H), 6.95 (dd, J = 8.9, 4.6 Hz, 1H), 7.05 (td, J = 8.9, 3.3 Hz, 1H) |
| 6-(2-Methoxy-5-methylphenyl)-5-(2-methoxyphenylaminomethyl)-2,2,4-trimethyl-1,2-dihydroquinoline (Compound No. 6-76)<br>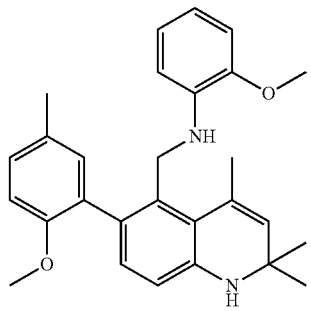 | $^1$H-NMR (400 MHz, DMSO-$d_6$)<br>δ 1.15 (s, 3H), 1.21 (s, 3H), 2.08 (s, 3H), 2.19 (s, 3H), 3.61 (s, 3H), 3.71 (s, 3H), 3.83 (dd, J = 12.1, 3.3 Hz, 1H), 4.01 (dd, J = 12.1, 6.6 Hz, 1H), 4.25 (dd, J = 6.6, 3.3 Hz, 1H), 5.39 (s, 1H), 5.95 (s, 1H), 6.34 (dd, J = 7.8, 1.4 Hz, 1H), 6.50 (td, J = 7.8, 1.4 Hz, 1H), 6.59 (d, J = 8.1 Hz, 1H), 6.67 (td, J = 7.8, 1.4 Hz, 1H), 6.68 (d, J = 8.1 Hz, 1H), 6.73 (dd, J = 7.8, 1.4 Hz, 1H), 6.84 (d, J = 8.3 Hz, 1H), 6.88 (d, J = 2.3 Hz, 1H), 7.02 (dd, J = 8.3, 2.3 Hz, 1H) |
| 6-(4-Fluoro-2-methoxyphenyl)-5-[2-(2-hydroxyethyl)phenylaminomethyl)-2,2,4-trimethyl-1,2-dihydroquinoline (Compound No. 6-77)<br>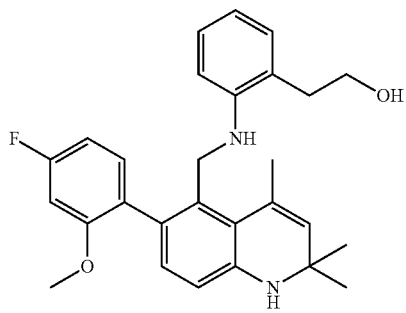 | $^1$H-NMR (400 MHz, DMSO-$d_6$)<br>δ 1.15 (s, 3H), 1.21 (s, 3H), 2.02 (s, 3H), 2.47-2.52 (m, 2H), 3.48 (ddd, J = 12.0, 6.7, 0.9 Hz, 2H), 3.72 (s, 3H), 3.79 (dd, J = 12.5, 4.4 Hz, 1H), 4.03 (dd, J = 12.5, 4.4 Hz, 1H), 4.28 (t, J = 4.4 Hz, 1H), 4.61 (t, J = 4.9 Hz, 1H), 5.38 (s, 1H), 5.99 (s, 1H), 6.31 (d, J = 7.5 Hz, 1H), 6.49 (td, J = 7.5, 1.1 Hz, 1H), 6.60 (d, J = 8.3 Hz, 1H), 6.69 (d, J = 8.3 Hz, 1H), 6.72 (td, J = 8.3, 2.6 Hz, 1H), 6.90 (dd, J = 11.4, 2.6 Hz, 1H), 6.90 (dd, J = 7.5, 1.1 Hz, 1H), 6.91-6.95 (m, 1H), 7.18 (dd, J = 8.3, 7.1 Hz, 1H) |

| | |
|---|---|
| 6-(5-Fluoro-2-methoxyphenyl)-5-(5-fluoro-2-methylphenylaminomethyl)-2,2,4-trimethyl-1,2-dihydroquinoline (Compound No. 6-78) 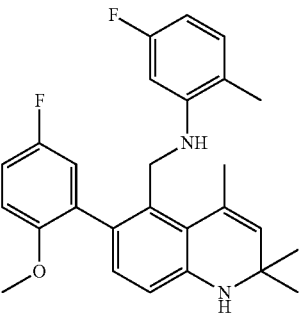 | $^1$H-NMR (400 MHz, DMSO-d$_6$) δ 1.12 (s, 3H), 1.19 (s, 3H), 1.90 (s, 3H), 2.05 (s, 3H), 3.68 (s, 3H), 3.88 (dd, J = 12.8, 5.1 Hz, 1H), 4.08 (dd, J = 12.8, 3.9 Hz, 1H), 4.29-4.30 (m, 1H), 5.41 (s, 1H), 6.05 (dd, J = 12.1, 2.4 Hz, 1H), 6.05 (s, 1H), 6.20 (td, J = 8.2, 2.4 Hz, 1H), 6.61 (d, J = 8.2 Hz, 1H), 6.73 (d, J = 8.2 Hz, 1H), 6.87 (dd, J = 8.2, 7.2 Hz, 1H), 7.02 (dd, J = 8.9, 4.8 Hz, 1H), 7.04 (dd, J = 9.2, 3.2 Hz, 1H), 7.08 (td, J = 8.9, 3.2 Hz, 1H) |
| 5-(5-Fluoro-2-methylphenylaminomethyl)-6-(2-methoxy-5-trifluoromethylphenyl)-2,2,4-trimethyl-1,2-dihydroquinoline (Compound No. 6-79) 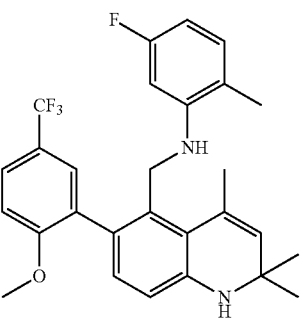 | $^1$H-NMR (400 MHz, DMSO-d$_6$) δ 1.13 (s, 3H), 1.19 (s, 3H), 1.87 (s, 3H), 2.06 (s, 3H), 3.76-3.82 (m, 1H), 3.80 (s, 3H), 4.11 (dd, J = 13.5 Hz, 1H), 4.39 (br s, 1H), 5.42 (s, 1H), 6.00 (dd, J = 11.2, 2.4 Hz, 1H), 6.07 (s, 1H), 6.18 (td, J = 8.4, 2.4 Hz, 1H), 6.62 (d, J = 8.1 Hz, 1H), 6.73 (d, J = 8.1 Hz, 1H), 6.83-6.86 (m, 1H), 7.19 (d, J = 8.7 Hz, 1H), 7.49 (d, J = 2.0 Hz, 1H), 7.62 (dd, J = 8.7, 2.0 Hz, 1H) |
| 6-(5-Chloro-2-methoxyphenyl)-5-(5-fluoro-2-methylphenylaminomethyl)-2,2,4-trimethyl-1,2-dihydroquinoline (Compound No. 6-80) 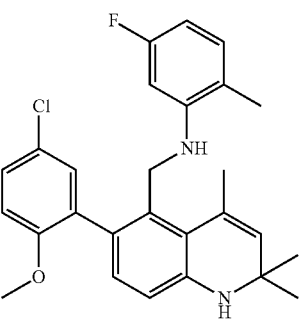 | $^1$H-NMR (400 MHz, DMSO-d$_6$) δ 1.12 (s, 3H), 1.19 (s, 3H), 1.90 (s, 3H), 2.05 (s, 3H), 3.70 (s, 3H), 3.84 (dd, J = 13.2, 4.6 Hz, 1H), 4.09 (dd, J = 13.2, 4.6 Hz, 1H), 4.30 (t, J = 4.6 Hz, 1H), 5.41 (s, 1H), 6.05 (dd, J = 11.2, 2.6 Hz, 1H), 6.05 (s, 1H), 6.20 (td, J = 8.4, 2.6 Hz, 1H), 6.60 (d, J = 8.1 Hz, 1H), 6.72 (d, J = 8.1 Hz, 1H), 6.85-6.89 (m, 1H), 7.03 (d, J = 8.7 Hz, 1H), 7.21 (d, J = 2.8 Hz, 1H), 7.30 (dd, J = 8.7, 2.8 Hz, 1H) |

| | |
|---|---|
| 6-(2-Methoxy-5-trifluoromethylphenyl)-5-(2-methylphenylaminomethyl)-2,2,4-trimethyl-1,2-dihydroquinoline (Compound No. 6-81)<br>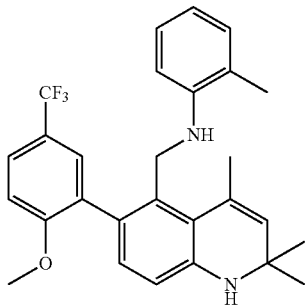 | $^1$H-NMR (400 MHz, DMSO-d$_6$) δ 1.15 (s, 3H), 1.21 (s, 3H), 1.92 (s, 3H), 2.04 (s, 3H), 3.79 (s, 3H), 3.78-3.84 (m, 1H), 3.96 (t, J = 4.4 Hz, 1H), 4.09 (dd, J = 12.7, 4.4 Hz, 1H), 5.42 (s, 1H), 6.08 (s, 1H), 6.27 (d, J = 7.6 Hz, 1H), 6.45 (t, J = 7.6 Hz, 1H), 6.62 (d, J = 8.2 Hz, 1H), 6.72 (d, J = 8.2 Hz, 1H), 6.87-6.91 (m, 2H), 7.20 (d, J = 8.6 Hz, 1H), 7.50 (d, J = 2.0 Hz, 1H), 7.62 (dd, J = 8.6, 2.0 Hz, 1H) |
| 5-(2,5-Dimethylphenylaminomethyl)-6-(2-methoxy-5-trifluoromethylphenyl)-2,2,4-trimethyl-1,2-dihydroquinoline (Compound No. 6-82)<br>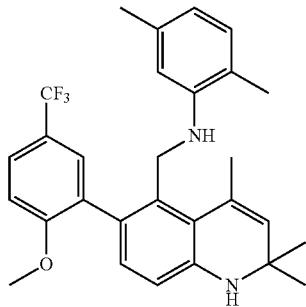 | $^1$H-NMR (500 MHz, DMSO-d$_6$) δ 1.12 (s, 3H), 1.21 (s, 3H), 1.87 (s, 3H), 2.05 (s, 3H), 2.09 (s, 3H), 3.79 (s, 3H), 3.83 (dd, J = 12.7, 4.2 Hz, 1H), 3.90 (t, J = 4.2 Hz, 1H), 4.09 (dd, J = 12.7, 4.2 Hz, 1H), 5.42 (s, 1H), 6.06 (br s, 2H), 6.26 (d, J = 7.3 Hz, 1H), 6.62 (d, J = 8.2 Hz, 1H), 6.73 (d, J = 8.2 Hz, 1H), 6.75 (d, J = 7.3 Hz, 1H), 7.21 (d, J = 8.7 Hz, 1H), 7.50 (d, J = 2.4 Hz, 1H), 7.63 (dd, J = 8.7, 2.4 Hz, 1H) |
| 6-(4-Chloro-2-methoxylphenyl)-5-(2-methoxy-5-methylphenylaminomethyl)-2,2,4-trimethyl-1,2-dihydroquinoline (Compound No. 6-83)<br>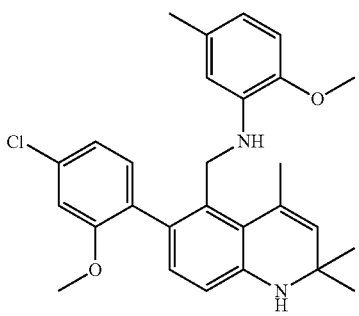 | $^1$H-NMR (400 MHz, DMSO-d$_6$) δ 1.14 (s, 3H), 1.21 (s, 3H), 2.07 (s, 3H), 2.10 (s, 3H), 3.67 (s, 3H), 3.68 (s, 3H), 3.81 (dd, J = 12.5, 3.7 Hz, 1H), 3.98-4.04 (m, 1H), 4.13-4.15 (m, 1H), 5.39 (s, 1H), 6.02 (s, 1H), 6.15 (s, 1H), 6.31 (d, J = 7.8 Hz, 1H), 6.59 (d, J = 8.2 Hz, 1H), 6.61 (d, J = 7.8 Hz, 1H), 6.67 (d, J = 8.2 Hz, 1H), 6.97 (dd, J = 8.1, 2.2 Hz, 1H), 7.04 (d, J = 2.2 Hz, 1H), 7.09 (d, J = 8.1 Hz, 1H) |

| | |
|---|---|
| 6-(4-Chloro-2-methoxylphenyl)-5-(2-methoxylphenylaminomethyl)-2,2,4-trimethyl-1,2-dihydroquinoline (Compound No. 6-84)<br>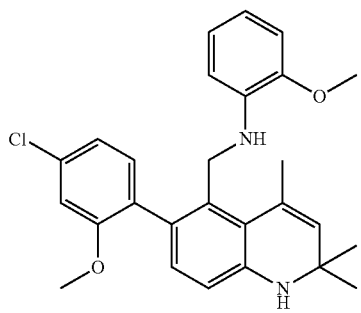 | $^1$H-NMR (400 MHz, DMSO-$d_6$) δ 1.14 (s, 3H), 1.21 (s, 3H), 2.06 (s, 3H), 3.68 (s, 3H), 3.71 (s, 3H), 3.81 (d, J = 12.2 Hz, 1H), 3.98-4.02 (m, 1H), 4.18-4.20 (m, 1H), 5.39 (s, 1H), 6.03 (s, 1H), 6.35 (d, J = 7.5 Hz, 1H), 6.51 (t, J = 7.6 Hz, 1H), 6.60 (d, J = 8.2 Hz, 1H), 6.66-6.70 (m, 1H), 6.68 (d, J = 8.2 Hz, 1H), 6.74 (dd, J = 7.5, 1.2 Hz, 1H), 6.96 (dd, J = 7.9, 2.0 Hz, 1H), 7.03 (d, J = 2.0 Hz, 1H), 7.09 (d, J = 7.9 Hz, 1H) |
| 6-(4-Chloro-2-methoxylphenyl)-5-(5-fluoro-2-methylphenylaminomethyl)-2,2,4-trimethyl-1,2-dihydroquinoline (Compund No. 6-85)<br>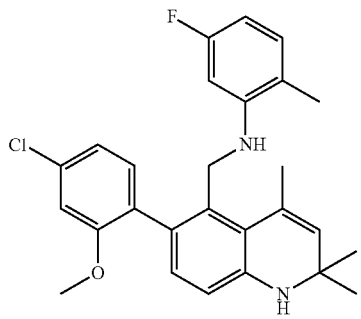 | $^1$H-NMR (400 MHz, DMSO-$d_6$) δ 1.11 (s, 3H), 1.19 (s, 3H), 1.89 (s, 3H), 2.03 (s, 3H), 3.73 (s, 3H), 3.88 (dd, J = 13.2, 4.7 Hz, 1H), 4.06 (dd, J = 13.2, 4.4 Hz, 1H), 4.23 (br s, 1H), 5.40 (s, 1H), 6.04 (s, 1H), 6.05 (dd, J = 12.5, 2.4 Hz, 1H), 6.20 (td, J = 8.4, 2.4 Hz, 1H), 6.60 (d, J = 8.2 Hz, 1H), 6.70 (d, J = 8.2 Hz, 1H), 6.86-6.89 (m, 1H), 6.99 (dd, J = 8.1, 2.1 Hz, 1H), 7.09 (d, J = 2.1 Hz, 1H), 7.18 (d, J = 8.1 Hz, 1H) |
| 5-[2-(2-t-Butoxycarbonylaminoethyl)phenylaminomethyl]-6-(4-fluoro-2-methoxylphenyl)-2,2,4-trimethyl-1,2-dihydroquinoline (Compound No. 6-86)<br>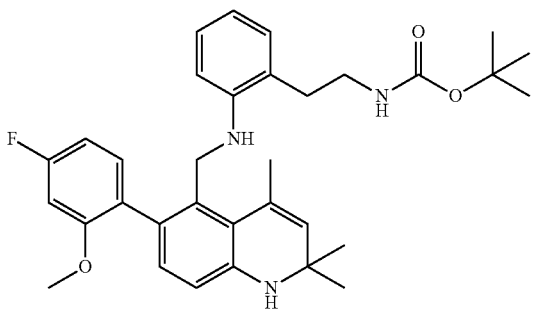 | $^1$H-NMR (400 MHz, DMSO-$d_6$) δ 1.11 (s, 3H), 1.18 (s, 3H), 1.34 (s, 9H), 2.03 (s, 3H), 2.49-2.51 (m, 2H), 2.96-2.99 (m, 2H), 3.72 (s, 3H), 4.09 (br s, 1H), 4.32-4.36 (m, 2H), 5.36 (s, 1H), 5.93 (s, 1H), 6.30-7.23 (m, 10H) |

Example 7

5-Acryloyloxymethyl-1-allyl-6-(2-methoxylphenyl)-2,2,4-trimethyl-1,2-dihydroquinoline (Compound No. 7-1)

A mixture of 5-acryloyloxymethyl-6-(2-methoxyphenyl)-2,2,4-trimethyl-1,2-dihydroquinoline (Compound No. 1-7, 50 mg, 0.14 mmol), allylbromide (111 μL, 1.28 mmol) and potassium carbonate (78 mg, 0.56 mmol) was suspended in anhydrous N,N-dimethylformamide (2 mL), and the reaction mixture was stirred at 60° C. for 4 days. After cooling down, it was diluted with ethyl acetate (25 mL). The whole was washed with water (30 mL, twice) and saturated brine (30 mL) successively, dried over anhydrous magnesium sulfate, and then the solvent was removed under reduced pressure. The obtained residue was purified by silica gel column chromatography (hexane-ethyl acetate) to give the titled compound (23 mg) as a pale yellow oil. (Yield 41%)

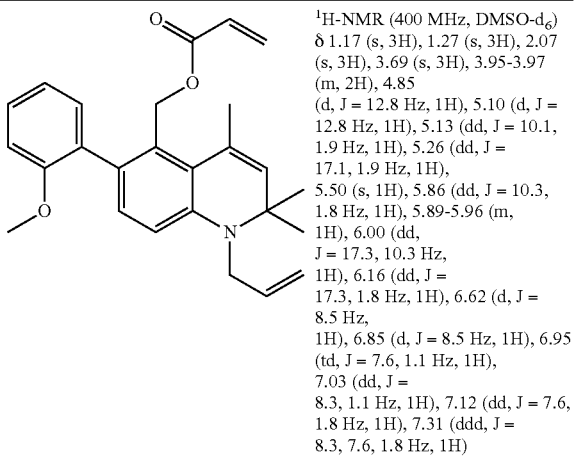

| | ¹H-NMR (400 MHz, DMSO-d₆) δ 1.17 (s, 3H), 1.27 (s, 3H), 2.07 (s, 3H), 3.69 (s, 3H), 3.95-3.97 (m, 2H), 4.85 (d, J = 12.8 Hz, 1H), 5.10 (d, J = 12.8 Hz, 1H), 5.13 (dd, J = 10.1, 1.9 Hz, 1H), 5.26 (dd, J = 17.1, 1.9 Hz, 1H), 5.50 (s, 1H), 5.86 (dd, J = 10.3, 1.8 Hz, 1H), 5.89-5.96 (m, 1H), 6.00 (dd, J = 17.3, 10.3 Hz, 1H), 6.16 (dd, J = 17.3, 1.8 Hz, 1H), 6.62 (d, J = 8.5 Hz, 1H), 6.85 (d, J = 8.5 Hz, 1H), 6.95 (td, J = 7.6, 1.1 Hz, 1H), 7.03 (dd, J = 8.3, 1.1 Hz, 1H), 7.12 (dd, J = 7.6, 1.8 Hz, 1H), 7.31 (ddd, J = 8.3, 7.6, 1.8 Hz, 1H) |

Using Compound No. 1-7 or 9-5, the following Compounds (No. 7-2 and 7-3) were obtained by a method similar to that of Compound No. 7-1.

Example 8

6-(2-Hydroxyphenyl)-5-[(pyrrolidin-1-yl)carbonyl]-2,2,4-trimethyl-1,2-dihydroquinoline (Compound No. 8-1)

Pyrrolidine (135 μL, 1.62 mmol) was dissolved in anhydrous tetrahydrofuran (1 mL), and 1.6 M hexane solution of n-butyl litium was added dropwise thereto at 0° C. After the reaction mixture was stirred at same temperature for 30 minutes, an anhydrous tetrahydrofuran solution (3 mL) of 2,2,4-trimethyl-1,2-dihydro-6-oxa-1-azachrysen-5-one (Reference Compound No. 1-1, 80 mg, 0.27 mmol) was dropped and then the reaction mixture was stirred for 30 minutes more. After the saturated aqueous NH₄Cl solution (5 mL) was added to the reaction mixture, the reaction mixture was diluted with ethyl acetate (100 mL). The whole was washed with water (100 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (80.2 mg) as a pale yellow solid. (Yield 82%)

| 5-Acryloyloxymethyl-1-ethyl-6-(2-methoxylphenyl)-2,2,4-trimethyl-1,2-dihydro quinoline (Compound No. 7-2) 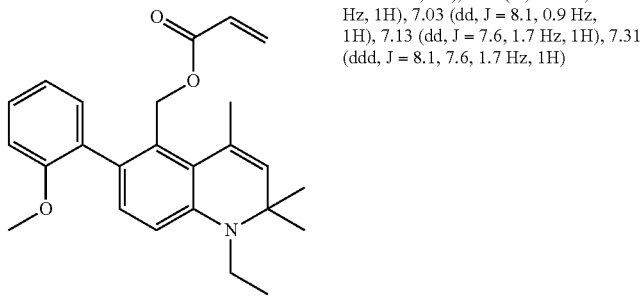 | ¹H-NMR (400 MHz, DMSO-d₆) δ 1.14 (t, J = 6.7 Hz, 3H), 1.16 (s, 3H), 1.28 (s, 3H), 2.04 (s, 3H), 3.30-3.38 (m, 2H), 3.69 (s, 3H), 4.85 (d, J = 12.9 Hz, 1H), 5.10 (d, J = 12.9 Hz, 1H), 5.46 (s, 1H), 5.86 (dd, J = 10.5, 1.7 Hz, 1H), 5.99 (dd, J = 17.2, 10.5 Hz, 1H), 6.16 (dd, J = 17.2, 1.7 Hz, 1H), 6.71 (d, J = 8.7 Hz, 1H), 6.89 (d, J = 8.7 Hz, 1H), 6.95 (td, J = 7.6, 0.9 Hz, 1H), 7.03 (dd, J = 8.1, 0.9 Hz, 1H), 7.13 (dd, J = 7.6, 1.7 Hz, 1H), 7.31 (ddd, J = 8.1, 7.6, 1.7 Hz, 1H) |
| 5-Benzylcarbamoyl-6-(2-methoxylphenyl)-1,2,2,4-tetramethyl-1,2-dihydroquinoline (Compound No. 7-3) 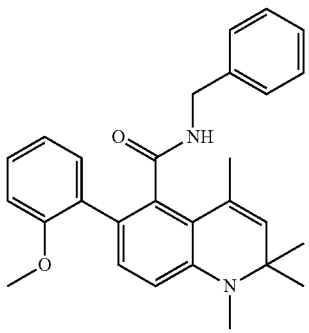 | ¹H-NMR (400 MHz, CDCl₃) δ 1.18 (s, 3H), 1.40 (s, 3H), 2.13 (s, 3H), 2.83 (s, 3H), 3.44 (s, 3H), 4.12 (br s, 2H), 5.44 (s, 1H), 6.11 (br s, 1H), 6.64 (d, J = 8.5 Hz, 1H), 6.75 (d, J = 7.5 Hz, 1H), 6.83-6.88 (m, 2H), 6.92 (d, J = 8.5 Hz, 1H), 6.97 (t, J = 7.5 Hz, 1H), 7.20-7.31 (m, 5H) |

| | |
|---|---|
| 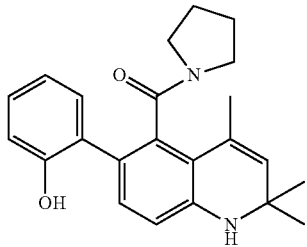 [SMILES: CC1=CC(C)(C)Nc2ccc(-c3ccccc3O)c(C(=O)N3CCCC3)c21] | ¹H-NMR (400 MHz, DMSO-d₆) δ 1.17 (s, 3H), 1.21-1.30 (m, 1H), 1.22 (s, 3H), 1.37-1.45 (m, 1H), 1.58-1.65 (m, 2H), 1.83 (s, 3H), 2.81-2.93 (m, 2H), 3.07-3.15 (m, 2H), 5.33 (s, 1H), 6.02 (s, 1H), 6.56 (d, J = 8.2 Hz, 1H), 6.70 (t, J = 7.4 Hz, 1H), 6.84 (d, J = 7.1 Hz, 1H), 6.85 (d, J = 8.2 Hz, 1H), 7.00 (d, J = 7.6 Hz, 1H), 7.02-7.07 (m, 1H), 9.05 (s, 1H) |

Using Reference Compound No. 1-1, the following Compounds (No. 8-2~8-8) were obtained by a method similar to that of Compound No. 8-1.

| | |
|---|---|
| 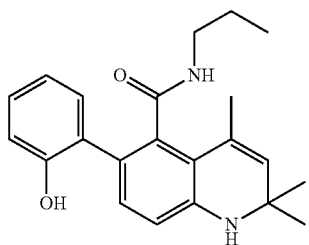<br>6-(2-Hydroxyphenyl)-5-propylcarbamoyl-2,2,4-trimethyl-1,2-dihydroquinoline (Compound No. 8-2) | ¹H-NMR (400 MHz, DMSO-d₆) δ 0.56 (t, J = 7.4 Hz, 3H), 1.01-1.06 (m, 2H), 1.21 (s, 6H), 1.94 (d, J = 1.5 Hz, 3H), 2.78 (br s, 2H), 5.30 (s, 1H), 5.97 (d, J = 1.5 Hz, 1H), 6.53 (d, J = 8.1 Hz, 1H), 6.67-6.71 (m, 1H), 6.72 (d, J = 8.1 Hz, 1H), 6.80 (dd, J = 7.7, 1.0 Hz, 1H), 6.99 (d, J = 7.7 Hz, 1H), 7.05 (td, J = 7.7, 1.5 Hz, 1H), 7.72 (br s, 1H), 8.77 (s, 1H) |
| 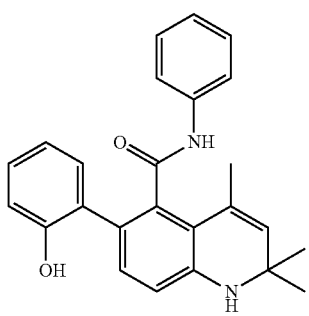<br>6-(2-Hydroxyphenyl)-5-phenylcarbamoyl-2,2,4-trimethyl-1,2-dihydroquinoline (Compound No. 8-3) | ¹H-NMR (400 MHz, DMSO-d₆) δ 1.24 (s, 6H), 1.95 (d, J = 1.2 Hz, 3H), 5.34 (s, 1H), 6.06 (d, J = 1.2 Hz, 1H), 6.60 (d, J = 8.2 Hz, 1H), 6.64 (t, J = 7.4 Hz, 1H), 6.77 (d, J = 7.3 Hz, 1H), 6.79 (d, J = 8.2 Hz, 1H), 6.95-6.99 (m, 2H), 7.09 (d, J = 7.1 Hz, 1H), 7.18 (t, J = 7.8 Hz, 2H), 7.33 (d, J = 7.8 Hz, 2H), 8.95 (s, 1H), 9.88 (br s, 1H) |

| Compound | NMR |
|---|---|
| 6-(2-Hydroxyphenyl)-5-[(N-methyl-N-phenyl)carbamoyl]-2,2,4-trimethyl-1,2-dihydroquinoline (Compound No. 8-4) 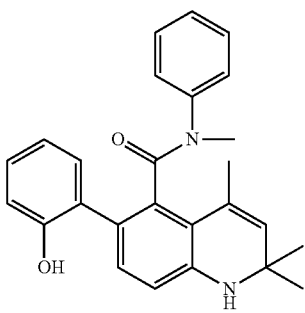 | $^1$H-NMR (500 MHz, CDCl$_3$) δ 1.33 (s, 6H), 2.17 (s, 3H), 3.03 (s, 3H), 5.48 (s, 1H), 6.59-6.61 (m, 1H), 6.64-6.65 (m, 2H), 6.88-6.99 (m, 4H), 7.06-7.08 (m, 1H), 7.17-7.21 (m, 2H), 7.24-7.32 (m, 3H) |
| 5-Benzylcarbamoyl-6-(2-hydroxyphenyl)-2,2,4-tetramethyl-1,2-dihydroquinoline (Compound No. 8-5) 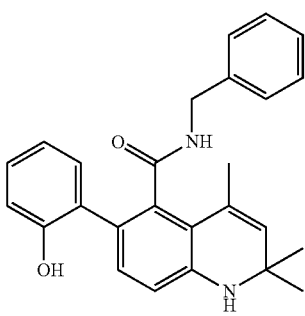 | $^1$H-NMR (400 MHz, CDCl$_3$) δ 1.26 (s, 3H), 1.33 (s, 3H), 2.10 (s, 3H), 3.91-4.09 (m, 2H), 4.54 (br s, 1H), 5.43 (s, 1H), 5.82 (br s, 1H), 6.55 (d, J = 8.2 Hz, 1H), 6.74-6.76 (m, 2H), 6.85 (d, J = 8.2 Hz, 1H), 6.94 (t, J = 7.5 Hz, 1H), 7.02 (d, J = 7.5 Hz, 1H), 7.09 (d, J = 7.5 Hz, 1H), 7.12-7.18 (m, 1H), 7.15 (d, J = 7.3 Hz, 2H), 7.25-7.30 (m, 2H) |
| 6-(2-Hydroxyphenyl)-5-(pyridin-3-yl)carbamoyl-2,2,4-trimethyl-1,2-dihydroquinoline (Compound No. 8-6) 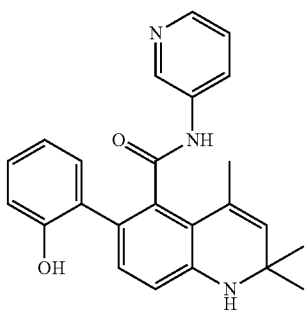 | $^1$H-NMR (400 MHz, CDCl$_3$) δ 1.24 (s, 3H), 1.31 (s, 3H), 2.12 (s, 3H), 4.10 (br s, 1H), 5.44 (s, 1H), 6.58 (d, J = 8.1 Hz, 1H), 6.74 (d, J = 7.6 Hz, 1H), 6.78 (t, J = 7.6 Hz, 1H), 6.88 (d, J = 8.1 Hz, 1H), 7.02 (t, J = 7.6 Hz, 1H), 7.10 (d, J = 7.6 Hz, 1H), 7.22-7.26 (m, 1H), 8.17 (dd, J = 4.9, 1.6 Hz, 1H), 8.23 (d, J = 1.6 Hz, 1H), 8.40 (d, J = 7.3 Hz, 1H), 9.34 (s, 1H), 11.06 (br s, 1H) |
| 5-Cyclohexylcarbamoyl-6-(2-hydroxyphenyl)-2,2,4-trimethyl-1,2-dihydroquinoline (Compound No. 8-7) 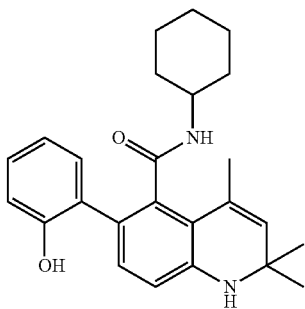 | $^1$H-NMR (400 MHz, DMSO-d$_6$) δ 0.97-1.24 (m, 10H), 1.46 (s, 3H), 1.56 (s, 3H), 2.11 (s, 3H), 3.27-3.42 (m, 1H), 5.47 (s, 1H), 6.68-6.86 (m, 3H), 6.96-7.15 (m, 4H) 7.55 (br s, 1H) |

| | |
|---|---|
| 6-(2-Hydroxyphenyl)-5-methoxyethylcarbamoyl-2,2,4-trimethyl-1,2-dihydroquinoline (Compound No. 8-8) 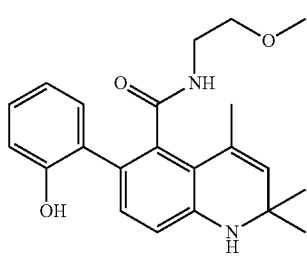 | $^1$H-NMR (400 MHz, CDCl$_3$) δ 1.28 (s, 3H), 1.32 (s, 3H), 2.08 (s, 3H), 2.90 (br s, 1H), 3.14 (br s, 1H), 3.15 (s, 3H), 3.38 (br s, 1H), 3.93 (br s, 1H), 5.44 (s, 1H), 5.98 (br s, 1H), 6.56 (d, J = 8.1 Hz, 1H), 6.85 (d, J = 8.1 Hz, 1H), 6.91 (t, J = 7.4 Hz, 1H), 6.98 (d, J = 7.4 Hz, 1H), 7.10 (d, J = 7.4 Hz, 1H), 7.21 (t, J = 7.4 Hz, 1H) |

Example 9

6-(2-Methoxyphenyl)-5-[(pyrrolidin-1-yl)carbonyl]-2,2,4-trimethyl-1,2-dihydroquinoline (Compound No. 9-1)

A mixture of 6-(2-hydroxyphenyl)-5-[(pyrrolidin-1-yl)carbonyl]-2,2,4-trimethyl-1,2-dihydroquinoline (Compound No. 8-1, 65.0 mg, 0.179 mmol), methyl iodide (11.1 μL, 0.178 mmol) and potassium carbonate (49.5 mg, 0.358 mmol) was suspended in anhydrous N,N-dimethylformamide (1.5 mL), and the reaction mixture was stirred at 50° C. overnight. After cooling down, it was diluted with ethyl acetate (100 mL). The whole was washed with water (100 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (42.5 mg) as a colorless solid. (Yield 63%)

$^1$H-NMR (500 MHz, DMSO-d$_6$) δ 1.15-1.27 (m, 1H), 1.17 (s, 3H), 1.22 (s, 3H), 1.35-1.46 (m, 1H), 1.56-1.67 (m, 2H), 1.82 (d, J = 1.5 Hz, 3H), 2.78-2.83 (m, 1H), 2.87-2.93 (m, 1H), 2.99-3.04 (m, 1H), 3.08-3.13 (m, 1H), 3.68 (s, 3H), 5.33 (s, 1H), 6.05 (d, J = 1.5 Hz, 1H), 6.55 (d, J = 8.2 Hz, 1H), 6.80 (d, J = 8.2 Hz, 1H), 6.85 (td, J = 7.4, 1.0 Hz, 1H), 7.01 (d, J = 7.9 Hz, 1H), 7.04 (br s, 1H), 7.21-7.24 (m, 1H)

Using any compounds among Compounds No. 8-2~8-8, the following Compounds (No. 9-2~9-8) were obtained by a method similar to that of Compound No. 9-1.

| | |
|---|---|
| 6-(2-Methoxyphenyl)-5-propylcarbamoyl-2,2,4-trimethyl-1,2-dihydroquinoline (Compound No. 9-2) 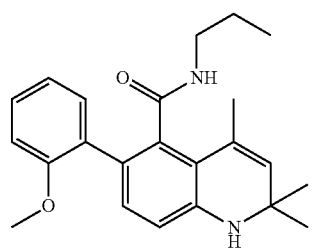 | $^1$H-NMR (400 MHz, DMSO-d$_6$) δ 0.56 (br s, 3H), 1.00 (br s, 2H), 1.21 (s, 6H), 1.93 (d, J = 1.3 Hz, 3H), 2.75 (br s, 2H), 3.66 (s, 3H), 5.29 (s, 1H), 5.97 (d, J = 1.3 Hz, 1H), 6.52 (d, J = 8.2 Hz, 1H), 6.69 (d, J = 8.2 Hz, 1H), 6.81 (t, J = 7.3 Hz, 1H), 6.95 (d, J = 8.3 Hz, 1H), 7.07 (d, J = 6.3 Hz, 1H), 7.18-7.23 (m, 1H), 7.66 (br s, 1H) |

| | |
|---|---|
| 6-(2-Methoxyphenyl)-5-phenylcarbamoyl-2,2,4-trimethyl-1,2-dihydroquinoline (Compound No. 9-3) 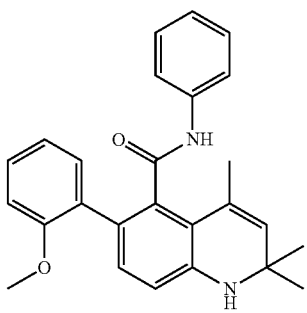 | ¹H-NMR (500 MHz, DMSO-d₆) δ 1.24 (s, 6H), 1.93 (s, 3H), 3.64 (s, 3H), 5.33 (s, 1H), 6.08 (d, J = 1.5 Hz, 1H), 6.59 (d, J = 8.2 Hz, 1H), 6.76 (d, J = 8.2 Hz, 1H), 6.78 (t, J = 7.5 Hz, 1H), 6.90 (d, J = 7.6 Hz, 1H), 6.96 (t, J = 7.5 Hz, 1H), 7.12-7.15 (m, 2H), 7.18 (t, J = 7.9 Hz, 2H), 7.33 (d, J = 7.6 Hz, 2H), 9.86 (br s, 1H) |
| 6-(2-Methoxyphenyl)-5-[(N-methyl-N-phenyl)carbamoyl]-2,2,4-trimethyl-1,2-dihydroquinoline (Compound No. 9-4) 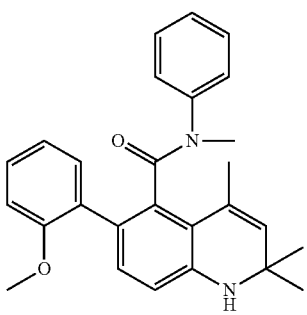 | ¹H-NMR (400 MHz, CDCl₃) δ 1.34 (s, 6H), 2.15 (s, 3H), 2.99 (s, 3H), 3.73 (s, 3H), 5.42 (s, 1H), 6.54-6.80 (m, 3H), 6.94-7.05 (m, 4H), 7.13-7.17 (m, 1H), 7.22-7.26 (m, 2H), 7.31-7.41 (m, 2H) |
| 5-Benzylcarbamoyl-6-(2-methoxyphenyl)-2,2,4-trimethyl-1,2-dihydroquinoline (Compound No. 9-5) 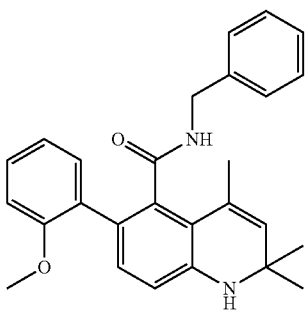 [SMILES: COc1ccccc1-c1ccc2c(c1C(=O)SCc1ccccc1)C(C)=CC(C)(C)N2] | ¹H-NMR (400 MHz, CDCl₃) δ 1.29 (s, 3H), 1.31 (br s, 3H), 2.12 (s, 3H), 3.45 (s, 3H), 3.87 (br s, 1H), 4.09-4.15 (m, 1H), 5.40 (s, 1H), 6.09 (br s, 1H), 6.50 (d, J = 8.1 Hz, 1H), 6.74 (d, J = 8.1 Hz, 1H), 6.78 (d, J = 8.1 Hz, 1H), 6.83-6.85 (m, 2H), 6.96 (t, J = 7.3 Hz, 1H), 7.20-7.22 (m, 4H), 7.28 (t, J = 8.1 Hz, 1H) |
| 6-(2-Methoxyphenyl)-5-(pyridin-3-yl)carbamoyl-2,2,4-trimethyl-1,2-dihydroquinline (Compound No. 9-6) 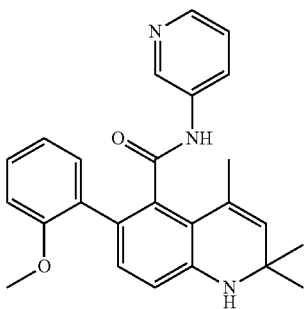 | ¹H-NMR (400 MHz, CDCl₃) δ 1.31 (s, 3H), 1.32 (s, 3H), 2.09 (s, 3H), 3.76 (s, 3H), 4.04 (br s, 1H), 5.44 (s, 1H), 6.58 (d, J = 8.1 Hz, 1H), 6.87 (d, J = 8.1 Hz, 1H), 6.86-6.88 (m, 1H), 6.91 (t, J = 7.4 Hz, 1H), 7.15-7.20 (m, 3H), 7.90 (d, J = 8.3 Hz, 1H), 7.94 (br s, 1H), 8.10 (d, J = 2.4 Hz, 1H), 8.23 (dd, J = 4.6, 2.4 Hz, 1H) |

| | |
|---|---|
| 5-Cyclohexylcarbamoyl-6-(2-methoxyphenyl)-2,2,4-trimethyl-1,2-dihydroquinoline (Compound No. 9-7) 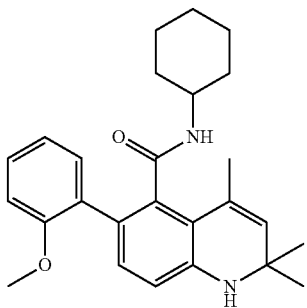 | ¹H-NMR (500 MHz, CDCl₃) 0.88-1.69 (m, 10H), 1.25 (s, 3H), 1.31 (s, 3H), 2.11 (s, 3H), 3.47-3.55 (m, 1H). 3.76 (s, 3H), 5.37 (s, 1H), 5.70 (br s, 1H), 6.49 (d, J = 8.1 Hz, 1H), 6.79 (d, J = 8.1 Hz, 1H), 6.88 (d, J = 7.9 Hz, 1H), 6.92 (t, J = 7.9 Hz, 1H), 7.14-7.19 (m, 1H), 7.25-7.28 (m, 1H) |
| 5-Methoxyethylcarbamoyl-6-(2-methoxyphenyl)-2,2,4-trimethyl-1,2-dihydroquinoline (Compound No. 9-8) 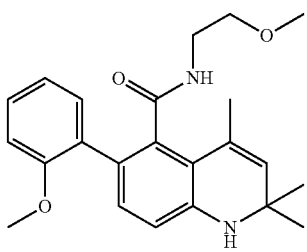 | ¹H-NMR (500 MHz, CDCl₃) δ 1.25 (s, 6H), 2.07 (s, 3H), 2.84 (br s, 1H), 3.13 (br s, 3H), 3.19 (s, 3H), 3.76 (s, 3H), 3.96 (br s, 1H), 5.37 (s, 1H), 6.22 (br s, 1H), 6.50 (d, J = 7.9 Hz, 1H), 6.81 (d, J = 8.0 Hz, 1H), 6.89 (d, J = 8.0 Hz, 1H), 6.92 (m, 1H), 7.17 (d, J = 7.9 Hz, 1H), 7.27 (t, J = 7.9 Hz, 1H) |

Example 10

6-(2-Methoxyphenyl)-5-phenylthiomethyl-2,2,4-trimethyl-1,2-dihydroquinoline (Compound No. 10-1)

A mixture of 5-chloromethyl-6-(2-methoxyphenyl)-2,2,4-trimethyl-1,2-dihydroquinoline (Reference Compound No. 5-1, 80 mg, 0.24 mmol), thiophenol (148 μL, 1.44 mmol) and potassium carbonate (266 mg, 1.92 mmol) was suspended in anhydrous N,N-dimethylformamide (2 mL), and the reaction mixture was stirred at 50° C. overnight. After cooling down, it was diluted with ethyl acetate (50 mL). The whole was washed with water (50 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled compound (53 mg) as a colorless solid. (Yield 55%)

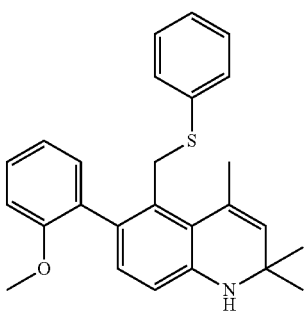

¹H-NMR (400 MHz, DMSO-d₆) δ 1.13 (s, 3H), 1.22 (s, 3H), 2.24 (s, 3H), 3.68 (s, 3H), 3.88 (d, J = 12.3 Hz, 1H), 4.28 (d, J = 12.3 Hz, 1H), 5.41 (s, 1H), 5.96 (s, 1H), 6.56 (d, J = 8.3 Hz, 1H), 6.66 (d, J = 8.3 Hz, 1H), 6.91 (td, J = 7.4, 1.1 Hz, 1H), 6.96-6.98 (m, 2H), 7.01 (d, J = 7.6 Hz, 1H), 7.05 (dd, J = 7.3, 1.7 Hz, 1H), 7.09 (t, J = 7.3 Hz, 1H), 7.17 (t, J = 7.3 Hz, 2H), 7.26-7.30 (m, 1H)

Using Reference Compound No. 5-2, the following Compounds (No. 10-2~10-5) were obtained by a method similar to that of Compound No. 10-1.

| | | |
|---|---|---|
| 6-(4-Fluoro-2-methoxyphenyl)-5-phenylthiomethyl-2,2,4-trimethyl-1,2-dihydroquinoline (Compound No. 10-2) 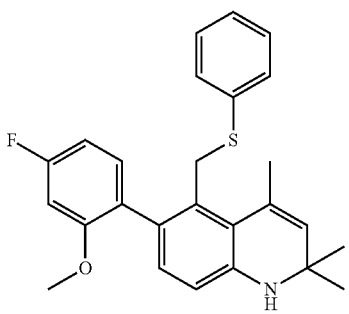 | | $^1$H-NMR (500 MHz, Solv. DMSO-$d_6$) δ 1.13 (s, 3H), 1.22 (s, 3H), 2.24 (s, 3H), 3.69 (s, 3H), 3.84 (d, J = 12.1 Hz, 1H), 4.26 (d, J = 12.1 Hz, 1H), 5.41 (s, 1H), 5.97 (s, 1H), 6.55 (d, J = 8.2 Hz, 1H), 6.64 (d, J = 8.2 Hz, 1H), 6.71 (td, J = 8.4, 2.4 Hz, 1H), 6.90 (dd, J = 11.6, 2.4 Hz, 1H), 6.99-7.01 (m, 2H), 7.03 (dd, J = 8.4, 7.2 Hz, 1H), 7.10-7.13 (m, 1H), 7.17-7.21 (m, 2H) |
| 6-(4-Fluoro-2-methoxyphenyl)-5-(2-methylphenylthiomethyl)-2,2,4-trimethyl-1,2-dihydroquinoline (Compound No. 10-3) 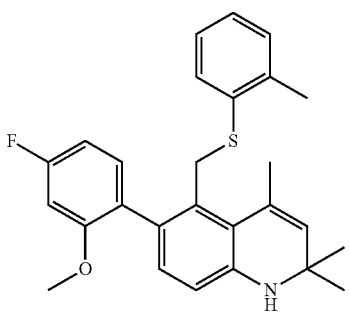 | | $^1$H-NMR (400 MHz, DMSO-$d_6$) δ 1.14 (s, 3H), 1.22 (s, 3H), 2.06 (s, 3H), 2.25 (s, 3H), 3.69 (s, 3H), 3.78 (d, J = 12.3 Hz, 1H), 4.20 (d, J = 12.3 Hz, 1H), 5.42 (s, 1H), 5.97 (s, 1H), 6.55 (d, J = 8.3 Hz, 1H), 6.62 (d, J = 8.3 Hz, 1H), 6.69 (dd, J = 8.5, 2.5 Hz, 1H), 6.89 (dd, J = 11.4, 2.5 Hz, 1H), 6.94-6.99 (m, 2H), 7.03-7.05 (m, 2H), 7.09-7.12 (m, 1H) |
| 5-(2,5-Dimethylphenylthiomethyl)-6-(4-fluoro-2-methoxyphenyl)-2,2,4-trimethyl-1,2-dihydroquinoline (Compound No. 10-4) 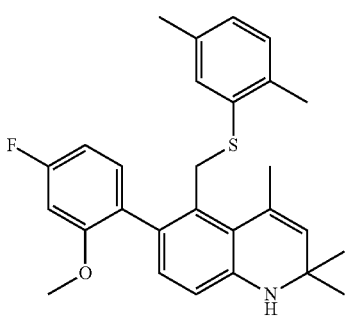 | | $^1$H-NMR (500 MHz, DMSO-$d_6$) δ 1.15 (s, 3H), 1.23 (s, 3H), 2.03 (s, 3H), 2.14 (s, 3H), 2.26 (s, 3H), 3.68 (s, 3H), 3.75 (d, J = 12.4 Hz, 1H), 4.20 (d, J = 12.4 Hz, 1H), 5.42 (s, 1H), 5.95 (s, 1H), 6.55 (d, J = 7.9 Hz, 1H), 6.62 (d, J = 7.9 Hz, 1H), 6.69 (dd, J = 8.3, 2.4 Hz, 1H), 6.70 (s, 1H), 6.85 (d, J = 7.8 Hz, 1H), 6.89 (dd, J = 11.6, 2.4 Hz, 1H), 6.95 (dd, J = 8.3, 7.0 Hz, 1H), 6.98 (d, J = 7.8 Hz, 1H) |
| 6-(4-Fluoro-2-methoxyphenyl)-5-(2-methoxyphenylthiomethyl)-2,2,4-trimethyl-1,2-dihydroquinoline (Compound No. 10-5) 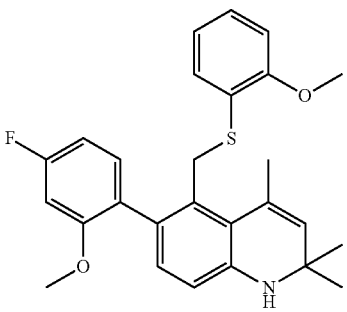 | | $^1$H-NMR (500 MHz, DMSO-$d_6$) δ 1.13 (s, 3H), 1.22 (s, 3H), 2.23 (s, 3H), 3.67 (s, 3H), 3.69 (s, 3H), 3.73 (d, J = 12.1 Hz, 1H), 4.15 (d, J = 12.1 Hz, 1H), 5.40 (s, 1H), 5.95 (s, 1H), 6.54 (d, J = 7.9 Hz, 1H), 6.62 (d, J = 7.9 Hz, 1H), 6.70 (td, J = 8.4, 2.4 Hz, 1H), 6.80 (t, J = 7.7 Hz, 1H), 6.86-6.94 (m, 2H), 6.89 (dd, J = 11.6, 2.4 Hz, 1H), 7.03 (t, J = 7.7 Hz, 1H), 7.11 (t, J = 7.7 Hz, 1H) |

Example 11

5-Benzylthiomethyl-6-(2-methoxyphenyl)-2,2,4-trimethyl-1,2-dihydroquinoline (Compound No. 11-1)

5-Chloromethyl-6-(2-methoxyphenyl)-2,2,4-trimethyl-1,2-dihydroquinoline (Reference Compound No. 5-1, 80 mg, 0.24 mmol) and benzylmercaptane (85 μL, 0.72 mmol) were dissolved in anhydrous tetrahydrofuran (2 mL), and 60% sodium hydride (38 mg, 0.95 mmol) was added thereto under argon atmosphere at 0° C. Anhydrous N,N-dimethylformamide (0.5 mL) was added thereto at room temperature and then the reaction mixture was stirred for 4 hours. The reaction mixture was diluted with ethyl acetate (50 mL). The whole was washed with water (50 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (65 mg) as a colorless solid. (Yield 65%)

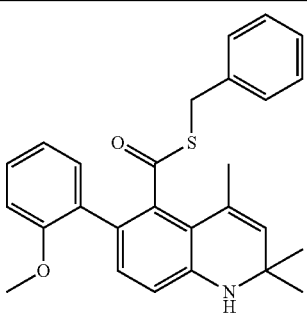

$^1$H-NMR (400 MHz, DMSO-$d_6$) δ 1.12 (s, 3H), 1.19 (s, 3H), 2.11 (s, 3H), 3.29 (d, J = 13.2 Hz, 1H), 3.35 (d, J = 13.2 Hz, 1H), 3.41 (d, J = 12.9 Hz, 1H), 3.64 (s, 3H), 3.76 (d, J = 12.9 Hz, 1H), 5.36 (s, 1H), 5.89 (s, 1H), 6.52 (d, J = 8.1 Hz, 1H), 6.64 (d, J = 8.1 Hz, 1H), 6.95-6.98 (m, 3H), 7.01 (d, J = 7.6 Hz, 1H), 7.12 (dd, J = 7.4, 1.8 Hz, 1H), 7.14-7.20 (m, 3H), 7.30-7.35 (m, 1H)

Using Reference Compound No. 5-2, the following Compounds (No. 11-2~11-3) were obtained by a method similar to that of Compound No. 11-1.

| | | |
|---|---|---|
| 6-(4-Fluoro-2-methoxyphenyl)-5-benzylthiomethyl-2,2,4-trimethyl-1,2-dihydroquinoline (Compound No. 11-2) 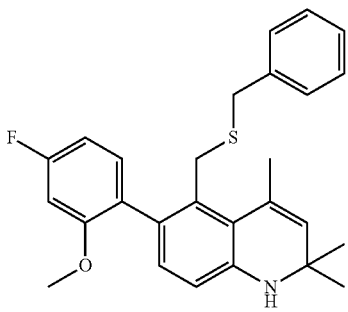 | | $^1$H-NMR (400 MHz, DMSO-$d_6$) δ 1.11 (s, 3H), 1.19 (s, 3H), 2.13 (s, 3H), 3.33 (d, J = 12.7 Hz, 1H), 3.36 (d, J = 13.2 Hz, 1H), 3.41 (d, J = 13.2 Hz, 1H), 3.64 (s, 3H), 3.72 (d, J = 12.7 Hz, 1H), 5.36 (s, 1H), 5.91 (s, 1H), 6.51 (d, J = 8.3 Hz, 1H), 6.61 (d, J = 8.3 Hz, 1H), 6.73 (td, J = 8.4, 2.4 Hz, 1H), 6.86 (dd, J = 11.5, 2.4 Hz, 1H), 6.99-7.01 (m, 2H), 7.08 (dd, J = 8.4, 7.1 Hz, 1H), 7.15-7.21 (m, 3H) |
| 6-(4-Fluoro-2-methoxyphenyl)-5-(2-phenylethylthiomethyl)-2,2,4-trimethyl-1,2-dihydroquinoline (Compound No. 11-3) 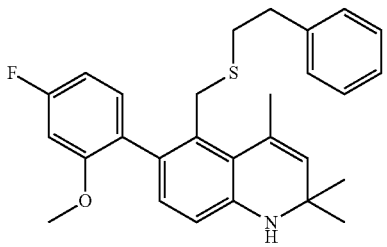 | | $^1$H-NMR (500 MHz, DMSO-$d_6$) δ 1.10 (s, 3H), 1.20 (s, 3H), 2.22 (s, 3H), 2.32-2.53 (m, 4H), 3.46 (d, J = 13.3 Hz, 1H), 3.67 (s, 3H), 3.86 (d, J = 13.3 Hz, 1H), 5.38 (s, 1H), 5.91 (s, 1H), 6.52 (d, J = 8.2 Hz, 1H), 6.64 (d, J = 8.2 Hz, 1H), 6.79 (td, J = 8.3, 2.4 Hz, 1H), 6.94 (dd, J = 11.6, 2.4 Hz, 1H), 7.00 (d, J = 7.2 Hz, 2H), 7.12 (dd, J = 8.3, 7.3 Hz, 1H), 7.15 (t, J = 7.2 Hz, 1H), 7.23 (t, J = 7.2 Hz, 2H) |

Example 12

6-(4-Fluoro-2-methoxyphenyl)-5-(4-methylthiobenzoyloxymethyl)-2,2,4-trimethyl-1,2-dihydroquinoline (Compound No. 12-1)

5-Chloromethyl-6-(4-fluoro-2-methoxyphenyl)-2,2,4-trimethyl-1,2-dihydroquinoline (Reference Compound No. 5-2, 50.0 mg, 0.145 mmol), 4-methylthiobenzoic acid (73.2 mg, 0.435 mmol), and potassium carbonate (80.2 mg, 0.580 mmol) were suspended in anhydrous N,N-dimethylformamide (1 mL), and the reaction mixture was stirred at 80° C. for 2.5 hours. Ethyl acetate (100 mL) was added to the reaction mixture, and the whole was washed with water (100 mL) and saturated brine (100 mL) successively, dried over anhydrous magnesium sulfate, and then the solvent was removed under reduced pressure. The obtained residue was purified by silica gel column chromatography (hexane-ethyl acetate) to give the titled compound (32.4 mg) as a colorless amorphous product. (Yield 47%)

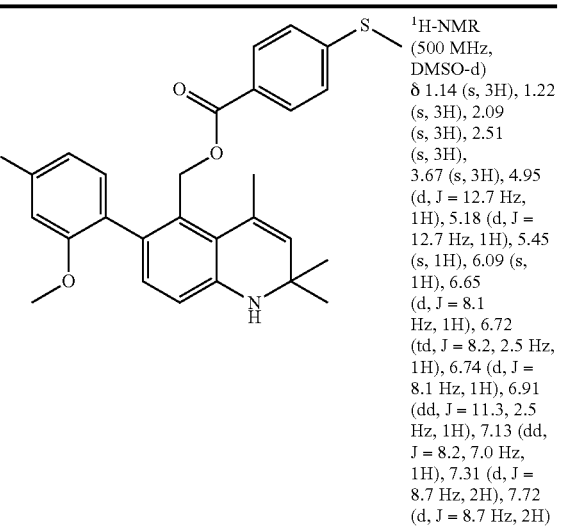

$^1$H-NMR (500 MHz, DMSO-d) δ 1.14 (s, 3H), 1.22 (s, 3H), 2.09 (s, 3H), 2.51 (s, 3H), 3.67 (s, 3H), 4.95 (d, J = 12.7 Hz, 1H), 5.18 (d, J = 12.7 Hz, 1H), 5.45 (s, 1H), 6.09 (s, 1H), 6.65 (d, J = 8.1 Hz, 1H), 6.72 (td, J = 8.2, 2.5 Hz, 1H), 6.74 (d, J = 8.1 Hz, 1H), 6.91 (dd, J = 11.3, 2.5 Hz, 1H), 7.13 (dd, J = 8.2, 7.0 Hz, 1H), 7.31 (d, J = 8.7 Hz, 2H), 7.72 (d, J = 8.7 Hz, 2H)

Using any compounds among Reference Compounds No. 5-2~5-3 and 5-5~5-16, the following Compounds (No. 12-2~12-80) were obtained by a method similar to that of Compound No. 12-1.

| | |
|---|---|
| 6-(4-Fluoro-2-methoxyphenyl)-5-(4-nitrobenzoyloxymethyl)-2,2,4-trimethyl-1,2-dihydroquinoline (Compound No. 12-2) 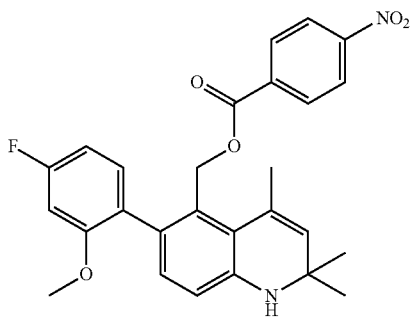 | $^1$H-NMR (400 MHz, DMSO-d$_6$) δ 1.14 (s, 3H), 1.22 (s, 3H), 2.11 (s, 3H), 3.65 (s, 3H), 5.05 (d, J = 12.7 Hz, 1H), 5.27 (d, J = 12.7 Hz, 1H), 5.47 (s, 1H), 6.12 (s, 1H), 6.67 (d, J = 8.1 Hz, 1H), 6.69-7.74 (m, 1H), 6.75 (d, J = 8.1 Hz, 1H), 6.91 (dd, J = 11.5, 2.4 Hz, 1H), 7.14 (dd, J = 8.3, 7.1 Hz, 1H), 8.03 (d, J = 9.0 Hz, 2H), 8.31 (d, J = 9.0 Hz, 2H) |
| 6-(4-Fluoro-2-methoxyphenyl)-5-(4-hydroxymethylbenzoyloxymethyl)-2,2,4-trimethyl-1,2-dihydroquinoline (Compound No. 12-3) 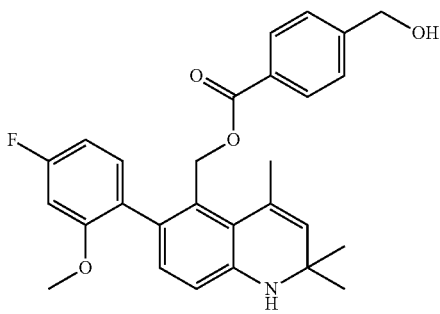 | $^1$H-NMR (400 MHz, DMSO-d$_6$) δ 1.15 (s, 3H), 1.22 (s, 3H), 2.09 (s, 3H), 3.67 (s, 3H), 4.55 (d, J = 5.7 Hz, 2H), 4.96 (d, J = 12.8 Hz, 1H), 5.19 (d, J = 12.8 Hz, 1H), 5.34 (t, J = 5.7 Hz, 1H), 5.45 (s, 1H), 6.10 (s, 1H), 6.66 (d, J = 8.1 Hz, 1H), 6.72 (td, J = 8.3, 2.4 Hz, 1H), 6.75 (d, J = 8.1 Hz, 1H), 6.92 (dd, J = 11.4, 2.4 Hz, 1H), 7.14 (dd, J = 8.3, 7.1 Hz, 1H), 7.40 (d, J = 8.5 Hz, 2H), 7.78 (d, J = 8.5 Hz, 2H) |
| 5-(4-Acetylbenzoyloxymethyl)-6-(4-fluoro-2-methoxyphenyl)-2,2,4-trimethyl-1,2-dihydroquinoline (Compound No. 12-4) 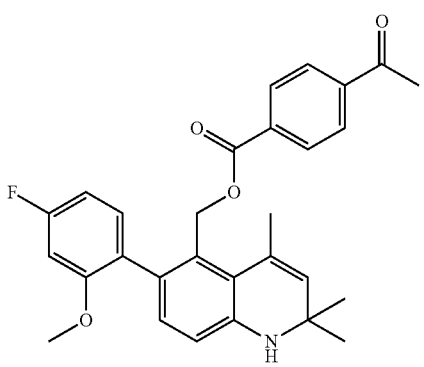 | $^1$H-NMR (400 MHz, DMSO-d$_6$) δ 1.15 (s, 3H), 1.23 (s, 3H), 2.11 (s, 3H), 2.61 (s, 3H), 3.66 (s, 3H), 5.02 (d, J = 12.8 Hz, 1H), 5.24 (d, J = 12.8 Hz, 1H), 5.47 (s, 1H), 6.12 (s, 1H), 6.67 (d, J = 8.3 Hz, 1H), 6.72 (td, J = 8.3, 2.5 Hz, 1H), 6.75 (d, J = 8.3 Hz, 1H), 6.92 (dd, J = 11.5, 2.5 Hz, 1H), 7.14 (dd, J = 8.3, 7.1 Hz, 1H), 7.93 (d, J = 8.7 Hz, 2H), 8.03 (d, J = 8.7 Hz, 2H) |

| | |
|---|---|
| 5-(4-Acetoxybenzoyloxymethyl)-6-(4-fluoro-2-methoxyphenyl)-2,2,4-trimethyl-1,2-dihydroquinoline (Compound No. 12-5)<br>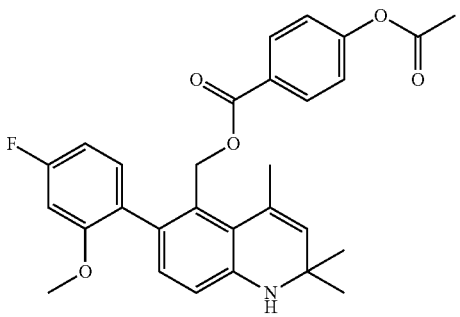 | $^1$H-NMR (400 MHz, DMSO-$d_6$) δ 1.14 (s, 3H), 1.22 (s, 3H), 2.10 (s, 3H), 2.28 (s, 3H), 3.67 (s, 3H), 4.98 (d, J = 12.8 Hz, 1H), 5.21 (d, J = 12.8 Hz, 1H), 5.46 (s, 1H), 6.10 (s, 1H), 6.66 (d, J = 8.2 Hz, 1H), 6.73 (td, J = 8.4, 2.5 Hz, 1H), 6.75 (d, J = 8.2 Hz, 1H), 6.92 (dd, J = 11.6, 2.5 Hz, 1H), 7.14 (dd, J = 8.4, 7.1 Hz, 1H), 7.24 (d, J = 8.9 Hz, 2H), 7.85 (d, J = 8.9 Hz, 2H) |
| 6-(4-Fluoro-2-methoxyphenyl)-5-(4-phenoxybenzoylmethyl)-2,2,4-trimethyl-1,2-dihydroquinoline (Compound No. 12-6)<br>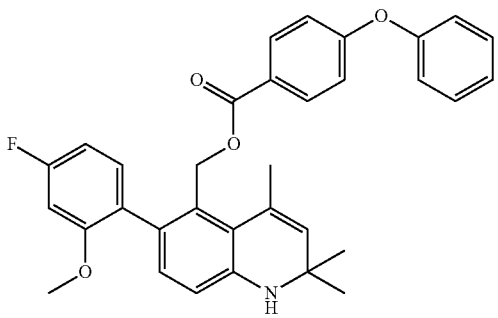 | $^1$H-NMR (400 MHz, DMSO-$d_6$) δ 1.13 (s, 3H), 1.21 (s, 3H), 2.09 (s, 3H), 3.66 (s, 3H), 4.94 (d, J = 12.7 Hz, 1H), 5.18 (d, J = 12.7 Hz, 1H), 5.45 (s, 1H), 6.09 (s, 1H), 6.65 (d, J = 8.3 Hz, 1H), 6.72 (td, J = 8.5, 2.8 Hz, 1H), 6.74 (d, J = 8.3 Hz, 1H), 6.92 (dd, J = 11.5, 2.8 Hz, 1H), 7.00 (dt, J = 8.9, 2.4 Hz, 2H), 7.11 (dd, J = 8.6, 1.1 Hz, 2H), 7.13 (dd, J = 8.5, 7.1 Hz, 1H), 7.24 (t, J = 7.0 Hz, 1H), 7.45 (dd, J = 8.6, 7.6 Hz, 2H), 7.81 (dt, J = 8.9, 2.4 Hz, 2H) |
| 5-(3-Fluoro-4-methoxybenzoyloxymethyl)-6-(4-fluoro-2-methoxyphenyl)-2,2,4-trimethyl-1,2-dihydroquinoline (Compound No. 12-7)<br>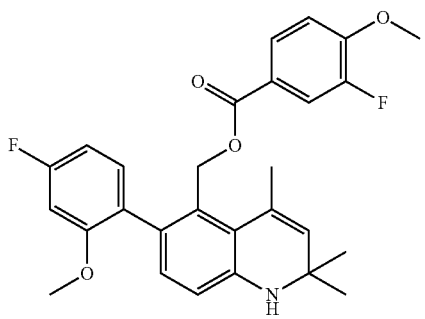 [SMILES: COc1cc(F)ccc1-c1ccc2c(c1COC(=O)c1ccc(SC)cc1)C(C)=CC(C)(C)N2] | $^1$H-NMR (500 MHz, DMSO-$d_6$) δ 1.14 (s, 3H), 1.23 (s, 3H), 2.09 (s, 3H), 3.67 (s, 3H), 3.90 (s, 3H), 4.97 (d, J = 12.8 Hz, 1H), 5.18 (d, J = 12.8 Hz, 1H), 5.46 (s, 1H), 6.10 (s, 1H), 6.66 (d, J = 8.1 Hz, 1H), 6.73 (td, J = 8.4, 2.4 Hz, 1H), 6.75 (d, J = 8.1 Hz, 1H), 6.92 (dd, J = 11.3, 2.4 Hz, 1H), 7.14 (dd, J = 8.4, 7.0 Hz, 1H), 7.25 (t, J = 8.6 Hz, 1H), 7.51 (dd, J = 11.9, 2.1 Hz, 1H), 7.63-7.65 (m, 1H) |
| 6-(4-Fluoro-2-methoxyphenyl)-5-(4-methoxy-3-methylbenzoyloxymethyl)-2,2,4-trimethyl-1,2-dihydroquinoline (Compound No. 12-8)<br>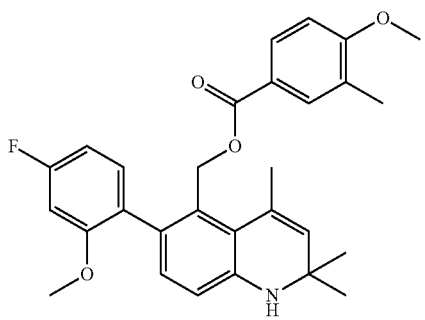 | $^1$H-NMR (500 MHz, DMSO-$d_6$) δ 1.16 (s, 3H) 1.23 (s, 3H), 2.07 (s, 3H), 2.13 (s, 3H), 3.67 (s, 3H), 3.84 (s, 3H), 4.92 (d, J = 12.7 Hz, 1H), 5.14 (d, J = 12.7 Hz, 1H), 5.46 (s, 1H), 6.10 (s, 1H), 6.65 (d, J = 8.1 Hz, 1H), 6.73 (td, J = 8.2, 2.4 Hz, 1H), 6.75 (d, J = 8.1 Hz, 1H), 6.92 (dd, J = 11.5, 2.4 Hz, 1H), 7.00 (d, J = 8.8 Hz, 1H), 7.14 (dd, J = 8.2, 7.3 Hz, 1H), 7.59 (d, J = 2.1 Hz, 1H), 7.68 (dd, J = 8.8, 2.1 Hz, 1H) |

6-(4-Fluoro-2-methoxyphenyl)-5-(4-methoxy-3-trifluoromethylbenzoyloxymethyl)-2,2,4-trimethyl-1,2-dihydroquinoline
(Compound No. 12-9)

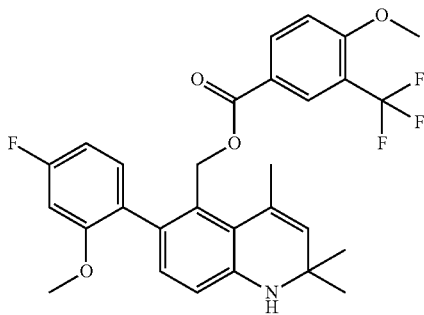

$^1$H-NMR (500 MHz, DMSO-d$_6$)
δ 1.10 (s, 3H), 1.22 (s, 3H), 2.10 (s, 3H), 3.67 (s, 3H), 3.96 (s, 3H), 5.03 (d, J = 12.8 Hz, 1H), 5.22 (d, J = 12.8 Hz, 1H), 5.46 (s, 1H), 6.11 (s, 1H), 6.66 (d, J = 8.1 Hz, 1H), 6.75 (td, J = 8.4, 2.5 Hz, 1H), 6.75 (d, J = 8.1 Hz, 1H), 6.92 (dd, J = 11.3, 2.5 Hz, 1H), 7.15 (dd, J = 8.4, 7.2 Hz, 1H), 7.37 (d, J = 8.8 Hz, 1H), 7.96 (d, J = 1.8 Hz, 1H), 8.07 (dd, J = 8.8, 1.8 Hz, 1H)

6-(4-Fluoro-2-methoxyphenyl)-5-(4-methoxy-3-nitrobenzoyloxymethyl)-2,2,4-trimethyl-1,2-dihydroquinoline
(Compound No. 12-10)

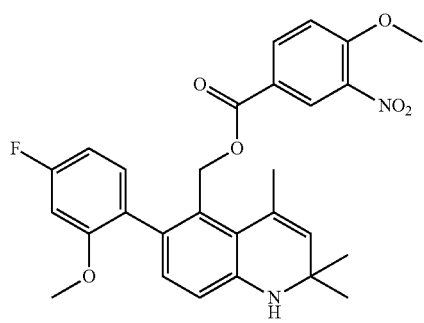

$^1$H-NMR (400 MHz, DMSO-d$_6$)
δ 1.12 (s, 3H), 1.22 (s, 3H), 2.09 (s, 3H), 3.67 (s, 3H), 3.99 (s, 3H), 5.01 (d, J = 12.8 Hz, 1H), 5.22 (d, J = 12.8 Hz, 1H), 5.46 (s, 1H), 6.12 (s, 1H), 6.66 (d, J = 8.2 Hz, 1H), 6.73 (td, J = 8.4, 2.5 Hz, 1H), 6.75 (d, J = 8.2 Hz, 1H), 6.92 (dd, J = 11.5, 2.5 Hz, 1H), 7.15 (dd, J = 8.4, 7.1 Hz, 1H), 7.47 (d, J = 8.9 Hz, 1H), 8.05 (dd, J = 8.9, 2.2 Hz, 1H), 8.19 (d, J = 2.2 Hz, 1H)

5-(2,4-Dimethoxybenzoyloxymethyl)-6-(4-fluoro-2-methoxyphenyl)-2,2,4-trimethyl-1,2-dihydroquinoline
(Compound No. 12-11)

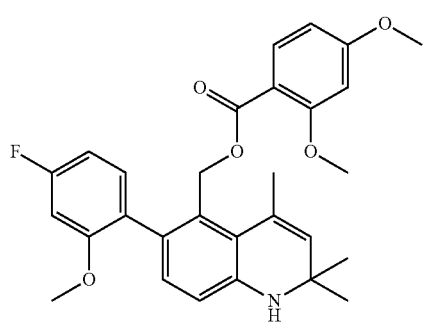

$^1$H-NMR (400 MHz, DMSO-d$_6$)
δ 1.15 (s, 3H), 1.22 (s, 3H), 2.11 (s, 3H), 3.68 (s, 3H), 3.75 (s, 3H), 3.80 (s, 3H), 4.84 (d, J = 12.7 Hz, 1H), 5.09 (d, J = 12.7 Hz, 1H), 5.45 (s, 1H), 6.05 (s, 1H), 6.52 (dd, J = 8.8, 2.4 Hz, 1H), 6.58 (d, J = 2.4 Hz, 1H), 6.63 (d, J = 8.1 Hz, 1H), 6.72 (d, J = 8.1 Hz, 1H), 6.74 (td, J = 8.5, 2.5 Hz, 1H), 6.93 (dd, J = 11.5, 2.5 Hz, 1H), 7.12 (dd, J = 8.5, 7.1 Hz, 1H), 7.54 (d, J = 8.8 Hz, 1H)

| | |
|---|---|
| 5-(3,4-Dimethoxybenzoyloxymethyl)-6-(4-fluoro-2-methoxyphenyl)-2,2,4-trimethyl-1,2-dihydroquinoline (Compound No. 12-12) 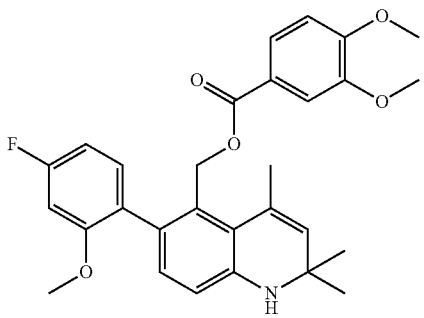 | $^1$H-NMR (400 MHz, DMSO-d$_6$) δ 1.13 (s, 3H), 1.22 (s, 3H), 2.10 (s, 3H), 3.68 (s, 3H), 3.75 (s, 3H), 3.81 (s, 3H), 4.95 (d, J = 12.7 Hz, 1H), 5.17 (d, J = 12.7 Hz, 1H), 5.46 (s, 1H), 6.09 (s, 1H), 6.65 (d, J = 8.1 Hz, 1H), 6.71-6.78 (m, 1H), 6.74 (d, J = 8.1 Hz, 1H), 6.93 (dd, J = 11.4, 2.6 Hz, 1H), 7.02 (d, J = 8.3 Hz, 1H), 7.15 (dd, J = 8.3, 7.1 Hz, 1H), 7.29 (d, J = 2.0 Hz, 1H), 7.45 (dd, J = 8.3, 2.0 Hz, 1H) |
| 6-(4-Fluoro-2-methoxyphenyl)-5-(4-methoxy-2-methylbenzoyloxymethyl)-2,2,4-trimethyl-1,2-dihydroquinoline (Compound No. 12-13) 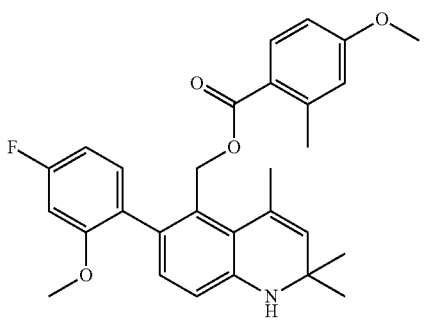 | $^1$H-NMR (400 MHz, DMSO-d$_6$) δ 1.16 (s, 3H), 1.22 (s, 3H), 2.08 (s, 3H), 2.40 (s, 3H), 3.66 (s, 3H), 3.78 (s, 3H), 4.91 (d, J = 12.7 Hz, 1H), 5.14 (d, J = 12.7 Hz, 1H), 5.45 (s, 1H), 6.09 (s, 1H), 6.65 (d, J = 8.2 Hz, 1H), 6.70-6.85 (m, 3H), 6.74 (d, J = 8.2 Hz, 1H), 6.92 (dd, J = 11.5, 2.4 Hz, 1H), 7.12 (dd, J = 8.3, 7.1 Hz, 1H), 7.72 (d, J = 8.8 Hz, 1H) |
| 5-(3-Chloro-4-methoxybenzoyloxymethyl)-6-(4-fluoro-2-methoxyphenyl)-2,2,4-trimethyl-1,2-dihydroquinoline (Compound No. 12-14) 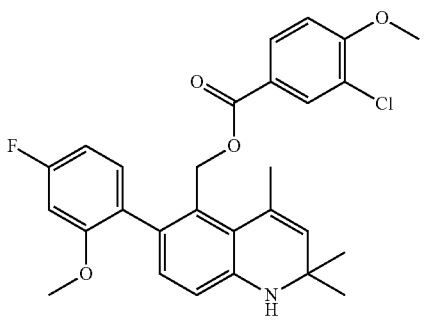 | $^1$H-NMR (400 MHz, DMSO-d$_6$) δ 1.15 (s, 3H), 1.24 (s, 3H), 2.08 (s, 3H), 3.67 (s, 3H), 3.92 (s, 3H), 4.98 (d, J = 12.8 Hz, 1H), 5.18 (d, J = 12.8 Hz, 1H), 5.47 (s, 1H), 6.13 (s, 1H), 6.66 (d, J = 8.2 Hz, 1H), 6.74 (td, J = 8.4, 2.4 Hz, 1H), 6.75 (d, J = 8.2 Hz, 1H), 6.93 (dd, J = 11.5, 2.4 Hz, 1H), 7.15 (dd, J = 8.4, 7.1 Hz, 1H), 7.24 (d, J = 8.5 Hz, 1H), 7.76-7.79 (m, 2H) |

6-(4-Fluoro-2-methoxyphenyl)-5-[(pyridin-4-yl)carbonyloxymethyl]-2,2,4-trimethyl-1,2-dihydroquinoline
(Compound No. 12-15)

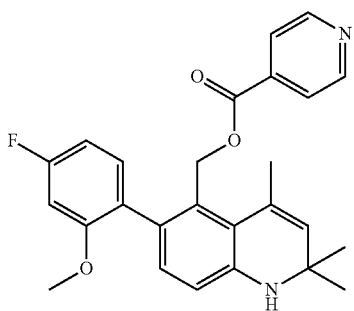

$^1$H-NMR (500 MHz, DMSO-$d_6$)
δ 1.12 (s, 3H), 1.22 (s, 3H), 2.12 (s, 3H), 3.66 (s, 3H), 5.05 (d, J = 12.8 Hz, 1H), 5.27 (d, J = 12.8 Hz, 1H), 5.47 (s, 1H), 6.12 (s, 1H), 6.66 (d, J = 8.1 Hz, 1H), 6.72 (td, J = 8.4, 2.6 Hz, 1H), 6.75 (d, J = 8.1 Hz, 1H), 6.91 (dd, J = 11.6, 2.6 Hz, 1H), 7.14 (dd, J = 8.4, 7.0 Hz, 1H), 7.67 (d, J = 6.1 Hz, 2H), 8.76 (d, J = 6.1 Hz, 2H)

6-(4-Fluoro-2-methoxyphenyl)-5-[(pyridin-2-yl)carbonyloxymethyl]-2,2,4-trimethyl-1,2-dihydroquinoline
(Compound No. 12-16)

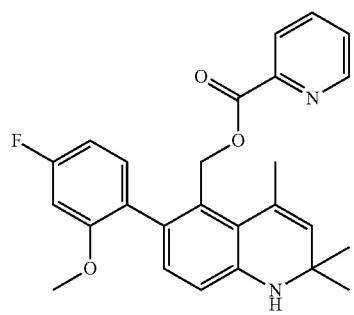

$^1$H-NMR (400 MHz, DMSO-$d_6$)
δ 1.15 (s, 3H), 1.20 (s, 3H), 2.12 (s, 3H), 3.65 (s, 3H), 4.98 (d, J = 12.6 Hz, 1H), 5.24 (d, J = 12.6 Hz, 1H), 5.45 (s, 1H), 6.09 (s, 1H), 6.65 (d, J = 8.2 Hz, 1H), 6.73 (td, J = 8.4, 2.4 Hz, 1H), 6.74 (d, J = 8.2 Hz, 1H), 6.91 (dd, J = 11.5, 2.4 Hz, 1H), 7.12 (dd, J = 8.4, 7.1 Hz, 1H), 7.61 (ddd, J = 7.5, 4.8, 1.1 Hz, 1H), 7.88 (dt, J = 7.5, 1.1 Hz, 1H), 7.94 (td, J = 7.5, 1.7 Hz, 1H), 8.67 (ddd, J = 4.8, 1.7, 1.1 Hz, 1H)

5-[(3-Chlorothiophen-2-yl)carbonyloxymethyl]-6-(4-fluoro-2-methoxyphenyl)-2,2,4-trimethyl-1,2-dihydroquinoline
(Compound No. 12-17)

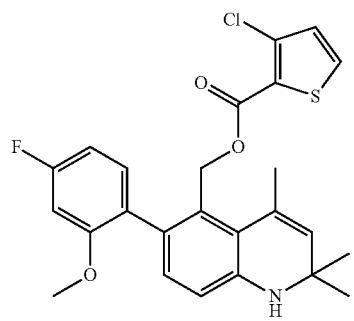

$^1$H-NMR (400 MHz, DMSO-$d_6$)
δ 1.13 (s, 3H), 1.20 (s, 3H), 2.10 (s, 3H), 3.67 (s, 3H), 4.96 (d, J = 12.7 Hz, 1H), 5.19 (d, J = 12.7 Hz, 1H), 5.44 (s, 1H), 6.09 (s, 1H), 6.65 (d, J = 8.2 Hz, 1H), 6.73 (d, J = 8.2 Hz, 1H), 6.74 (td, J = 8.3, 2.8 Hz, 1H), 6.93 (dd, J = 11.5, 2.8 Hz, 1H), 7.12 (dd, J = 8.3, 7.1 Hz, 1H), 7.20 (d, J = 5.2 Hz, 1H), 7.97 (d, J = 5.2 Hz, 1H)

5-[(4-Acetylthiophen-2-yl)carbonyloxy methyl]-6-(4-fluoro-2-methoxyphenyl)-2,2,4-trimethyl-1,2-dihydroquinoline (Compound No. 12-18)

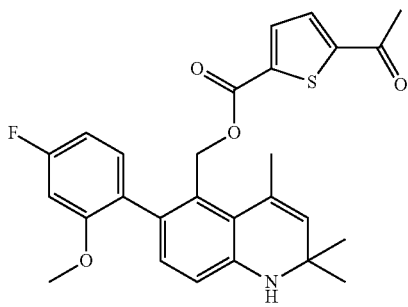

¹H-NMR (400 MHz, DMSO-d₆) δ 1.13 (s, 3H), 1.21 (s, 3H), 2.10 (s, 3H), 2.56 (s, 3H), 3.70 (s, 3H), 4.99 (d, J = 12.7 Hz, 1H), 5.22 (d, J = 12.7 Hz, 1H), 5.46 (s, 1H), 6.12 (s, 1H), 6.66 (d, J = 8.2 Hz, 1H), 6.73 (td, J = 8.4, 2.5 Hz, 1H), 6.74 (d, J = 8.2 Hz, 1H), 6.93 (dd, J = 11.5, 2.5 Hz, 1H), 7.13 (dd, J = 8.4, 7.1 Hz, 1H), 7.70 (d, J = 4.2 Hz, 1H), 7.91 (d, J = 4.2 Hz, 1H)

6-(4-fluoro-2-methoxyphenyl)-5-[(5-methylthiophen-2-yl)carbonyloxymethyl]-2,2,4-trimethyl-1,2-dihydroquinoline (Compound No. 12-19)

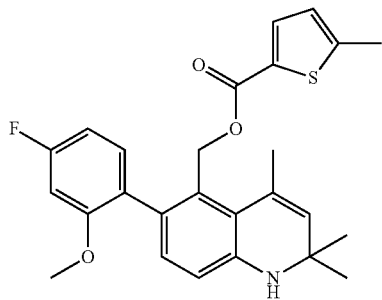

¹H-NMR (400 MHz, DMSO-d₆) δ 1.14 (s, 3H), 1.21 (s, 3H), 2.09 (s, 3H), 2.47 (s, 3H), 3.67 (s, 3H), 4.88 (d, J = 12.7 Hz, 1H), 5.14 (d, J = 12.7 Hz, 1H), 5.44 (s, 1H), 6.09 (s, 1H), 6.64 (d, J = 8.2 Hz, 1H), 6.73 (d, J = 8.2 Hz, 1H), 6.72-6.75 (m, 1H), 6.88 (d, J = 3.5 Hz, 1H), 6.92 (d, J = 11.6, 2.5 Hz, 1H), 7.12 (dd, J = 8.5, 7.1 Hz, 1H), 7.47 (d, J = 3.5 Hz, 1H)

5-[(5-Ethylthiophen-2-yl)carbonyloxymethyl]-6-(4-fluoro-2-methoxyphenyl)-2,2,4-trimethyl-1,2-dihydroquinoline (Compound No. 12-20)

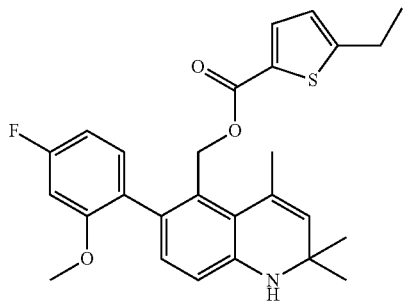

¹H-NMR (400 MHz, DMSO-d₆) δ 1.15 (s, 3H), 1.21 (s, 3H), 1.22 (t, J = 7.6 Hz, 3H), 2.09 (s, 3H), 2.82 (q, J = 7.6 Hz, 2H), 3.67 (s, 3H), 4.89 (d, J = 12.5 Hz, 1H), 5.15 (d, J = 12.5 Hz, 1H), 5.44 (s, 1H), 6.10 (s, 1H), 6.65 (d, J = 8.1 Hz, 1H), 6.69-6.76 (m, 1H), 6.74 (d, J = 8.1 Hz, 1H), 6.89-6.96 (m, 2H), 7.12 (dd, J = 8.3, 7.1 Hz, 1H), 7.50 (d, J = 3.7 Hz, 1H)

| | |
|---|---|
| 6-(4-Fluoro-2-methoxyphenyl)-5-[(4-methylthiophen-2-yl)carbonyloxymethyl]-2,2,4-trimethyl-1,2-dihydroquinoline (Compound No. 12-21) 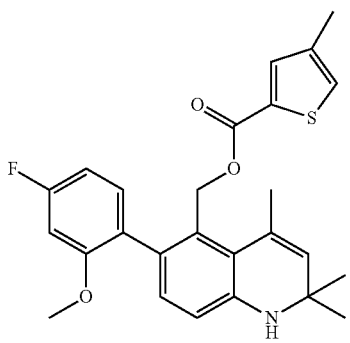 | $^1$H-NMR (400 MHz, DMSO-$d_6$) δ 1.15 (s, 3H), 1.21 (s, 3H), 2.09 (s, 3H), 2.20 (s, 3H), 3.67 (s, 3H), 4.90 (d, J = 12.6 Hz, 1H), 5.15 (d, J = 12.6 Hz, 1H), 5.44 (s, 1H), 6.09 (s, 1H), 6.65 (d, J = 8.2 Hz, 1H), 6.70-6.75 (m, 1H), 6.73 (d, J = 8.2 Hz, 1H), 6.92 (dd, J = 11.5, 2.4 Hz, 1H), 7.12 (dd, J = 8.3, 7.1 Hz, 1H), 7.48-7.49 (m, 2H) |
| 5-[(5-Chlorothiophen-2-yl)carbonyloxymethyl]-6-(4-fluoro-2-methoxyphenyl)-2,2,4-trimethyl-1,2-dihydroquinoline (Compound No. 12-22) 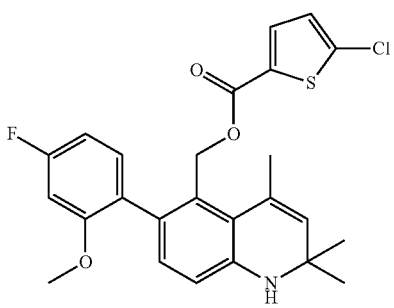 | $^1$H-NMR (400 MHz, DMSO-$d_6$) δ 1.13 (s, 3H), 1.21 (s, 3H), 2.09 (s, 3H), 3.67 (s, 3H), 4.95 (d, J = 12.7 Hz, 1H), 5.18 (d, J = 12.7 Hz, 1H), 5.46 (s, 1H), 6.11 (s, 1H), 6.65 (d, J = 8.3 Hz, 1H), 6.73 (d, J = 8.3 Hz, 1H), 6.74 (td, J = 8.3, 2.4 Hz, 1H), 6.92 (dd, J = 11.5, 2.4 Hz, 1H), 7.12 (dd, J = 8.3, 7.1 Hz, 1H), 7.24 (d, J = 4.2 Hz, 1H), 7.54 (d, J = 4.2 Hz, 1H) |
| 5-[(5-t-Butylthiophen-2-yl)carbonyloxymethyl]-6-(4-fluoro-2-methoxyphenyl)-2,2,4-trimethyl-1,2-dihydroquinoline (Compound No. 12-23) 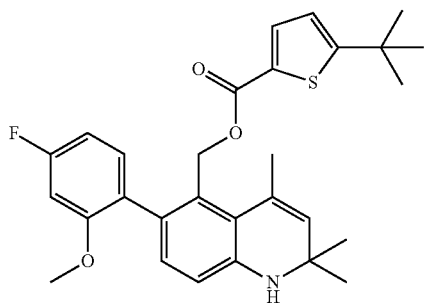 | $^1$H-NMR (500 MHz, DMSO-$d_6$) δ 1.15 (s, 3H), 1.21 (s, 3H), 1.32 (s, 9H), 2.07 (s, 3H), 3.67 (s, 3H), 4.88 (d, J = 12.8 Hz, 1H), 5.14 (d, J = 12.8 Hz, 1H), 5.44 (s, 1H), 6.09 (s, 1H), 6.65 (d, J = 8.2 Hz, 1H), 6.73 (d, J = 8.2 Hz, 1H), 6.72-6.75 (m, 1H), 6.92 (dd, J = 11.3, 2.5 Hz, 1H), 6.98 (d, J = 4.0 Hz, 1H), 7.12 (dd, J = 8.3, 7.0 Hz, 1H), 7.49 (d, J = 4.0 Hz, 1H) |

| | |
|---|---|
| 6-(4-Fluoro-2-methoxyphenyl)-5-[(3-methylthiophen-2-yl)carbonyloxymethyl]-2,2,4-trimethyl-1,2-dihydroquinoline (Compound No. 12-24)<br />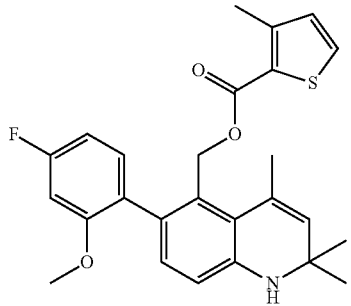 | $^1$H-NMR (500 MHz, CDCl$_3$)<br />δ 1.29 (s, 3H), 1.32 (s, 3H), 2.19 (s, 3H), 2.46 (s, 3H), 3.69 (s, 3H), 5.01 (d, J = 13.0 Hz, 1H), 5.31 (d, J = 13.0 Hz, 1H), 5.54 (s, 1H), 6.61-6.64 (m, 3H), 6.64-6.75 (m, 1H), 6.85-6.89 (m, 2H), 7.14 (t, J = 7.8 Hz, 1H), 7.34 (d, J = 4.9 Hz, 1H) |
| 5-[(5-Bromothiophen-2-yl)carbonyloxymethyl]-6-(4-fluoro-2-methoxyphenyl)-2,2,4-trimethyl-1,2-dihydroquinoline (Compound No. 12-25)<br />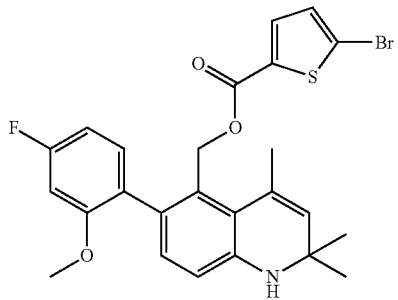 | $^1$H-NMR (400 MHz, DMSO-d$_6$)<br />δ 1.13 (s, 3H), 1.21 (s, 3H), 2.09 (s, 3H), 3.67 (s, 3H), 4.94 (d, J = 12.7 Hz, 1H), 5.18 (d, J = 12.7 Hz, 1H), 5.46 (s, 1H), 6.11 (s, 1H), 6.65 (d, J = 8.2 Hz, 1H), 6.74 (d, J = 8.2 Hz, 1H), 6.74 (td, J = 8.3, 2.5 Hz, 1H), 6.92 (dd, J = 11.5, 2.4 Hz, 1H), 7.12 (dd, J = 8.3, 7.1 Hz, 1H), 7.33 (d, J = 3.9 Hz, 1H), 7.49 (d, J = 3.9 Hz, 1H) |
| 6-(4-Fluoro-2-methoxyphenyl)-5-[(4-phenylthiophen-2-yl)carbonyloxymethyl]-2,2,4-trimethyl-1,2-dihydroquinoline (Compound No. 12-26)<br />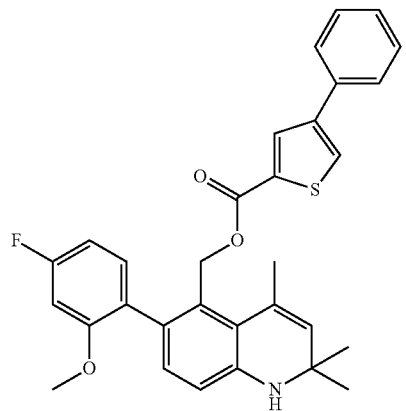 | $^1$H-NMR (400 MHz, DMSO-d$_6$)<br />δ 1.15 (s, 3H), 1.22 (s, 3H), 2.12 (s, 3H), 3.69 (s, 3H), 4.96 (d, J = 12.7 Hz, 1H), 5.21 (d, J = 12.7 Hz, 1H), 5.47 (s, 1H), 6.11 (s, 1H), 6.66 (d, J = 8.3 Hz, 1H), 6.74 (td, J = 8.2, 2.4 Hz, 1H), 6.75 (d, J = 8.3 Hz, 1H), 6.93 (dd, J = 11.5, 2.4 Hz, 1H), 7.16 (dd, J = 8.2, 7.7 Hz, 1H), 7.33 (t, J = 7.4 Hz, 1H), 7.42 (t, J = 7.4 Hz, 2H), 7.71 (d, J = 7.4 Hz, 2H), 8.04 (d, J = 1.4 Hz, 1H), 8.22 (d, J = 1.4 Hz, 1H) |

| | | |
|---|---|---|
| 5-[(3-Chloro-4-methylthiophen-2-yl)carbonyloxymethyl]-6-(4-fluoro-2-methoxyphenyl)-2,2,4-trimethyl-1,2-dihydroquinoline (Compound No. 12-27) 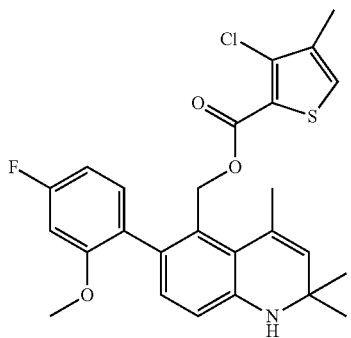 | ¹H-NMR (500 MHz, DMSO-d₆) δ 1.14 (s, 3H), 1.20 (s, 3H), 2.09 (s, 3H), 2.15 (s, 3H), 3.67 (s, 3H), 4.95 (d, J = 12.8 Hz, 1H), 5.18 (d, J = 12.8 Hz, 1H), 5.43 (s, 1H), 6.08 (s, 1H), 6.65 (d, J = 8.2 Hz, 1H), 6.70-6.77 (m, 1H), 6.74 (d, J = 8.2 Hz, 1H), 6.93 (dd, J = 11.3, 2.4 Hz, 1H), 7.12 (dd, J = 8.2, 7.0 Hz, 1H), 7.70 (s, 1H) | |
| 6-(4-Fluoro-2-methoxyphenyl)-5-[(5-phenylthiophen-2-yl)carbonyloxymethyl]-2,2,4-trimethyl-1,2-dihydroquinoline (Compound No. 12-28) 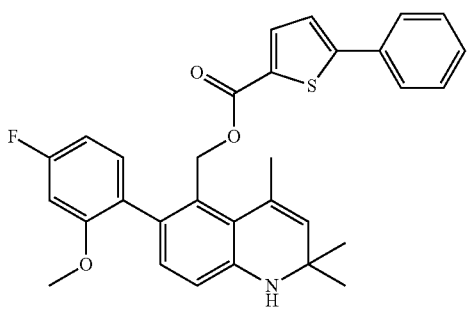 | ¹H-NMR (500 MHz, DMSO-d₆) δ 1.16 (s, 3H), 1.22 (s, 3H), 2.12 (s, 3H), 3.69 (s, 3H), 4.94 (d, J = 12.8 Hz, 1H), 5.20 (d, J = 12.8 Hz, 1H), 5.47 (s, 1H), 6.10 (s, 1H), 6.66 (d, J = 8.2 Hz, 1H), 6.70-6.78 (m, 1H), 6.75 (d, J = 8.2 Hz, 1H), 6.93 (dd, J = 11.5, 2.6 Hz, 1H), 7.15 (dd, J = 8.2, 7.0 Hz, 1H), 7.37-7.42 (m, 1H), 7.43-7.48 (m, 2H), 7.57 (d, J = 4.0 Hz, 1H), 7.66 (d, J = 4.0 Hz, 1H), 7.69-7.74 (m, 2H) | |
| 6-(4-Fluoro-2-methoxyphenyl)-5-[(3,4,5-trichlorothiophen-2-yl)carbonyloxymethyl]-2,2,4-trimethyl-1,2-dihydroquinoline (Compound No. 12-29) 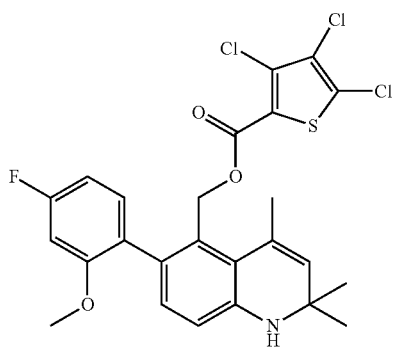 | ¹H-NMR (400 MHz, DMSO-d₆) δ 1.14 (s, 3H), 1.21 (s, 3H), 2.10 (s, 3H), 3.67 (s, 3H), 5.03 (d, J = 12.7 Hz, 1H), 5.23 (d, J = 12.7 Hz, 1H), 5.46 (s, 1H), 6.12 (s, 1H), 6.66 (d, J = 8.2 Hz, 1H), 6.74 (d, J = 8.2 Hz, 1H), 6.76 (td, J = 8.3, 2.4 Hz, 1H), 6.93 (dd, J = 11.4, 2.4 Hz, 1H), 7.12 (dd, J = 8.3, 7.1 Hz, 1H) | |

| | |
|---|---|
| 6-(4-Fluoro-2-methoxyphenyl)-5-[(5-methylthiothiophen-2-yl)carbonyloxymethyl]-2,2,4-trimethyl-1,2-dihydroquinoline (Compound No. 12-30) 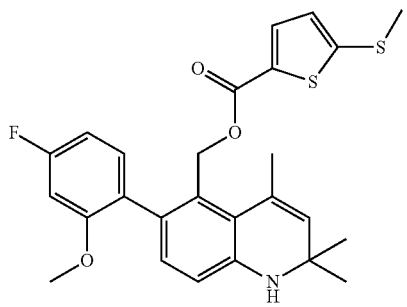 | $^1$H-NMR (500 MHz, DMSO-d$_6$) δ 1.14 (s, 3H), 1.21 (s, 3H), 2.08 (s, 3H), 2.58 (s, 3H), 3.67 (s, 3H), 4.89 (d, J = 12.5 Hz, 1H), 5.15 (d, J = 12.5 Hz, 1H), 5.45 (s, 1H), 6.09 (s, 1H), 6.65 (d, J = 8.2 Hz, 1H), 6.73 (td, J = 8.4, 2.4 Hz, 1H), 6.73 (d, J = 8.2 Hz, 1H), 6.92 (dd, J = 11.3, 2.4 Hz, 1H), 7.06 (d, J = 4.0 Hz, 1H), 7.12 (dd, J = 8.2, 7.0 Hz, 1H), 7.54 (d, J = 4.0 Hz, 1H) |
| 5-[(3-Acetylaminothiophen-2-yl)carbonyloxymethyl]-6-(4-fluoro-2-methoxyphenyl)-2,2,4-trimethyl-1,2-dihydroquinoline (Compound No. 12-31) 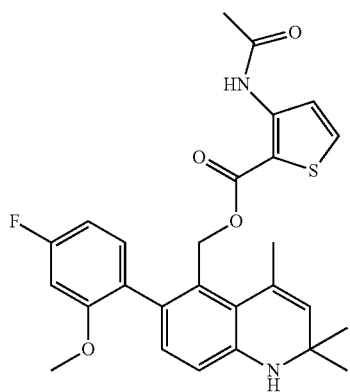 | $^1$H-NMR (400 MHz, DMSO-d$_6$) δ 1.15 (s, 3H), 1.21 (s, 3H), 2.08 (s, 3H), 2.09 (s, 3H), 3.68 (s, 3H), 4.95 (d, J = 12.7 Hz, 1H), 5.20 (d, J = 12.7 Hz, 1H), 5.45 (s, 1H), 6.12 (s, 1H), 6.66 (d, J = 8.2 Hz, 1H), 6.72-6.77 (m, 1H), 6.75 (d, J = 8.2 Hz, 1H), 6.94 (dd, J = 11.7, 2.4 Hz, 1H), 7.13 (dd, J = 8.3, 7.1 Hz, 1H), 7.84 (d, J = 5.4 Hz, 1H), 7.88 (d, J = 5.4 Hz, 1H), 9.85 (s, 1H) |
| 5-[(3,5-Dimethylthiothiophen-2-yl)carbonyloxymethyl]-6-(4-fluoro-2-methoxyphenyl)-2,2,4-trimethyl-1,2-dihydroquinoline (Compound No. 12-32) 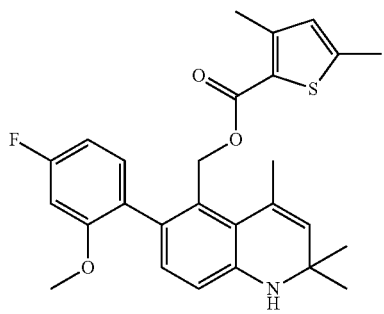 | $^1$H-NMR (400 MHz, DMSO-d$_6$) δ 1.16 (s, 3H), 1.20 (s, 3H), 2.07 (s, 3H), 2.29 (s, 3H), 2.39 (s, 3H), 3.66 (s, 3H), 4.87 (d, J = 12.7 Hz, 1H), 5.12 (d, J = 12.7 Hz, 1H), 5.43 (s, 1H), 6.08 (s, 1H), 6.65 (d, J = 8.3 Hz, 1H), 6.70-6.77 (m, 3H), 6.93 (dd, J = 11.5, 2.4 Hz, 1H), 7.11 (dd, J = 8.3, 7.1 Hz, 1H) |

| Compound | NMR |
|---|---|
| 6-(4-Fluoro-2-methoxyphenyl)-5-[(5-methoxythiophen-2-yl)carbonyloxymethyl]-2,2,4-trimethyl-1,2-dihydroquinoline (Compound No. 12-33) 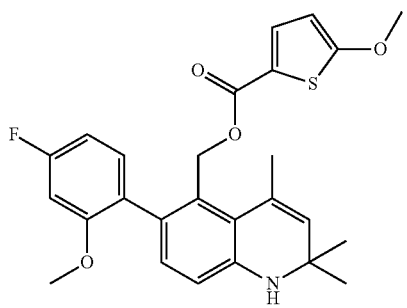 | $^1$H-NMR (400 MHz, DMSO-d$_6$) δ 1.15 (s, 3H), 1.21 (s, 3H), 2.07 (s, 3H), 3.68 (s, 3H), 3.91 (s, 3H), 4.85 (d, J = 12.5 Hz, 1H), 5.12 (d, J = 12.5 Hz, 1H), 5.44 (s, 1H), 6.09 (s, 1H), 6.41 (d, J = 4.2 Hz, 1H), 6.64 (d, J = 8.3 Hz, 1H), 6.70-6.77 (m, 1H), 6.73 (d, J = 8.3 Hz, 1H), 6.92 (dd, J = 11.6, 2.6 Hz, 1H), 7.12 (dd, J = 8.3, 7.1 Hz, 1H), 7.41 (d, J = 4.2 Hz, 1H) |
| 6-(4-Fluoro-2-methoxyphenyl)-5-[(pyrrol-2-yl)carbonyloxymethyl]-2,2,4-trimethyl-1,2-dihydroquinoline (Compound No. 12-34) 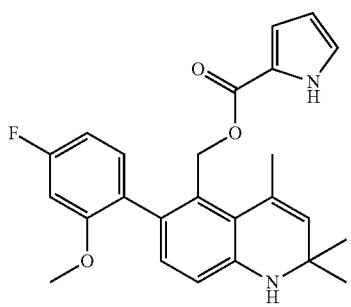 | $^1$H-NMR (400 MHz, DMSO-d$_6$) δ 1.16 (s, 3H), 1.20 (s, 3H), 2.09 (s, 3H), 3.67 (s, 3H), 4.79 (d, J = 12.5 Hz, 1H), 5.10 (d, J = 12.5 Hz, 1H), 5.43 (s, 1H), 6.05 (s, 1H), 6.10-6.12 (m, 1H), 6.61-6.65 (m, 1H), 6.63 (d, J = 8.2 Hz, 1H), 6.69 (td, J = 8.4, 2.5 Hz, 1H), 6.72 (d, J = 8.2 Hz, 1H), 6.91 (dd, J = 11.5, 2.5 Hz, 1H), 6.95-6.97 (m, 1H), 7.14 (dd, J = 8.4, 7.1 Hz, 1H), 11.8 (s, 1H) |
| 6-(4-Fluoro-2-methoxyphenyl)-5-[(furan-2-yl)carbonyloxymethyl]-2,2,4-trimethyl-1,2-dihydroquinoline (Compound No. 12-35) 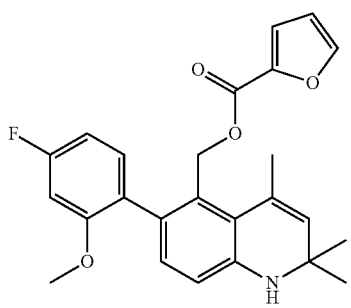 | $^1$H-NMR (400 MHz, DMSO-d$_6$) δ 1.14 (s, 3H), 1.20 (s, 3H), 2.09 (s, 3H), 3.66 (s, 3H), 4.90 (d, J = 12.6 Hz, 1H), 5.17 (d, J = 12.6 Hz, 1H), 5.45 (s, 1H), 6.08 (s, 1H), 6.64 (d, J = 8.2 Hz, 1H), 6.65 (dd, J = 3.4, 1.7 Hz, 1H), 6.71 (td, J = 8.6, 2.4 Hz, 1H), 6.72 (dd, J = 8.2 Hz, 1H), 6.91 (dd, J = 11.5, 2.4 Hz, 1H), 7.11 (dd, J = 8.6, 7.0 Hz, 1H), 7.11 (dd, J = 3.4, 0.9 Hz, 1H), 7.93 (dd, J = 1.7, 0.9 Hz, 1H) |
| 6-(4-Fluoro-2-methoxyphenyl)-5-[(thiophen-2-yl)carbonyloxymethyl]-2,2,4-trimethyl-1,2-dihydroquinoline (Compound No. 12-36) 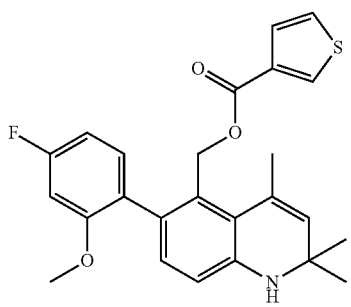 | $^1$H-NMR (400 MHz, DMSO-d$_6$) δ 1.13 (s, 3H), 1.21 (s, 3H), 2.10 (s, 3H), 3.67 (s, 3H), 4.89 (d, J = 12.6 Hz, 1H), 5.15 (d, J = 12.6 Hz, 1H), 5.45 (s, 1H), 6.08 (s, 1H), 6.65 (d, J = 8.2 Hz, 1H), 6.72 (td, J = 8.4, 2.5 Hz, 1H), 6.74 (d, J = 8.2 Hz, 1H), 6.91 (dd, J = 11.5, 2.5 Hz, 1H), 7.14 (dd, J = 8.4, 7.1 Hz, 1H), 7.31 (dd, J = 5.0, 1.3 Hz, 1H), 7.61 (dd, J = 5.0, 3.0 Hz, 1H), 8.16 (dd, J = 3.0, 1.3 Hz, 1H) |

6-(4-Fluoro-2-methoxyphenyl)-
5-[(4-methoxythiophen-3-yl)carbonyloxymethyl]-
2,2,4-trimethyl-1,2-dihydroquinoline
(Compound No. 12-37)

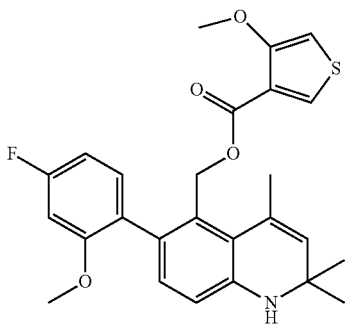

$^1$H-NMR (500 MHz, DMSO-d$_6$)
δ 1.13 (s, 3H), 1.20 (s, 3H), 2.10 (s, 3H), 3.67 (s, 3H), 3.72 (s, 3H), 4.83 (d, J = 12.7 Hz, 1H), 5.09 (d, J = 12.7 Hz, 1H), 5.44 (s, 1H), 6.05 (s, 1H), 6.63 (d, J = 7.9 Hz, 1H), 6.67 (d, J = 3.7 Hz, 1H), 6.72 (td, J = 8.3, 2.4 Hz, 1H), 6.72 (d, J = 7.9 Hz, 1H), 6.92 (dd, J = 11.3, 2.4 Hz, 1H), 7.14 (dd, J = 8.3, 7.0 Hz, 1H), 7.98 (d, J = 3.7 Hz, 1H)

5-[(5-Ethylthiophen-3-yl)carbonyloxymethyl]-
6-(4-fluoro-2-methoxyphenyl)-
2,2,4-trimethyl-1,2-dihydroquinoline
(Compound No. 12-38)

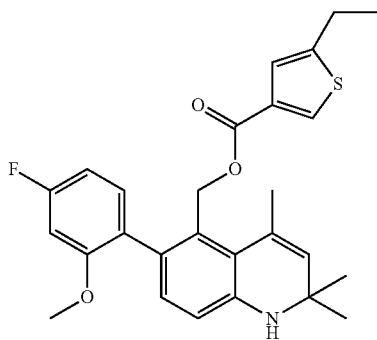

$^1$H-NMR (400 MHz, DMSO-d$_6$)
δ 1.15 (s, 3H), 1.17 (t, J = 7.5 Hz, 3H), 1.22 (s, 3H), 2.08 (s, 3H), 2.78 (q, J = 7.5 Hz, 2H), 3.67 (s, 3H), 4.86 (d, J = 12.6 Hz, 1H), 5.12 (d, J = 12.6 Hz, 1H), 5.45 (s, 1H), 6.08 (s, 1H), 6.64 (d, J = 8.3 Hz, 1H), 6.70-6.74 (m, 1H), 6.73 (d, J = 8.3 Hz, 1H), 6.92 (dd, J = 11.6, 2.6 Hz, 1H), 7.02 (d, J = 1.2 Hz, 1H), 7.13 (dd, J = 8.4, 7.2 Hz, 1H), 7.94 (d, J = 1.2 Hz, 1H)

6-(4-Fluoro-2-methoxyphenyl)-5-
[(thiazol-5-yl)carbonyloxymethyl]-
2,2,4-trimethyl-1,2-dihydroquinoline
(Compound No. 12-39)

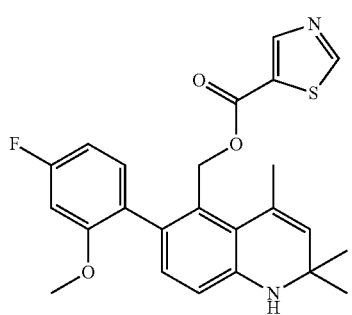

$^1$H-NMR (500 MHz, DMSO-d$_6$)
δ 1.12 (s, 3H), 1.21 (s, 3H), 2.10 (s, 3H), 3.69 (s, 3H), 4.99 (d, J = 12.7 Hz, 1H), 5.22 (d, J = 12.7 Hz, 1H), 5.46 (s, 1H), 6.11 (s, 1H), 6.66 (d, J = 8.3 Hz, 1H), 6.73 (td, J = 8.4, 2.6 Hz, 1H), 6.74 (d, J = 8.3 Hz, 1H), 6.92 (dd, J = 11.5, 2.6 Hz, 1H), 7.13 (dd, J = 8.4, 7.2 Hz, 1H), 8.37 (d, J = 0.6 Hz, 1H), 9.33 (d, J = 0.6 Hz, 1H)

| Compound | <sup>1</sup>H-NMR |
|---|---|
| 6-(4-Fluoro-2-methoxyphenyl)-5-[(thiazol-4-yl)carbonyloxymethyl]-2,2,4-trimethyl-1,2-dihydroquinoline (Compound No. 12-40) 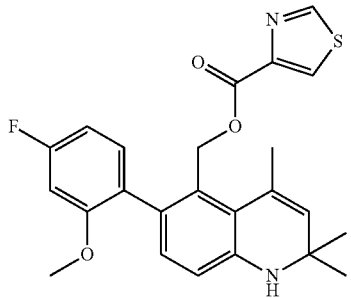 | ¹H-NMR (400 MHz, DMSO-d₆) δ 1.14 (s, 3H), 1.20 (s, 3H), 2.11 (s, 3H), 3.65 (s, 3H), 4.91 (d, J = 12.5 Hz, 1H), 5.20 (d, J = 12.5 Hz, 1H), 5.44 (s, 1H), 6.08 (s, 1H), 6.65 (d, J = 8.2 Hz, 1H), 6.68 (td, J = 8.5, 2.5 Hz, 1H), 6.73 (d, J = 8.2 Hz, 1H), 6.91 (dd, J = 11.5, 2.5 Hz, 1H), 7.13 (dd, J = 8.5, 7.2 Hz, 1H), 8.37 (d, J = 1.8 Hz, 1H), 9.13 (d, J = 1.8 Hz, 1H) |
| 6-(4-Fluoro-2-methoxyphenyl)-5-[(thiazol-2-yl)carbonyloxymethyl]-2,2,4-trimethyl-1,2-dihydroquinoline (Compound No. 12-41) 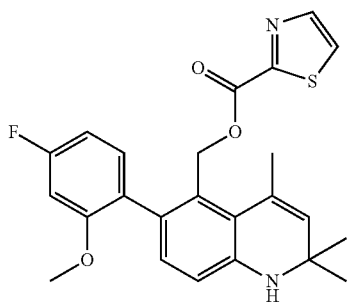 | ¹H-NMR (400 MHz, DMSO-d₆) δ 1.13 (s, 3H), 1.21 (s, 3H), 2.12 (s, 3H), 3.65 (s, 3H), 5.04 (d, J = 12.6 Hz, 1H), 5.29 (d, J = 12.6 Hz, 1H), 5.45 (s, 1H), 6.12 (s, 1H), 6.66 (d, J = 8.3 Hz, 1H), 6.71 (td, J = 8.4, 2.4 Hz, 1H), 6.74 (d, J = 8.3 Hz, 1H), 6.92 (dd, J = 11.5, 2.4 Hz, 1H), 7.12 (dd, J = 8.4, 7.2 Hz, 1H), 8.09 (d, J = 3.1. Hz, 1H), 8.12 (d, J = 3.1 Hz, 1H) |
| 5-[(1,3-Benzodioxol-5-yl)carbonyloxymethyl]-6-(4-fluoro-2-methoxyphenyl)-2,2,4-trimethyl-1,2-dihydroquinoline (Compound No. 12-42) 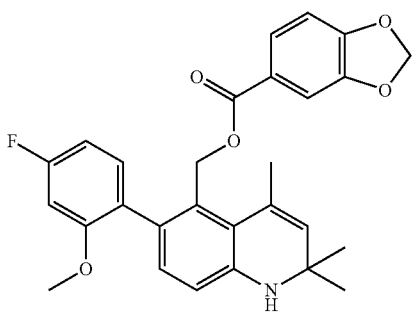 | ¹H-NMR (400 MHz, DMSO-d₆) δ 1.14 (s, 3H), 1.23 (s, 3H), 2.08 (s, 3H), 3.68 (s, 3H), 4.94 (d, J = 12.7 Hz, 1H), 5.15 (d, J = 12.7 Hz, 1H), 5.46 (s, 1H), 6.10 (s, 1H), 6.11 (s, 2H), 6.65 (d, J = 8.3 Hz, 1H), 6.70-6.78 (m, 2H), 6.92 (dd, J = 11.5, 2.4 Hz, 1H), 6.98 (d, J = 8.1 Hz, 1H), 7.14 (dd, J = 8.3, 7.1 Hz, 1H), 7.20 (d, J = 1.7 Hz, 1H), 7.42 (dd, J = 8.1, 1.7 Hz, 1H) |

| | |
|---|---|
| 5-[(Benzothiazol-6-yl)carbonyloxymethyl]-6-(4-fluoro-2-methoxyphenyl)-2,2,4-trimethyl-1,2-dihydroquinoline (Compound No. 12-43)<br />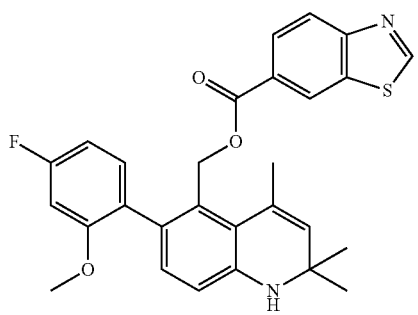 | $^1$H-NMR (400 MHz, DMSO-$d_6$)<br />δ 1.16 (s, 3H), 1.23 (s, 3H), 2.13 (s, 3H), 3.66 (s, 3H), 5.03 (d, J = 12.7 Hz, 1H), 5.26 (d, J = 12.7 Hz, 1H), 5.48 (s, 1H), 6.12 (s, 1H), 6.67 (d, J = 8.3 Hz, 1H), 6.71 (td, J = 8.3, 2.6 Hz, 1H), 6.76 (d, J = 8.3 Hz, 1H), 6.91 (dd, J = 11.4, 2.6 Hz, 1H), 7.17 (dd, J = 8.3, 7.1 Hz, 1H), 7.95 (dd, J = 8.5, 1.5 Hz, 1H), 8.15 (d, J = 8.5 Hz, 1H), 8.67 (d, J = 1.5 Hz, 1H), 9.59 (s, 1H) |
| 5-[(2,3-Dihydrobenzofuran-5-yl)carbonyloxymethyl]-6-(4-fluoro-2-methoxyphenyl)-2,2,4-trimethyl-1,2-dihydroquinoline (Compound No. 12-44)<br />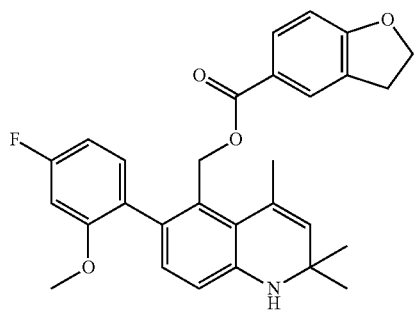 | $^1$H-NMR (500 MHz, DMSO-$d_6$)<br />δ 1.16 (s, 3H), 1.23 (s, 3H), 2.07 (s, 3H), 3.18 (t, J = 8.7 Hz, 2H), 3.67 (s, 3H), 4.60 (t, J = 8.7 Hz, 2H), 4.91 (d, J = 12.5 Hz, 1H), 5.14 (d, J = 12.5 Hz, 1H), 5.45 (s, 1H), 6.08 (s, 1H), 6.65 (d, J = 8.2 Hz, 1H), 6.73 (td, J = 8.3, 2.4 Hz, 1H), 6.74 (d, J = 8.2 Hz, 1H), 6.80 (d, J = 8.2 Hz, 1H), 6.92 (dd, J = 11.3, 2.4 Hz, 1H), 7.13 (dd, J = 8.3, 7.0 Hz, 1H), 7.62 (dd, J = 8.2, 1.5 Hz, 1H), 7.66 (d, J = 1.5 Hz, 1H) |
| 5-[(2,2-Difluoro-1,3-benzodioxol-5-yl)carbonyloxymethyl]-6-(4-fluoro-2-methoxyphenyl)-2,2,4-trimethyl-1,2-dihydroquinoline (Compound No. 12-45)<br />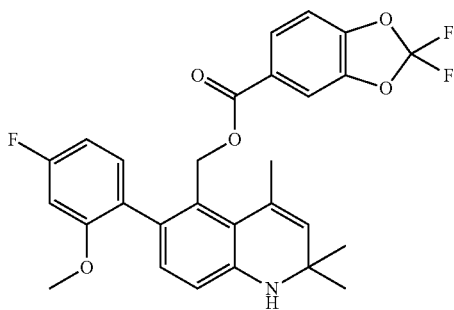 | $^1$H-NMR (500 MHz, DMSO-$d_6$)<br />δ 1.14 (s, 3H), 1.22 (s, 3H), 2.10 (s, 3H), 3.67 (s, 3H), 5.01 (d, J = 12.7 Hz, 1H), 5.22 (d, J = 12.7 Hz, 1H), 5.47 (s, 1H), 6.11 (s, 1H), 6.66 (d, J = 8.2 Hz, 1H), 6.71-6.74 (m, 1H), 6.75 (d, J = 8.2 Hz, 1H), 6.92 (dd, J = 11.6, 2.4 Hz, 1H), 7.15 (dd, J = 8.2, 7.0 Hz, 1H), 7.52 (d, J = 8.5 Hz, 1H), 7.69 (d, J = 1.6 Hz, 1H), 7.72 (dd, J = 8.5, 1.6 Hz, 1H) |

5-[1,4-Benzodioxan-6-yl)carbonyloxymethyl]-6-(4-fluoro-2-methoxyphenyl)-2,2,4-trimethyl-1,2-dihydroquinoline
(Compound No. 12-46)

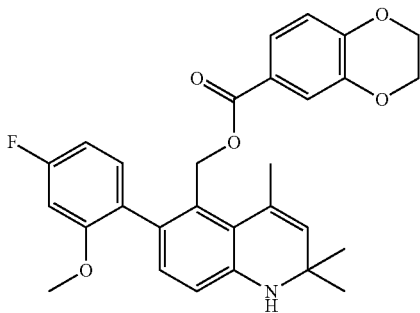

$^1$H-NMR (400 MHz, DMSO-d$_6$)
δ 1.15 (s, 3H), 1.23 (s, 3H), 2.07 (s, 3H), 3.67 (s, 3H), 4.25-4.26 (m, 2H), 4.29-4.30 (m, 2H), 4.93 (d, J = 12.8 Hz, 1H), 5.14 (d, J = 12.8 Hz, 1H), 5.45 (s, 1H), 6.10 (s, 1H), 6.65 (d, J = 8.2 Hz, 1H), 6.72-6.76 (m, 1H), 6.74 (d, J = 8.2 Hz, 1H), 6.90-6.93 (m, 1H), 6.91 (d, J = 8.4 Hz, 1H), 7.13 (dd, J = 8.4, 7.1 Hz, 1H), 7.25 (d, J = 2.1 Hz, 1H), 7.32 (dd, J = 8.4, 2.1 Hz, 1H)

5-Cinnamoyloxymethyl-6-(4-fluoro-2-methoxyphenyl)-2,2,4-trimethyl-1,2-dihydroquinoline
(Compound No. 12-47)

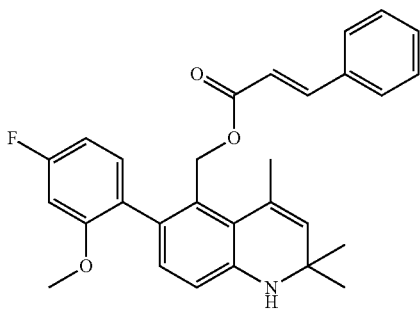

$^1$H-NMR (400 MHz, DMSO-d$_6$)
δ 1.18 (s, 3H), 1.22 (s, 3H), 2.09 (s, 3H), 3.70 (s, 3H), 4.81 (d, J = 12.7 Hz, 1H), 5.08 (d, J = 12.7 Hz, 1H), 5.45 (s, 1H), 6.07 (s, 1H), 6.51 (d, J = 16.0 Hz, 1H), 6.64 (d, J = 8.2 Hz, 1H), 6.73 (d, J = 8.2 Hz, 1H), 6.74 (td, J = 8.4, 2.5 Hz, 1H), 6.92 (dd, J = 11.4, 2.5 Hz, 1H), 7.13 (dd, J = 8.4, 7.3 Hz, 1H), 7.40-7.42 (m, 3H), 7.50 (d, J = 16.0 Hz, 1H), 7.64-7.67 (m, 2H)

5-[(Benzothiophen-2-yl)carbonyloxymethyl]-6-(4-fluoro-2-methoxyphenyl)-2,2,4-trimethyl-1,2-dihydroquinoline
(Compound No. 12-48)

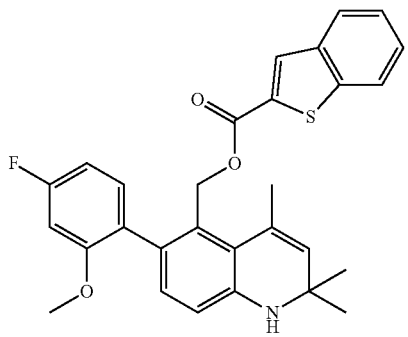

$^1$H-NMR (500 MHz, DMSO-d$_6$)
δ 1.16 (s, 3H), 1.22 (s, 3H), 2.15 (s, 3H), 3.67 (s, 3H), 5.00 (d, J = 12.5 Hz, 1H), 5.25 (d, J = 12.5 Hz, 1H), 5.47 (s, 1H), 6.11 (s, 1H), 6.67 (d, J = 8.2 Hz, 1H), 6.72 (td, J = 8.5, 2.5 Hz, 1H), 6.75 (d, J = 8.2 Hz, 1H), 6.92 (dd, J = 11.6, 2.5 Hz, 1H), 7.15 (dd, J = 8.5, 7.2 Hz, 1H), 7.46 (ddd, J = 8.0, 7.0, 1.2 Hz, 1H), 7.52 (ddd, J = 8.0, 7.0, 1.2 Hz, 1H), 7.99 (d, J = 8.0 Hz, 1H), 8.04 (d, J = 8.0 Hz, 1H), 8.06 (s, 1H)

5-[(Benzothiophen-3-yl)carbonyloxymethyl]-
6-(4-fluoro-2-methoxyphenyl)-
2,2,4-trimethyl-1,2-dihydroquinoline
(Compound No. 12-49)

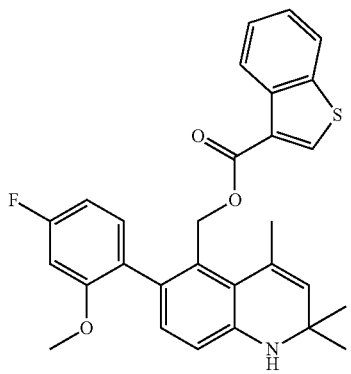

$^1$H-NMR (500 MHz, DMSO-d$_6$)
δ 1.18 (s, 3H), 1.24 (s, 3H), 2.14 (s, 3H), 3.64 (s, 3H), 5.05 (d, J = 12.7 Hz, 1H), 5.26 (d, J = 12.7 Hz, 1H), 5.48 (s, 1H), 6.11 (s, 1H), 6.68 (d, J = 8.2 Hz, 1H), 6.72 (td, J = 8.4, 2.5 Hz, 1H), 6.76 (d, J = 8.2 Hz, 1H), 6.91 (dd, J = 11.5, 2.5 Hz, 1H), 7.15 (dd, J = 8.4, 7.2 Hz, 1H), 7.42-7.45 (m, 2H), 8.06-8.09 (m, 1H), 8.28-8.31 (m, 1H), 8.54 (s, 1H)

5-Benzoyloxymethyl-6-(3,4-difluoro-2-methoxyphenyl)-2,2,4-trimethyl-1,2-dihydroquinoline
(Compound No. 12-50)

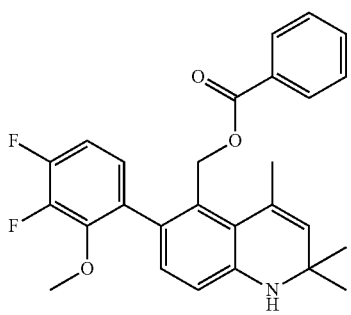

$^1$H-NMR (400 MHz, CDCl$_3$)
δ 1.14 (s, 3H), 1.21 (s, 3H), 2.12 (s, 3H), 3.61 (s, 3H), 5.05 (d, J = 12.9 Hz, 1H), 5.27 (d, J = 12.9 Hz, 1H), 5.48 (s, 1H), 6.22 (s, 1H), 6.70 (d, J = 8.2 Hz, 1H), 6.83 (d, J = 8.2 Hz, 1H), 7.03 (ddd, J = 9.0, 6.3, 2.0 Hz, 1H), 7.10-7.14 (m, 1H), 7.47 (t, J = 7.8 Hz, 2H), 7.62 (t, J = 7.8 Hz, 1H), 7.81 (d, J = 7.8 Hz, 2H)

6-(3,5-Difluoro-2-methoxyphenyl)-5-[(thiophen-2-yl)carbonyloxymethyl]-2,2,4-trimethyl-1,2-dihydroquinoline
(Compound No. 12-51)

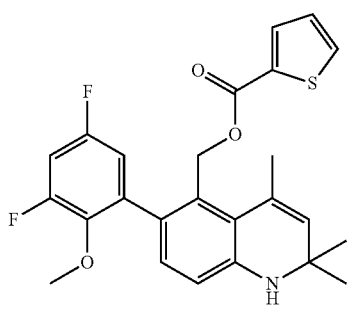

$^1$H-NMR (400 MHz, DMSO-d$_6$)
δ 1.14 (s, 3H), 1.20 (s, 3H), 2.12 (s, 3H), 3.50 (s, 3H), 5.02 (d, J = 12.9 Hz, 1H), 5.27 (d, J = 12.9 Hz, 1H), 5.47 (s, 1H), 6.26 (s, 1H), 6.70 (d, J = 8.3 Hz, 1H), 6.87 (d, J = 8.3 Hz, 1H), 6.93 (ddd, J = 9.0, 2.9, 1.7 Hz, 1H), 7.17 (dd, J = 4.9, 3.8 Hz, 1H), 7.25-7.31 (m, 1H), 7.67 (dd, J = 3.8, 1.3 Hz, 1H), 7.91 (dd, J = 4.9, 1.3 Hz, 1H)

| Compound | NMR |
|---|---|
| 6-(3,5-Difluoro-2-methoxyphenyl)-5-[(5-methylthiophen-2-yl)carbonyloxymethyl]-2,2,4-trimethyl-1,2-dihydroquinoline (Compound No. 12-52) 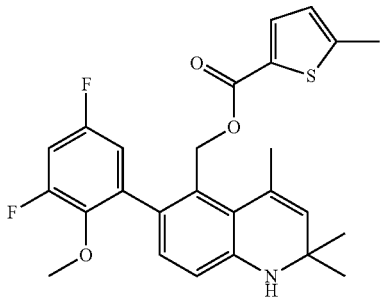 | $^1$H-NMR (400 MHz, DMSO-d$_6$) δ 1.15 (s, 3H), 1.20 (s, 3H), 2.11 (s, 3H), 2.47 (s, 3H), 3.49 (s, 3H), 4.98 (d, J = 12.9 Hz, 1H), 5.23 (d, J = 12.9 Hz, 1H), 5.47 (s, 1H), 6.24 (s, 1H), 6.70 (d, J = 8.3 Hz, 1H), 6.86 (d, J = 8.3 Hz, 1H), 6.88 (d, J = 3.7 Hz, 1H), 6.91 (ddd, J = 9.0, 2.9, 1.7 Hz, 1H), 7.25-7.31 (m, 1H), 7.49 (d, J = 3.7 Hz, 1H) |
| 6-(4,5-Difluoro-2-methoxyphenyl)-5-[(thiophen-2-yl)carbonyloxymethyl]-2,2,4-trimethyl-1,2-dihydroquinoline (Compound No. 12-53) 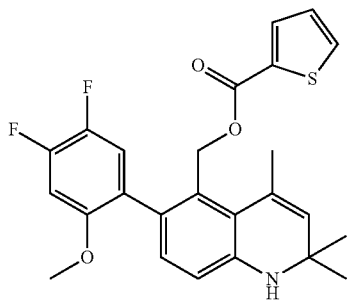 | $^1$H-NMR (500 MHz, DMSO-d$_6$) δ 1.13 (s, 3H), 1.21 (s, 3H), 2.11 (s, 3H), 3.66 (s, 3H), 4.95 (d, J = 12.8 Hz, 1H), 5.20 (d, J = 12.8 Hz, 1H), 5.46 (s, 1H), 6.15 (s, 1H), 6.65 (d, J = 8.2 Hz, 1H), 6.76 (d, J = 8.2 Hz, 1H), 7.14-7.22 (m, 3H), 7.67 (dd, J = 3.8, 1.4 Hz, 1H), 7.91 (dd, J = 5.0, 1.4 Hz, 1H) |
| 6-(4,5-Difluoro-2-methoxyphenyl)-5-[(5-methylthiophen-2-yl)carbonyloxymethyl]-2,2,4-trimethyl-1,2-dihydroquinoline (Compound No. 12-54) 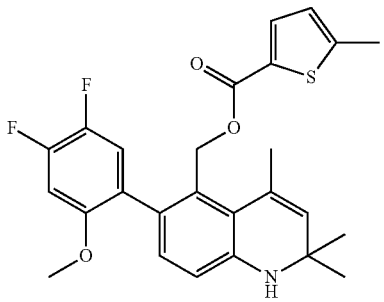 | $^1$H-NMR (500 MHz, DMSO-d$_6$) δ 1.13 (s, 3H), 1.21 (s, 3H), 2.10 (s, 3H), 2.47 (s, 3H), 3.66 (s, 3H), 4.91 (d, J = 12.8 Hz, 1H), 5.16 (d, J = 12.8 Hz, 1H), 5.45 (s, 1H), 6.15 (s, 1H), 6.65 (d, J = 8.2 Hz, 1H), 6.75 (d, J = 8.2 Hz, 1H), 6.89 (d, J = 3.7 Hz, 1H), 7.16 (dd, J = 13.0, 7.2 Hz, 1H), 7.16 (dd, J = 13.0, 7.2 Hz, 1H), 7.19 (dd, J = 11.0, 9.5 Hz, 1H), 7.48 (d, J = 3.7 Hz, 1H) |
| 6-(4-Fluoro-2-methoxyphenyl)-5-[(5-methylthiophen-2-yl)carbonyloxymethyl]-2,2,4,7-tetramethyl-1,2-dihydroquinoline (Compound No. 12-55) 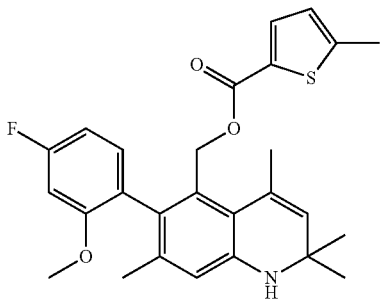 | $^1$H-NMR (400 MHz, DMSO-d$_6$) δ 1.17 (s, 3H), 1.19 (s, 3H), 1.75 (s, 3H), 2.05 (s, 3H), 2.48 (s, 3H), 3.63 (s, 3H), 4.71 (d, J = 12.2 Hz, 1H), 5.02 (d, J = 12.2 Hz, 1H), 5.39 (s, 1H), 5.96 (s, 1H), 6.53 (s, 1H), 6.67 (td, J = 8.3, 2.4 Hz, 1H), 6.88-6.93 (m, 2H), 6.98 (dd, J = 8.3, 7.2 Hz, 1H), 7.49 (d, J = 3.7 Hz, 1H) |

| | |
|---|---|
| 6-(4-Fluoro-2-methoxyphenyl)-7-methoxy-5-[(thiophen-2-yl)carbonyloxymethyl]-2,2,4-trimethyl-1,2-dihydroquinoline (Compound No. 12-56) 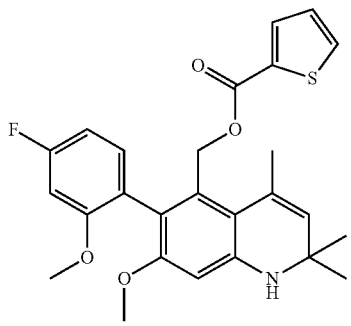 | $^1$H-NMR (400 MHz, DMSO-d$_6$) δ 1.18 (s, 6H), 2.05 (s, 3H), 3.55 (s, 3H), 3.61 (s, 3H), 4.77 (d, J = 12.3 Hz, 1H), 5.05 (d, J = 12.3 Hz, 1H), 5.30 (s, 1H), 6.13 (s, 1H), 6.35 (s, 1H), 6.63 (td, J = 8.4, 2.4 Hz, 1H), 6.86 (dd, J = 11.6, 2.4 Hz, 1H), 6.99 (dd, J = 8.4, 7.1 Hz, 1H), 7.18 (dd, J = 4.9, 3.9 Hz, 1H), 7.67 (dd, J = 3.9, 1.0 Hz, 1H), 7.91 (dd, J = 4.9, 1.0 Hz, 1H) |
| 6-(4-Fluoro-2-methoxyphenyl)-7-methoxy-5-[(5-methylthiophen-2-yl)carbonyloxymethyl]-2,2,4-trimethyl-1,2-dihydroquinoline (Compound No. 12-57) 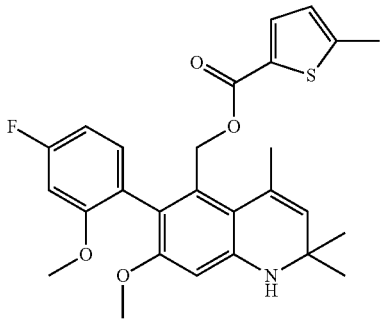 | $^1$H-NMR (400 MHz, CDCl$_3$) δ 1.28 (s, 6H), 2.14 (s, 3H), 2.49 (s, 3H), 3.65 (s, 3H), 3.67 (s, 3H), 4.84 (d, J = 12.2 Hz, 1H), 5.19 (d, J = 12.2 Hz, 1H), 5.37 (s, 1H), 6.21 (s, 1H), 6.56-6.64 (m, 2H), 6.72 (d, J = 3.8 Hz, 1H), 7.08 (dd, J = 8.3, 6.8 Hz, 1H), 7.51 (d, J = 3.8 Hz, 1H) |
| 6-(2-Ethoxy-4-fluorophenyl)-5-[(5-methylthiophen-2-yl)carbonyloxymethyl]-2,2,4-trimethyl-1,2-dihydroquinoline (Compound No. 12-58) 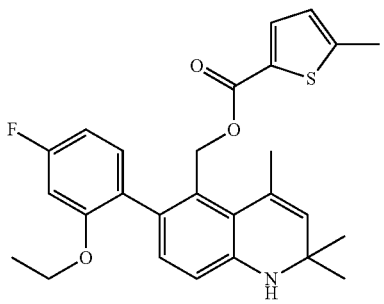 | $^1$H-NMR (400 MHz, DMSO-d$_6$) δ 1.10 (s, 3H), 1.19 (t, J = 6.9 Hz, 3H), 1.24 (s, 3H), 2.08 (s, 3H), 2.46 (s, 3H), 3.95-4.01 (m, 2H), 4.91 (d, J = 12.8 Hz, 1H), 5.22 (d, J = 12.8 Hz, 1H), 5.44 (s, 1H), 6.09 (s, 1H), 6.65 (d, J = 8.2 Hz, 1H), 6.75 (d, J = 8.2 Hz, 1H), 6.75 (td, J = 8.4, 2.4 Hz, 1H), 6.87 (d, J = 3.7 Hz, 1H), 6.91 (dd, J = 11.5, 2.4 Hz, 1H), 7.16 (dd, J = 8.4, 7.1 Hz, 1H), 7.45 (d, J = 3.7 Hz, 1H) |

| | |
|---|---|
| 6-(4-Fluoro-2-propoxyphenyl)-5-[(5-methylthiophen-2-yl)carbonyloxymethyl]-2,2,4-trimethyl-1,2-dihydroquinoline (Compound No. 12-59)<br />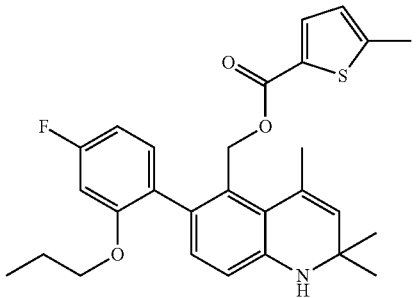 | $^1$H-NMR (400 MHz, DMSO-d$_6$) δ 0.80 (t, J = 7.3 Hz, 3H), 1.11 (s, 3H), 1.22 (s, 3H), 1.51-1.63 (m, 2H), 2.07 (s, 3H), 2.46 (s, 3H), 3.80-3.93 (m, 2H), 4.89 (d, J = 12.7 Hz, 1H), 5.21 (d, J = 12.7 Hz, 1H), 5.44 (s, 1H), 6.08 (s, 1H), 6.65 (d, J = 8.1 Hz, 1H), 6.70-6.77 (m, 1H), 6.74 (d, J = 8.1 Hz, 1H), 6.87 (d, J = 3.7 Hz, 1H), 6.92 (dd, J = 11.5, 2.4 Hz, 1H), 7.16 (dd, J = 8.3, 7.1 Hz, 1H), 7.45 (d, J = 3.7 Hz, 1H) |
| 6-(4-Fluoro-2-isopropoxyphenyl)-5-[(5-methylthiophen-2-yl)carbonyloxymethyl]-2,2,4-trimethyl-1,2-dihydroquinoline (Compound No. 12-60)<br />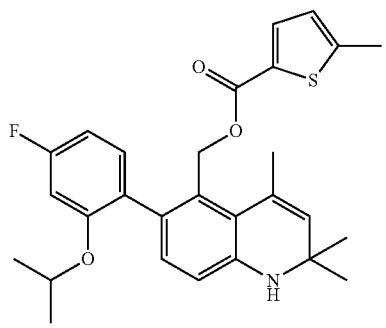 | $^1$H-NMR (400 MHz, DMSO-d$_6$) δ 1.09 (d, J = 6.1 Hz, 3H), 1.09 (s, 3H), 1.21 (d, J = 6.1 Hz, 3H), 1.24 (s, 3H), 2.06 (s, 3H), 2.45 (s, 3H), 4.52-4.56 (m, 1H), 4.88 (d, J = 13.1 Hz, 1H), 5.25 (d, J = 13.1 Hz, 1H), 5.44 (s, 1H), 6.09 (s, 1H), 6.65 (d, J = 8.2 Hz, 1H), 6.74 (d, J = 8.2 Hz, 1H), 6.75 (td, J = 8.3, 2.6 Hz, 1H), 6.87 (d, J = 3.7 Hz, 1H), 6.94 (dd, J = 11.7, 2.6 Hz, 1H), 7.18 (dd, J = 8.3, 7.1 Hz, 1H), 7.45 (d, J = 3.7 Hz, 1H) |
| 5-(4-Ethylbenzoyloxymethyl)-6-(4-fluoro-2-methoxyphenyl)-2,2,4-trimethyl-1,2-dihydroquinoline (Compound No. 12-61)<br />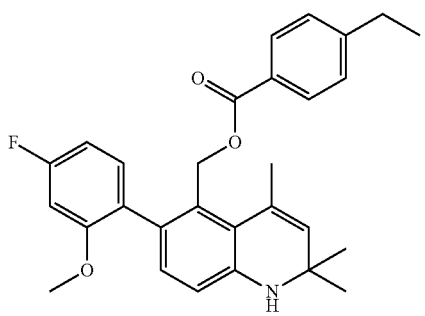 | $^1$H-NMR (500 MHz, DMSO-d$_6$) δ 1.15 (s, 3H), 1.17 (t, J = 7.6 Hz, 3H), 1.22 (s, 3H), 2.08 (s, 3H), 2.65 (q, J = 7.6 Hz, 2H), 3.67 (s, 3H), 4.95 (d, J = 12.5 Hz, 1H), 5.18 (d, J = 12.5 Hz, 1H), 5.45 (s, 1H), 6.10 (s, 1H), 6.66 (d, J = 8.2 Hz, 1H), 6.69-6.76 (m, 1H), 6.75 (d, J = 8.2 Hz, 1H), 6.92 (dd, J = 11.3, 2.4 Hz, 1H), 7.14 (dd, J = 8.2, 7.0 Hz, 1H), 7.31 (d, J = 8.2 Hz, 2H), 7.74 (d, J = 8.2 Hz, 2H) |

| Compound | NMR |
|---|---|
| 6-(4-Fluoro-2-methoxyphenyl)-5-(4-propylbenzoyloxymethyl)-2,2,4-trimethyl-1,2-dihydroquinoline (Compound No. 12-62)<br>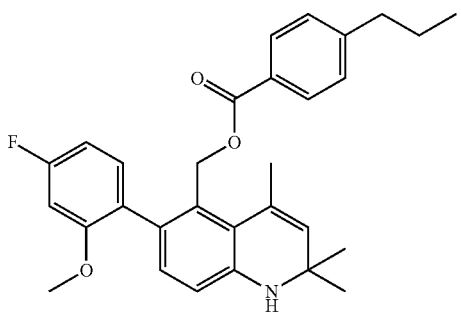 | $^1$H-NMR (500 MHz, DMSO-d$_6$) δ 0.87 (t, J = 7.3 Hz, 3H), 1.14 (s, 3H), 1.22 (s, 3H), 1.53-1.64 (m, 2H), 2.09 (s, 3H), 2.60 (t, J = 7.3 Hz, 2H), 3.66 (s, 3H), 4.95 (d, J = 12.8 Hz, 1H), 5.18 (d, J = 12.8 Hz, 1H), 5.45 (s, 1H), 6.10 (s, 1H), 6.65 (d, J = 8.2 Hz, 1H), 6.70-6.75 (m, 1H), 6.74 (d, J = 8.2 Hz, 1H), 6.92 (dd, J = 11.3, 2.4 Hz, 1H), 7.14 (dd, J = 8.4, 7.2 Hz, 1H), 7.29 (d, J = 8.2 Hz, 2H), 7.73 (d, J = 8.2 Hz, 2H) |
| 5-(4-Chlorobenzoyloxymethyl)-6-(4-fluoro-2-methoxyphenyl)-2,2,4-trimethyl-1,2-dihydroquinoline (Compound No. 12-63)<br>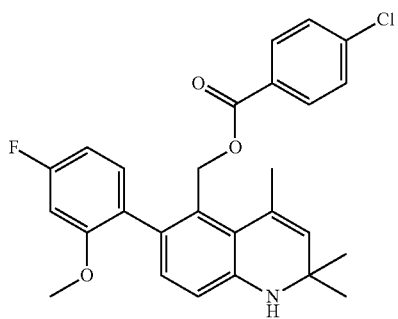 | $^1$H-NMR (400 MHz, DMSO-d$_6$) δ 1.13 (s, 3H), 1.22 (s, 3H), 2.10 (s, 3H), 3.66 (s, 3H), 4.99 (d, J = 12.7 Hz, 1H), 5.21 (d, J = 12.7 Hz, 1H), 5.46 (s, 1H), 6.11 (s, 1H), 6.65 (d, J = 8.3 Hz, 1H), 6.72 (td, J = 8.4, 2.6 Hz, 1H), 6.74 (d, J = 8.3 Hz, 1H), 6.91 (dd, J = 11.5, 2.6 Hz, 1H), 7.13 (dd, J = 8.4, 7.1 Hz, 1H), 7.56 (dt, J = 9.1, 2.2 Hz, 2H), 7.80 (dt, J = 9.1, 2.2 Hz, 2H) |
| 8-Chloro-6-(4-fluoro-2-methoxyphenyl)-5-(thiophen-2-ylcarbonyloxymethyl)-2,2,4-trimethyl-1,2-dihydroquinoline (Compound No. 12-64)<br>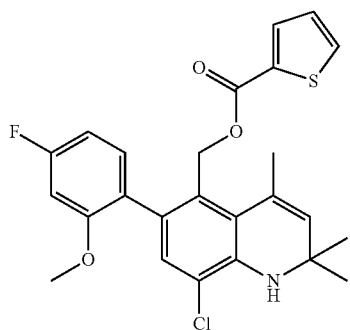 | $^1$H-NMR (400 MHz, DMSO-d$_6$) δ 1.18 (s, 3H), 1.29 (s, 3H), 2.13 (s, 3H), 3.69 (s, 3H), 4.95 (d, J = 12.9 Hz, 1H), 5.18 (d, J = 12.9 Hz, 1H), 5.53 (s, 1H), 5.58 (s, 1H), 6.71-6.81 (m, 1H), 6.90-7.00 (m, 2H), 7.14-7.23 (m, 2H), 7.66 (dd, J = 3.8, 1.3 Hz, 1H), 7.91 (dd, J = 5.0, 1.3 Hz, 1H) |
| 6-(4-Fluoro-2-methoxyphenyl)-5-(thiophen-2-ylacetoxymethyl)-2,2,4-trimethyl-1,2-dihydroquinoline (Compound No. 12-65)<br>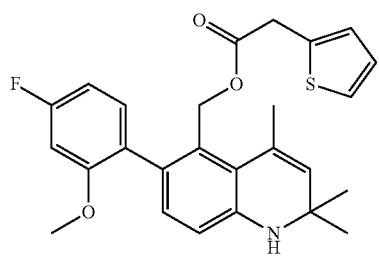 | $^1$H-NMR (400 MHz, DMSO-d$_6$) δ 1.18 (s, 6H), 1.99 (s, 3H), 3.68 (s, 3H), 3.78 (s, 2H), 4.69 (d, J = 12.5 Hz, 1H), 4.98 (d, J = 12.5 Hz, 1H), 5.40 (s, 1H), 6.04 (s, 1H), 6.61 (d, J = 8.3 Hz, 1H), 6.66-6.74 (m, 1H), 6.69 (d, J = 8.3 Hz, 1H), 6.88 (dd, J = 3.4, 1.2 Hz, 1H), 6.91 (dd, J = 11.6, 2.6 Hz, 1H), 6.95 (dd, J = 5.1, 3.4 Hz, 1H), 7.03 (dd, J = 8.3, 7.1 Hz, 1H), 7.39 (dd, J = 5.1, 1.2 Hz, 1H) |

| | |
|---|---|
| 6-(4-Fluoro-2-methoxyphenyl)-5-[(2-hydroxyphenyl)acetoxymethyl]-2,2,4-trimethyl-1,2-dihydroquinoline (Compound No. 12-66)<br>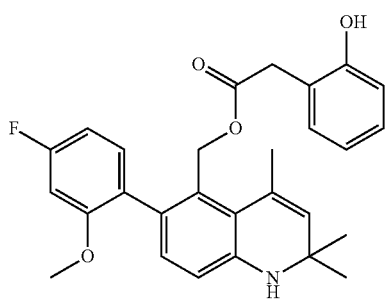 | $^1$H-NMR (400 MHz, DMSO-d$_6$) δ 1.17 (s, 6H), 2.00 (s, 3H), 3.42 (s, 2H), 3.69 (s, 3H), 4.59 (d, J = 12.5 Hz, 1H), 4.92 (d, J = 12.5 Hz, 1H), 5.38 (s, 1H), 6.02 (s, 1H), 6.60 (d, J = 8.2 Hz, 1H), 6.68 (d, J = 8.2 Hz, 1H), 6.68 (d, J = 8.3 Hz, 1H), 6.72 (dd, J = 8.3, 2.4 Hz, 1H), 6.77 (d, J = 8.1 Hz, 1H), 6.91 (dd, J = 11.5, 2.4 Hz, 1H), 6.99-7.03 (m, 2H), 7.06 (t, J = 7.6 Hz, 1H), 9.42 (s, 1H) |
| 6-(2-Methoxy-5-methylphenyl)-5-(5-methylthiophen-2-ylcarbonyloxymethyl)-2,2,4-trimethyl-1,2-dihydroquinoline (Compound No. 12-67)<br>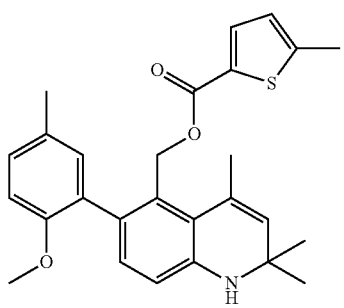 | $^1$H-NMR (500 MHz, DMSO-d$_6$) δ 1.16 (s, 3H), 1.20 (s, 3H), 2.08 (s, 3H), 2.13 (s, 3H), 2.47 (s, 3H), 3.62 (s, 3H), 4.87 (d, J = 12.5 Hz, 1H), 5.15 (d, J = 12.5 Hz, 1H), 5.44 (s, 1H), 6.04 (s, 1H), 6.65 (d, J = 8.2 Hz, 1H), 6.75 (d, J = 8.2 Hz, 1H), 6.88 (d, J = 3.7 Hz, 1H), 6.90 (d, J = 7.9 Hz, 1H), 6.92 (d, J = 2.3 Hz, 1H), 7.07 (dd, J = 7.9, 2.3 Hz, 1H), 7.48 (d, J = 3.7 Hz, 1H) |
| 5-(4-Methoxybenzoyloxymethyl)-6-(2-methoxy-5-methylphenyl)-2,2,4-trimethyl-1,2-dihydroquinoline (Compound No. 12-68)<br>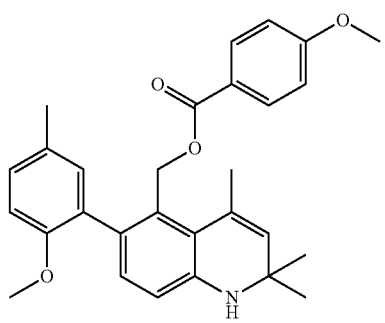 | $^1$H-NMR (400 MHz, DMSO-d$_6$) δ 1.17 (s, 3H), 1.22 (s, 3H), 2.07 (s, 3H), 2.12 (s, 3H), 3.62 (s, 3H), 3.81 (s, 3H), 4.91 (d, J = 12.7 Hz, 1H), 5.17 (d, J = 12.7 Hz, 1H), 5.45 (s, 1H), 6.05 (s, 1H), 6.65 (d, J = 8.2 Hz, 1H), 6.76 (d, J = 8.2 Hz, 1H), 6.89 (d, J = 8.5 Hz, 1H), 6.93 (d, J = 2.3 Hz, 1H), 6.99 (dt, J = 9.5, 2.5 Hz, 2H), 7.06 (dd, J = 8.5, 2.3 Hz, 1H), 7.78 (dt, J = 9.5, 2.5 Hz, 2H) |

| | |
|---|---|
| 6-(5-Chloro-2-methoxyphenyl)-5-(5-methylthiophen-2-ylcarbonyloxymethyl)-2,2,4-trimethyl-1,2-dihydroquinoline (Compound No. 12-69) 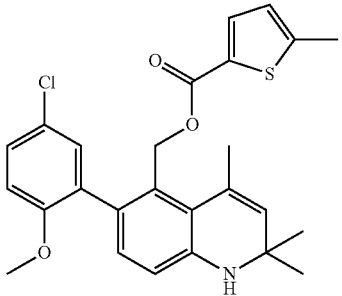 | $^1$H-NMR (400 MHz, DMSO-d$_6$) δ 1.14 (s, 3H), 1.21 (s, 3H), 2.10 (s, 3H), 2.47 (s, 3H), 3.66 (s, 3H), 4.88 (d, J = 12.7 Hz, 1H), 5.16 (d, J = 12.7 Hz, 1H), 5.45 (s, 1H), 6.13 (s, 1H), 6.65 (d, J = 8.3 Hz, 1H), 6.76 (d, J = 8.3 Hz, 1H), 6.88 (dd, J = 3.7, 1.0 Hz, 1H), 7.04 (d, J = 8.9 Hz, 1H), 7.13 (d, J = 2.8 Hz, 1H), 7.32 (dd, J = 8.9, 2.8 Hz, 1H), 7.47 (d, J = 3.7 Hz, 1H) |
| 6-(5-Chloro-2-methoxyphenyl)-5-(4-methoxybenzoyloxymethyl)-2,2,4-trimethyl-1,2-dihydroquinoline (Compound No. 12-70) 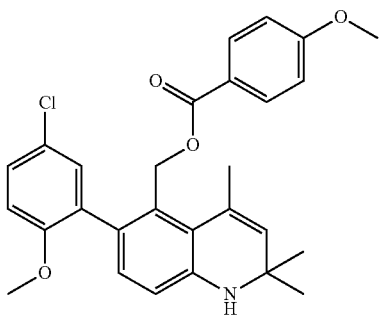 | $^1$H-NMR (400 MHz, DMSO-d$_6$) δ 1.14 (s, 3H), 1.22 (s, 3H), 2.10 (s, 3H), 3.66 (s, 3H), 3.81 (s, 3H), 4.93 (d, J = 12.8 Hz, 1H), 5.18 (d, J = 12.8 Hz, 1H), 5.46 (s, 1H), 6.14 (s, 1H), 6.66 (d, J = 8.3 Hz, 1H), 6.77 (d, J = 8.3 Hz, 1H), 6.99 (d, J = 9.0 Hz, 2H), 7.03 (d, J = 8.8 Hz, 1H), 7.15 (d, J = 2.8 Hz, 1H), 7.32 (dd, J = 8.8, 2.8 Hz, 1H), 7.77 (d, J = 9.0 Hz, 2H) |
| 6-(2-Methoxy-5-trifluoromethylphenyl)-5-(4-methylbenzoyloxymethyl)-2,2,4-trimethyl-1,2-dihydroquinoline (Compound No. 12-71) 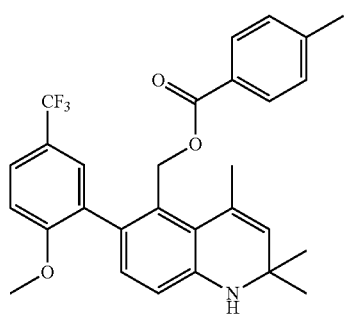 | $^1$H-NMR (400 MHz, DMSO-d$_6$) δ 1.15 (s, 3H), 1.21 (s, 3H), 2.10 (s, 3H), 2.34 (s, 3H), 3.75 (s, 3H), 4.89 (d, J = 12.8 Hz, 1H), 5.20 (d, J = 12.8 Hz, 1H), 5.46 (s, 1H), 6.17 (s, 1H), 6.68 (d, J = 8.3 Hz, 1H), 6.80 (d, J = 8.3 Hz, 1H), 7.21 (d, J = 8.4 Hz, 1H), 7.26 (d, J = 8.1 Hz, 2H), 7.42 (d, J = 1.8 Hz, 1H), 7.64 (dd, J = 8.4, 1.8 Hz, 1H), 7.69 (d, J = 8.1 Hz, 2H) |

5-(4-Methoxybenzoyloxymethyl)-6-(2-methoxy-5-trifluoromethylphenyl)-2,2,4-trimethyl-1,2-dihydroquinoline
(Compound No. 12-72)

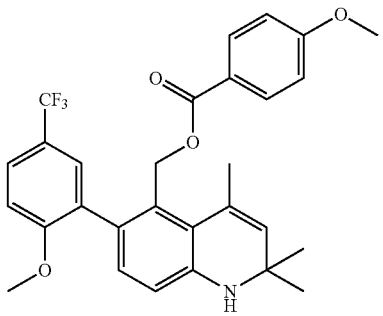

$^1$H-NMR (400 MHz, DMSO-d$_6$)
δ 1.16 (s, 3H), 1.22 (s, 3H), 2.10 (s, 3H), 3.74 (s, 3H), 3.81 (s, 3H), 4.89 (d, J = 12.8 Hz, 1H), 5.17 (d, J = 12.8 Hz, 1H), 5.49 (s, 1H), 6.17 (s, 1H), 6.68 (d, J = 8.3 Hz, 1H), 6.80 (d, J = 8.3 Hz, 1H), 6.98 (d, J = 9.0 Hz, 2H), 7.21 (d, J = 8.5 Hz, 1H), 7.41 (d, J = 2.2 Hz, 1H), 7.64 (d, J = 8.5, 2.2 Hz, 1H), 7.75 (d, J = 9.0 Hz, 2H)

6-(2-Methoxy-5-trifluoromethylphenyl)-5-(5-methylthiophen-2-ylcarbonyloxymethyl)-2,2,4-trimethyl-1,2-dihydroquinoline
(Compound No. 12-73)

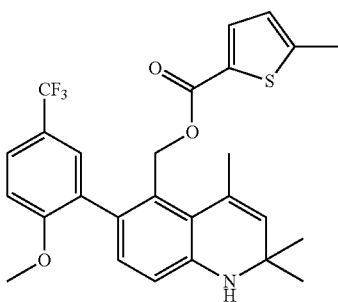

$^1$H-NMR (400 MHz, DMSO-d$_6$)
δ 1.15 (s, 3H), 1.20 (s, 3H), 2.11 (s, 3H), 2.46 (s, 3H), 3.75 (s, 3H), 4.84 (d, J = 12.6 Hz, 1H), 5.15 (d, J = 12.6 Hz, 1H), 5.46 (s, 1H), 6.16 (s, 1H), 6.67 (d, J = 8.2 Hz, 1H), 6.79 (d, J = 8.2 Hz, 1H), 6.87 (dd, J = 3.7, 1.0 Hz, 1H), 7.21 (d, J = 8.6 Hz, 1H), 7.40 (d, J = 2.1 Hz, 1H), 7.46 (d, J = 3.7 Hz, 1H), 7.65 (dd, J = 8.6, 2.1 Hz, 1H)

5-(5-Chlorothiophen-2-ylcarbonyloxymethyl)-6-(2-methoxy-5-trifluoromethylphenyl)-2,2,4-trimethyl-1,2-dihydroquinoline
(Compound No. 12-74)

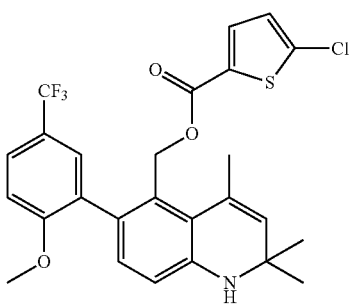

$^1$H-NMR (400 MHz, DMSO-d$_6$)
δ 1.15 (s, 3H), 1.20 (s, 3H), 2.11 (s, 3H), 3.76 (s, 3H), 4.91 (d, J = 12.7 Hz, 1H), 5.19 (d, J = 12.7 Hz, 1H), 5.47 (s, 1H), 6.18 (s, 1H), 6.68 (d, J = 8.2 Hz, 1H), 6.79 (d, J = 8.2 Hz, 1H), 7.21-7.23 (m, 1H), 7.22 (d, J = 4.2 Hz, 1H), 7.39 (d, J = 2.2 Hz, 1H), 7.54 (d, J = 4.2 Hz, 1H), 7.65 (dd, J = 8.5, 2.2 Hz, 1H)

6-(5-Fluoro-2-methoxyphenyl)-5-(4-metoxybenzoyloxymethyl)-2,2,4-trimethyl-1,2-dihydroquinoline (Compound No. 12-75)

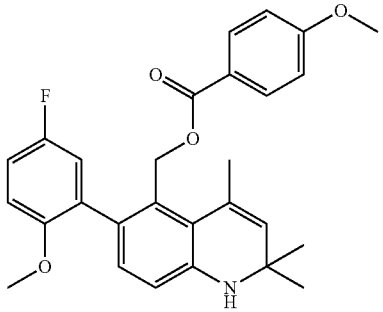

¹H-NMR (400 MHz, DMSO-d₆)
δ 1.14 (s, 3H), 1.23 (s, 3H), 2.10 (s, 3H), 3.64 (s, 3H), 3.81 (s, 3H), 4.96 (d, J = 12.8 Hz, 1H), 5.19 (d, J = 12.8 Hz, 1H), 5.46 (s, 1H), 6.13 (s, 1H), 6.66 (d, J = 8.2 Hz, 1H), 6.78 (d, J = 8.2 Hz, 1H), 6.96-7.02 (m, 2H), 6.99 (d, J = 9.0 Hz, 1H), 7.11 (td, J = 8.6, 3.3 Hz, 1H), 7.77 (d, J = 9.0 Hz, 2H)

6-(5-Fluoro-2-methoxyphenyl)-5-(5-methylthiophenyl-2-ylcarbonyloxymethyl)-2,2,4-trimethyl-1,2-dihydroquinoline (Compound No. 12-76)

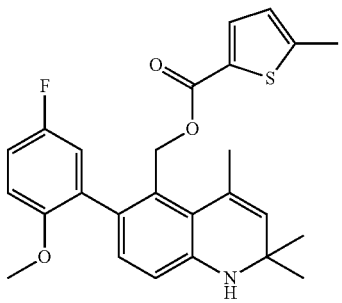

¹H-NMR (500 MHz, DMSO-d₆)
δ 1.14 (s, 3H), 1.21 (s, 3H), 2.09 (s, 3H), 2.47 (s, 3H), 3.65 (s, 3H), 4.91 (d, J = 12.8 Hz, 1H), 5.17 (d, J = 12.8 Hz, 1H), 5.45 (s, 1H), 6.12 (s, 1H), 6.66 (d, J = 7.9 Hz, 1H), 6.77 (d, J = 7.9 Hz, 1H), 6.88 (dd, J = 3.7, 0.9 Hz, 1H), 6.96 (dd, J = 9.0, 3.2 Hz, 1H), 7.01 (dd, J = 8.8, 4.7 Hz, 1H), 7.11 (td, J = 8.8, 3.2 Hz, 1H), 7.47 (d, J = 3.7 Hz, 1H)

6-(2-Methoxy-5-trifluoromethylphenyl)-5-(4-methylthiophen-2-ylcarbonyloxymethyl)-2,2,4-trimethyl-1,2-dihydroquinoline (Compound No. 12-77)

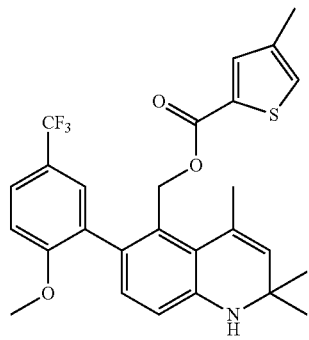

¹H-NMR (500 MHz, DMSO-d₆)
δ 1.16 (s, 3H), 1.20 (s, 3H), 2.10 (s, 3H), 2.19 (s, 3H), 3.75 (s, 3H), 4.85 (d, J = 12.7 Hz, 1H), 5.17 (d, J = 12.7 Hz, 1H), 5.46 (s, 1H), 6.16 (s, 1H), 6.67 (d, J = 8.2 Hz, 1H), 6.79 (d, J = 8.2 Hz, 1H), 7.21 (d, J = 8.8 Hz, 1H), 7.40 (d, J = 2.2 Hz, 1H), 7.46 (d, J = 1.5 Hz, 1H), 7.49 (d, J = 1.5 Hz, 1H), 7.65 (dd, J = 8.8, 2.2 Hz, 1H)

| Compound | ¹H-NMR |
|---|---|
| 5-(5-Ethylthiophen-2-ylcarbonylmethyl)-6-(2-methoxy-5-trifluoromethylphenyl)-2,2,4-trimethyl-1,2-dihydroquinoline (Compound No. 12-78) 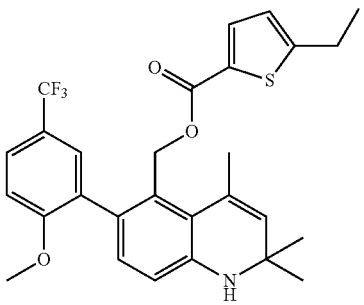 | ¹H-NMR (400 MHz, DMSO-d₆) δ 1.16 (s, 3H), 1.20 (s, 3H), 1.22 (t, J = 7.6 Hz, 3H), 2.10 (s, 3H), 2.82 (q, J = 7.6 Hz, 2H), 3.76 (s, 3H), 4.84 (d, J = 12.5 Hz, 1H), 5.16 (d, J = 12.5 Hz, 1H), 5.46 (s, 1H), 6.17 (s, 1H), 6.68 (d, J = 8.1 Hz, 1H), 6.78 (d, J = 8.1 Hz, 1H), 6.91 (d, J = 3.8 Hz, 1H), 7.21 (d, J = 8.8 Hz, 1H), 7.39 (d, J = 2.1 Hz, 1H), 7.48 (d, J = 3.8 Hz, 1H), 7.65 (dd, J = 8.8, 2.1 Hz, 1H) |
| 6-(4-Chloro-2-methoxyphenyl)-5-(5-methylthiophen-2-ylcarbonyloxymethyl)-2,2,4-trimethyl-1,2-dihydroquinoline (Compound No. 12-79) 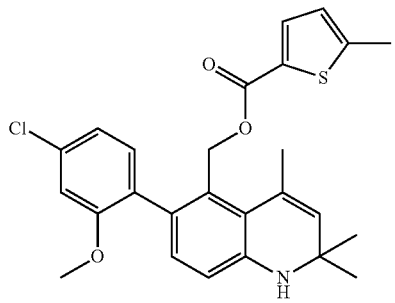 | ¹H-NMR (400 MHz, DMSO-d₆) δ 1.14 (s, 3H), 1.21 (s, 3H), 2.09 (s, 3H), 2.47 (s, 3H), 3.69 (s, 3H), 4.88 (d, J = 12.7 Hz, 1H), 5.15 (d, J = 12.7 Hz, 1H), 5.44 (s, 1H), 6.11 (s, 1H), 6.65 (d, J = 8.3 Hz, 1H), 6.73 (d, J = 8.3 Hz, 1H), 6.88 (dd, J = 3.7, 1.0 Hz, 1H), 6.97 (dd, J = 8.1, 2.0 Hz, 1H), 7.09 (d, J = 2.0 Hz, 1H), 7.12 (d, J = 8.1 Hz, 1H), 7.47 (d, J = 3.7 Hz, 1H) |
| 6-(4-Chloro-2-methoxyphenyl)-5-(4-metoxylbenzoyloxymethyl)-2,2,4-trimethyl-1,2-dihydroquinoline (Compound No. 12-80) 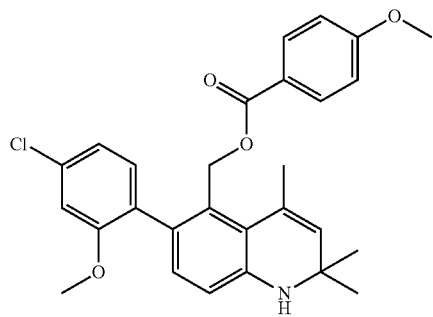 | ¹H-NMR (500 MHz, DMSO-d₆) δ 1.14 (s, 3H), 1.22 (s, 3H), 2.09 (s, 3H), 3.68 (s, 3H), 3.81 (s, 3H), 4.93 (d, J = 12.8 Hz, 1H), 5.16 (d, J = 12.8 Hz, 1H), 5.46 (s, 1H), 6.11 (s, 1H), 6.66 (d, J = 8.3 Hz, 1H), 6.74 (d, J = 8.3 Hz, 1H), 6.97 (dd, J = 8.1, 1.9 Hz, 1H), 6.99 (d, J = 8.9 Hz, 2H), 7.08 (d, J = 1.9 Hz, 1H), 7.14 (d, J = 8.1 Hz, 1H), 7.76 (d, J = 8.9 Hz, 2H) |

Example 13

5-(3-Aminobenzoyloxymethyl)-6-(4-fluoro-2-methoxyphenyl)-2,2,4-trimethyl-1,2-dihydroquinoline (Compound No. 13-1)

6-(4-Fluoro-2-methoxyphenyl)-5-hydroxymethyl-2,2,4-trimethyl-1,2-dihydroquinoline (Reference Compound No. 4-3, 49.7 mg, 0.15 mmol), 3-aminobenzoic acid (49.0 mg, 0.35 mmol), tri-n-butylphosphine (87.0 μL, 0.35 mmol), and 1,1'-(azodicarbonyl)dipiperidine (89.4 mg, 0.35 mmol) were dissolved in anhydrous benzene (2 mL), and then the mixture was stirred under argon atmosphere at room temperature overnight. Hexane (3 mL)—ethyl acetate (3 mL) were added to the reaction mixture, and unsoluble materials were filtered. The filtrate was concentrated under reduced pressure and the residue was purified by silica gel column chromatography (hexane-ethyl acetate) to give the titled compound (28.0 mg) as a colorless amorphous product (Yield 42%)

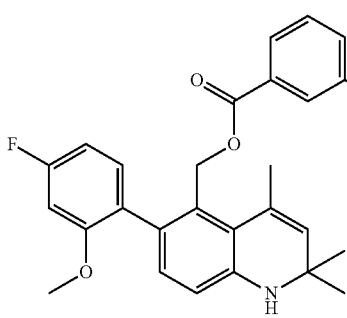

¹H-NMR (400 MHz, DMSO-d₆)
δ 1.17 (s, 3H), 1.21 (s, 3H), 2.08 (s, 3H), 3.66 (s, 3H), 4.86 (d, J = 12.7 Hz, 1H), 5.13 (d, J = 12.7 Hz, 1H), 5.30-5.32 (m, 2H), 5.45 (s, 1H), 6.08 (s, 1H), 6.65 (d, J = 8.2 Hz, 1H), 6.68-6.76 (m, 2H), 6.73 (d, J = 8.2 Hz, 1H), 6.91 (dd, J = 11.5, 2.7 Hz, 1H), 6.95-6.97 (m, 1H), 7.05-7.09 (m, 2H), 7.12 (d d, J = 8.3, 7.1 Hz, 1H)

Using any compounds among Reference Compounds No. 4-1, 4-3, and 4-31, the following Compounds (No. 13-2~13-4) were obtained by a method similar to that of Compound No. 13-1.

6-(4-Fluoro-2-methoxyphenyl)-5-(3-hydroxybenzoyloxy-methyl)-2,2,4-trimethyl-1,2-dihydroquinoline (Compound No. 13-2)

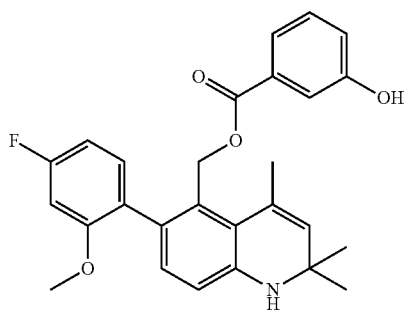

¹H-NMR (400 MHz, DMSO-d₆) δ 1.15 (s, 3H), 1.22 (s, 3H), 2.09 (s, 3H), 3.66 (s, 3H), 4.93 (d, J = 12.7 Hz, 1H), 5.17 (d, J = 12.7 Hz, 1H), 5.46 (s, 1H), 6.09 (s, 1H), 6.65 (d, J = 8.2 Hz, 1H), 6.72 (td, J = 8.4, 2.6 Hz, 1H), 6.74 (d, J = 8.2 Hz, 1H), 6.91 (dd, J = 11.5, 2.6 Hz, 1H), 6.97-7.01 (m, 1H), 7.12 (dd, J = 8.4, 7.1 Hz, 1H), 7.22-7.28 (m, 3H), 9.75 (s, 1H)

6-(2-Methoxyphenyl)-5-(4-methylbenzoyloxy-methyl)-2,2,4-trimethyl-1,2-dihydroquinoline (Compound No. 13-3)

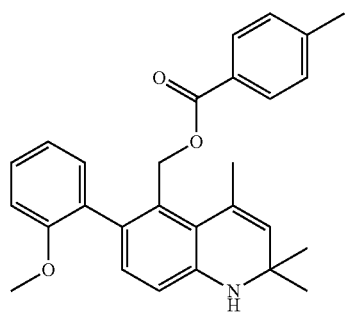

¹H-NMR (500 MHz, DMSO-d₆) δ 1.15 (s, 3H), 1.23 (s, 3H), 2.07 (s, 3H), 2.35 (s, 3H), 3.66 (s, 3H), 4.96 (d, J = 12.8 Hz, 1H), 5.20 (d, J = 12.8 Hz, 1H), 5.45 (s, 1H), 6.07 (s, 1H), 6.66 (d, J = 8.2 Hz, 1H), 6.77 (d, J = 8.2 Hz, 1H), 6.91 (td, J = 7.4, 1.0 Hz, 1H), 7.02 (d, J = 7.4 Hz, 1H), 7.13 (dd, J = 7.4, 1.8 Hz, 1H), 7.27-7.30 (m, 1H), 7.27 (d, J = 8.1 Hz, 2H), 7.71 (d, J = 8.1 Hz, 2H)

6-(2-Methoxy-4-methoxyphenyl)-5-(4-methylbenzoyloxy-methyl)-2,2,4-trimethyl-1,2-dihydroquinoline (Compound No. 13-4)

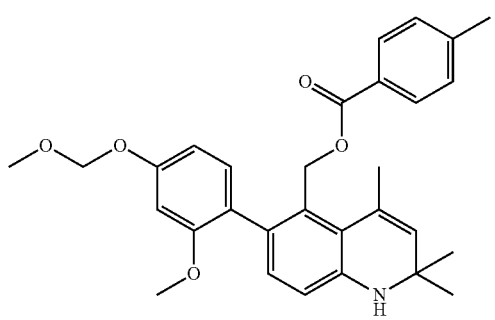

$^1$H-NMR (400 MHz, DMSO-d$_6$) δ 1.14 (s, 3H), 1.23 (s, 3H), 2.07 (s, 3H), 2.35 (s, 3H), 3.39 (s, 3H), 3.64 (s, 3H), 4.97 (d, J = 12.8 Hz, 1H), 5.20 (d, J = 12.8 Hz, 1H), 5.20 (s, 2H), 5.44 (s, 1H), 6.05 (s, 1H), 6.58 (d, J = 8.3, 2.3 Hz, 1H), 6.65 (d, J = 8.2 Hz, 1H), 6.66 (d, J = 2.3 Hz, 1H), 6.75 (d, J = 8.2 Hz, 1H), 7.04 (d, J = 8.3 Hz, 1H), 7.27 (d, J = 7.9 Hz, 2H), 7.71 (d, J = 7.9 Hz, 2H)

Example 14

6-(4-Fluoro-2-methoxyphenyl)-5-(2-methoxycarbonylmethylphenoxymethyl)-2,2,4-trimethyl-1,2-dihydroquinoline (Compound No. 14-1)

6-(4-Fluoro-2-methoxyphenyl)-5-hydroxymethyl-2,2,4-trimethyl-1,2-dihydroquinoline (Reference Compound No. 4-3, 100.1 mg, 0.31 mmol), methyl 2-hydroxyphenylacetate (76.1 mg, 0.46 mmol), tri-n-butylphosphine (114 μL, 0.46 mmol), and 1,1'-(azodicarbonyl)dipiperidine (117 mg, 0.46 mmol) were dissolved in anhydrous benzene (2 mL), and the mixture was stirred under argon atmosphere at room temperature for 1 hour. Hexane (5 mL) was added to the reaction mixture and unsoluble materials were filtered. The filtrate was concentrated under reduced pressure and the residue was purified by silica gel column chromatography (hexane-ethyl acetate) to give the titled compound (107.1 mg) as a colorless amorphous product (Yield 74%)

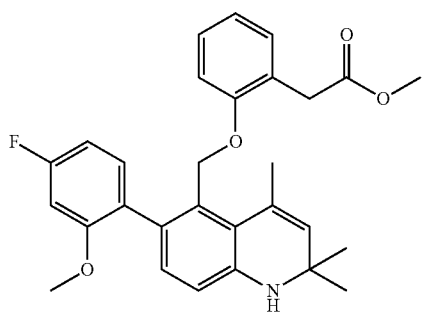 [SMILES: COC(=O)Cc1ccccc1OCc1c(-c2ccc(F)cc2OC)ccc2c1C(C)=CC(C)(C)N2]

$^1$H-NMR (500 MHz, DMSO-d$_6$) δ 1.09 (s, 3H), 1.17 (s, 3H), 2.00 (s, 3H), 3.49 (d, J = 16.2 Hz, 1H), 3.49 (s, 3H), 3.54 (d, J = 16.2 Hz, 1H), 3.72 (s, 3H), 4.52 (d, J = 11.6 Hz, 1H), 5.02 (d, J = 11.6 Hz, 1H), 5.37 (s, 1H), 6.00 (s, 1H), 6.59 (d, J = 8.2 Hz, 1H), 6.62 (d, J = 8.2 Hz, 1H), 6.71 (td, J = 8.4, 2.3 Hz, 1H), 6.74 (d, J = 8.2 Hz, 1H), 6.79 (t, J = 7.0 Hz, 1H), 6.93 (dd, J = 11.3, 2.3 Hz, 1H), 7.06-7.12 (m, 2H), 7.15 (dd, J = 8.4, 7.2 Hz, 1H)

Using any compounds among Reference Compounds No. 4-3~4-4, 4-6, 4-17, 4-27 and 4-29~4-32, the following Compounds (No. 14-2~14-56) were obtained by a method similar to that of Compound No. 14-1.

5-(2-Dimethylaminomethylphenoxymethyl)-6-(4-fluoro-2-methoxyphenyl)-2,2,4-trimethyl-1,2-dihydroquinoline (Compound No. 14-2)

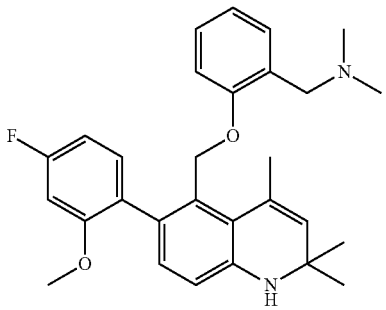

$^1$H-NMR (400 MHz, CDCl$_3$) δ 1.17 (s, 3H), 1.28 (s, 3H), 2.15 (s, 3H), 2.20 (s, 6H), 3.35 (d, J = 13.7 Hz, 1H), 3.45 (d, J = 13.7 Hz, 1H), 3.73 (s, 3H), 4.74 (d, J = 11.8 Hz, 1H), 5.11 (d, J = 11.8 Hz, 1H), 5.46 (s, 1H), 6.49 (d, J = 7.3 Hz, 1H), 6.58 (d, J = 8.1 Hz, 1H), 6.63-6.67 (m, 2H), 6.81-6.85 (m, 1H), 6.86 (d, J = 8.1 Hz, 1H), 7.02-7.06 (m, 1H), 7.18 (dd, J = 8.9, 7.0 Hz, 1H), 7.25-7.27 (m, 1H)

6-(4-Fluoro-2-methoxyphenyl)-5-[2-(2-methoxycarbonylethyl)phenoxymethyl]-2,2,4-trimethyl-1,2-dihydroquinoline (Compound No. 14-3)

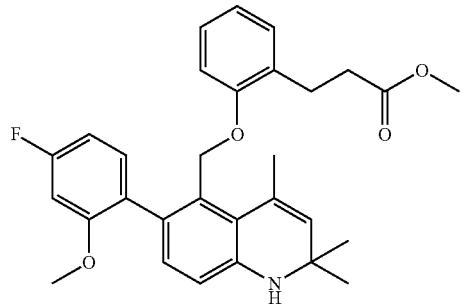

$^1$H-NMR (500 MHz, DMSO-d$_6$) δ 1.07 (s, 3H), 1.17 (s, 3H), 2.01 (s, 3H), 2.45 (td, J = 7.7, 2.1 Hz, 2H), 2.71 (t, J = 7.7 Hz, 2H), 3.53 (s, 3H), 3.72 (s, 3H), 4.59 (d, J = 11.6 Hz, 1H), 5.01 (d, J = 11.6 Hz, 1H), 5.37 (s, 1H), 6.02 (s, 1H), 6.59 (d, J = 7.9 Hz, 1H), 6.64 (d, J = 8.1 Hz, 1H), 6.73-6.77 (m, 2H), 6.75 (d, J = 8.1 Hz, 1H), 6.94 (dd, J = 11.3, 2.4 Hz, 1H), 7.01-7.07 (m, 2H), 7.17 (dd, J = 8.4, 7.2 Hz, 1H)

5-(3-Acetylaminophenoxymethyl)-6-(4-fluoro-2-methoxyphenyl)-2,2,4-trimethyl-1,2-dihydroquinoline (Compound No. 14-4)

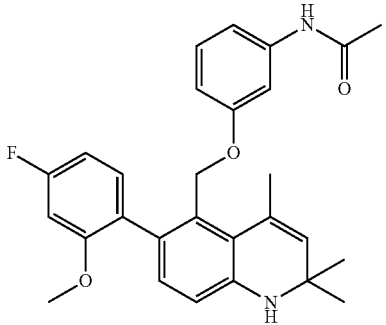

$^1$H-NMR (400 MHz, DMSO-d$_6$) δ 1.15 (s, 3H), 1.19 (s, 3H), 1.99 (s, 3H), 2.03 (s, 3H), 3.72 (s, 3H), 4.48 (d, J = 10.9 Hz, 1H), 4.92 (d, J = 10.9 Hz, 1H), 5.39 (s, 1H), 6.01 (s, 1H), 6.37 (d, J = 6.8 Hz, 1H), 6.62 (d, J = 8.3 Hz, 1H), 6.70 (td, J = 8.5, 2.4 Hz, 1H), 6.73 (d, J = 8.3 Hz, 1H), 6.91 (dd, J = 11.5, 2.4 Hz, 1H), 7.02-7.15 (m, 4H), 9.81 (s, 1H)

6-(4-Fluoro-2-methoxyphenyl)-5-2-hydroxyphenoxymethyl)-2,2,4-trimethyl-1,2-dihydroquinoline (Compound No. 14-5)

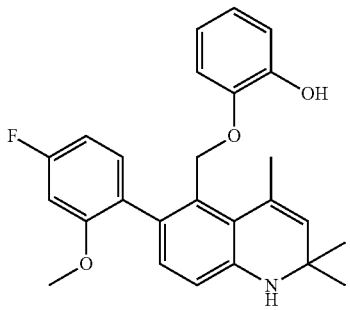

$^1$H-NMR (400 MHz, DMSO-d$_6$) δ 1.16 (s, 3H), 1.17 (s, 3H), 2.11 (s, 3H), 3.70 (s, 3H), 4.37 (d, J = 11.0 Hz, 1H), 5.02 (d, J = 11.0 Hz, 1H), 5.38 (s, 1H), 5.98 (s, 1H), 6.54-6.73 (m, 5H), 6.61 (d, J = 8.3 Hz, 1H), 6.72 (d, J = 8.3 Hz, 1H), 6.88 (dd, J = 11.5, 2.4 Hz, 1H), 7.21 (dd, J = 8.5, 7.2 Hz, 1H), 8.66 (s, 1H)

| | |
|---|---|
| 5-(2-Acetylaminophenoxymethyl)-6-(4-fluoro-2-methoxyphenyl)-2,2,4-trimethyl-1,2-dihydroquinoline (Compound No. 14-6)<br>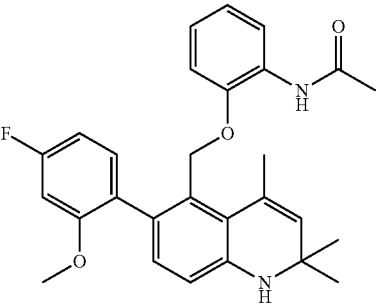 | $^1$H-NMR (500 MHz, DMSO-d$_6$) δ 1.09 (s, 3H), 1.17 (s, 3H), 2.03 (s, 3H), 2.09 (s, 3H), 3.74 (s, 3H), 4.59 (d, J = 11.8 Hz, 1H), 5.11 (d, J = 11.8 Hz, 1H), 5.42 (s, 1H), 6.02 (s, 1H), 6.60 (d, J = 7.5 Hz, 1H), 6.62 (d, J = 8.1 Hz, 1H), 6.72 (dt, J = 8.5, 2.6 Hz, 1H), 6.75 (d, J = 8.1 Hz, 1H), 6.79 (t, J = 7.5 Hz, 1H), 6.87 (t, J = 7.5 Hz, 1H), 6.94 (dd, J = 11.3, 2.6 Hz, 1H), 7.22 (dd, J = 8.5, 7.2 Hz, 1H), 7.85 (d, J = 7.5 Hz, 1H), 8.47 (s, 1H) |
| 5-(5-Amino-2-methylphenoxymethyl)-6-(4-fluoro-2-methoxyphenyl)-2,2,4-trimethyl-1,2-dihydroquinoline (Compound No. 14-7)<br>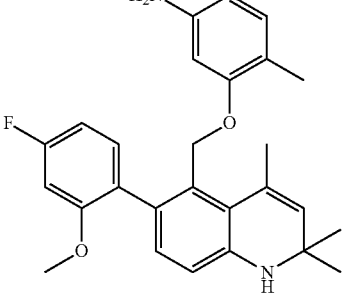 | $^1$H-NMR (400 MHz, DMSO-d$_6$) δ 1.13 (s, 3H), 1.20 (s, 3H), 1.87 (s, 3H), 1.96 (s, 3H), 3.75 (s, 3H), 4.42 (d, J = 11.2 Hz, 1H), 4.71 (br s, 2H), 4.85 (d, J = 11.2 Hz, 1H), 5.37 (s, 1H), 5.89 (s, 1H), 5.97 (dd, J = 8.1, 2.0 Hz, 1H), 6.01 (s, 1H), 6.63 (d, J = 8.1 Hz, 1H), 6.66 (d, J = 8.1 Hz, 1H), 6.73-6.77 (m, 1H), 6.74 (d, J = 8.1 Hz, 1H), 6.95 (dd, J = 11.6, 2.6 Hz, 1H), 7.19 (dd, J = 8.3, 7.1 Hz, 1H) |
| 5-(5-Amino-2-methoxyphenoxymethyl)-6-(4-fluoro-2-methoxyphenyl)-2,2,4-trimethyl-1,2-dihydroquinoline (Compound No. 14-8)<br>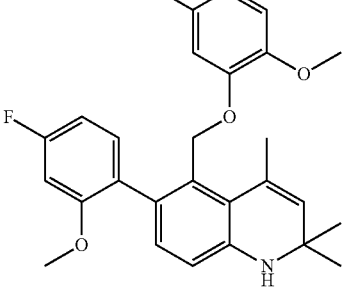 | $^1$H-NMR (400 MHz, DMSO-d$_6$) δ 1.17 (s, 3H), 1.19 (s, 3H), 2.04 (s, 3H), 3.52 (s, 3H), 3.71 (s, 3H), 4.36 (d, J = 11.0 Hz, 1H), 4.64 (br s, 2H), 4.89 (d, J = 11.0 Hz, 1H), 5.37 (s, 1H), 5.97-6.01 (m, 3H), 6.59 (d, J = 8.7 Hz, 1H), 6.63 (d, J = 8.1 Hz, 1H), 6.69 (td, J = 8.4, 2.5 Hz, 1H), 6.73 (d, J = 8.1 Hz, 1H), 6.92 (dd, J = 11.2, 2.5 Hz, 1H), 7.17 (dd, J = 8.4, 7.1 Hz, 1H) |
| 5-(3-Aminophenoxymethyl)-6-(4-fluoro-2-methoxyphenyl)-2,2,4-trimethyl-1,2-dihydroquinoline (Compound No. 14-9)<br>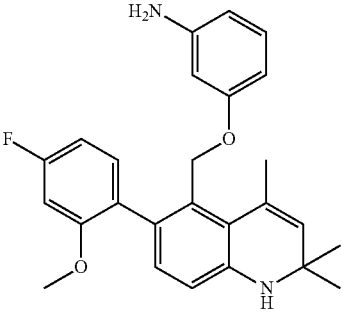 | $^1$H-NMR (500 MHz, DMSO-d$_6$) δ 1.16 (s, 3H), 1.19 (s, 3H), 2.03 (s, 3H), 3.71 (s, 3H), 4.39 (d, J = 10.9 Hz, 1H), 4.85 (d, J = 10.9 Hz, 1H), 4.94 (s, 2H), 5.38 (s, 1H), 5.86 (dd, J = 7.9, 2.0 Hz, 1H), 5.95 (t, J = 2.0 Hz, 1H), 5.98 (s, 1H), 6.07 (dd, J = 7.9, 2.0 Hz, 1H), 6.61 (d, J = 8.2 Hz, 1H), 6.71 (td, J = 8.4, 2.5 Hz, 1H), 6.72 (d, J = 8.2 Hz, 1H), 6.78 (t, J = 7.9 Hz, 1H), 6.91 (dd, J = 11.3, 2.5 Hz, 1H), 7.14 (dd, J = 8.4, 7.2 Hz, 1H) |

| Compound | NMR |
|---|---|
| 6-(2-Methoxy-5-methylphenyl)-5-(2-methyl-5-nitrophenoxymethyl)-2,2,4-trimethyl-1,2-dihydroquinoline (Compound No. 14-10) 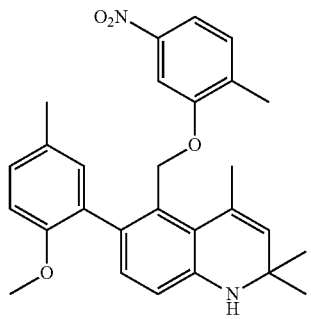 | $^1$H-NMR (500 MHz, DMSO-$d_6$) δ 0.86 (s, 3H), 1.19 (s, 3H), 2.16 (s, 3H), 2.19 (s, 3H), 2.24 (s, 3H), 3.70 (s, 3H), 4.76 (d, J = 12.8 Hz, 1H), 5.34 (d, J = 12.8 Hz, 1H), 5.39 (s, 1H), 5.98 (s, 1H), 6.60 (d, J = 8.2 Hz, 1H), 6.77 (d, J = 8.2 Hz, 1H), 6.93 (d, J = 8.5 Hz, 1H), 7.07 (d, J = 2.1 Hz, 1H), 7.09 (d, J = 2.2 Hz, 1H), 7.10 (dd, J = 8.5, 2.1 Hz, 1H), 7.32 (d, J = 8.5 Hz, 1H), 7.62 (dd, J = 8.5, 2.2 Hz, 1H) |
| 5-(5-Fluoro-2-methphenoxymethyl)-6-(2-methoxy-5-methylphenyl)-2,2,4-trimethyl-1,2-dihydroquinoline (Compound No. 14-11) 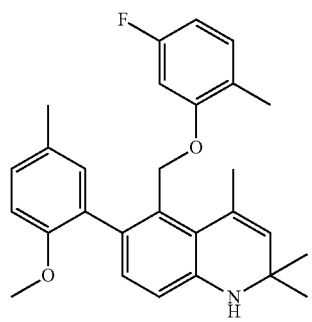 | $^1$H-NMR (400 MHz, DMSO-$d_6$) δ 1.05 (s, 3H), 1.15 (s, 3H), 2.02 (s, 3H), 2.09 (s, 3H), 2.18 (s, 3H), 3.68 (s, 3H), 4.57 (d, J = 12.1 Hz, 1H), 5.09 (d, J = 12.1 Hz, 1H), 5.39 (s, 1H), 5.99 (s, 1H), 6.32 (dd, J = 11.5, 2.4 Hz, 1H), 6.52 (td, J = 8.4, 2.4 Hz, 1H), 6.62 (d, J = 8.2 Hz, 1H), 6.77 (d, J = 8.2 Hz, 1H), 6.93 (d, J = 8.3 Hz, 1H), 6.96 (d, J = 2.2 Hz, 1H), 7.01-7.05 (m, 1H), 7.08 (dd, J = 8.3, 2.2 Hz, 1H) |
| 6-(5-Chloro-2-methoxyphenyl)-5-(2-methyl-5-nitrophenoxymethyl)-2,2,4-trimethyl-1,2-dihydroquinoline (Compound No. 14-12) 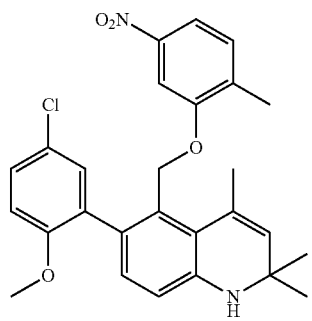 | $^1$H-NMR (400 MHz, DMSO-$d_6$) δ 0.92 (s, 3H), 1.18 (s, 3H), 2.13 (s, 3H), 2.19 (s, 3H), 3.74 (s, 3H), 4.71 (d, J = 12.6 Hz, 1H), 5.32 (d, J = 12.6 Hz, 1H), 5.41 (s, 1H), 6.09 (s, 1H), 6.62 (d, J = 8.2 Hz, 1H), 6.80 (d, J = 8.2 Hz, 1H), 7.06 (d, J = 8.8 Hz, 1H), 7.17 (d, J = 2.2 Hz, 1H), 7.25 (d, J = 2.7 Hz, 1H), 7.33 (dd, J = 8.8, 2.7 Hz, 1H), 7.33 (d, J = 8.4 Hz, 1H), 7.64 (dd, J = 8.4, 2.2 Hz, 1H) |
| 6-(5-Chloro-2-methoxyphenyl)-5-(5-fluoro-2-methylphenoxymethyl)-2,2,4-trimethyl-1,2-dihydroquinoline (Compound No. 14-13) 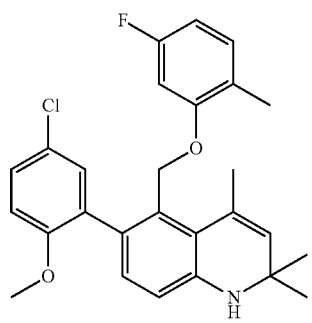 | $^1$H-NMR (400 MHz, DMSO-$d_6$) δ 1.10 (s, 3H), 1.15 (s, 3H), 2.03 (s, 3H), 2.07 (s, 3H), 3.72 (s, 3H), 4.52 (d, J = 12.0 Hz, 1H), 5.08 (d, J = 12.0 Hz, 1H), 5.41 (s, 1H), 6.09 (s, 1H), 6.42 (dd, J = 11.5, 2.4 Hz, 1H), 6.54 (dd, J = 8.4, 2.4 Hz, 1H), 6.64 (d, J = 8.2 Hz, 1H), 6.78 (d, J = 8.2 Hz, 1H), 7.03-7.07 (m, 1H), 7.06 (d, J = 8.8 Hz, 1H), 7.16 (d, J = 2.8 Hz, 1H), 7.32 (dd, J = 8.8, 2.8 Hz, 1H) |

| Compound | NMR |
|---|---|
| 6-(2-Methoxy-5-trifluoromethylphenyl)-5-(2-methyl-5-nitrophenoxymethyl)-2,2,4-trimethyl-1,2-dihydroquinoline (Compound No. 14-14)<br />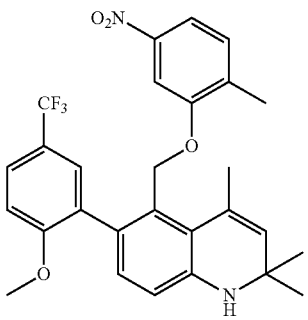 | $^1$H-NMR (400 MHz, DMSO-d$_6$) δ 0.95 (s, 3H), 1.18 (s, 3H), 2.13 (s, 3H), 2.17 (s, 3H), 3.82 (s, 3H), 4.67 (d, J = 12.5 Hz, 1H), 5.31 (d, J = 12.5 Hz, 1H), 5.42 (s, 1H), 6.13 (s, 1H), 6.64 (d, J = 8.2 Hz, 1H), 6.82 (d, J = 8.2 Hz, 1H), 7.17 (d, J = 2.3 Hz, 1H), 7.24 (d, J = 8.5 Hz, 1H), 7.33 (d, J = 8.2 Hz, 1H), 7.52 (d, J = 2.1 Hz, 1H), 7.63 (d, J = 8.2, 2.3 Hz, 1H), 7.65 (dd, J = 8.5, 2.1 Hz, 1H) |
| 5-(5-Fluoro-2-methylphenoxymethyl)-6-(2-methoxy-5-trifluoromethylphenyl)-2,2,4-trimethyl-1,2-dihydroquinoline (Compound No. 14-15)<br />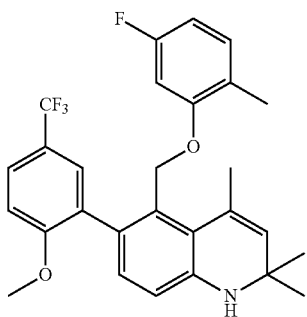 | $^1$H-NMR (400 MHz, DMSO-d$_6$) δ 1.11 (s, 3H), 1.16 (s, 3H), 2.01 (s, 3H), 2.08 (s, 3H), 3.81 (s, 3H), 4.47 (d, J = 11.8 Hz, 1H), 5.07 (d, J = 11.8 Hz, 1H), 5.42 (s, 1H), 6.12 (s, 1H), 6.39 (dd, J = 11.4, 2.3 Hz, 1H), 6.53 (td, J = 8.5, 2.3 Hz, 1H), 6.66 (d, J = 8.3 Hz, 1H), 6.81 (d, J = 8.3 Hz, 1H), 7.02-7.06 (m, 1H), 7.23 (d, J = 8.6 Hz, 1H), 7.44 (d, J = 2.0 Hz, 1H), 7.64 (dd, J = 8.6, 2.0 Hz, 1H) |
| 6-(2-Methoxy-5-methylphenyl)-5-(2-methoxy-5-nitrophenoxymethyl)-2,2,4-trimethyl-1,2-dihydroquinoline (Compound No. 14-16)<br />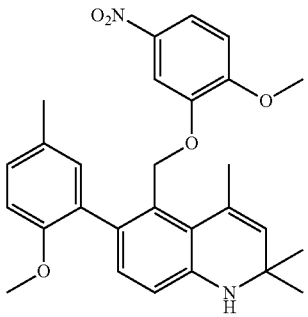 | $^1$H-NMR (400 MHz, DMSO-d$_6$) δ 1.02 (s, 3H), 1.18 (s, 3H), 2.12 (s, 3H), 2.16 (s, 3H), 3.65 (s, 3H), 3.82 (s, 3H), 4.58 (d, J = 11.9 Hz, 1H), 5.30 (d, J = 11.9 Hz, 1H), 5.39 (s, 1H), 5.97 (s, 1H), 6.60 (d, J = 8.3 Hz, 1H), 6.74 (d, J = 8.3 Hz, 1H), 6.87 (d, J = 8.3 Hz, 1H), 6.95 (d, J = 2.2 Hz, 1H), 7.03 (dd, J = 8.3, 2.2 Hz, 1H), 7.09 (d, J = 9.0 Hz, 1H), 7.27 (d, J = 2.7 Hz, 1H), 7.80 (dd, J = 9.00, 2.7 Hz, 1H) |
| 5-(5-Chloro-2-methylphenoxymethyl)-6-(2-methoxy-5-methylphenyl)-2,2,4-trimethyl-1,2-dihydroquinoline (Compound No. 14-17)<br />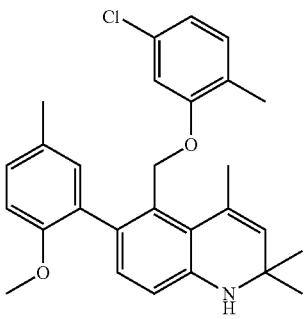 | $^1$H-NMR (500 MHz, DMSO-d$_6$) δ 0.96 (s, 3H), 1.18 (s, 3H), 2.04 (s, 3H), 2.14 (s, 3H), 2.21 (s, 3H), 3.69 (s, 3H), 4.60 (d, J = 12.5 Hz, 1H), 5.18 (d, J = 12.5 Hz, 1H), 5.39 (s, 1H), 5.97 (s, 1H), 6.39 (d, J = 2.2 Hz, 1H), 6.61 (d, J = 8.2 Hz, 1H), 6.74 (dd, J = 8.5, 2.2 Hz, 1H), 6.76 (d, J = 8.2 Hz, 1H), 6.94 (d, J = 8.5 Hz, 1H), 7.00 (d, J = 2.2 Hz, 1H), 7.03 (d, J = 8.2 Hz, 1H), 7.11 (dd, J = 8.2, 2.2 Hz, 1H) |

| Compound | NMR |
|---|---|
| 5-(5-Fluoro-2-methoxyphenoxymethyl)-6-(2-methoxy-5-methylphenyl)-2,2,4-trimethyl-1,2-dihydroquinoline (Compound No. 14-18) 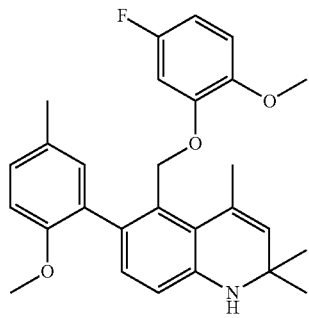 | $^1$H-NMR (500 MHz, DMSO-$d_6$) δ 1.15 (s, 6H), 2.08 (s, 3H), 2.12 (s, 3H), 3.64 (s, 3H), 3.66 (s, 3H), 4.42 (d, J = 11.5 Hz, 1H), 5.10 (d, J = 11.5 Hz, 1H), 5.39 (s, 1H), 5.96 (s, 1H), 6.52 (dd, J = 10.5, 2.9 Hz, 1H), 6.59 (td, J = 8.8, 2.9 Hz, 1H), 6.62 (d, J = 7.9 Hz, 1H), 6.75 (d, J = 7.9 Hz, 1H), 6.89 (dd, J = 8.8, 5.5 Hz, 1H), 6.88 (d, J = 8.3 Hz, 1H), 6.95 (d, J = 2.2 Hz, 1H), 7.02 (dd, J = 8.3, 2.2 Hz, 1H) |
| 5-(2-Methoxycarbonylmethylphenoxymethyl)-6-(2-methoxy-5-methylphenyl)-2,2,4-trimethyl-1,2-dihydroquinoline (Compound No. 14-19) 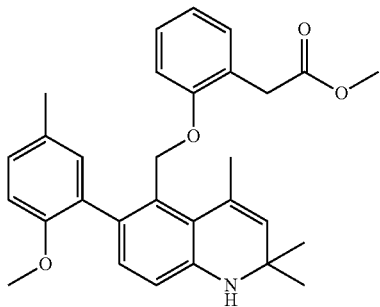 | $^1$H-NMR (400 MHz, DMSO-$d_6$) δ 1.09 (s, 3H), 1.17 (s, 3H), 2.02 (s, 3H), 2.16 (s, 3H), 3.49 (s, 3H), 3.49 (d, J = 16.3 Hz, 1H), 3.55 (d, J = 16.3 Hz, 1H), 3.66 (s, 3H), 4.57 (d, J = 11.7 Hz, 1H), 5.04 (d, J = 11.7 Hz, 1H), 5.37 (s, 1H), 5.96 (s, 1H), 6.56 (d, J = 7.7 Hz, 1H), 6.62 (d, J = 8.2 Hz, 1H), 6.75 (d, J = 8.2 Hz, 1H), 6.79 (td, J = 7.7, 1.6 Hz, 1H), 6.90 (d, J = 8.2 Hz, 1H), 6.94 (d, J = 1.9 Hz, 1H), 7.06 (dd, J = 8.2, 1.9 Hz, 1H), 7.06 (td, J = 7.7, 1.6 Hz, 1H), 7.10 (dd, J = .7.7, 1.6 Hz, 1H) |
| 6-(4-Fluoro-2-methoxyphenyl)-5-(3-hydroxyphenoxymethyl)-2,2,4-trimethyl-1,2-dihydroquinoline (Compound No. 14-20) 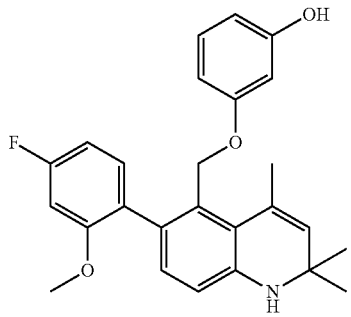 | $^1$H-NMR (400 MHz, DMSO-$d_6$) δ 1.14 (s, 3H), 1.18 (s, 3H), 2.05 (s, 3H), 3.71 (s, 3H), 4.44 (d, J = 11.2 Hz, 1H), 4.90 (d, J = 11.2 Hz, 1H), 5.38 (s, 1H), 5.98 (s, 1H), 6.10-6.15 (m, 2H), 6.27 (ddd, J = 8.1, 0.9, 0.5 Hz, 1H), 6.61 (d, J = 8.2 Hz, 1H), 6.70 (td, J = 8.2, 2.6 Hz, 1H), 6.72 (d, J = 8.2 Hz, 1H), 6.91 (dd, J = 11.7, 2.6 Hz, 1H), 6.93 (t, J = 8.1 Hz, 1H), 7.14 (dd, J = 8.4, 7.1 Hz, 1H), 9.26 (s, 1H) |
| 5-(2-Allylphenoxymethyl)-6-(2-methoxy-5-methylphenyl)-2,2,4-trimethyl-1,2-dihydroquinoline (Compound No. 14-21) 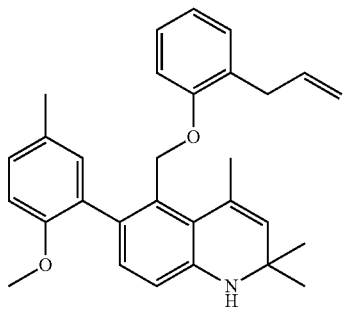 | $^1$H-NMR (400 MHz, DMSO-$d_6$) δ 1.10 (s, 3H), 1.18 (s, 3H), 2.03 (s, 3H), 2.17 (s, 3H), 3.19 (dd, J = 15.0, 6.9 Hz, 1H), 3.25 (dd, J = 15.0, 6.9 Hz, 1H), 3.67 (s, 3H), 4.60 (d, J = 11.7 Hz, 1H), 4.91-4.99 (m, 2H), 5.05 (d, J = 11.7 Hz, 1H), 5.38 (s, 1H), 5.88 (ddt, J = 16.1, 10.0, 6.9 Hz, 1H), 5.98 (s, 1H), 6.57 (d, J = 7.8 Hz, 1H), 6.63 (d, J = 8.2 Hz, 1H), 6.76 (d, J = 8.2 Hz, 1H), 6.78 (td, J = 7.8, 0.9 Hz, 1H), 6.91 (d, J = 8.0 Hz, 1H), 6.96 (d, J = 1.8 Hz, 1H), 7.01 (td, J = 8.0, 1.8 Hz, 1H), 7.03 (d, J = 7.8 Hz, 1H), 7.06 (dd, J = 7.8, 0.9 Hz, 1H) |

| | |
|---|---|
| 6-(5-Chloro-2-methoxyphenyl)-5-(2-methoxy-5-nitrophenoxymethyl)-2,2,4-trimethyl-1,2-dihydroquinoline (Compound No. 14-22) 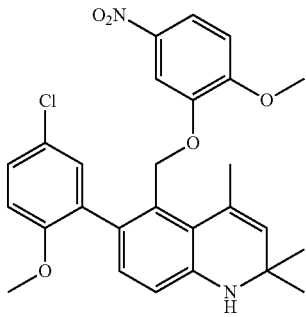 | $^1$H-NMR (400 MHz, DMSO-$d_6$) δ 1.08 (s, 3H), 1.17 (s, 3H), 2.15 (s, 3H), 3.69 (s, 3H), 3.84 (s, 3H), 4.50 (d, J = 11.7 Hz, 1H), 5.31 (d, J = 11.7 Hz, 1H), 5.41 (s, 1H), 6.07 (s, 1H), 6.62 (d, J = 8.2 Hz, 1H), 6.76 (d, J = 8.2 Hz, 1H), 7.00 (d, J = 8.9 Hz, 1H), 7.10 (d, J = 9.0 Hz, 1H), 7.14 (d, J = 2.7 Hz, 1H), 7.25 (dd, J = 8.9, 2.7 Hz, 1H), 7.36 (d, J = 2.7 Hz, 1H), 7.82 (dd, J = 9.0, 2.7 Hz, 1H) |
| 5-(2-Methoxy-5-nitrophenoxymethyl)-6-(2-methoxy-5-trifluoromethylphenyl)-2,2,4-trimethyl-1,2-dihydroquinoline (Compound No. 14-23) 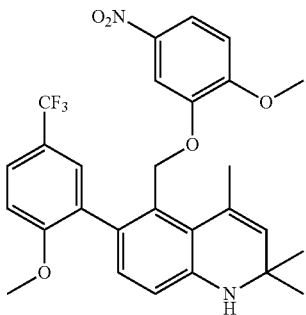 | $^1$H-NMR (400 MHz, DMSO-$d_6$) δ 1.12 (s, 3H), 1.17 (s, 3H), 2.14 (s, 3H), 3.78 (s, 3H), 3.82 (s, 3H), 4.43 (d, J = 11.7 Hz, 1H), 5.29 (d, J = 11.7 Hz, 1H), 5.42 (s, 1H), 6.11 (s, 1H), 6.65 (d, J = 8.3 Hz, 1H), 6.80 (d, J = 8.3 Hz, 1H), 7.09 (d, J = 9.1 Hz, 1H), 7.18 (d, J = 8.8 Hz, 1H), 7.36 (d, J = 2.7 Hz, 1H), 7.43 (d, J = 2.3 Hz, 1H), 7.57 (dd, J = 9.1, 2.3 Hz, 1H), 7.82 (dd, J = 8.8, 2.7 Hz, 1H) |
| 5-(5-Chloro-2-methylphenoxymethyl)-6-(2-methoxy-5-trifluoromethylphenyl)-2,2,4-trimethyl-1,2-dihydroquinoline (Compound No. 14-24) 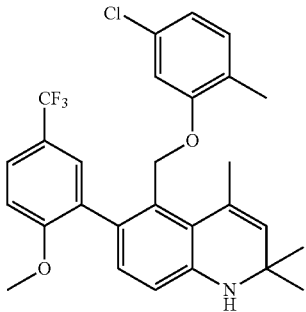 | $^1$H-NMR (500 MHz, DMSO-$d_6$) δ 1.04 (s, 3H), 1.17 (s, 3H), 2.02 (s, 3H), 2.10 (s, 3H), 3.82 (s, 3H), 4.51 (d, J = 12.4 Hz, 1H), 5.15 (d, J = 12.4 Hz, 1H), 5.42 (s, 1H), 6.11 (s, 1H), 6.47 (d, J = 2.0 Hz, 1H), 6.65 (d, J = 8.1 Hz, 1H), 6.75 (dd, J = 8.0, 2.0 Hz, 1H), 6.81 (d, J = 8.1 Hz, 1H), 7.04 (d, J = 8.0 Hz, 1H), 7.24 (d, J = 8.7 Hz, 1H), 7.46 (d, J = 2.3 Hz, 1H), 7.61 (dd, J = 8.7, 2.3 Hz, 1H) |
| 5-(5-Fluoro-2-methoxyphenoxymethyl)-6-(2-methoxy-5-trifluoromethylphenyl)-2,2,4-trimethyl-1,2-dihydroquinoline (Compound No. 14-25) 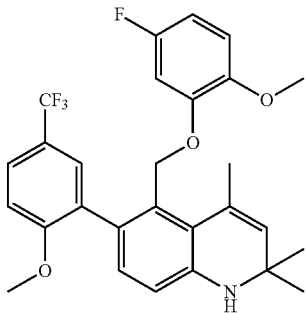 | $^1$H-NMR (500 MHz, DMSO-$d_6$) δ 1.16 (s, 3H), 1.19 (s, 3H), 2.10 (s, 3H), 3.64 (s, 3H), 3.77 (s, 3H), 4.30 (d, J = 11.2 Hz, 1H), 5.09 (d, J = 11.2 Hz, 1H), 5.42 (s, 1H), 6.10 (s, 1H), 6.55-6.60 (m, 2H), 6.66 (d, J = 8.3 Hz, 1H), 6.79 (d, J = 8.3 Hz, 1H), 6.83 (dd, J = 8.7, 5.7 Hz, 1H), 7.19 (d, J = 8.8 Hz, 1H), 7.42 (d, J = 2.3 Hz, 1H), 7.58 (dd, J = 8.8, 2.3 Hz, 1H) |

| | |
|---|---|
| 5-(2-Methoxycarbonylmethylphenoxymethyl)-6-(2-methoxy-5-trifluoromethylphenyl)-2,2,4-trimethyl-1,2-dihydroquinoline (Compound No. 14-26) 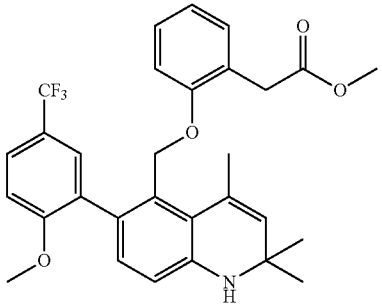 | $^1$H-NMR (500 MHz, DMSO-d$_6$) δ 1.12 (s, 3H), 1.18 (s, 3H), 2.02 (s, 3H), 3.45 (d, J = 16.4 Hz, 1H), 3.46 (s, 3H), 3.53 (d, J = 16.4 Hz, 1H), 3.79 (s, 3H), 4.57 (d, J = 11.8 Hz, 1H), 5.05 (d, J = 11.8 Hz, 1H), 5.40 (s, 1H), 6.08 (s, 1H), 6.57 (d, J = 8.3 Hz, 1H), 6.65 (d, J = 8.3 Hz, 1H), 6.73-6.80 (m, 1H), 6.79 (d, J = 8.3 Hz, 1H), 7.05 (td, J = 7.6, 2.3 Hz, 1H), 7.11 (dd, J = 7.6, 1.7 Hz, 1H), 7.21 (d, J = 8.8 Hz, 1H), 7.43 (d, J = 2.3 Hz, 1H), 7.63 (dd, J = 8.8, 2.3 Hz, 1H) |
| 6-(5-Chloro-2-methoxyphenyl)-5-(5-chloro-2-methylphenoxymethyl)-2,2,4-trimethyl-1,2-dihydroquinoline (Compound No. 14-27) 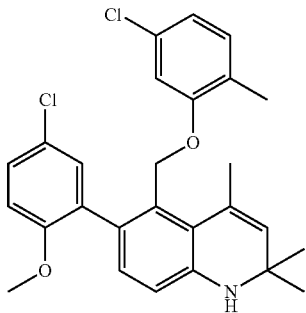 | $^1$H-NMR (500 MHz, DMSO-d$_6$) δ 1.01 (s, 3H), 1.17 (s, 3H), 2.04 (s, 3H), 2.11 (s, 3H), 3.73 (s, 3H), 4.55 (d, J = 12.4 Hz, 1H), 5.16 (d, J = 12.4 Hz, 1H), 5.41 (s, 1H), 6.07 (s, 1H), 6.48 (d, J = 1.8 Hz, 1H), 6.63 (d, J = 8.3 Hz, 1H), 6.75-6.79 (m, 1H), 6.78 (d, J = 8.3 Hz, 1H), 7.05 (d, J = 8.1 Hz, 1H), 7.07 (d, J = 8.8 Hz, 1H), 7.18 (d, J = 2.6 Hz, 1H), 7.34 (dd, J = 8.8, 2.6 Hz, 1H) |
| 6-(5-Chloro-2-methoxyphenyl)-5-(5-fluoro-2-methoxyphenoxymethyl)-2,2,4-trimethyl-1,2-dihydroquinoline (Compound No. 14-28) 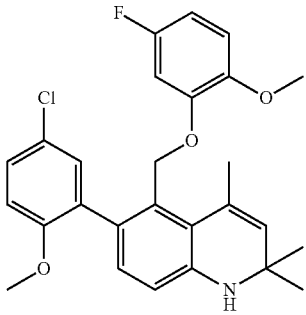 | $^1$H-NMR (400 MHz, DMSO-d$_6$) δ 1.16 (s, 3H), 1.18 (s, 3H), 2.11 (s, 3H), 3.67 (s, 3H), 3.68 (s, 3H), 4.36 (d, J = 11.4 Hz, 1H), 5.10 (d, J = 11.4 Hz, 1H), 5.41 (s, 1H), 6.07 (s, 1H), 6.57-6.63 (m, 2H), 6.63 (d, J = 8.1 Hz, 1H), 6.76 (d, J = 8.1 Hz, 1H), 6.86 (dd, J = 8.5, 5.6 Hz, 1H), 7.01 (d, J = 8.9 Hz, 1H), 7.14 (d, J = 2.7 Hz, 1H), 7.25 (dd, J = 8.9, 2.7 Hz, 1H) |
| 6-(2-Methoxy-5-trifluoromethylphenyl)-5-(3-methylphenoxymethyl)-2,2,4-trimethyl-1,2-dihydroquinoline (Compound No. 14-29) 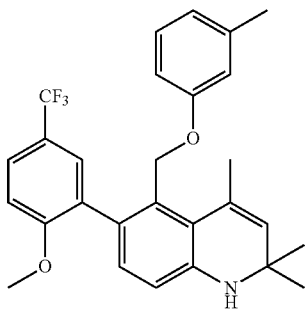 | $^1$H-NMR (400 MHz, DMSO-d$_6$) δ 1.15 (s, 3H), 1.17 (s, 3H), 2.10 (s, 3H), 2.17 (s, 3H), 3.78 (s, 3H), 4.38 (d, J = 11.4 Hz, 1H), 5.04 (d, J = 11.4 Hz, 1H), 5.42 (s, 1H), 6.07 (s, 1H), 6.47-6.48 (m, 2H), 6.62-6.65 (m, 1H), 6.63 (d, J = 8.2 Hz, 1H), 6.78 (d, J = 8.2 Hz, 1H), 7.01 (dd, J = 8.8, 7.6 Hz, 1H), 7.20 (d, J = 8.8 Hz, 1H), 7.43 (d, J = 2.2 Hz, 1H), 7.61 (dd, J = 8.8, 2.2 Hz, 1H) |

| | |
|---|---|
| 6-(2-Methoxy-5-trifluoromethylphenyl)-5-(2-methyl-phenoxymethyl)-2,2,4-trimethyl-1,2-dihydroquinoline (Compound No. 14-30)<br>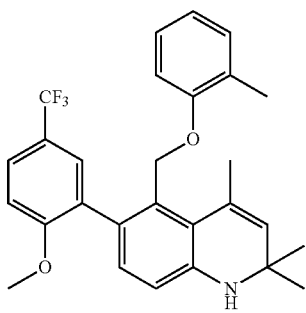 | $^1$H-NMR (400 MHz, DMSO-d$_6$) δ 1.13 (s, 3H), 1.17 (s, 3H), 2.04 (s, 3H), 2.05 (s, 3H), 3.81 (s, 3H), 4.46 (d, J = 11.5 Hz, 1H), 5.04 (d, J = 11.5 Hz, 1H), 5.41 (s, 1H), 6.11 (s, 1H), 6.55 (d, J = 7.2 HZ, 1H), 6.65 (d, J = 8.3 Hz, 1H), 6.72 (t, J = 7.2 Hz, 1H), 6.80 (d, J = 8.3 Hz, 1H), 6.96 (t, J = 7.2 Hz, 1H), 7.04 (d, J = 7.2 Hz, 1H), 7.22 (d, J = 8.8 Hz, 1H), 7.45 (d, J = 2.2 Hz, 1H), 7.64 (dd, J = 8.8, 2.2 Hz, 1H) |
| 5-(2-Ethylphenoxymethyl)-6-(2-methoxy-5-trifluoro-methylphenyl)-2,2,4-trimethyl-1,2-dihydroquinoline (Compound No. 14-31)<br>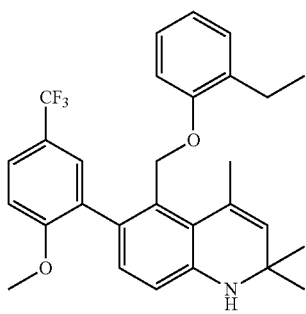 | $^1$H-NMR (400 MHz, DM SO-d$_6$) δ 1.03 (t, J = 7.6 Hz, 3H), 1.14 (s, 3H), 1.18 (s, 3H), 2.04 (s, 3H), 2.42-2.49 (m, 2H), 3.79 (s, 3H), 4.48 (d, J = 11.5 Hz, 1H), 5.03 (d, J = 11.5 Hz, 1H), 5.40 (s, 1H), 6.11 (s, 1H), 6.58 (d, J = 7.5 Hz, 1H), 6.66 (d, J = 8.2 Hz, 1H), 6.76 (t, J = 7.5 Hz, 1H), 6.80 (d, J = 8.2 Hz, 1H), 6.97 (td, J = 7.5, 1.6 Hz, 1H), 7.05 (dd, J = 7.5, 1.6 Hz, 1H), 7.22 (d, J = 8.5 Hz, 1H), 7.44 (d, J = 2.0 Hz, 1H), 7.63 (dd, J = 8.5, 2.0 Hz, 1H) |
| 6-(2-Methoxy-5-trifluoromethylphenyl)-5-(2,3,5-tri-methylphenoxymethyl)-2,2,4-trimethyl-1,2-dihydroquinoline (Compound No. 14-32)<br>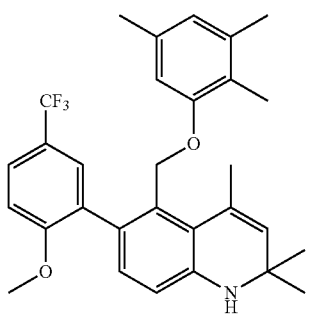 | $^1$H-NMR (400 MHz, DMSO-d$_6$) δ 1.08 (s, 3H), 1.19 (s, 3H), 1.91 (s, 3H), 2.07 (s, 6H), 2.08 (s, 3H), 3.81 (s, 3H), 4.46 (d, J = 11.9 Hz, 1H), 5.04 (d, J = 11.9 Hz, 1H), 5.40 (s, 1H), 6.09 (s, 1H), 6.15 (s, 1H), 6.44 (s, 1H), 6.64 (d, J = 8.3 Hz, 1H), 6.79 (d, J = 8.3 Hz, 1H), 7.23 (d, J = 8.5 Hz, 1H), 7.46 (d, J = 2.2 Hz, 1H), 7.65 (dd, J = 8.5, 2.2 Hz, 1H) |
| 5-(2-Isopropylphenoxymethyl)-6-(2-methoxy-5-tri-fluoromethylphenyl)-2,2,4-trimethyl-1,2-dihydroquinoline (Compound No. 14-33)<br>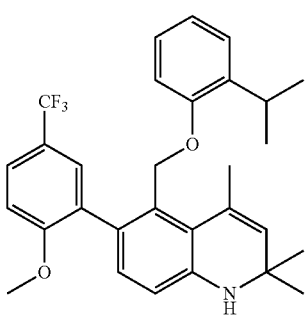 | $^1$H-NMR (500 MHz, DMSO-d$_6$) δ 1.06 (d, J = 6.7 Hz, 6H), 1.15 (s, 3H), 1.19 (s, 3H), 2.02 (s, 3H), 3.12-3.16 (m, 1H), 3.79 (s, 3H), 4.51 (d, J = 11.5 Hz, 1H), 5.02 (d, J = 11.5 Hz, 1H), 5.39 (s, 1H), 6.11 (s, 1H), 6.60 (d, J = 7.8 Hz, 1H), 6.67 (d, J = 8.1 Hz, 1H), 6.79-6.82 (m, 1H), 6.80 (d, J = 8.1 Hz, 1H), 6.98 (td, J = 7.8, 2.2 Hz, 1H), 7.11 (dd, J = 7.8, 2.2 Hz, 1H), 7.22 (d, J = 8.8 Hz, 1H), 7.42 (d, J = 2.3 Hz, 1H), 7.63 (dd, J = 8.8, 2.3 Hz, 1H) |

| Compound | NMR |
|---|---|
| 5-(2,5-Dimethylphenoxymethyl)-6-(2-methoxy-5-tri-fluoromethylphenyl)-2,2,4-trimethyl-1,2-dihydroquinoline (Compound No. 14-34) 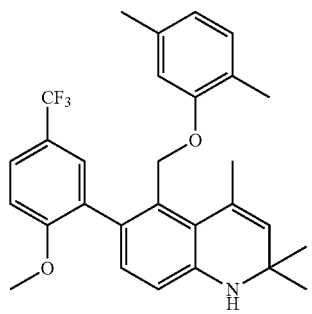 | $^1$H-NMR (400 MHz, DMSO-d$_6$) δ 1.06 (s, 3H), 1.18 (s, 3H), 1.99 (s, 3H), 2.09 (s, 3H), 2.10 (s, 3H), 3.81 (s, 3H), 4.47 (d, J = 12.0 Hz, 1H), 5.08 (d, J = 12.0 Hz, 1H), 5.41 (s, 1H), 6.09 (s, 1H), 6.27 (s, 1H), 6.51 (d, J = 7.7 Hz, 1H), 6.64 (d, J = 8.2 Hz, 1H), 6.79 (d, J = 8.2 Hz, 1H), 6.89 (d, J = 7.7 Hz, 1H), 7.24 (d, J = 8.5 Hz, 1H), 7.48 (d, J = 2.2 Hz, 1H), 7.66 (dd, J = 8.5, 2.2 Hz, 1H) |
| 5-(2-Methoxy-5-methylphenoxymethyl)-6-(2-methoxy-5-tri-fluoromethylphenyl)-2,2,4-trimethyl-1,2-dihydroquinoline (Compound No. 14-35) 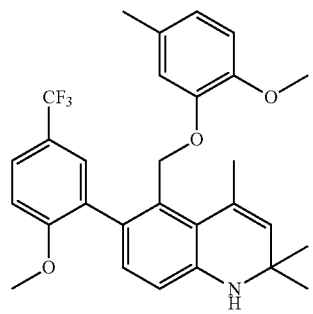 | $^1$H-NMR (400 MHz, DMSO-d$_6$) δ 1.17 (s, 3H), 1.18 (s, 3H), 2.09 (s, 3H), 2.13 (s, 3H), 3.59 (s, 3H), 3.77 (s, 3H), 4.32 (d, J = 11.2 Hz, 1H), 5.08 (d, J = 11.2 Hz, 1H), 5.41 (s, 1H), 6.07 (s, 1H), 6.41 (s, 1H), 6.58 (d, J = 8.3 Hz, 1H), 6.64 (d, J = 8.3 Hz, 1H), 6.72 (d, J = 8.3 Hz, 1H), 6.77 (d, J = 8.3 Hz, 1H), 7.19 (d, J = 8.5 Hz, 1H), 7.44 (d, J = 2.2 Hz, 1H), 7.61 (dd, J = 8.5, 2.2 Hz, 1H) |
| 6-(2-Methoxy-5-trifluoromethylphenyl)-5-[2-(1-prophenyl)phenoxymethyl]-2,2,4-trimethyl-1,2-dihydroquinoline (Compound No. 14-36) 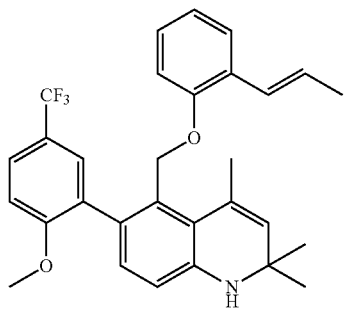 | $^1$H-NMR (400 MHz, DMSO-d$_6$) δ 1.19 (s, 3H), 1.21 (s, 3H), 1.76 (dd, J = 6.6, 1.7 Hz, 3H), 2.02 (s, 3H), 3.78 (s, 3H), 4.53 (d, J = 11.2 Hz, 1H), 5.01 (d, J = 11.2 Hz, 1H), 5.42 (s, 1H), 6.10-6.18 (m, 1H), 6.14 (s, 1H), 6.52 (d, J = 17.8 Hz, 1H), 6.63 (d, J = 7.3 Hz, 1H), 6.68 (d, J = 8.3 Hz, 1H), 6.77-6.63 (m, 1H), 6.80 (d, J = 8.3 Hz, 1H), 7.01 (t, J = 7.3 Hz, 1H), 7.21 (d, J = 8.9 Hz, 1H), 7.34 (d, J = 7.3 Hz, 1H), 7.43 (d, J = 2.2 Hz, 1H), 7.62 (dd, J = 8.9, 2.2 Hz, 1H) |
| 5-(2-Allylphenoxymethyl)-6-(2-methoxy-5-trifluoro-methylphenyl)-2,2,4-trimethyl-1,2-dihydroquinoline (Compound No. 14-37) 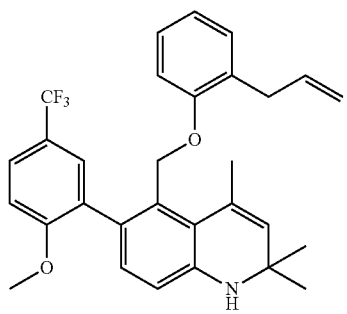 | $^1$H-NMR (400 MHz, DMSO-d$_6$) δ 1.13 (s, 3H), 1.18 (s, 3H), 2.04 (s, 3H), 3.19-3.23 (m, 2H), 3.80 (s, 3H), 4.52 (d, J = 11.6 Hz, 1H), 4.91-4.97 (m, 2H), 5.05 (d, J = 11.6 Hz, 1H), 5.41 (s, 1H), 5.80-5.90 (m, 1H), 6.11 (s, 1H), 6.59 (d, J = 8.3 Hz, 1H), 6.66 (d, J = 8.2 Hz, 1H), 6.76-6.81 (m, 1H), 6.80 (d, J = 8.2 Hz, 1H), 6.98-7.02 (m, 1H), 7.02 (d, J = 7.4 Hz, 1H), 7.23 (d, J = 8.6 Hz, 1H), 7.43 (d, J = 2.1 Hz, 1H), 7.62 (dd, J = 8.6, 2.1 Hz, 1H) |

| Compound | NMR |
|---|---|
| 5-(2,5-Dichlorophenoxymethyl)-6-(2-methoxy-5-trifluoromethylphenyl)-2,2,4-trimethyl-1,2-dihydroquinoline (Compound No. 14-38) 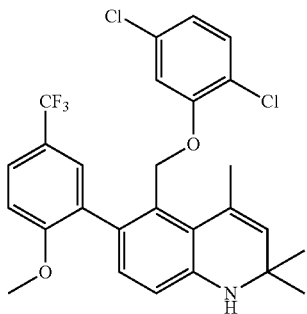 | $^1$H-NMR (400 MHz, DMSO-$d_6$) δ 1.09 (s, 3H), 1.16 (s, 3H), 2.12 (s, 3H), 3.80 (s, 3H), 4.50 (d, J = 12.1 Hz, 1H), 5.22 (d, J = 12.1 Hz, 1H), 5.42 (s, 1H), 6.14 (s, 1H), 6.66 (d, J = 8.2 Hz, 1H), 6.76 (d, J = 2.3 Hz, 1H), 6.82 (d, J = 8.2 Hz, 1H), 6.91 (dd, J = 8.5, 2.3 Hz, 1H), 7.23 (d, J = 8.6 Hz, 1H), 7.35 (d, J = 8.5 Hz, 1H), 7.46 (d, J = 2.0 Hz, 1H), 7.64 (dd, J = 8.6, 2.0 Hz, 1H) |
| 5-(2,5-Dimethylphenoxymethyl)-6-(2-methoxy-5-methylphenyl)-2,2,4-trimethyl-1,2-dihydroquinoline (Compound No. 14-39) 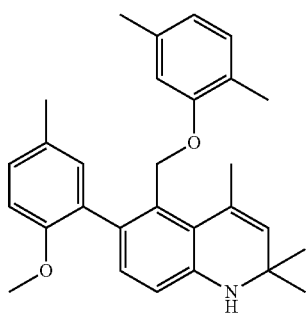 | $^1$H-NMR (400 MHz, DMSO-$d_6$) δ 1.02 (s, 3H), 1.19 (s, 3H), 2.01 (s, 3H), 2.10 (s, 3H), 2.11 (s, 3H), 2.21 (s, 3H), 3.69 (s, 3H), 4.58 (d, J = 12.1 Hz, 1H), 5.09 (d, J = 12.1 Hz, 1H), 5.38 (s, 1H), 5.95 (s, 1H), 6.24 (s, 1H), 6.50 (d, J = 7.3 Hz, 1H), 6.60 (d, J = 8.3 Hz, 1H), 6.75 (d, J = 8.3 Hz, 1H), 6.88 (d, J = 7.3 Hz, 1H), 6.94 (d, J = 8.3 Hz, 1H), 7.01 (d, J = 1.8 Hz, 1H), 7.10 (dd, J = 8.3, 1.8 Hz, 1H) |
| 5-(2,5-Dimethylphenoxymethyl)-6-(5-fluoro-2-methoxyphenyl)-2,2,4-trimethyl-1,2-dihydroquinoline (Compound No. 14-40) 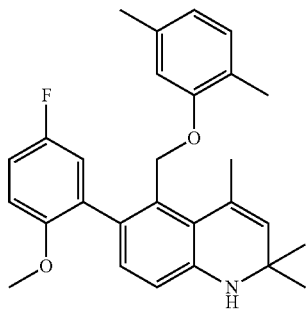 | $^1$H-NMR (400 MHz, DMSO-$d_6$) δ 1.06 (s, 3H), 1.19 (s, 3H), 2.00 (s, 3H), 2.08 (s, 3H), 2.13 (s, 3H), 3.71 (s, 3H), 4.57 (d, J = 12.1 Hz, 1H), 5.08 (d, J = 12.1 Hz, 1H), 5.39 (s, 1H), 6.05 (s, 1H), 6.30 (s, 1H), 6.52 (d, J = 7.3 Hz, 1H), 6.62 (d, J = 8.3 Hz, 1H), 6.78 (d, J = 8.3 Hz, 1H), 6.89 (d, J = 7.3 Hz, 1H), 7.02 (dd, J = 9.3, 3.2 Hz, 1H), 7.05 (dd, J = 8.7, 4.3 Hz, 1H), 7.13 (td, J = 8.7, 3.2 Hz, 1H) |
| 5-(5-Chloro-2-methylphenoxymethyl)-6-(5-fluoro-2-methoxyphenyl)-2,2,4-trimethyl-1,2-dihydroquinoline (Compound No. 14-41) 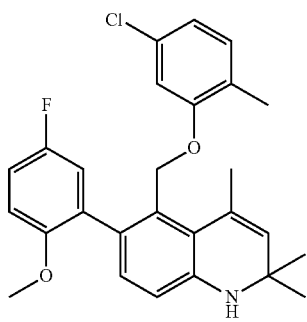 | $^1$H-NMR (400 MHz, DMSO-$d_6$) δ 1.01 (s, 3H), 1.17 (s, 3H), 2.03 (s, 3H), 2.10 (s, 3H), 3.71 (s, 3H), 4.61 (d, J = 12.4 Hz, 1H), 5.15 (d, J = 12.4 Hz, 1H), 5.40 (s, 1H), 6.07 (s, 1H), 6.48 (d, J = 2.1 Hz, 1H), 6.63 (d, J = 8.3 Hz, 1H), 6.76 (dd, J = 8.1, 2.1 Hz, 1H), 6.79 (d, J = 8.3 Hz, 1H), 7.00 (dd, J = 9.0, 3.2 Hz, 1H), 7.04 (d, J = 8.1 Hz, 1H), 7.05 (dd, J = 9.0, 4.2 Hz, 1H), 7.13 (td, J = 9.0, 3.2 Hz, 1H) |

| Compound | ¹H-NMR |
|---|---|
| 6-(5-Fluoro-2-methoxyphenyl)-5-(2-methoxy-5-nitrophenoxymethyl)-2,2,4-trimethyl-1,2-dihydroquinoline (Compound No. 14-42)<br>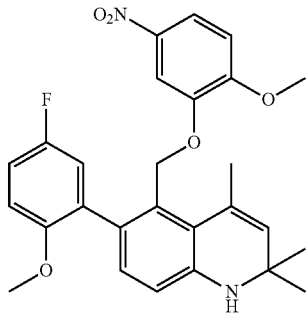 | ¹H-NMR (400 MHz, DMSO-$d_6$) δ 1.06 (s, 3H), 1.18 (s, 3H), 2.15 (s, 3H), 3.67 (s, 3H), 3.82 (s, 3H), 4.58 (d, J = 12.0 Hz, 1H), 5.30 (d, J = 12.0 Hz, 1H), 5.41 (s, 1H), 6.06 (s, 1H), 6.62 (d, J = 8.2 Hz, 1H), 6.77 (d, J = 8.2 Hz, 1H), 6.96 (dd, J = 9.3, 3.2 Hz, 1H), 6.98 (dd, J = 8.9, 4.6 Hz, 1H), 7.05 (td, J = 8.9, 3.2 Hz, 1H), 7.09 (d, J = 8.9 Hz, 1H), 7.34 (d, J = 2.7 Hz, 1H), 7.81 (dd, J = 8.9, 2.7 Hz, 1H) |
| 6-(5-Fluoro-2-methoxyphenyl)-5-(5-fluoro-2-methylphenoxymethyl)-2,2,4-trimethyl-1,2-dihydroquinoline (Compound No. 14-43)<br>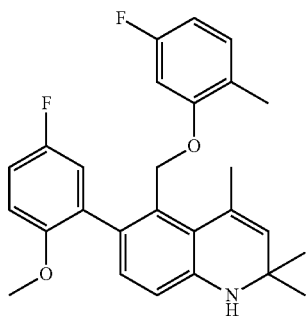 | ¹H-NMR (500 MHz, DMSO-$d_6$) δ 1.08 (s, 3H), 1.15 (s, 3H), 2.01 (s, 3H), 2.07 (s, 3H), 3.70 (s, 3H), 4.58 (d, J = 12.1 Hz, 1H), 5.08 (d, J = 12.1 Hz, 1H), 5.41 (s, 1H), 6.07 (s, 1H), 6.39 (dd, J = 11.3, 2.4 Hz, 1H), 6.53 (td, J = 8.4, 2.4 Hz, 1H), 6.63 (d, J = 8.1 Hz, 1H), 6.79 (d, J = 8.1 Hz, 1H), 6.98 (dd, J = 9.2, 3.1 Hz, 1H), 7.02-7.06 (m, 2H), 7.11 (td, J = 8.6, 3.1 Hz, 1H) |
| 6-(5-Fluoro-2-methoxyphenyl)-5-(2-methyl-5-nitrophenoxymethyl)-2,2,4-trimethyl-1,2-dihydroquinoline (Compound No. 14-44)<br>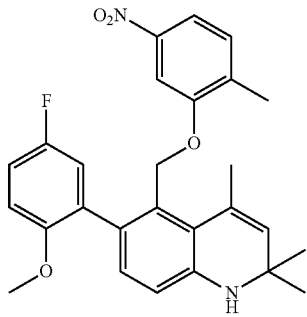 | ¹H-NMR (400 MHz, DMSO-$d_6$) δ 0.90 (s, 3H), 1.19 (s, 3H), 2.14 (s, 3H), 2.18 (s, 3H), 3.72 (s, 3H), 4.77 (d, J = 12.9 Hz, 1H), 5.33 (d, J = 12.9 Hz, 1H), 5.41 (s, 1H), 6.08 (s, 1H), 6.62 (d, J = 8.3 Hz, 1H), 6.80 (d, J = 8.3 Hz, 1H), 7.05 (dd, J = 8.7, 4.6 Hz, 1H), 7.07 (dd, J = 9.3, 2.9 Hz, 1H), 7.13 (td, J = 8.7, 2.9 Hz, 1H), 7.15 (d, J = 2.3 Hz, 1H), 7.33 (d, J = 8.2 Hz, 1H), 7.63 (dd, J = 8.2, 2.3 Hz, 1H) |
| 5-(2-Allylphenoxymethyl)-6-(5-fluoro-2-methoxyphenyl)-2,2,4-trimethyl-1,2-dihydroquinoline (Compound No. 14-45)<br>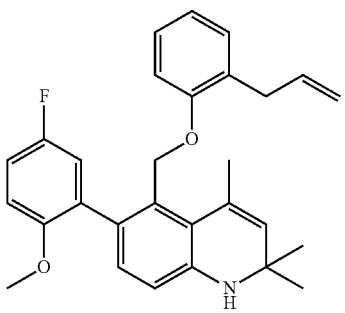 | ¹H-NMR (500 MHz, DMSO-$d_6$) δ 1.11 (s, 3H), 1.18 (s, 3H), 2.03 (s, 3H), 3.17-3.26 (m, 2H), 3.69 (s, 3H), 4.60 (d, J = 11.6 Hz, 1H), 4.91-4.97 (m, 2H), 5.05 (d, J = 11.6 Hz, 1H), 5.39 (s, 1H), 5.87 (ddt, J = 16.1, 10.1, 6.6 Hz, 1H), 6.06 (s, 1H), 6.61 (d, J = 7.7 Hz, 1H), 6.64 (d, J = 8.2 Hz, 1H), 6.78 (d, J = 8.2 Hz, 1H), 6.78 (td, J = 7.7, 0.8 Hz, 1H), 6.99 (dd, J = 9.0, 3.2 Hz, 1H), 7.01-7.05 (m, 3H), 7.10 (td, J = 8.6, 3.2 Hz, 1H) |

| Compound | ¹H-NMR |
|---|---|
| 6-(5-Chloro-2-methoxyphenyl)-5-(2,5-dimethyl-phenoxymethyl)-2,2,4-trimethyl-1,2-dihydroquinoline (Compound No. 14-46) 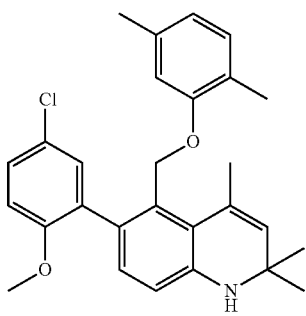 | ¹H-NMR (400 MHz, DMSO-d₆) δ 1.05 (s, 3H), 1.18 (s, 3H), 2.01 (s, 3H), 2.09 (s, 3H), 2.13 (s, 3H), 3.73 (s, 3H), 4.52 (d, J = 12.1 Hz, 1H), 5.09 (d, J = 12.1 Hz, 1H), 5.40 (s, 1H), 6.05 (s, 1H), 6.29 (s, 1H), 6.52 (d, J = 7.7 Hz, 1H), 6.62 (d, J = 8.2 Hz, 1H), 6.76 (d, J = 8.2 Hz, 1H), 6.89 (d, J = 7.7 Hz, 1H), 7.07 (d, J = 8.8 Hz, 1H), 7.20 (d, J = 2.7 Hz, 1H), 7.34 (dd, J = 8.8, 2.7 Hz, 1H) |
| 5-(2-Allylphenoxymethyl)-6-(5-chloro-2-methoxy-phenyl)-2,2,4-trimethyl-1,2-dihydroquinoline (Compound No. 14-47) 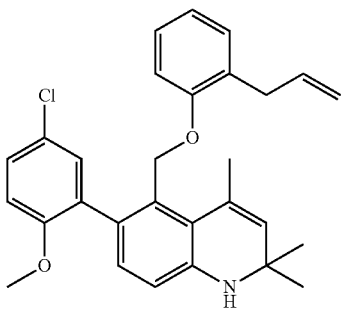 | ¹H-NMR (400 MHz, DMSO-d₆) δ 1.12 (s, 3H), 1.17 (s, 3H), 2.02 (s, 3H), 3.21-3.24 (m, 2H), 3.71 (s, 3H), 4.55 (d, J = 11.6 Hz, 1H), 4.92-4.98 (m, 2H), 5.04 (d, J = 11.6 Hz, 1H), 5.40 (s, 1H), 5.82-5.92 (m, 1H), 6.08 (s, 1H), 6.61-6.65 (m, 1H), 6.64 (d, J = 8.3 Hz, 1H), 6.76-6.80 (m, 1H), 6.77 (d, J = 8.3 Hz, 1H), 7.02-7.06 (m, 2H), 7.05 (d, J = 8.8 Hz, 1H), 7.16 (d, J = 2.7 Hz, 1H), 7.31 (dd, J = 8.8, 2.7 Hz, 1H) |
| 5-(5-Fluoro-2-methylphenoxymethyl)-6-(2-methoxy-5-nitrophenyl)-2,2,4-trimethyl-1,2-dihydroquinoline (Compound No. 14-48) 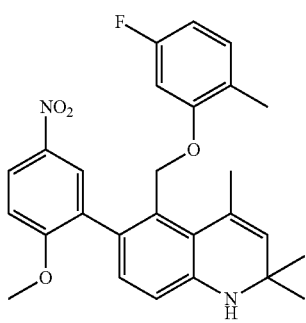 | ¹H-NMR (400 MHz, DMSO-d₆) δ 1.14 (s, 3H), 1.16 (s, 3H), 2.02 (s, 3H), 2.06 (s, 3H), 3.87 (s, 3H), 4.47 (d, J = 12.0 Hz, 1H), 5.06 (d, J = 12.0 Hz, 1H), 5.43 (s, 1H), 6.17 (s, 1H), 6.46 (dd, J = 11.4, 2.4 Hz, 1H), 6.53 (td, J = 8.4, 2.4 Hz, 1H), 6.67 (d, J = 8.3 Hz, 1H), 6.83 (d, J = 8.3 Hz, 1H), 7.01-7.05 (m, 1H), 7.27 (d, J = 9.2 Hz, 1H), 7.97 (d, J = 2.9 Hz, 1H), 8.21 (dd, J = 9.2, 2.9 Hz, 1H) |
| 5-(5-Fluoro-2-methylphenoxymethyl)-6-(2-methoxy-4-methoxymethoxyphenyl)-2,2,4-trimethyl-1,2-dihydroquinoline (Compound No. 14-49) 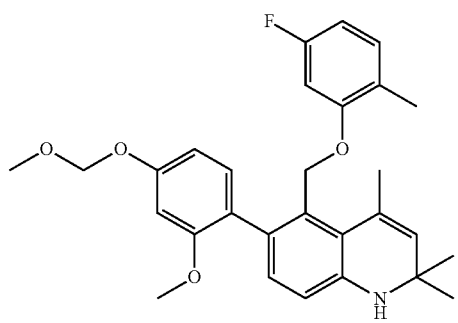 | ¹H-NMR (400 MHz, DMSO-d₆) δ 1.02 (s, 3H), 1.14 (s, 3H), 2.01 (s, 3H), 2.07 (s, 3H), 3.39 (s, 3H), 3.71 (s, 3H), 4.64 (d, J = 12.2 Hz, 1H), 5.08 (d, J = 12.2 Hz, 1H), 5.21 (s, 2H), 5.38 (s, 1H), 5.96 (s, 1H), 6.31 (dd, J = 11.5, 2.6 Hz, 1H), 6.51 (td, J = 8.5, 2.6 Hz, 1H), 6.60 (d, J = 8.1 Hz, 1H), 6.62 (dd, J = 8.3, 2.4 Hz, 1H), 6.70 (d, J = 2.4 Hz, 1H), 6.74 (d, J = 8.1 Hz, 1H), 7.01-7.05 (m, 1H), 7.07 (d, J = 8.3 Hz, 1H) |

| Compound | NMR |
|---|---|
| 5-(5-Fluoro-2-methylphenoxymethyl)-6-(2-methoxy-5-methoxymethoxyphenyl)-2,2,4-trimethyl-1,2-dihydroquinoline (Compound No. 14-50) 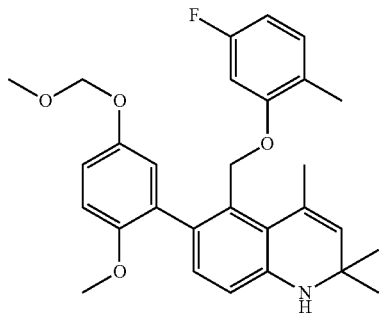 | $^1$H-NMR (500 MHz, DMSO-d$_6$) δ 1.05 (s, 3H), 1.15 (s, 3H), 2.02 (s, 3H), 2.08 (s, 3H), 3.29 (s, 3H), 3.67 (s, 3H), 4.62 (d, J = 12.1 Hz, 1H), 5.02 (d, J = 6.7 Hz, 1H), 5.06 (d, J = 6.7 Hz, 1H), 5.10 (d, J = 12.1 Hz, 1H), 5.39 (s, 1H), 6.02 (s, 1H), 6.35 (dd, J = 11.6, 2.4 Hz, 1H), 6.52 (td, J = 8.4, 2.4 Hz, 1H), 6.63 (d, J = 8.2 Hz, 1H), 6.79 (d, J = 8.2 Hz, 1H), 6.86 (d, J = 2.7 Hz, 1H), 6.95 (dd, J = 8.9, 2.7 Hz, 1H), 6.97 (d, J = 8.9 Hz, 1H), 7.02-7.05 (m, 1H) |
| 6-(4-Chloro-2-methoxyphenyl)-5-(2,5-dimethyl-phenoxymethyl)-2,2,4-trimethyl-1,2-dihydroquinoline (Compound No. 14-51) 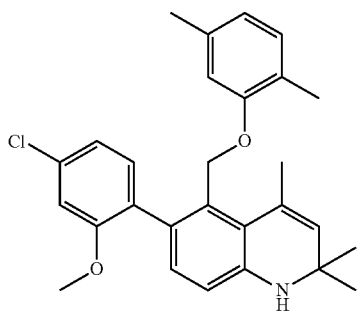 | $^1$H-NMR (400 MHz, DMSO-d$_6$) δ 1.05 (s, 3H), 1.18 (s, 3H), 1.99 (s, 3H), 2.06 (s, 3H), 2.13 (s, 3H), 3.76 (s, 3H), 4.56 (d, J = 12.1 Hz, 1H), 5.04 (d, J = 12.1 Hz, 1H), 5.38 (s, 1H), 6.03 (s, 1H), 6.29 (s, 1H), 6.52 (d, J = 7.6 Hz, 1H), 6.61 (d, J = 8.3 Hz, 1H), 6.74 (d, J = 8.3 Hz, 1H), 6.89 (d, J = 7.6 Hz, 1H), 7.01 (dd, J = 8.1, 2.1 Hz, 1H), 7.12 (d, J = 2.1 Hz, 1H), 7.19 (d, J = 8.1 Hz, 1H) |
| 6-(4-Chloro-2-methoxyphenyl)-5-(5-chloro-2-methyl-phenoxymethyl)-2,2,4-trimethyl-1,2-dihydroquinoline (Compound No. 14-52) 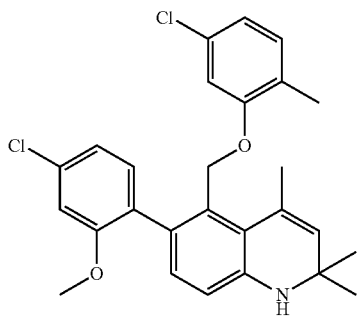 | $^1$H-NMR (400 MHz, DMSO-d$_6$) δ 1.01 (s, 3H), 1.17 (s, 3H), 2.02 (s, 3H), 2.08 (s, 3H), 3.76 (s, 3H), 4.60 (d, J = 12.5 Hz, 1H), 5.11 (d, J = 12.5 Hz, 1H), 5.40 (s, 1H), 6.06 (s, 1H), 6.47 (d, J = 2.1 Hz, 1H), 6.62 (d, J = 8.3 Hz, 1H), 6.75 (d, J = 8.3 Hz, 1H), 6.76 (dd, J = 7.9, 2.1 Hz, 1H), 7.02 (dd, J = 8.1, 2.0 Hz, 1H), 7.04 (d, J = 7.9 Hz, 1H), 7.12 (d, J = 2.0 Hz, 1H), 7.18 (d, J = 8.1 Hz, 1H) |
| 6-(4-Chloro-2-methoxyphenyl)-5-(2-methoxy-5-nitro-phenoxymethyl)-2,2,4-trimethyl-1,2-dihydroquinoline (Compound No. 14-53) 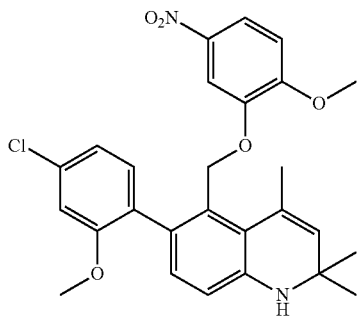 | $^1$H-NMR (500 MHz, DMSO-d$_6$) δ 1.05 (s, 3H), 1.18 (s, 3H), 2.13 (s, 3H), 3.71 (s, 3H), 3.82 (s, 3H), 4.63 (d, J = 12.1 Hz, 1H), 5.24 (d, J = 12.1 Hz, 1H), 5.40 (s, 1H), 6.03 (s, 1H), 6.61 (d, J = 8.2 Hz, 1H), 6.73 (d, J = 8.2 Hz, 1H), 6.92 (dd, J = 8.0, 2.1 Hz, 1H), 7.06 (d, J = 2.1 Hz, 1H), 7.08 (d, J = 9.1 Hz, 1H), 7.12 (d, J = 8.0 Hz, 1H), 7.31 (d, J = 2.7 Hz, 1H), 7.81 (dd, J = 9.1, 2.7 Hz, 1H) |

| Compound | ¹H-NMR |
|---|---|
| 6-(4-Chloro-2-methoxyphenyl)-5-(5-fluoro-2-methyl-phenoxymethyl)-2,2,4-trimethyl-1,2-dihydroquinoline (Compound No. 14-54) 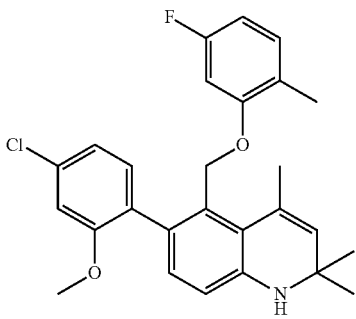 | ¹H-NMR (400 MHz, DMSO-d$_6$) δ 1.06 (s, 3H), 1.15 (s, 3H), 2.01 (s, 3H), 2.05 (s, 3H), 3.75 (s, 3H), 4.58 (d, J = 12.0 Hz, 1H), 5.05 (d, J = 12.0 Hz, 1H), 5.40 (s, 1H), 6.06 (s, 1H), 6.38 (dd, J = 11.4, 2.4 Hz, 1H), 6.53 (td, J = 8.4, 2.4 Hz, 1H), 6.63 (d, J = 8.2 Hz, 1H), 6.75 (d, J = 8.2 Hz, 1H), 7.00 (dd, J = 8.1, 2.2 Hz, 1H), 7.02-7.06 (m, 1H), 7.11 (d, J = 2.2 Hz, 1H), 7.16 (d, J = 8.1 Hz, 1H) |
| 6-(4-Chloro-2-methoxyphenyl)-5-(2-methoxy-5-nitro-phenoxymethyl)-2,2,4-trimethyl-1,2-dihydroquinoline (Compound No. 14-55) 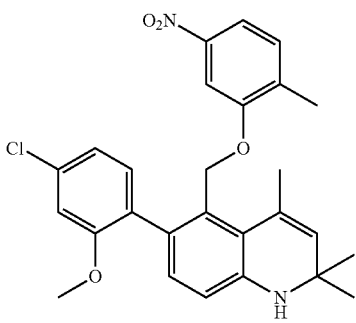 | ¹H-NMR (400 MHz, DMSO-d$_6$) δ 0.91 (s, 3H), 1.18 (s, 3H), 2.12 (s, 3H), 2.17 (s, 3H), 3.76 (s, 3H), 4.76 (d, J = 12.8 Hz, 1H), 5.29 (d, J = 12.8 Hz, 1H), 5.40 (s, 1H), 6.07 (s, 1H), 6.61 (d, J = 8.2 Hz, 1H), 6.76 (d, J = 8.2 Hz, 1H), 7.03 (dd, J = 8.1, 2.0 Hz, 1H), 7.12 (d, J = 2.0 Hz, 1H), 7.14 (d, J = 2.2 Hz, 1H), 7.25 (d, J = 8.1 Hz, 1H), 7.33 (d, J = 8.2 Hz, 1H), 7.64 (dd, J = 8.2, 2.2 Hz, 1H) |
| 5-(2-Allylphenoxymethyl)-6-(4-chloro-2-methoxyphenyl)-2,2,4-trimethyl-1,2-dihydroquinoline (Compound No. 14-56) 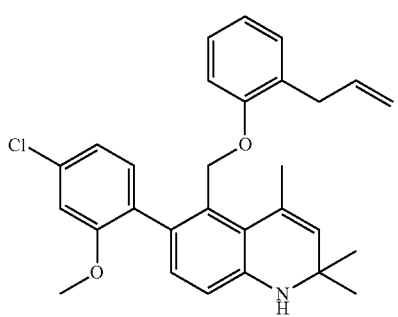 | ¹H-NMR (500 MHz, DMSO-d$_6$) δ 1.09 (s, 3H), 1.18 (s, 3H), 2.02 (s, 3H), 3.19 (dd, J = 14.0, 6.2 Hz, 1H), 3.23 (dd, J = 14.0, 6.2 Hz, 1H), 3.74 (s, 3H), 4.58 (d, J = 11.8 Hz, 1H), 4.92-4.97 (m, 2H), 5.02 (d, J = 11.8 Hz, 1H), 5.39 (s, 1H), 5.88 (ddt, J = 16.8, 10.0, 6.2 Hz, 1H), 6.05 (s, 1H), 6.60 (d, J = 8.6 Hz, 1H), 6.63 (d, J = 8.1 Hz, 1H), 6.75 (d, J = 8.1 Hz, 1H), 6.78 (td, J = 7.5, 0.8 Hz, 1H), 6.97 (dd, J = 7.9, 2.0 Hz, 1H), 7.01-7.05 (m, 2H), 7.10 (d, J = 2.0 Hz, 1H), 7.16 (d, J = 7.9 Hz, 1H) |

Example 15

6-(4-Benzyloxy-2-methoxyphenyl)-5-(5-fluoro-2-methylphenoxymethyl)-2,2,4-trimethyl-1,2-dihydroquinoline (Compound No. 15-1)

5-(5-Fluoro-2-methylphenoxymethyl)-6-(4-hydroxy-2-methoxyphenyl)-2,2,4-trimethyl-1,2-dihydroquinoline (Reference Compound No. 5-3, 20.1 mg, 0.046 mmol), potassium carbonate (16.7 mg, 0.12 mmol) and benzyl bromide (6.6 µL, 0.055 mmol) were dissolved in anhydrous N,N-dimethylformamide (0.5 mL), and the mixture was stirred at 60° C. for 40 minutes. Ethyl acetate (50 mL) was added to the reaction mixture, and the whole was washed with water (50 mL) and saturated brine (30 mL), dried over anhydrous magnesium sulfate, and then the solvent was removed under reduced pressure. The residue was purified by silica gel column chromatography (hexane-ethyl acetate) to give the titled compound (5.1 mg) as a colorless oil. (Yield 19%)

| | |
|---|---|
| 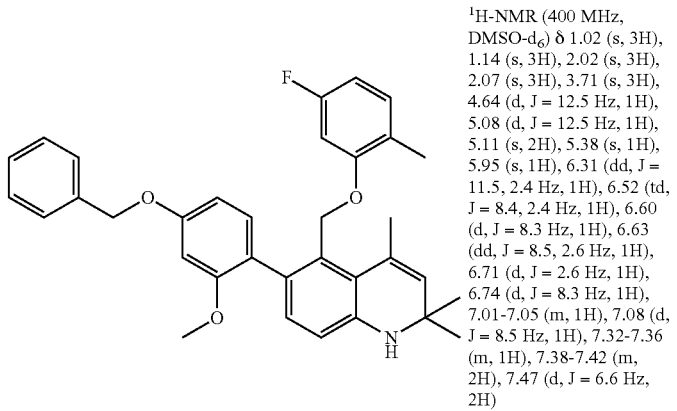 | ¹H-NMR (400 MHz, DMSO-d₆) δ 1.02 (s, 3H), 1.14 (s, 3H), 2.02 (s, 3H), 2.07 (s, 3H), 3.71 (s, 3H), 4.64 (d, J = 12.5 Hz, 1H), 5.08 (d, J = 12.5 Hz, 1H), 5.11 (s, 2H), 5.38 (s, 1H), 5.95 (s, 1H), 6.31 (dd, J = 11.5, 2.4 Hz, 1H), 6.52 (td, J = 8.4, 2.4 Hz, 1H), 6.60 (d, J = 8.3 Hz, 1H), 6.63 (dd, J = 8.5, 2.6 Hz, 1H), 6.71 (d, J = 2.6 Hz, 1H), 6.74 (d, J = 8.3 Hz, 1H), 7.01-7.05 (m, 1H), 7.08 (d, J = 8.5 Hz, 1H), 7.32-7.36 (m, 1H), 7.38-7.42 (m, 2H), 7.47 (d, J = 6.6 Hz, 2H) |

Using a Reference Compound No. 5-3 or 5-4, the following Compounds (No. 15-2~15-18) were obtained by a method similar to that of Compound No. 15-1.

| | |
|---|---|
| 6-(5-Benzyloxy-2-methoxyphenyl)-5-(5-fluoro-2-methylphenoxymethyl)-2,2,4-trimethyl-1,2-dihydroquinoline (Compound No. 15-2) 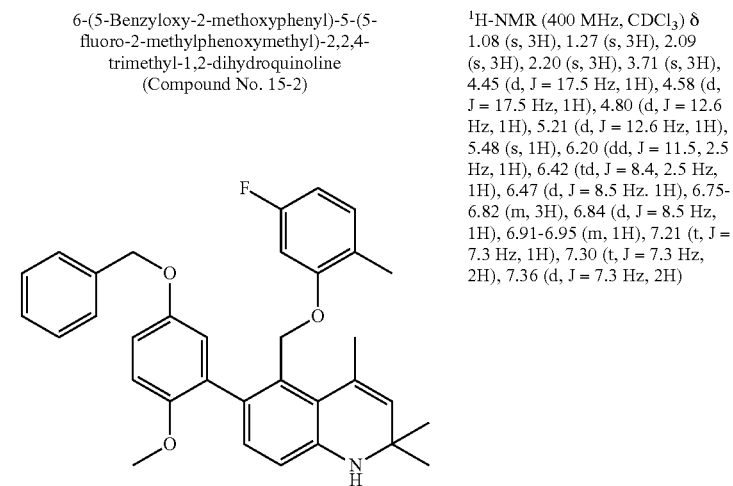 | ¹H-NMR (400 MHz, CDCl₃) δ 1.08 (s, 3H), 1.27 (s, 3H), 2.09 (s, 3H), 2.20 (s, 3H), 3.71 (s, 3H), 4.45 (d, J = 17.5 Hz, 1H), 4.58 (d, J = 17.5 Hz, 1H), 4.80 (d, J = 12.6 Hz, 1H), 5.21 (d, J = 12.6 Hz, 1H), 5.48 (s, 1H), 6.20 (dd, J = 11.5, 2.5 Hz, 1H), 6.42 (td, J = 8.4, 2.5 Hz, 1H), 6.47 (d, J = 8.5 Hz, 1H), 6.75-6.82 (m, 3H), 6.84 (d, J = 8.5 Hz, 1H), 6.91-6.95 (m, 1H), 7.21 (t, J = 7.3 Hz, 1H), 7.30 (t, J = 7.3 Hz, 2H), 7.36 (d, J = 7.3 Hz, 2H) |
| 6-[5-(2-Chlorobenzyloxy)-2-methoxyphenyl]-5-(5-fluoro-2-methylphenoxymethyl)-2,2,4-trimethyl-1,2-dihydroquinoline (Compound No. 15-3) 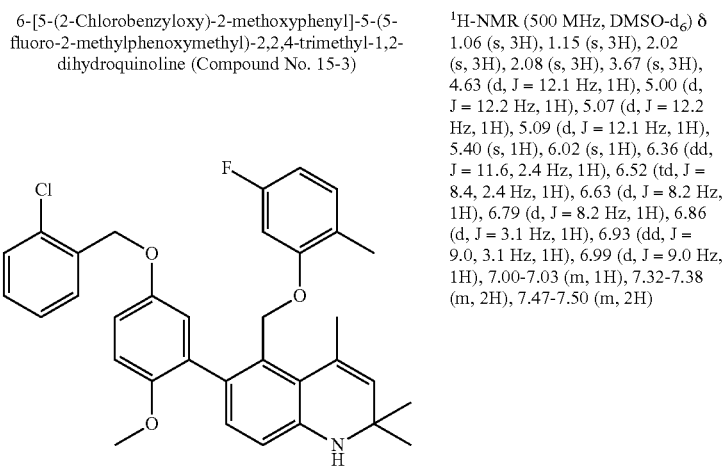 | ¹H-NMR (500 MHz, DMSO-d₆) δ 1.06 (s, 3H), 1.15 (s, 3H), 2.02 (s, 3H), 2.08 (s, 3H), 3.67 (s, 3H), 4.63 (d, J = 12.1 Hz, 1H), 5.00 (d, J = 12.2 Hz, 1H), 5.07 (d, J = 12.2 Hz, 1H), 5.09 (d, J = 12.1 Hz, 1H), 5.40 (s, 1H), 6.02 (s, 1H), 6.36 (dd, J = 11.6, 2.4 Hz, 1H), 6.52 (td, J = 8.4, 2.4 Hz, 1H), 6.63 (d, J = 8.2 Hz, 1H), 6.79 (d, J = 8.2 Hz, 1H), 6.86 (d, J = 3.1 Hz, 1H), 6.93 (dd, J = 9.0, 3.1 Hz, 1H), 6.99 (d, J = 9.0 Hz, 1H), 7.00-7.03 (m, 1H), 7.32-7.38 (m, 2H), 7.47-7.50 (m, 2H) |

-continued

| | | |
|---|---|---|
| 6-[5-(3-Chlorobenzyloxy)-2-methoxyphenyl]-5-(5-fluoro-2-methylphenoxymethyl)-2,2,4-trimethyl-1,2-dihydroquinoline (Compound No. 15-4) | 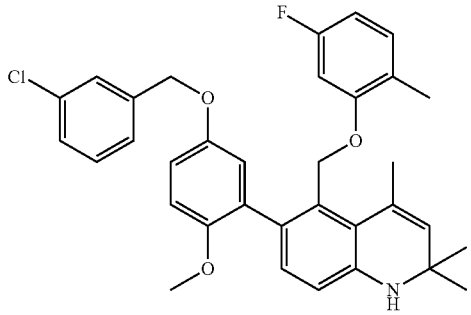 [SMILES: COc1ccc(OCc2cccc(Cl)c2)cc1-c1ccc2c(c1COc1cc(F)ccc1C)C(C)=CC(C)(C)N2] | $^1$H-NMR (500 MHz, DMSO-$d_6$) δ 1.07 (s, 3H), 1.14 (s, 3H), 2.03 (s, 3H), 2.08 (s, 3H), 3.66 (s, 3H), 4.62 (d, J = 12.1 Hz, 1H), 4.95 (d, J = 12.5 Hz, 1H), 5.03 (d, J = 12.5 Hz, 1H), 5.06 (d, J = 12.1 Hz, 1H), 5.40 (s, 1H), 6.01 (s, 1H), 6.35 (dd, J = 11.5, 2.5 Hz, 1H), 6.53 (td, J = 8.6, 2.5 Hz, 1H), 6.62 (d, J = 8.2 Hz, 1H), 6.78 (d, J = 8.2 Hz, 1H), 6.85 (d, J = 3.1 Hz, 1H), 6.92 (dd, J = 8.9, 3.1 Hz, 1H), 6.97 (d, J = 8.9 Hz, 1H), 7.02-7.05 (m, 1H), 7.31 (d, J = 7.0 Hz, 1H), 7.35-7.40 (m, 2H), 7.43 (s, 1H) |
| 6-[5-(4-Chlorobenzyloxy)-2-methoxyphenyl]-5-(5-fluoro-2-methylphenoxymethyl)-2,2,4-trimethyl-1,2-dihydroquinoline (Compound No. 15-5) | 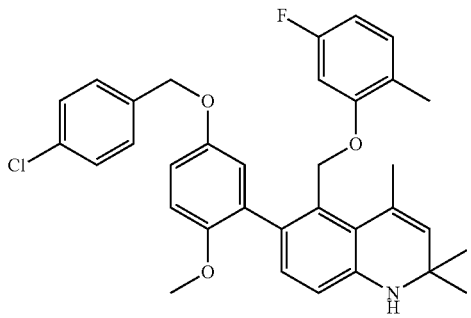 [SMILES: COc1ccc(OCc2ccc(Cl)cc2)cc1-c1ccc2c(c1COc1cc(F)ccc1C)C(C)=CC(C)(C)N2] | $^1$H-NMR (500 MHz, DMSO-$d_6$) δ 1.07 (s, 3H), 1.14 (s, 3H), 2.03 (s, 3H), 2.08 (s, 3H), 3.66 (s, 3H), 4.60 (d, J = 12.2 Hz, 1H), 4.92 (d, J = 12.5 Hz, 1H), 5.02 (d, J = 12.5 Hz, 1H), 5.06 (d, J = 12.2 Hz, 1H), 5.40 (s, 1H), 6.01 (s, 1H), 6.36 (dd, J = 11.5, 2.4 Hz, 1H), 6.55 (td, J = 8.4, 2.4 Hz, 1H), 6.62 (d, J = 8.3 Hz, 1H), 6.78 (d, J = 8.3 Hz, 1H), 6.84 (d, J = 3.1 Hz, 1H), 6.91 (dd, J = 8.9, 3.1 Hz, 1H), 6.96 (d, J = 8.9 Hz, 1H), 7.03-7.06 (m, 1H), 7.36 (d, J = 8.5 Hz, 2H), 7.40 (d, J = 8.5 Hz, 2H) |
| 6-(2,4-Dimethoxyphenyl)-5-(5-fluoro-2-methylphenoxymethyl)-2,2,4-trimethyl-1,2-dihydroquinoline (Compound No. 15-6) | 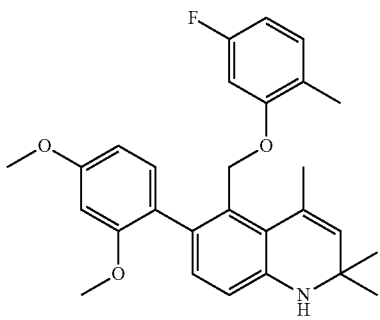 | $^1$H-NMR (400 MHz, DMSO-$d_6$) δ 1.01 (s, 3H), 1.14 (s, 3H), 2.02 (s, 3H), 2.07 (s, 3H), 3.72 (s, 3H), 3.78 (s, 3H), 4.63 (d, J = 12.4 Hz, 1H), 5.08 (d, J = 12.4 Hz, 1H), 5.38 (s, 1H), 5.95 (s, 1H), 6.30 (dd, J = 11.5, 2.4 Hz, 1H), 6.51 (td, J = 8.4, 2.4 Hz, 1H), 6.54 (dd, J = 8.4, 2.0 Hz, 1H), 6.60 (d, J = 8.3 Hz, 1H), 6.61 (d, J = 2.0 Hz, 1H), 6.74 (d, J = 8.3 Hz, 1H), 7.00-7.04 (m, 1H), 7.07 (d, J = 8.3 Hz, 1H) |
| 6-(4-Allyloxy-2-methoxyphenyl)-5-(5-fluoro-2-methylphenoxymethyl)-2,2,4-trimethyl-1,2-dihydroquinoline (Compound No. 15-7) | 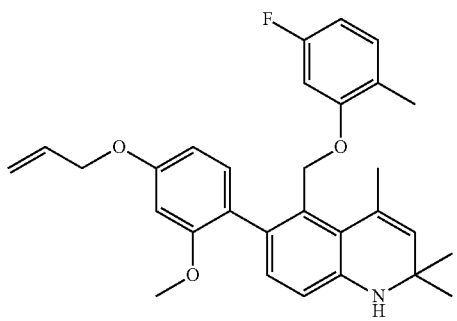 [SMILES: C=CCOc1ccc(-c2ccc3c(c2COc2cc(F)ccc2C)C(C)=CC(C)(C)N3)c(OC)c1] | $^1$H-NMR (400 MHz, DMSO-$d_6$) δ 1.02 (s, 3H), 1.14 (s, 3H), 2.01 (s, 3H), 2.08 (s, 3H), 3.71 (s, 3H), 4.58 (dt, J = 5.1, 1.6 Hz, 2H), 4.63 (d, J = 12.2 Hz, 1H), 5.08 (d, J = 12.2 Hz, 1H), 5.26 (dq, J = 10.6, 1.6 Hz, 1H), 5.38 (s, 1H), 5.42 (dq, J = 17.3, 1.6 Hz, 1H), 5.95 (s, 1H), 6.05 (ddt, J = 17.3, 10.6, 5.1 Hz, 1H), 6.30 (dd, J = 11.5, 2.5 Hz, 1H), 6.50 (td, J = 8.4, 2.5 Hz, 1H), 6.55 (dd, J = 8.3, 2.4 Hz, 1H), 6.60 (d, J = 8.1 Hz, 1H), 6.64 (d, J = 2.4 Hz, 1H), 6.74 (d, J = 8.1 Hz, 1H), 7.00-7.04 (m, 1H), 7.06 (d, J = 8.3 Hz, 1H) |

| | |
|---|---|
| 6-(5-Allyloxy-2-methoxyphenyl)-5-(5-fluoro-2-methylphenoxymethyl)-2,2,4-trimethyl-1,2-dihydroquinoline (Compound No. 15-8)<br>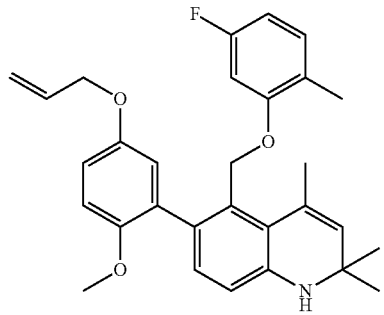 [SMILES: C=CCOc1ccc(OC)c(-c2ccc3c(c2COc2cc(F)ccc2C)C(C)=CC(C)(C)N3)c1] | $^1$H-NMR (400 MHz, DMSO-d$_6$) δ 1.05 (s, 3H), 1.15 (s, 3H), 2.02 (s, 3H), 2.08 (s, 3H), 3.66 (s, 3H), 4.38 (ddt, J = 13.2, 5.3, 1.5 Hz, 1H), 4.47 (ddt, J =13.3, 5.3, 1.5 Hz, 1H), 4.63 (d, J = 12.0 Hz, 1H), 5.09 (d, J = 12.0 Hz, 1H), 5.18 (dq, J = 10.6, 1.5 Hz 1H), 5.29 (dq, J = 17.3, 1.5 Hz, 1H), 5.39 (s, 1H), 5.96 (ddt, J = 17.3, 10.6, 5.3 Hz, 1H), 6.01 (s, 1H), 6.35 (dd, J = 11.5, 2.4 Hz, 1H), 6.53 (td, J = 8.3, 2.4 Hz, 1H), 6.62 (d, J = 8.3 Hz, 1H), 6.77 (d, J = 3.2 Hz, 1H), 6.79 (d, J = 8.3 Hz, 1H), 6.87 (dd, J = 8.9, 3.2 Hz, 1H), 6.96 (d, J = 8.9 Hz, 1H), 7.01-7.05 (m, 1H) |
| 5-(5-Fluoro-2-methylphenoxymethyl)-6-[2-methoxy-5-(2-methoxybenzyloxy)phenyl]-2,2,4-trimethyl-1,2-dihydroquinoline (Compound No. 15-9)<br>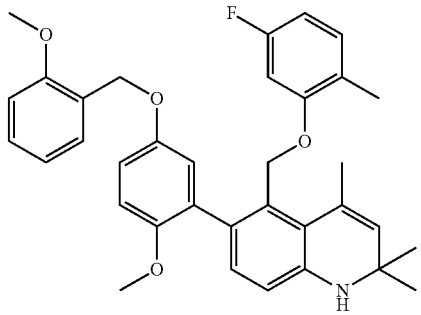 | $^1$H-NMR (500 MHz, DMSO-d$_6$) δ 1.06 (s, 3H), 1.15 (s, 3H), 2.02 (s, 3H), 2.08 (s, 3H), 3.66 (s, 3H), 3.79 (s, 3H), 4.62 (d, J = 11.9 Hz, 1H), 4.90 (d, J = 12.1 Hz, 1H), 4.97 (d, J = 12.1 Hz, 1H), 5.08 (d, J = 11.9 Hz, 1H), 5.39 (s, 1H), 6.01 (s, 1H), 6.35 (dd, J = 11.5, 2.4 Hz, 1H), 6.53 (td, J = 8.3, 2.4 Hz, 1H), 6.62 (d, J = 8.3 Hz, 1H), 6.79 (d, J = 8.3 Hz, 1H), 6.82 (d, J = 3.0 Hz, 1H), 6.89 (dd, J = 9.1, 3.0 Hz, 1H), 6.90-6.93 (m, 1H), 6.96 (d, J = 9.1 Hz, 1H), 7.01-7.04 (m, 2H), 7.28-7.31 (m, 2H) |
| 5-(5-Fluoro-2-methylphenoxymethyl)-6-[2-methoxy-5-(3-methoxybenzyloxy)phenyl]-2,2,4-trimethyl-1,2-dihydroquinoline (Compound No. 15-10)<br>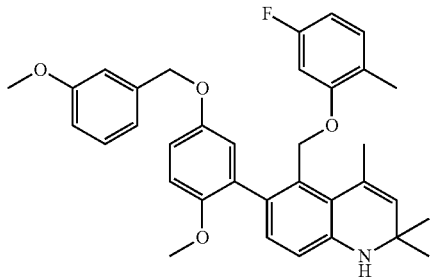 | 1H-NMR (500 MHz, DMSO-d$_6$) δ 1.06 (s, 3H), 1.14 (s, 3H), 2.03 (s, 3H), 2.08 (s, 3H), 3.66 (s, 3H), 3.74 (s, 3H), 4.62 (d, J = 12.2 Hz, 1H), 4.90 (d, J = 12.2 Hz, 1H), 4.99 (d, J = 12.2 Hz, 1H), 5.06 (d, J = 12.2 Hz, 1H), 5.39 (s, 1H), 6.01 (s, 1H), 6.35 (dd, J = 11.3, 2.4 Hz, 1H), 6.53 (td, J = 8.4, 2.4 Hz, 1H), 6.62 (d, J = 8.3 Hz, 1H), 6.78 (d, J = 8.3 Hz, 1H), 6.84 (d, J = 2.8 Hz, 1H), 6.89 (dd, J = 8.7, 2.8 Hz, 1H), 6.90-6.94 (m, 2H), 6.92 (s, 1H), 6.96 (d, J = 8.7 Hz, 1H), 7.01-7.05 (m, 1H), 7.26 (t, J = 7.8 Hz, 1H) |
| 5-(5-Fluoro-2-methylphenoxymethyl)-6-[2-methoxy-5-(4-methoxybenzyloxy)phenyl]-2,2,4-trimethyl-1,2-dihydroquinoline (Compound No. 15-11)<br>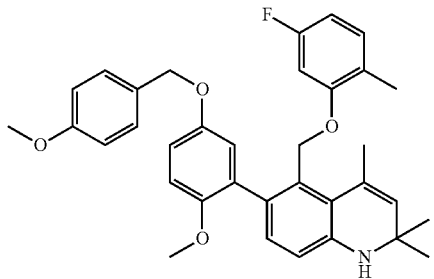 | $^1$H-NMR (400 MHz, DMSO-d$_6$) δ 1.06 (s, 3H), 1.14 (s, 3H), 2.03 (s, 3H), 2.08 (s, 3H), 3.66 (s, 3H), 3.74 (s, 3H), 4.61 (d, J = 12.1 Hz, 1H), 4.83 (d, J = 11.5 Hz, 1H), 4.93 (d, J = 11.5 Hz, 1H), 5.07 (d, J = 12.1 Hz, 1H), 5.39 (s, 1H), 6.01 (s, 1H), 6.36 (dd, J = 11.4, 2.5 Hz, 1H), 6.54 (td, J = 8.4, 2.5 Hz, 1H), 6.62 (d, J = 8.3 Hz, 1H), 6.78 (d, J = 8.3 Hz, 1H), 6.83 (d, J = 2.9 Hz, 1H), 6.88-7.92 (m, 1H), 6.90 (d, J = 8.8 Hz, 2H), 6.96 (d, J = 9.0 Hz, 1H), 7.02-7.06 (m, 1H), 7.25 (d, J = 8.8 Hz, 2H) |

-continued 6-(2,5-Dimethoxyphenyl)-5-(5-fluoro-2-methylphenoxy-methyl)-2,2,4-trimethyl-1,2-dihydroquinoline (Compound No. 15-12)

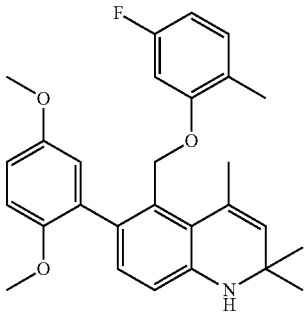 [SMILES: COc1ccc(OC)c(-c2ccc3c(c2COc2cc(F)ccc2C)C(C)=CC(C)(C)N3)c1]

¹H-NMR (400 MHz, DMSO-d₆) δ 1.03 (s, 3H), 1.16 (s, 3H), 2.01 (s, 3H), 2.08 (s, 3H), 3.65 (s, 3H), 3.66 (s, 3H), 4.64 (d, J = 12.2 Hz, 1H), 5.11 (d, J = 12.2 Hz, 1H), 5.39 (s, 1H), 6.01 (s, 1H), 6.33 (dd, J = 11.5, 2.4 Hz, 1H), 6.52 (td, J = 8.5, 2.4 Hz, 1H), 6.62 (d, J = 8.3 Hz, 1H), 6.63 (d, J = 3.1 Hz, 1H), 6.79 (d, J = 8.3 Hz, 1H), 6.86 (dd, J = 9.0, 3.1 Hz, 1H), 6.97 (d, J = 9.0 Hz, 1H), 7.01-7.05 (m, 1H)

6-[4-(2-Chlorobenzyloxy)-2-methoxyphenyl]-5-(5-fluoro-2-methylphenoxymethyl)-2,2,4-trimethyl-1,2-dihydroquinoline (Compound No. 15-13)

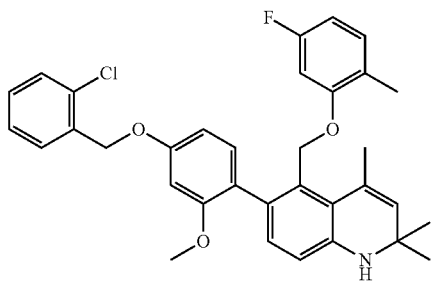 [SMILES: COc1cc(OCc2ccccc2Cl)ccc1-c1ccc2c(c1COc1cc(F)ccc1C)C(C)=CC(C)(C)N2]

¹H-NMR (500 vMHz, DMSO-d₆) δ 1.02 (s, 3H), 1.14 (s, 3H), 2.02 (s, 3H), 2.08 (s, 3H), 3.72 (s, 3H), 4.65 (d, J = 12.2 Hz, 1H), 5.09 (d, J = 12.2 Hz, 1H), 5.18 (s, 2H), 5.38 (s, 1H), 5.95 (s, 1H), 6.32 (dd, J = 11.5, 2.4 Hz, 1H), 6.52 (td, J = 8.4, 2.4 Hz, 1H), 6.61 (d, J = 8.1 Hz, 1H), 6.64 (dd, J = 8.2, 2.4 Hz, 1H), 6.73 (d, J = 2.4 Hz, 1H), 6.75 (d, J = 8.1 Hz, 1H), 7.01-7.04 (m, 1H), 7.09 (d, J = 8.2 Hz, 1H), 7.39-7.42 (m, 2H), 7.51-7.53 (m, 1H), 7.62-7.64 (m, 1H)

6-[4-(3-Chlorobenzyloxy)-2-methoxyphenyl]-5-(5-fluoro-2-methylphenoxymethyl)-2,2,4-trimethyl-1,2-dihydroquinoline (Compound No. 15-14)

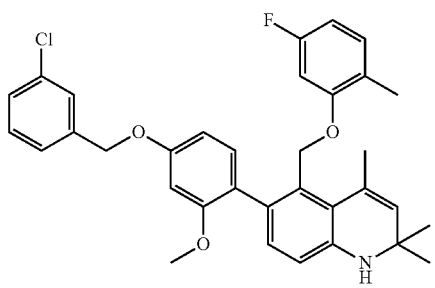 [SMILES: COc1cc(OCc2cccc(Cl)c2)ccc1-c1ccc2c(c1COc1cc(F)ccc1C)C(C)=CC(C)(C)N2]

¹H-NMR (400 MHz, DMSO-d₆) δ 1.02 (s, 3H), 1.14 (s, 3H), 2.01 (s, 3H), 2.07 (s, 3H), 3.72 (s, 3H), 4.64 (d, J = 12.2 Hz, 1H), 5.08 (d, J = 12.2 Hz, 1H), 5.14 (s, 2H), 5.38 (s, 1H), 5.95 (s, 1H), 6.31 (dd, J = 11.5, 2.5 Hz, 1H), 6.52 (td, J = 8.4, 2.5 Hz, 1H), 6.60 (d, J = 8.2 Hz, 1H), 6.61-6.64 (m, 1H), 6.72 (d, J = 2.4 Hz, 1H), 6.74 (d, J = 8.2 Hz, 1H), 7.01-7.04 (m, 1H), 7.08 (d, J = 8.3 Hz, 1H), 7.39-7.44 (m, 3H), 7.55 (s, 1H)

6-[4-(4-Chlorobenzyloxy)-2-methoxyphenyl]-5-(5-fluoro-2-methylphenoxymethyl)-2,2,4-trimethyl-1,2-dihydroquinoline (Compound No. 15-15)

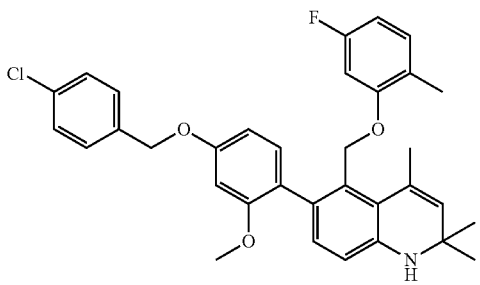 [SMILES: COc1cc(OCc2ccc(Cl)cc2)ccc1-c1ccc2c(c1COc1cc(F)ccc1C)C(C)=CC(C)(C)N2]

¹H-NMR (500 vMHz, DMSO-d₆) δ 1.02 (s, 3H), 1.14 (s, 3H), 2.01 (s, 3H), 2.07 (s, 3H), 3.71 (s, 3H), 4.63 (d, J = 12.5 Hz, 1H), 5.08 (d, J = 12.5 Hz, 1H), 5.12 (s, 2H), 5.38 (s, 1H), 5.94 (s, 1H), 6.31 (dd, J = 11.3, 2.4 Hz, 1H), 6.52 (td, J = 8.4, 2.4 Hz, 1H), 6.60 (d, J = 8.2 Hz, 1H), 6.61 (dd, J = 8.4, 2.4 Hz, 1H), 6.70 (d, J = 2.4 Hz, 1H), 6.74 (d, J = 8.2 Hz, 1H), 7.01-7.04 (m, 1H), 7.07 (d, J = 8.4 Hz, 1H), 7.46 (d, J = 8.6 Hz, 2H), 7.50 (d, J = 8.6 Hz, 2H)

| Compound | 1H-NMR |
|---|---|
| 5-(5-Fluoro-2-methylphenoxymethyl)-6-[2-methoxy-5-(2-methylbenzyloxy)phenyl]-2,2,4-trimethyl-1,2-dihydroquinoline (Compound No. 15-16) 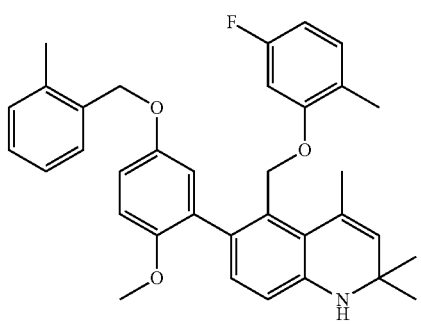 | $^1$H-NMR (400 MHz, DMSO-d$_6$) δ 1.06 (s, 3H), 1.15 (s, 3H), 2.02 (s, 3H), 2.08 (s, 3H), 2.25 (s, 3H), 3.67 (s, 3H), 4.64 (d, J = 11.8 Hz, 1H), 4.89 (d, J = 11.6 Hz, 1H), 4.99 (d, J = 11.6 Hz, 1H), 5.10 (d, J = 11.8 Hz, 1H), 5.40 (s, 1H), 6.01 (s, 1H), 6.37 (dd, J = 11.5, 2.4 Hz, 1H), 6.53 (td, J = 8.4, 2.4 Hz, 1H), 6.63 (d, J = 8.2 Hz, 1H), 6.80 (d, J = 8.2 Hz, 1H), 6.87 (d, J = 2.9 Hz, 1H), 6.93 (dd, J = 8.9, 2.9 Hz, 1H), 6.98 (d, J = 8.9 Hz, 1H), 7.00-7.04 (m, 1H), 7.16-7.22 (m, 3H), 7.31 (d, J = 7.6 Hz, 1H) |
| 5-(5-Fluoro-2-methylphenoxymethyl)-6-[2-methoxy-5-(3-methylbenzyloxy)phenyl]-2,2,4-trimethyl-1,2-dihydroquinoline (Compound No. 15-17) 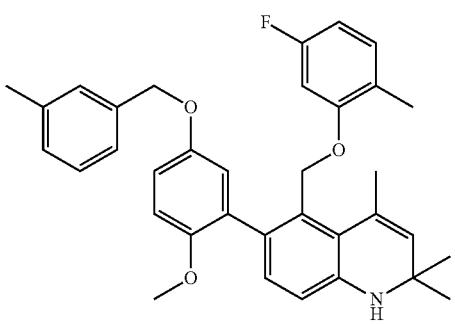 | $^1$H-NMR (400 MHz, DMSO-d$_6$) δ 1.06 (s, 3H), 1.14 (s, 3H), 2.03 (s, 3H), 2.08 (s, 3H), 2.30 (s, 3H), 3.66 (s, 3H), 4.62 (d, J = 12.2 Hz, 1H), 4.87 (d, J = 12.0 Hz, 1H), 4.97 (d, J = 12.0 Hz, 1H), 5.07 (d, J = 12.2 Hz, 1H), 5.39 (s, 1H), 6.01 (s, 1H), 6.35 (dd, J = 11.5, 2.4 Hz, 1H), 6.53 (td, J = 8.5, 2.4 Hz, 1H), 6.63 (d, J = 8.2 Hz, 1H), 6.79 (d, J = 8.2 Hz, 1H), 6.84 (d, J = 3.0 Hz, 1H), 6.91 (dd, J = 8.9, 3.0 Hz, 1H), 6.97 (d, J = 8.9 Hz, 1H), 7.02-7.06 (m, 1H), 7.11 (d, J = 7.3 Hz, 1H), 7.13 (d, J = 7.3 Hz, 1H), 7.17 (s, 1H), 7.23 (t, J = 7.3 Hz, 1H) |
| 5-(5-Fluoro-2-methylphenoxymethyl)-6-[2-methoxy-5-(4-methylbenzyloxy)phenyl]-2,2,4-trimethyl-1,2-dihydroquinoline (Compound No. 15-18) 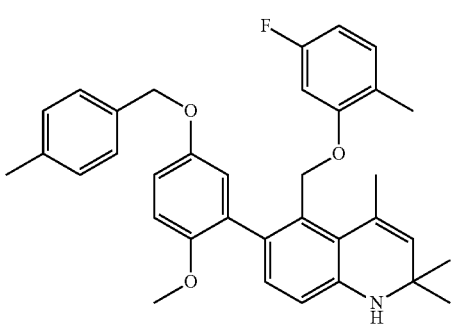 | $^1$H-NMR (400 MHz, CDCl$_3$) δ 1.12 (s, 3H), 1.23 (s, 3H), 2.08 (s, 3H), 2.16 (s, 3H), 2.34 (s, 3H), 3.69 (s, 3H), 4.74 (d, J = 12.1 Hz, 1H), 4.88 (d, J = 11.4 Hz, 1H), 4.96 (d, J = 11.4 Hz, 1H), 5.11 (d, J = 12.1 Hz, 1H), 5.46 (s, 1H), 6.21 (dd, J = 11.2, 2.4 Hz, 1H), 6.42 (td, J = 8.3, 2.4 Hz, 1H), 6.58 (d, J = 8.3 Hz, 1H), 6.84-6.95 (m, 5H), 7.16 (d, J = 7.7 Hz, 2H), 7.27 (d, J = 7.7 Hz, 2H) |

Example 16

6-(4-Fluoro-2-methoxyphenyl)-5-(4-hydroxybenzoyloxymethyl)-2,2,4-trimethyl-1,2-dihydroquinoline (Compound No. 16)

5-(4-Acetoxybenzoyloxymethyl)-6-(4-fluoro-2-methoxyphenyl)-2,2,4-trimethyl-1,2-dihydroquinoline (Compound No. 12-5, 40.9 mg, 0.0835 mmol) and potassium carbonate (24.0 mg, 0.174 mmol) were suspended in anhydrous methanol (1 mL), and the mixture was stirred at room temperature for 1.5 hours. After the unsoluble materials were filtered, the filtrate was concentrated under reduced pressure, and ethyl acetate (50 mL) and water (50 mL) were added thereto, and then separated. The organic layer was washed with water (30 mL) and saturated brine (30 mL) successively, dried over anhydrous magnesium sulfate, and then the solvent was removed under reduced pressure. The obtained residue was filtered with hexane to give the titled compound (28.8 mg) as a colorless solid. (Yield 78%)

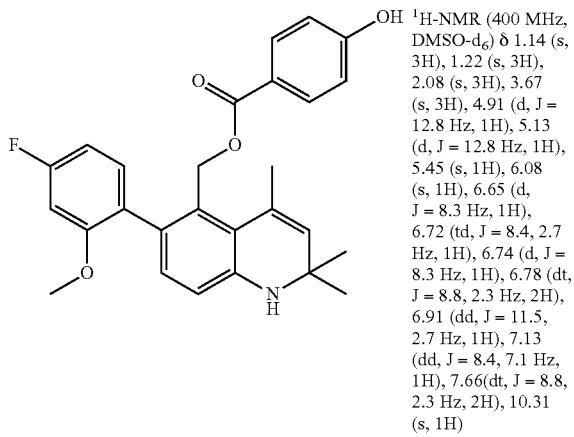

¹H-NMR (400 MHz, DMSO-d₆) δ 1.14 (s, 3H), 1.22 (s, 3H), 2.08 (s, 3H), 3.67 (s, 3H), 4.91 (d, J = 12.8 Hz, 1H), 5.13 (d, J = 12.8 Hz, 1H), 5.45 (s, 1H), 6.08 (s, 1H), 6.65 (d, J = 8.3 Hz, 1H), 6.72 (td, J = 8.4, 2.7 Hz, 1H), 6.74 (d, J = 8.3 Hz, 1H), 6.78 (dt, J = 8.8, 2.3 Hz, 2H), 6.91 (dd, J = 11.5, 2.7 Hz, 1H), 7.13 (dd, J = 8.4, 7.1 Hz, 1H), 7.66 (dt, J = 8.8, 2.3 Hz, 2H), 10.31 (s, 1H)

Example 17

5-Benzoylaminomethyl-6-(4-fluoro-2-methoxyphenyl)-2,2,4-trimethyl-1,2-dihydro quinoline (Compound No. 17-1)

60% Sodium hydride (23.2 mg, 0.580 mmol) was suspended in anhydrous N,N-dimethylformamide (3 mL) and benzamide (70.3 mg, 0.580 mmol) was added thereto at 0° C. After the reaction mixture was stirred at room temperature for 25 minutes, 5-chloromethyl-6-(4-fluoro-2-methoxyphenyl)-2,2,4-trimethyl-1,2-dihydroquinoline (Reference Compound No. 5-2, 50.0 mg, 0.145 mmol) was added thereto and the reaction mixture was stirred at 50° C. for 1 hour. Ethyl acetate (100 mL) was added to the reaction mixture, then the whole was washed with water (100 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (34.1 mg) as a pale yellow amorphous product. (Yield 55%)

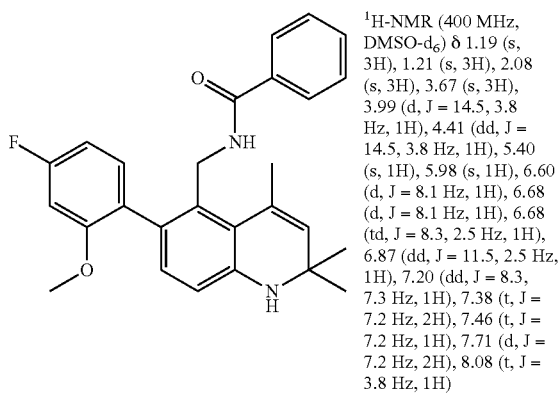

¹H-NMR (400 MHz, DMSO-d₆) δ 1.19 (s, 3H), 1.21 (s, 3H), 2.08 (s, 3H), 3.67 (s, 3H), 3.99 (d, J = 14.5, 3.8 Hz, 1H), 4.41 (dd, J = 14.5, 3.8 Hz, 1H), 5.40 (s, 1H), 5.98 (s, 1H), 6.60 (d, J = 8.1 Hz, 1H), 6.68 (d, J = 8.1 Hz, 1H), 6.68 (td, J = 8.3, 2.5 Hz, 1H), 6.87 (dd, J = 11.5, 2.5 Hz, 1H), 7.20 (dd, J = 8.3, 7.3 Hz, 1H), 7.38 (t, J = 7.2 Hz, 2H), 7.46 (t, J = 7.2 Hz, 1H), 7.71 (d, J = 7.2 Hz, 2H), 8.08 (t, J = 3.8 Hz, 1H)

Using Reference Compound No. 5-2, the following Compounds (No. 17-2~17-4) were obtained by a method similar to that of Compound No. 17-1.

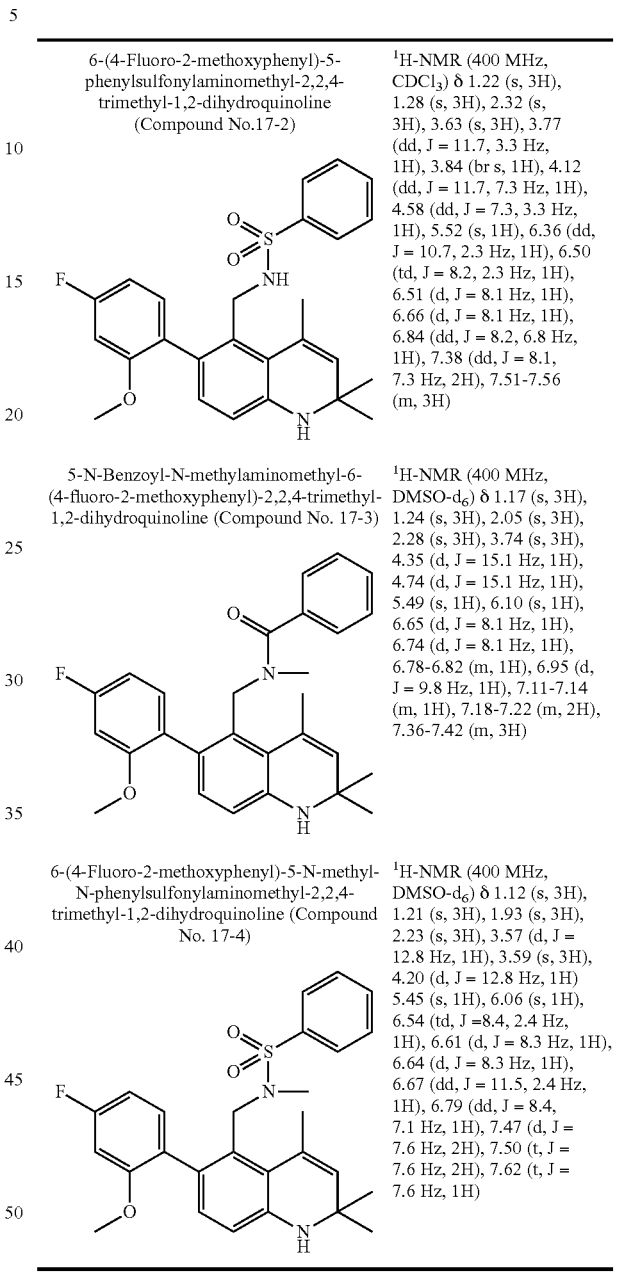

6-(4-Fluoro-2-methoxyphenyl)-5-phenylsulfonylaminomethyl-2,2,4-trimethyl-1,2-dihydroquinoline (Compound No.17-2)

¹H-NMR (400 MHz, CDCl₃) δ 1.22 (s, 3H), 1.28 (s, 3H), 2.32 (s, 3H), 3.63 (s, 3H), 3.77 (dd, J = 11.7, 3.3 Hz, 1H), 3.84 (br s, 1H), 4.12 (dd, J = 11.7, 7.3 Hz, 1H), 4.58 (dd, J = 7.3, 3.3 Hz, 1H), 5.52 (s, 1H), 6.36 (dd, J = 10.7, 2.3 Hz, 1H), 6.50 (td, J = 8.2, 2.3 Hz, 1H), 6.51 (d, J = 8.1 Hz, 1H), 6.66 (d, J = 8.1 Hz, 1H), 6.84 (dd, J = 8.2, 6.8 Hz, 1H), 7.38 (dd, J = 8.1, 7.3 Hz, 2H), 7.51-7.56 (m, 3H)

5-N-Benzoyl-N-methylaminomethyl-6-(4-fluoro-2-methoxyphenyl)-2,2,4-trimethyl-1,2-dihydroquinoline (Compound No. 17-3)

¹H-NMR (400 MHz, DMSO-d₆) δ 1.17 (s, 3H), 1.24 (s, 3H), 2.05 (s, 3H), 2.28 (s, 3H), 3.74 (s, 3H), 4.35 (d, J = 15.1 Hz, 1H), 4.74 (d, J = 15.1 Hz, 1H), 5.49 (s, 1H), 6.10 (s, 1H), 6.65 (d, J = 8.1 Hz, 1H), 6.74 (d, J = 8.1 Hz, 1H), 6.78-6.82 (m, 1H), 6.95 (d, J = 9.8 Hz, 1H), 7.11-7.14 (m, 1H), 7.18-7.22 (m, 2H), 7.36-7.42 (m, 3H)

6-(4-Fluoro-2-methoxyphenyl)-5-N-methyl-N-phenylsulfonylaminomethyl-2,2,4-trimethyl-1,2-dihydroquinoline (Compound No. 17-4)

¹H-NMR (400 MHz, DMSO-d₆) δ 1.12 (s, 3H), 1.21 (s, 3H), 1.93 (s, 3H), 2.23 (s, 3H), 3.57 (d, J = 12.8 Hz, 1H), 3.59 (s, 3H), 4.20 (d, J = 12.8 Hz, 1H), 5.45 (s, 1H), 6.06 (s, 1H), 6.54 (td, J =8.4, 2.4 Hz, 1H), 6.61 (d, J = 8.3 Hz, 1H), 6.64 (d, J = 8.3 Hz, 1H), 6.67 (dd, J = 11.5, 2.4 Hz, 1H), 6.79 (dd, J = 8.4, 7.1 Hz, 1H), 7.47 (d, J = 7.6 Hz, 2H), 7.50 (t, J = 7.6 Hz, 2H), 7.62 (t, J = 7.6 Hz, 1H)

Example 18

6-(4-Fluoro-2-methoxyphenyl)-5-phenylaminocarbonyloxymethyl-2,2,4-trimethyl-1,2-dihydroquinoline (Compound No. 18)

6-(4-Fluoro-2-methoxyphenyl)-5-hydroxymethyl-2,2,4-trimethyl-1,2-dihydroquinoline (Reference Compound No. 4-3, 50.0 mg, 0.153 mmol) and 4-dimethylaminopyridine (1.87 mg, 0.0153 mmol) were dissolved in anhydrous tetrahydrofuran (1 mL), then 1,1'-carbonyldiimidazole (32.3 mg, 0.199 mmol) was added thereto, and then the mixture was stirred at room temperature overnight [Solution 1].

1.6M n-Butyllithium solution in hexane (430 μL, 0.688 mmol) was added to a solution of aniline (69.7 μL, 0.765 mmol) in anhydrous tetrahydrofuran (2 mL) dropwise and the mixture was stirred at 0° C. for 30 minutes [Solution 2].

After the Solution 2 was cooled to −78° C., the Solution 1 was added dropwise thereto, and the reaction mixture was stirred at −78° C. for 30 minutes. After a saturated aqueous NH$_4$Cl solution (5 mL) was added to the reaction mixture, the mixture was diluted with ethyl acetate (100 mL). The whole was washed with water (100 mL), 0.02N aqueous HCl solution (100 mL), water (50 mL), and saturated brine (50 mL) successively, dried over anhydrous magnesium sulfate, and then the solvent was removed under reduced pressure. The obtained residue was purified by silica gel column chromatography (toluene-ethyl acetate) to give the titled compound (66.0 mg) as a pale yellow amorphous product. (Yield 97%)

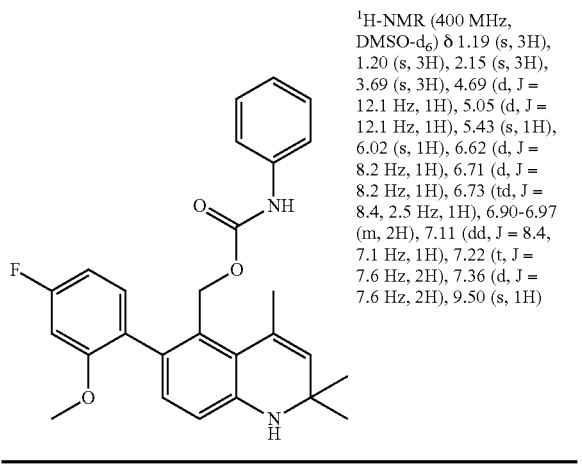

$^1$H-NMR (400 MHz, DMSO-d$_6$) δ 1.19 (s, 3H), 1.20 (s, 3H), 2.15 (s, 3H), 3.69 (s, 3H), 4.69 (d, J = 12.1 Hz, 1H), 5.05 (d, J = 12.1 Hz, 1H), 5.43 (s, 1H), 6.02 (s, 1H), 6.62 (d, J = 8.2 Hz, 1H), 6.71 (d, J = 8.2 Hz, 1H), 6.73 (td, J = 8.4, 2.5 Hz, 1H), 6.90-6.97 (m, 2H), 7.11 (dd, J = 8.4, 7.1 Hz, 1H), 7.22 (t, J = 7.6 Hz, 2H), 7.36 (d, J = 7.6 Hz, 2H), 9.50 (s, 1H)

Example No. 19

5-(2-Carboxymethylphenoxymethyl)-6-(4-fluoro-2-methoxyphenyl)-2,2,4-trimethyl-1,2-dihydroquinoline (Compound No. 19-1)

6-(4-Fluoro-2-methoxyphenyl)-5-(2-methoxycarbonylmethylphenoxymethyl)-2,2,4-trimethyl-1,2-dihydroquinoline (Compound No. 14-1, 84.0 mg, 0.18 mmol) was dissolved in methanol (2 mL)—tetrahydrofuran mL) and 1N aqueous NaOH solution (0.56 mL) was added thereto and the mixture was stirred at room temperature overnight. After ethyl acetate (100 mL) was added to the reaction mixture, the whole was washed with 0.01N aqueous HCl solution (100 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (74.1 mg) as a colorless solid. (Yield 89%)

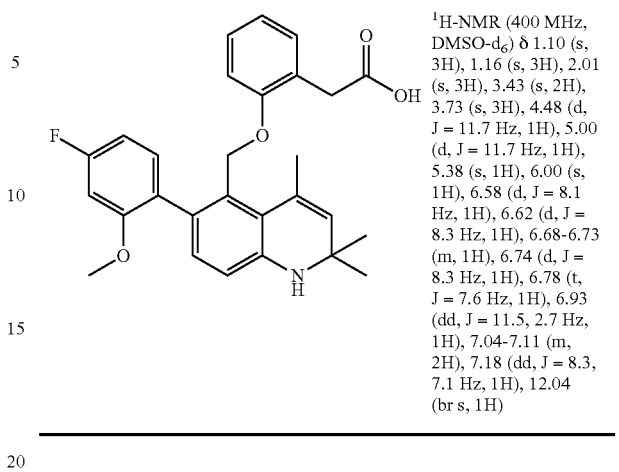

$^1$H-NMR (400 MHz, DMSO-d$_6$) δ 1.10 (s, 3H), 1.16 (s, 3H), 2.01 (s, 3H), 3.43 (s, 2H), 3.73 (s, 3H), 4.48 (d, J = 11.7 Hz, 1H), 5.00 (d, J = 11.7 Hz, 1H), 5.38 (s, 1H), 6.00 (s, 1H), 6.58 (d, J = 8.1 Hz, 1H), 6.62 (d, J = 8.3 Hz, 1H), 6.68-6.73 (m, 1H), 6.74 (d, J = 8.3 Hz, 1H), 6.78 (t, J = 7.6 Hz, 1H), 6.93 (dd, J = 11.5, 2.7 Hz, 1H), 7.04-7.11 (m, 2H), 7.18 (dd, J = 8.3, 7.1 Hz, 1H), 12.04 (br s, 1H)

Using any compounds among Compounds No. 3-51, 3-53 and 14-3, the following Compounds (No. 19-2~19-4) were obtained by a method similar to that of Compound No. 19-1.

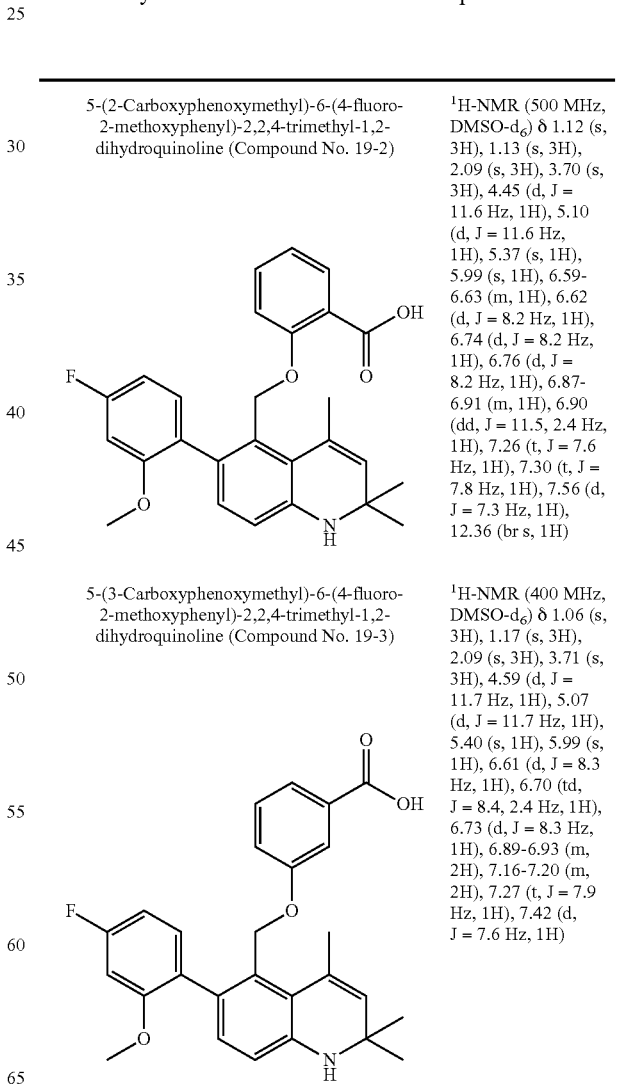

5-(2-Carboxyphenoxymethyl)-6-(4-fluoro-2-methoxyphenyl)-2,2,4-trimethyl-1,2-dihydroquinoline (Compound No. 19-2)

$^1$H-NMR (500 MHz, DMSO-d$_6$) δ 1.12 (s, 3H), 1.13 (s, 3H), 2.09 (s, 3H), 3.70 (s, 3H), 4.45 (d, J = 11.6 Hz, 1H), 5.10 (d, J = 11.6 Hz, 1H), 5.37 (s, 1H), 5.99 (s, 1H), 6.59-6.63 (m, 1H), 6.62 (d, J = 8.2 Hz, 1H), 6.74 (d, J = 8.2 Hz, 1H), 6.76 (d, J = 8.2 Hz, 1H), 6.87-6.91 (m, 1H), 6.90 (dd, J = 11.5, 2.4 Hz, 1H), 7.26 (t, J = 7.6 Hz, 1H), 7.30 (t, J = 7.8 Hz, 1H), 7.56 (d, J = 7.3 Hz, 1H), 12.36 (br s, 1H)

5-(3-Carboxyphenoxymethyl)-6-(4-fluoro-2-methoxyphenyl)-2,2,4-trimethyl-1,2-dihydroquinoline (Compound No. 19-3)

$^1$H-NMR (400 MHz, DMSO-d$_6$) δ 1.06 (s, 3H), 1.17 (s, 3H), 2.09 (s, 3H), 3.71 (s, 3H), 4.59 (d, J = 11.7 Hz, 1H), 5.07 (d, J = 11.7 Hz, 1H), 5.40 (s, 1H), 5.99 (s, 1H), 6.61 (d, J = 8.3 Hz, 1H), 6.70 (td, J = 8.4, 2.4 Hz, 1H), 6.73 (d, J = 8.3 Hz, 1H), 6.89-6.93 (m, 2H), 7.16-7.20 (m, 2H), 7.27 (t, J = 7.9 Hz, 1H), 7.42 (d, J = 7.6 Hz, 1H)

5-[2-(2-Carboxyethyl)phenoxymethyl]-6-(4-fluoro-2-methoxyphenyl)-2,2,4-trimethyl-1,2-dihydroquinoline (Compound No. 19-4)

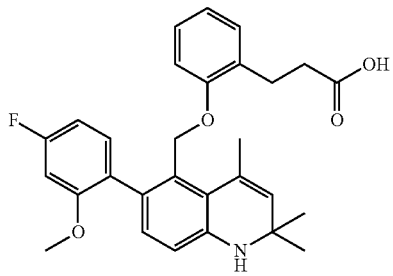 [SMILES: COc1cc(F)ccc1-c1ccc2c(c1COc1ccccc1CCC(=O)O)C(C)=CC(C)(C)N2]

$^1$H-NMR (400 MHz, DMSO-$d_6$) δ 1.09 (s, 3H), 1.17 (s, 3H), 2.01 (s, 3H), 2.36 (t, J = 8.0 Hz, 2H), 2.68 (t, J = 8.0 Hz, 2H), 3.73 (s, 3H), 4.57 (d, J = 11.7 Hz, 1H), 5.01 (d, J = 11.7 Hz, 1H), 5.38 (s, 1H), 6.01 (s, 1H), 6.58 (d, J = 7.8 Hz, 1H), 6.63 (d, J = 8.2 Hz, 1H), 6.72-6.77 (m, 2H), 6.75 (d, J = 8.2 Hz, 1H), 6.94 (dd, J = 11.5, 2.4 Hz, 1H), 7.02 (td, J = 7.8, 1.5 Hz, 1H), 7.07 (dd, J = 7.3, 1.5 Hz, 1H), 7.17 (dd, J = 8.3, 7.1 Hz, 1H), 12.00 (br s, 1H)

Example 20

5-(2-Aminophenoxymethyl)-6-(4-fluoro-2-methoxyphenyl)-2,2,4-trimethyl-1,2-dihydroquinoline (Compound No. 20-1)

4N HCl/1,4-dioxane solution (1 mL) was added to 5-(2-t-Butoxycarbonylaminophenoxymethyl)-6-(4-fluoro-2-methoxyphenyl)-2,2,4-trimethyl-1,2-dihydroquinoline (Compound No. 3-79, 9.6 mg, 0.019 mmol), then the reaction mixture was stirred at room temperature for 1 hour. The reaction mixture was concentrated under reduced pressure. Ethyl acetate (10 mL) and saturated aqueous NaHCO$_3$ solution (10 mL) were added to the residue and separated. The organic layer was dried over anhydrous magnesium sulfate. The solvent was removed under reduced pressure to give the titled compound (5.4 mg) as a yellow oil. (Yield 70%)

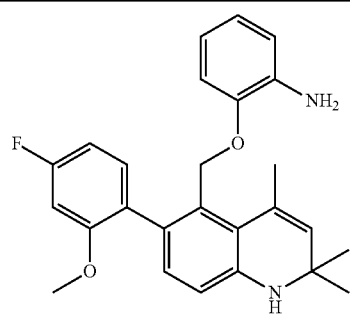

$^1$H-NMR (400 MHz, DMSO-$d_6$) δ 1.14 (s, 3H), 1.20 (s, 3H), 2.04 (s, 3H), 3.72 (s, 3H), 4.45 (s, 2H), 4.52 (d, J = 11.2 Hz, 1H), 4.95 (d, J = 11.2 Hz, 1H), 5.40 (s, 1H), 6.03 (s, 1H), 6.34-6.42 (m, 1H), 6.47 (d, J = 7.1 Hz, 1H), 6.52-6.61 (m, 2H), 6.63 (d, J = 8.3 Hz, 1H), 6.70 (td, J = 8.4, 2.4 Hz, 1H), 6.74 (d, J = 8.3 Hz, 1H), 6.92 (dd, J = 11.5, 2.4 Hz, 1H), 7.18 (dd, J = 8.4, 7.2 Hz, 1H)

Using Compound No. 6-86, the following Compound No. 20-2 was obtained by a method similar to that of Compound No. 20-1.

6-(4-Fluoro-2-methoxyphenyl)-5-[2-(2-aminoethyl)phenylaminomethyl]-2,2,4-trimethyl-1,2-dihydroquinoline (Compound No. 20-2)

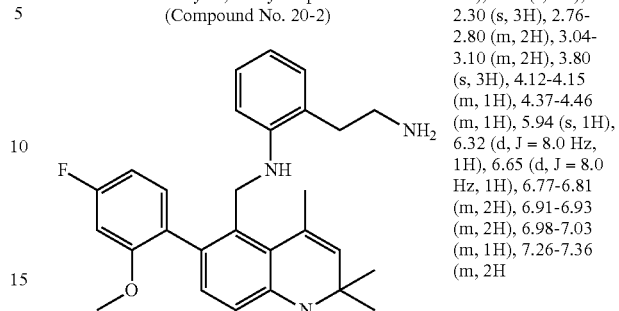

$^1$H-NMR (400 MHz, DMSO-$d_6$) δ 1.32 (s, 3H), 1.45 (s, 3H), 2.30 (s, 3H), 2.76-2.80 (m, 2H), 3.04-3.10 (m, 2H), 3.80 (s, 3H), 4.12-4.15 (m, 1H), 4.37-4.46 (m, 1H), 5.94 (s, 1H), 6.32 (d, J = 8.0 Hz, 1H), 6.65 (d, J = 8.0 Hz, 1H), 6.77-6.81 (m, 2H), 6.91-6.93 (m, 2H), 6.98-7.03 (m, 1H), 7.26-7.36 (m, 2H)

Example 21

6-(5-Amino-2-methoxyphenyl)-5-(5-fluoro-2-methylphenoxymethyl)-2,2,4-trimethyl-1,2-dihydroquinoline (Compound No. 21-1)

5-(5-Fluoro-2-methylphenoxymethyl)-6-(2-methoxy-5-nitrophenyl)-2,2,4-trimethyl-1,2-dihydroquinoline (Compound No. 14-48, 100.4 mg, 0.217 mmol) was dissolved in 4N aqueous NaOH solution (405 µL, 1.62 mmol)—ethanol (5 mL), and zinc (292.9 mg, 4.48 mmol) was added thereto, and then the reaction mixture was stirred at 110° C. overnight. Ethyl acetate (20 mL) was added to the reaction mixture and the unsoluble materials were filtered. After ethyl acetate (50 mL) was added to the filtrate, the whole was washed with water (100 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (12.1 mg) as a yellow amorphous product. (Yield 13%)

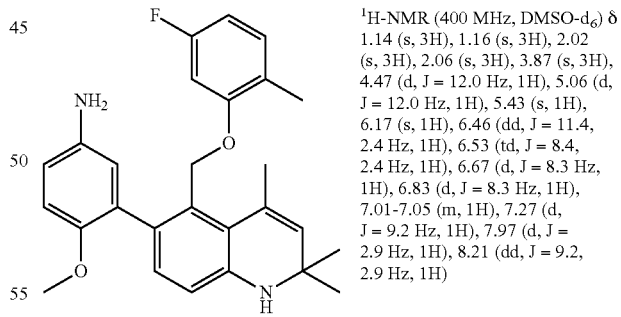

$^1$H-NMR (400 MHz, DMSO-$d_6$) δ 1.14 (s, 3H), 1.16 (s, 3H), 2.02 (s, 3H), 2.06 (s, 3H), 3.87 (s, 3H), 4.47 (d, J = 12.0 Hz, 1H), 5.06 (d, J = 12.0 Hz, 1H), 5.43 (s, 1H), 6.17 (s, 1H), 6.46 (dd, J = 11.4, 2.4 Hz, 1H), 6.53 (td, J = 8.4, 2.4 Hz, 1H), 6.67 (d, J = 8.3 Hz, 1H), 6.83 (d, J = 8.3 Hz, 1H), 7.01-7.05 (m, 1H), 7.27 (d, J = 9.2 Hz, 1H), 7.97 (d, J = 2.9 Hz, 1H), 8.21 (dd, J = 9.2, 2.9 Hz, 1H)

Example 22

6-(2-Methoxy-5-phenylacetylphenyl)-5-(4-methylbenzoyloxymethyl)-2,2,4-trimethyl-1,2-dihydroquinoline (Compound No. 22)

Aluminum chloride (97.0 mg, 0.73 mmol) was added to anhydrous dichloroethane (0.5 mL) and the solution was cooled to 0° C. Phenylacetyl chloride (97 µL, 0.73 mmol) and 6-(2-methoxyphenyl)-5-(4-methylbenzoyloxymethyl)-2,2,4-trimethyl-1,2-dihydroquinoline (Compound No. 13-3, 49.7 mg, 0.12 mmol) were added thereto and the reaction mixture was stirred at room temperature for 1.5 hours. Ethyl acetate (100 mL) was added to the reaction mixture, and the whole was washed with water (100 mL) and saturated brine (50 mL) successively, dried over anhydrous magnesium sulfate, and then the solvent was removed under reduced pressure. The residue was purified by silica gel column chromatography (hexane-ethyl acetate) to give the titled compound (53.6 mg) as a pale yellow amorphous product. (Yield 82%)

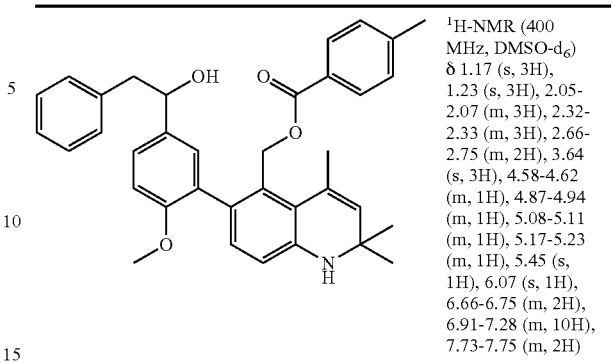

$^1$H-NMR (400 MHz, DMSO-$d_6$) δ 1.17 (s, 3H), 1.23 (s, 3H), 2.05-2.07 (m, 3H), 2.32-2.33 (m, 3H), 2.66-2.75 (m, 2H), 3.64 (s, 3H), 4.58-4.62 (m, 1H), 4.87-4.94 (m, 1H), 5.08-5.11 (m, 1H), 5.17-5.23 (m, 1H), 5.45 (s, 1H), 6.07 (s, 1H), 6.66-6.75 (m, 2H), 6.91-7.28 (m, 10H), 7.73-7.75 (m, 2H)

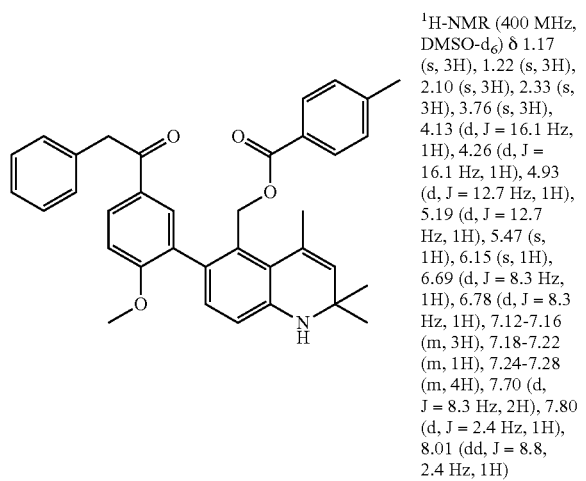

$^1$H-NMR (400 MHz, DMSO-$d_6$) δ 1.17 (s, 3H), 1.22 (s, 3H), 2.10 (s, 3H), 2.33 (s, 3H), 3.76 (s, 3H), 4.13 (d, J = 16.1 Hz, 1H), 4.26 (d, J = 16.1 Hz, 1H), 4.93 (d, J = 12.7 Hz, 1H), 5.19 (d, J = 12.7 Hz, 1H), 5.47 (s, 1H), 6.15 (s, 1H), 6.69 (d, J = 8.3 Hz, 1H), 6.78 (d, J = 8.3 Hz, 1H), 7.12-7.16 (m, 3H), 7.18-7.22 (m, 1H), 7.24-7.28 (m, 4H), 7.70 (d, J = 8.3 Hz, 2H), 7.80 (d, J = 2.4 Hz, 1H), 8.01 (dd, J = 8.8, 2.4 Hz, 1H)

Example No. 23

6-[5-(1-Hydroxy-2-phenylethyl)-2-methoxyphenyl]-5-(4-methylbenzoyloxymethyl)-2,2,4-trimethyl-1,2-dihydroquinoline (Compound No. 23)

6-(2-Methoxy-5-phenylacetylphenyl)-5-(4-methylbenzoyloxymethyl)-2,2,4-trimethyl-1,2-dihydroquinoline (Compound No. 22, 34.0 mg. 0.0623 mmol) was dissolved in tetrahydrofuran (0.5 mL)—methanol (0.5 mL), and sodium borohydride (6.8 mg, 0.180 mmol) was added thereto, and then the reaction mixture was stirred at room temperature for 45 minutes. 1N aqueous HCl solution (0.5 mL) and ethyl acetate (50 mL) were added to the reaction mixture, the whole was washed with water (50 mL, twice) and saturated brine (50 mL) successively, dried over anhydrous magnesium sulfate, and then the solvent was removed under reduced pressure. The residue was purified by silica gel column chromatography (hexane-ethyl acetate) to give the titled compound (31.8 mg) as a colorless amorphous product (yield: 93%)

Preparation Examples

Hereinafter, typical preparation examples of the present compound are shown.

| 1) Tablet (in 100 mg) | |
|---|---|
| Present Compound | 1 mg |
| Lactose | 66.4 mg |
| Cornstarch | 20 mg |
| Carboxymethyl cellulose calcium | 6 mg |
| Hydroxypropyl cellulose | 4 mg |
| Magnesium stearate | 0.6 mg |

A tablet of the above-mentioned formulation is coated with 2 mg of a coating agent (for example, a conventional coating agent such as hydroxypropylmethyl cellulose, macrogol or a silicone resin), whereby an objective tablet can be obtained. In addition, a desired tablet can be obtained by appropriately changing the kind and/or amount of the present compound and additives.

| 2) Capsule (in 150 mg) | |
|---|---|
| Present Compound | 5 mg |
| Lactose | 145 mg |

A desired capsule can be obtained by appropriately changing the mixing ratio of the present compound to lactose.

| 3) Eye drop (in 100 mL) | |
|---|---|
| Present Compound | 100 mg |
| Sodium chloride | 900 mg |
| Polysorbate 80 | 200 mg |
| Sodium hydroxide | q.s. |
| Hydrochloric acid | q.s. |
| Sterile purified water | q.s. |

A desired eye drop can be obtained by appropriately changing the kind and/or amount of the present compound and additives.

[Pharmacological Test]

1. Evaluation Test for Binding Activity to Glucocorticoid Receptor (Hereinafter Referred to as "GR")

In order to evaluate a binding activity to GR, a receptor competitor assay was carried out by a fluorescence polarization method. In the assay, a GR competitor assay kit (manufactured by Invitrogen, cat No. P2816) was used, and a procedure was carried out according to the protocol attached to the kit. Hereinafter, the specific method will be described.
(Preparation of Reagents)

GR screening buffer: A buffer containing 10 mM potassium phosphate (pH 7.4), 20 mM sodium molybdate ($Na_2MoO_4$), 0.1 mM ethylene diamine tetraacetic acid (EDTA), 5 mM dithiothreitol (DTT), 0.1 mM stabilizing peptide and 2% dimethylsulfoxide was prepared.

4×GS1 solution: Fluormone™ GS1, which is a fluorescent glucocorticoid ligand, was diluted with GR screening buffer, whereby a 4 nM solution was prepared.

4×GR solution: Recombinant human GR was diluted with GR screening buffer, whereby a 16 nM solution was prepared.
(Preparation of Test Compound Solution)

After a test compound was dissolved in dimethylsulfoxide, the resulting solution was diluted with GR screening buffer, whereby a 20 µM test compound solution was prepared.
(Test Method and Measurement Method)

1) The test compound solution was added in an amount of 25 µL or 10 µL into each well of a 96-well or 384-well plate, and then, 4×GS1 solution and 4×GR solution were added in an amount of 12.5 µL or 5 µL into each well, respectively.

2) The plate was incubated in a dark place at room temperature for 2 to 4 hours.

3) By using a multimode plate reader, Analyst™ HT (manufactured by LJL Biosystems), fluorescence polarization of each well was measured. As the blank, a well containing GR screening buffer in place of the test compound and 4×GS1 solution was used.

4) The same procedure as that in the above 1) to 3) was carried out except that GR screening buffer was used in place of the test compound solution, and the obtained result was taken as the negative control.

5) The same procedure as that in the above 1) to 3) was carried out except that 2 mM dexamethasone was used in place of the test compound solution, and the obtained result was taken as the positive control.
(Calculation Equation of GR Binding Ratio)

A GR binding ratio (%) was calculated from the following equation.

GR binding ratio(%)=100×[1−(fluorescence polarization of test compound solution−fluorescence polarization of positive control solution)/(fluorescence polarization of negative control solution−fluorescence polarization of positive control solution)]

(Test Results and Discussion)

As an example of the test results, the GR binding ratios (%) of the test compounds (Compound 1-19, Compound 1-21, Compound 1-46, Compound 3-21, Compound 3-22, Compound 3-33, Compound 3-44, Compound 3-45, Compound 3-48, Compound 3-56, Compound 3-57, Compound 3-58, Compound 3-59, Compound 3-61, Compound 3-62, Compound 3-67, Compound 3-68, Compound 3-69, Compound 3-72, Compound 3-74, Compound 3-85, Compound 3-91, Compound 3-94, Compound 3-98, Compound 3-99, Compound 5-3, Compound 5-4, Compound 6-20, Compound 6-24, Compound 6-27, Compound 6-36, Compound 6-37, Compound 6-40, Compound 6-43, Compound 6-45, Compound 6-47, Compound 6-53, Compound 6-57, Compound 6-59, Compound 6-75, Compound 6-76, Compound 6-77, Compound 6-78, Compound 6-79, Compound 12-17, Compound 12-19, Compound 12-20, Compound 12-21, Compound 12-22, Compound 12-25, Compound 12-33, Compound 12-42, Compound 12-53, Compound 12-54, Compound 12-58, Compound 12-67, Compound 12-69, Compound 12-73, Compound 12-75, Compound 12-76, Compound 14-1, Compound 14-11, Compound 14-12, Compound 14-13, Compound 14-15, Compound 14-21, Compound 14-40, Compound 14-41, Compound 14-43, Compound 14-45, Compound 14-47, Compound 14-48, Compound 15-2, and Compound 15-7) are shown in Table I.

TABLE I

| Test Compound | GR Binding ratio (%) |
|---|---|
| Compound 1-19 | 100 |
| Compound 1-21 | 82 |
| Compound 1-46 | 100 |
| Compound 3-21 | 97 |
| Compound 3-22 | 99 |
| Compound 3-33 | 100 |
| Compound 3-44 | 98 |
| Compound 3-45 | 98 |
| Compound 3-48 | 100 |
| Compound 3-56 | 98 |
| Compound 3-57 | 98 |
| Compound 3-58 | 100 |
| Compound 3-59 | 100 |
| Compound 3-61 | 100 |
| Compound 3-62 | 100 |
| Compound 3-67 | 100 |
| Compound 3-68 | 100 |
| Compound 3-69 | 100 |
| Compound 3-72 | 100 |
| Compound 3-74 | 100 |
| Compound 3-85 | 95 |
| Compound 3-91 | 100 |
| Compound 3-94 | 100 |
| Compound 3-98 | 100 |
| Compound 3-99 | 100 |
| Compound 5-3 | 100 |
| Compound 5-4 | 95 |
| Compound 6-20 | 100 |
| Compound 6-24 | 100 |
| Compound 6-27 | 100 |
| Compound 6-36 | 98 |
| Compound 6-37 | 100 |
| Compound 6-40 | 99 |
| Compound 6-43 | 100 |
| Compound 6-45 | 96 |
| Compound 6-47 | 100 |
| Compound 6-53 | 95 |
| Compound 6-57 | 100 |
| Compound 6-59 | 96 |
| Compound 6-75 | 100 |
| Compound 6-76 | 100 |
| Compound 6-77 | 100 |
| Compound 6-78 | 100 |
| Compound 6-79 | 100 |
| Compound 12-17 | 100 |
| Compound 12-19 | 100 |
| Compound 12-20 | 100 |
| Compound 12-21 | 100 |
| Compound 12-22 | 100 |
| Compound 12-25 | 100 |
| Compound 12-33 | 100 |
| Compound 12-42 | 99 |
| Compound 12-53 | 100 |
| Compound 12-54 | 100 |
| Compound 12-58 | 100 |
| Compound 12-67 | 100 |
| Compound 12-69 | 100 |
| Compound 12-73 | 100 |
| Compound 12-75 | 100 |
| Compound 12-76 | 100 |
| Compound 14-1 | 100 |
| Compound 14-11 | 100 |
| Compound 14-12 | 100 |
| Compound 14-13 | 100 |
| Compound 14-15 | 99 |
| Compound 14-21 | 99 |
| Compound 14-40 | 100 |

TABLE I-continued

| Test Compound | GR Binding ratio (%) |
|---|---|
| Compound 14-41 | 100 |
| Compound 14-43 | 100 |
| Compound 14-45 | 100 |
| Compound 14-47 | 100 |
| Compound 14-48 | 100 |
| Compound 15-2 | 76 |
| Compound 15-7 | 100 |

Incidentally, a GR binding ratio of 100% or more is indicated by 100%.

INDUSTRIAL APPLICABILITY

As is apparent from Table I, the present compound shows an excellent GR receptor binding activity. Accordingly, the present compound can be used as a GR receptor modulator, and is useful for a preventive or therapeutic agent particularly for GR-related diseases, that is, metabolic disorders, inflammatory diseases, autoimmune diseases, allergic diseases, central nervous system diseases, cardiovascular diseases, homeostasis-related diseases, glaucoma and the like.

The invention claimed is:

1. A method for treating a glucocorticoid receptor-related disease selected from the group consisting of diabetes, obesity, enteritis, a chronic obstructive pulmonary disease, a connective tissue disease, asthma, atopic dermatitis, allergic rhinitis, a psychiatric disorder, Alzheimer's disease, a drug use disorder, hypertension, hypercalcemia, hyperinsulinemia, hyperlipidemia, a homeostasis-related disease causing an abnormality of neuro-immune-endocrine balance and glaucoma, the method comprising administering a therapeutically effective amount of a compound of formula (1) or a pharmaceutically acceptable salt thereof to a patient, the compound of formula (1) being:

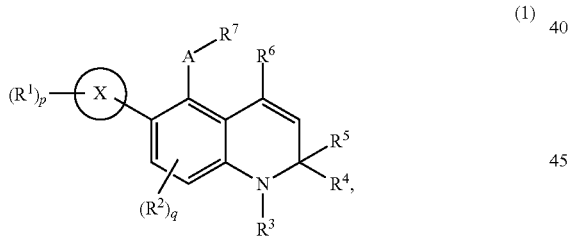

(1)

wherein the ring X represents a benzene ring or a pyridine ring;

$R^1$ represents a halogen atom, a lower alkyl group which optionally has a substituent, a hydroxy group, a lower alkoxy group which optionally has a substituent, a lower alkenyloxy group which optionally has a substituent, a lower alkylcarbonyl group, an amino group, a nitro group or a cyano group;

p represents an integer of 0 to 5;

in the case where p is 2 to 5, each $R^1$ is the same or different;

$R^2$ represents a halogen atom, a lower alkyl group which optionally has a substituent, a hydroxy group, an ester of a hydroxy group or a lower alkoxy group which optionally has a substituent;

q represents an integer of 0 to 2;

in the case where q is 2, each $R^2$ is the same or different;

$R^3$ represents a hydrogen atom, a lower alkyl group which optionally has a substituent, a lower alkenyl group which optionally has a substituent, a lower alkynyl group which optionally has a substituent, an aryl group which optionally has a substituent, a lower alkylcarbonyl group which optionally has a substituent, a lower alkenylcarbonyl group which optionally has a substituent, a lower alkynylcarbonyl group which optionally has a substituent or an arylcarbonyl group which optionally has a substituent;

$R^4$ and $R^5$ are the same or different and represent a hydrogen atom or a lower alkyl group; or $R^4$ and $R^5$ are combined together to form a 3- to 8-membered lower cycloalkane ring;

$R^6$ represents a hydrogen atom or a lower alkyl group;

A represents a lower alkylene group or a carbonyl group;

$R^7$ represents $OR^8$, $NR^8R^9$, $SR^8$, $S(O)R^8$ or $S(O)_2R^8$;

$R^8$ represents a lower alkyl group which optionally has a substituent, a lower alkenyl group which optionally has a substituent, a lower alkynyl group which optionally has a substituent, a lower cycloalkyl group optionally has a substituent, an aryl group which optionally has a substituent, a heterocyclic group which optionally has a substituent, a formyl group, a lower alkylcarbonyl group which optionally has a substituent, a lower alkenylcarbonyl group which optionally has a substituent, a lower alkynylcarbonyl group which optionally has a substituent, a lower cycloalkylcarbonyl group which optionally has a substituent, an arylcarbonyl group which optionally has a substituent, a heterocyclic carbonyl group which optionally has a substituent, a carboxy group, a lower alkoxycarbonyl group which optionally has a substituent, a lower alkenyloxycarbonyl group which optionally has a substituent, a lower alkynyloxycarbonyl group which optionally has a substituent, a lower cycloalkyloxycarbonyl group which optionally has a substituent, an aryloxycarbonyl group which optionally has a substituent, a heterocyclic oxycarbonyl group which optionally has a substituent, a lower alkylsulfonyl group which optionally has a substituent, a lower alkenylsulfonyl group which optionally has a substituent, a lower alkynylsulfonyl group which optionally has a substituent, a lower cycloalkylsulfonyl group which optionally has a substituent, an arylsulfonyl group which optionally has a substituent, a heterocyclic sulfonyl group which optionally has a substituent, an aminocarbonyl group, a lower alkylaminocarbonyl group which optionally has a substituent, a lower alkenylaminocarbonyl group which optionally has a substituent, a lower alkynylaminocarbonyl group which optionally has a substituent, a lower cycloalkylaminocarbonyl group which optionally has a substituent, an arylaminocarbonyl group which optionally has a substituent or a heterocyclic aminocarbonyl group which optionally has a substituent;

$R^9$ represents a hydrogen atom, a lower alkyl group which optionally has a substituent, a lower alkenyl group which optionally has a substituent, a lower alkynyl group which optionally has a substituent, a lower cycloalkyl group which optionally has a substituent, an aryl group which optionally has a substituent, a heterocyclic group which optionally has a substituent, a formyl group, a lower alkylcarbonyl group which optionally has a substituent, a lower alkenylcarbonyl group which optionally has a substituent, a lower alkynylcarbonyl group which optionally has a substituent, a lower cycloalkylcarbonyl group which optionally has a substituent, an arylcarbonyl group which optionally has a substituent, a heterocyclic carbonyl group which optionally has a substituent, a carboxy group, a lower alkoxycarbonyl group optionally has a substituent, a lower alkenyloxycarbonyl group which optionally has a substituent, a lower alkynyloxycarbonyl group which optionally has a substituent, a lower cycloalkyloxycarbonyl group which optionally has a substituent, an aryloxycarbonyl group which optionally has a substituent, a heterocyclic oxycarbonyl group which optionally has a substituent, a lower alkylsulfonyl group which optionally has a substituent, a lower alkenylsulfonyl group which optionally has a substituent, a lower alkynylsulfonyl group which optionally has a substituent, a lower cycloalkylsulfonyl group which optionally has a substituent, an arylsulfonyl group which optionally has a substituent, a heterocyclic sulfonyl group which optionally has a substituent, an aminocarbonyl group, a lower alkylaminocarbonyl group which optionally has a substituent, a lower alkenylaminocarbonyl group which optionally has a substituent, a lower alkynylaminocarbonyl group which optionally has a substituent, a lower cycloalkylaminocarbonyl group which optionally has a substituent, an arylaminocarbonyl group which optionally has a substituent or a heterocyclic aminocarbonyl group which optionally has a substituent;

in the case where $R^7$ is $NR^8R^9$, $R^8$ and $R^9$ may be combined together to form a 3- to 8-membered nitrogen-containing heterocyclic ring which optionally has a substituent.

2. The method according to claim 1, wherein in the formula (I), the ring X represents a benzene ring or a pyridine ring;

$R^1$ represents a halogen atom, a lower alkyl group, a hydroxy group, a lower alkoxy group, a lower alkenyloxy group, a lower alkylcarbonyl group, an amino group, a nitro group or a cyano group;

in the case where $R^1$ is a lower alkyl group or a lower alkoxy group, the lower alkyl group or the lower alkoxy group optionally has one or a plurality of substituents selected from the group consisting of a halogen atom, an aryl group, an aryl group substituted by a halogen atom, an aryl group substituted by a lower alkyl group, an aryl group substituted by a hydroxy group, an aryl group substituted by a lower alkoxy group, a hydroxyl group, an ester of a hydroxy group, a lower alkoxy group, an aryloxy group, a carboxy group and an ester of a carboxy group;

p represents an integer of 0 to 3;

in the case where p is 2 or 3, each $R^1$ is the same or different;

$R^2$ represents a halogen atom, a lower alkyl group, a hydroxy group, an ester of a hydroxy group or a lower alkoxy group;

q represents an integer of 0 to 2;

in the case where q is 2, each $R^2$ is the same or different;

$R^3$ represents a hydrogen atom, a lower alkyl group, a lower alkenyl group, a lower alkynyl group, an aryl group, a lower alkylcarbonyl group, a lower alkenylcarbonyl group, a lower alkynylcarbonyl group or an arylcarbonyl group; in the case where $R^3$ is a lower alkyl group or a lower alkylcarbonyl group, the lower alkyl group or lower alkylcarbonyl group optionally has one or a plurality of substituents comprising aryl groups;

in the case where $R^3$ is an aryl group or an arylcarbonyl group, the aryl group or the arylcarbonyl group optionally has one or a plurality of substituents selected from the group consisting of a halogen atom and a lower alkyl group;

$R^4$ and $R^5$ are the same or different and represent a hydrogen atom or a lower alkyl group;

$R^6$ represents a hydrogen atom or a lower alkyl group;

A represents a lower alkylene group or a carbonyl group;

$R^7$ represents $OR^8NR^8R^9$ or $SR^8$;

$R^8$ represents a lower alkyl group, a lower alkenyl group, a lower alkynyl group, a lower cycloalkyl group, an aryl group, a heterocyclic group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfonyl group, a lower alkenylsulfonyl group, a lower alkynylsulfonyl group, a lower cycloalkylsulfonyl group, an arylsulfonyl group, a heterocyclic sulfonyl group, an aminocarbonyl group, a lower alkylaminocarbonyl group, a lower alkenylaminocarbonyl group, a lower alkynylaminocarbonyl group, a lower cycloalkylaminocarbonyl group, an arylaminocarbonyl group or a heterocyclic aminocarbonyl group;

$R^9$ represents a hydrogen atom, a lower alkyl group, a lower alkenyl group, a lower alkynyl group, a lower cycloalkyl group, an aryl group, a heterocyclic group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfonyl group, a lower alkenylsulfonyl group, a lower alkynylsulfonyl group, a lower cycloalkylsulfonyl group, an arylsulfonyl group, a heterocyclic sulfonyl group, an aminocarbonyl group, a lower alkylaminocarbonyl group, a lower alkenylaminocarbonyl group, a lower alkynylaminocarbonyl group, a lower cycloalkylaminocarbonyl group, an arylaminocarbonyl group or a heterocyclic aminocarbonyl group;

in the case where $R^8$ or $R^9$ is a lower alkyl group, a lower alkenyl group, a lower alkynyl group, a lower alkylcarbonyl group, a lower alkenylcarbonyl group, a lower alkynylcarbonyl group, a lower alkoxycarbonyl group, a lower alkenyloxycarbonyl group, a lower alkynyloxycarbonyl group, a lower alkylsulfonyl group, a lower alkenylsulfonyl group, a lower alkynylsulfonyl group, a lower alkylaminocarbonyl group, a lower alkenylaminocarbonyl group or a lower alkynylaminocarbonyl group, the lower alkyl group, the lower alkenyl group, the lower alkynyl group, the lower alkylcarbonyl group, the lower alkenylcarbonyl group, the lower alkynylcarbonyl group, the lower alkoxycarbonyl group, the lower alkenyloxycarbonyl group, the lower alkynyloxycarbonyl group, the lower alkylsulfonyl group, the lower alkenylsulfonyl group, lower alkynylsulfonyl group, the lower alkylaminocarbonyl group, lower alkenylaminocarbonyl group or the lower alkynylaminocarbonyl group optionally has one or a plurality of substituents selected from the group consisting of a halogen atom, a lower cycloalkyl group, an aryl group, a heterocyclic group, a hydroxy group, an ester of a hydroxy group, a lower alkoxy group, a lower alkoxy group substituted by a halogen atom, a lower alkenyloxy group, a lower alkynyloxy group, a lower cycloalkyloxy group, an aryloxy group, a heterocyclic oxy group, a mercapto group, an ester of a mercapto group, a lower alkylthio group, a lower alkenylthio group, a lower alkynylthio group, a lower cycloalkylthio group, an arylthio group, a heterocyclic thio group, an amino group, an amide of an amino group, a lower alkylamino group, an amide of a lower alkylamino group, an arylamino group, an amide of an arylamino group, a heterocyclic amino group, an amide of a heterocyclic amino group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, an amide of a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfinyl group, an arylsulfinyl group, a lower alkylsulfonyl group, an arylsulfonyl group, a sulfinic acid group, an ester of a sulfinic acid group, an amide of a sulfinic acid group, a sulfonic acid group, an ester of a sulfonic acid group, an amide of a sulfonic acid group, a nitro group and a cyano group;

in the case where $R^8$ or $R^9$ is a lower cycloalkyl group, an aryl group, a heterocyclic group, a lower cycloalkylcarbonyl group, an arylcarbonyl group, a heterocyclic carbonyl group, a lower cycloalkyloxycarbonyl group, an aryloxycarbonyl group, a heterocyclic oxycarbonyl group, a lower cycloalkylsulfonyl group, an arylsulfonyl group, a heterocyclic sulfonyl group, a lower cycloalkylaminocarbonyl group, an arylaminocarbonyl group or a heterocyclic aminocarbonyl group, the lower cycloalkyl group, aryl group, the heterocyclic group, the lower cycloalkylcarbonyl group, the arylcarbonyl group, the heterocyclic carbonyl group, the lower cycloalkyloxycarbonyl group, the aryloxycarbonyl group, the heterocyclic oxycarbonyl group, the lower cycloalkylsulfonyl group, the arylsulfonyl group, the heterocyclic sulfonyl group, the lower cycloalkylaminocarbonyl group, the arylaminocarbonyl group or the heterocyclic aminocarbonyl group optionally has one or a plurality of substituents selected from the group consisting of a halogen atom, a lower alkyl group, a lower alkyl group substituted by a halogen atom, a lower alkyl group substituted by a hydroxy group, a lower alkyl group substituted by a lower alkoxy group, a lower alkyl group substituted by an amino group, a lower alkyl group substituted by a lower alkylamino group, a lower alkyl group substituted by a carboxy group, a lower alkyl group substituted by a lower alkoxycarbonyl group, a lower alkenyl group, a lower alkynyl group, a lower cycloalkyl group, an aryl group, a heterocyclic group, a hydroxy group, an ester of a hydroxy group, a lower alkoxy group, a lower alkoxy group substituted by a halogen atom, a lower alkenyloxy group, a lower alkynyloxy group, a lower cycloalkyloxy group, an aryloxy group, a heterocyclic oxy group, a mercapto group, an ester of a mercapto group, a lower alkylthio group, a lower alkenylthio group, a lower alkynylthio group, a lower cycloalkylthio group, an arylthio group, a heterocyclic thio group, an amino group, an amide of an amino group, a lower alkylamino group, an amide of a lower alkylamino group, an arylamino group, an amide of an arylamino group, a heterocyclic amino group, an amide of a heterocyclic amino group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, an amide of a carboxy group, a lower alkoxycarbonyl group, a lower alkynyloxycarbonyl group, a lower alkynyloxycarbonyl group, a lower cycloalkyloxycarbonyl group, an aryloxycarbonyl group, a heterocyclic oxycarbonyl group, a lower alkylsulfinyl group, an arylsulfinyl group, a lower alkylsulfonyl group, an arylsulfonyl group, a sulfinic acid group, an ester of a sulfinic acid group, an amide of a sulfinic acid group, a sulfonic acid group, an ester of a sulfonic acid group, an amide of a sulfonic acid group, a nitro group, a cyano group, an aminocarbonyloxy group, a lower alkylaminocarbonyloxy group and an arylaminocarbonyloxy group;

in the case where $R^7$ is $NR^8R^9$, $R^8$ and $R^9$ may be combined together to form a 5- or 6-membered nitrogen-containing heterocyclic ring.

3. The method according to claim 1, wherein in the formula (1), the ring X represents a benzene ring or a pyridine ring;

$R^1$ represents a halogen atom, a lower alkyl group, a hydroxy group, a lower alkoxy group, a lower alkenyloxy group, a lower alkylcarbonyl group, an amino group or a nitro group;

in the case where $R^1$ is a lower alkyl group or a lower alkoxy group, the lower alkyl group or the lower alkoxy group optionally has one or a plurality of substituents selected from the group consisting of a halogen atom, an aryl group, an aryl group substituted by a halogen atom, an aryl group substituted by a lower alkyl group, an aryl group substituted by a lower alkoxy group, a hydroxy group, a lower alkoxy group, an aryloxy group, a carboxy group and an ester of a carboxy group;

p represents an integer of 0 to 3;

in the case where p is 2 or 3, each $R^1$ is the same or different;

$R^2$ represents a halogen atom, a lower alkyl group, a hydroxy group or a lower alkoxy group;

q represents an integer of 0 to 2;

in the case where q is 2, each $R^2$ is the same or different;

$R^3$ represents a hydrogen atom, a lower alkyl group, a lower alkenyl group, an aryl group, a lower alkylcarbonyl group, a lower alkenylcarbonyl group or an arylcarbonyl group;

in the case where $R^3$ is a lower alkyl group or a lower alkylcarbonyl group, the lower alkyl group or the lower alkylcarbonyl group optionally has one or a plurality of substituents comprising aryl groups;

in the case where $R^3$ is an aryl group or an arylcarbonyl group, the aryl group or the arylcarbonyl group optionally has one or a plurality of substituents selected from the group consisting of a halogen atom and a lower alkyl group;

$R^4$ and $R^5$ are the same or different and represent a hydrogen atom or a lower alkyl group;

$R^6$ represents a hydrogen atom or a lower alkyl group;

A represents a lower alkylene group or a carbonyl group;

$R^7$ represents $OR^8$, $NR^8R^9$ or $SR^8$;

$R^8$ represents a lower alkyl group, a lower alkenyl group, a lower alkynyl group, a lower cycloalkyl group, an aryl group, a heterocyclic group, a lower alkylcarbonyl group, a lower alkenylcarbonyl group, a lower alkynylcarbonyl group, a lower cycloalkylcarbonyl group, an arylcarbonyl group or a heterocyclic carbonyl group;

$R^9$ represents a hydrogen atom, a lower alkyl group, a lower alkenyl group, a lower alkynyl group, a lower cycloalkyl group, an aryl group, a heterocyclic group, a lower alkylcarbonyl group, a lower alkenylcarbonyl group, a lower alkynylcarbonyl group, a lower cycloalkylcarbonyl group, an arylcarbonyl group or a heterocyclic carbonyl group;

in the case where $R^8$ or $R^9$ is a lower alkyl group, a lower alkenyl group, a lower alkynyl group, a lower alkylcarbonyl group, a lower alkenylcarbonyl group or a lower alkynylcarbonyl group, the lower alkyl group, the lower alkenyl group, the lower alkynyl group, the lower alkylcarbonyl group, the lower alkenylcarbonyl group or the lower alkynylcarbonyl group optionally has one or a plurality of substituents selected from the group consisting of an aryl group, a hydroxy group and a lower alkoxy group;

in the case where $R^8$ or $R^9$ is a lower cycloalkyl group, an aryl group, a heterocyclic group, a lower cycloalkylcarbonyl group, an arylcarbonyl group or a heterocyclic carbonyl group, the lower cycloalkyl group, aryl group, the heterocyclic group, the lower cycloalkylcarbonyl group, the arylcarbonyl group or the heterocyclic carbonyl group optionally has one or a plurality of substituents selected from the group consisting of a halogen atom, a lower alkyl group, a lower alkyl group substituted by a halogen atom, a lower alkyl group substituted by a hydroxy group, a lower alkyl group substituted by a lower alkoxy group, a lower alkyl group substituted by an amino group, a lower alkyl group substituted by a lower alkylamino group, a lower alkyl group substituted by a carboxy group, a lower alkyl group substituted by a lower alkoxycarbonyl group, a lower alkenyl group, a lower alkynyl group, an aryl group, a heterocyclic group, a hydroxy group, an ester of a hydroxy group, a lower alkoxy group, a lower alkoxy group substituted by a halogen atom, an aryloxy group, a mercapto group, a lower alkylthio group, an amino group, an amide of an amino group, a lower alkylamino group, an amide of a lower alkylamino group, a formyl group, a lower alkylcarbonyl group, a carboxy group, an amide of a carboxy group, a lower alkoxycarbonyl group, a nitro group, a cyano group, an aminocarbonyloxy group and a lower alkylaminocarbonyloxy group;

in the case where $R^7$ is $NR^8R^9$, $R^8$ and $R^9$ may be combined together to form a 5- or 6-membered nitrogen-containing heterocyclic ring.

4. The method according to claim 1, wherein in the formula (I), the ring X represents a benzene ring or a pyridine ring;

$R^1$ represents a halogen atom, a lower alkyl group, a hydroxy group, a lower alkoxy group, a lower alkenyloxy group, a lower alkylcarbonyl group, an amino group or a nitro group;

in the case where $R^1$ is a lower alkyl group or a lower alkoxy group, the lower alkyl group or the lower alkoxy group optionally has one or a plurality of substituents selected from the group consisting of a halogen atom, an aryl group, an aryl group substituted by a halogen atom, an aryl group substituted by a lower alkyl group, an aryl group substituted by a lower alkoxy group, a hydroxy group, a lower alkoxy group and an ester of a carboxy group;

p represents an integer of 0 to 3;

in the case where p is 2 or 3, each $R^1$ is the same or different;

$R^2$ represents a halogen atom, a lower alkyl group or a lower alkoxy group;

q represents 0 or 1;

$R^3$ represents a hydrogen atom, a lower alkyl group, a lower alkenyl group, a lower alkylcarbonyl group, a lower alkenylcarbonyl group or an arylcarbonyl group;

in the case where $R^3$ is a lower alkyl group, the lower alkyl group optionally has one or a plurality of substituents comprising aryl groups;

in the case where $R^3$ is an arylcarbonyl group, the arylcarbonyl group optionally has one or a plurality of substituents selected from group consisting of a halogen atom and a lower alkyl group;

$R^4$ and $R^5$ both represent a lower alkyl group;

$R^6$ represents a lower alkyl group;

A represents a lower alkylene group or a carbonyl group;

$R^7$ represents $OR^8$, $NR^8R^9$ or $SR^8$;

$R^8$ represents a lower alkyl group, a lower cycloalkyl group, an aryl group, a heterocyclic group, a lower alkylcarbonyl group, a lower alkenylcarbonyl group, a lower cycloalkylcarbonyl group, an arylcarbonyl group or a heterocyclic carbonyl group;

$R^9$ represents a hydrogen atom, a lower alkyl group, a lower cycloalkyl group, an aryl group, a heterocyclic group, an arylcarbonyl group or a heterocyclic carbonyl group;

in the case where $R^8$ or $R^9$ is a lower alkyl group, the lower alkyl group optionally has one or a plurality of substituents selected from the group consisting of a lower alkoxy group and an aryl group;

in the case where $R^8$ or $R^9$ is an aryl group, an arylcarbonyl group or a heterocyclic carbonyl group, the aryl group, the arylcarbonyl group or the heterocyclic carbonyl group optionally has one or a plurality of substituents selected from the group consisting of a halogen atom, a lower alkyl group, a lower alkyl group substituted by a halogen atom, a lower alkyl group substituted by a hydroxy group, a lower alkyl group substituted by an amino group, a lower alkyl group substituted by a lower alkylamino group, a lower alkyl group substituted by a carboxy group, a lower alkyl group substituted by a lower alkoxycarbonyl group, a lower alkenyl group, a lower alkynyl group, an aryl group, a hydroxy group, an ester of a hydroxy group, a lower alkoxy group, a lower alkoxy group substituted by a halogen atom, an aryloxy group, a lower alkylthio group, an amino group, an amide of an amino group, a lower alkylamino group, an amide of a lower alkylamino group, a formyl group, a lower alkylcarbonyl group, a carboxy group, an amide of a carboxy group, a lower alkoxycarbonyl group, a nitro group, a cyano group and a lower alkylaminocarbonyloxy group;

in the case where $R^7$ is $NR^8R^9$, $R^8$ and $R^9$ may be combined together to form a 5- or 6-membered nitrogen-containing heterocyclic ring.

5. The method according to claim 1, wherein in the formula (I), the ring X represents a benzene ring;

$R^1$ represents a halogen atom, a lower alkyl group, a hydroxy group, a lower alkoxy group, a lower alkenyloxy group, an amino group or a nitro group;

in the case where $R^1$ is a lower alkyl group, the lower alkyl group optionally has one or a plurality of substituents comprising halogen atoms;

in the case where $R^1$ is a lower alkoxy group, the lower alkoxy group optionally has one or a plurality of substituents selected from the group consisting of an aryl group, an aryl group substituted by a halogen atom, an aryl group substituted by a lower alkyl group, an aryl group substituted by a lower alkoxy group and a lower alkoxy group;

p represents 2 or 3, and in this case, each $R^1$ is the same or different;

R² represents a halogen atom, a lower alkyl group or a lower alkoxy group;

q represents 0 or 1;

R³ represents a hydrogen atom;

R⁴ and R⁵ both represent a lower alkyl group;

R⁶ represents a lower alkyl group;

A represents a lower alkylene group;

R⁷ represents OR⁸, NR⁸R⁹ or SR⁸;

R⁸ represents an aryl group, an arylcarbonyl group or a heterocyclic carbonyl group;

R⁹ represents a hydrogen atom or a lower alkyl group;

in the case where R⁸ is an aryl group, an arylcarbonyl group or a heterocyclic carbonyl group, the aryl group, arylcarbonyl group or the heterocyclic carbonyl group optionally has one or a plurality of substituents selected from the group consisting of a halogen atom, a lower alkyl group, a lower alkyl group substituted by a halogen atom, a lower alkyl group substituted by a hydroxy group, a lower alkyl group substituted by an amino group, a lower alkyl group substituted by a lower alkylamino group, a lower alkyl group substituted by a carboxy group, a lower alkyl group substituted by a lower alkoxycarbonyl group, a lower alkenyl group, a lower alkynyl group, an aryl group, a hydroxy group, an ester of a hydroxy group, a lower alkoxy group, a lower alkoxy group substituted by a halogen atom, an aryloxy group, a lower alkylthio group, an amino group, an amide of an amino group, a lower alkylamino group, an amide of a lower alkylamino group, a formyl group, a lower alkylcarbonyl group, a carboxy group, an amide of a carboxy group, a lower alkoxycarbonyl group, a nitro group, a cyano group and a lower alkylaminocarbonyloxy group.

6. The method according to claim 1, wherein in the formula (1), R⁷ is OR⁸.

7. The method according to claim 6, wherein R⁸ represents a phenyl group, a phenylcarbonyl group or a thiophenecarbonyl group.

8. The method according to claim 1, wherein in the formula (1), R⁷ is NR⁸R⁹.

9. The method according to claim 8, wherein R⁸ represents a phenyl group.

10. The method according to claim 1, wherein in the formula (1), R⁷ is SR⁸.

11. The method according to claim 1, wherein in the formula (1), the ring X is a benzene ring.

12. The method according to claim 1, wherein in the formula (1), A is a lower alkylene group.

13. The method according to claim 12, wherein in the formula (1), A represents a methylene group.

14. The method according to claim 1, wherein in the formula (1), R³ is a hydrogen atom.

15. The method according to claim 1, wherein in the formula (1), R⁴, R⁵ and R⁶ are a lower alkyl group.

16. The method according to claim 1, wherein in the formula (1), R⁴, R⁵ and R⁶ represent a methyl group.

17. The method according to claim 1, wherein the compound of formula (I) is selected from the group consisting of 5-acetoxymethyl-6-(2-methoxyphenyl)-2,2,4-trimethyl-1,2-dihydroquinoline, 5-benzoyloxymethyl-6-(2-methoxyphenyl)-2,2,4-trimethyl-1,2-dihydroquinoline, 6-(2-methoxyphenyl)-5-[(thiophene-2-yl)carbonyloxymethyl]-2,2,4-trimethyl-1,2-dihydroquinoline, 5-(4-t-butylbenzoyloxymethyl)-6-(2-methoxyphenyl)-2,2,4-trimethyl-1,2-dihydroquinoline, 5-benzoyloxymethyl-6-(4-fluoro-2-methoxyphenyl)-2,2,4-trimethyl-1,2-dihydroquinoine, 6-(4-fluoro-2-methoxyphenyl)-5-(3-methoxybenzoyloxymethyl)-2,2,4-trimethyl-1,2-dihydroquinoline, 6-(4-fluoro-2-methoxyphenyl)-5-(2-methoxybenzoyloxymethyl)-2,2,4-trimethyl-1,2-dihydroquinoline, 6-(4-fluoro-2-methoxyphenyl)-5-(4-methoxybenzoyloxymethyl)-2,2,4-trimethyl-1,2-dihydroquinoline, 6-(4-fluoro-2-methoxyphenyl)-5-[(thiophene-2-yl)carbonyl-oxymethyl]-2,2,4-trimethyl-1,2-dihydroquinoline, 6-(4-fluoro-2-methoxyphenyl)-5-(4-methylbenzoyloxymethyl)-2,2,4-trimethyl-1,2-dihydroquinoline, 6-(4-fluoro-2-methoxyphenyl)-5-(3-methylbenzoyloxymethyl)-2,2,4-trimethyl-1,2-dihydroquinoline, 6-(4-fluoro-2-methoxyphenyl)-5-(2-methylbenzoyloxymethyl)-2,2,4-trimethyl-1,2-dihydroquinoline, 6-(4-fluoro-2-methoxyphenyl)-5-phenoxymethyl-2,2,4-tri-methyl-1,2-dihydroquinoline, 6-(4-fluoro-2-methoxyphenyl)-5-(4-methoxyphenoxymethyl)-2,2,4-trimethyl-1,2-dihydroquinoline, 6-(4-fluoro-2-methoxyphenyl)-5-(4-fluorophenoxymethyl)-2,2,4-trimethyl-1,2-dihydroquinoline, 6-(4-fluoro-2-methoxyphenyl)-5-(3-fluorophenoxymethyl)-2,2,4-trimethyl-1,2-dihydroquinoline, 6-(4-fluoro-2-methoxyphenyl)-5-(2-fluorophenoxymethyl)-2,2,4-trimethyl-1,2-dihydroquinoline, 6-(4-fluoro-2-methoxyphenyl)-5-(3-methoxyphenoxymethyl)-2,2,4-trimethyl-1,2-dihydroquinoline, 6-(4-fluoro-2-methoxyphenyl)-5-(2-methoxyphenoxymethyl)-2,2,4-trimethyl-1,2-dihydroquinoline, 6-(4,5-difluoro-2-methoxyphenyl)-5-(3-fluorophenoxymethyl)-2,2,4-trimethyl-1,2-dihydroquinoline, 6-(4-fluoro-2-methoxyphenyl)-5-(4-methylphenoxymethyl)-2,2,4-trimethyl-1,2-dihydroquinoline, 6-(4-fluoro-2-methoxyphenyl)-5-(3-methylphenoxymethyl)-2,2,4-trimethyl-1,2-dihydroquinoline, 6-(4-fluoro-2-methoxyphenyl)-5-(2-methylphenoxymethyl)-2,2,4-trimethyl-1,2-dihydroquinoline, 6-(4-fluoro-2-methoxyphenyl)-5-(2-hydroxymethylphenoxy-methyl)-2,2,4-trimethyl-1,2-dihydroquinoline, 6-(4-fluoro-2-methoxyphenyl)-5-(5-fluoro-2-methylphenoxy-methyl)-2,2,4-trimethyl-1,2-dihydroquinoline, 6-(4-fluoro-2-methoxyphenyl)-5-(5-chloro-2-methylphenoxy-methyl)-2,2,4-trimethyl-1,2-dihydroquinoline, 6-(4,5-difluoro-2-methoxyphenyl)-5-(5-fluoro-2-methylphen-oxymethyl)-2,2,4-trimethyl-1,2-dihydroquinoline, 6-(4-fluoro-2-methoxyphenyl)-5-(2-methoxy-5-nitrophenoxy-methyl)-2,2,4-trimethyl-1,2-dihydroquinoline, 6-(4-fluoro-2-methoxyphenyl)-5-[2-(2-hydroxyethyl)phenoxy-methyl]-2,2,4-trimethyl-1,2-dihydroquinoline, 6-(4-fluoro-2-methoxyphenyl)-5-(2-methyl-5-nitrophenoxy-methyl)-2,2,4-trimethyl-1,2-dihydroquinoline, 6-(4-fluoro-2-methoxyphenyl)-5-(2-alkylphenoxymethyl)-2,2,4-trimethyl-1,2-dihydroquinoline, 6-(5-chloro-2-methoxyphenyl)-5-[2-(2-hydroxyethyl)phenoxy-methyl]-2,2,4-trimethyl-1,2-dihydroquinoline, 5-(5-fluoro-2-methylphenoxymethyl)-6-(4-hydroxy-2-methoxyphenyl)-2,2,4-trimethyl-1,2-dihydroquinoline, 5-(5-fluoro-2-methylphenoxymethyl)-6-(5-hydroxy-2-methoxyphenyl)-2,2,4-trimethyl-1,2-dihydroquinoline, 6-(4-hydroxy-2-methoxyphenyl)-5-(4-methybenzoyloxymethyl)-2,2,4-trimethyl-1,2-dihydroquinoline, 6-(2-methoxyphenyl)-5-phenylaminomethyl-2,2,4-trimethyl-1, 2-dihydroquinoline, 6-(4-fluoro-2-methoxyphenyl)-5-phenylaminomethyl-2,2,4-trimethyl-1,2-dihydroquinoline, 6-(4-fluoro-2-methoxyphenyl)-5-(4-methoxyphenylaminomethyl)-2,2,4-trimethyl-1,2-dihydroquinoline, 6-(4-fluoro-2-methoxyphenyl)-5-(4-fluorophenylaminomethyl)-2,2,4-trimethyl-1,2-dihydroquinoline, 6-(4-fluoro-2-methoxyphenyl)-5-(3-fluorophenylaminomethyl)-2,2,4-trimethyl-1,2-dihydroquinoline, 6-(4-fluoro-2- methoxyphenyl)-5-(2-fluorophenylaminomethyl)-2,2,4-trimethyl-1,2-dihydroquinoline, 6-(4-fluoro-2-methoxyphenyl)-5-(3-methoxyphenylamino-methyl)-2,2,4-trimethyl-1,2-dihydroquinoline, 6-(4-fluoro-2-methoxyphenyl)-5-(2-methoxyphenylamino-methyl)-2,2,4-trimethyl-1,2-dihydroquinoline, 6-(4,5-difluoro-2-methoxyphenyl)-5-(2-methoxyphenylamino-methyl)-2,2,4-trimethyl-1,2-dihydroquinoline, 6-(4-fluoro-2-methoxyphenyl)-5-(2-hydroxymethyl-phenylaminomethyl)-2,2,4-trimethyl-1,2-dihydroquinoline, 6-(4-fluoro-2-methoxyphenyl)-5-(2-methoxy-5-methylphenyl-aminomethyl)-2,2,4-trimethyl-1,2-dihydroquinoline, 6-(4-fluoro-2-methoxyphenyl)-5-(5-fluoro-2-methylphenyl-aminomethyl)-2,2,4-trimethyl-1,2-dihydroquinoline, 6-(5-chloro-2-methoxyphenyl)-5-(2-methoxyphenylamino-methyl)-2,2,4-trimethyl-1,2-dihydroquinoline, 6-(5-chloro-2-methoxyphenyl)-5-(5-fluoro-2-methylphenyl-aminomethyl)-2,2,4-trimethyl-1,2-dihydroquinoline, 6-(2-methoxyphenyl)-5-phenylthiomethyl-2,2,4-trimethyl-1,2-dihydroquinoline, 6-(4-fluoro-2-methoxyphenyl)-5-phenylthiomethyl-2,2,4-trimethyl-1,2-dihydroquinoline, 6-(4-fluoro-2-methoxyphenyl)-5-(2-methoxyphenylthiomethyl)-2,2,4-trimethyl-1,2-dihydroquinoline, 6-(4-fluoro-2-methoxyphenyl)-5-[(5-methylthiophen-2-yl) carbonyloxymethyl]-2,2,4-trimethyl-1,2-dihydroquinoline, 6-(4-fluoro-2-methoxyphenyl)-5-[(4-methylthiophen-2-yl) carbonyloxymethyl]-2,2,4-trimethyl-1,2-dihydroquinoline, 5-[(5-chlorothiophen-2-yl)carbonyloxymethyl]-6-(4-fluoro-2-methoxyphenyl)-2,2,4-trimethyl-1,2-dihydroquinoline, 6-(4-fluoro-2-methoxyphenyl)-5-[(3-methylthiophen-2-yl) carbonyloxymethyl]-2,2,4-trimethyl-1,2-dihydroquinoline, 5-[(5-bromothiophen-2-yl)carbonyloxymethyl]-6-(4-fluoro-2-methoxyphenyl)-2,2,4-trimethyl-1,2-dihydroquinoline, 6-(4-fluoro-2-methoxyphenyl)-5-[(5-methoxythiophen-2-yl) carbonyloxymethyl]-2,2,4-trimethyl-1,2-dihydroquinoline, 6-(4-fluoro-2-methoxyphenyl)-5-[(thiophen-3-yl)carbonyloxymethyl]-2,2,4-trimethyl-1,2-dihydroquinoline, 6-(4,5-difluoro-2-methoxyphenyl)-5-[(5-methylthiophen-2-yl)carbonyloxymethyl]-2,2,4-trimethyl-1,2-dihydroquinoline, 6-(5-chloro-2-methoxyphenyl)-5-(5-methylthiophen-2-ylcarbonyloxymethyl)-2,2,4-trimethyl-1,2-dihydroquinoline, 6-(5-chloro-2-methoxyphenyl)-5-(4-methoxybenzoyloxymethyl)-2,2,4-trimethyl-1,2-dihydroquinoline, 6-(5-chloro-2-methoxyphenyl)-5-(2-methyl-5-nitrophenoxy-methyl)-2,2,4-trimethyl-1,2-dihydroquinoline, 6-(5-chloro-2-methoxyphenyl)-5-(5-fluoro-2-methylphenoxy-methyl)-2,2,4-trimethyl-1,2-dihydroquinoline, 6-(5-chloro-2-methoxyphenyl)-5-(2-methoxy-5-nitrophenoxy-methyl)-2,2,4-trimethyl-1,2-dihydroquinoline, 6-(5-chloro-2-methoxyphenyl)-5-(5-chloro-2-methylphenoxy-methyl)-2,2,4-trimethyl-1,2-dihydroquinoline, 6-(5-chloro-2-methoxyphenyl)-5-(5-fluoro-2-methoxyphenoxy-methyl)-2,2,4-trimethyl-1,2-dihydroquinoline, 6-(5-chloro-2-methoxyphenyl)-5-(2,5-dimethylphenoxymethyl)-2,2,4-trimethyl-1,2-dihydroquinoline, 5-(2-allylphenoxymethyl)-6-(5-chloro-2-methoxyphenyl)-2,2,4-trimethyl-1,2-dihydroquinoline, 5-(5-fluoro-2-methylphenoxymethyl)-6-(2-methoxy-5-nitro-phenyl)-2,2,4-trimethyl-1,2-dihydroquinoline, 6-(4-allyloxy-2-methoxyphenyl)-5-(5-fluoro-2-methylphenoxy-methyl)-2,2,4-trimethyl-1,2-dihydroquinoline, 6-(5-allyloxy-2-methoxyphenyl)-5-(5-fluoro-2-methylphenoxy-methyl)-2,2,4-trimethyl-1,2-dihydroquinoline, 6-(5-amino-2-methoxyphenyl)-5-(5-fluoro-2-methylphenoxy-methyl)-2,2,4-trimethyl-1,2-dihydroquinoline, 5-(2-fluorobenzoyloxymethyl)-6-(4-fluoro-2-methoxyphenyl)-2,2,4-trimethyl-1,2-dihydroquinoline, 5-(3-fluorobenzoyloxymethyl)-6-(4-fluoro-2-methoxyphenyl)-2,2,4-trimethyl-1,2-dihydroquinoline, 5-(4-fluorobenzoyloxymethyl)-6-(4-fluoro-2-methoxyphenyl)-2,2,4-trimethyl-1,2-dihydroquinoline, 6-(4-fluoro-2-methoxyphenyl)-5-(4-methylphenylaminomethyl)-2,2,4-trimethyl-1,2-dihydroquinoline, 6-(4-fluoro-2-methoxyphenyl)-5-(3-methylphenylaminomethyl)-2,2,4-trimethyl-1,2-dihydroquinoline, 6-(4-fluoro-2-methoxyphenyl)-5-(2-methylphenylaminomethyl)-2,2,4-trimethyl-1,2-dihydroquinoline and 6-(4-fluoro-2-methoxyphenyl)-5-(2-methylphenylthiomethyl)-2,2,4-trimethyl-1,2-dihydroquinoline, or a pharmaceutically acceptable salt thereof.

18. The method according to claim 1, wherein the compound is 5-(5-fluoro-2-methylphenoxymethyl)-6-(4-hydroxy-2-methoxyphenyl)-2,2,4-trimethyl-1,2-dihydroquinoline.

19. The method according to claim 1, wherein the compound is 5-(5-fluoro-2-methylphenoxymethyl)-6-(2-methoxy-4-methoxymethoxyphenyl)-2,2,4-trimethyl-1,2-dihydroquinoline.

20. The method according to claim 1, wherein the compound is 5-(5-fluoro-2-methylphenoxymethyl)-6-(2-methoxy-5-methoxymethoxyphenyl)-2,2,4-trimethyl-1,2-dihydroquinoline.

21. The method according to claim 1, wherein the compound is 6-(4-benzyloxy-2-methoxyphenyl)-5-(5-fluoro-2-methylphenoxymethyl)-2,2,4-trimethyl-1,2-dihydroquinoline.

22. The method according to claim 1, wherein the compound is 6-(5-benzyloxy-2-methoxyphenyl)-5-(5-fluoro-2-methylphenoxymethyl)-2,2,4-trimethyl-1,2-dihydroquinoline.

23. The method according to claim 1, wherein the compound is 6-[5-(2-chlorobenzyloxy)-2-methoxy-phenyl]-5-(5-fluoro-2-methylphenoxymethyl)-2,2,4-trimethyl-1,2-dihydroquinoline.

24. The method according to claim 1, wherein the compound is 6-[5-(3-chlorobenzyloxy)-2-methoxy-phenyl]-5-(5-fluoro-2-methylphenoxymethyl)-2,2,4-trimethyl-1,2-dihydroquinoline.

25. The method according to claim 1, wherein the compound is 6-[5-(4-chlorobenzyloxy)-2-methoxy-phenyl]-5-(5-fluoro-2-methylphenoxymethyl)-2,2,4-trimethyl-1,2-dihydroquinoline.

26. The method according to claim 1, wherein the compound is 5-(5-fluoro-2-methylphenoxymethyl)-6-[2-methoxy-5-(2-methoxybenzyloxy)phenyl]-2,2,4-trimethyl-1,2-dihydroquinoline.

27. The method according to claim 1, wherein the compound is 5-(5-fluoro-2-methylphenoxymethyl)-6-[2-methoxy-5-(3-methoxybenzyloxy)phenyl]-2,2,4-trimethyl-1,2-dihydroquinoline.

28. The method according to claim 1, wherein the compound is 5-(5-fluoro-2-methylphenoxymethyl)-6-[2-methoxy-5-(4-methoxybenzyloxy)phenyl]-2,2,4-trimethyl-1,2-dihydroquinoline.

29. The method according to claim 1, wherein the compound is 6-[4-(2-chlorobenzyloxy)-2-methoxy-phenyl]-5-(5-fluoro-2-methylphenoxymethyl)-2,2,4-trimethyl-1,2-dihydroquinoline.

30. The method according to claim 1, wherein the compound is 6-[4-(3-chlorobenzyloxy)-2-methoxy-phenyl]-5-(5-fluoro-2-methylphenoxy-methyl)-2,2,4-trimethyl-1,2-dihydroquinoline.

31. The method according to claim 1, wherein the compound is 6-[4-(4-chlorobenzyloxy)-2-methoxy-phenyl]-5-(5-fluoro-2-methylphenoxymethyl)-2,2,4-trimethyl-1,2-dihydroquinoline.

32. The method according to claim 1, wherein the compound is 5-(5-fluoro-2-methylphenoxymethyl)-6-[2-methoxy-5-(2-methylbenzyloxy)phenyl]-2,2,4-trimethyl-1,2-dihydroquinoline.

33. The method according to claim 1, wherein the compound is 5-(5-fluoro-2-methylphenoxymethyl)-6-[2-methoxy-5-(3-methylbenzyloxy)phenyl]-2,2,4-trimethyl-1,2-dihydroquinoline.

34. The method according to claim 1, wherein the compound is 5-(5-fluoro-2-methylphenoxymethyl)-6-[2-methoxy-5-(4-methylbenzyloxy)phenyl]-2,2,4-trimethyl-1,2-dihydroquinoline.

\* \* \* \* \*